US012643903B2

(12) United States Patent
Lei et al.

(10) Patent No.: US 12,643,903 B2
(45) Date of Patent: Jun. 2, 2026

(54) BIFUNCTIONAL COMPOUNDS FOR DEGRADATION OF EGFR AND RELATED METHODS OF USE

(71) Applicant: BeiGene, Ltd., Grand Cayman (KY)

(72) Inventors: Bailin Lei, Beijing (CN); Huaqing Liu, Beijing (CN); Songzhe Han, Beijing (CN); Zhiwei Wang, Beijing (CN)

(73) Assignee: BeOne Medicines I GmbH, Basel (CH)

( * ) Notice: Subject to any disclaimer, the term of this patent is extended or adjusted under 35 U.S.C. 154(b) by 519 days.

(21) Appl. No.: 18/029,227

(22) PCT Filed: Sep. 29, 2021

(86) PCT No.: PCT/CN2021/121563

§ 371 (c)(1),
(2) Date: Mar. 29, 2023

(87) PCT Pub. No.: WO2022/068849

PCT Pub. Date: Apr. 7, 2022

(65) Prior Publication Data

US 2024/0025902 A1 Jan. 25, 2024

(30) Foreign Application Priority Data

Sep. 30, 2020 (WO) ................ PCT/CN2020/119276
Sep. 2, 2021 (WO) ................ PCT/CN2021/116268

(51) Int. Cl.
*C07D 487/04* (2006.01)
*C07D 401/14* (2006.01)
*C07D 405/14* (2006.01)

(52) U.S. Cl.
CPC ......... *C07D 487/04* (2013.01); *C07D 401/14* (2013.01); *C07D 405/14* (2013.01)

(58) Field of Classification Search
None
See application file for complete search history.

(56) References Cited

U.S. PATENT DOCUMENTS

| | | | |
|---|---|---|---|
| 2013/0225527 | A1 | 8/2013 | Wang |
| 2014/0066406 | A1 | 3/2014 | Wang |
| 2016/0045607 | A1 | 2/2016 | Crew |
| 2017/0008904 | A1 | 1/2017 | Crew |
| 2018/0050021 | A1 | 2/2018 | Ciulli |
| 2018/0072711 | A1 | 3/2018 | Crew |
| 2019/0106417 | A1 | 4/2019 | Gray |

FOREIGN PATENT DOCUMENTS

| | | | |
|---|---|---|---|
| CN | 101374818 | A | 2/2009 |
| CN | 102105150 | A | 6/2011 |
| CN | 103153064 | A | 6/2013 |
| CN | 107257800 | A | 10/2017 |
| CN | 109422733 | A | 3/2019 |
| CN | 109912655 | A | 6/2019 |
| CN | 109928956 | A | 6/2019 |
| CN | 110357889 | A | 10/2019 |
| CN | 110684015 | A | 1/2020 |
| CN | 110753693 | A | 2/2020 |
| CN | 110818690 | A | 2/2020 |
| CN | 112079866 | A | 12/2020 |
| CN | 114286678 | A | 4/2022 |
| WO | 2002020740 | A2 | 3/2002 |
| WO | 2012051587 | A1 | 4/2012 |
| WO | 2014108452 | A1 | 7/2014 |
| WO | 2016105518 | A1 | 6/2016 |
| WO | 2016146985 | A1 | 9/2016 |
| WO | 2016149668 | A1 | 9/2016 |
| WO | 2016197032 | A1 | 12/2016 |
| WO | 2016197114 | A1 | 12/2016 |
| WO | 2017011590 | A1 | 1/2017 |
| WO | 2017030814 | A1 | 2/2017 |
| WO | 2017079267 | A1 | 5/2017 |
| WO | 2017182418 | A1 | 10/2017 |
| WO | 2017197036 | A1 | 11/2017 |
| WO | 2017197046 | A1 | 11/2017 |
| WO | 2017197051 | A1 | 11/2017 |
| WO | 2017197056 | A1 | 11/2017 |
| WO | 2017201449 | A1 | 11/2017 |
| WO | 2017204445 | A2 | 11/2017 |
| WO | 2018071606 | A1 | 4/2018 |
| WO | 2018119441 | A1 | 6/2018 |
| WO | 2019015655 | A1 | 1/2019 |
| WO | 2019040274 | A1 | 2/2019 |
| WO | 2019042444 | A1 | 3/2019 |
| WO | 2019060742 | A1 | 3/2019 |
| WO | 2019113071 | A1 | 6/2019 |
| WO | 2019114770 | A1 | 6/2019 |

(Continued)

OTHER PUBLICATIONS

Ardley, H.C. et al., "E3 ubiquitin ligases," Essays Biochemistry, 41:15-30, 2005.
Cermakova, K. et al., "Next-Generation Drugs and Probes for Chromatin Biology: From Targeted Protein Degradation to Phase Separation," Molecules, 23(1958):26 pages, 2018.
Chen, Y. et al., "The cullin 4A/B-DDB1-cereblon E3 ubiquitin ligase complex mediates the degradation of CLC-1 chloride channels," Scientific Reports, 5(10667):1-13, 2015.
Chu, T. T. et al., "Specific knockdown of endogenous tau protein by peptide-directed ubiquitin-proteasome degradation", Cell Chemical Biology, 23(4):453-461, 2016.
Chung Hyo Kang et al., "Induced protein degradation of anaplastic lymphoma kinase (ALK) by proteolysis targeting chimera (PROTAC)", Biochemical and Biophysical Research Communications, 505(2):542-547, 2018, Abstract.
Crews, Craig M. et al., "Inducing Protein Degradation as a Therapeutic Strategy," J. Med. Chem., 61(2):403-404, 2018.
Extended European Search Report dated Feb. 3, 2025 issued for European Pat. No. 22795025 (8 pages).

(Continued)

*Primary Examiner* — Adam C Milligan
*Assistant Examiner* — Jason M. Nolan
(74) *Attorney, Agent, or Firm* — Foley & Lardner LLP

(57) ABSTRACT

Disclosed herein are bifunctional compounds formed by conjugating EGFR inhibitor moieties with E3 ligase Ligand moieties, which function to recruit targeted proteins to E3 ubiquitin ligase for degradation of mutant EGFR kinase, and methods of preparation and uses thereof.

38 Claims, No Drawings

(56) References Cited

FOREIGN PATENT DOCUMENTS

| | | | | |
|---|---|---|---|---|
| WO | 2019121562 A1 | | 6/2019 | |
| WO | 2019133531 A1 | | 7/2019 | |
| WO | 2019149922 A1 | | 8/2019 | |
| WO | 2019183523 A1 | | 9/2019 | |
| WO | 2019196812 A1 | | 10/2019 | |
| WO | WO-2019190259 A1 | * | 10/2019 | ........... C07D 403/14 |
| WO | 2020010210 A1 | | 1/2020 | |
| WO | 2020051564 A1 | | 3/2020 | |
| WO | 2020051572 A1 | | 3/2020 | |
| WO | 2020113233 A1 | | 6/2020 | |
| WO | 2020200291 A1 | | 10/2020 | |
| WO | 2020216371 A1 | | 10/2020 | |
| WO | 2020253862 A1 | | 12/2020 | |
| WO | 2021011871 A1 | | 1/2021 | |
| WO | 2021011913 A1 | | 1/2021 | |
| WO | 2021023233 A1 | | 2/2021 | |
| WO | 2021036922 A1 | | 3/2021 | |
| WO | 2021057882 A1 | | 4/2021 | |
| WO | 2021073498 A1 | | 4/2021 | |
| WO | 2021123087 A1 | | 6/2021 | |
| WO | 2021127190 A1 | | 6/2021 | |
| WO | 2021127283 A2 | | 6/2021 | |
| WO | 2021127561 A1 | | 6/2021 | |
| WO | 2021133809 A1 | | 7/2021 | |
| WO | 2021168074 A1 | | 8/2021 | |
| WO | 2021173677 A1 | | 9/2021 | |
| WO | 2021178920 A1 | | 9/2021 | |
| WO | 2021208918 A1 | | 10/2021 | |
| WO | 2021216440 A1 | | 10/2021 | |
| WO | 2022012622 A1 | | 1/2022 | |
| WO | 2022012623 A1 | | 1/2022 | |
| WO | 2022063106 A1 | | 3/2022 | |
| WO | 2022068849 A1 | | 4/2022 | |
| WO | 2022171123 A1 | | 8/2022 | |
| WO | 2022228556 A1 | | 11/2022 | |

OTHER PUBLICATIONS

Grice, G. L. et al., "The Proteasome Distinguishes between Heterotypic and Homotypic Lysine-11-Linked Polyubiquitin Chains," Cell Rep., 12(4):545-553, 2015.

He, Kailun, et al., "Discovery and biological evaluation of proteolysis targeting chimeras (PROTACs) as an EGFR degraders based on osimertinib and lenalidomide", Bioorganic & Medicinal Chemistry Letters, 30(12):127167, 2020.

International Search Report and Written Opinion for PCT/CN2022/075651 issued May 9, 2022 (14 pages).

International Search Report and Written Opinion for PCT/CN2022/090342 issued on Jul. 27, 2022 (18 pages).

Komander, D. et al., "The Ubiquitin Code," Annu. Rev. Biochem., 81:203-229, 2012.

Konduri et al., "EGFR fusions as novel therapeutic targets in lung cancer", Cancer Discovery, 6(6):601-611, 2016.

Lebraud, H. et al., "Protein degradation by in-cell self-assembly of proteolysis targeting chimeras," ACS Central Science, 2(12):927-934, 2016.

Lebraud, H. et al., "Protein degradation: a validated therapeutic strategy with exciting prospects," Essays Biochem., 61(5):517-527, 2017.

Lim, K. M. H. et al., "Dynamic Kinetic Resolution in Rhodium-Catalyzed Asymmetric Arylation of Phospholene Oxides", Journal of the American Chemical Society, 139(24):8122-8125, 2017.

Liu, S. et al., "Targeted selective degradation of Bruton's tyrosine kinase by PROTACs", Medicinal Chemistry Research, 29:802-808, 2020.

Lochmuller, C. H. et al., "Chromatographic Resolution of Enantiomers," Journal of Chromatography, 113:283-302, 1975.

Lu, J. et al., "Hijacking the E3 Ubiquitin ligase cereblon to efficiently target BRD4," Chemistry and Biology, 22(6):755-763, 2015.

Lu, X. et al., "Targeting EGFRL858R/T790M and EGFRL858R/T790M/C797S resistance mutations in NSCLC: Current developments in medicinal chemistry," Medicinal Research Reviews, 38(5):1550-1581, 2018.

Maemondo, M. et al., "Gefitinib or chemotherapy for non-small-cell lung cancer with mutated EGFR," New England Journal of Medicine, 362(25):2380-2388, 2010.

Matyskiela, M. E. et al., "SALL4 mediates teratogenicity as a thalidomide-dependent cereblon substrate," Nature Chemical Biology, 14(10):981-987, 2018.

Neklesa, T. K. et al., "Targeted protein degradation by PROTACs," Pharmacology & Therapeutics, 174:138-144, 2017.

Ottis, P. et al., "Assessing Different E3 Ligases for Small Molecule Induced Protein Ubiquitination and Degradation," ACS Chem. Biol., 12(10):2570-2578, 2017.

Ottis, P. et al., "Proteolysis-Targeting Chimeras: Induced Protein Degradation as a Therapeutic Strategy," ACS Chem. Biol., 12(4):892-898, 2017.

Pav, O. et al., "Novel phosphanucleoside analogs of dideoxynucleosides", Tetrahedron, 73: 5220-5228, 2017.

Qin, C. et al., "Discovery of QCA570 as an exceptionally potent and efficacious proteolysis targeting chimera (PROTAC) degrader of the bromodomain and extra-terminal (BET) proteins capable of inducing complete and durable tumor regression", Journal of Medicinal Chemistry, 61(15):6685-6704, 2018.

Qu, X. et al., "Effective degradation of EGFRL858R+T790M mutant proteins by CRBN-based PROTACs through both proteosome and autophagy/lysosome degradation systems," European Journal of Medicinal Chemistry, 218(113328):1-14, 2021.

Sainan, A. et al., "Small-molecule PROTACs: An emerging and promising approach for the development of targeted therapy drugs", EBioMedicine, 36:552-562, 2018.

Sakamoto, Kathleen M., "Chimeric molecules to target proteins for ubiquitination and degradation," Methods Enzymol., 399:833-847, 2005.

Sakamoto, Kathleen M., "Protacs: chimeric molecules that target proteins to the Skp1-Cullin-F box complex for ubiquitination and degradation," Proc Natl Acad Sci USA, 98(15):8554-8559, 2001.

Spradlin, J. N. et al., "Harnessing the anti-cancer natural product nimbolide for targeted protein degradation," Nat. Chem. Biol, 15(7):747-755, 2019.

Sun, N. et al., "Development of a Brigatinib degrader (SIAIS117) as a potential treatment for ALK positive cancer resistance", European Journal of Medicinal Chemistry, vol. 193, 7 pages, 2020.

Sun, Y. et al., "PROTAC-induced BTK degradation as a novel therapy for mutated BTK C481S induced ibrutinib-resistant B-cell malignancies", Cell Research, 28(7):779-781, 2018.

Sun, Y. et al., "Degradation of Bruton's tyrosine kinase mutants by PROTACs for potential treatment of ibrutinib-resistant non-Hodgkin lymphomas", Leukemia, 33:2105-2110, 2019.

Swatek, K. N. et al., "Ubiquitin modifications," Cell Research, 26(4):399-422, 2016.

Thress, K. S. et al., "Acquired EGFR C797S mutation mediates resistance to AZD9291 in non-small cell lung cancer harboring EGFR T790M," Nature Medicine, 21(6):560-562, 2015.

Tinworth, C. P. et al., "PROTAC-mediated degradation of Bruton's tyrosine kinase is inhibited by covalent binding", ACS Chemical Biology, 14(3):342-347, 2019.

Toure, M. et al., "Small-Molecule PROTACS: New Approaches to Protein Degradation," Angew. Chem. Int. Ed., 55(6):1966-1973, 2016.

Winter, G. E. et al., "Phthalimide conjugation as a strategy for in vivo target protein degradation," Science, 348(6241):1376-1381, 2015.

Xu, Y. et al., "Acquired resistance of lung adenocarcinoma to EGFR-tyrosine kinase inhibitors gefitinib and erlotinib," Cancer Biology & Therapy, 9(8):572-582, 2010.

Yarden, Y. et al., "Untangling the ErbB signalling network," Nature Reviews Molecular Cell Biology, 2(2):127-137, 2001.

Yewale, C. et al., "Epidermal growth factor receptor targeting in cancer: a review of trends and strategies", Biomaterials, 34(34):8690-8707, 2013.

(56) References Cited

OTHER PUBLICATIONS

Zhang, H. et al., "Design, synthesis and biological evaluation of novel EGFR PROTACs targeting Del19/T790M/C797S mutation," ACS Medicinal Chemistry Letters, 13:278-283, 2022.
Zhang, H. et al., "Discovery of potent epidermal growth factor receptor (EGFR) degraders by proteolysis targeting chimera (PROTAC)", European Journal of Medicinal Chemistry, 189, p. 112061, 2020.
Zhang, X. et al., "Design and synthesis of selective degraders of EGFRL858R/T790M mutant", European Journal of Medicinal Chemistry, 192, p. 112199, 2020.
Zhang, X. et al., "Electrophilic PROTACs that degrade nuclear proteins by engaging DCAF16", Nat. Chem. Biol., 15(7):737-746, 2019.
International Search Report issued Dec. 30, 2021 in PCT/CN2021/121563.
Written Opinion issued Dec. 30, 2021 in PCT/CN2021/121563.

* cited by examiner

BIFUNCTIONAL COMPOUNDS FOR DEGRADATION OF EGFR AND RELATED METHODS OF USE

CROSS-REFERENCE TO RELATED APPLICATION

This application is a Section 371 of International Application No. PCT/CN2021/121563 filed Sep. 29, 2021, which was published in the English language Apr. 7, 2022, under International Publication No. WO 2022/068849 A1, which claims priority to International Patent Application No. PCT/CN2020/119276 Filed Sep. 30, 2020, and International Application No. PCT/CN2021/116268 filed Sep. 2, 2021, the disclosures of which are incorporated herein by reference in their entireties.

FIELD OF THE INVENTION

Disclosed herein are novel bifunctional compounds formed by conjugating EGFR inhibitor moieties with E3 ligase Ligand moieties, which function to recruit targeted proteins to E3 ubiquitin ligase for degradation of mutant EGFR kinase, and methods of preparation and uses thereof.

BACKGROUND OF THE INVENTION

Proteolysis targeting chimera (PROTAC) consists of two covalently linked protein-binding molecules: one capable of engaging an E3 ubiquitin ligase, and another that binds to the protein of interest (POI) a target meant for degradation (Sakamoto K M et al., *Proc. Natl. Acad. Sci.* 2001, 98: 8554-9.; Sakamoto K. M. et al., *Methods Enzymol.* 2005; 399:833-847.). Rather than inhibiting the target protein's enzymatic activity, recruitment of the E3 ligase to the specific unwanted proteins results in ubiquitination and subsequent degradation of the target protein by the proteasome. The whole process of ubiquitination and proteasomal degradation is known as the ubiquitin-proteasome pathway (UPP) (Ardley H. et al., *Essays Biochem.* 2005, 41, 15-30; Komander D. et al., *Biochem.* 2012, 81, 203-229; Grice G. L. et al., *Cell Rep.* 2015, 12, 545-553; Swatek K. N. et al., *Cell Res.* 2016, 26, 399-422). Proteasomes are protein complexes which degrade unneeded, misfolded or abnormal proteins into small peptides to maintain health and productivity of the cells. Ubiquitin ligases, also called an E3 ubiquitin ligase, directly catalyze the transfer of ubiquitin from the E2 to the target protein for degradation. Although the human genome encodes over 600 putative E3 ligases, only a limited number of E3 ubiquitin ligases have been widely applied by small molecule PROTAC technology: cereblon (CRBN), Von Hippel-Lindau (VHL), mouse double minute 2 homologue (MDM2) cellular inhibitor of apoptosis protein (cIAP) (Philipp O. et al., *Chem. Biol.* 2017, 12, 2570-2578), recombinant Human Ring Finger Protein 114 (RNF114) (Spradlin, J. N. et al. *Nat. Chem. Biol.* 2019, 15, 747-755) and DDB1 And CUL4 Associated Factor 16 (DCAF16) (Zhang, X. et al. *Nat. Chem. Biol.* 2019, 15, 737-746). For example, cereblon (CRBN) forms an E3 ubiquitin ligase complex with damaged DNA binding protein 1 (DDB1) and Cullin-4A (CUL4A) to ubiquitinate a number of other proteins followed by the degradation via proteasomes. (Yi-An Chen, et al., *Scientific Reports* 2015, 5, 1-13). Immunomodulatory drugs (IMiDs), including thalidomide, lenalidomide, and pomalidomide, function as monovalent promoters of PPIs by binding to the cereblon (CRBN) subunit of the $CRL4A^{CRBN}$ E3 ligase complex and recruiting neosubstrate proteins. (Matyskiela, M. E. et al., *Nat Chem Biol* 2018, 14, 981-987.) As a consequence, the ability of thalidomide, and its derivatives, to recruit CRBN has been widely applied in proteolysis-targeting chimeras (PROTACs) related studies (Christopher T. et al. *ACS Chem. Biol.* 2019, 14, 342-347.; Honorine L. et al, *ACS Cent. Sci.* 2016, 2, 927-934). PROTACs have great potential to eliminate protein targets that are "undruggable" by traditional inhibitors or are non-enzymatic proteins. (Chu T T. et al., *Cell Chem Biol.* 2016; 23:453-461. Qin C. et al., *J Med Chem* 2018; 61: 6685-6704. Winter G E. et al., *Science* 2015; 348:1376-1381.) In the recent years, PROTACs as useful modulators promote the selective degradation of a wide range of target proteins have been reported in antitumor studies. (Lu J. et al., *Chem Biol.* 2015; 22(6):755-763; Ottis P. et al., *Chem Biol.* 2017; 12(4):892-898.; Crews C. M. et al., *J Med Chem.* 2018; 61(2):403-404; Neklesa T. K. et al., *Pharmacol Ther.* 2017, 174:138-144.; Cermakova K. et al., *Molecules,* 2018.23(8).; An S. et al., *EBioMedicine,* 2018.; Lebraud H. et al., *Essays Biochem.* 2017; 61(5): 517-527.; Sun Y H. et al., *Cell Res.* 2018; 28:779-81; Toure M. et al., *Angew Chem Int Ed Engl.* 2016; 55(6):1966-1973; Yonghui Sun et al., *Leukemia*, volume 33, pages 2105-2110 (2019); Shaodong Liu et al., *Medicinal Chemistry Research*, volume 29, pages 802-808(2020); and has been disclosed or discussed in patent publications, e.g., US20160045607, US20170008904, US20180050021, US20180072711, WO2002020740, WO2014108452, WO2016146985, WO2016149668, WO2016197032, WO2016197114, WO2017011590, WO2017030814, WO2017079267, WO2017182418, WO2017197036, WO2017197046, WO2017197051, WO2017197056, WO2017201449, and WO2018071606.

Epidermal growth factor receptor (EGFR) that belongs to the ErbB family is a transmembrane receptor tyrosine kinase (RTK), which plays a fundamentally key role in cell proliferation, differentiation, and motility (Y Yarden, et al., *Nat. Rev. Mol. Cell Biol.* 2001; 2:127-137.). Homo- or heterodimerization of EGFR and other ErbB family members activates cytoplasmic tyrosine kinase domains to initiate intracellular signaling. Overexpression or activating mutations of EGFR are associated the development of many types of cancers, such as pancreatic cancer, breast cancer, glioblastoma multiforme, head and neck cancer, and non-small cell lung cancer (Yewale C., et al. *Biomaterials.* 2013, 34 (34): 8690-8707.). The activating mutations in the EGFR tyrosine kinase domain (L858R mutation and exon-19 deletion) have been identified as oncogenic drivers for NSCLC (Konduri, K., et al. *Cancer Discovery* 2016, 6 (6), 601-611.). The first-generation EGFR tyrosine kinase inhibitors (EGFR-TKIs) gefitinib and erlotinib have been approved for NSCLC patients with EGFR activation mutations (M. Maemondo, *N. Engl. J. Med.* 362 (2010) 2380-2388.). Although most patients with EGFR mutant NSCLC respond to these therapies, patients typically develop resistance after an average of one year on treatment. There are several mechanisms of acquired resistance to gefitinib and erlotinib, including a secondary threonine 790 to methionine 790 mutation (T790M), is also called "gatekeeper" T790M mutation (Xu Y, et al. *Cancer Biol Ther.* 2010, 9 (8): 572-582.). Therefore, the second-generation EGFR-TKIs afatinib and the third-generation EGFR-TKIs osimertinib (AZD9291) were developed as irreversible EGFR inhibitors that bind to Cys797 for the treatment of patients with T790M mutation. In particular, osimertinib that largely spares WT EGFR has achieved a greater clinical response rate in NSCLC patients with EGFR T790M. However, several recent studies have reported a tertiary Cys797 to Ser797 (C797S) point mutation with osimertinib clinical therapy (Thress K S, et al. *Nat. Med.* 2015, 21 (6): 560-562.). There is a need for drugs which can overcome EGFR (C797S) resistance obstacle in non-small cell lung cancer (NSCLC). EGFR-Targeting PROTACs serve as a potential strategy to overcome drug resistance mediated by these mutants, which has been disclosed or discussed in patent publications, e.g. WO2018119441, WO2019149922, WO2019183523, WO2019121562 and US20190106417.

Although, a number of EGFR-targeting PROTACs which were designed to degrade EGFR mutant proteins have been published (Zhang X., et al. *Eur. J Med Chem.* 2020, 192, 112199.; Zhang H, et al. *Eur. J Med Chem.* 2020, 189, 112061.; Lu X, *Med Res. Rev.* 2018, 38(5):1550-1581. He K., et al. *Bioorg. Med Chem. Lett.* 2020, 15, 127167.). Most of the published molecules are based on the first, second, and third generations of EGFR inhibitors. However, there were no data which showed those EGFR-Targeting PROTACs degrading all the main EGFR mutations.

The present application provides novel bifunctional compounds which degrade mutant EGFR kinase and compositions for the treatment of serious diseases.

SUMMARY OF THE INVENTION

One objective of the present invention is to provide compounds and derivatives formed by conjugating EGFR inhibitor moieties with E3 ligase Ligand moieties, which function to recruit targeted proteins to E3 ubiquitin ligase for degradation, and methods of preparation and uses thereof.

Aspect 1. A compound of Formula (I):

(I)

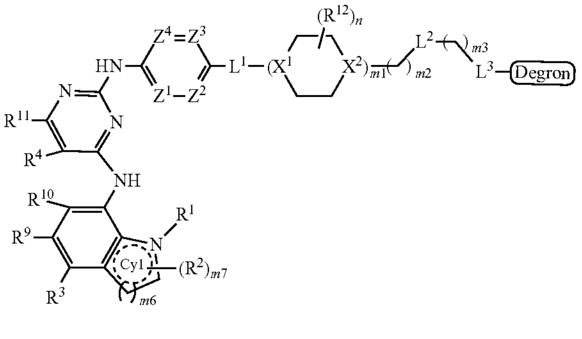

or an N-oxide thereof, or a pharmaceutically acceptable salt thereof, or a stereoisomer thereof, or a tautomer or a prodrug thereof, wherein:

Cy1 is selected from an aromatic ring or non-aromatic ring;

$R^1$ is selected from $-S(O)R^{1a}$, $-S(O)_2R^{1a}$, $-C(O)R^{1a}$ or $-P(O)R^{1a}R^{1b}$, wherein $R^{1a}$ and $R^{1b}$ are each independently selected from $-C_{1-8}$alkyl, $-C_{2-8}$alkenyl, $-C_{2-8}$alkynyl, cycloalkyl, heterocyclyl, aryl, heteroaryl, $-CN$, $-OR^{1d}$, $-CH_2CONR^{1d}R^{1e}$, $-CH_2CH_2CONR^{1d}R^{1e}$, $-CH_2CH_2CH_2CONR^{1d}R^{1e}$, $-NR^{1d}R^{1e}$, $-CH_2NR^{1d}R^{1e}$, $-CH_2CH_2NR^{1d}R^{1e}$, $-CH_2CH_2CH_2NR^{1d}R^{1e}$ or $-NR^{1d}COR^{1e}$, wherein each of said $-C_{1-8}$alkyl, $-C_{2-8}$alkenyl, $-C_{2-8}$alkynyl, cycloalkyl, heterocyclyl, aryl or heteroaryl is optionally substituted with at least one substituent $R^{1f}$;

$R^{1d}$ and $R^{1e}$ are each independently hydrogen, $-C_{1-8}$alkyl, $-C_{1-8}$haloalkyl, $-C_{2-8}$alkenyl, $-C_{2-8}$alkynyl, cycloalkyl, heterocyclyl, aryl, or heteroaryl; or $R^{1d}$ and $R^{1e}$ together with the atom(s) to which they are attached, form a 3- to 12-membered ring, said ring comprising 0, 1 or 2 additional heteroatom(s) independently selected from nitrogen, oxygen or optionally oxidized sulfur as ring member(s), said ring is optionally substituted with at least one substituent $R^{1f}$;

$R^{1f}$, at each of its occurrences, is independently hydrogen, halogen, hydroxyl, $-C_{1-8}$alkyl, $-C_{1-8}$haloalkyl, $-C_{2-8}$alkenyl, $-C_{2-8}$alkynyl, cycloalkyl, heterocyclyl, aryl, heteroaryl, oxo, $-CN$, $-OR^{1g}$, $-COR^{1g}$, $-CO_2R^{1g}$, $-CONR^{1g}R^{1h}$, $-NR^{1g}R^{1h}$, $-NR^{1g}COR^{1h}$, or $-NR^{1g}CO_2R^{1h}$, wherein each of said cycloalkyl, heterocyclyl, aryl or heteroaryl is optionally substituted with 1, 2 or 3 substituents selected from halogen and $-C_{1-8}$alkyl;

$R^{1g}$ and $R^{1h}$ are each independently hydrogen, halogen, hydroxyl, $-C_{1-8}$alkyl, $C_{1-8}$alkoxy-$C_{1-8}$alkyl-, $-C_{1-8}$haloalkyl, $-C_{2-8}$alkenyl, $-C_{2-8}$alkynyl, cycloalkyl, heterocyclyl, aryl or heteroaryl;

$R^2$, at each of their occurrences, is selected from hydrogen, halogen, oxo, $-C_{1-8}$alkyl, cycloalkyl, heterocyclyl, $-C_6$-$C_{12}$aryl, 5- to 12-membered heteroaryl, $-CN$, $-OR^{2a}$, $-COR^{2a}$, $-CO_2R^{2a}$, $-CONR^{2a}R^{2b}$, $-NR^{2a}R^{2b}$, $-NR^{2a}COR^{2b}$ or $-NR^{2a}CO_2R^{2b}$, wherein each of said $-C_{1-8}$alkyl, cycloalkyl, heterocyclyl, aryl or heteroaryl is optionally substituted with at least one substituent $R^{2c}$; or when $m \geq 2$, two $R^2$ together with the atom(s) to which they are attached, form a 3- to 12-membered ring, said ring comprising 0, 1 or 2 heteroatom(s) independently selected from nitrogen, oxygen, or optionally oxidized sulfur as ring member(s), said ring is optionally substituted with at least one substituent $R^{2c}$;

$R^{2a}$ and $R^{2b}$ are each independently selected from hydrogen, $-C_{1-8}$alkyl, $-C_{2-8}$alkenyl, $-C_{2-8}$alkynyl, $C_{1-8}$alkoxy-$C_{1-8}$alkyl-, cycloalkyl, heterocyclyl, aryl or heteroaryl, wherein each of said $-C_{1-8}$alkyl, $-C_{2-8}$alkenyl, $-C_{2-8}$alkynyl, $C_{1-8}$alkoxy-$C_{1-8}$alkyl-, cycloalkyl, heterocyclyl, aryl or heteroaryl is optionally substituted with at least one substituent $R^{2c}$;

$R^{2c}$, at each of its occurrence, is independently halogen, hydroxyl, $-C_{1-8}$alkyl, -halo$C_{1-8}$alkyl, $-C_{2-8}$alkenyl, $-C_{2-8}$alkynyl, cycloalkyl, heterocyclyl, aryl, heteroaryl, oxo, $-CN$, $-OR^{2d}$, $-COR^{2d}$, $-CO_2R^{2d}$, $-CONR^{2d}R^{2e}$, $-NR^{2d}R^{2e}$, $-NR^{2d}COR^{2e}$, or $-NR^{2d}CO_2R^{2e}$;

$R^{2d}$ and $R^{2e}$ are each independently hydrogen, $-C_{1-8}$alkyl, -halo$C_{1-8}$alkyl, $-C_{2-8}$alkenyl, $-C_{2-8}$ alkynyl, cycloalkyl, heterocyclyl, aryl or heteroaryl;

$R^3$, $R^9$ and $R^{10}$ are each independently selected from hydrogen, halogen, $-C_{1-8}$alkyl, $-NR^{3a}R^{3b}$, $-OR^{3a}$, cycloalkyl, heterocyclyl, aryl, heteroaryl, $-CN$, $-COR^{3a}$ or $-CO_2R^{3a}$, wherein each of said $-C_{1-8}$alkyl, cycloalkyl, heterocyclyl, aryl, or heteroaryl is optionally substituted with at least one substituent $R^{3c}$;

$R^{3a}$ and $R^{3b}$ are each independently selected from hydrogen, $-C_{1-8}$alkyl, $-C_{2-8}$alkenyl, $-C_{2-8}$alkynyl, $C_{1-8}$alkoxy-$C_{1-8}$alkyl-, cycloalkyl, heterocyclyl, aryl or heteroaryl, wherein each of said $-C_{1-8}$alkyl, $-C_{2-8}$alkenyl, $-C_{2-8}$alkynyl, cycloalkyl, heterocyclyl, aryl or heteroaryl is optionally substituted with at least one substituent $R^{3d}$; or $R^{3c}$ and $R^{3d}$ are each independently halogen, hydroxy, —$C_{1-8}$alkyl, -halo$C_{1-8}$alkyl, —$C_{1-8}$alkoxy, —$C_{2-8}$alkenyl, —$C_{2-8}$alkynyl, cycloalkyl, heterocyclyl, aryl or heteroaryl;

$R^4$ and $R^{11}$ are each independently selected from hydrogen, halogen, —$C_{1-8}$alkyl, —$C_{2-8}$alkynyl, —$C_{1-8}$alkoxy, cycloalkyl, heterocyclyl, aryl, heteroaryl, —CN, —$OR^{4a}$, —$NR^{4a}R^{4b}$, —$NR^{4a}COR^{4b}$, or $CONR^{4a}R^{4b}$, wherein each of said —$C_{1-8}$alkyl, —$C_{2-8}$alkynyl, —$C_{1-8}$alkoxy, cycloalkyl, heterocyclyl, aryl, or heteroaryl is optionally substituted with at least one $R^{40}$, or $R^{4a}$ and $R^{4b}$ are each independently hydrogen, —$C_{1-8}$alkyl, -halo$C_{1-8}$alkyl, —$C_{2-8}$alkenyl, —$C_{2-8}$ alkynyl, cycloalkyl, heterocyclyl, aryl, or heteroaryl; or $R^4$ and $R^{11}$, together with the atom(s) to which they are attached, form a 3- to 12-membered ring, said ring comprising 0, 1 or 2 heteroatom(s) independently selected from nitrogen, oxygen, or optionally oxidized sulfur as ring member(s), said ring is optionally substituted with at least one substituent $R^{4e}$;

$R^{4c}$ is selected from halogen, —$C_{1-8}$alkyl, -halo$C_{1-8}$alkyl, cycloalkyl, heterocyclyl, aryl, heteroaryl, oxo, —CN, —$OR^{4c}$, —$SO_2R^{4c}$, —$SO_2NR^{4c}R^{4d}$, —$COR^{4c}$, —$CO_2R^{4c}$, —$CONR^{4c}R^{4d}$, —$NR^{4c}R^{4d}$, —$NR^{4c}COR^{4d}$, —$NR^{4c}CO_2R^{4d}$, or —$NR^{4c}SO_2R^{4d}$;

$R^{4c}$ and $R^{4d}$ are each independently hydrogen, —$C_{1-8}$alkyl, -halo$C_{1-8}$alkyl, —$C_{2-8}$alkenyl, —$C_{2-8}$ alkynyl, cycloalkyl, heterocyclyl, aryl, or heteroaryl;

$R^{12}$ is independently selected from hydrogen, halogen, —$C_{1-8}$alkyl, —$NR^{12a}R^{12b}$, —$OR^{12a}$, cycloalkyl, heterocyclyl, aryl, heteroaryl, oxo or —CN, wherein each of said —$C_{1-8}$alkyl, cycloalkyl, heterocyclyl, aryl, or heteroaryl is optionally substituted with at least one substituent $R^{12c}$; or two $R^{12}$ together with the atom(s) to which they are attached, form a 3- to 12-membered ring, said ring comprising 0, 1 or 2 heteroatom(s) independently selected from nitrogen, oxygen, or optionally oxidized sulfur as ring member(s), said ring is optionally substituted with at least one substituent $R^{12c}$;

$R^{12a}$ and $R^{12b}$ are each independently selected from hydrogen, —$C_{1-8}$alkyl, —$C_{2-8}$alkenyl, —$C_{2-8}$alkynyl, cycloalkyl, heterocyclyl, aryl or heteroaryl, wherein each of said —$C_{1-8}$alkyl, —$C_{2-8}$alkenyl, —$C_{2-8}$alkynyl, cycloalkyl, heterocyclyl, aryl or heteroaryl is optionally substituted with at least one substituent $R^{12d}$; or $R^{12c}$ and $R^{12d}$ are each independently halogen, hydroxy, —$C_{1-8}$alkyl, -halo$C_{1-8}$alkyl, —$C_{1-8}$alkoxy, —$C_{2-8}$alkenyl, —$C_{2-8}$alkynyl, cycloalkyl, heterocyclyl, aryl or heteroaryl;

$Z^1$, $Z^2$, $Z^3$ and $Z^4$ are each independently selected from —$CR^Z$, or N;

$R^Z$, at each of its occurrences, is independently selected from hydrogen, halogen, —$C_{1-8}$alkyl, —$NR^{Za}R^{Zb}$, —$OR^{Za}$, cycloalkyl, heterocyclyl, aryl, heteroaryl, or CN, wherein each of said —$C_{1-8}$alkyl, cycloalkyl, heterocyclyl, aryl, or heteroaryl is optionally substituted with at least one $R^{Zc}$;

or two $R^Z$, when attached to adjacent carbon atoms of the ring, together with the two carbon atoms to which they are attached, form a 3- to 12-membered ring comprising 0, 1 or 2 heteroatom(s) independently selected from nitrogen, oxygen or optionally oxidized sulfur as ring member(s), said ring is optionally substituted with at least one substituent $R^{Zc}$;

$R^{Za}$ and $R^{Zb}$ are each independently selected from hydrogen, —$C_{1-8}$alkyl, —$C_{2-8}$alkenyl, —$C_{2-8}$alkynyl, cycloalkyl, heterocyclyl, aryl, or heteroaryl, wherein each of said —$C_{1-8}$alkyl, —$C_{2-8}$alkenyl, —$C_{2-8}$alkynyl, cycloalkyl, heterocyclyl, aryl, or heteroaryl is optionally substituted with at least one substituent $R^{Zd}$;

$R^{Zc}$ is independently halogen, hydroxy, —$C_{1-8}$alkyl, -halo$C_{1-8}$alkyl, —$C_{1-8}$alkoxy, —$C_{2-8}$alkenyl, —$C_{2-8}$alkynyl, cycloalkyl, heterocyclyl, aryl, or heteroaryl; or two $R^{Zc}$, together with the atom(s) to which they are attached, form a 3- to 12-membered ring, said ring comprising 0, 1 or 2 heteroatom(s) independently selected from nitrogen, oxygen, or optionally oxidized sulfur as ring member(s), said ring is optionally substituted with at least one substituent $R^{Zd}$;

$R^{Zd}$ is independently halogen, hydroxy, —$C_{1-8}$alkyl, -halo$C_{1-8}$alkyl, —$C_{1-8}$alkoxy, —$C_{2-8}$alkenyl, —$C_{2-8}$alkynyl, cycloalkyl, heterocyclyl, aryl, or heteroaryl;

$L^1$ is selected from a single bond, —O—, —$SO_2$—, —C(O)—, —$NR^{L1a}$—, —$C_3$-$C_8$cycloalkylene-, $*^{L1}$—O—$C_{1-8}$alkylene-$**^{L1}$, $*^{L1}$—$C_{1-8}$alkylene-O—$**^{L1}$, $*^{L1}$—$SO_2$—$C_{1-8}$alkylene-$*^{L1}$, $*^{L1}$—$C_{1-8}$alkylene-$SO_2$—$**^{L1}$, $*^{L1}$—C(O)—$C_{1-8}$alkylene-$**^{L1}$, $*^{L1}$—$C_{1-8}$alkylene-C(O)—$**^{L1}$, $*^{L1}$—$NR^{1a}$—$C_{1-8}$alkylene-$**^{L1}$, $*^{L1}$ $C_{1-8}$alkylene-$NR^{L1a}$—$**^{L1}$, $*^{L1}$—$NR^{1a}$C(O)—$**^{L1}$, $*^{L1}$—C(O)$NR^{L1a}$—$**^{L1}$, —$C_{1-8}$alkylene-, —$C_{2-8}$alkenylene-, —$C_{2-8}$alkynylene-, —[O$(CR^{L1a}R^{L1b})_{m4}]_{m5}$—,

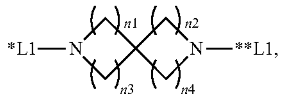

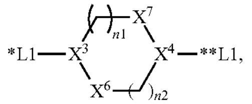

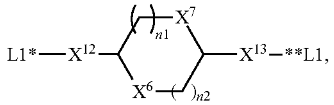

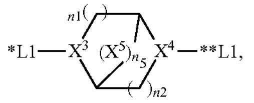

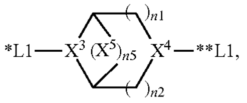

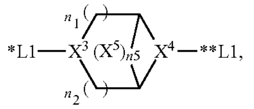

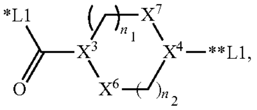

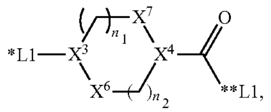

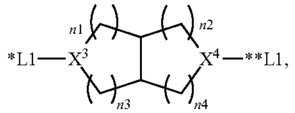

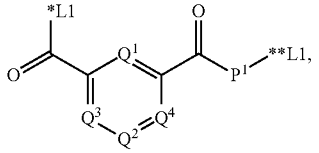

-continued
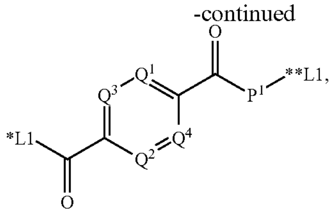
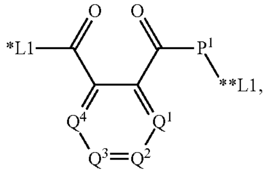
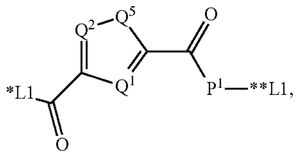
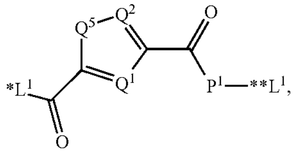
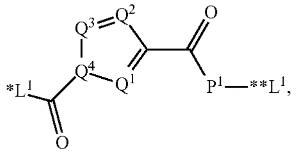
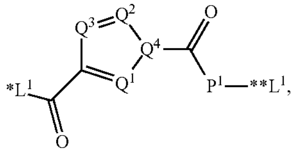
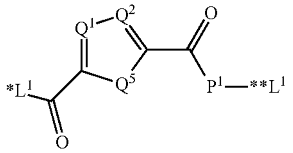
or
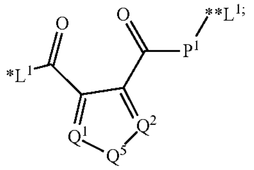
each of said —$C_3$-$C_8$cycloalkylene-, $*^{L1}$—O—$C_{1-8}$alkylene-$**^{L1}$, $*^{L1}$—$C_{1-8}$alkylene-O—$**^{L1}$, $*^{L1}$—S—$C_{1-8}$alkylene-$**^{L1}$,$*^{L1}$—$SO_2$—$C_{1-8}$alkylene-$**^{L1}$, $*^{L1}$—$C_{1-8}$alkylene-$SO_2$—$**^{L1}$, $*^{L1}$—$C_{1-8}$alkylene-$**^{L1}$, $*^{L1}$—$C_{1-8}$alkylene-CO—$**^{L1}$, $*^{L1}$—$NR^{L1a}$—$C_{1-8}$alkylene-$**^{L1}$, —$*^{L1}$—$C_{1-8}$alkylene-$NR^{L1a}$—$**^{L1}$, —$C_{1-8}$alkylene-, —$C_{2-8}$alkenylene-, —$C_{2-8}$alkynylene-,
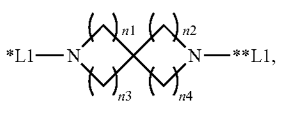
-continued
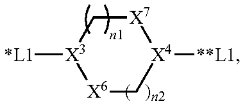
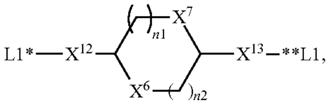
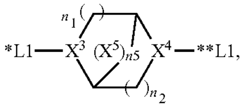
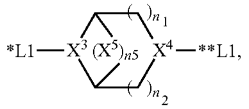
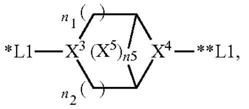
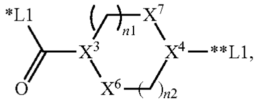
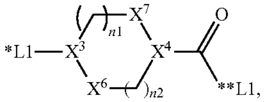
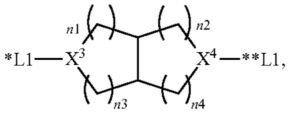
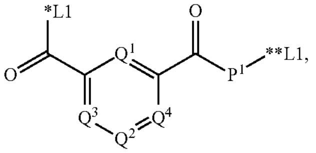
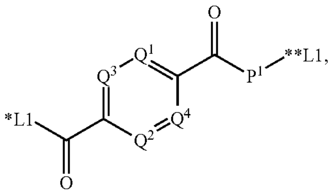
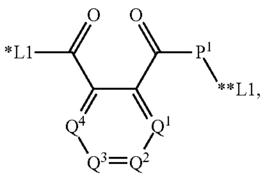
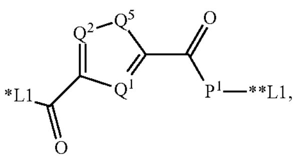
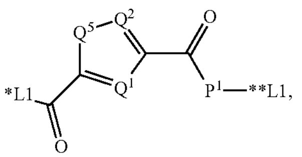
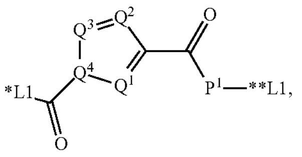

-continued

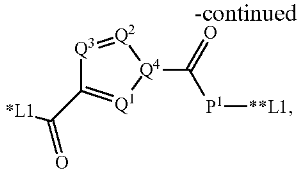

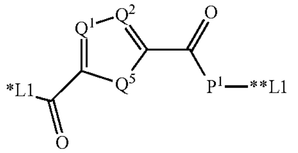

or

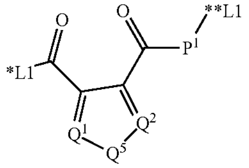

are optionally substituted with at least one $R^{L1c}$; wherein $*^{L1}$ refers to the position attached to the

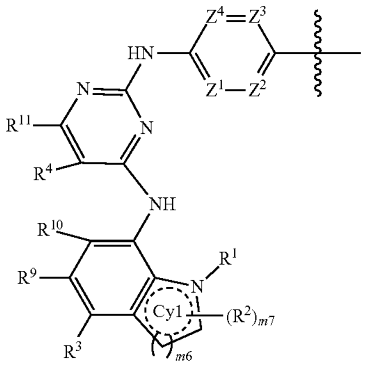

moiety, and $**^{L1}$ refers to the position attached to the

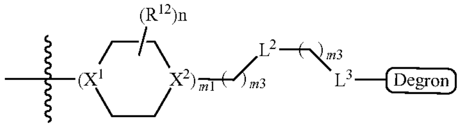

moiety;

$R^{L1a}$ and $R^{L1b}$ are each independently selected from hydrogen, $—C_{1-8}$alkyl, $—C_{2-8}$alkenyl, $—C_{2-8}$alkynyl, cycloalkyl, heterocyclyl, aryl or heteroaryl, wherein each of said $—C_{1-8}$alkyl, $—C_{2-8}$alkenyl, $—C_{2-8}$alkynyl, cycloalkyl, heterocyclyl, aryl or heteroaryl is optionally substituted with at least one substituent $R^{L1d}$;

each of said $R^{L1c}$ and $R^{L1d}$ are independently halogen, hydroxy, $—C_{1-8}$alkyl, -halo$C_{1-8}$alkyl, $—C_{1-8}$alkoxy, $—C_{2-8}$alkenyl, $—C_{2-8}$alkynyl, cycloalkyl, heterocyclyl, aryl or heteroaryl; $L_2$ is selected from a single bond, —O—, $—SO_2—$, —CO—, $—NR^{L2a}—$, $—C_3$-$C_8$cycloalkylene-, $*^{L2}—O—C_{1-8}$alkylene_$**^{L2}$, $*^{L2}—C_{1-8}$alkylene-O—$**^{L2}$, $*^{L2}—SO_2—C_{1-8}$alkylene_$**^{L2}$, $*^{L2}—C_{1-8}$alkylene-$SO_2—**^{L2}*^{L2}—C_{1-8}$alkylene-$**^{L2}$, $*^{L2}—C_{1-8}$alkylene-CO—$**^{L2}$, $*^{L2}—NR^{L2a}—C_{1-8}$alkylene, $^{L2}—C_{1-8}$alkylene- $NR^{L2a}—$, $^{L2}$, $*^{L2}—NR^{L2a}C(O)—**^{L2}$, $*^{L2}C(O)NR^{L2a}—**^{L2}—C_{1-8}$alkylene-, $—C_{2-8}$alkenylene-, $—C_{2-8}$alkynylene-, $—[O(CR^{L2a}R^{L2b})_{m4}]_{m5}—$,

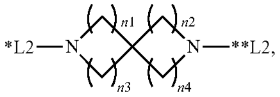

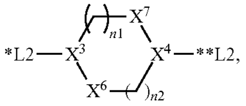

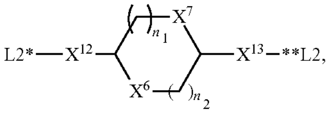

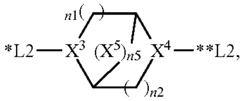

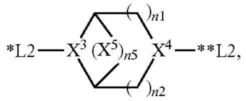

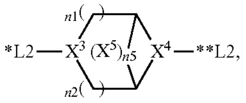

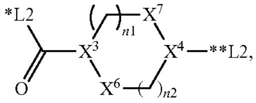

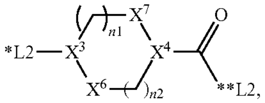

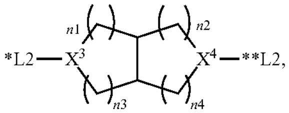

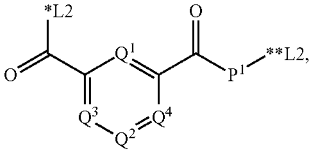

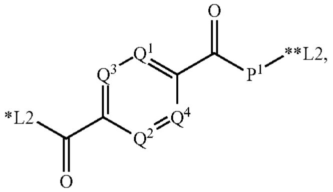

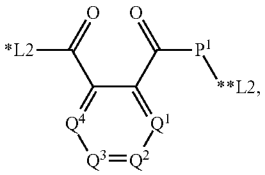

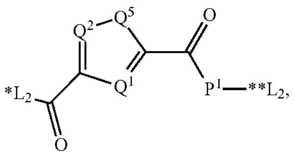

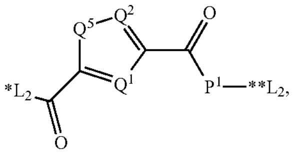

-continued

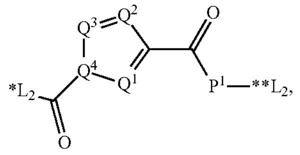

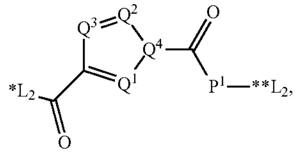

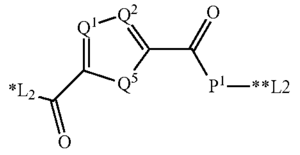

or

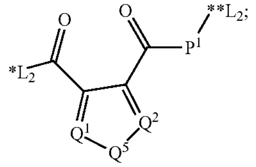

each of said —$C_3$-$C_8$cycloalkylene-, $*^{L2}$—O—$C_{1-8}$alkylene-$**^{L2}$, $*^{L2}$—$C_{1-8}$alkylene-O—$**^{L2}$, $*^{L2}$—$SO_2$—$C_{1-8}$alkylene-$**^{L2}$, $*^{L2}$—$C_{1-8}$alkylene-$SO_2$—$**^{L2}$, $*^{L2}$—$C_{1-8}$alkylene-$**^{L2}$, $*^{L2}$—$C_{1-8}$alkylene-CO—$**^{L2}$, $*^{L2}$—$NR^{L2a}$—$C_{1-8}$alkylene-$**^{L2}$, $*^{L2}$—$C_{1-8}$alkylene-$NR^{L2a}$—$**^{L2}$, —$C_{1-8}$alkylene-, —$C_{2-8}$alkenylene-, —$C_{2-8}$alkynylene-,

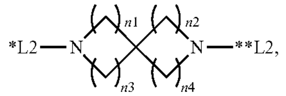

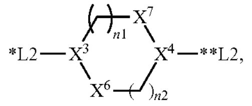

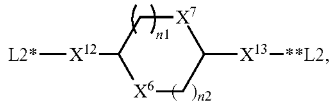

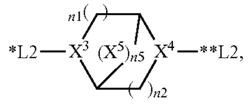

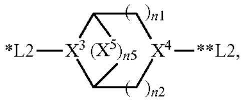

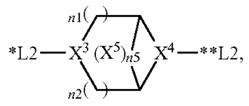

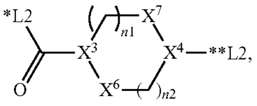

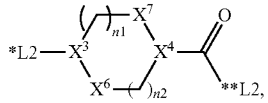

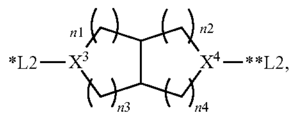

-continued

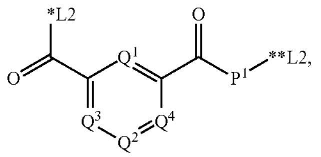

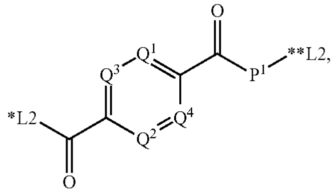

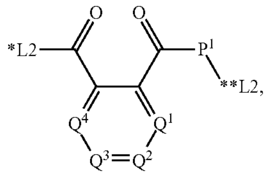

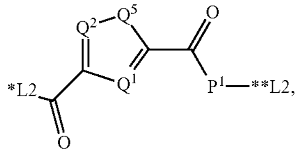

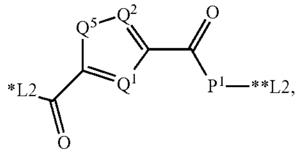

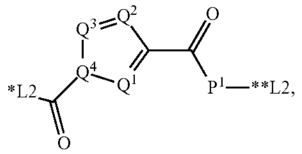

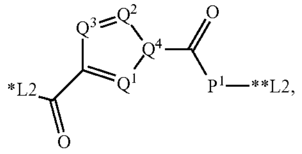

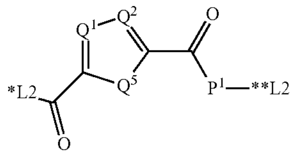

or

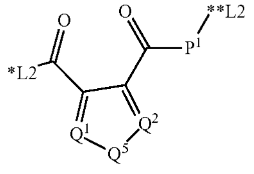

are optionally substituted with at least one substituent $R^{L2c}$;

wherein $*^{L2}$ refers to the position attached to the

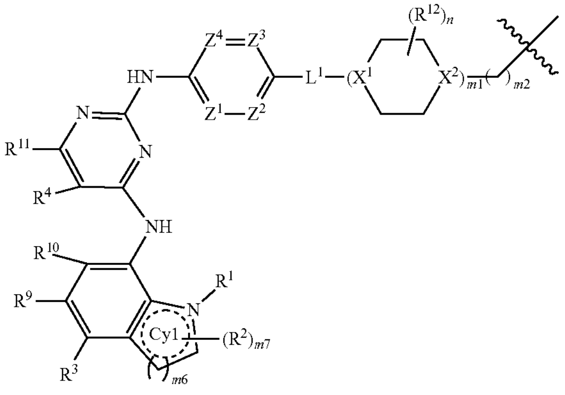

moiety, and $**^{L2}$ refers to the position attached to the

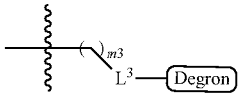

moiety;

$R^{L2a}$ and $R^{L2b}$ are each independently selected from hydrogen, —$C_{1-8}$alkyl, —$C_{2-8}$alkenyl, —$C_{2-8}$alkynyl, cycloalkyl, heterocyclyl, aryl or heteroaryl, wherein each of said —$C_{1-8}$alkyl, —$C_{2-8}$alkenyl, —$C_{2-8}$alkynyl, cycloalkyl, heterocyclyl, aryl or heteroaryl is optionally substituted with at least one substituent $R^{L2d}$;

each of said $R^{L2c}$ and $R^{L2d}$ are independently halogen, hydroxy, —$C_{1-8}$alkyl, -halo$C_{1-8}$alkyl, —$C_{1-8}$alkoxy, —$C_{2-8}$alkenyl, —$C_{2-8}$alkynyl, cycloalkyl, heterocyclyl, aryl or heteroaryl; $L^3$ is selected from a single bond, —O—, —$SO_2$—, —CO—, —$NR^{L3a}$—, —$C_3$-$C_8$cycloalkylene-, $*^{L3}$—O—$C_{1-8}$alkylene_$**^{L3}$, $*^{L3}$—$C_{1-8}$alkylene-O—$**^{L3}$, $*^{L3}$—$SO_2$—$C_{1-8}$alkylene_$**^{L3}$, $*^{L3}$—$C_{1-8}$alkylene-$SO_2$—$**^{L3}$$*^{L3}$—$C_{1-8}$alkylene_$**^{L3}$, $*^{L3}$—$C_{1-8}$alkylene-CO—$**^{L3}$, $*^{L3}$—$NR^{L3a}$—$C_{1-8}$alkylene_$**^{L3}$, $*^{L3}$—$C_{1-8}$alkylene-$NR^{L3a}$—$**^{L3}$, $*^{L3}$—$NR^{L3a}$C(O)—$**^{L3}$, $*^{L3}$-C(O)$NR^{L3a}$—$**^{L3}$, —$C_{1-8}$alkylene-, —$C_{2-8}$alkenylene-, —$C_{2-8}$alkynylene-, —$[O(CR^{L3a}R^{L3b})_{m4}]_{m5}$—,

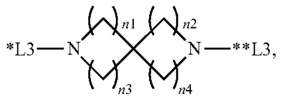

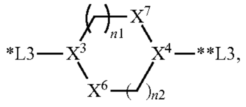

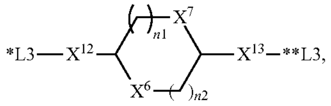

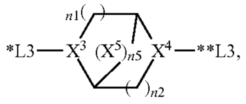 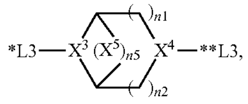

-continued

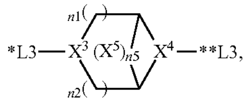 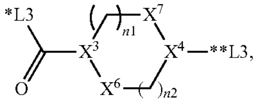

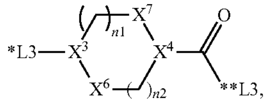

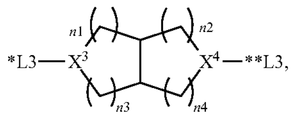

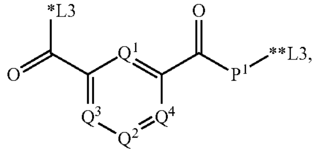

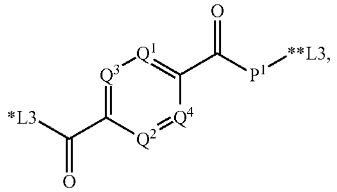

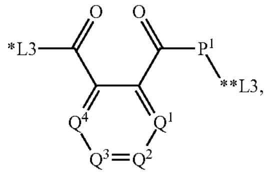

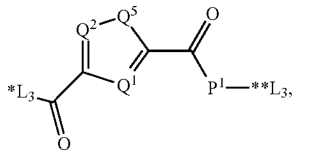

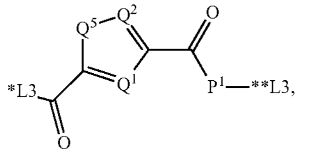

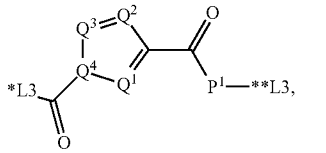

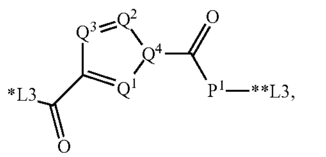

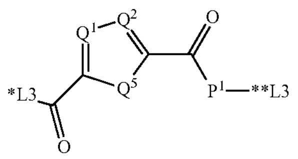

or

-continued

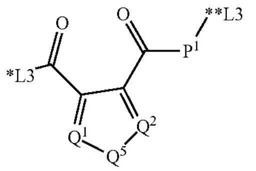

each of said —$C_3$-$C_8$cycloalkylene-, $*^{L3}$—O—$C_{1-8}$alkylene-$**^{L3}$, $*^{L3}$—$C_{1-8}$alkylene-O—$**^{L3}$, $*^{L3}$—$SO_2$—$C_{1-8}$alkylene-$**^{L3}$, $*^{L3}$—$C_{1-8}$alkylene-$SO_2$—$**^{L3}$, $*^{L3}$—$C_{1-8}$alkylene-$**^{L3}$, $*^{L3}$-$C_{1-8}$alkylene-CO—$**^{L3}$, $*^{L3}$—$NR^{L3a}$—$C_8$alkylene-$**^{L3}$, $*^{L3}$-alkylene-$NR^{L3a}$—$**^{L3}$, —$C_{1-8}$alkylene, —$C_{2-8}$alkenylene-,

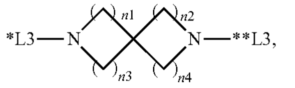

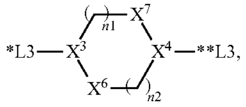

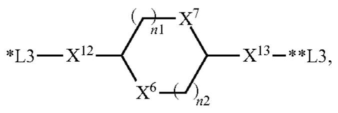

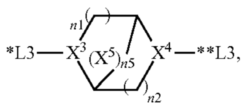

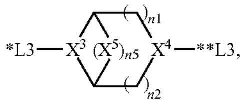

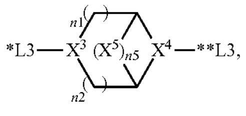

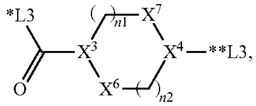

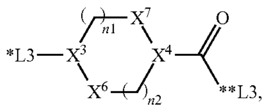

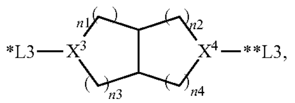

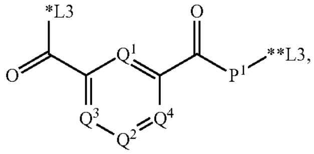

-continued

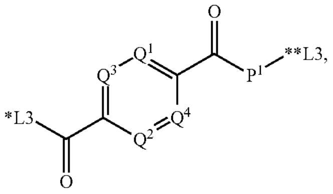

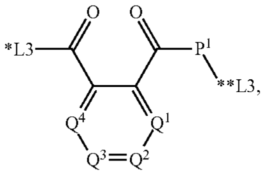

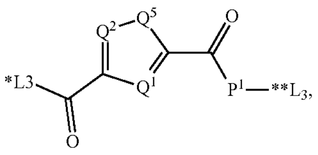

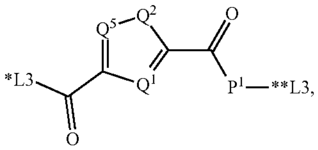

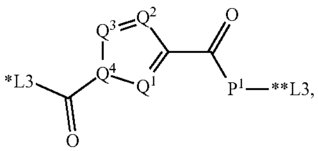

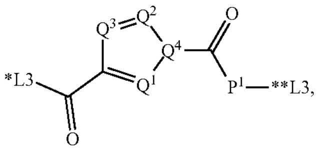

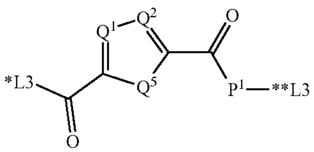

or

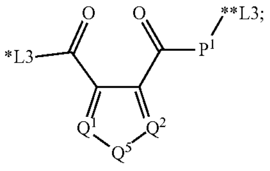

are optionally substituted with at least one substituent $R^{L3c}$; wherein $*^{L3}$ refers to the position attached to the

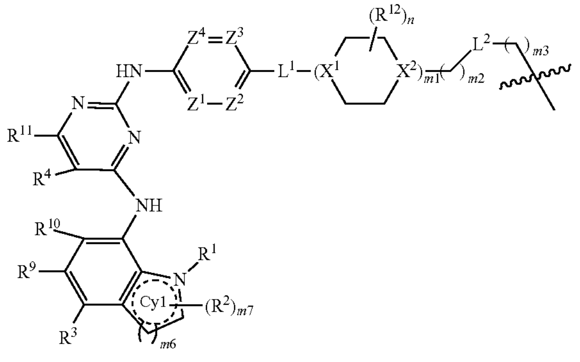

moiety, and **$^{L3}$ refers to the position attached to the

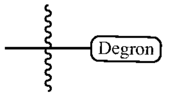

moiety;

$R^{L3a}$ and $R^{L3b}$ are each independently selected from hydrogen, —$C_{1-8}$alkyl, —$C_{2-8}$alkenyl, —$C_{2-8}$alkynyl, cycloalkyl, heterocyclyl, aryl or heteroaryl, wherein each of said —$C_{1-8}$alkyl, —$C_{2-8}$alkenyl, —$C_{2-8}$alkynyl, cycloalkyl, heterocyclyl, aryl or membered heteroaryl is optionally substituted with at least one substituent $R^{L3d}$;

each of said $R^{L3c}$ and $R^{L3d}$ are independently halogen, hydroxy, —$C_{1-8}$alkyl, -halo$C_{1-8}$alkyl, —$C_{1-8}$alkoxy, —$C_{2-8}$alkenyl, —$C_{2-8}$alkynyl, cycloalkyl, heterocyclyl, aryl or heteroaryl;

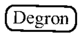

is selected from

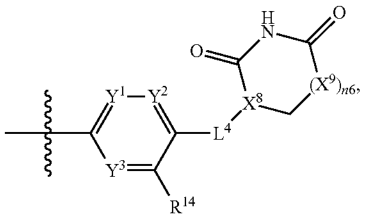

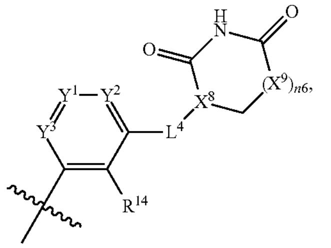

-continued

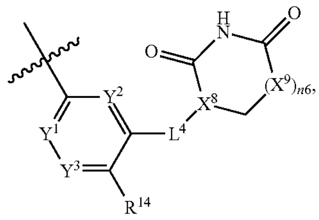

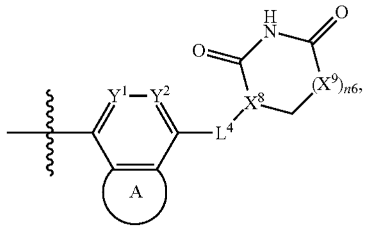

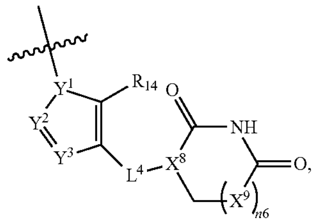

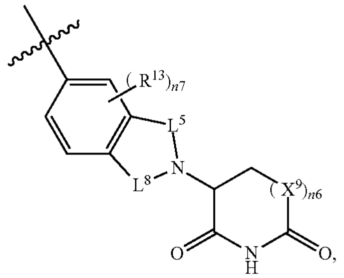

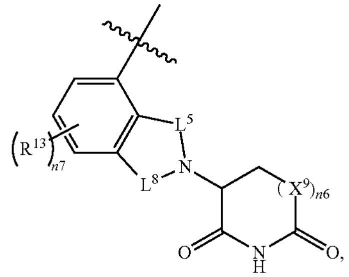

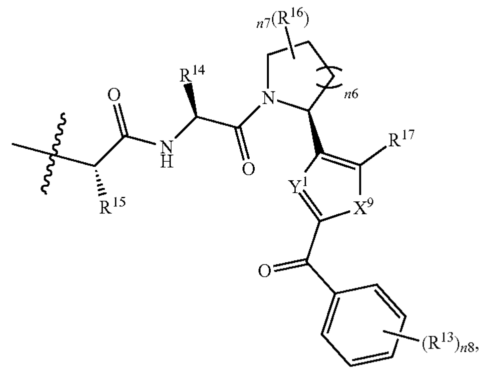

-continued

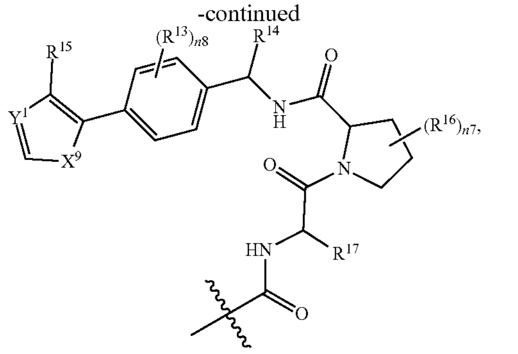

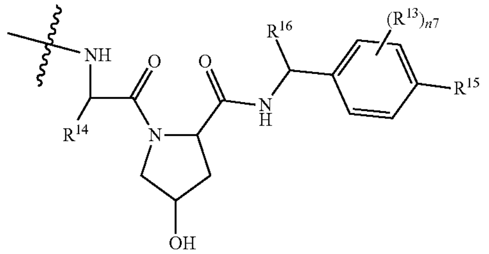

or

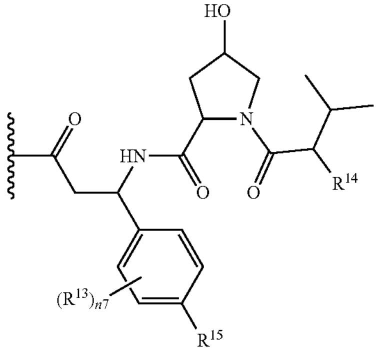

, wherein Ring A is selected from 3-12 membered cycloalkyl, 3-12 membered heterocyclyl, aryl, or heteroaryl;

$R^{13}$, $R^{14}$, $R^{15}$, $R^{16}$ and $R^{17}$ are independently selected from hydrogen, halogen, CN, —$C_{1-8}$alkyl, —$C_{1-8}$alkoxy, cycloalkyl, heterocyclyl, aryl, heteroaryl, —$OR^{13a}$, —$COR^{13a}$, —$CO_2R^{13a}$, —$NR^{13a}R^{13b}$, —$NR^{13a}COR^{13b}$ or —$NR^{13a}CO_2R^{13b}$ wherein each of said —$C_{1-8}$alkyl, —$C_{1-8}$alkoxy, cycloalkyl, heterocyclyl, aryl or heteroaryl is optionally substituted with at least one substituent halogen, —$C_{1-8}$alkyl, -halo$C_{1-8}$alkyl, $C_{1-8}$alkoxy-$C_{1-8}$alkyl-, —$C_{2-8}$alkenyl, —$C_{2-8}$alkynyl, cycloalkyl, heterocyclyl, aryl or heteroaryl;

$R^{13a}$ and $R^{13b}$ are each independently selected from hydrogen, —$C_{1-8}$alkyl, —$C_{2-8}$alkenyl, —$C_{2-8}$alkynyl, $C_{1-8}$alkoxy-$C_{1-8}$alkyl-, cycloalkyl, heterocyclyl, aryl or heteroaryl, wherein each of said —$C_{1-8}$alkyl, —$C_{2-8}$alkenyl, —$C_{2-8}$alkynyl, $C_{1-8}$alkoxy-$C_{1-8}$alkyl-, cycloalkyl, heterocyclyl, aryl or heteroaryl is optionally substituted with at least one substituent halogen, —$C_{1-8}$alkyl, -halo$C_{1-8}$alkyl, $C_{1-8}$alkoxy-$C_{1-8}$alkyl-, —$C_{2-8}$alkenyl, —$C_{2-8}$alkynyl, cycloalkyl, heterocyclyl, aryl or heteroaryl;

$X^1$, $X^2$, $X^3$, $X^4$ and $X^8$ are each independently selected from —$CR^a$ or N;

$X^5$, $X^6$, $X^7$ and $X^9$ are each independently selected from —$NR^a$—, —O—, —S— and —$CR^aR^b$—;

$X^{12}$ and $X^{13}$ are each independently selected from a single bond, —$NR^a$— and —O—;

$L^4$ is each independently selected from a single bond, —O—, —$NR^a$—, —$(CR^aR^b)_{n9}$—, —$O(CR^aR^b)_{n9}$—, —$NR^a(CR^aR^b)_{n9}$— or —C(O)—;

$L^5$ and $L^6$ are each independently selected from —$CR^aR^b$— or —C(O)—;

$Q^1$, $Q^2$, $Q^3$, $Q^4$, $Y^1$, $Y^2$ and $Y^3$ are each independently selected from $CR^a$ or N;

$Q^5$ is each independently selected from —O—, —$NR^a$—, —$CR^aR^b$—, —S— or —C(O)—;

$P^1$ is a single bond, —O—, —NH—, —$CH_2$—, —S—, —SO— or —$SO_2$—;

$R^a$ and $R^b$ are each independently selected from oxo, hydrogen, halogen, CN, —$C_{1-8}$alkyl, —$C_{1-8}$alkoxy, —$C_{2-8}$alkenyl, —$C_{2-8}$alkynyl, cycloalkyl, heterocyclyl, aryl or heteroaryl, wherein each of said —$C_{1-8}$alkyl, —$C_{1-8}$alkoxy, —$C_{2-8}$alkenyl, —$C_{2-8}$alkynyl, cycloalkyl, heterocyclyl, aryl or heteroaryl is optionally substituted with at least one substituent halogen, hydroxy, halogen, —$C_{1-8}$alkyl, —$C_{1-8}$alkoxy, —$C_{2-8}$alkenyl, —$C_{2-8}$alkynyl, cycloalkyl, heterocyclyl, aryl or heteroaryl;

m1 is 0, 1 or 2;

m2 and m3 are each independently 0, 1, 2, 3, 4, 5, 6, 7 or 8;

m4, m5 are each independently 0, 1, 2 or 3;

m6 is each independently 0, 1, 2 or 3;

m7 each independently 0, 1, 2, 3 or 4;

n, n1, n2, n3, n4 and n5 are each independently 0, 1, 2 or 3; and n6, n7, n8 and n9 are each independently 0, 1, 2, 3 or 4.

Aspect 2. The compound of aspect 1, wherein $R^1$ is —$SO_2R^{1a}$, wherein $R^{1a}$ is each independently selected from —$C_{1-5}$alkyl, —$C_{6-8}$aryl, —$C_{3-7}$cycloalkyl, or 4- to 7-membered heterocyclyl or —$NR^{1d}R^{1e}$, wherein each of said —$C_{1-5}$alkyl, —$C_{6-8}$aryl, —$C_{3-7}$cycloalkyl, or 4- to 7-membered heterocyclyl is optionally substituted with at least one substituent $R^f$;

$R^{1d}$ and $R^{1e}$ are each independently hydrogen, —$C_{1-8}$alkyl, —$C_{1-8}$haloalkyl, —$C_{2-8}$alkenyl, —$C_{2-8}$alkynyl, cycloalkyl, heterocyclyl, aryl, or heteroaryl;

$R^{1f}$, at each of its occurrences, is independently hydrogen, halogen, —$C_{1-8}$alkyl, —$C_{1-8}$haloalkyl, —$C_{2-8}$alkenyl, —$C_{2-8}$alkynyl, cycloalkyl, halocycloalkyl, heterocyclyl, phenyl, heteroaryl, —CN, or —$OR^{1g}$, wherein each of said cycloalkyl, heterocyclyl, aryl or heteroaryl is optionally substituted with 1, 2 or 3 substituents selected from halogen and —$C_{1-8}$alkyl;

$R^{1g}$ is hydrogen, —$C_{1-8}$alkyl, —$C_{1-8}$haloalkyl, $C_{1-8}$alkoxy-$C_{1-8}$alkyl-, —$C_{2-8}$alkenyl, —$C_{2-8}$alkynyl, cycloalkyl, heterocyclyl, aryl, or heteroaryl.

Aspect 3. The compound of aspect 1, wherein $R^{1a}$ is selected from —$CH_3$, —$C_2H_5$, —$C_3H_7$, -tert-butyl, -n-butyl, -iso-butyl, —$C_5H_{11}$, -cyclopropyl,

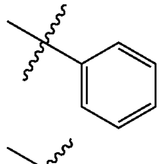

,

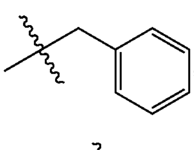

,

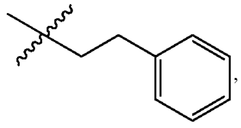

,

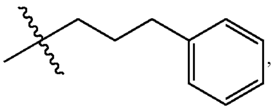

,

-continued

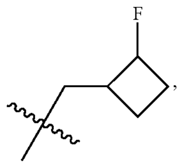,
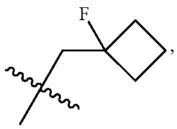,
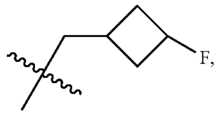,
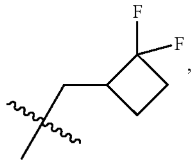,
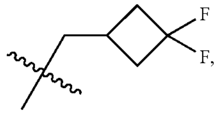,

—$CH_2F$, —$CHF_2$, —$CF_3$, —$N(CH_3)_2$, —$NHCH_3$, —$NHC_2H_5$, or —$NHC_3H_7$.

Aspect 4. The compound of aspect 1, wherein $R^2$ is independently selected from hydrogen, —F, —Cl, —Br, —I, methyl, ethyl, propyl, butyl, pentyl, hexyl, heptyl, octyl, cyclopropyl, cyclobutyl, cyclopentyl, cyclohexyl, cycloheptyl, cyclooctyl, —CN, —$OR^2$a or —$COR^{2a}$, wherein each of said methyl, ethyl, propyl, butyl, pentyl, hexyl, heptyl, octyl, cyclopropyl, cyclobutyl, cyclopentyl, cyclohexyl, cycloheptyl, or cyclooctyl is optionally substituted with at least one substituent $R^{2c}$, or two germinal $R^2$ together with the atom to which they are attached, form a spiro 3-, 4-, 5- or 6-membered cycloalkyl, said cycloalkyl is optionally substituted with at least one substituent $R^{2c}$; or two $R^2$ on different atoms, together with the atoms to which they are attached, form a 3-, 4-, 5- or 6-membered cycloalkyl, said cycloalkyl is optionally substituted with at least one substituent $R^{2c}$;

$R^{2a}$ is selected from hydrogen, —$C_{1-8}$alkyl, —$C_{2-8}$alkenyl, —$C_{2-8}$alkynyl, $C_{1-8}$alkoxy-$C_{1-8}$alkyl-, or $C_{3-8}$cycloalkyl;

$R^{2c}$, at each of its occurrences, is independently —F, —Cl, —Br, —I, —OH, —$C_{1-8}$alkyl, -halo$C_{1-8}$alkyl, —$C_{2-8}$alkenyl, —$C_{2-8}$alkynyl, or —$C_{3-8}$cycloalkyl.

Aspect 5. The compound of aspect 1, wherein $R^2$ is selected from hydrogen, —F, —Cl, —Br, —I, methyl, ethyl, propyl, butyl, pentyl, hexyl, heptyl, or octyl; or two germinal $R^2$, together with the atom to which they are attached, form a spiro 3-, 4-membered cycloalkyl.

Aspect 6. The compound of aspect 1, wherein $R^2$ is selected from hydrogen, F, Cl, Br, I, —$CH_3$, —$C_2H_5$, —$C_3H_7$, —$C_4H_9$, or —$C_5H_{11}$; or two germinal $R^2$, together with the atom to which they are attached, form a spiro cyclopropyl or a spiro cyclobutyl.

Aspect 7. The compound of aspect 1, wherein $R^3$, $R^9$ and $R^{10}$ are independently selected from hydrogen, —F, —Cl, —Br, —I, methyl, ethyl, propyl, butyl, pentyl, hexyl, heptyl, octyl, cyclopropyl, cyclobutyl, cyclopentyl, cyclohexyl, cycloheptyl, cyclooctyl, —$NR^{3a}R^{3b}$, —CN, —$OR^3$a, —$COR^3$a or —$CO_2R^{3a}$, wherein each of methyl, ethyl, propyl, butyl, pentyl, hexyl, heptyl, octyl, cyclopropyl, cyclobutyl, cyclopentyl, cyclohexyl, cycloheptyl, cyclooctyl is optionally substituted with at least one substituent $R^{3c}$ $R^{3a}$ is each independently selected from hydrogen, —$C_{1-8}$alkyl, —$C_{2-8}$alkenyl, —$C_{2-8}$alkynyl, $C_{1-8}$alkoxy-$C_{1-8}$alkyl-, or $C_{3-8}$cycloalkyl, wherein each of said —$C_{1-8}$alkyl, —$C_{2-8}$alkenyl, —$C_{2-8}$alkynyl, $C_{1-8}$alkoxy-$C_{1-8}$alkyl-, or $C_{3-8}$cycloalkyl is optionally substituted with at least one substituent $R^{3d}$;

$R^{3c}$ and $R^{3d}$, at each of their occurrences, is independently halogen, —$C_{1-8}$alkyl, —$C_{2-8}$alkenyl, —$C_{2-8}$alkynyl, or —$C_{3-8}$cycloalkyl.

Aspect 8. The compound of aspect 1, wherein $R^3$, $R^9$ and $R^{10}$ are each independently selected from H, F, Br, Cl, I, —$CH_3$, —$C_2H_5$, —$C_3H_7$, —$C_4H_9$, —$C_5H_{11}$, —$CF_3$, cyclopropyl, cyclobutyl, cyclopentyl, cyclohexyl, cycloheptyl, cyclooctyl, —$NH_2$, —$N(CH_3)_2$, —$N(CH_3)C_2H_5$, —$N(C_2H_5)_2$, —$OCH_3$, —$OC_2H_5$, —$OC_3H_7$, —$OC_4H_9$, or —$OC_5H_{11}$.

Aspect 9. The compound of aspect 1, wherein the

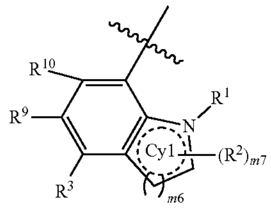

moiety is selected from

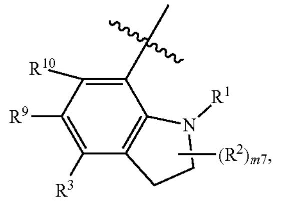

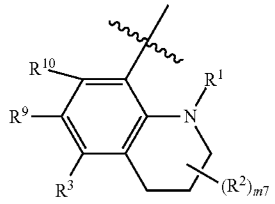

or

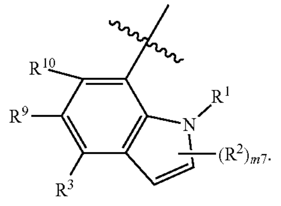

Aspect 10. The compound of aspect 1, wherein the

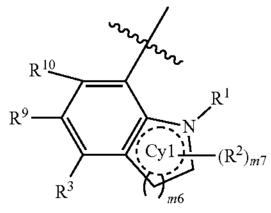

moiety is

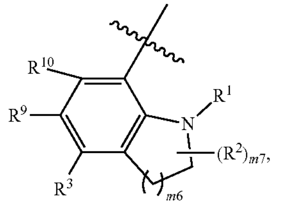

preferred

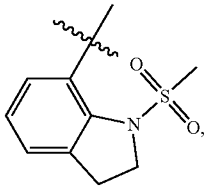

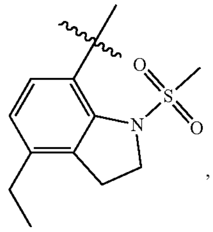

,

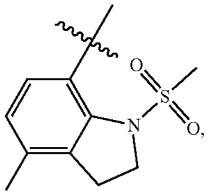

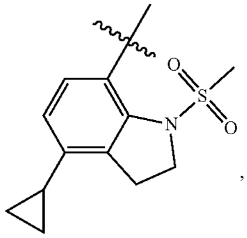

,

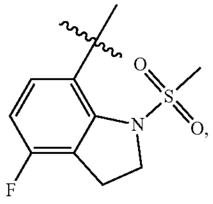

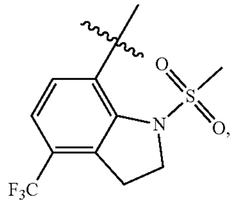

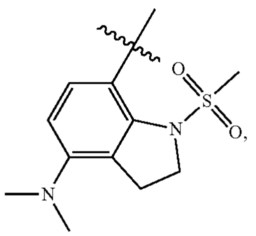

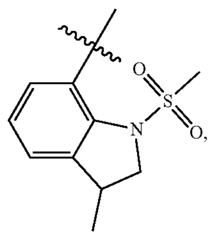

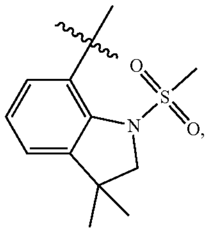

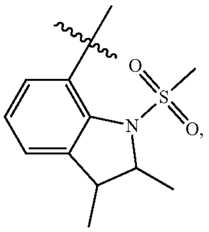

-continued

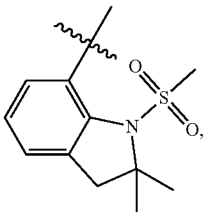

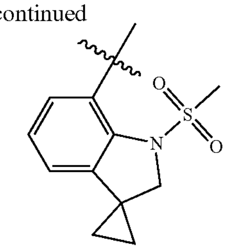

,

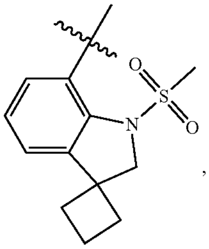

,

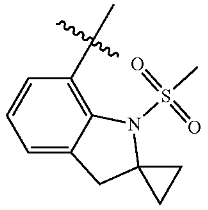

or

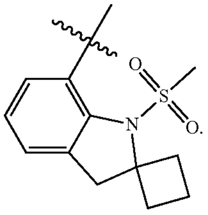 [SMILES: *c1cccc2c1N(S(C)(=O)=O)C1(CCC1)C2]

Aspect 11. The compound of aspect 1, wherein $R^4$ and $R^{11}$ are each independently selected from hydrogen, F, Br, Cl, I, methyl, ethyl, propyl, butyl, pentyl, hexyl, heptyl, octyl, cyclopropyl, cyclobutyl, cyclopentyl, cyclohexyl, cycloheptyl, cyclooctyl, 3- to 8-membered heterocyclyl, —CN, —$OR^{4a}$, or —$NR^{4a}R^{4b}$, wherein each of said methyl, ethyl, propyl, butyl, pentyl, hexyl, heptyl, octyl, cyclopropyl, cyclobutyl, cyclopentyl, cyclohexyl, cycloheptyl, cyclooctyl or 3- to 8-membered heterocyclyl is optionally substituted with at least one $R^{4e}$;

$R^{4a}$ and $R^{4b}$ are each independently hydrogen, —$C_{1-8}$alkyl, -halo$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl, or 5- to 12-membered heteroaryl;

$R^{4c}$ is selected from F, Br, Cl, I, methyl, ethyl, propyl, butyl, pentyl, hexyl, heptyl, octyl, cyclopropyl, cyclobutyl, cyclopentyl, cyclohexyl, cycloheptyl, cyclooctyl, 3- to 8-membered heterocyclyl, phenyl, 5- to 12-membered heteroaryl, oxo, —CN, or —$OR^{4c}$;

$R^{4c}$ is independently hydrogen, methyl, ethyl, propyl, butyl, pentyl, hexyl, heptyl, octyl, or phenyl.

Aspect 12. The compound of aspect 1, wherein $R^4$ and $R^{11}$, together with the atom(s) to which they are attached, form a 3-, 4-, 5-, 6-, 7- or 8-membered ring, said ring comprising 0, 1 or 2 heteroatom(s) independently selected from nitrogen, oxygen, or optionally oxidized sulfur as ring member(s), said ring is optionally substituted with at least one substituent $R^{4e}$;

$R^{4c}$ is selected from —F, —Cl, —Br, —I, methyl, ethyl, propyl, butyl, pentyl, hexyl, heptyl, octyl, cyclopropyl, cyclobutyl, cyclopentyl, cyclohexyl, cycloheptyl, cyclooctyl, 3- to 8-membered heterocyclyl, phenyl, 5- to 12-membered heteroaryl, oxo, —CN, or —$OR^{4c}$;

$R^{4c}$ is independently hydrogen, —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl, or 5- to 12-membered heteroaryl;

Aspect 13. The compound of aspect 1, wherein $R^4$ and $R^{11}$, together with the atom(s) to which they are attached, form a 5- or 6-membered ring, said ring comprising 1 or 2 heteroatom(s) independently selected from nitrogen, oxygen, or optionally oxidized sulfur, said ring is optionally substituted with at least one substituent $R^{4e}$;

$R^{4c}$ is selected from —F, —Cl, —Br, —I, methyl, ethyl, propyl, butyl, pentyl, hexyl, heptyl, octyl, cyclopropyl, cyclobutyl, cyclopentyl, cyclohexyl, cycloheptyl, cyclooctyl, phenyl, 5- to 12-membered heteroaryl, oxo, —CN, $—OCH_3$, $—OC_2H_5$, $—OC_3H_7$, $—OC_4H_9$, and $—OC_5H_{11}$.

Aspect 14. The compound of aspect 1, wherein

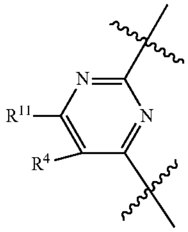

moiety is selected from

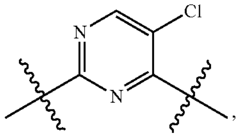, 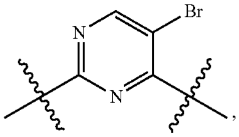, 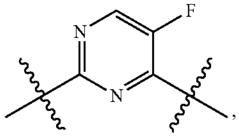, 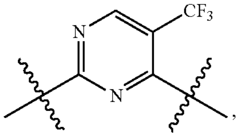, 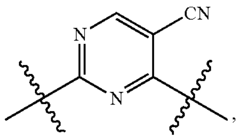, 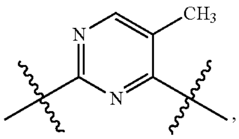, 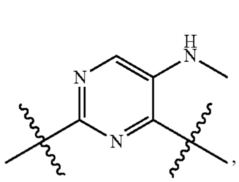, 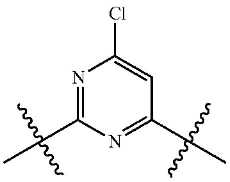, 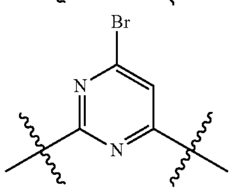, 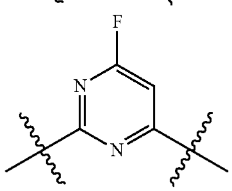, 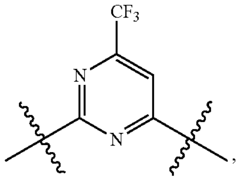, 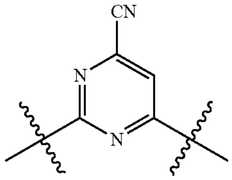

-continued

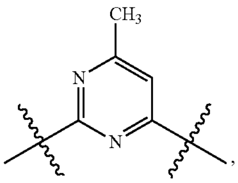, 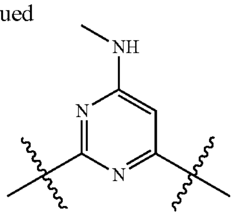, 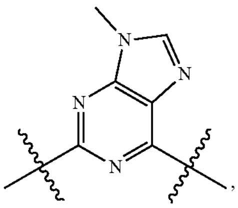, 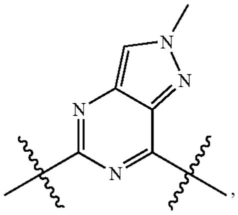, 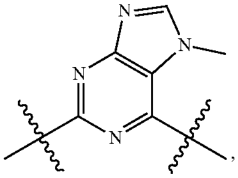, 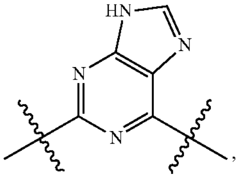, 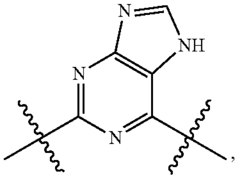, 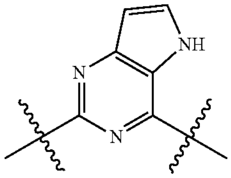, 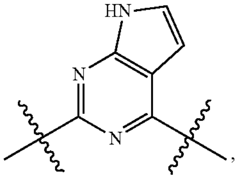, 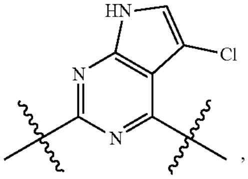, 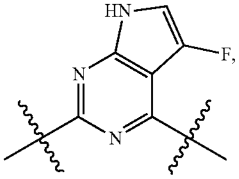 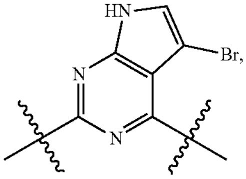 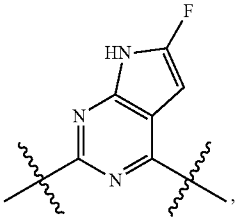, 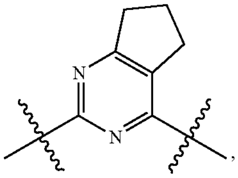, 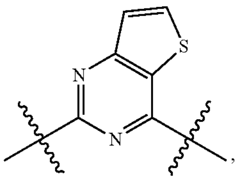, 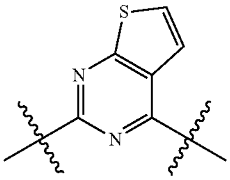 or 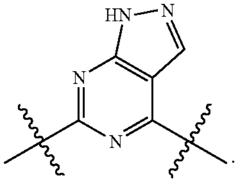.

Aspect 15. The compound of aspect 1, wherein $R^{12}$ independently selected from hydrogen, F, Cl, Br, I, OH, methyl, ethyl, propyl, butyl, pentyl, hexyl, methoxy, ethoxy, propoxy, butoxy, pentoxy, hexoxy, phenyl, cyclopropyl, cyclobutyl, cyclopentyl, cyclohexyl, oxo or —CN; or two germinal $R^{12}$ together with the atom to which they are attached, form a spiro 3-, 4-, 5-, 6-membered cycloalkyl, said cycloalkyl is optionally substituted with at least one substituent $R^{12c}$; or two $R^{12}$ on different atoms, together with the atoms to which they are attached, form a 3-, 4-, 5-, 6-membered cycloalkyl, said cycloalkyl is optionally substituted with at least one substituent $R^{12c}$;

$R^{12c}$ is independently halogen, hydroxy, —$C_{1-8}$alkyl, -halo$C_{1-8}$alkyl, —$C_{1-8}$alkoxy, —$C_{2-8}$alkenyl, —$C_{2-8}$alkynyl, cycloalkyl, heterocyclyl, aryl or heteroaryl.

Aspect 16. The compound of aspect 1, wherein

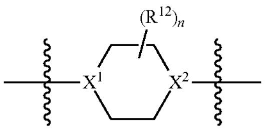

is selected from

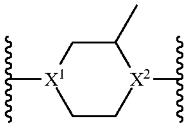,
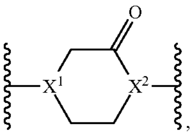,
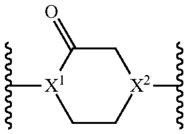,
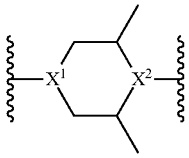,
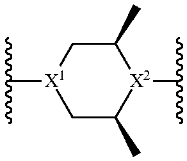,
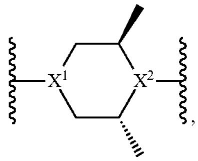,
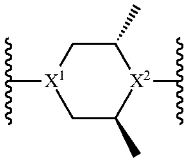,
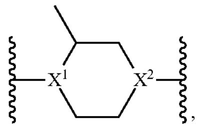,
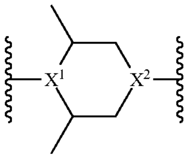,
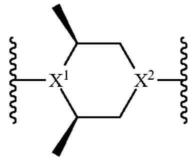,
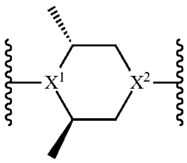,
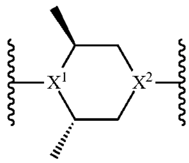, -continued

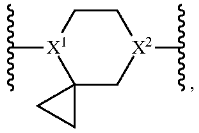,
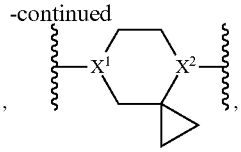,
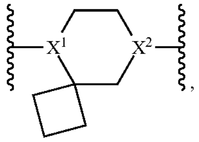,
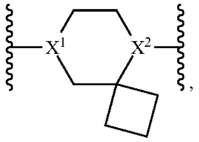,
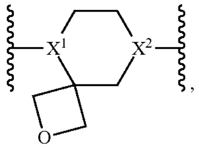, or
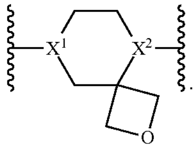.

Aspect 17. The compound of aspect 1, wherein $Z^1$, $Z^2$, $Z^3$ and $Z^4$ are each independently selected from —$CR^Z$, or N;

$R^Z$, at each of its occurrences, is independently selected from hydrogen, —F, —Cl, —Br, —I, methyl, ethyl, propyl, butyl, pentyl, hexyl, heptyl, octyl, —$NR^{Za}R^{Zb}$, —$OR^{Za}$, cyclopropyl, cyclobutyl, cyclopentyl, cyclohexyl, cycloheptyl, cyclooctyl, 3- to 8-membered heterocyclyl, phenyl, 5- to 12-membered heteroaryl, or CN, wherein each of said methyl, ethyl, propyl, butyl, pentyl, hexyl, heptyl, octyl, cyclopropyl, cyclobutyl, cyclopentyl, cyclohexyl, cycloheptyl, cyclooctyl, 3- to 8-membered heterocyclyl, phenyl, or 5- to 12-membered heteroaryl is optionally substituted with at least one $R^{Zc}$; or or two $R^Z$, when attached to adjacent carbon atoms of the ring, together with the two carbon atoms to which they are attached, form a 3- to 12-membered ring comprising 0, 1 or 2 heteroatom(s) independently selected from nitrogen, oxygen or optionally oxidized sulfur as ring member(s), said ring is optionally substituted with at least one substituent $R^{Ze}$;

$R^{Za}$ and $R^{Zb}$ are each independently selected from hydrogen, methyl, ethyl, propyl, butyl, pentyl, hexyl, heptyl, octyl, cyclopropyl, cyclobutyl, cyclopentyl, cyclohexyl, cycloheptyl, cyclooctyl, or phenyl, wherein each of said methyl, ethyl, propyl, butyl, pentyl, hexyl, heptyl, octyl, cyclopropyl, cyclobutyl, cyclopentyl, cyclohexyl, cycloheptyl, cyclooctyl, or phenyl is optionally substituted with at least one substituent $R^{Zd}$;

$R^{Zc}$ and $R^{Zd}$ are each independently —F, —Cl, —Br, —I, —OH, methyl, ethyl, propyl, butyl, pentyl, hexyl, heptyl, octyl, —$OCH_3$, —$OC_2H_5$, —$OC_3H_7$, —$OC_4H_9$, —$OC_5H_{11}$, cyclopropyl, cyclobutyl, cyclopentyl, cyclohexyl, cycloheptyl, cyclooctyl, or phenyl, or two $R^{Zc}$, together with the atom(s) to which they are attached, form a 3- to 8-membered ring, said ring comprising 0, 1 or 2 heteroatom(s) independently selected from nitrogen, oxygen, or optionally oxidized sulfur as ring member(s).

Aspect 18. The compound of aspect 1, wherein $Z^1$, $Z^2$, $Z^3$ and $Z^4$ are each independently —$CR^z$;

$R^Z$, at each of its occurrences, is independently selected from hydrogen, —F, —Cl, —Br, —I, methyl, ethyl, propyl, butyl, pentyl, hexyl, heptyl, octyl, —$OCH_3$, —$OC_2H_5$, —$OC_3H_7$, —$OC_4H_9$, or —$OC_5H_{11}$; or two $R^Z$, when attached to adjacent carbon atoms of the ring, together with the atoms to which they are attached, form a 4-, 5-, 6- or 7-membered ring, said ring comprising 0, 1 or 2 heteroatom(s) independently selected from nitrogen or oxygen, said ring is optionally substituted with at least one substituent $R^{Zc}$, wherein two germinal $R^{Zc}$, together with the atom to which they are attached, form a spiro 3-, 4-, 5- or 6-membered cycloalkyl or, two $R^{Zc}$ on different atoms, together with the atoms to which they are attached, form a 3-, 4-, 5- or 6-membered cycloalkyl.

Aspect 19. The compound of aspect 1, wherein the

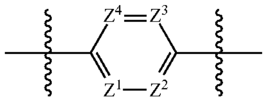

moiety is selected from

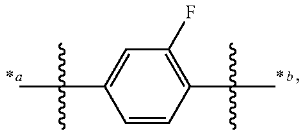

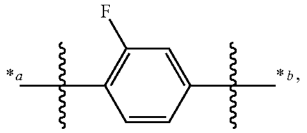

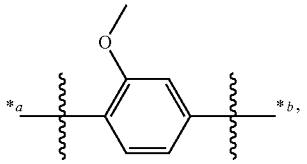

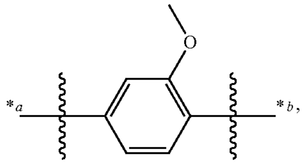

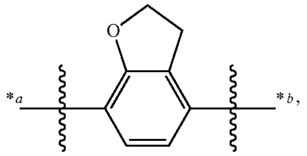

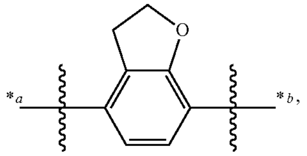

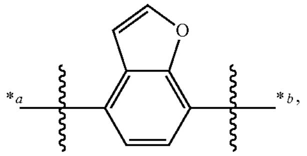

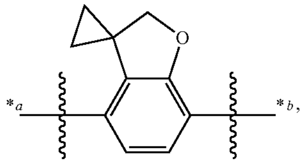

-continued

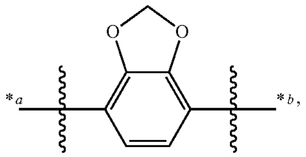

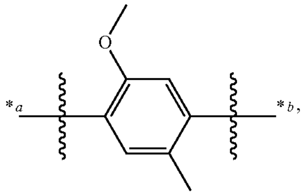

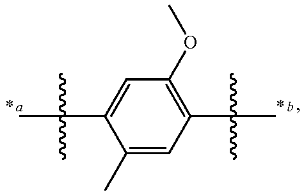

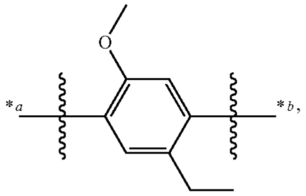

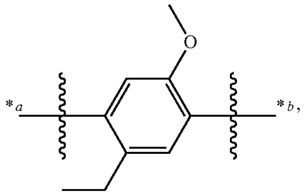

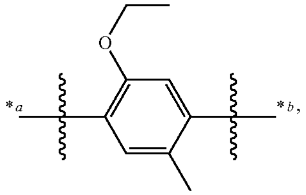

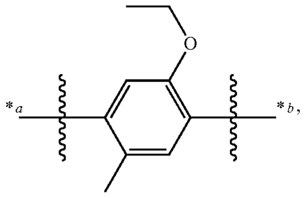

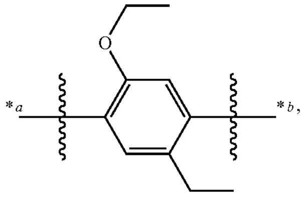

-continued

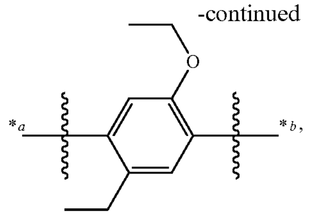

wherein *a refers to the position attached to

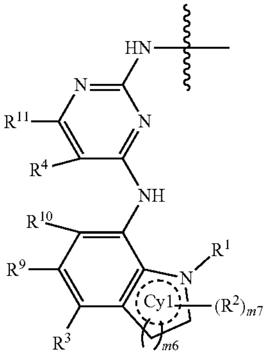

moiety, and *b refers to the position attached to the

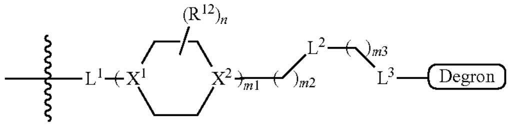

moiety.

Aspect 20. The compound of aspect 1, wherein $L^1$ is selected from a single bond —$C_{1-8}$alkylene- (preferably —$CH_2$—, —$C_2H_4$—, —$C_3H_6$—),

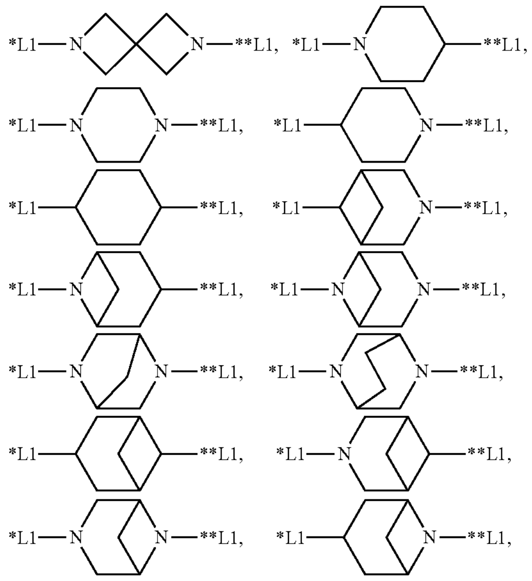

-continued

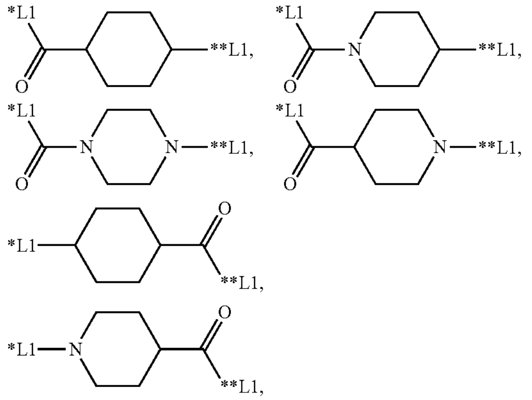

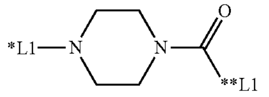

or

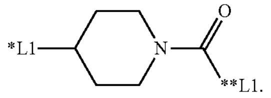

Aspect 21. The compound of aspect 1, wherein $X^1$ and $X^2$ are each independently selected from CH or N; m1=1 or 0; and $R^{12}$ is hydrogen or —$CH_3$.

Aspect 22. The compound of aspect 1, wherein m2 and m3 are selected from 0, 1, 2, 3, 4 or 5.

Aspect 23. The compound of aspect 1, wherein $L^2$ is selected from a single bond, —CO—, —O—, —$NR^{L2a}$—, —$C_{1-8}$alkylene- (preferably —$CH_2$—, —$C_2H_4$—, —$C_3H_6$—),

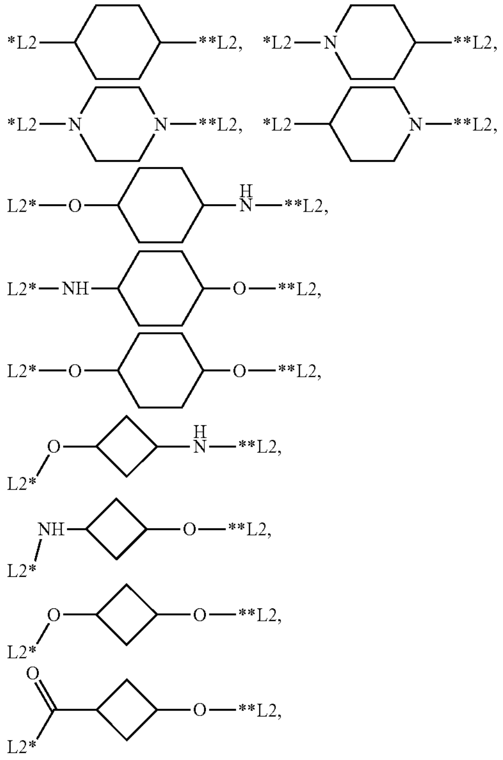

-continued
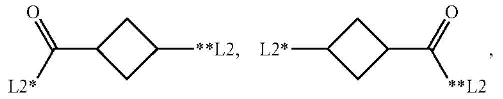
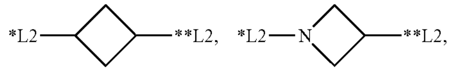
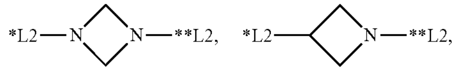
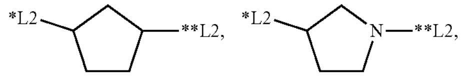
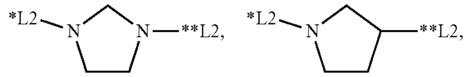
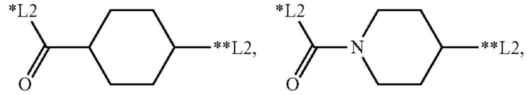
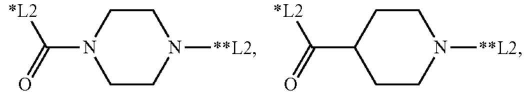
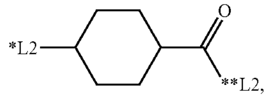
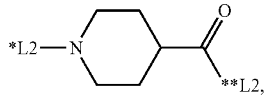
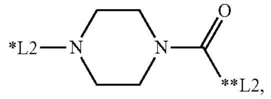
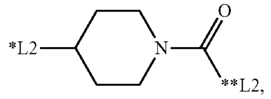
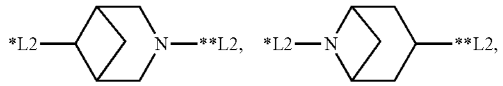
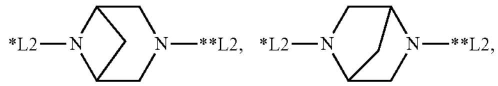
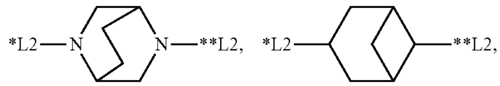
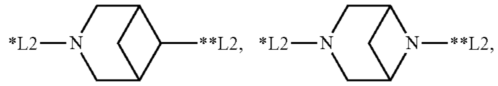 or
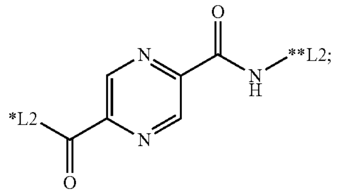
wherein $R^{L2a}$ is selected from hydrogen, methyl, ethyl or propyl.
Aspect 24. The compound of aspect 1, wherein $L^3$ is selected from a single bond, —O—, —$NR^{L3a}$—$C_{1-8}$alkylene- (preferably —$CH_2$—, —$C_2H_4$—, —$C_3H_6$—),
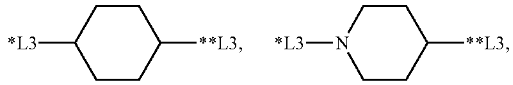
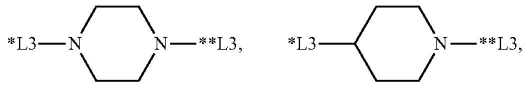
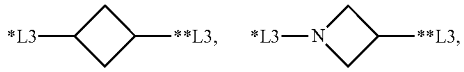
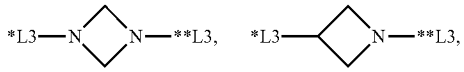
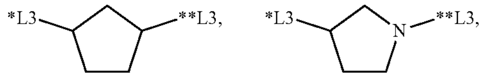
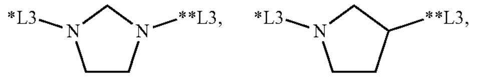 or
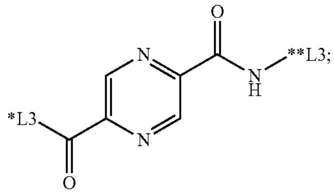
wherein $R^{L3a}$ is selected from hydrogen, methyl, ethyl or propyl.
Aspect 25. The compound of aspect 1, wherein
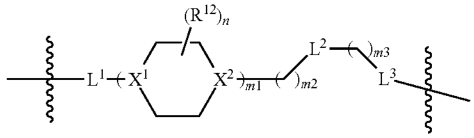
is selected from
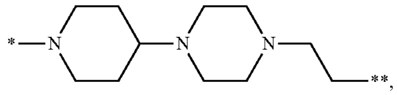
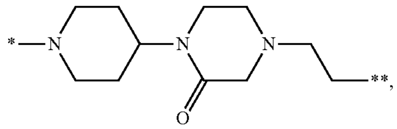
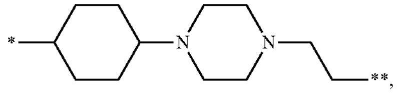
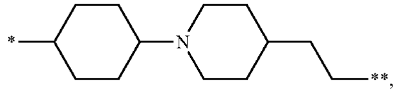
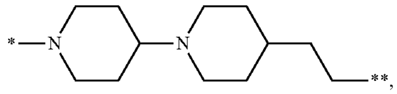
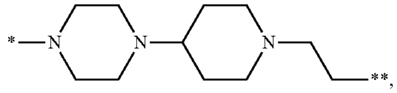

-continued
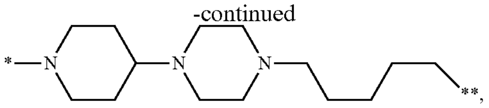
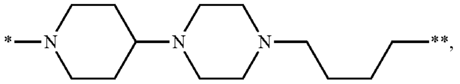
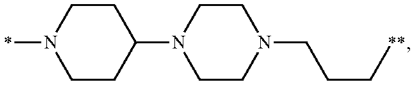
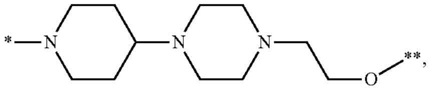
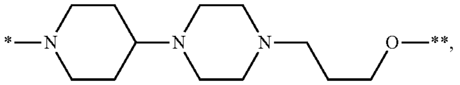
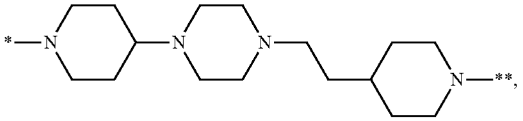
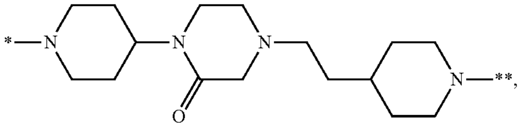
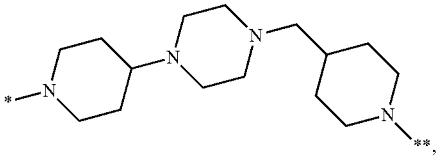
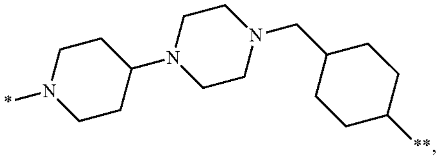
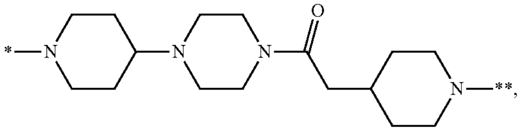
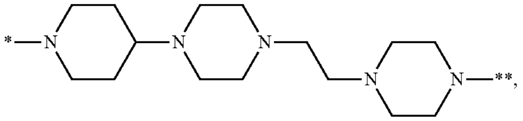
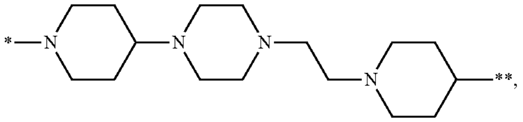
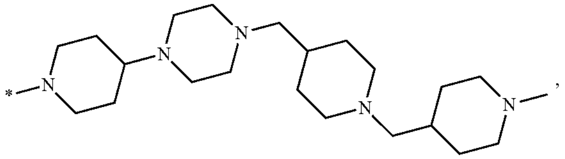
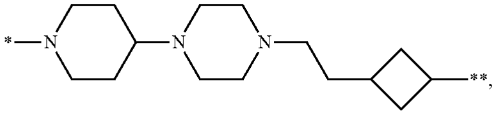
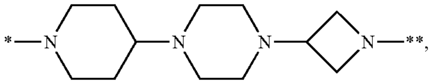
-continued
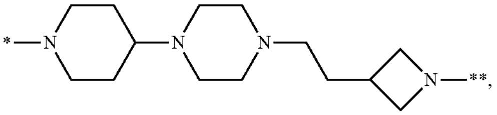
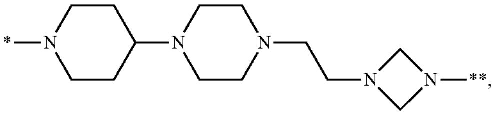
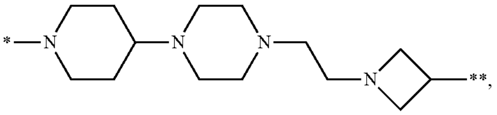
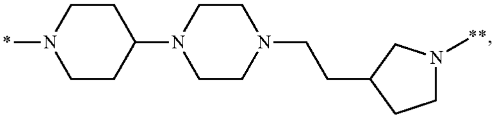
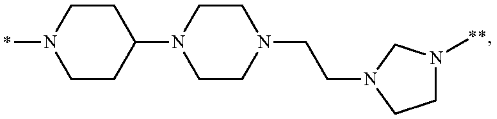
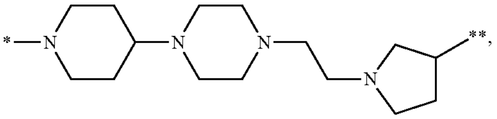
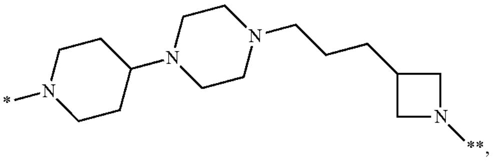
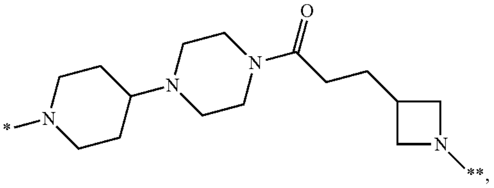
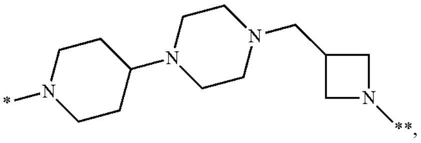
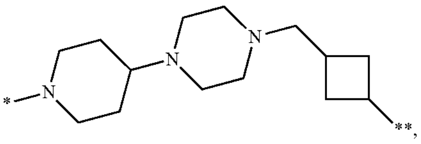
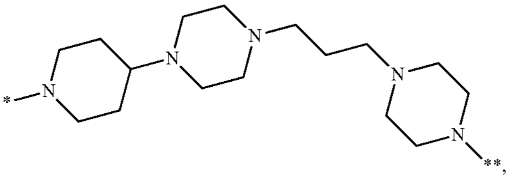
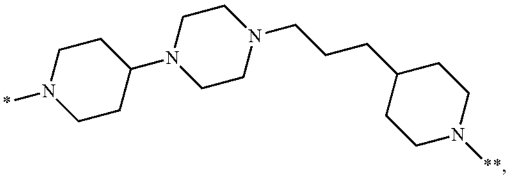

-continued
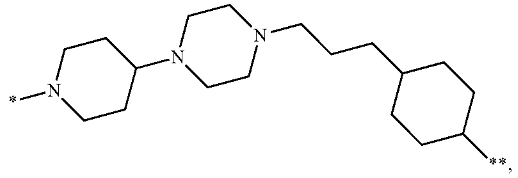
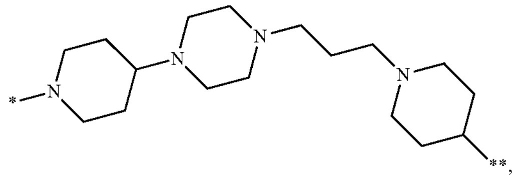
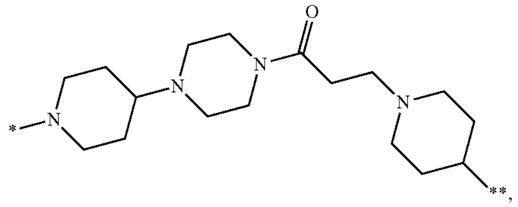
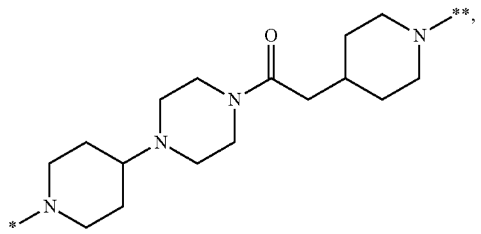
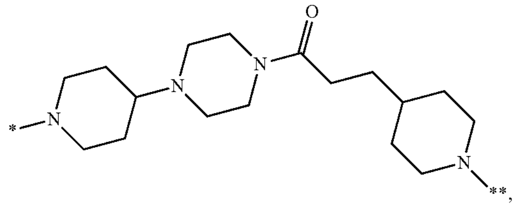
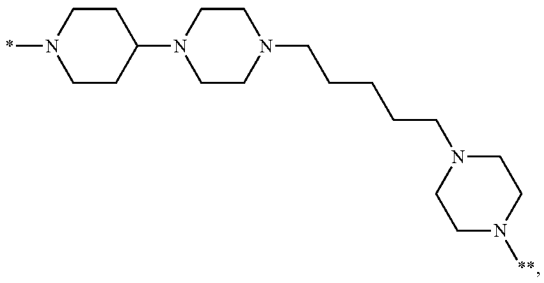
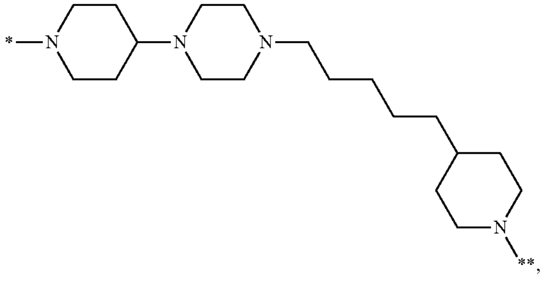
-continued
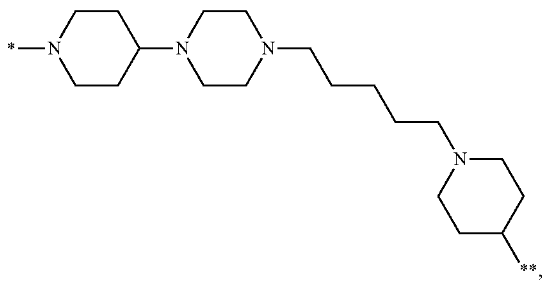
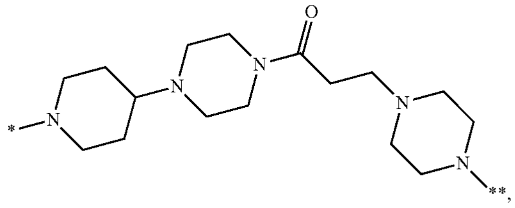
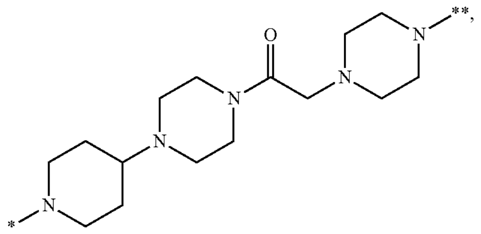
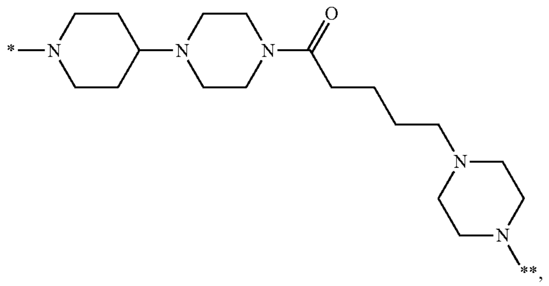
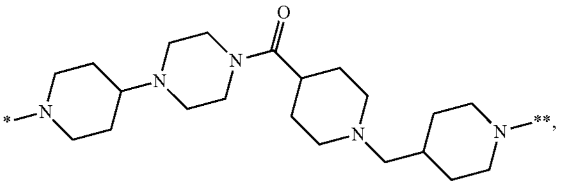
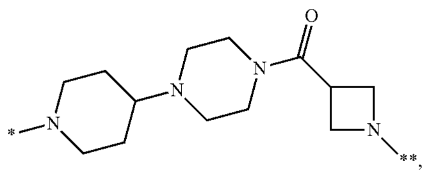
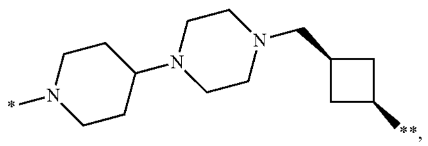
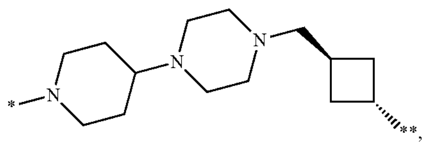

-continued
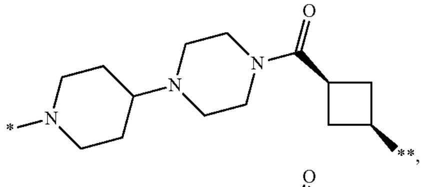
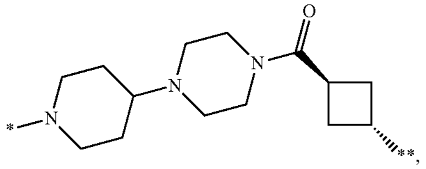
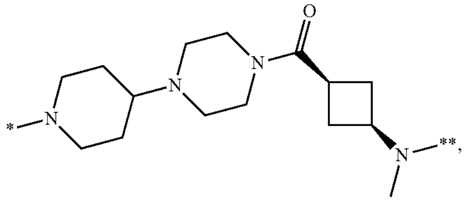
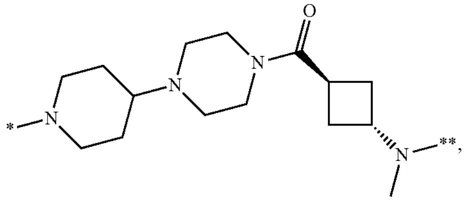
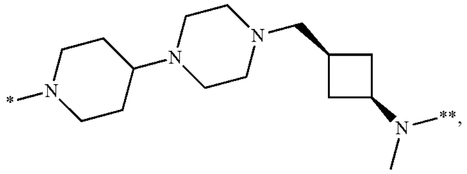
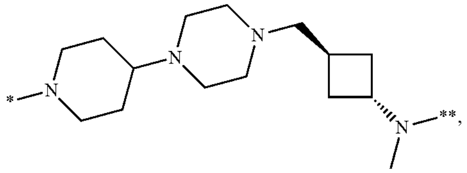
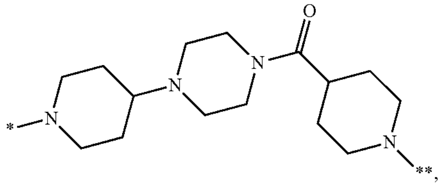
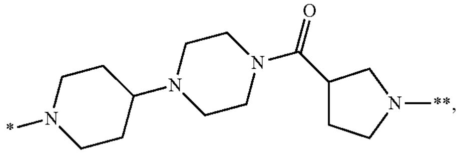
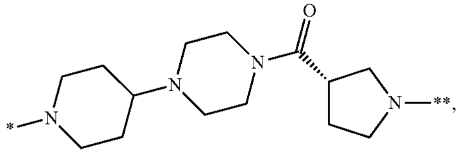
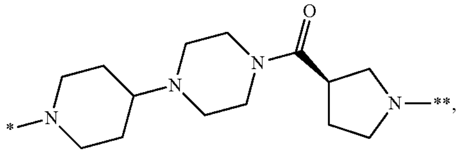
-continued
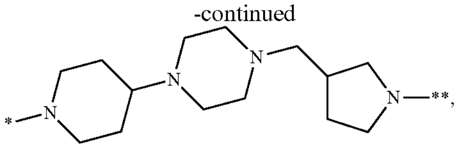
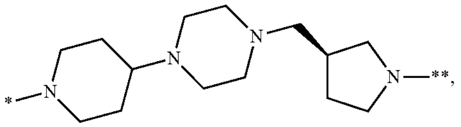
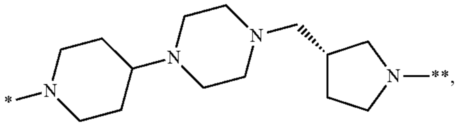
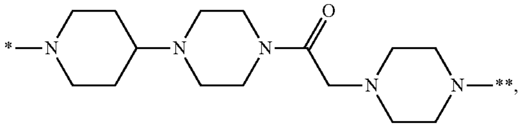
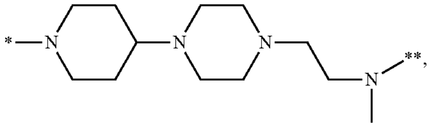
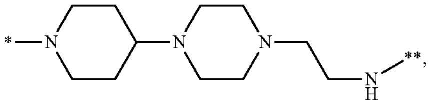
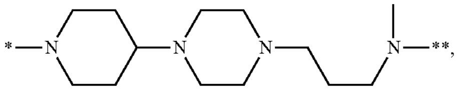
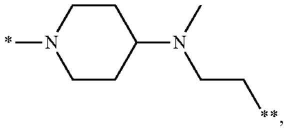
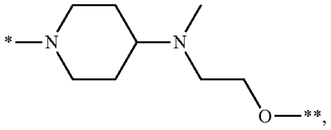
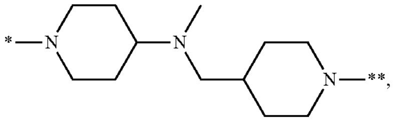
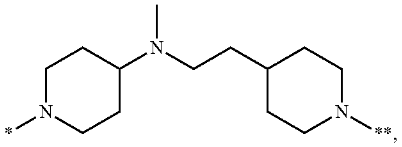
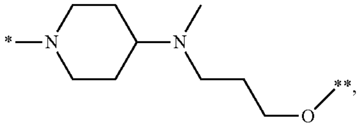
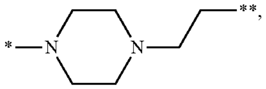
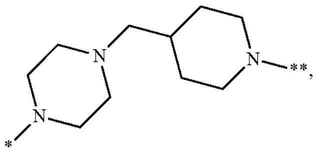

-continued
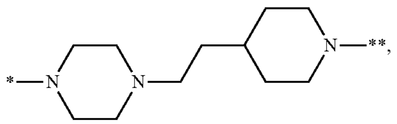
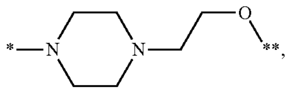
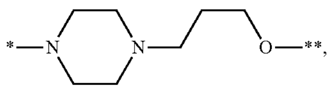
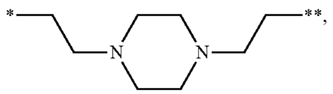
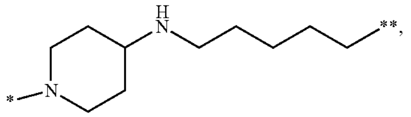
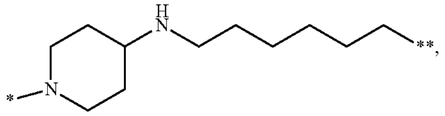
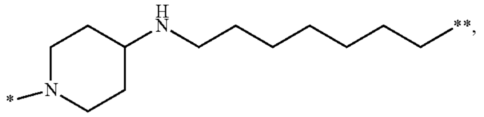
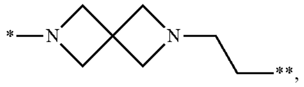
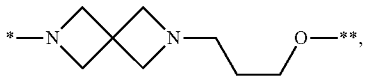
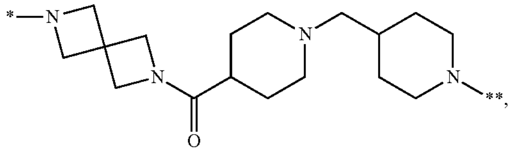
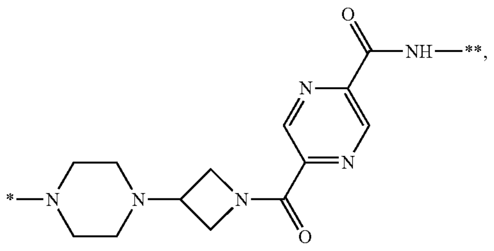
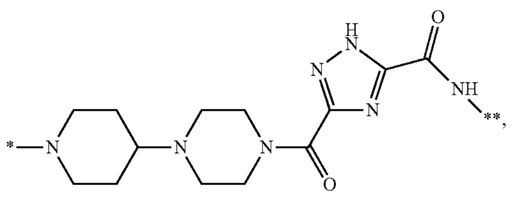
-continued
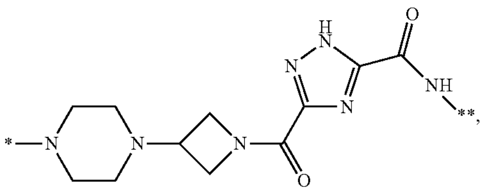
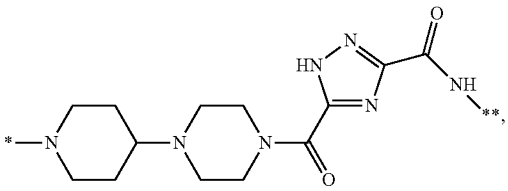
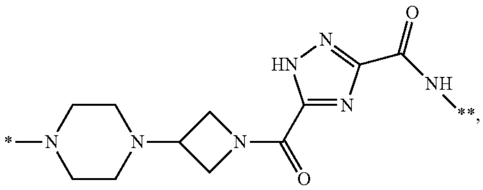
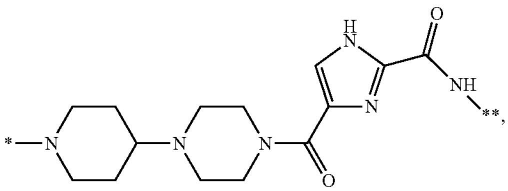
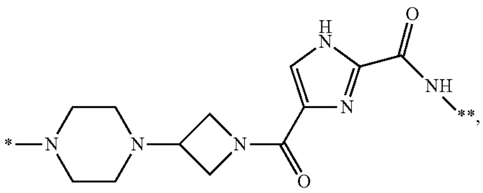
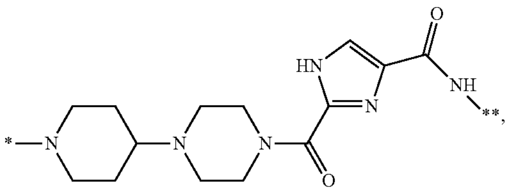
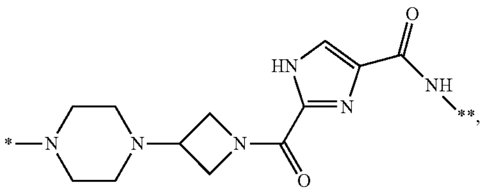
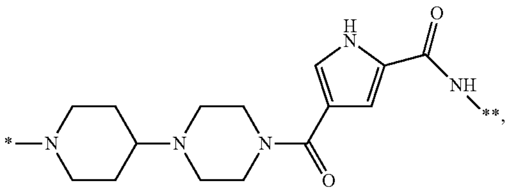
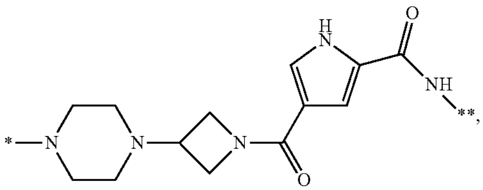

-continued
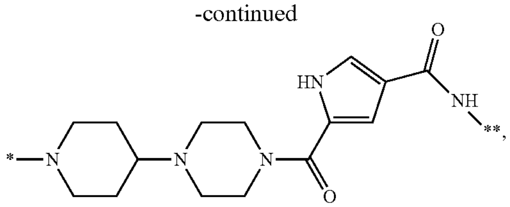
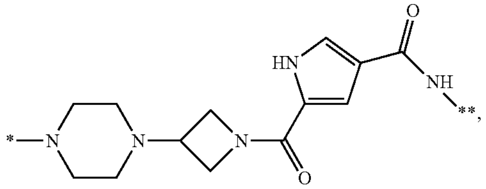
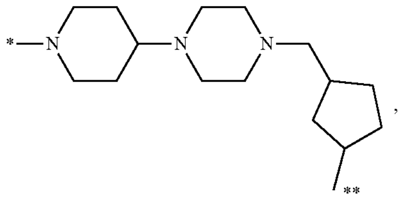
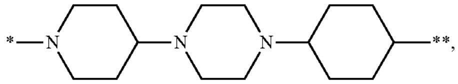
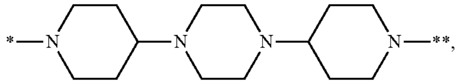
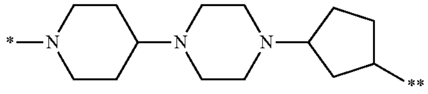
or
-continued
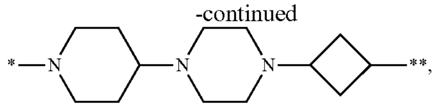
wherein * refers to the position attached to
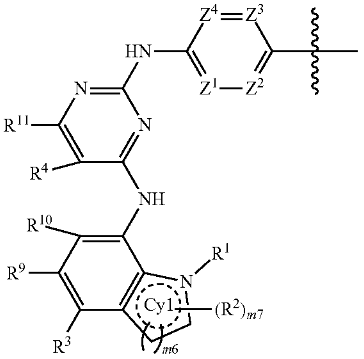
moiety, and ** refers to the position attached to the
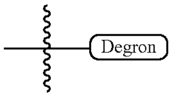
moiety.
Aspect 26. The compound of aspect 1, wherein the compound is Formula (II):
(II)
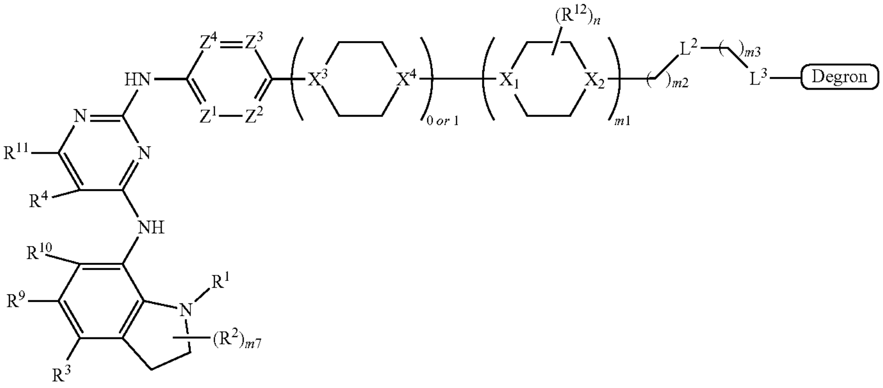

or an N-oxide thereof, or a pharmaceutically acceptable salt thereof, or a stereoisomer thereof, or a tautomer or a prodrug thereof, wherein: $R^{1f}$, $R^2$, $R^3$, $R^4$, $R^9$, $R^{10}$, $R^{11}$, $R^{12}$, $Z^1$, $Z^2$, $Z^3$, $Z^4$, $X^1$, $X^2$, $X^3$, $X^4$, $L^2$, $L^3$, Degron, n, m1, m2, m3 and m7 have the same meaning with Aspect 1.

Aspect 27. The compound of aspect 1, wherein the compound is Formula (III):

(III)

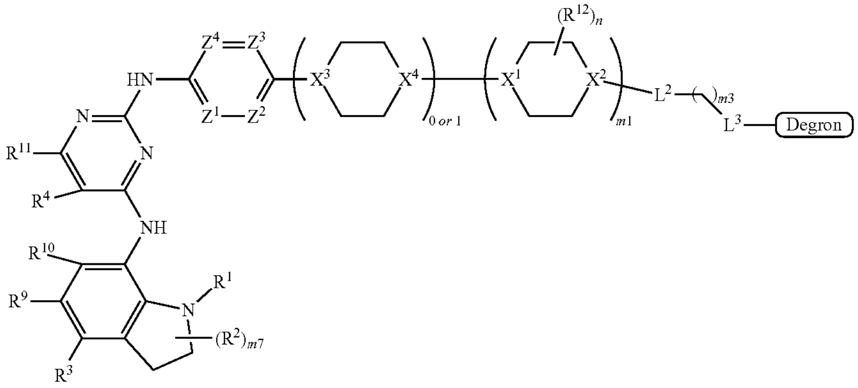

or an N-oxide thereof, or a pharmaceutically acceptable salt thereof, or a stereoisomer thereof, or a tautomer or a prodrug thereof, wherein: $R^1$, $R^2$, $R^3$, $R^4$, $R^9$, $R^{10}$, $R^{11}$, $R^{12}$, $Z^1$, $Z^2$, $Z^3$, $Z^4$, $X^1$, $X^2$, $X^3$, $X^4$, $L^2$, $L^3$, Degron, n, m1, m3 and m7 have the same meaning with Aspect 1, preferred $m_1$ is 0 or 1.

Aspect 28. The compound of aspect 1, wherein

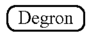

is selected from

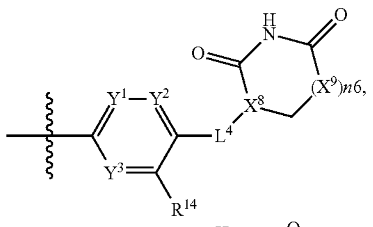

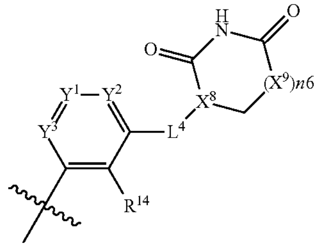 or

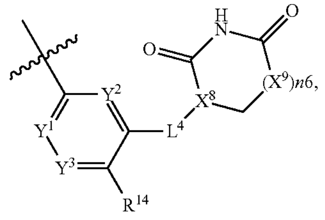

$R^{14}$ is independently selected from hydrogen, halogen, —$C_{1-8}$alkyl, —$C_{1-8}$alkoxy, or CN, wherein each of said —$C_{1-8}$alkyl or —$C_{1-8}$alkoxy is optionally substituted by one or more halogen or —$C_{1-8}$alkyl; preferably $R^{14}$ is independently selected from H, F, Cl, Br, I, $CH_3$, —$OCH_3$, $CH_2F$, CN, $CHF_2$, or $CF_3$;

$X^8$ is independently selected from CF, CH, $C(CH_3)$, $C(C_2H_5)$, $C(C_3H_7)$, C(CN) or N;

$L^4$ is independently selected from a single bond, —O—, —NH—, —$CH_2$—, —CHF—, or —$CF_2$—;

$Y^1$, $Y^2$, and $Y^3$ are each independently selected from $CR^a$ or N, wherein $R^a$ is each independently selected from hydrogen, halogen, —$C_{1-8}$alkyl or —$C_{1-8}$alkoxy, wherein each of said —$C_{1-8}$alkyl or —$C_{1-8}$alkoxy is optionally substituted with at least one or more halogen, hydroxy, halogen, —$C_{1-8}$alkyl, or —$C_{1-8}$alkoxy;

$X^9$ is $CH_2$;

n6 is independently 0, 1 or 2.

Aspect 29. The compound of aspect 1, wherein

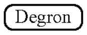 is 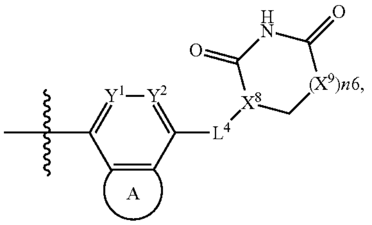

wherein Ring A is selected from 5-7 membered cycloalkyl, 5-7 membered heterocyclyl, aryl, or heteroaryl;

$X^8$ is independently selected from CF, CH, $C(CH_3)$, $C(C_2H_5)$, $C(C_3H_7)$, C(CN) or N;

$L^4$ is independently selected from a single bond, —O—, —NH—, —$CH_2$—, —CHF—, or —$CF_2$—;

$Y^1$ and $Y^2$ are each independently selected from $CR^a$ or N;

$R^a$ is each independently selected from hydrogen, halogen, —$C_{1-8}$alkyl, or —$C_{1-8}$alkoxy, each of said —$C_{1-8}$alkyl or —$C_{1-8}$alkoxy is optionally substituted with at least one or more halogen, hydroxy, halogen, —$C_{1-8}$alkyl, or —$C_{1-8}$alkoxy;

$X^9$ is $CH_2$; and $n_6$ is independently 0, 1 or 2.

Aspect 30. The compound of aspect 1, wherein

Degron is 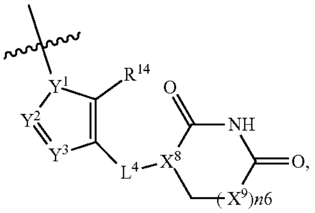

Wherein $R^{14}$ is independently selected from hydrogen, halogen, —$C_{1-8}$alkyl, or —$C_{1-8}$alkoxy, wherein each of said each —$C_{1-8}$alkyl or —$C_{1-8}$alkoxy is optionally substituted by one or more halogen, —$C_{1-8}$alkyl, or $C_{1-8}$alkoxy-$C_{1-8}$alkyl-;

$X^8$ is independently selected from CH, $C(CH_3)$, $C(C_2H_5)$, $C(C_3H_7)$, C(CN) or N;

$L^4$ is independently selected from a single bond, —O—, —NH—, —$CH_2$—, —CHF—, or —$CF_2$—;

$Y^1$, $Y^2$, and $Y^3$ are each independently selected from $CR^a$, or N;

$R^a$ is each independently selected from hydrogen, halogen, —$C_{1-8}$alkyl, or —$C_{1-8}$alkoxy, each of said —$C_{1-8}$alkyl, or —$C_{1-8}$alkoxy is optionally substituted with at least one or more halogen, hydroxy, halogen, —$C_{1-8}$alkyl, or —$C_{1-8}$alkoxy;

$X^9$ is $CH_2$; and n6 is independently 0, 1 or 2.

Aspect 31. The compound of aspect 1, wherein

Degron is 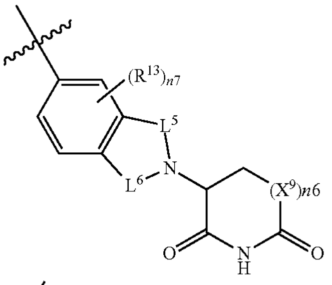 or

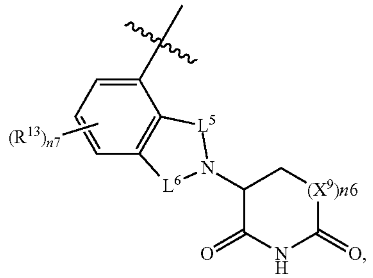

wherein $L^5$ and $L^6$ are each independently selected from —$CH_2$ or —CO—;

$X^9$ is $CH_2$;

each $R^{13}$ is independently selected from hydrogen, halogen, CN, —$C_{1-8}$alkyl, or —$C_{1-8}$alkoxy;

$n_6$ is 0 or 1; and $n_7$ is 0, 1 or 2.

Aspect 32. The compound of aspect 1, wherein

Degron is

-continued

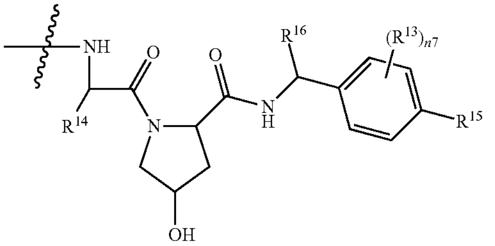 or

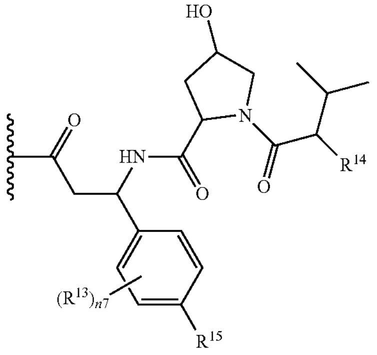 , wherein $R^{13}$ and $R^{16}$ are independently selected from hydrogen, halogen, —$C_{1-8}$alkyl, or —$C_{1-8}$alkoxy; said each —$C_{1-8}$alkyl or —$C_{1-8}$alkoxy is optionally substituted by one or more halogen, —$C_{1-8}$alkyl, or $C_{1-8}$alkoxy-$C_{1-8}$alkyl-;

$R^{15}$ and $R^{14}$ is selected from the group consisting of 5- to 12-membered heteroaryl, 3- to 8-membered heterocyclyl, and $C_6$-$C_{12}$aryl, and $R^{15}$ is optionally substituted by one or more halogen, —$C_{1-8}$alkyl, or $C_{1-8}$alkoxy-$C_{1-8}$alkyl-; and n7 is independently 0, 1, 2, 3 or 4.

Aspect 33. The compound of aspect 1, wherein

Degron is selected from

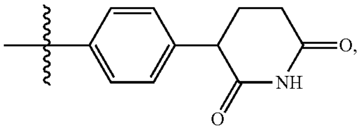

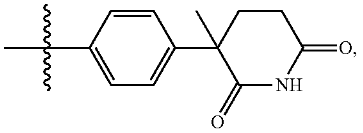

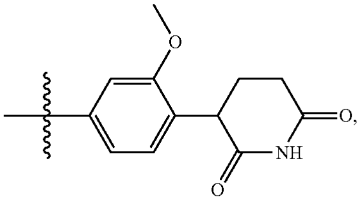

-continued
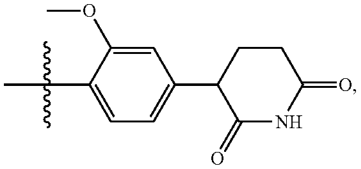
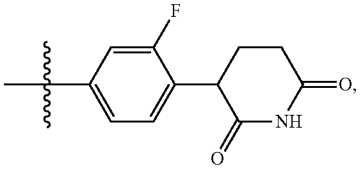
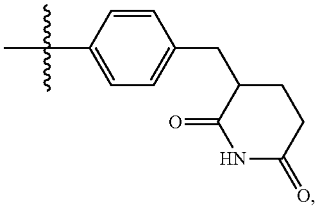
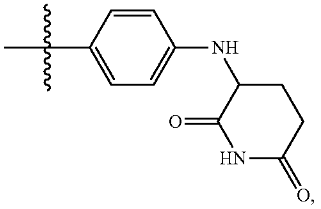
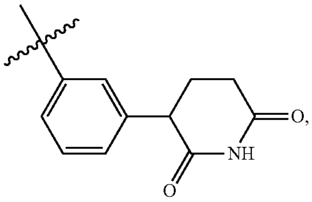
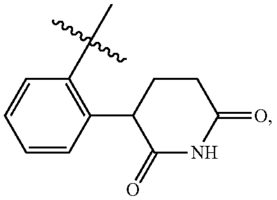
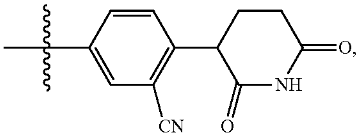
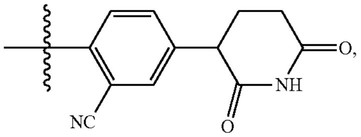
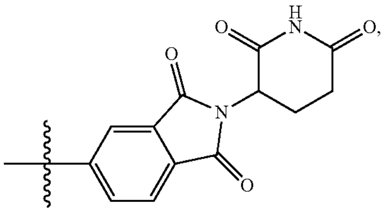
-continued
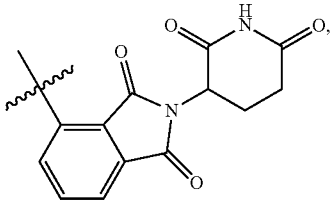
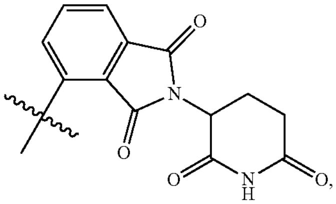
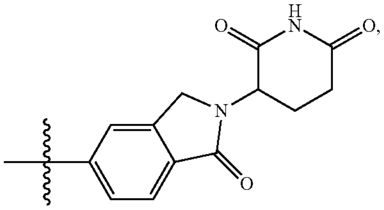
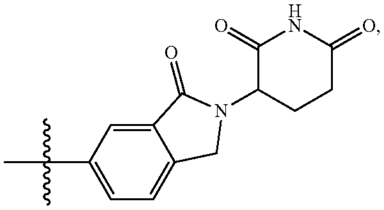
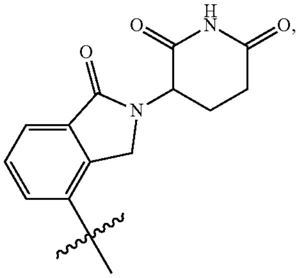
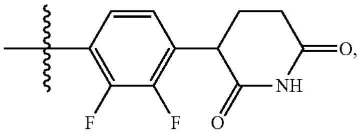
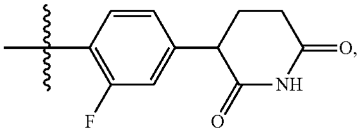
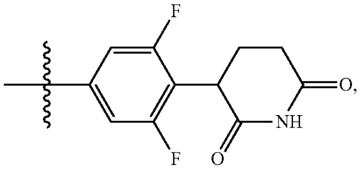
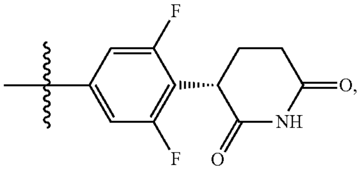

-continued
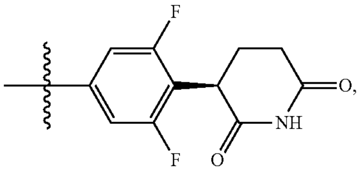
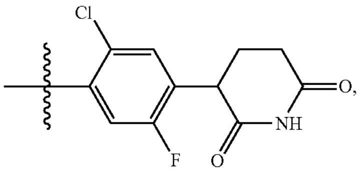
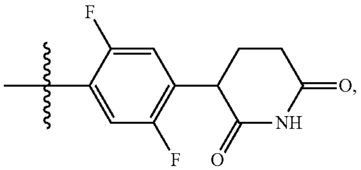
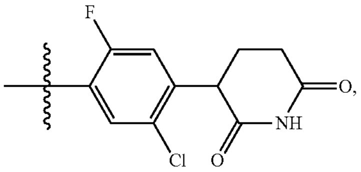
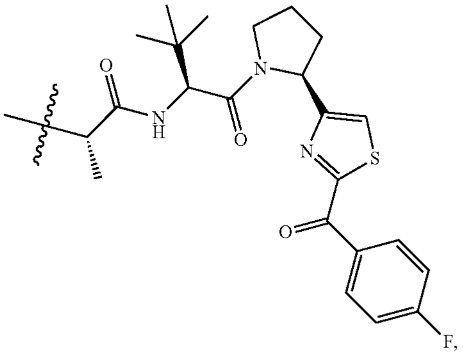
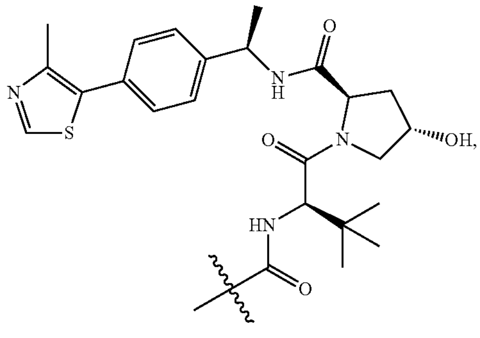
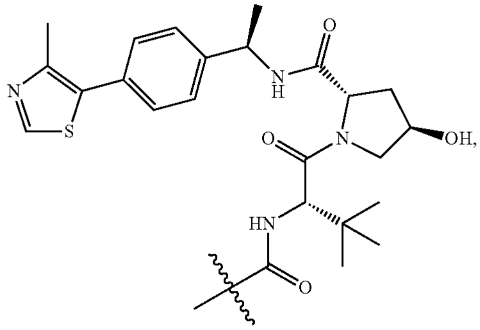
-continued
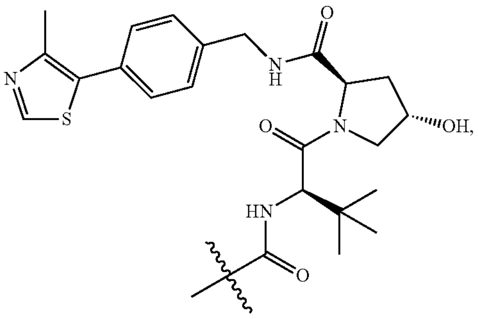
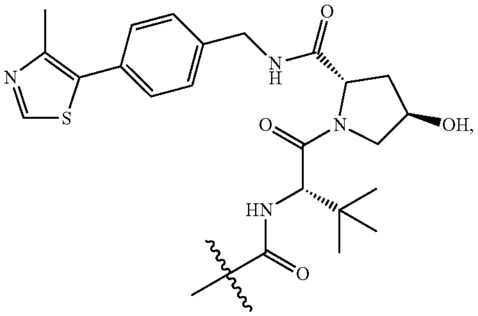
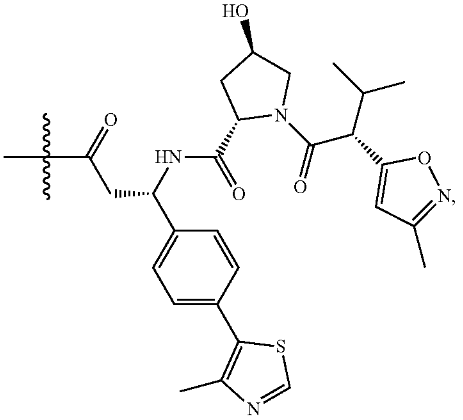
or
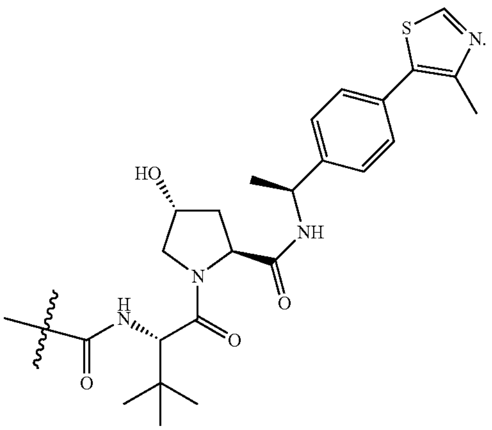

Aspect 34. The compound of aspect 1 selected from
1
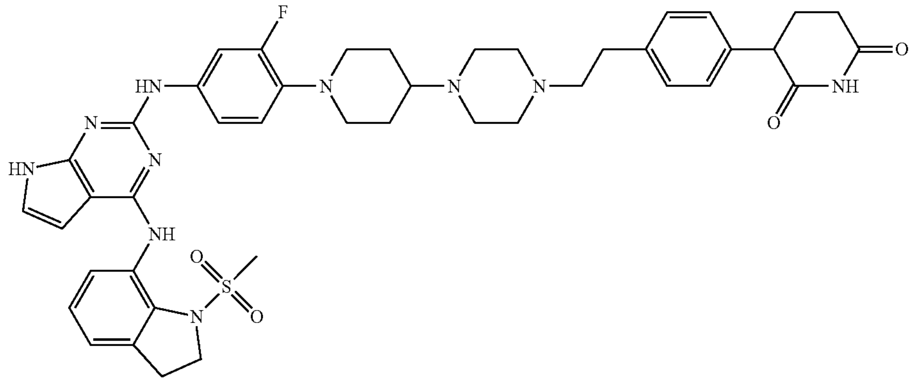
2
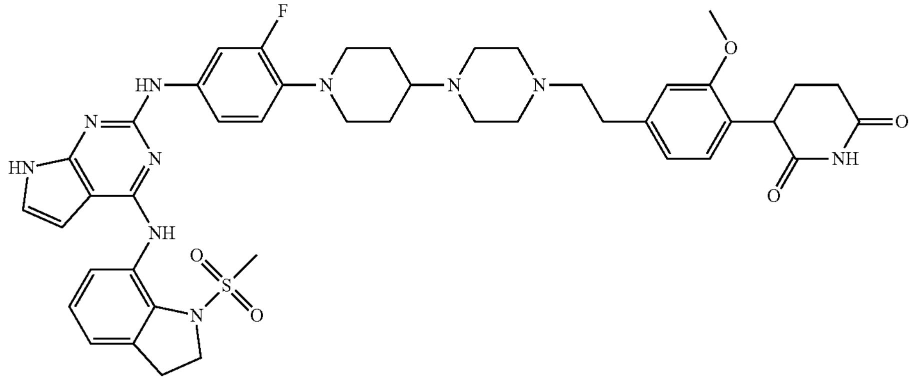
3
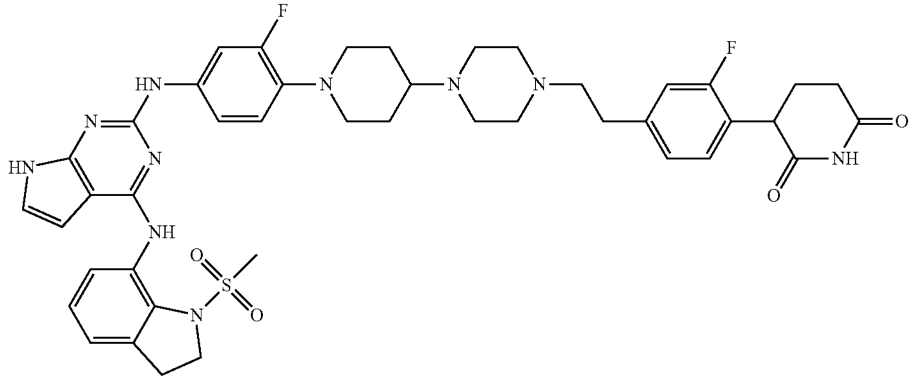
4
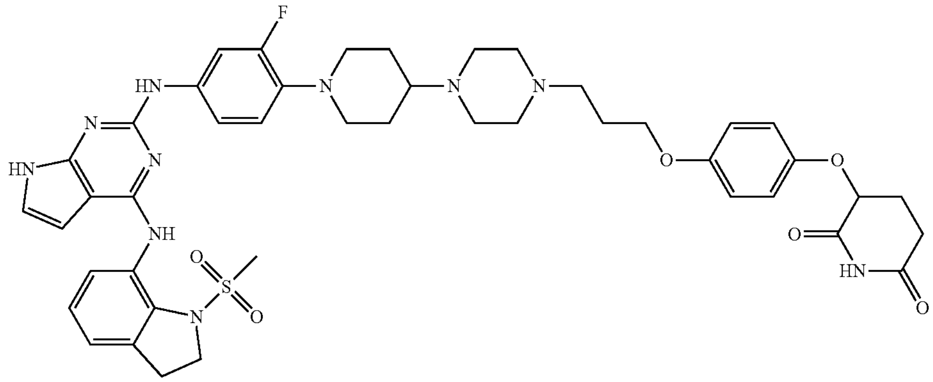

-continued
5
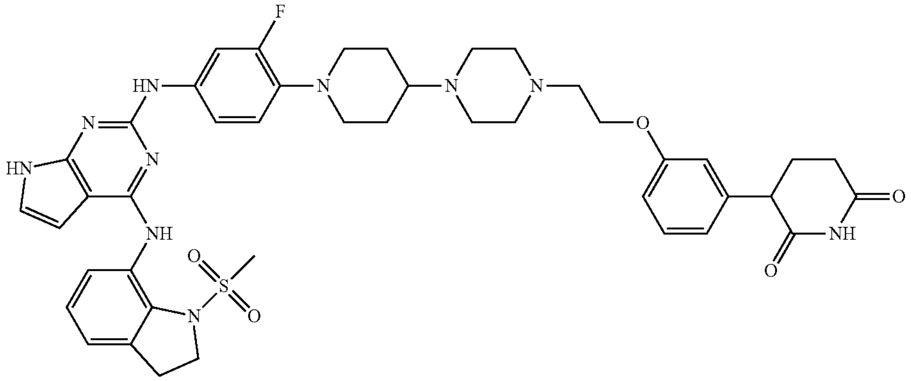
6
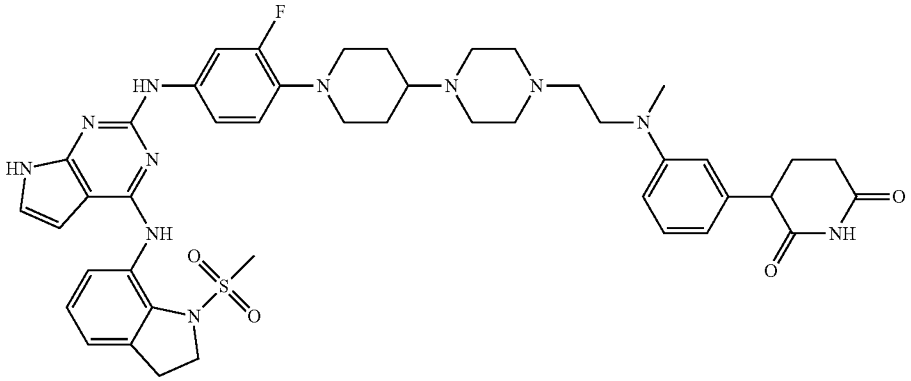
7
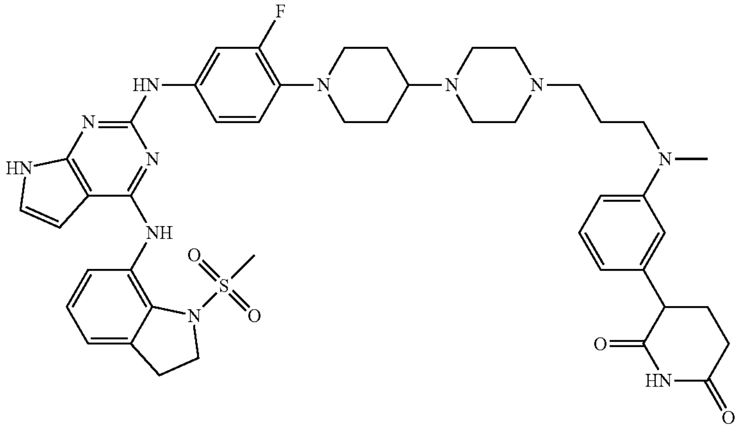
8
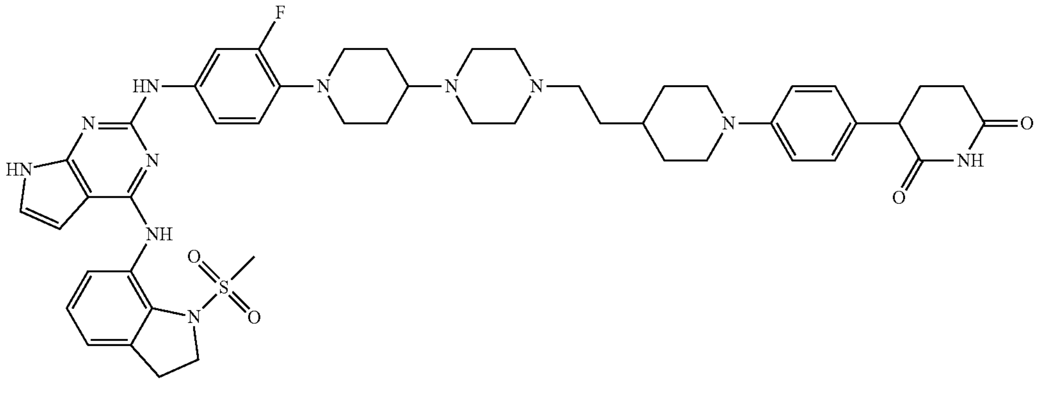

-continued
9
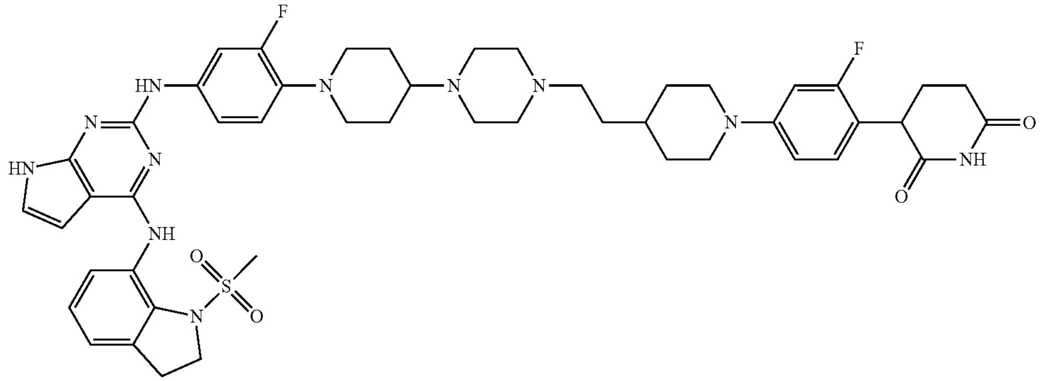
10
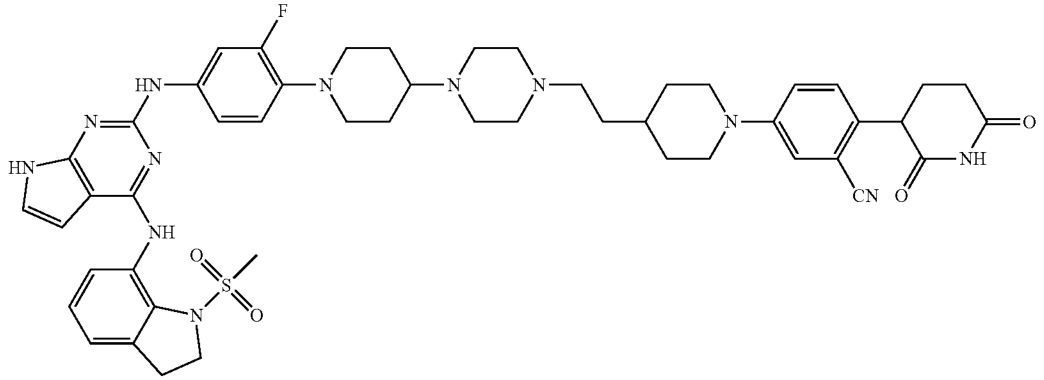
11
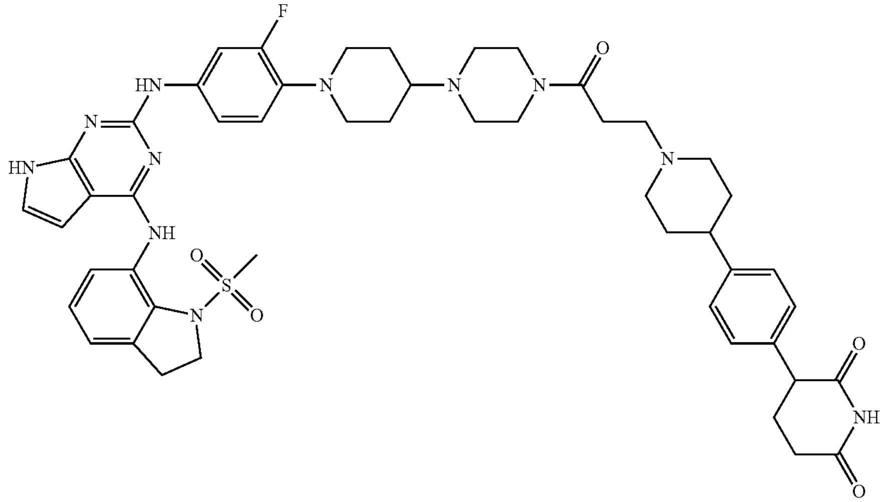
12
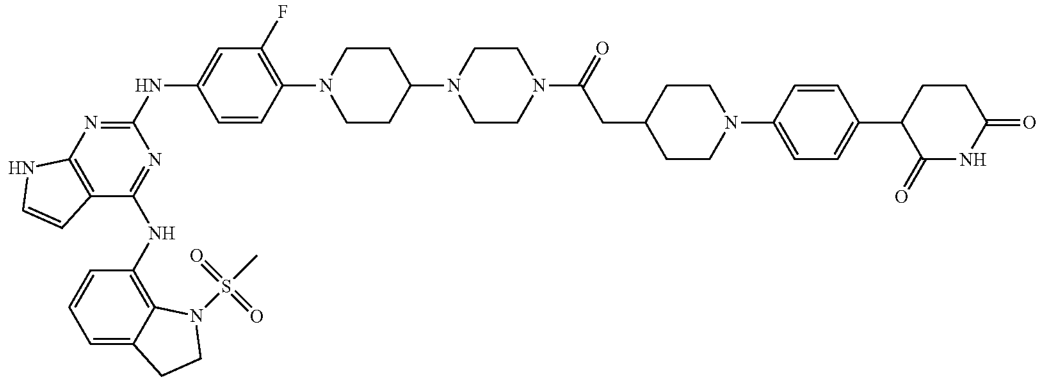

-continued
13
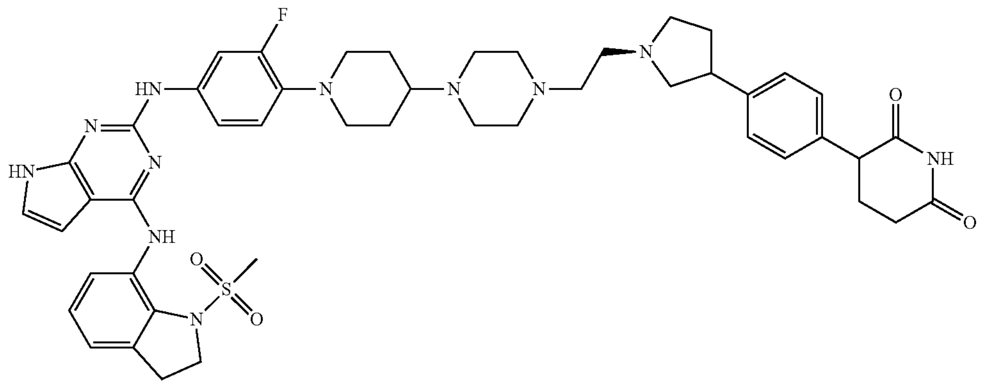
14
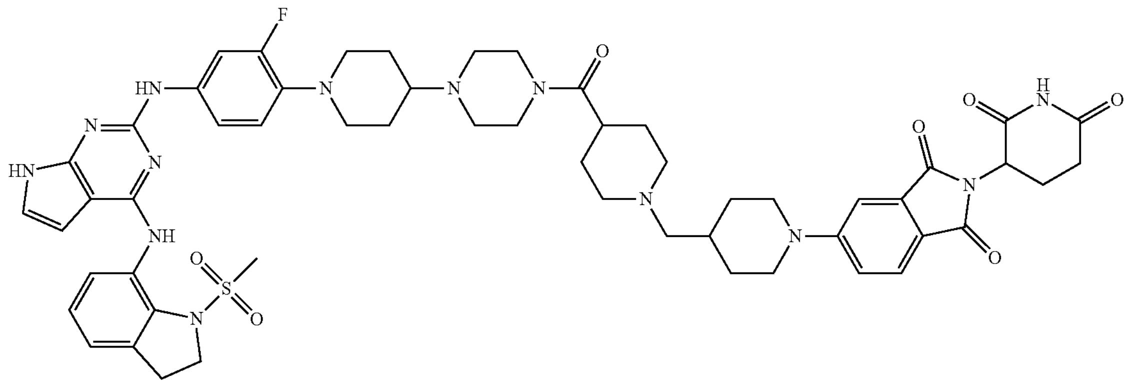
15
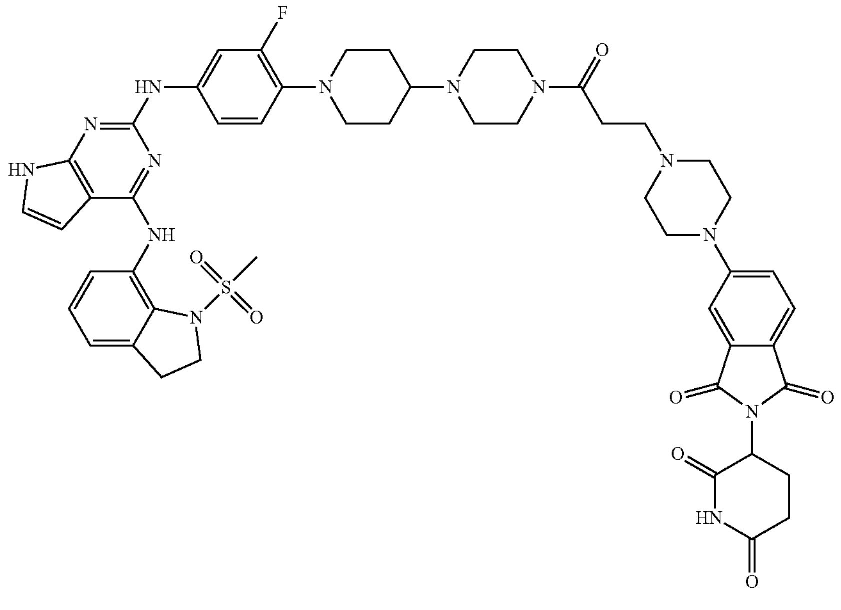

-continued
16
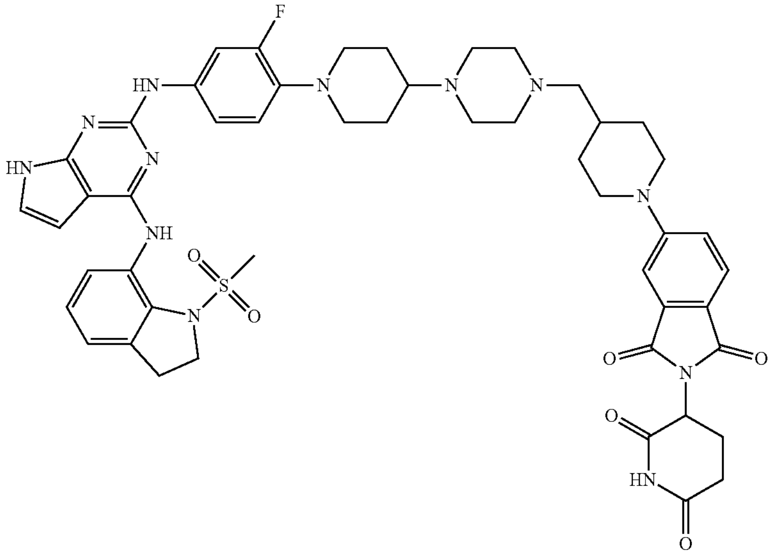
17
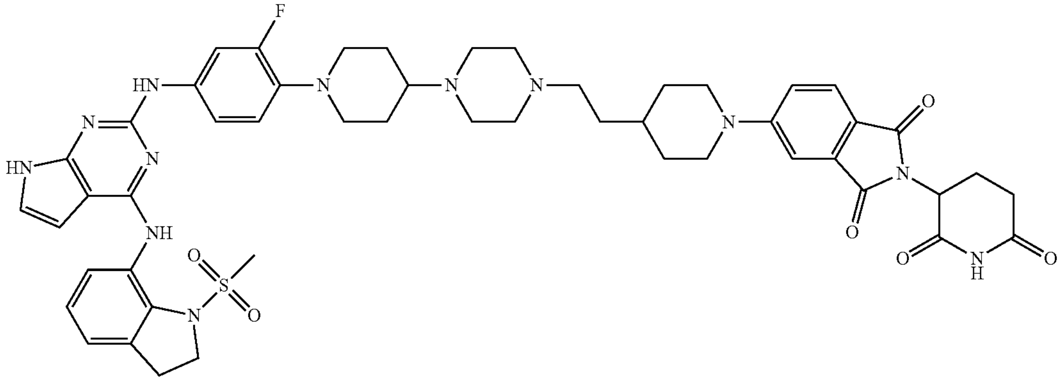
18
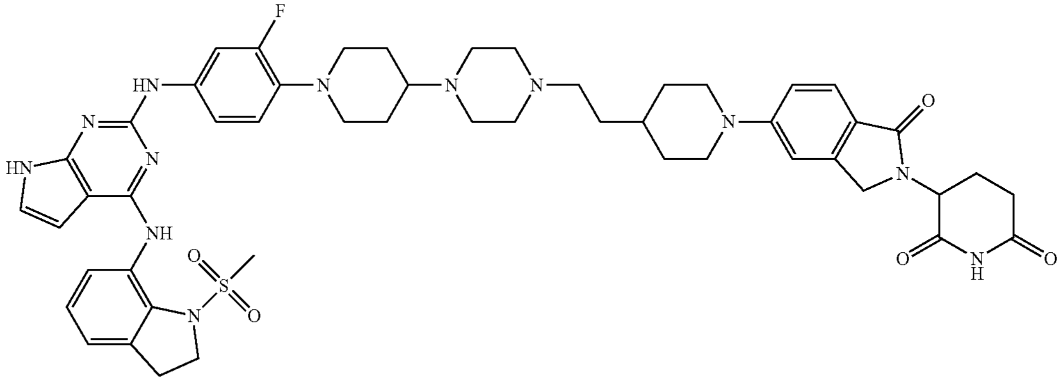

-continued
19
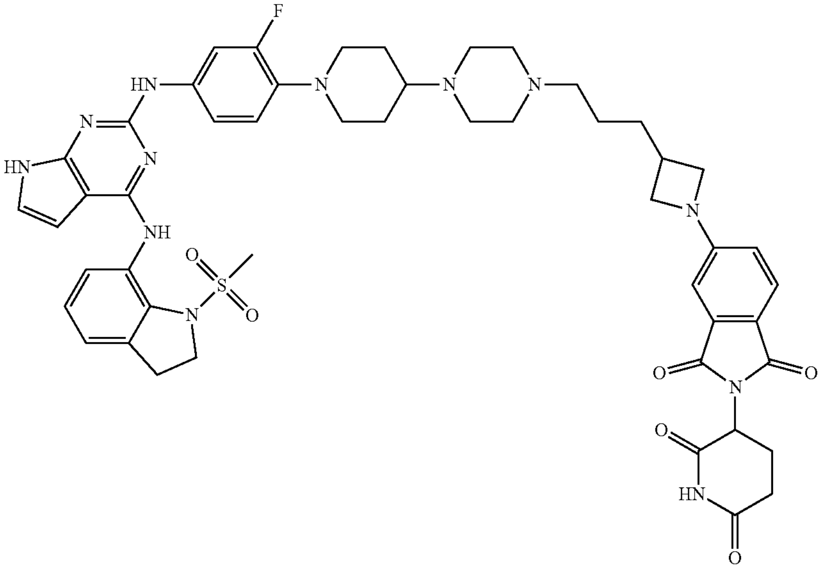
20
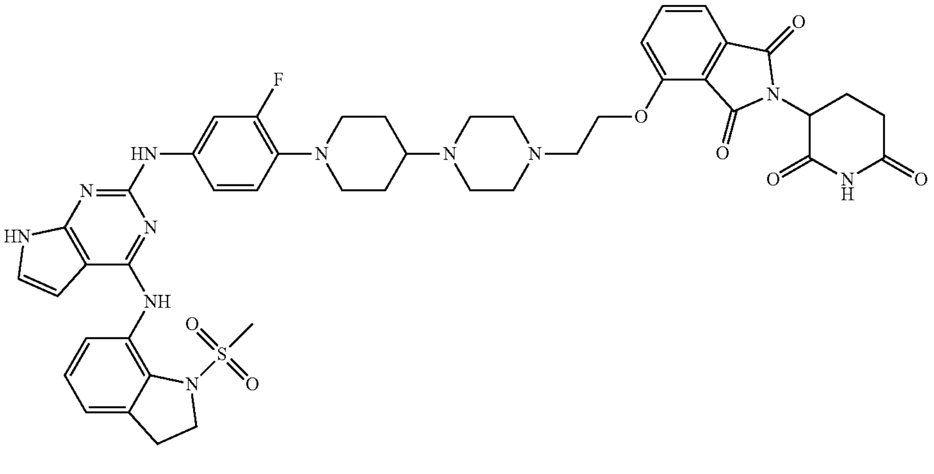
21
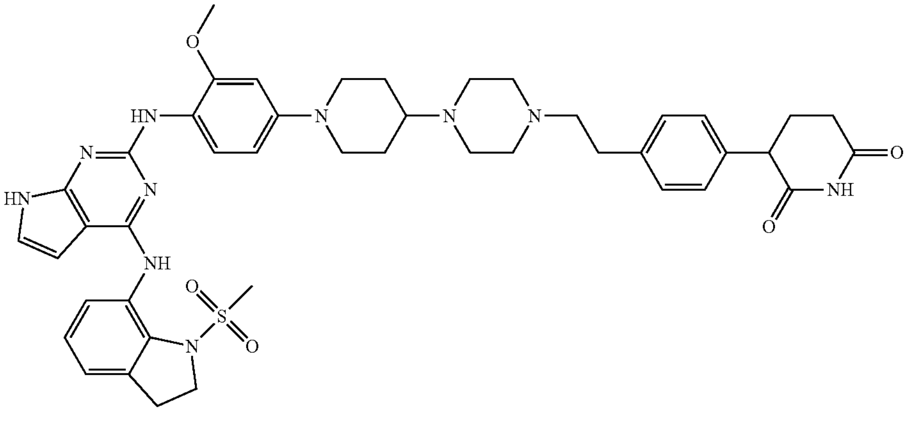

-continued
22
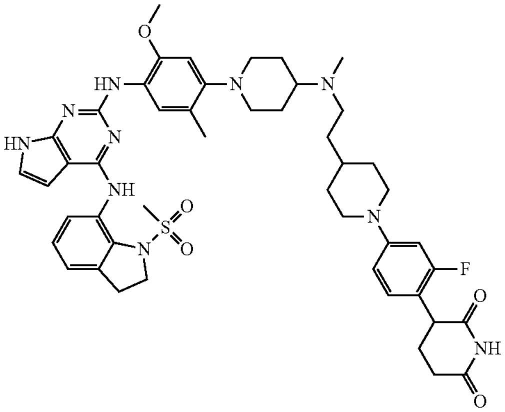
23
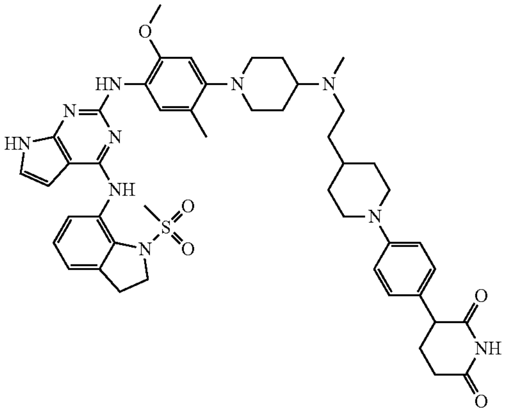
24
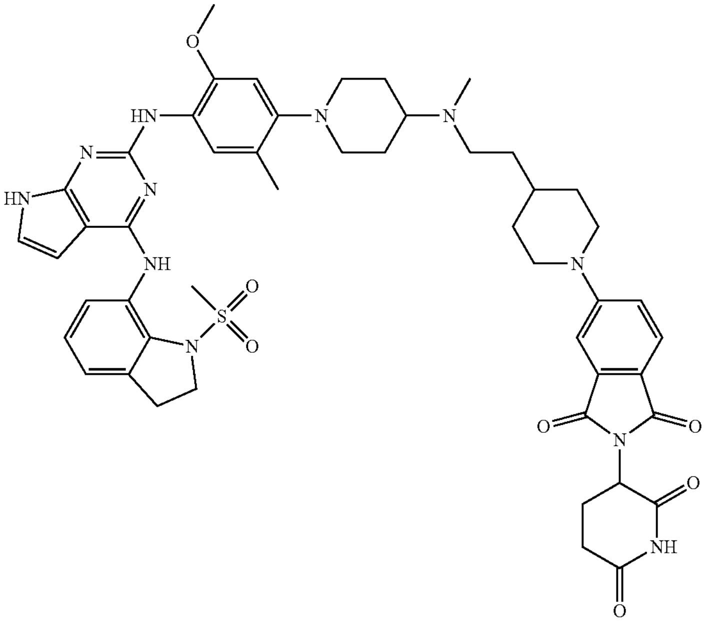
25
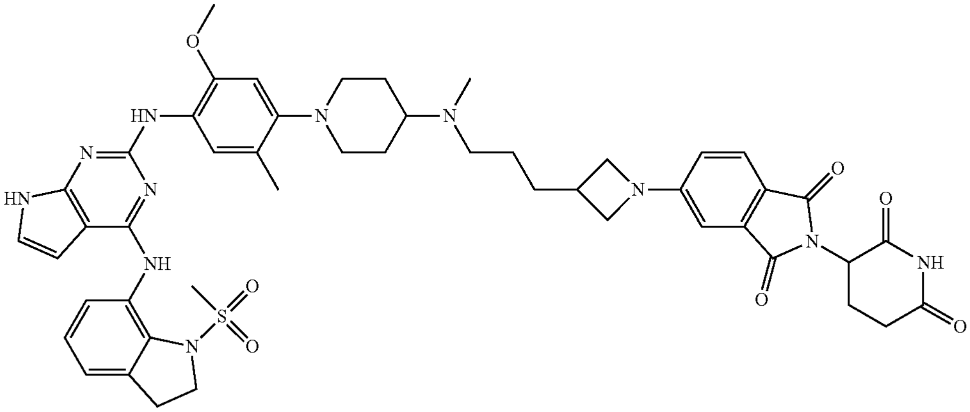

-continued
26
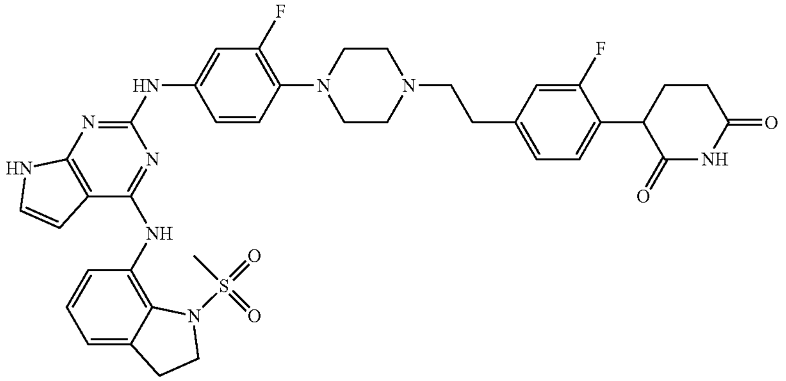
27
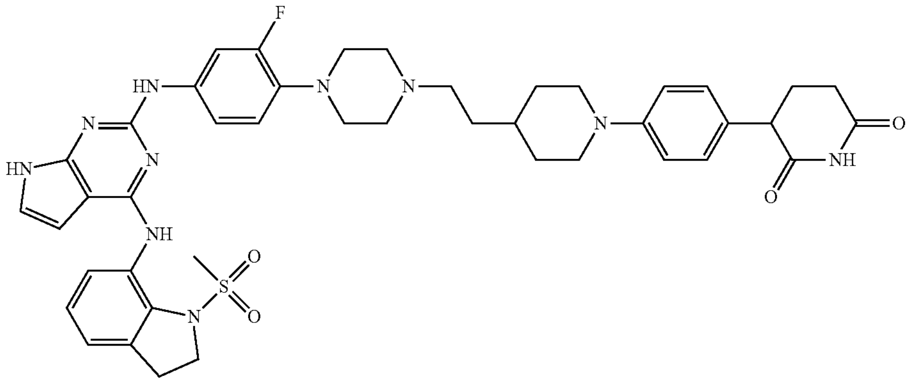
28
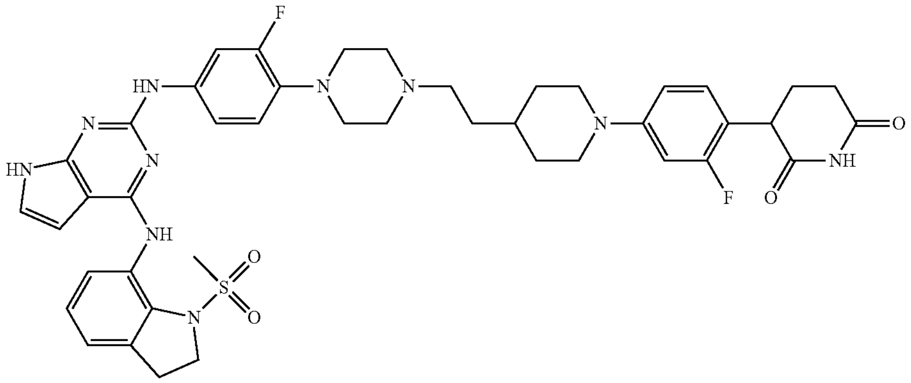
29
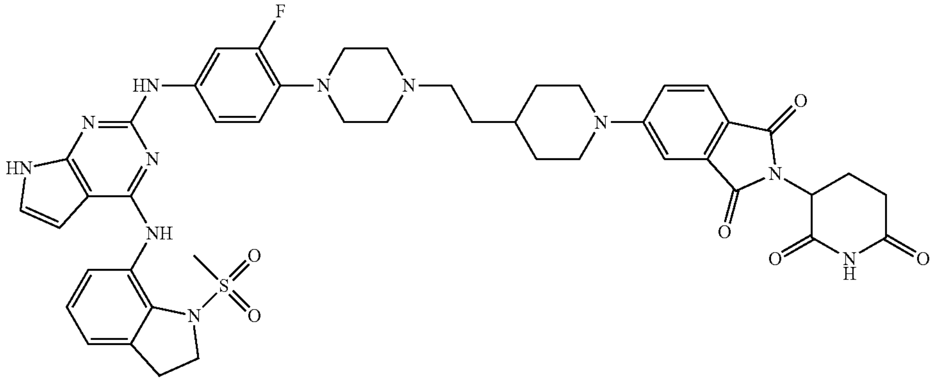

-continued
30
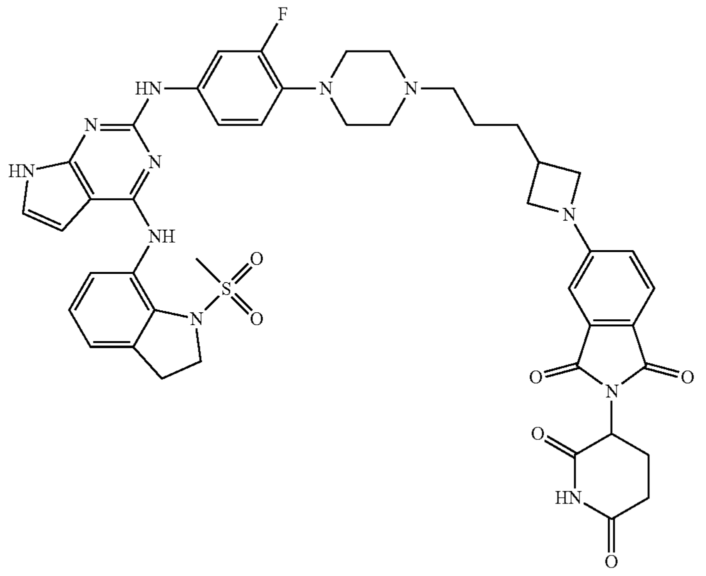
31
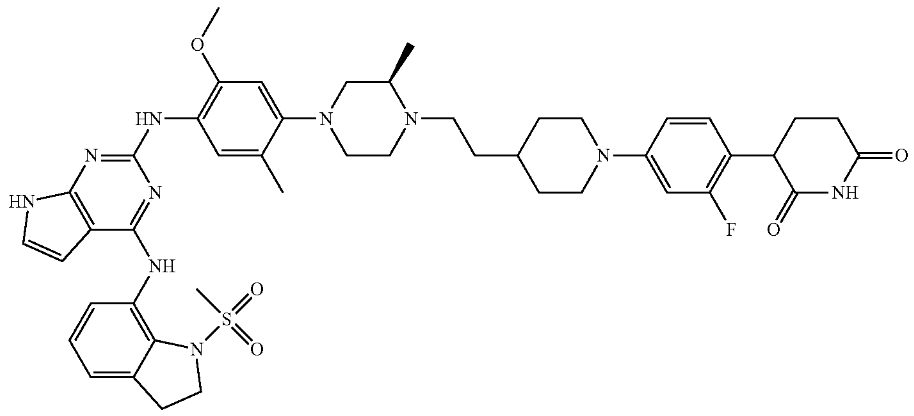
32
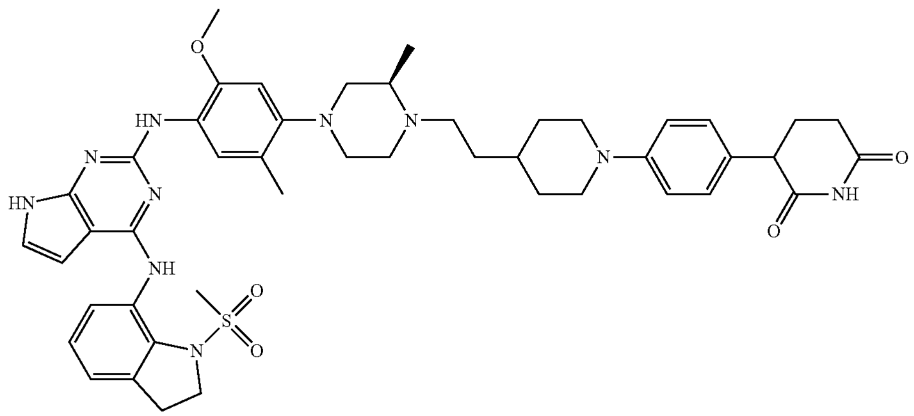

-continued
33
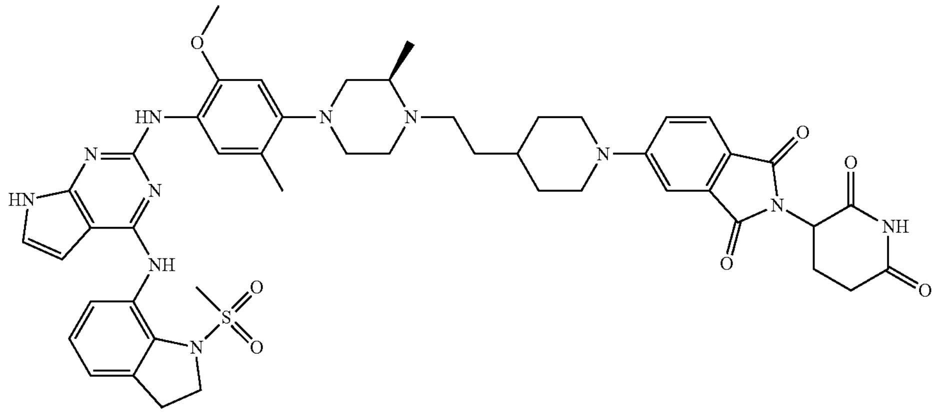
34
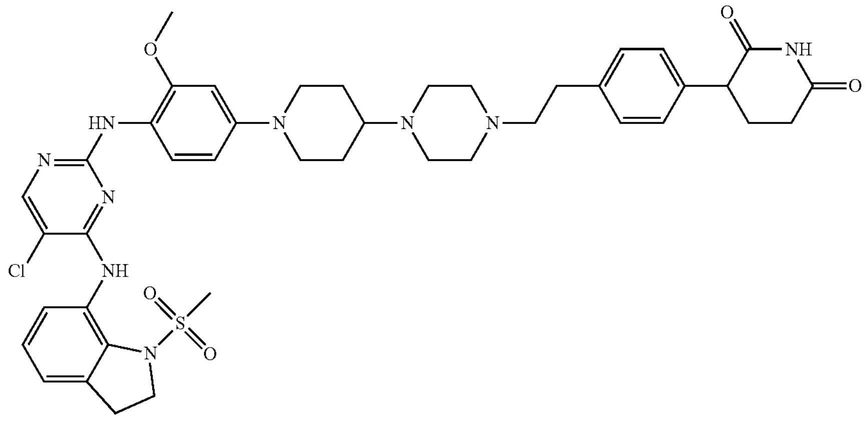
35
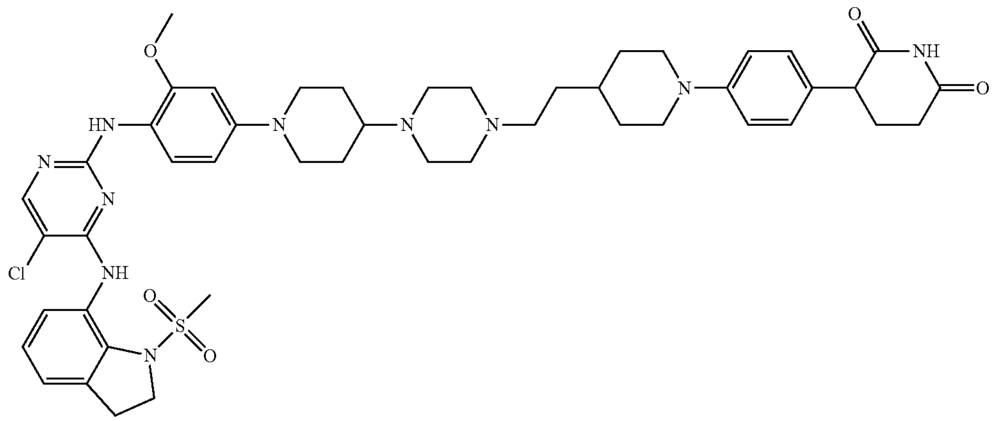

-continued
36
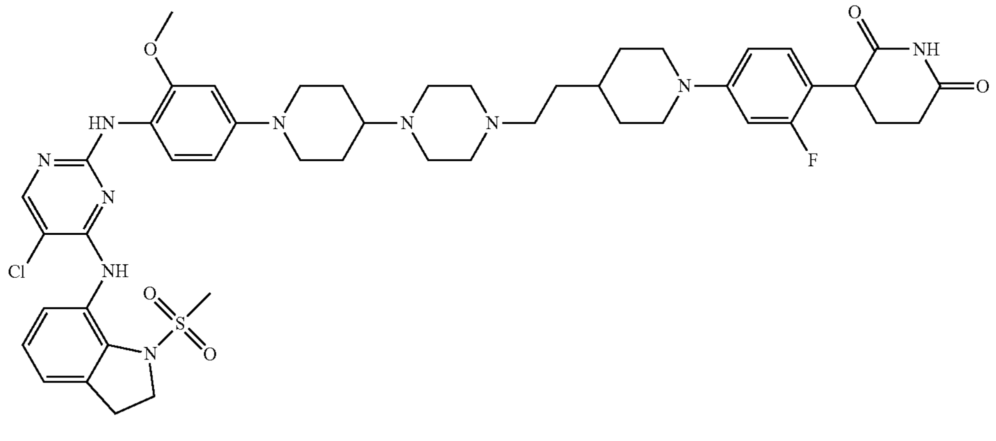
37
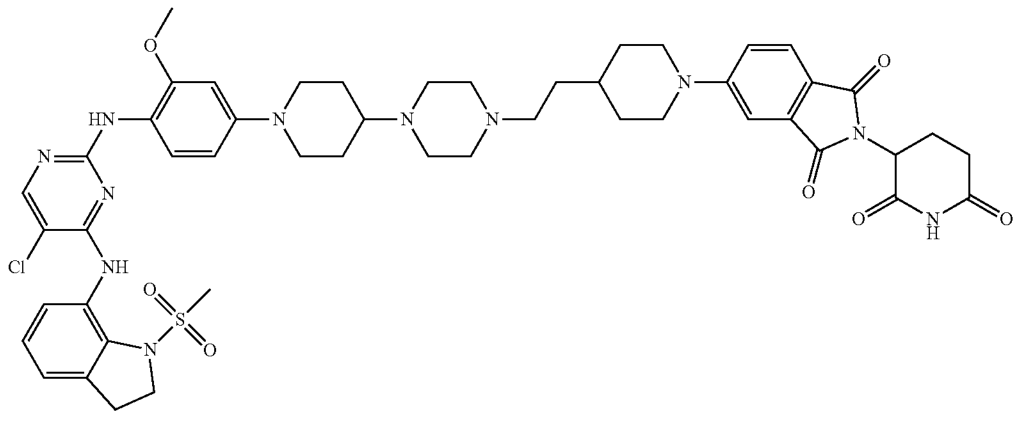
38
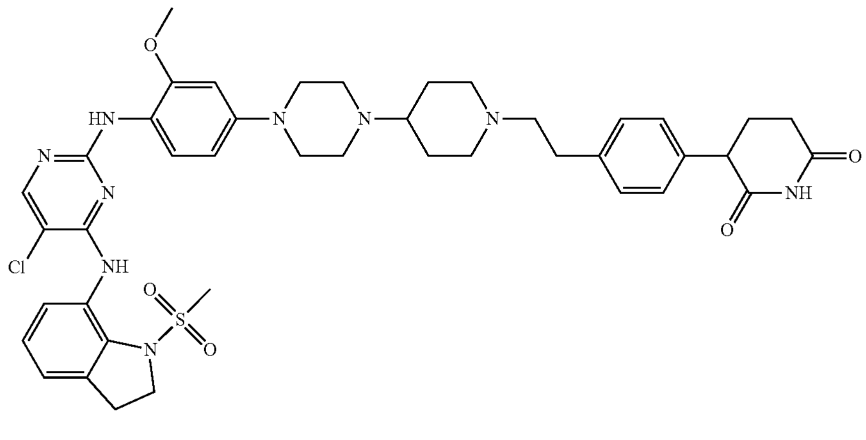

-continued
39
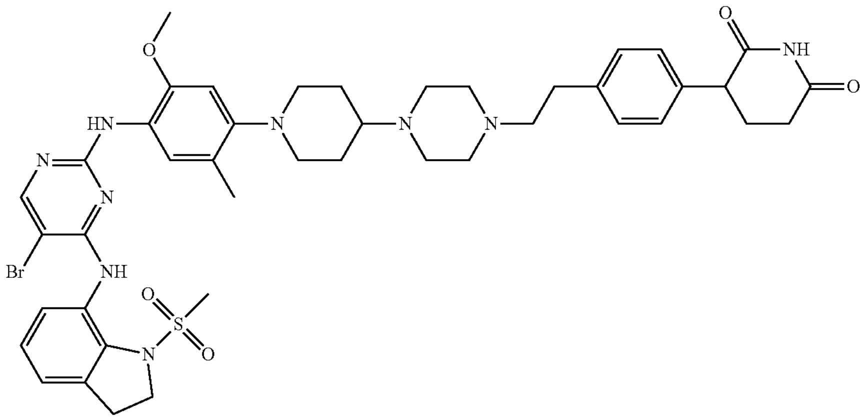
40
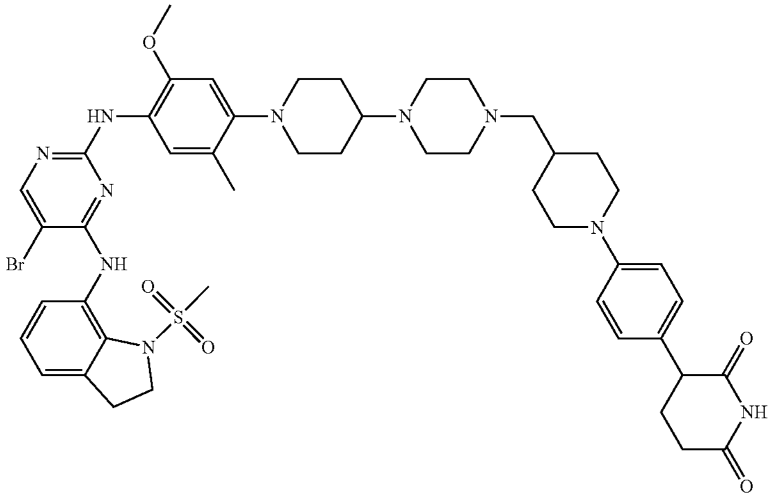
41
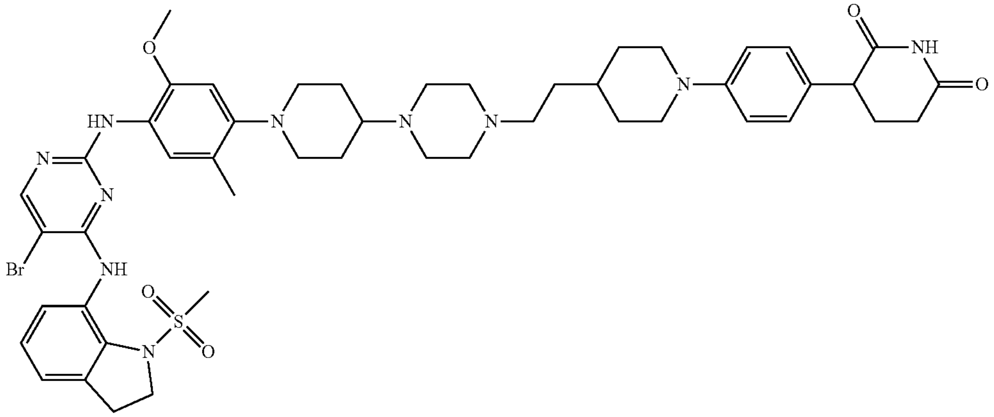

-continued
42
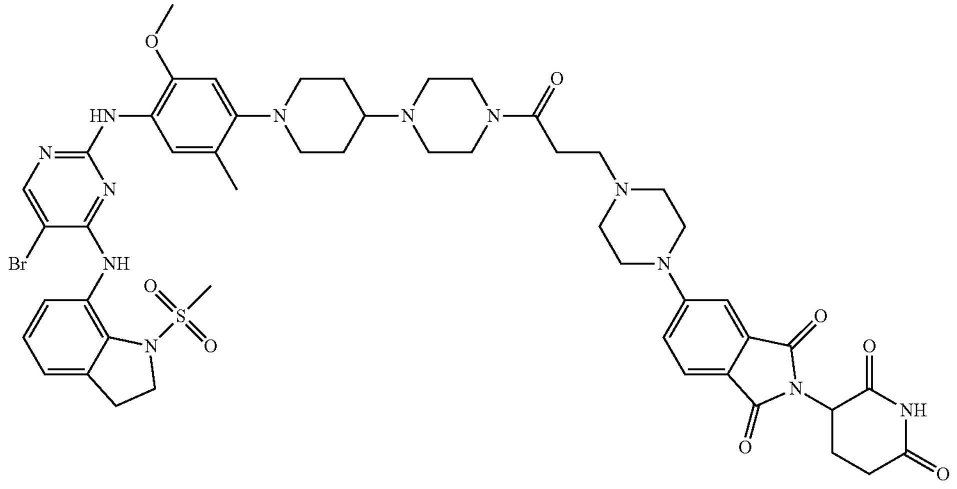
43
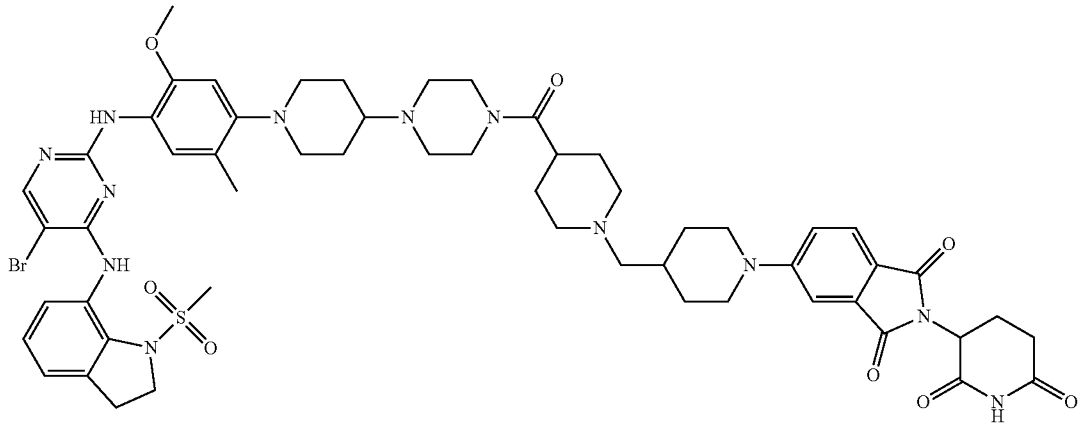
44
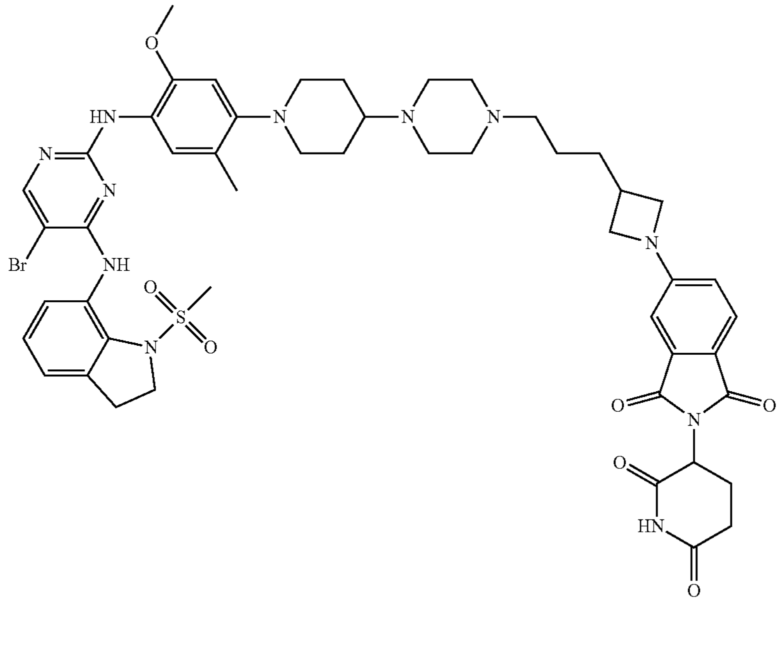

-continued
45
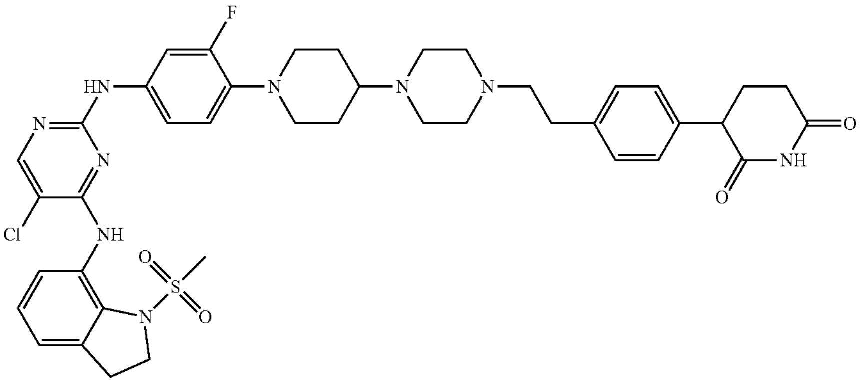
46
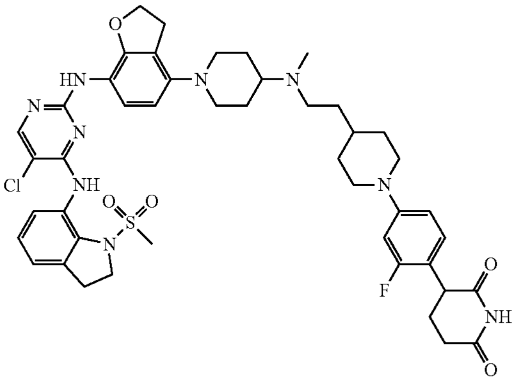
47
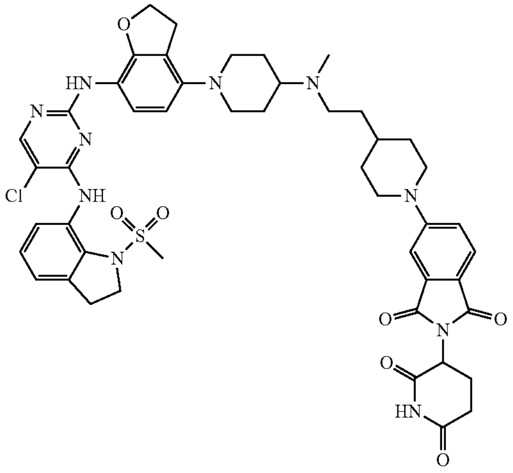
48
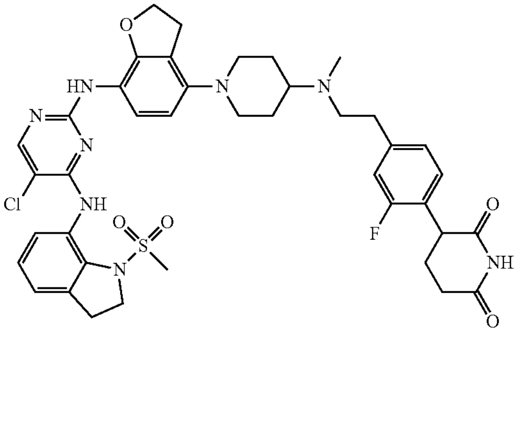
49
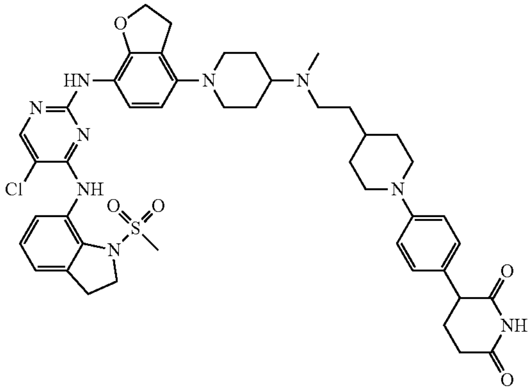

-continued
50
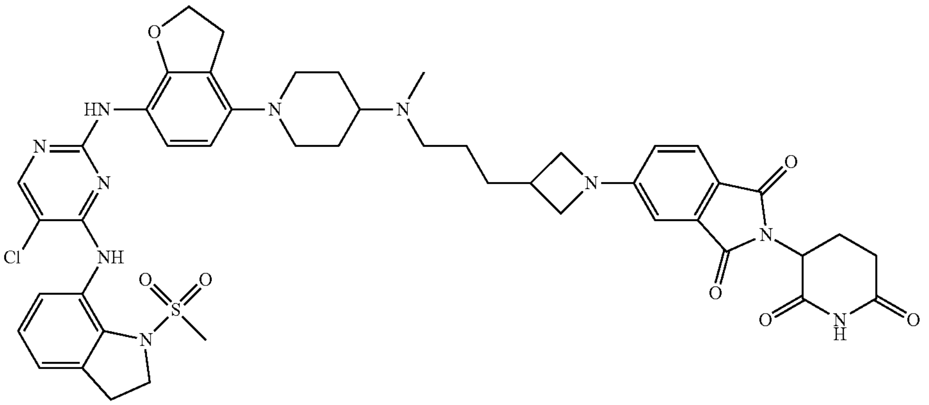
51
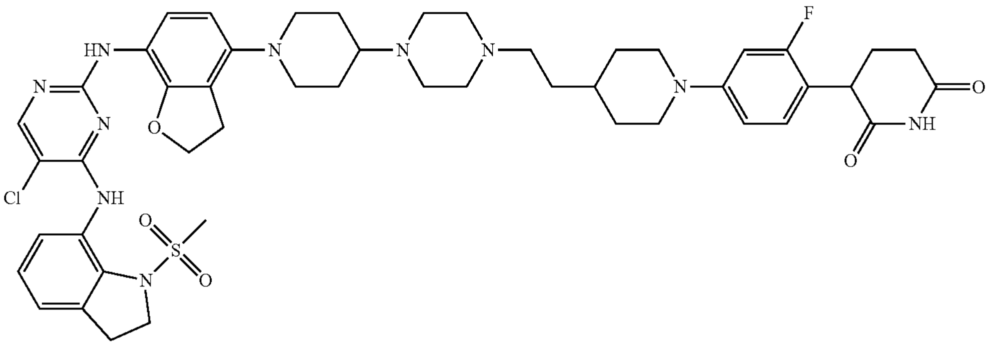
52
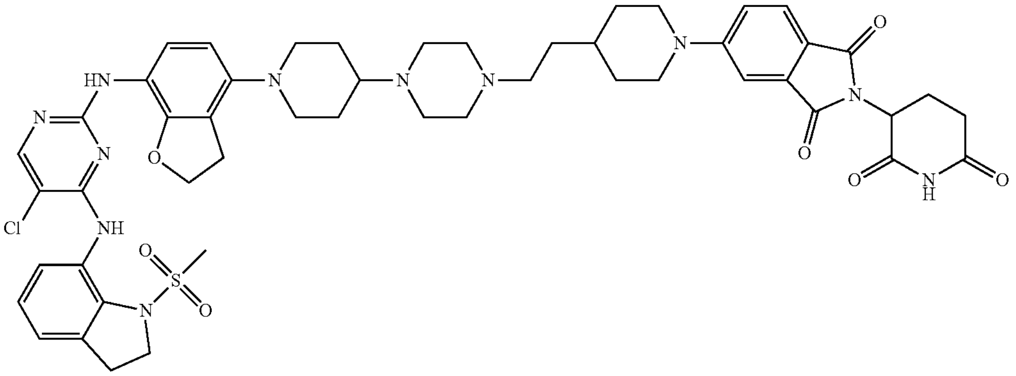
53
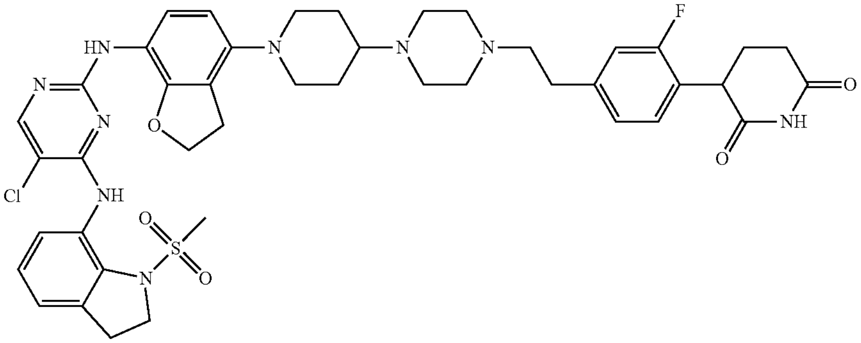

-continued
54
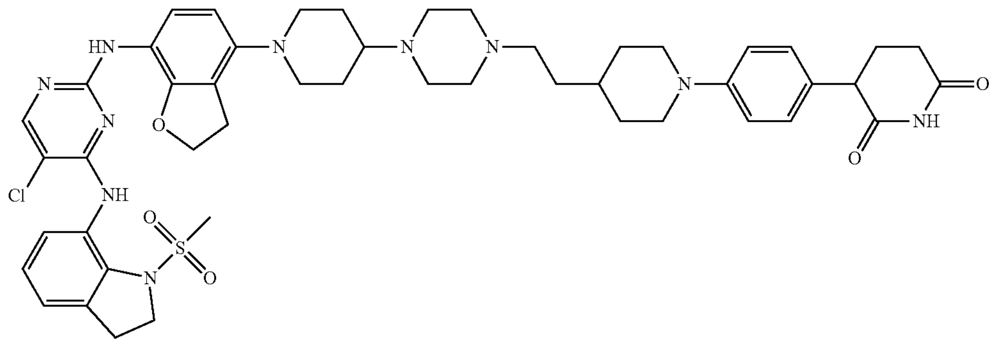
55
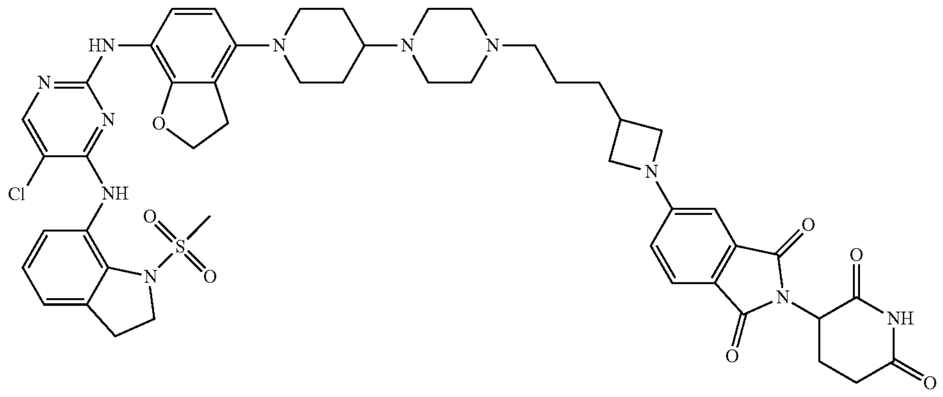
56
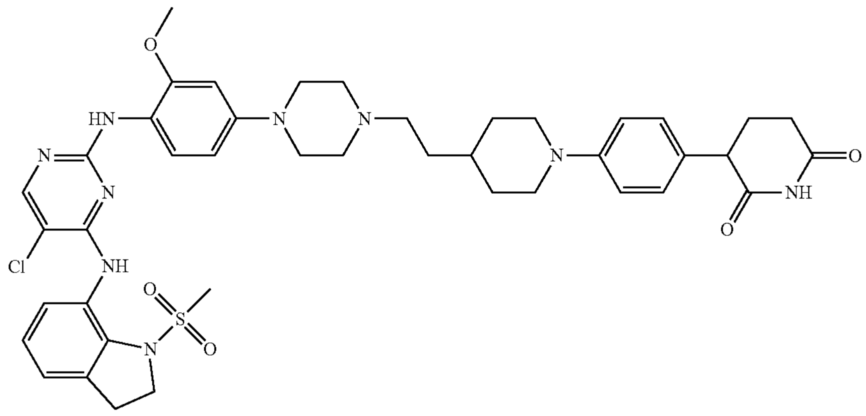
57
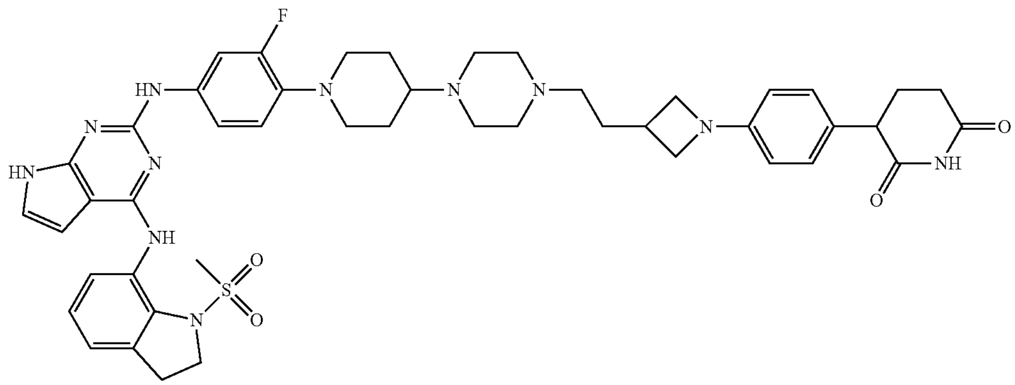

-continued
58
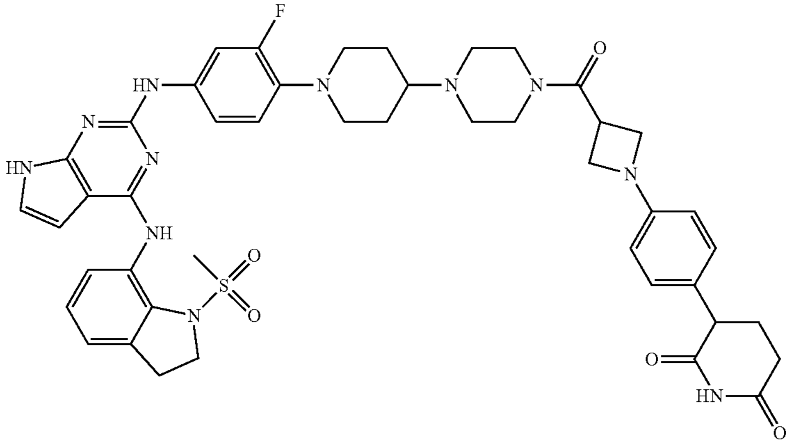
59
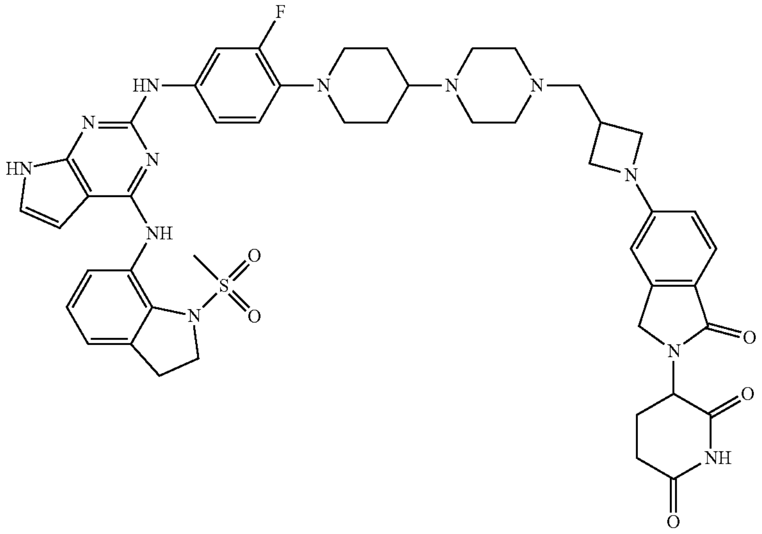
60
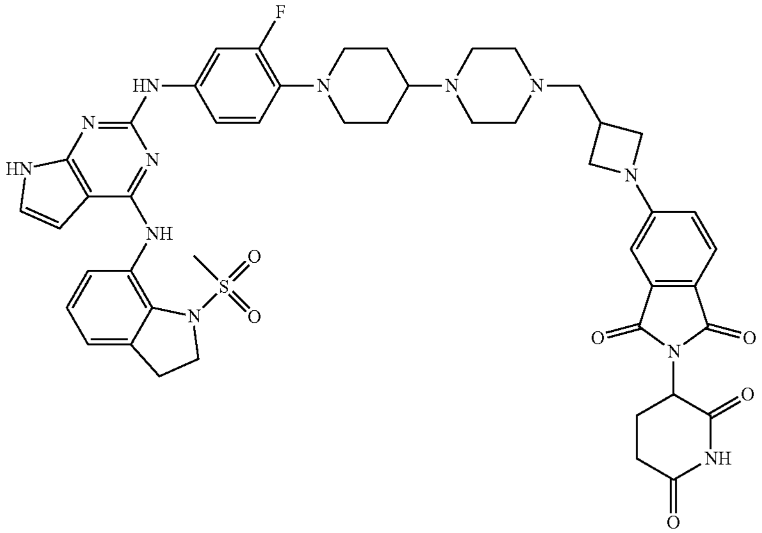

-continued
61
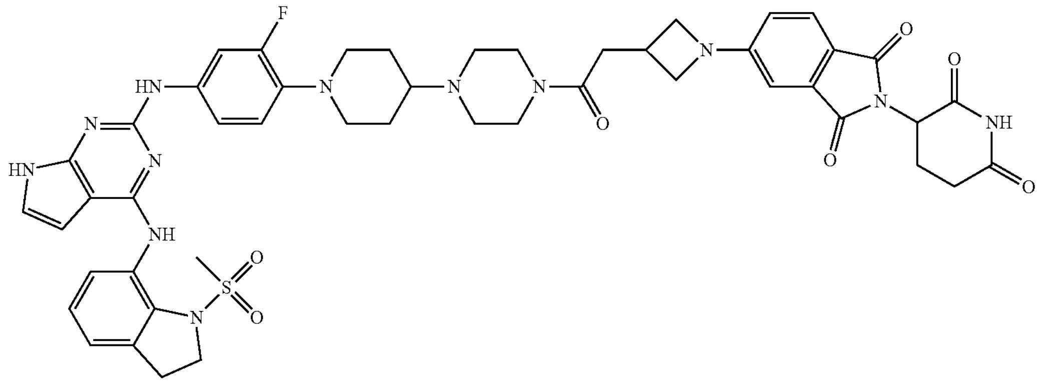
62
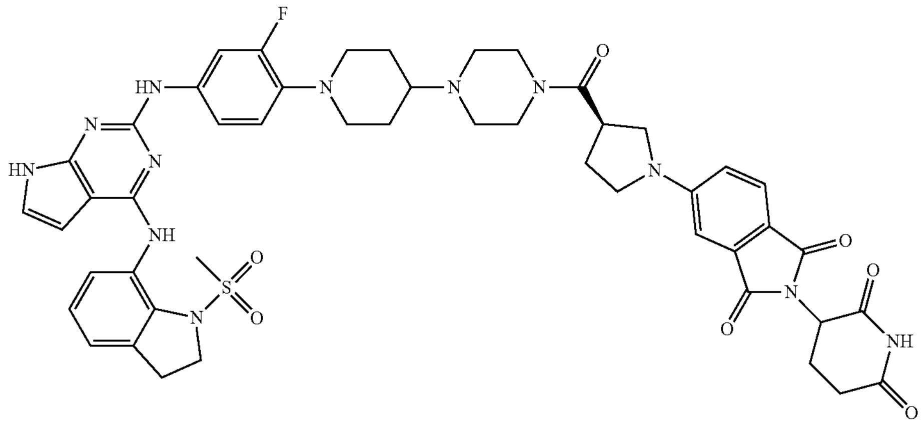
63
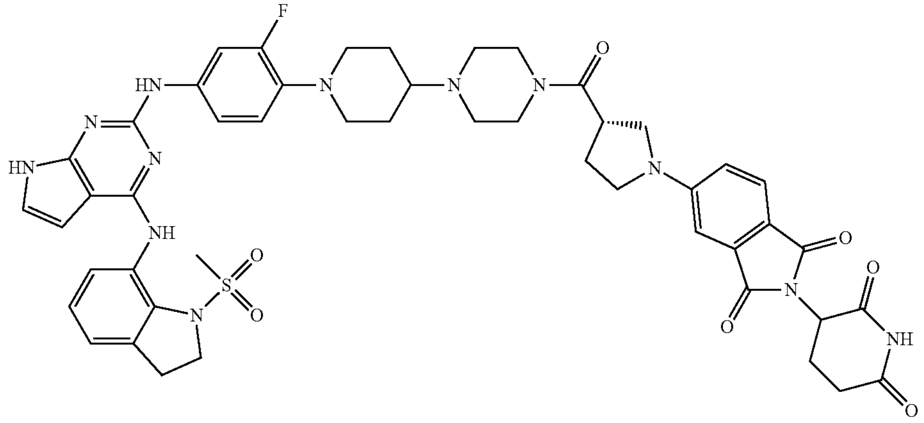

-continued
64
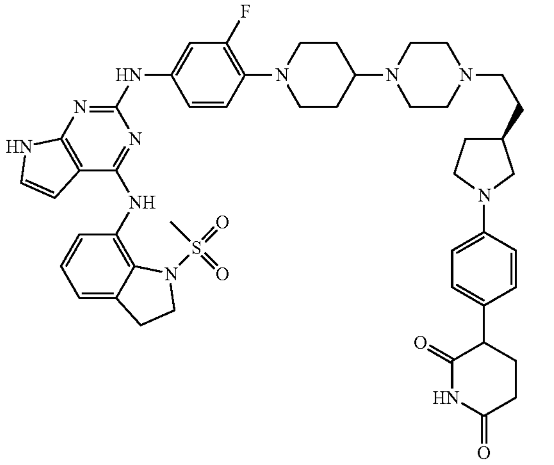
65
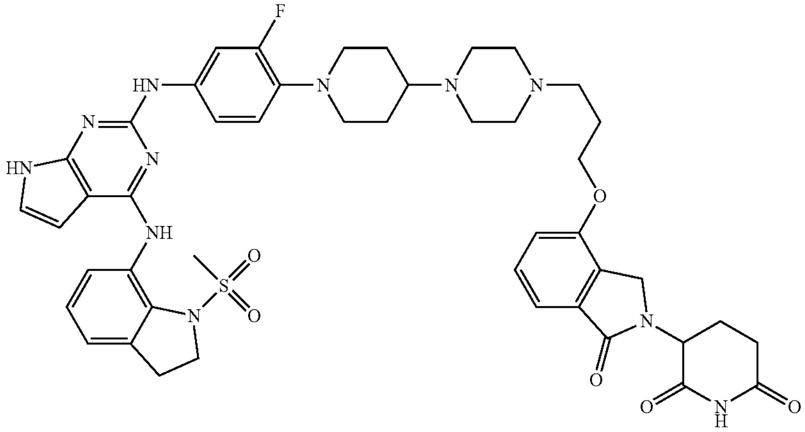
66
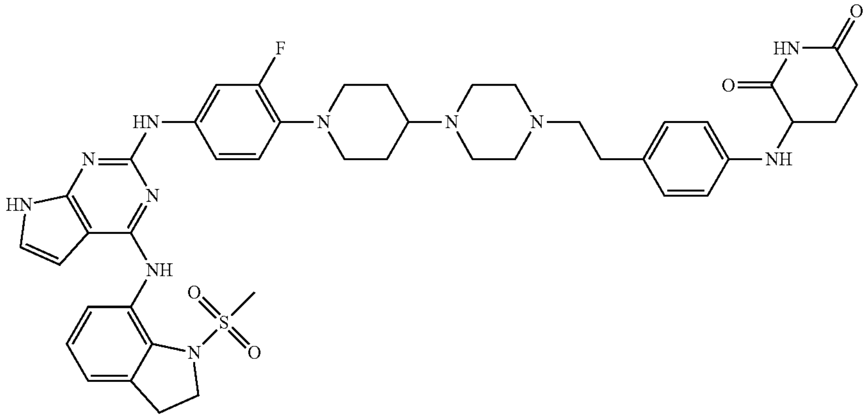

-continued
67
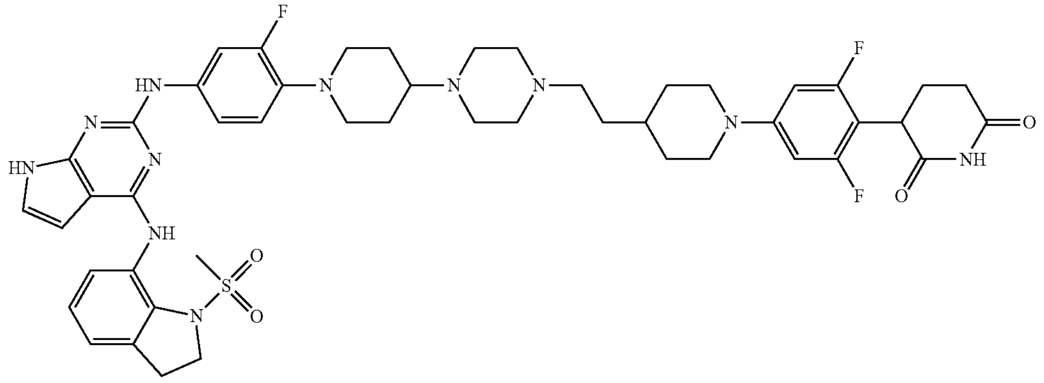
68
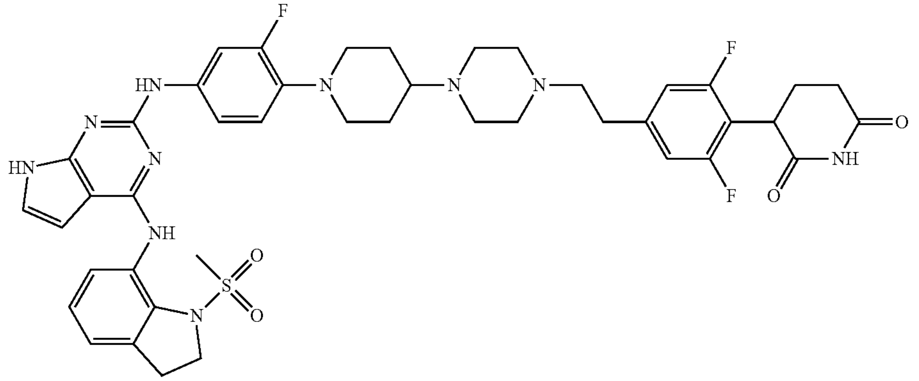
69
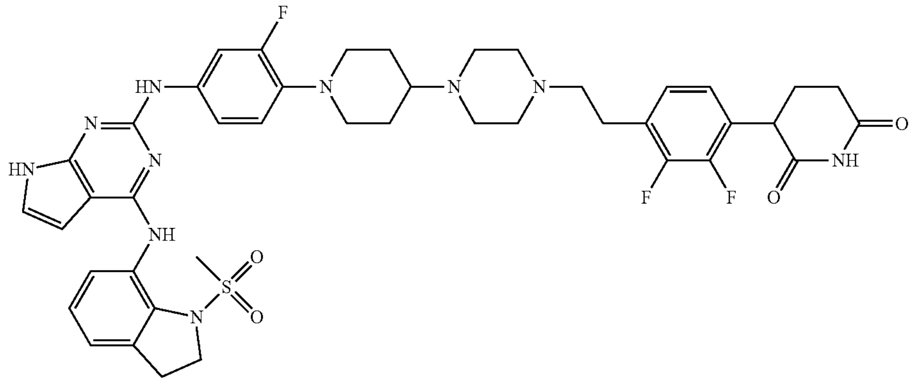
70
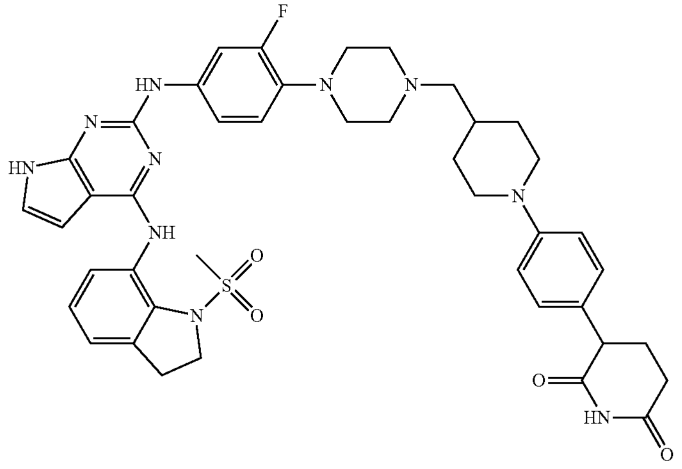

-continued
71
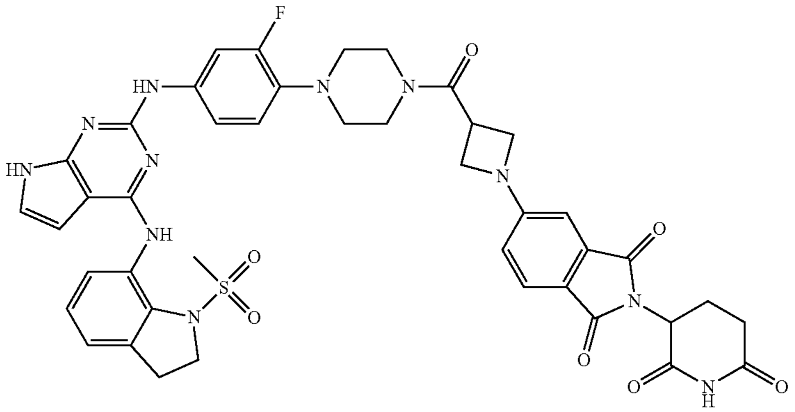
72
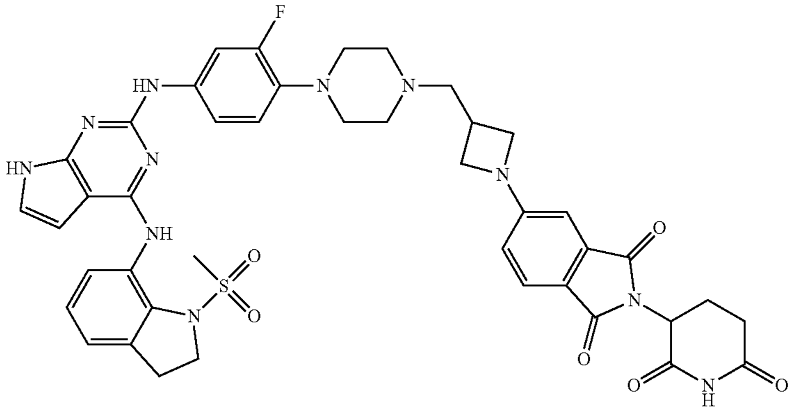
73
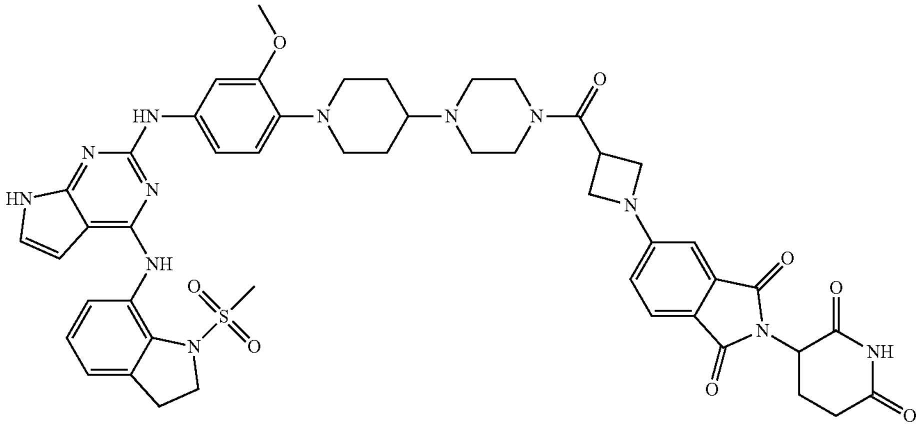

-continued
74
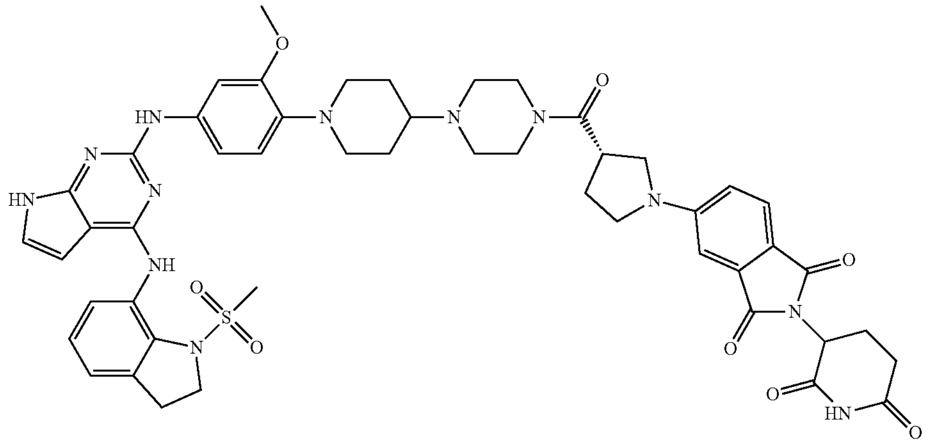
75
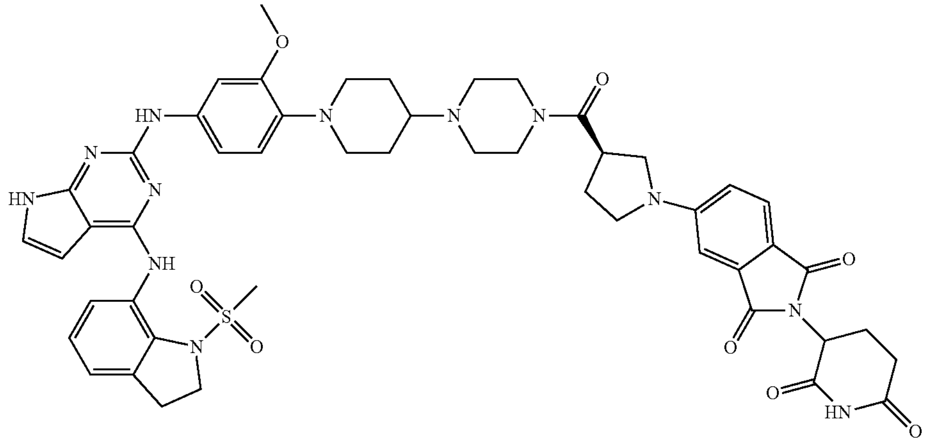
76
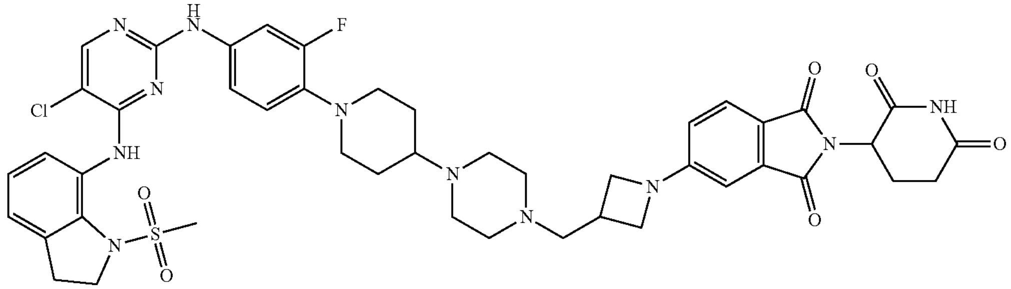
77
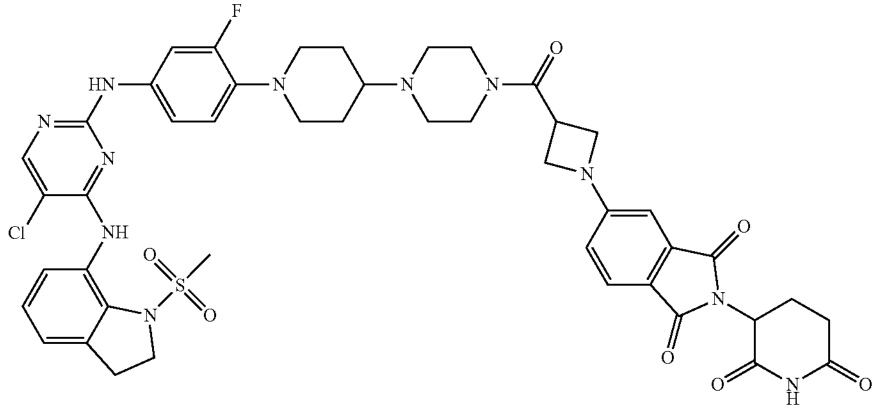

-continued
78
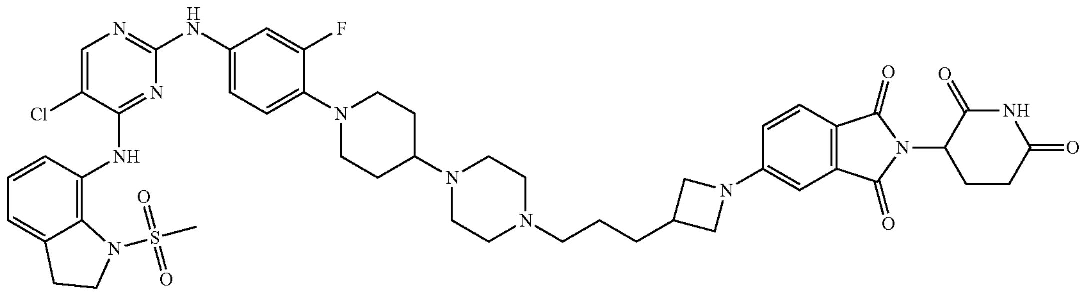
79
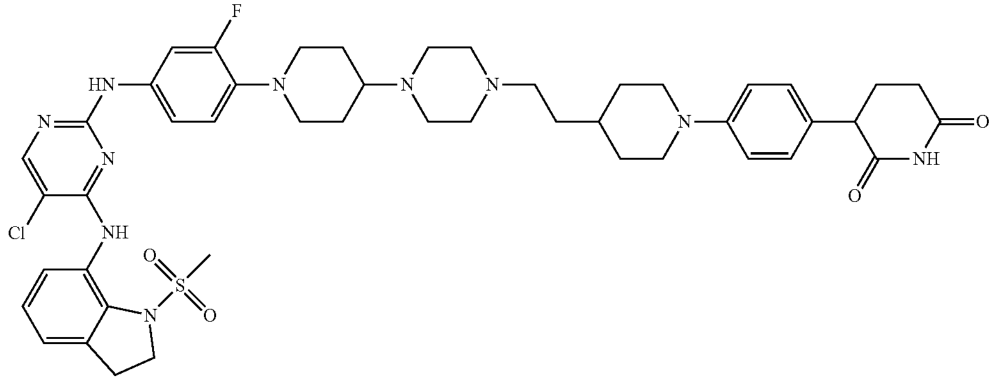
80
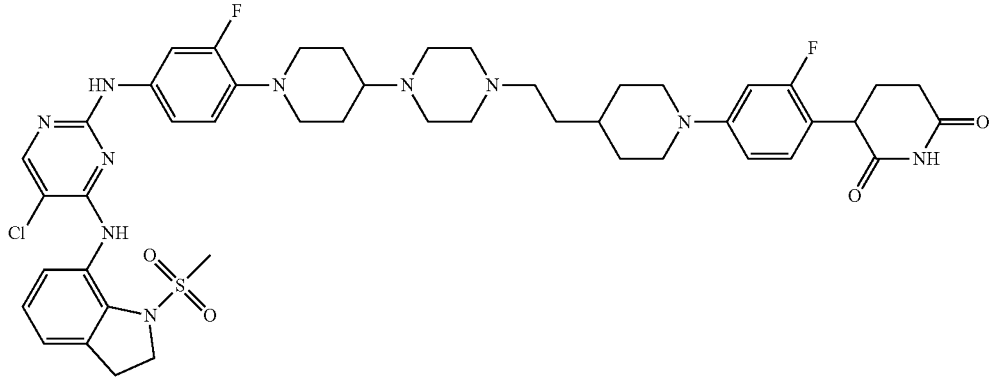
81
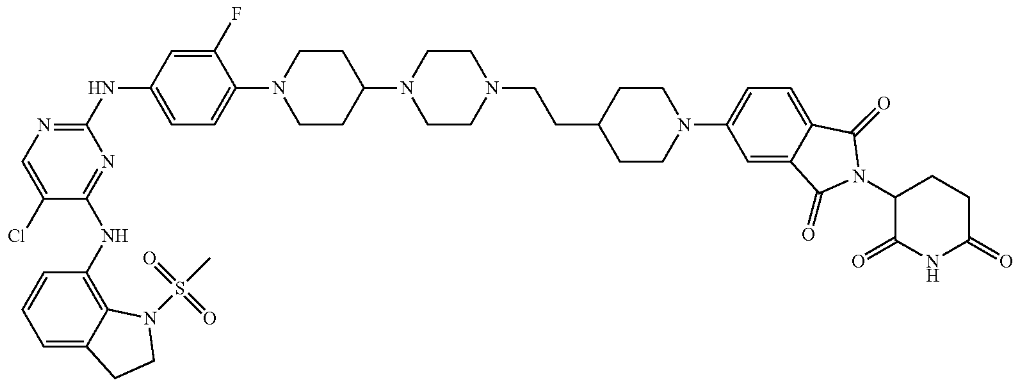

-continued
82
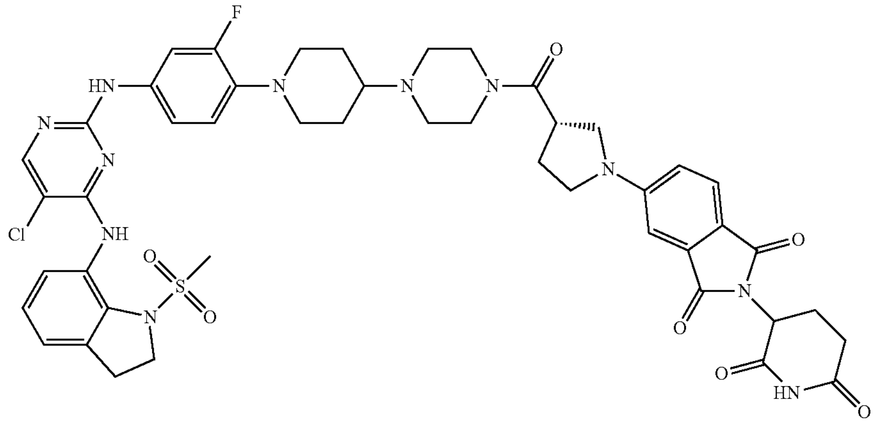
83
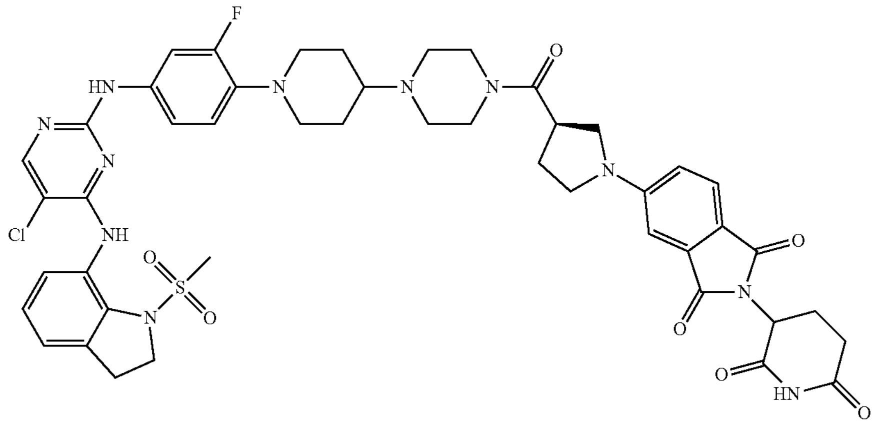
84
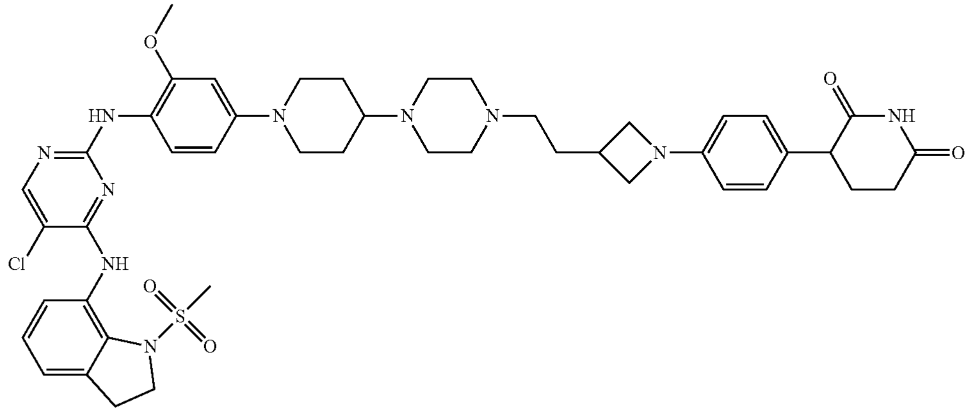

-continued
85
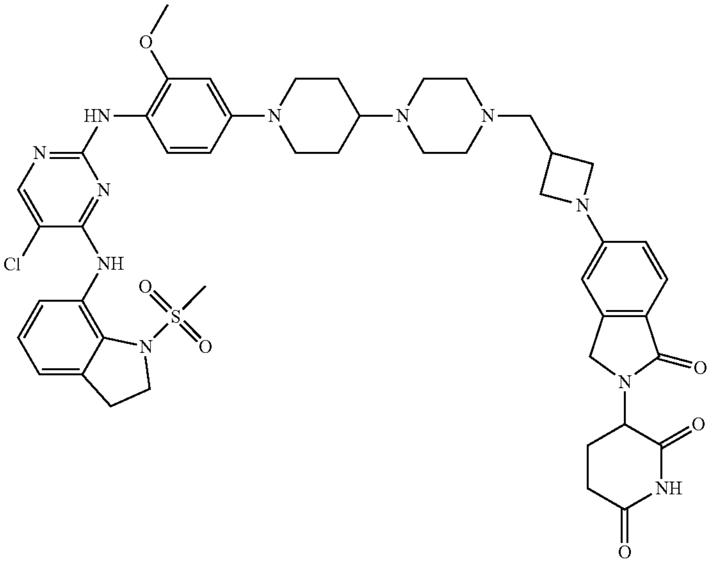
86
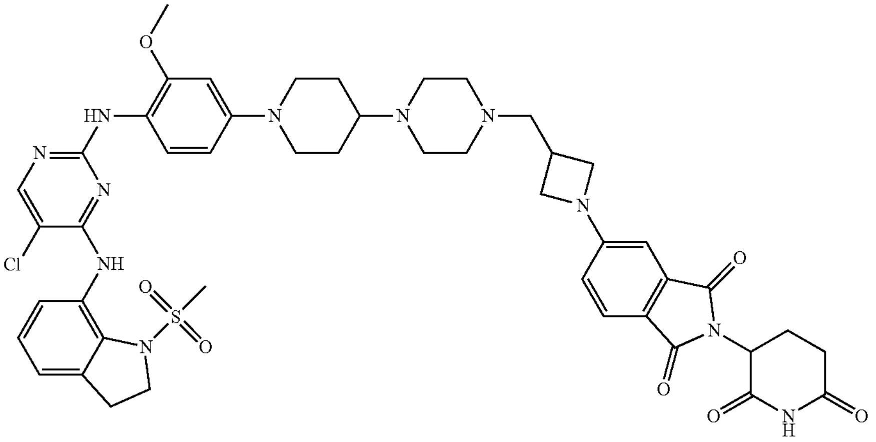
87
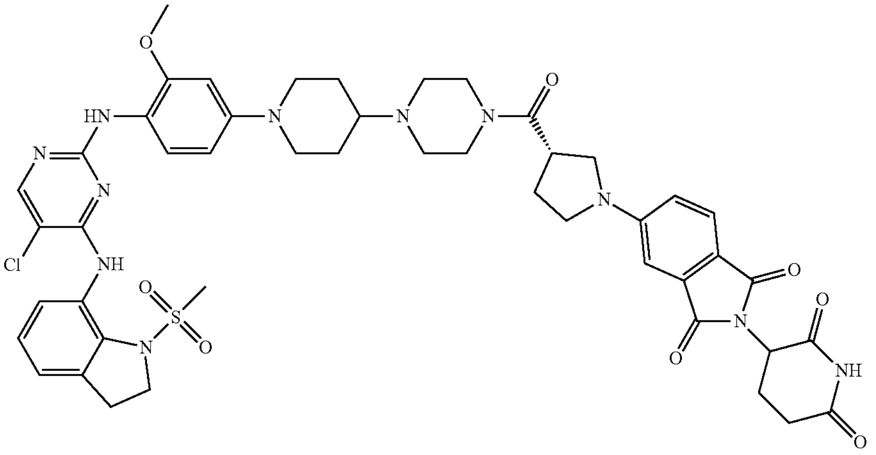

-continued
88
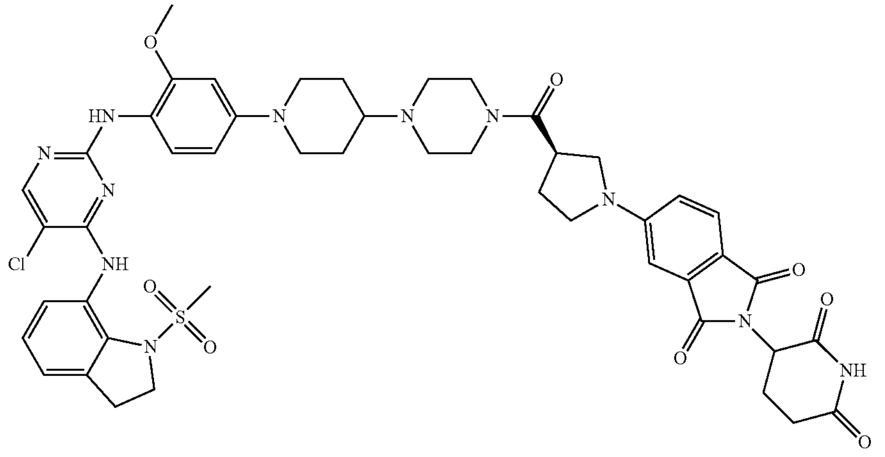
89
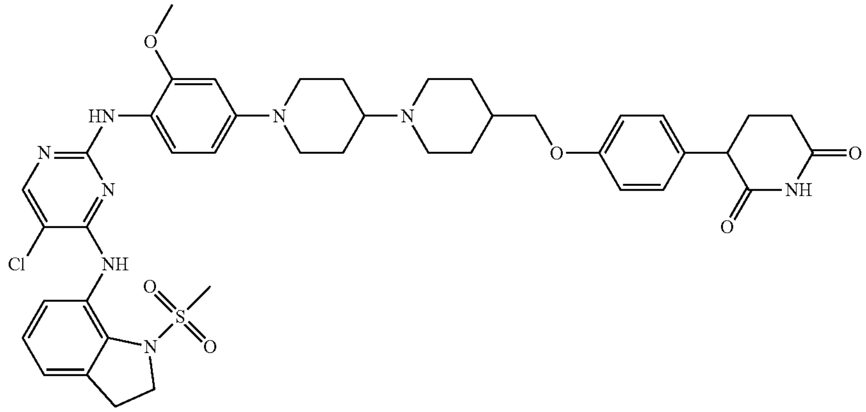
90
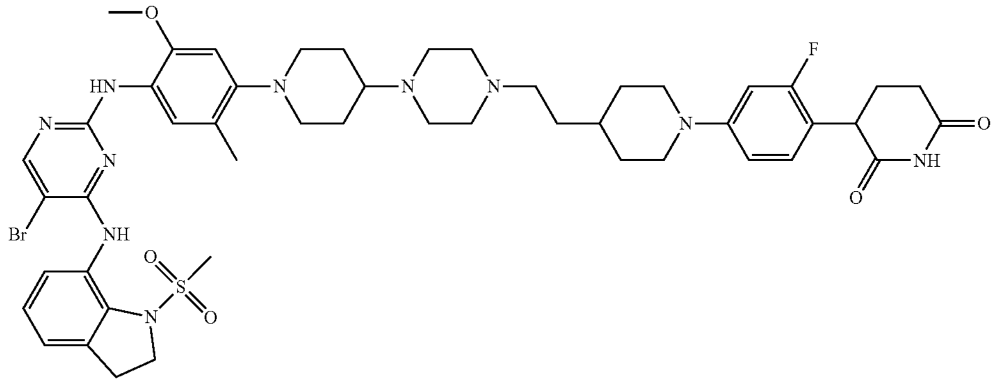
91
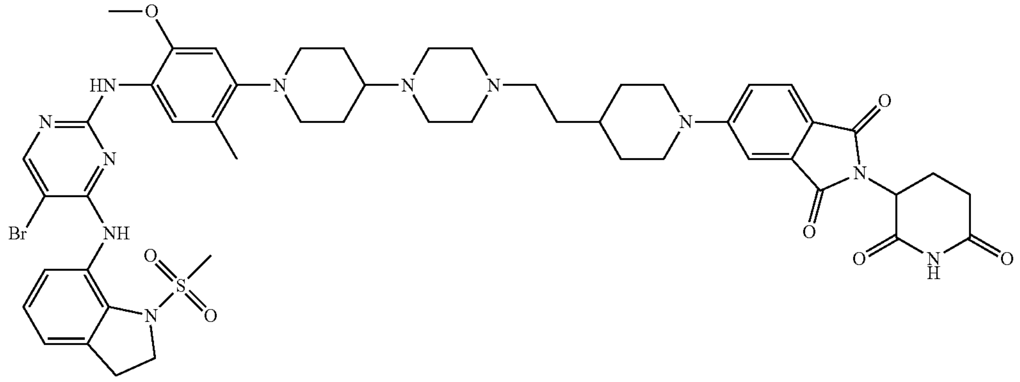

-continued
92
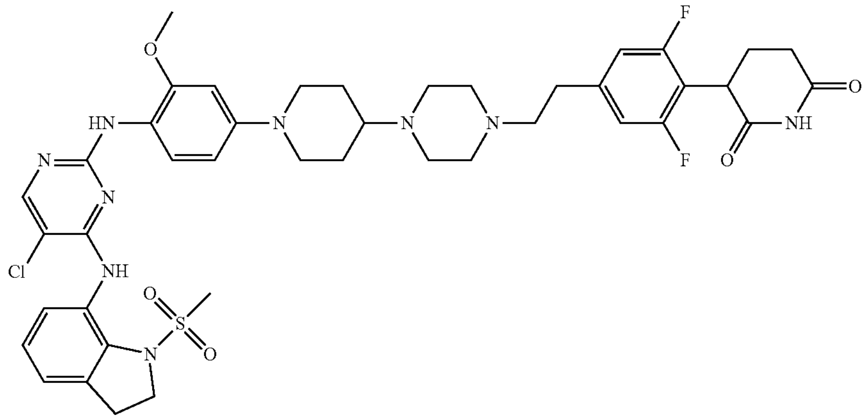
93
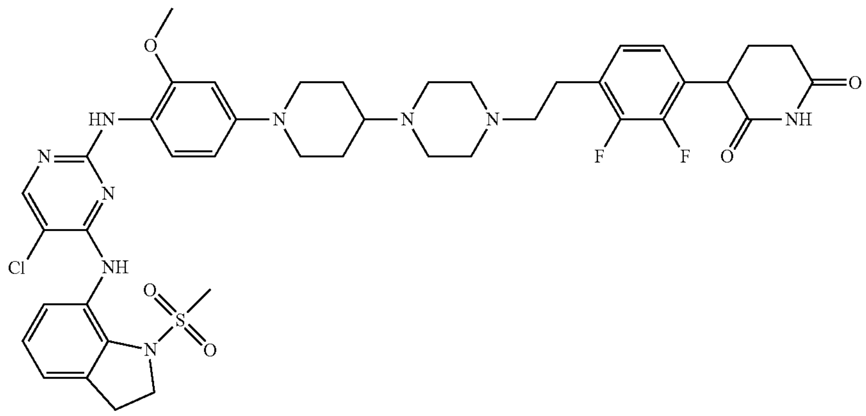
94
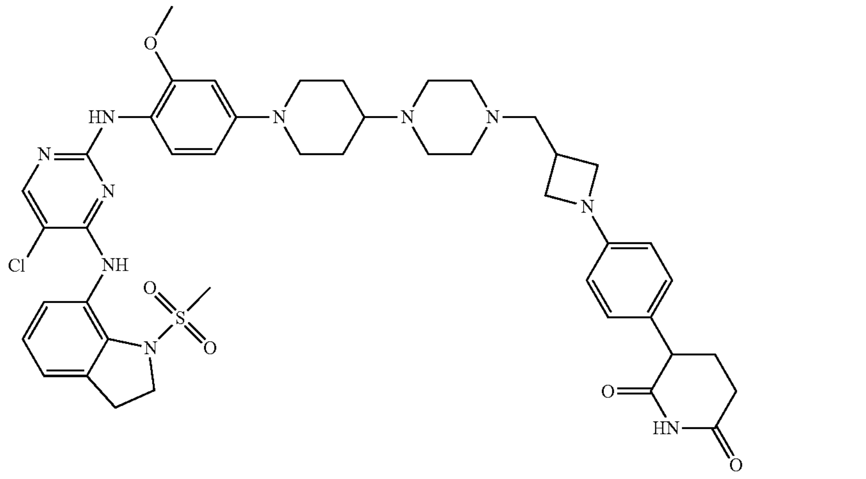

-continued
95
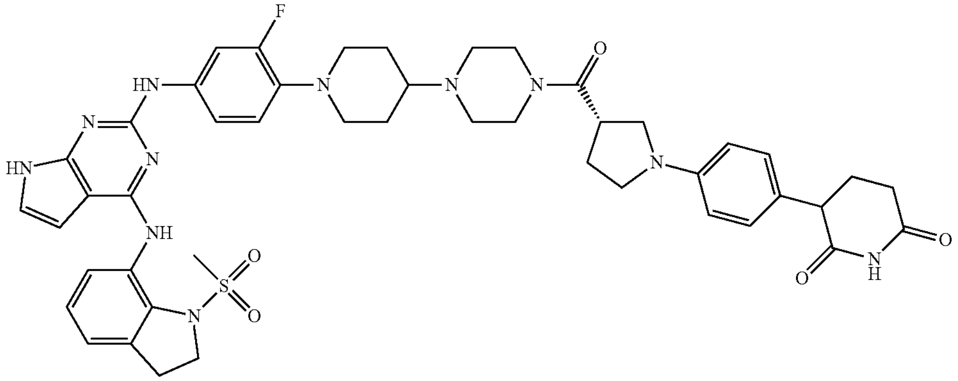
96
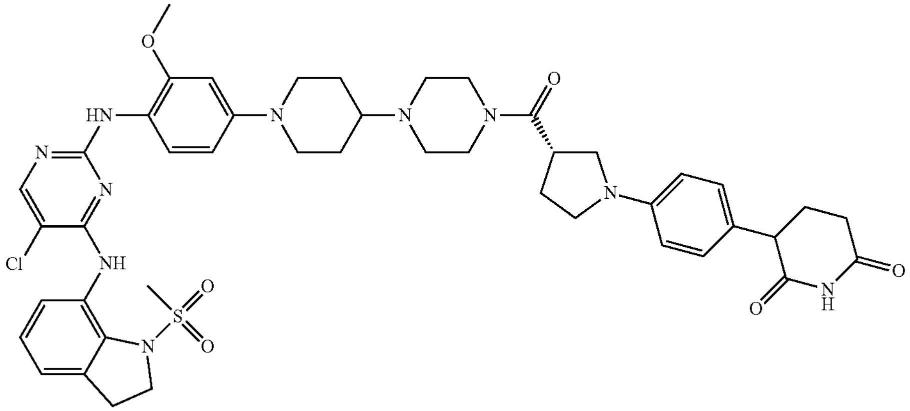
97
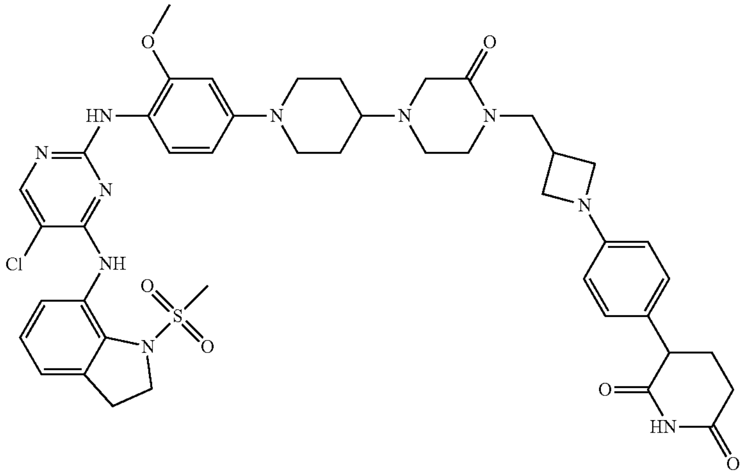
98
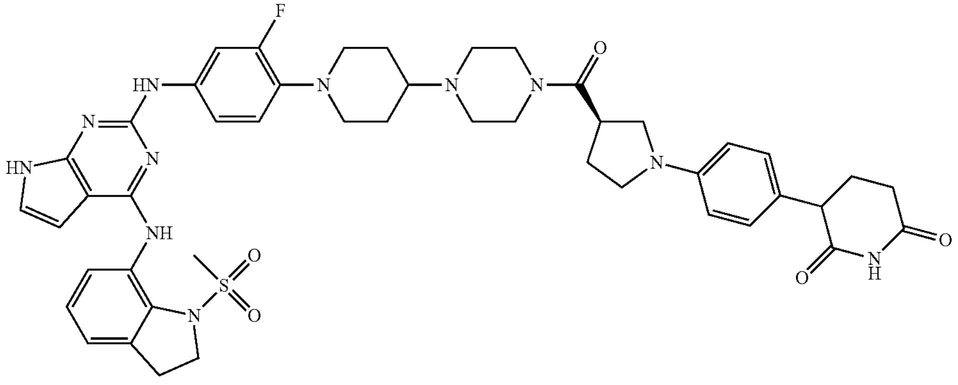

-continued
99
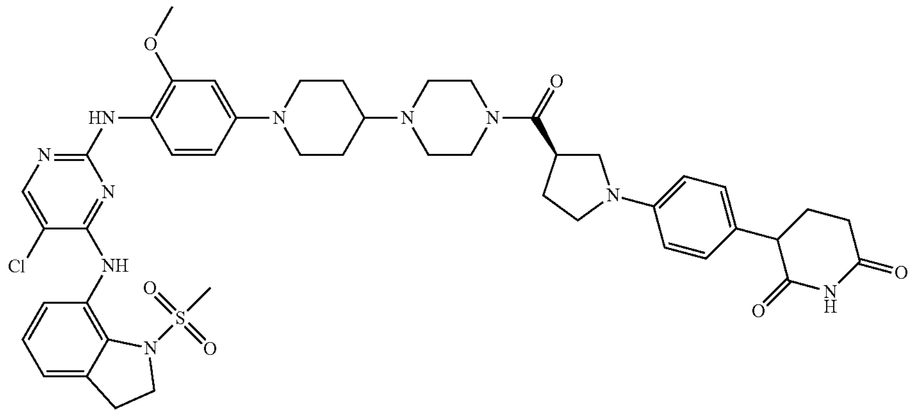
100
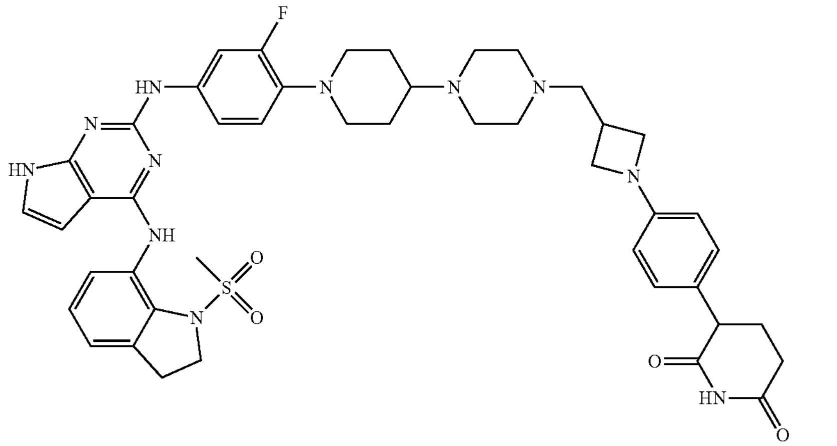
101
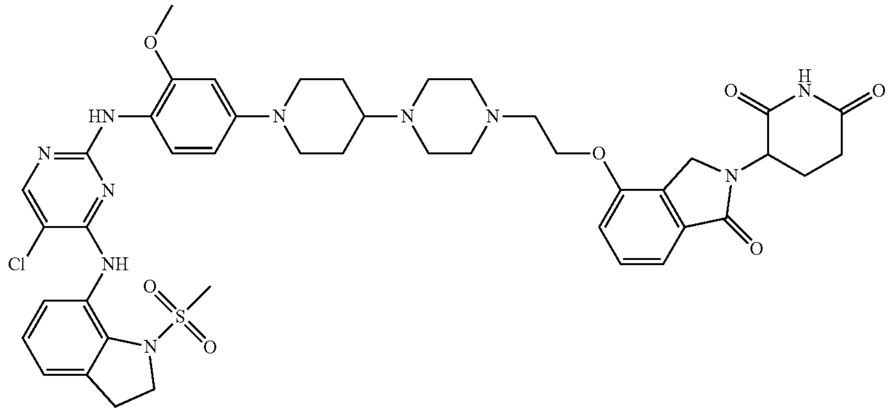

-continued
102
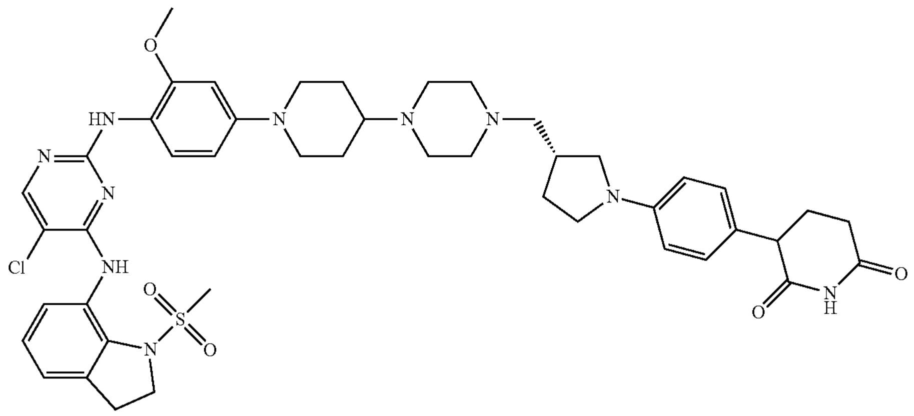
103
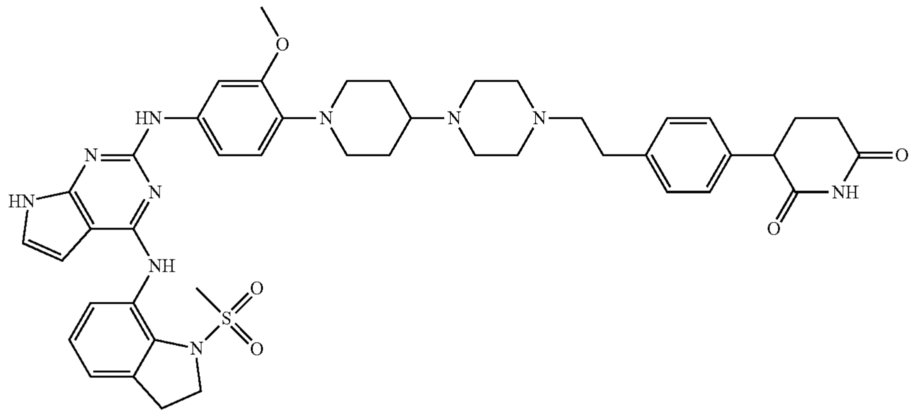
104
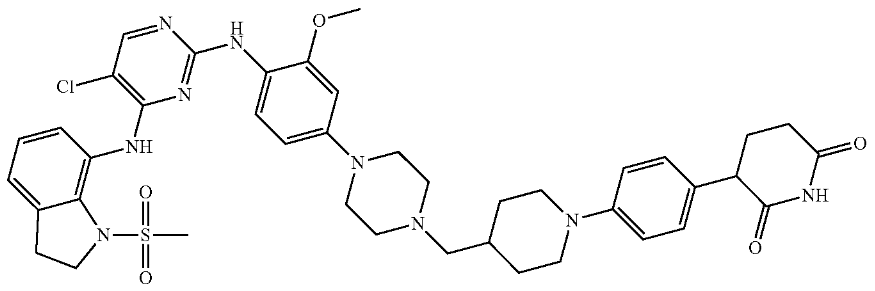
105
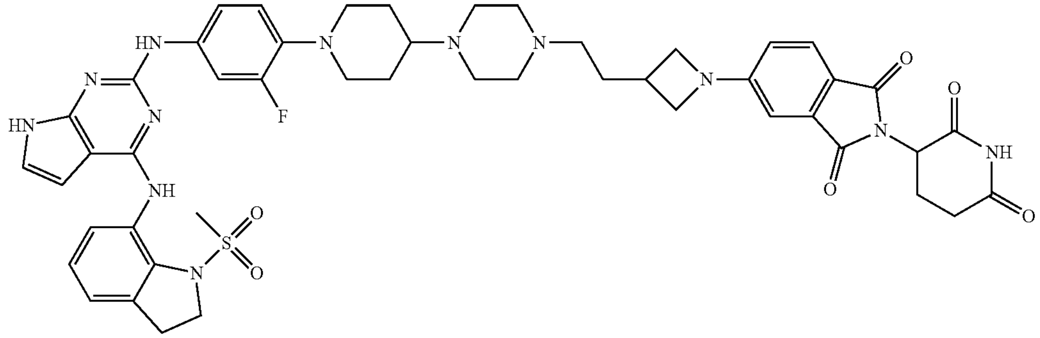

-continued
106
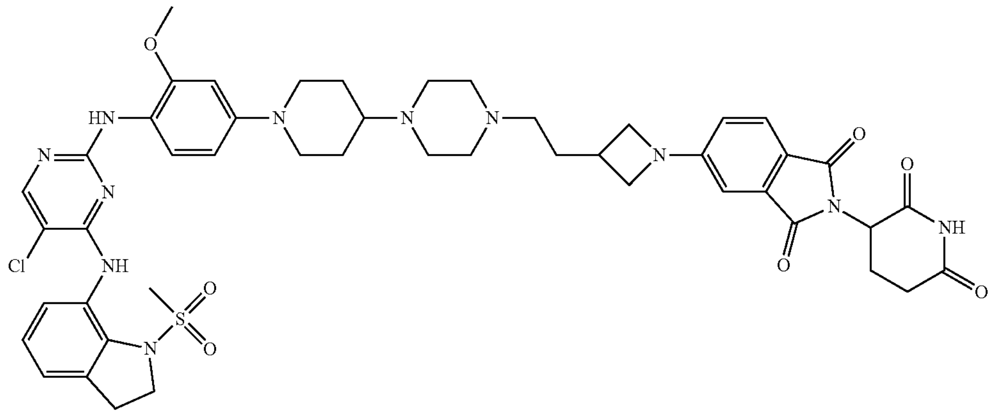
107
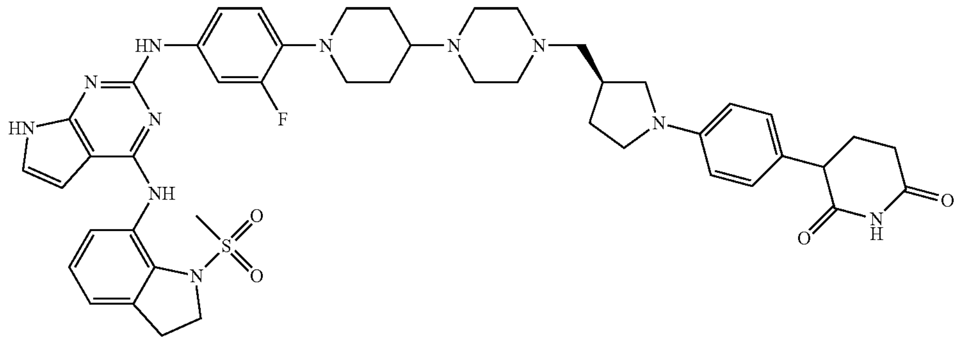
108
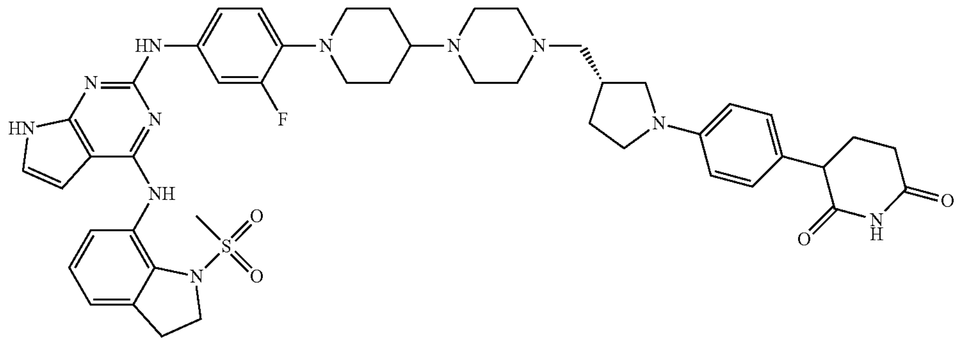
109
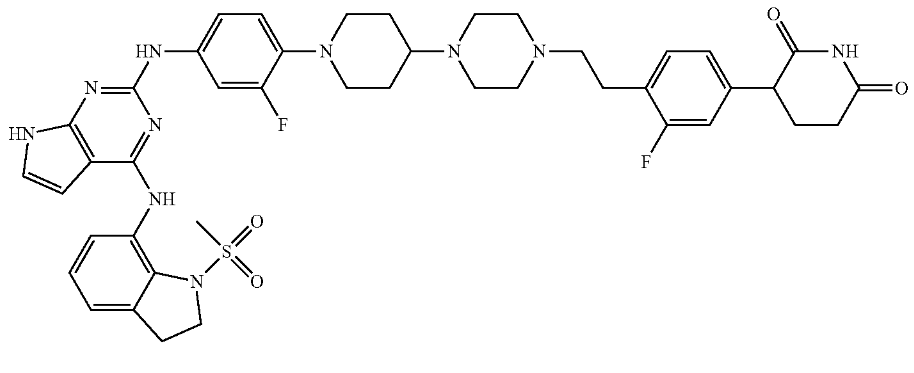

-continued
110
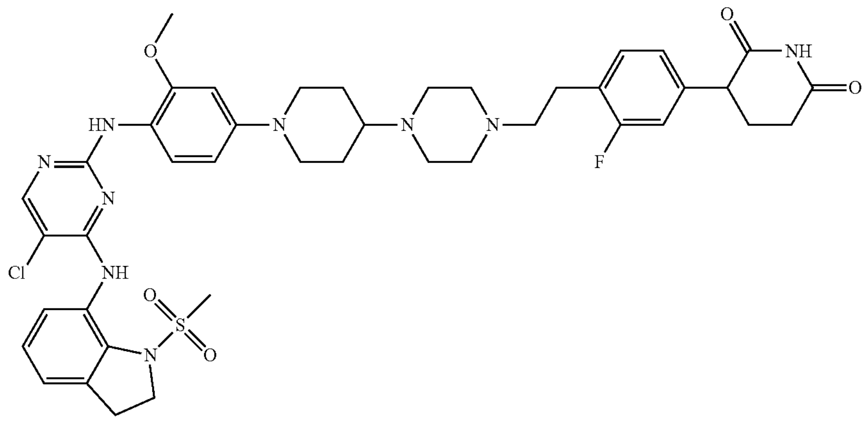
111
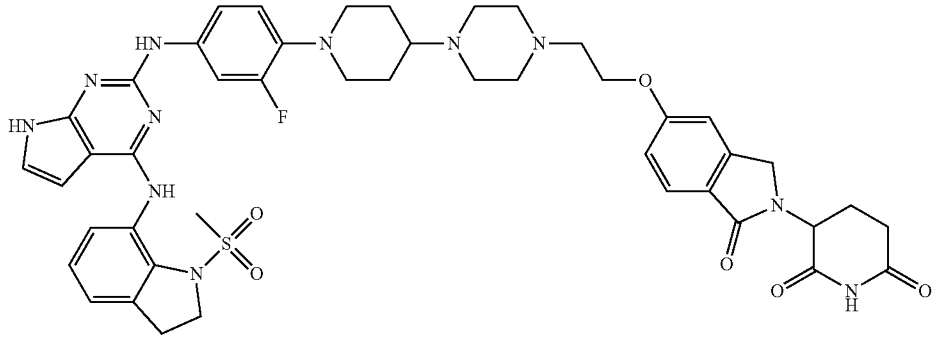
112
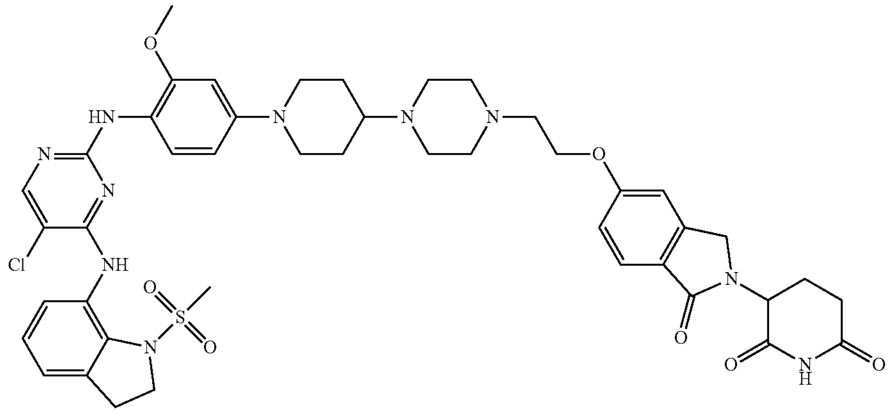
113
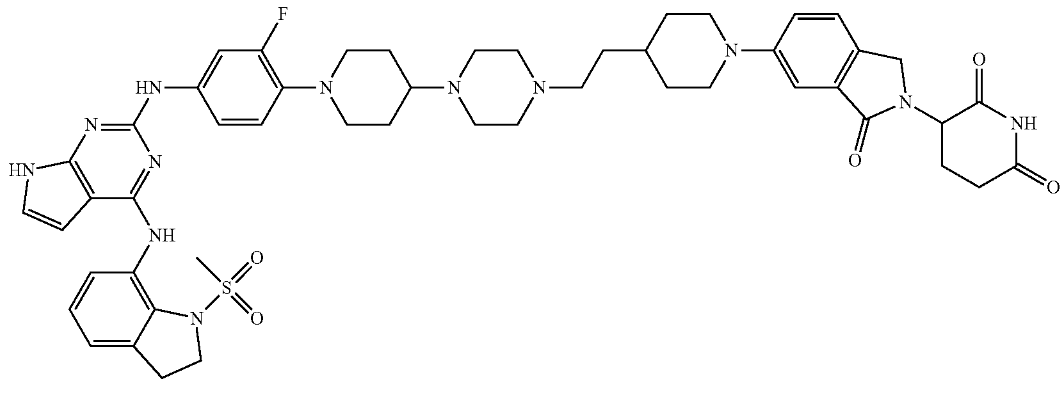

-continued
114
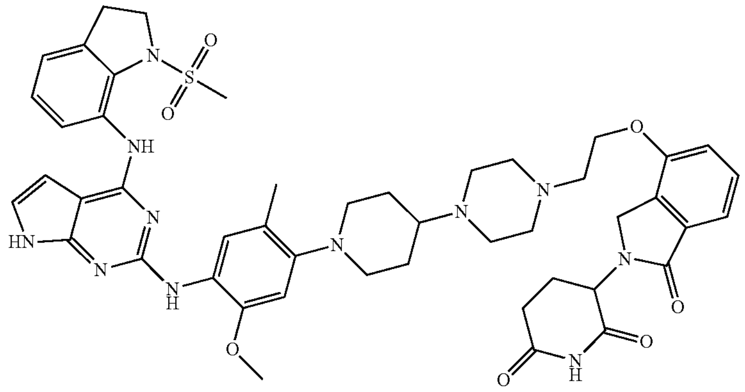
115
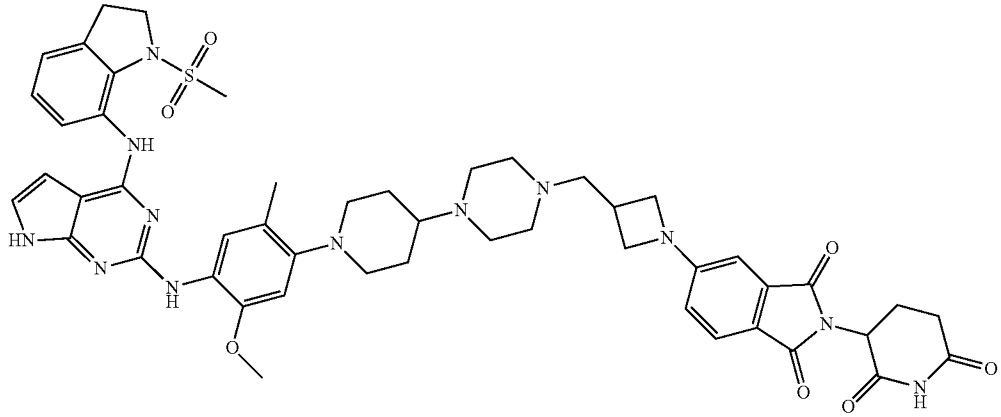
116
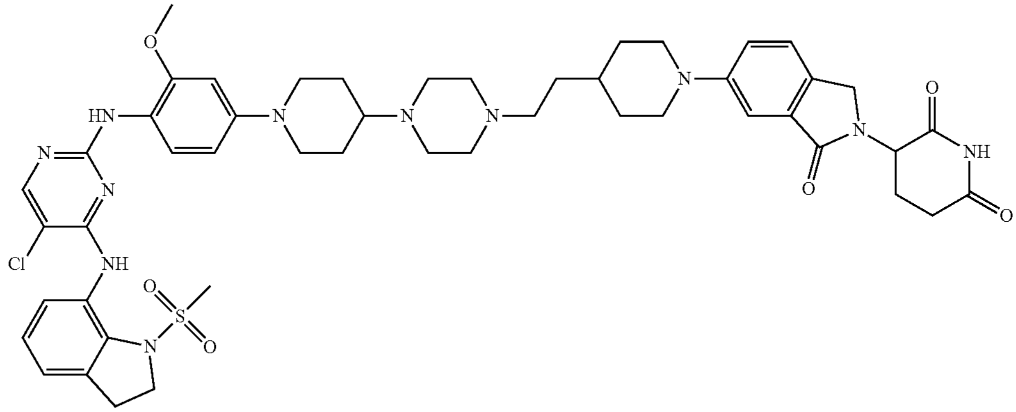
117
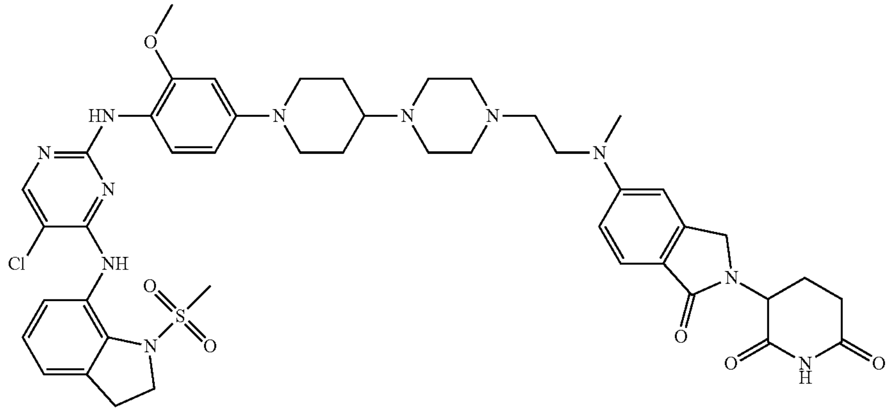

-continued
118
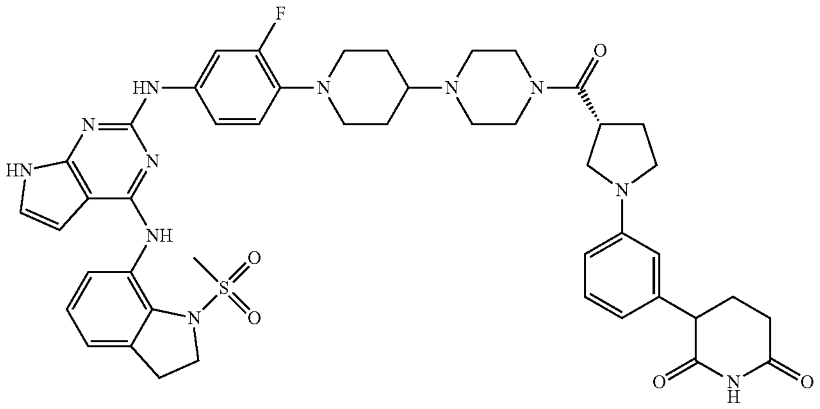
119
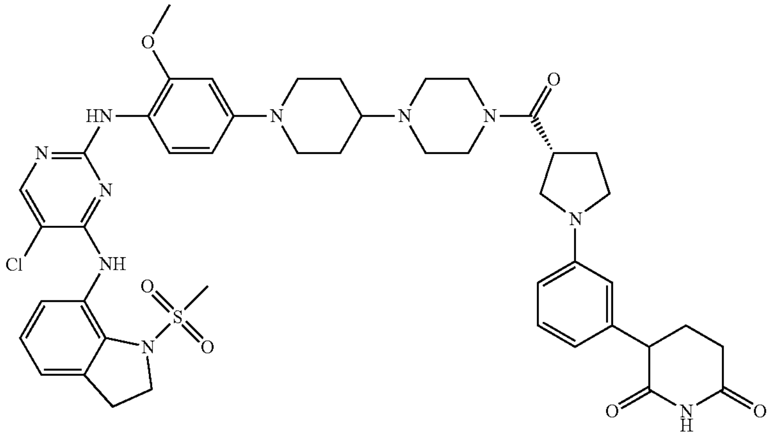
120
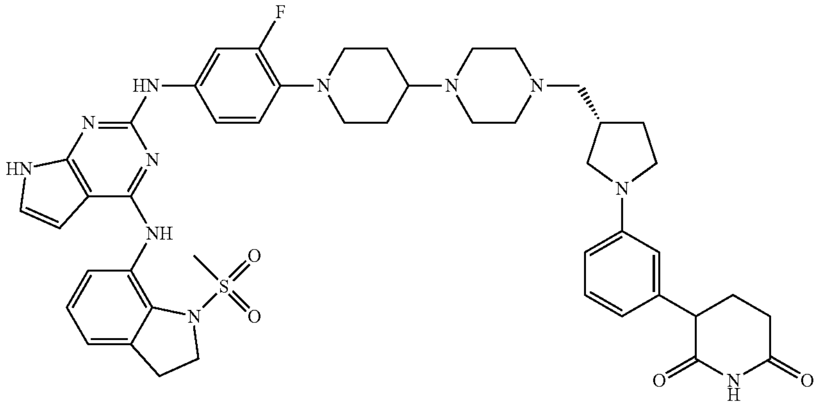

-continued
121
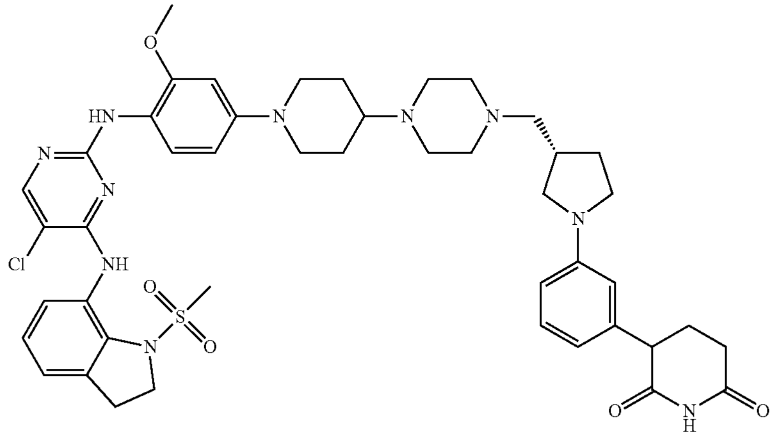
122
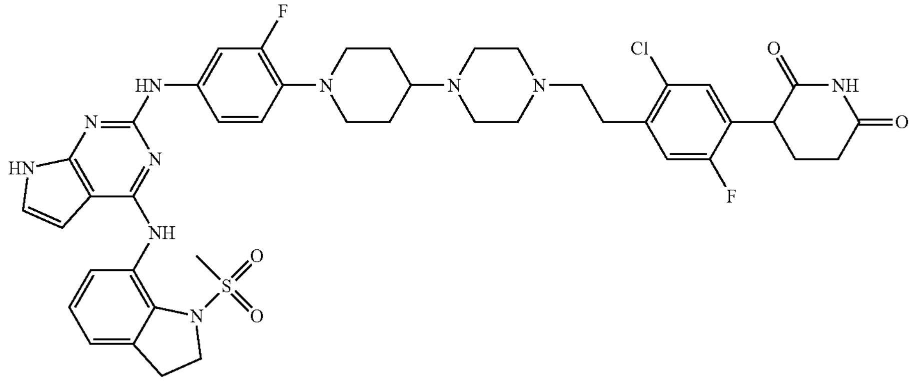
123
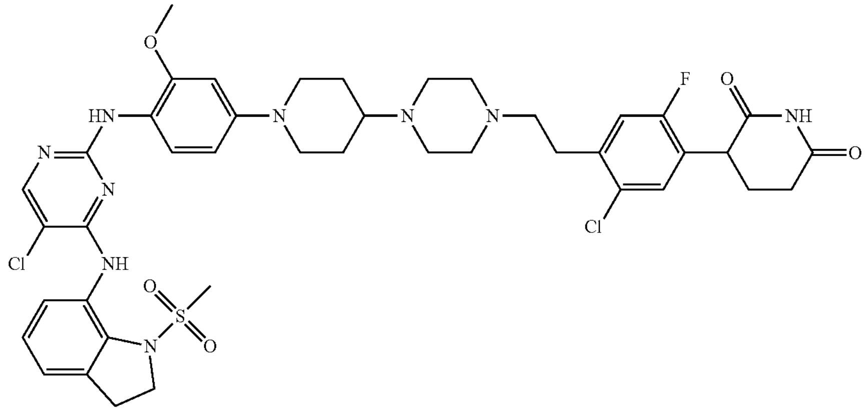
124
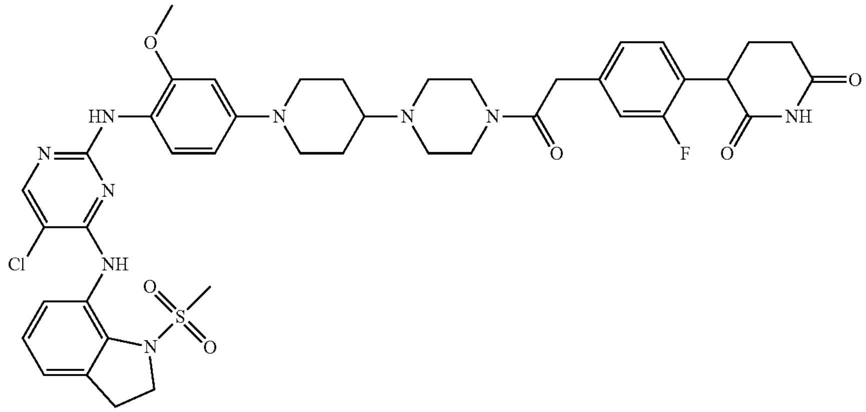

-continued
125
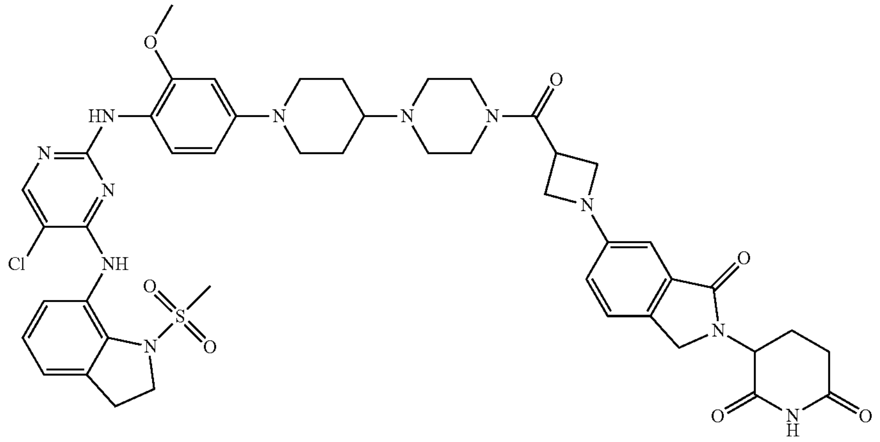
126
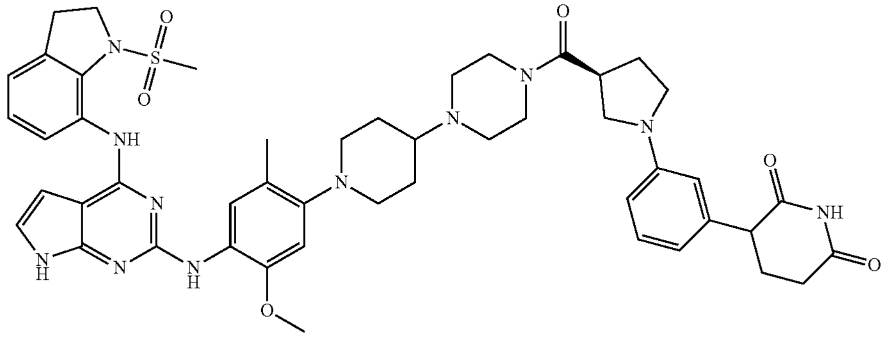
127
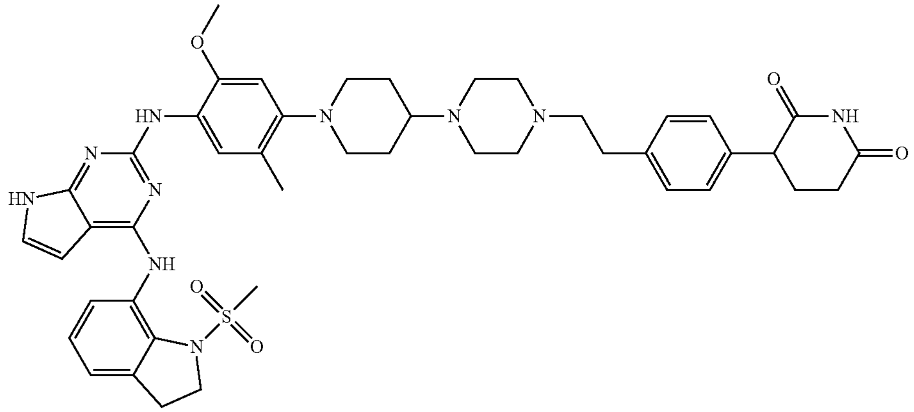
128
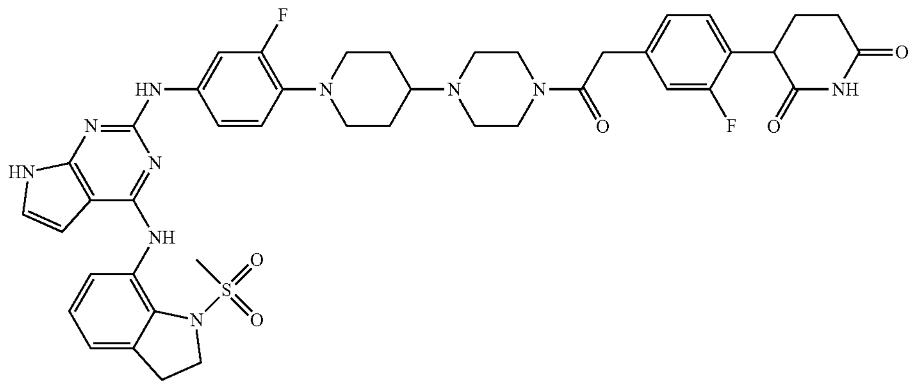

-continued
129
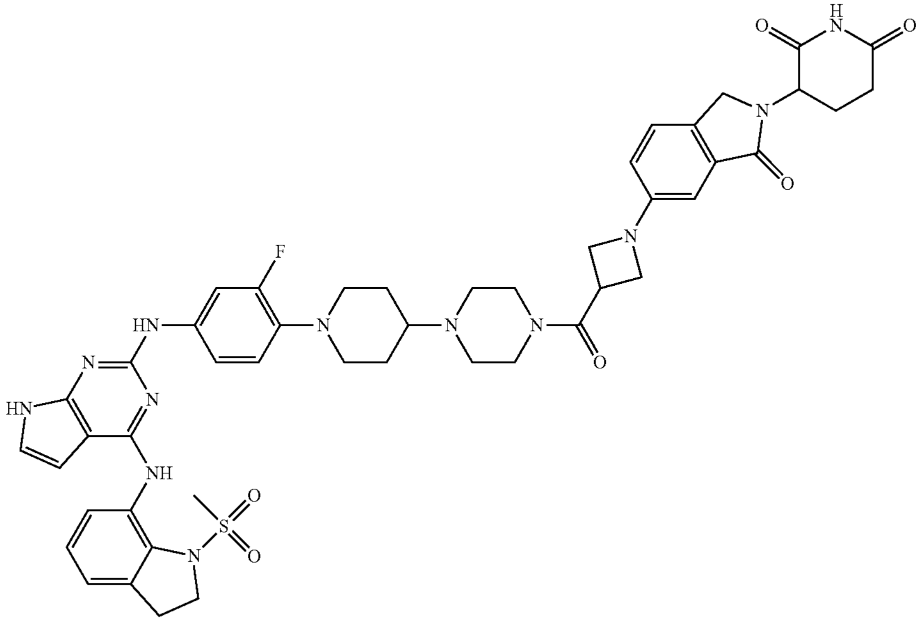
130
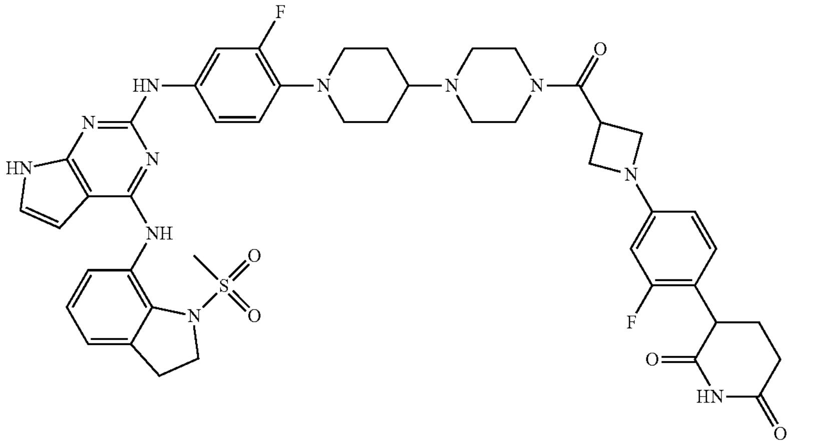
131
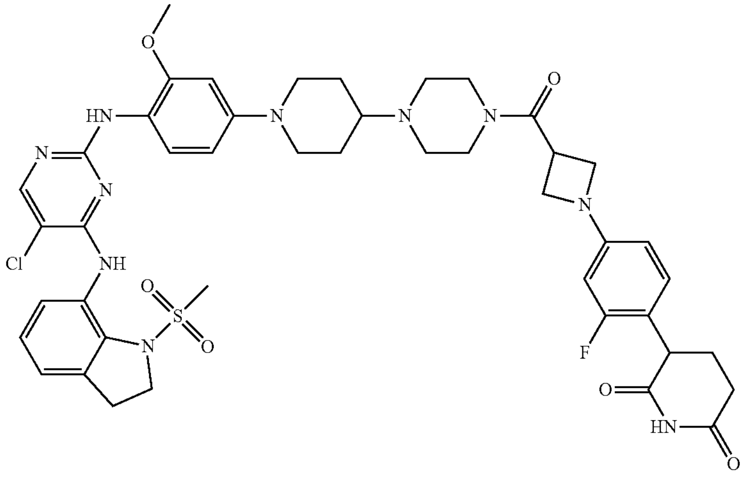

-continued
132
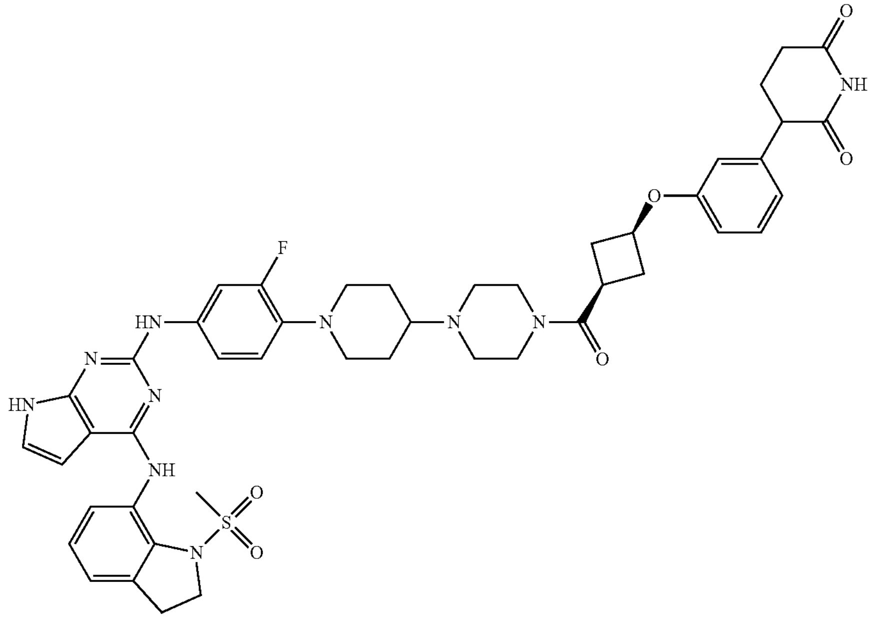
133
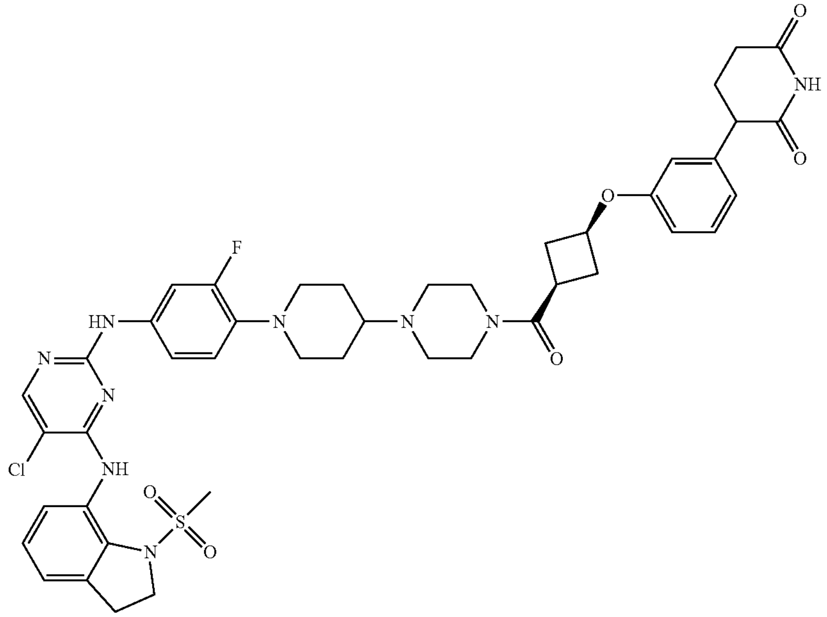
134
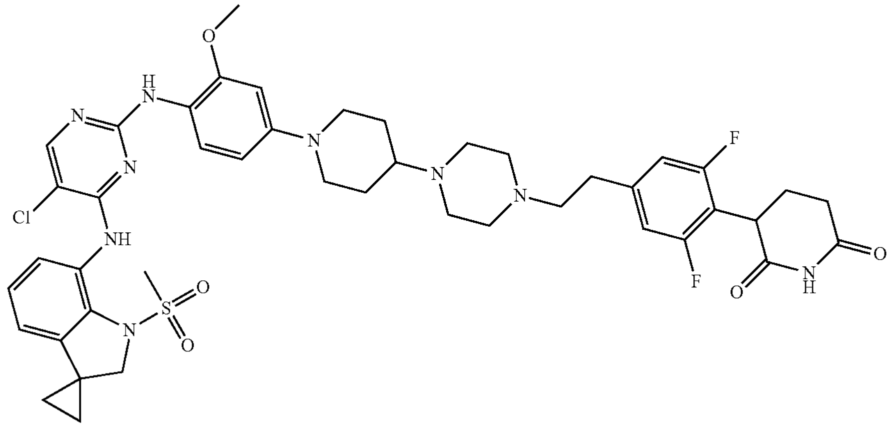

-continued
135
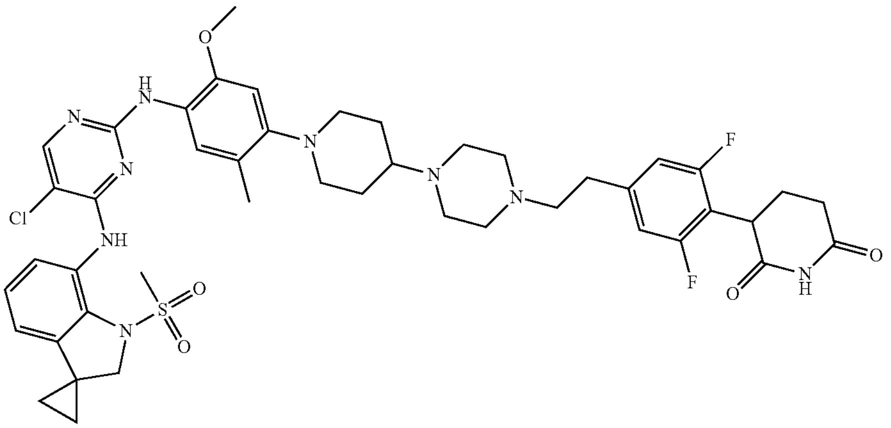
136
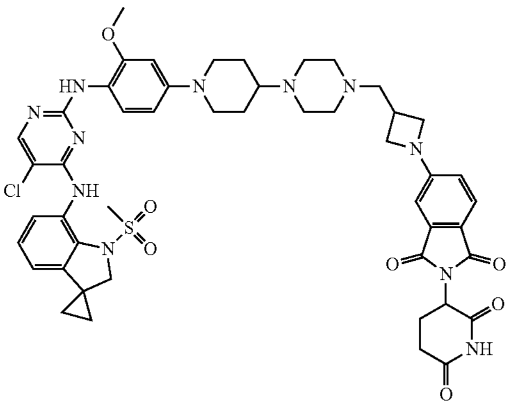
137
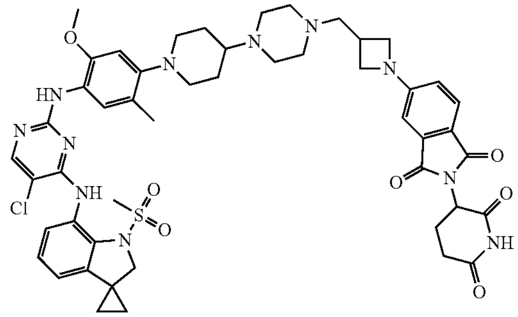
138
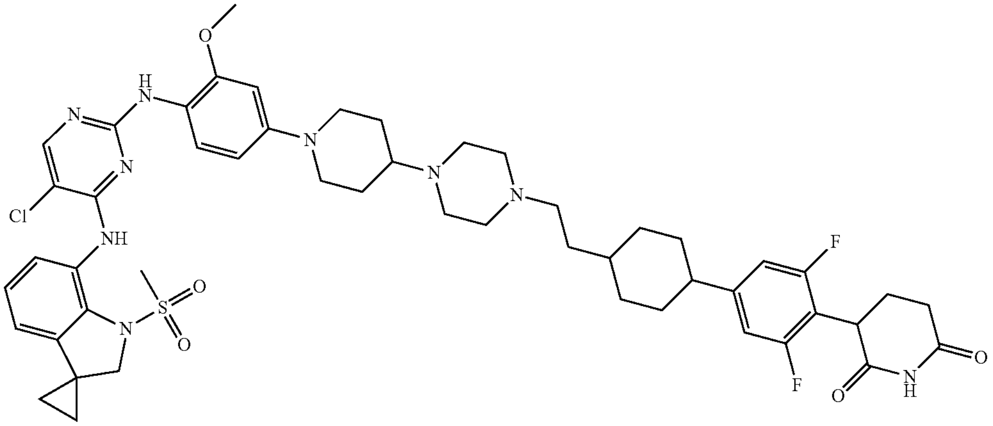

-continued
139
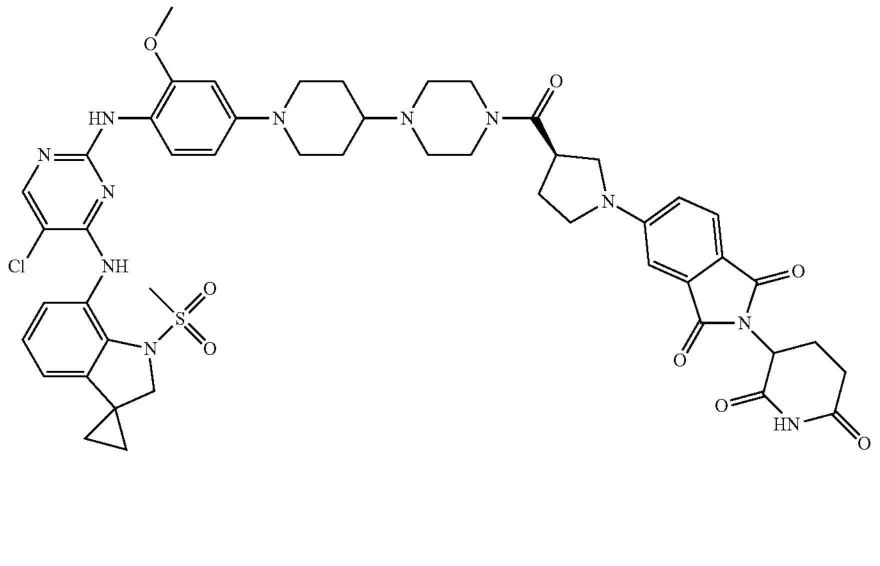
140
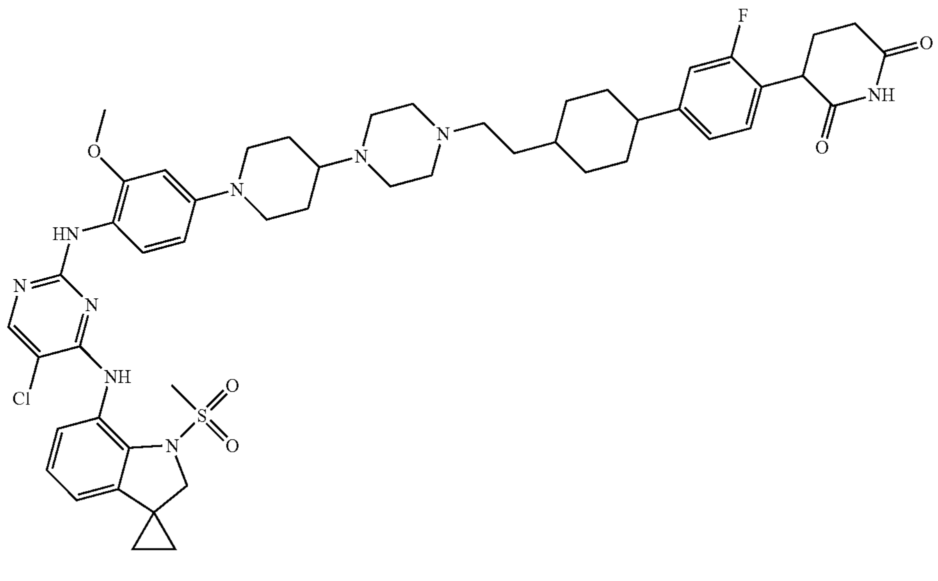
141
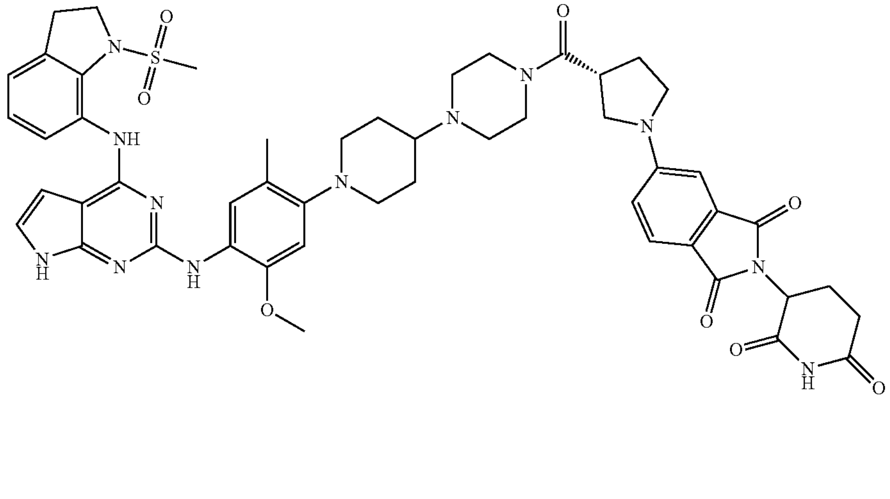

-continued
142
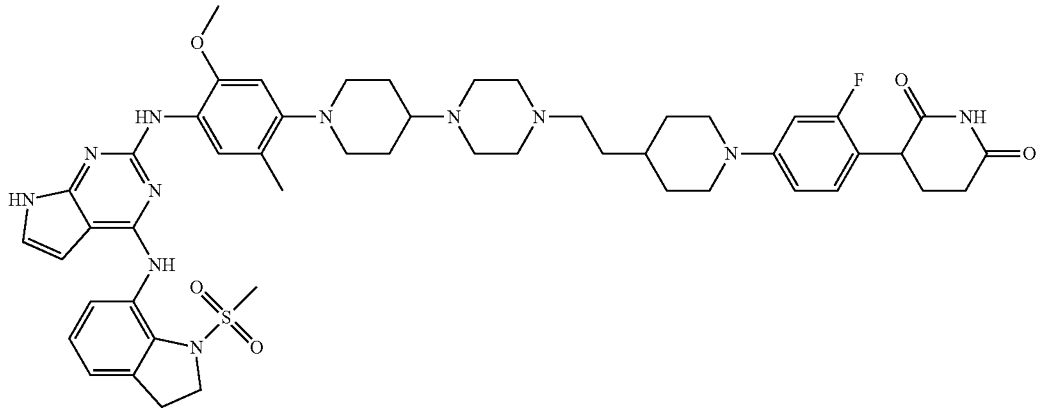
143
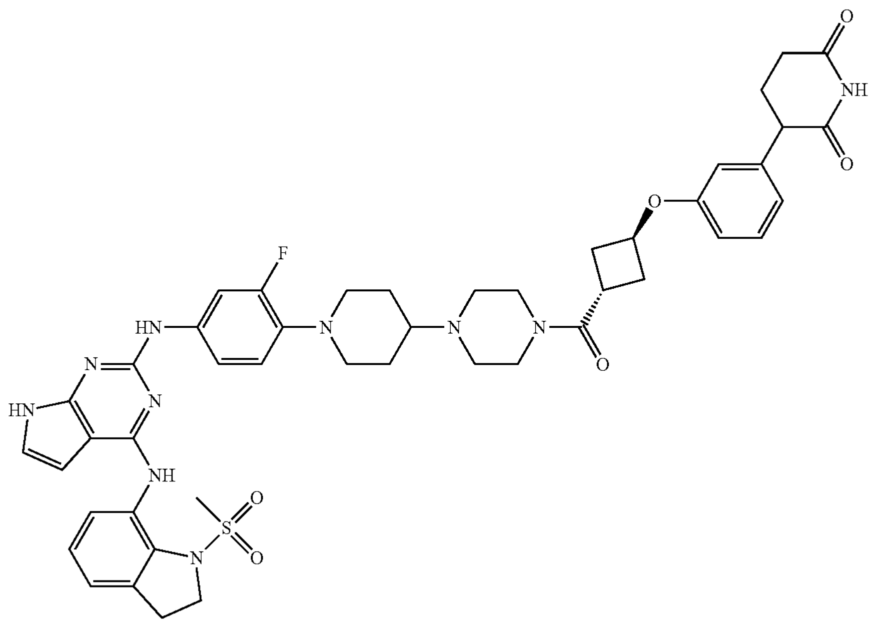
144
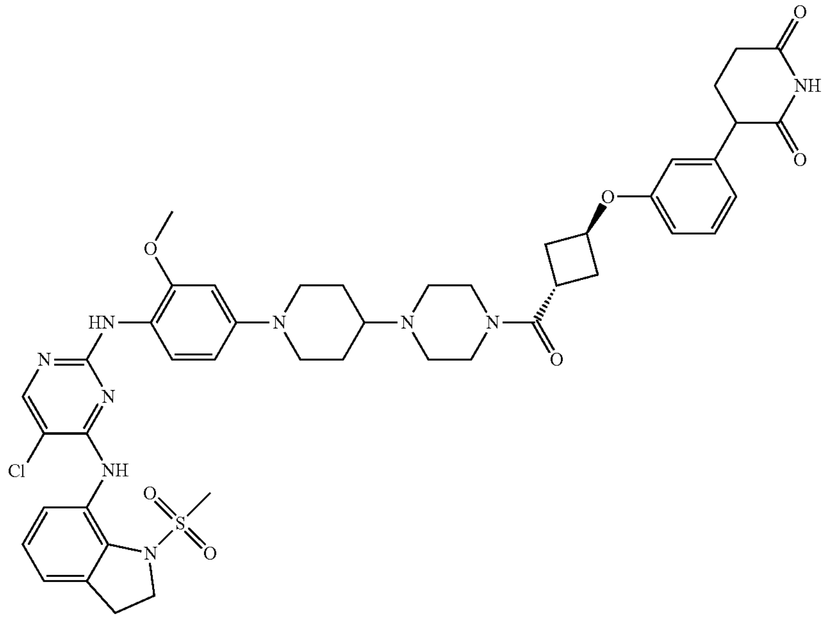

-continued
145
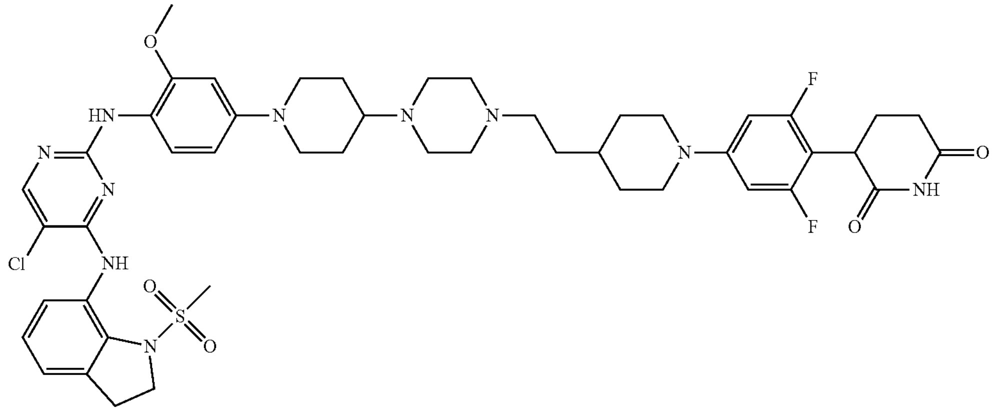
146
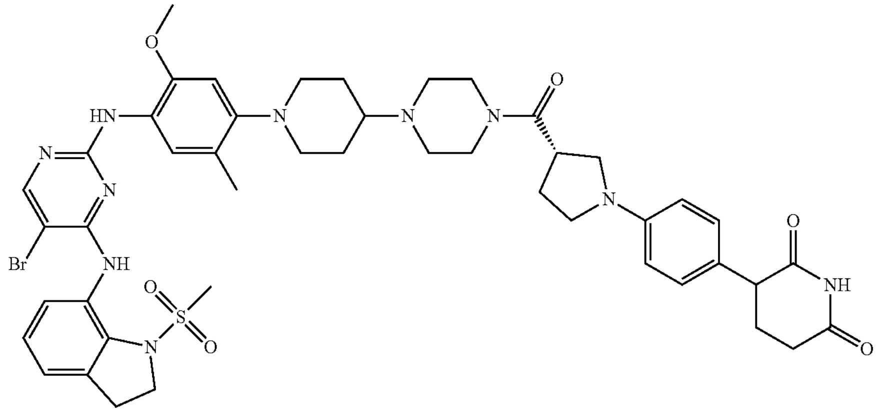
147
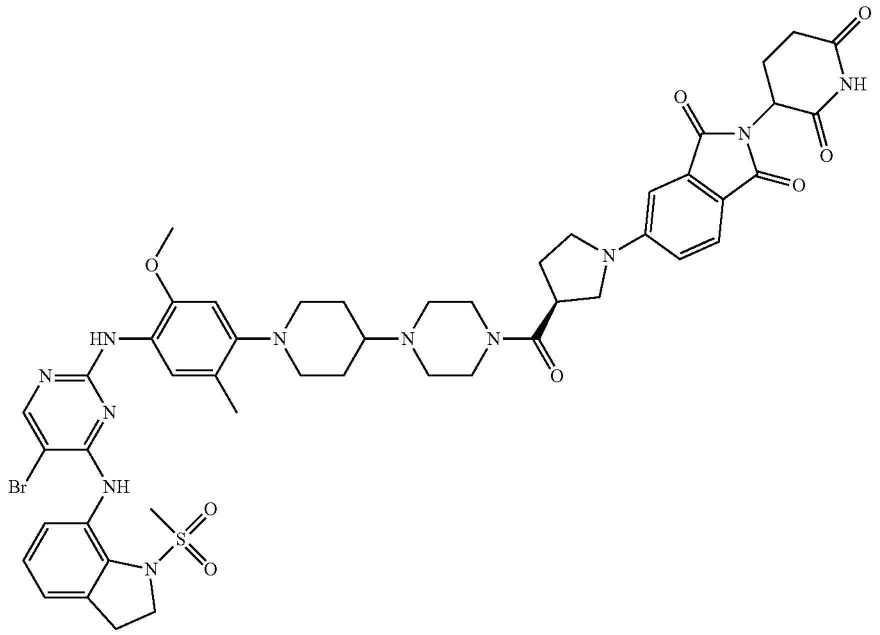

-continued
148
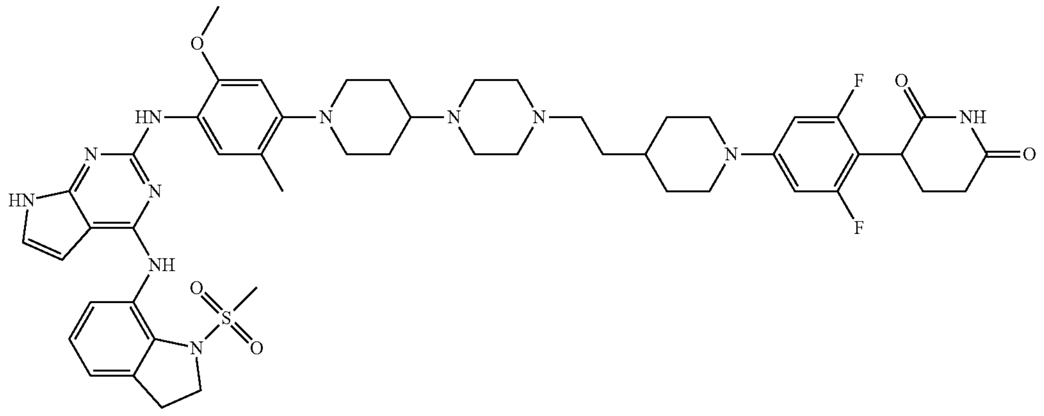
149
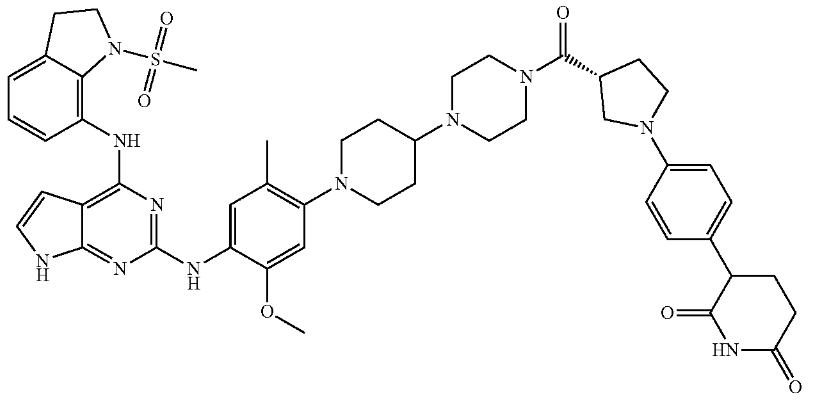
150
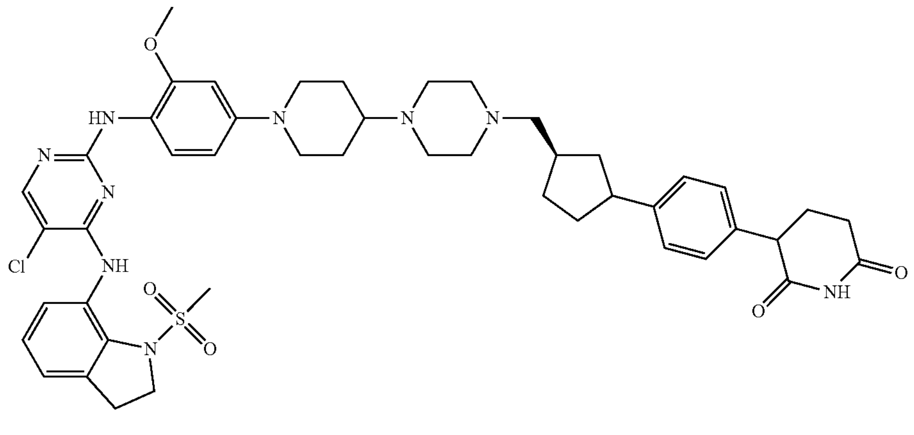

-continued
151
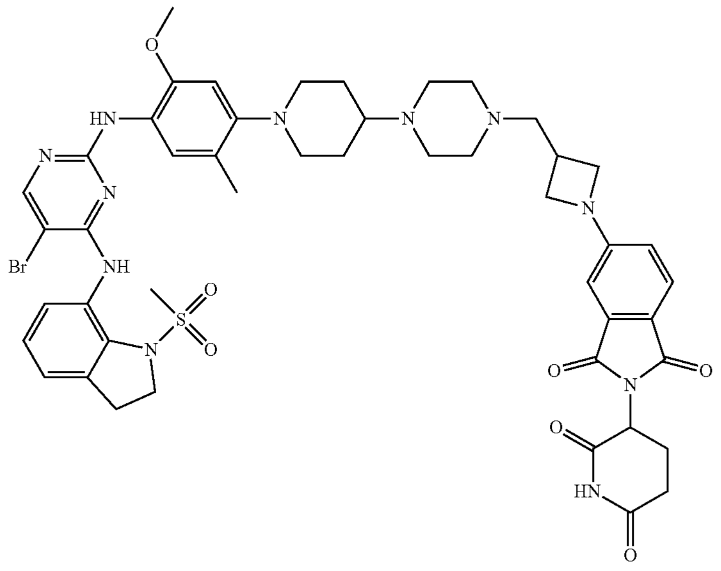
152
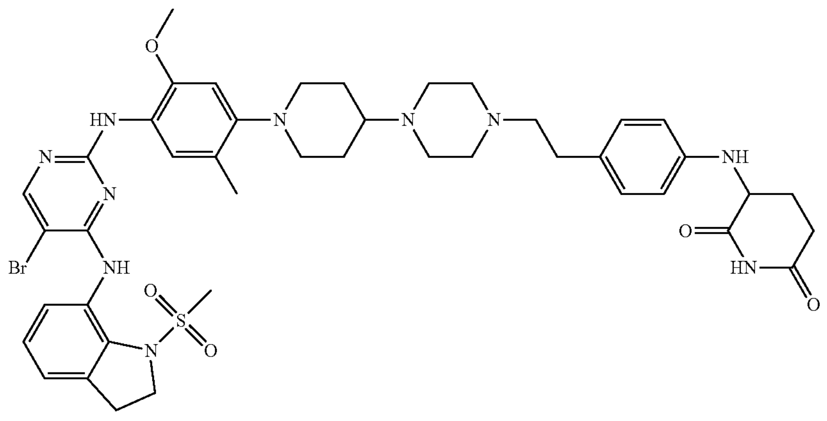
153
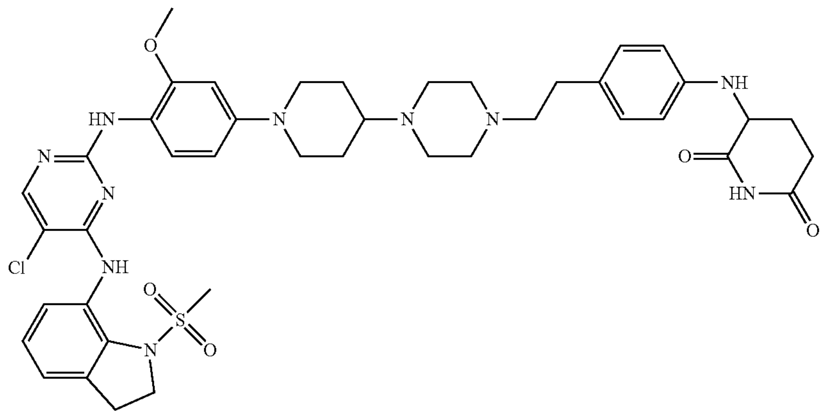

-continued
154
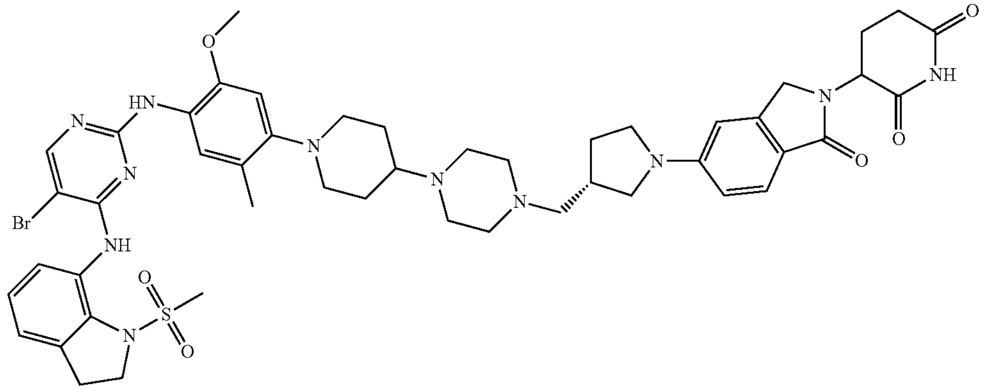
155
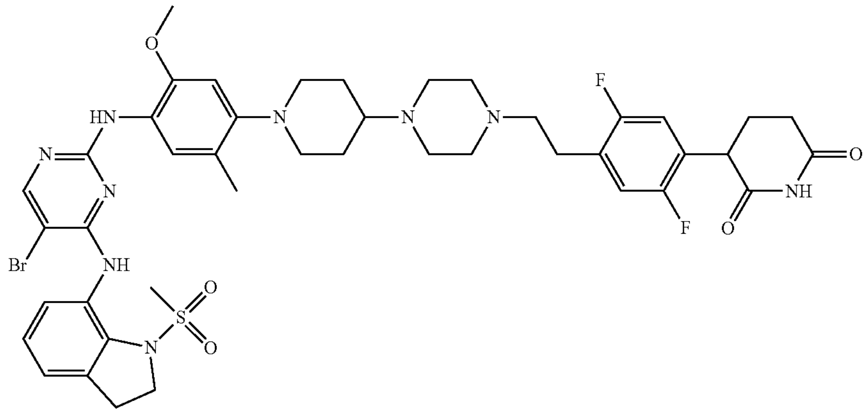
156
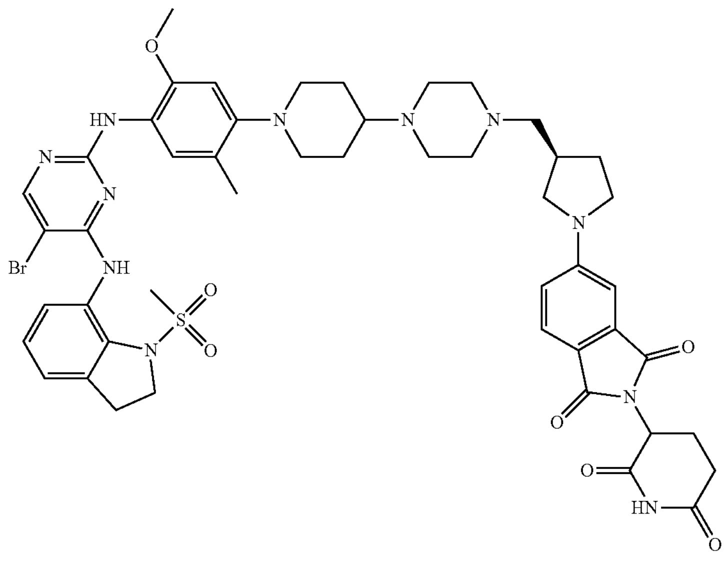

-continued
157
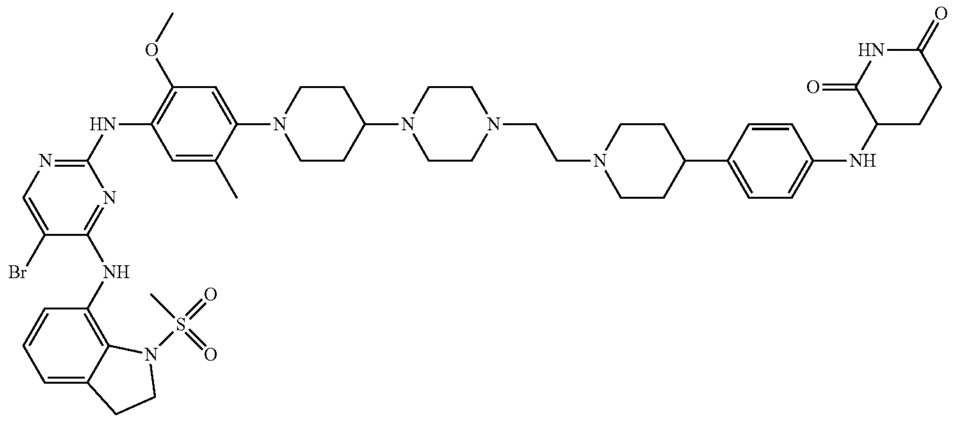
158
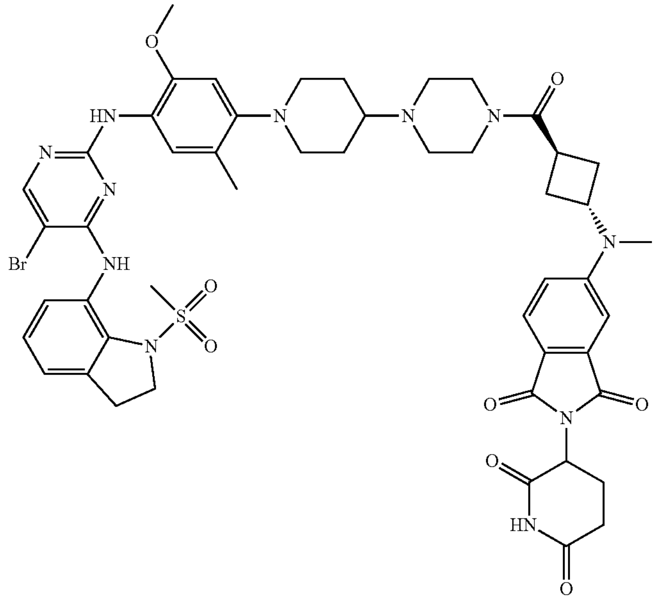
159
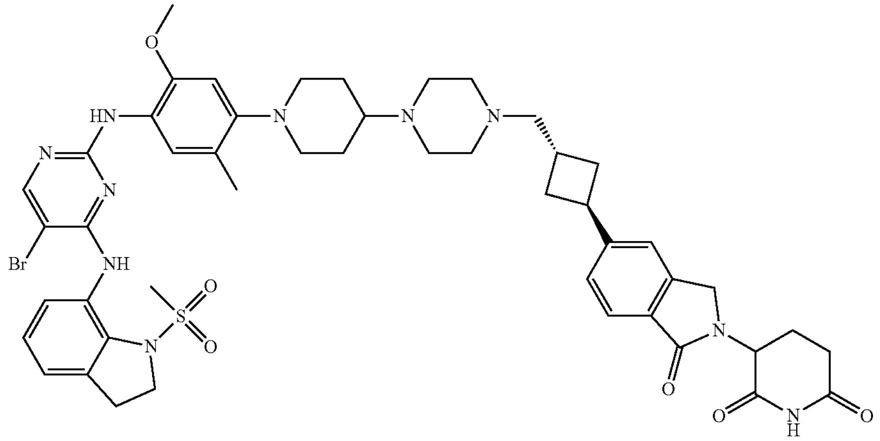

-continued
160
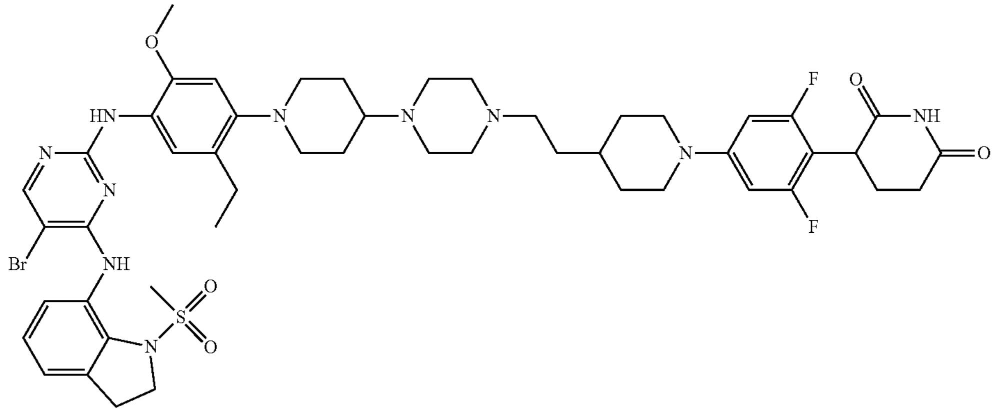
161
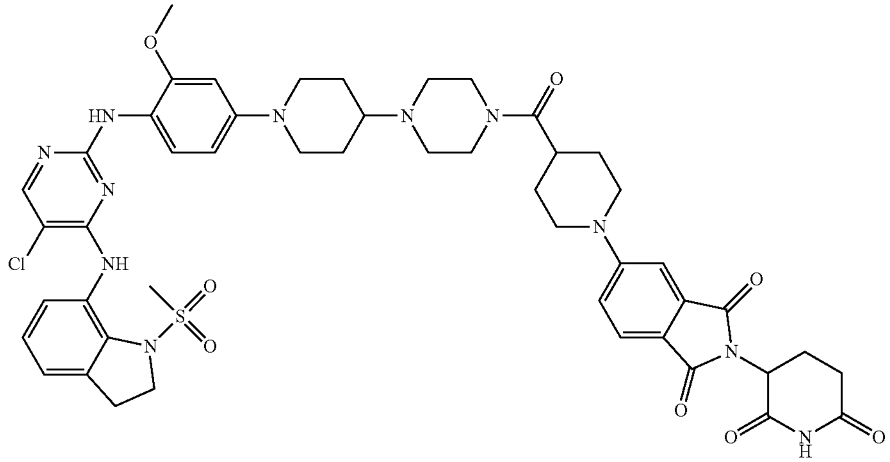
162
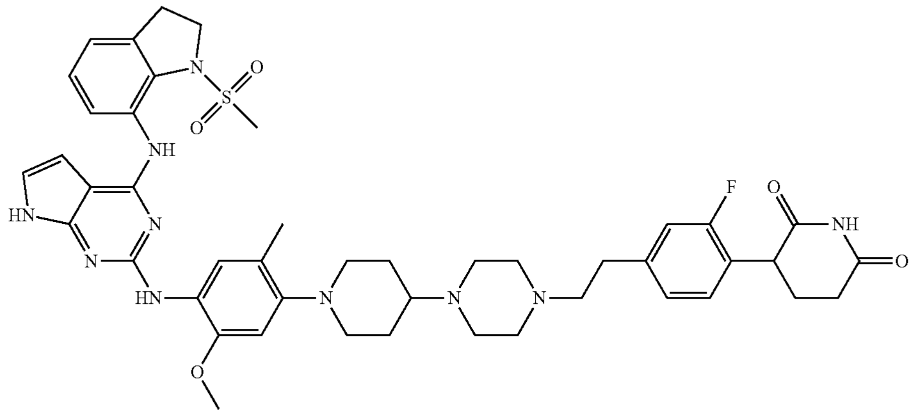

-continued
163
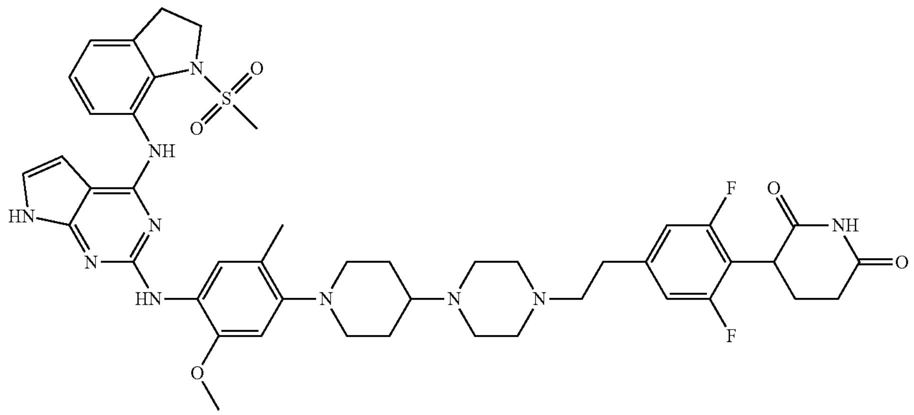
164
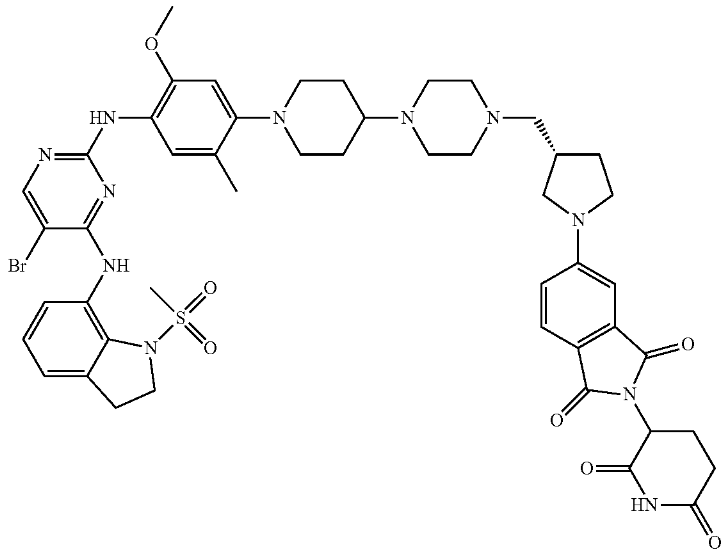
165
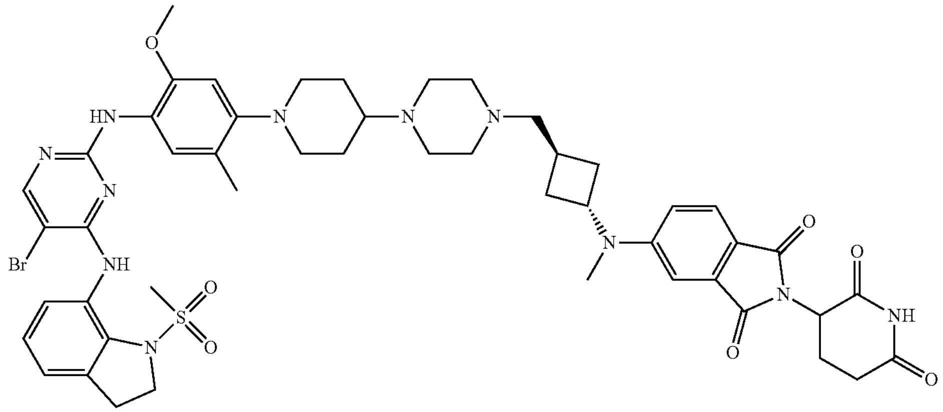

-continued
166
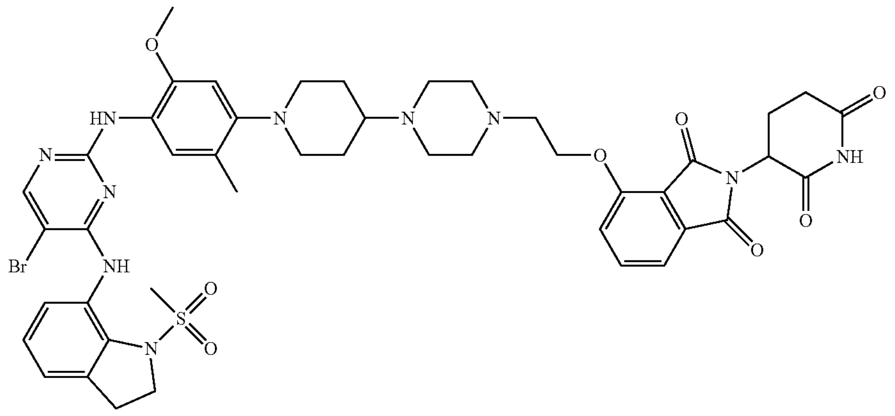
167
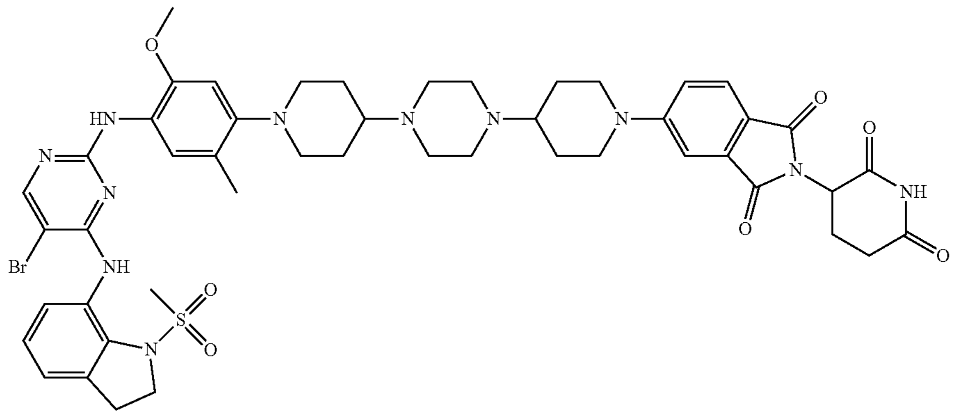
168
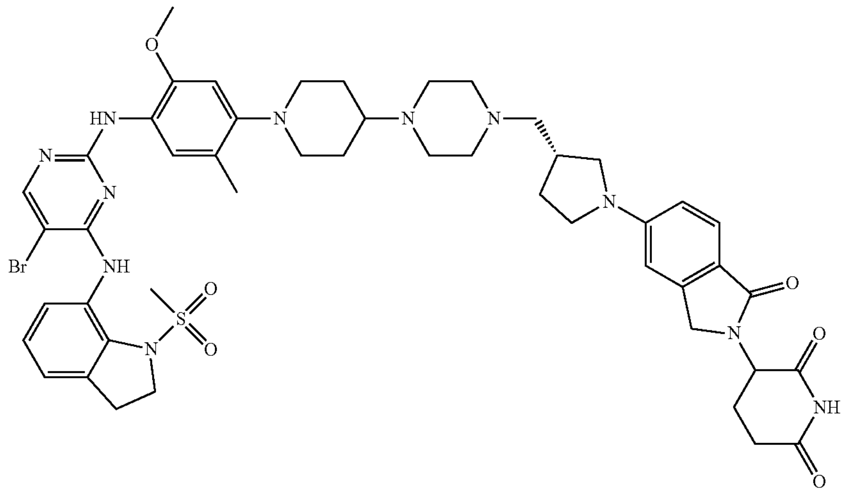

-continued
169
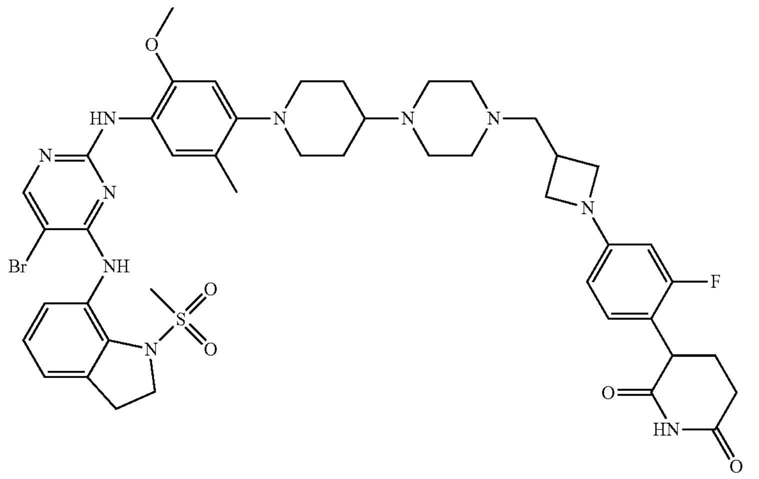
170
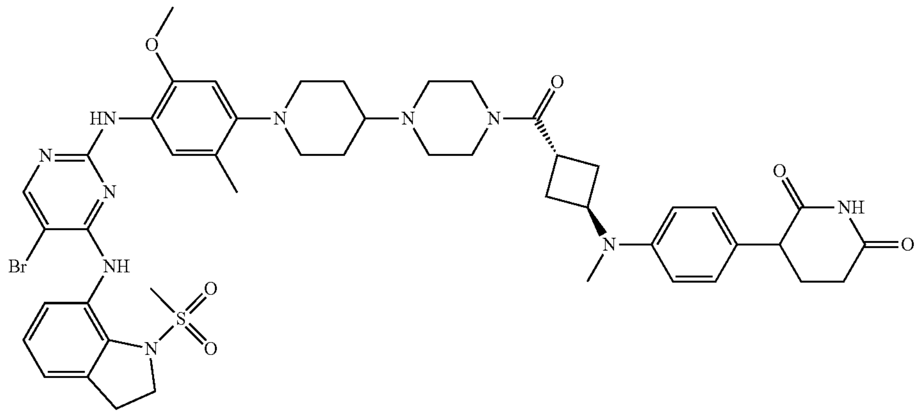
171
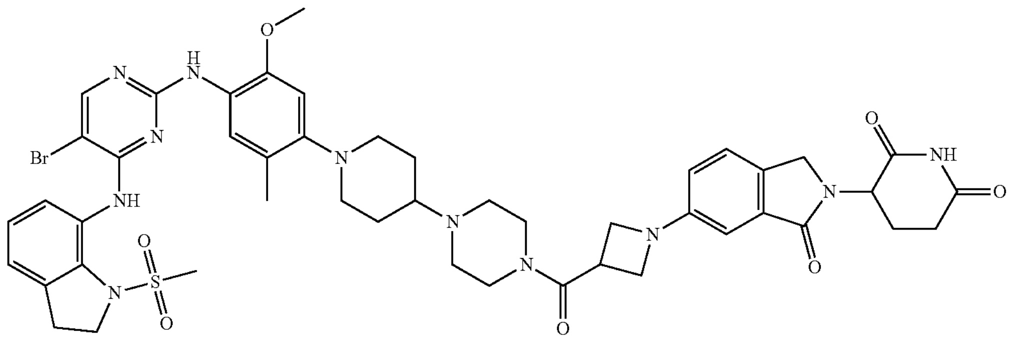
172
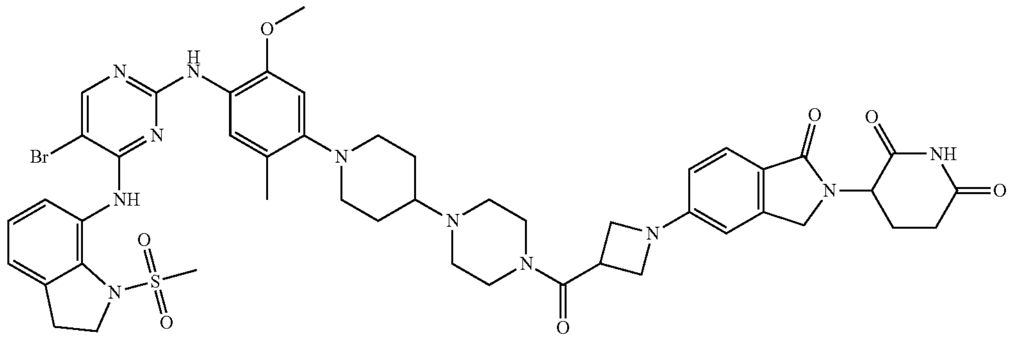

-continued
173
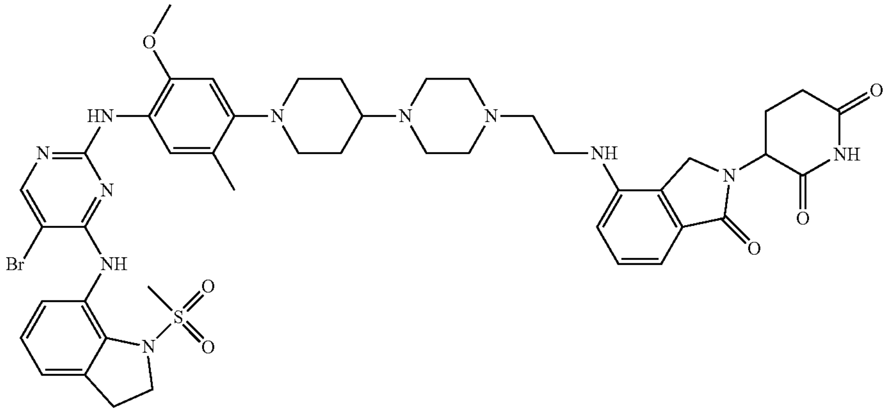
174
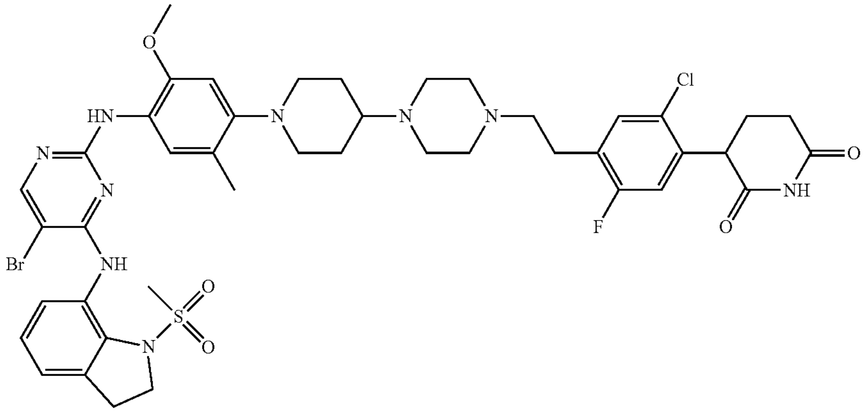
175
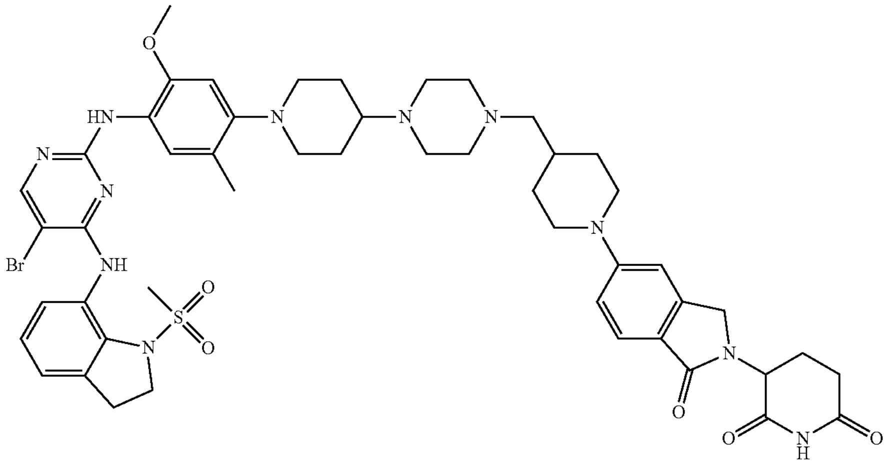

-continued
176
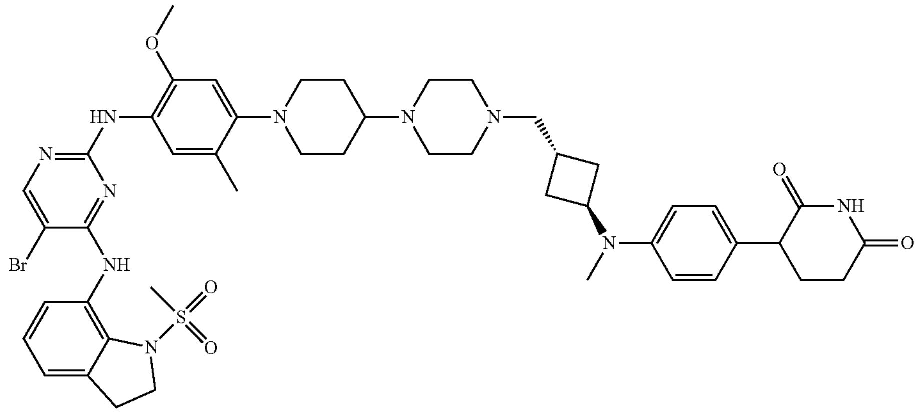
177
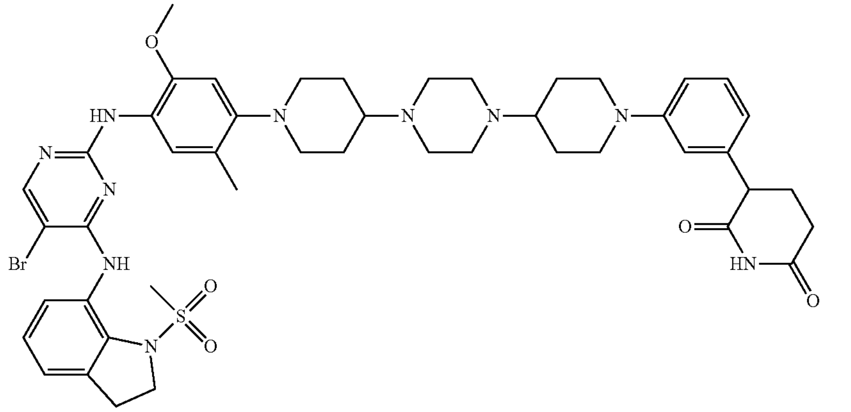
178
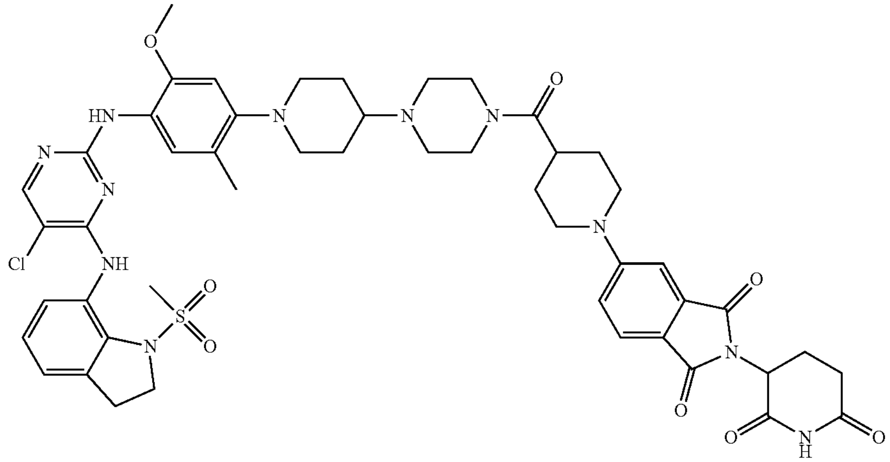
180
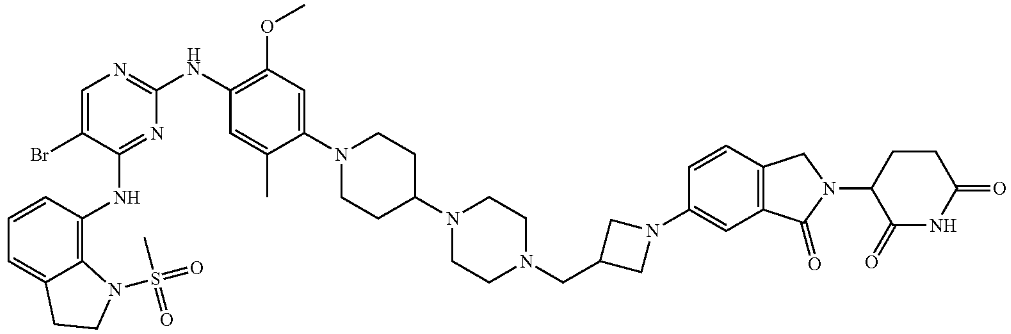

-continued
181
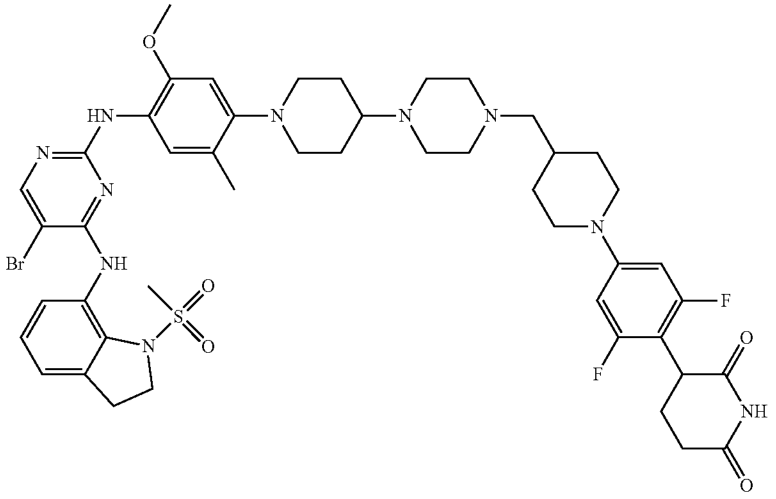
182
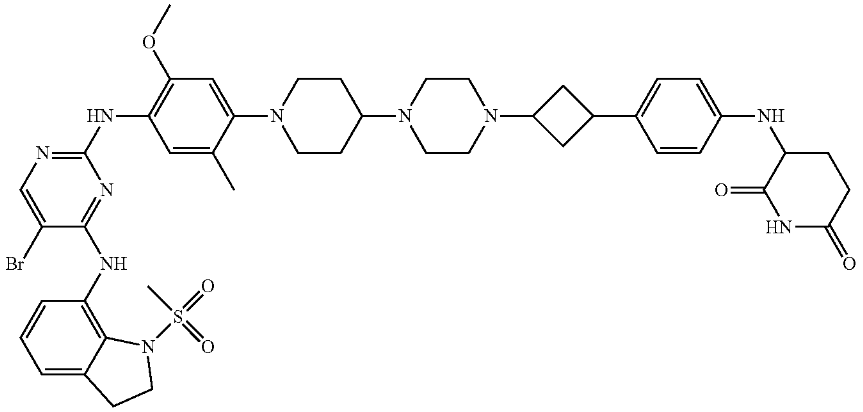
183
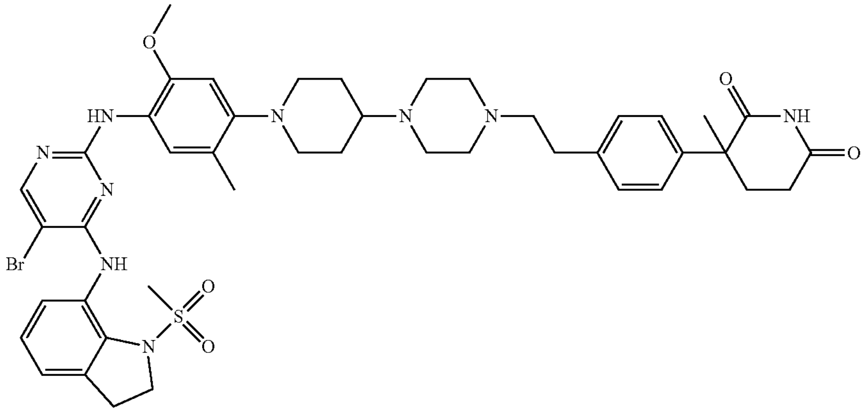

-continued
184
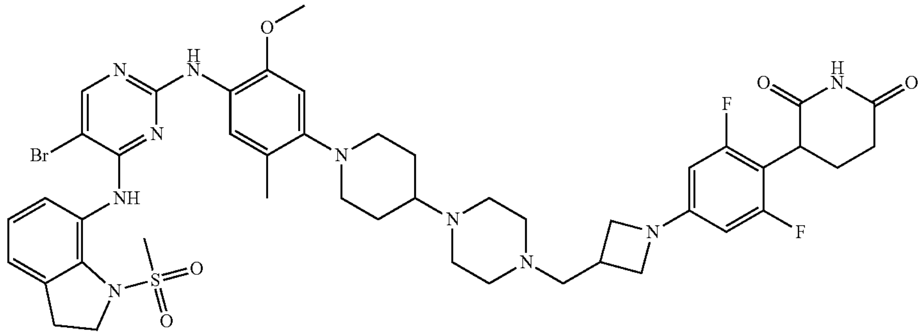
185
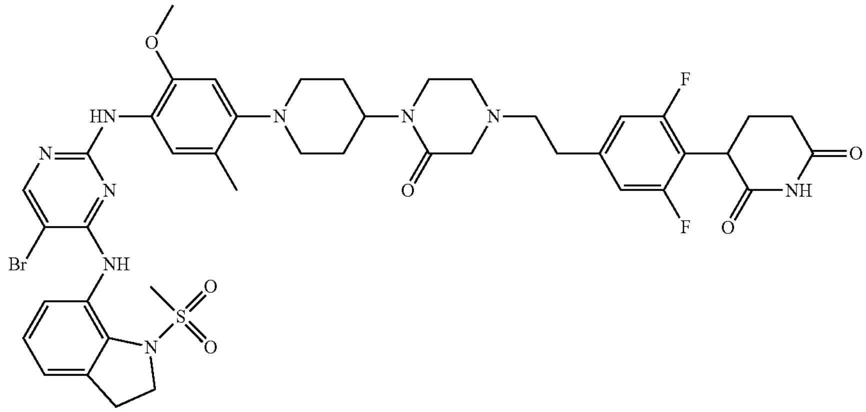
186
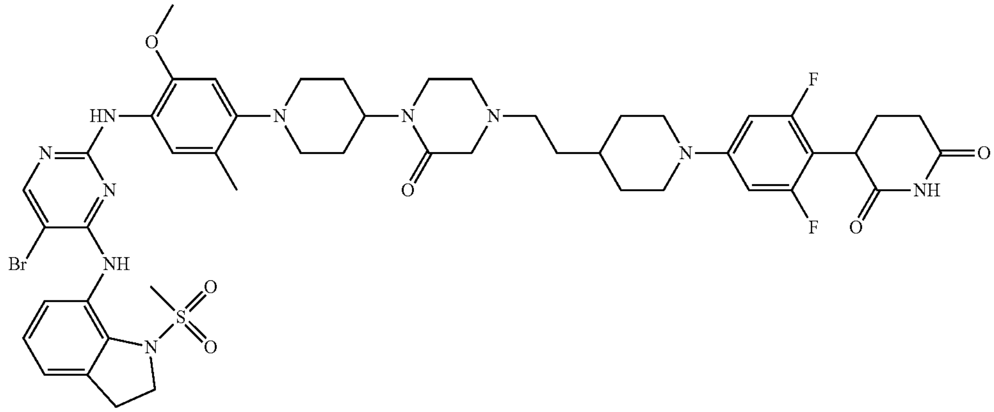

-continued
187
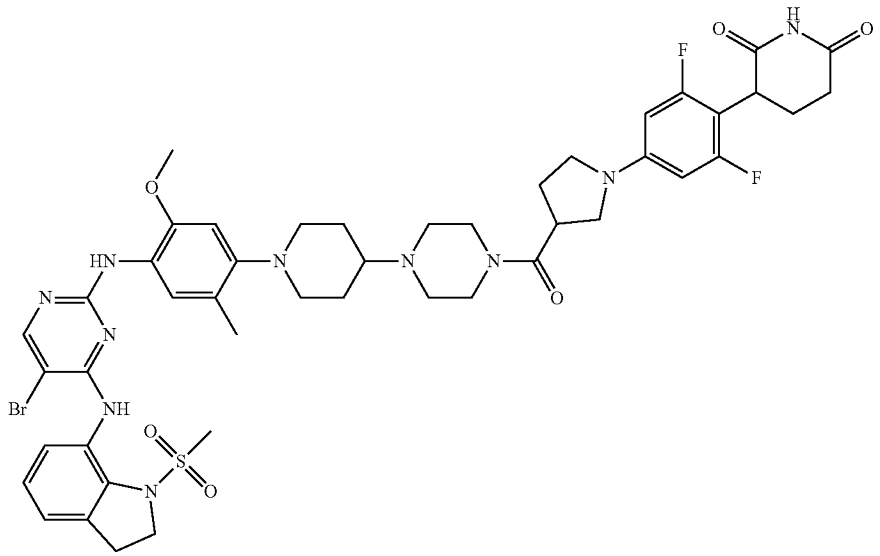
188
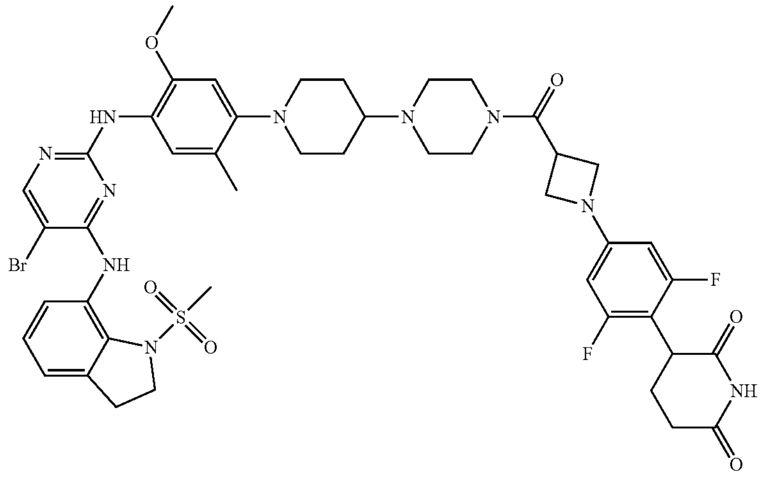
192
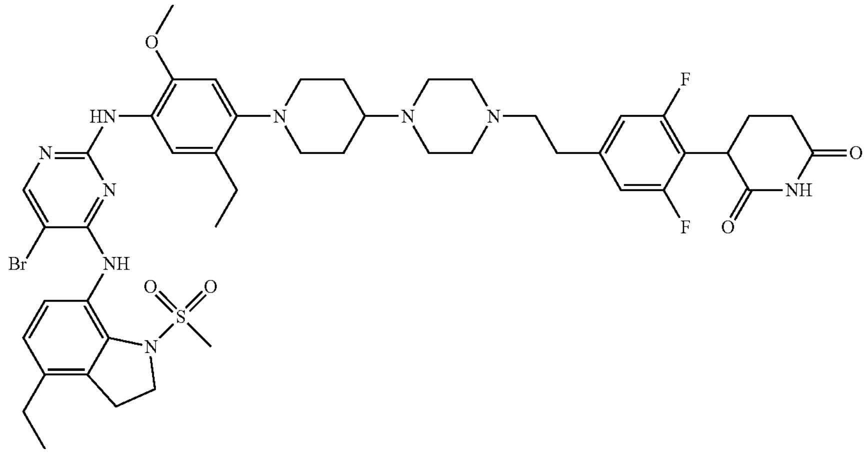

-continued
193
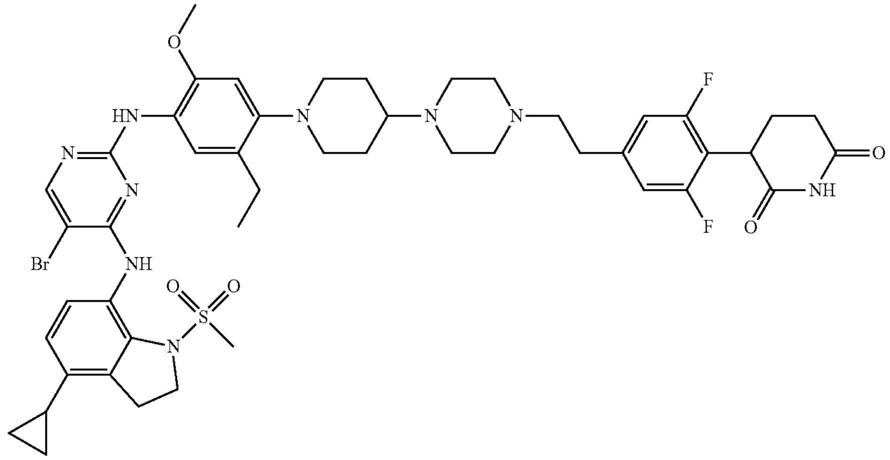
194
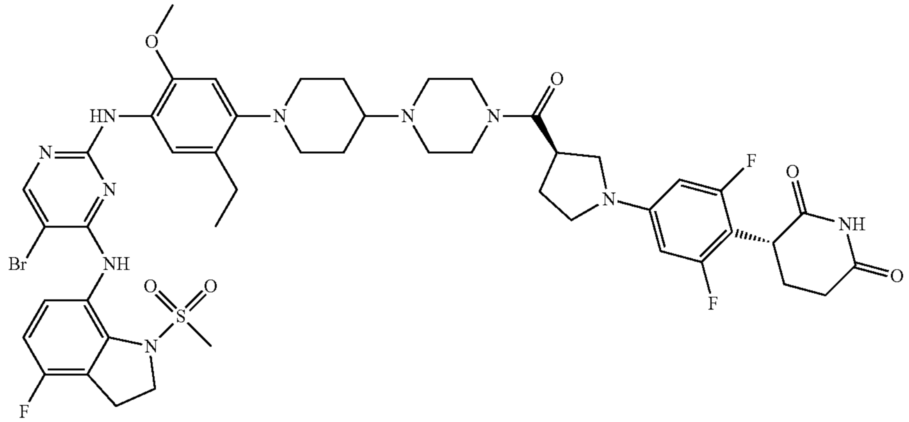
195
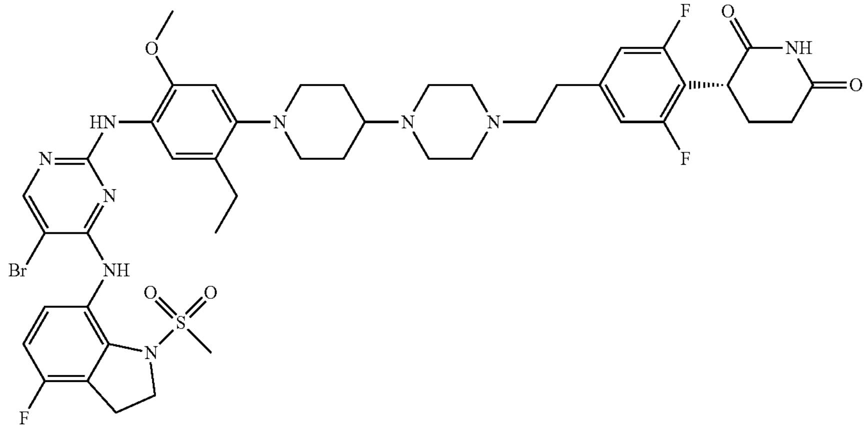

-continued
196
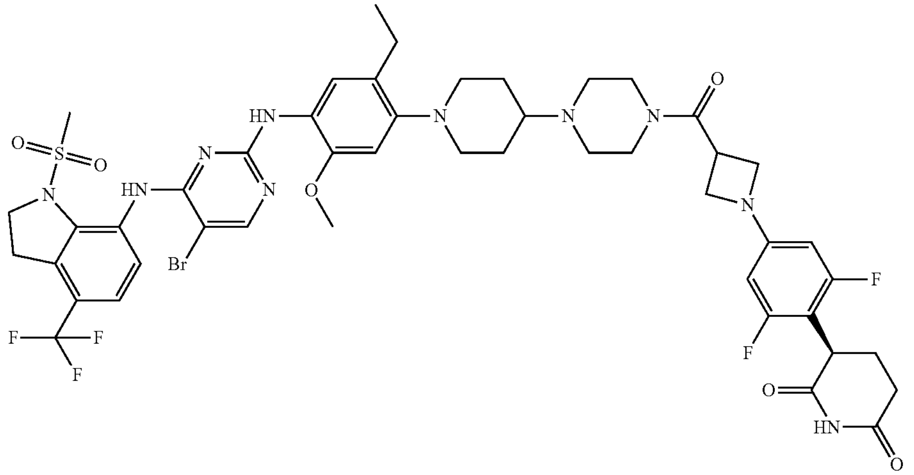
197
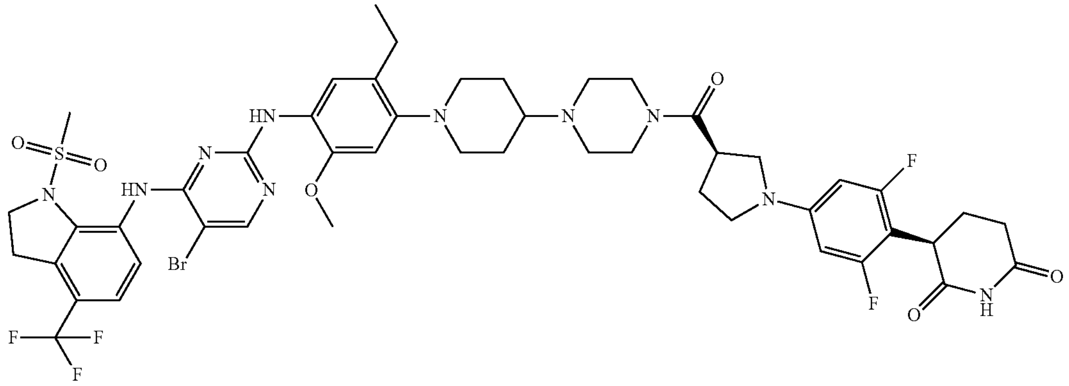
198
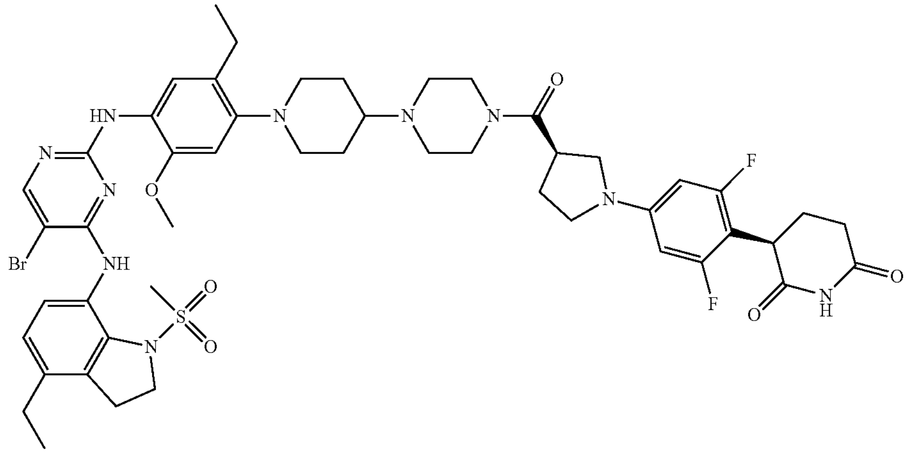

-continued

200

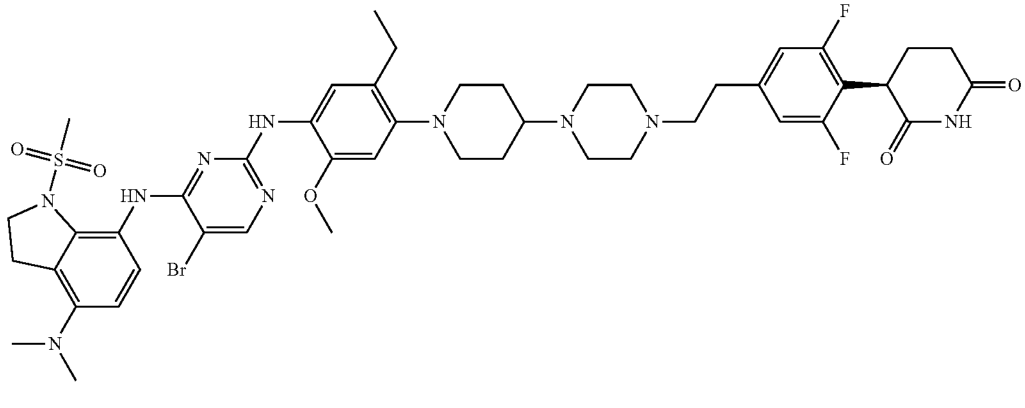

203

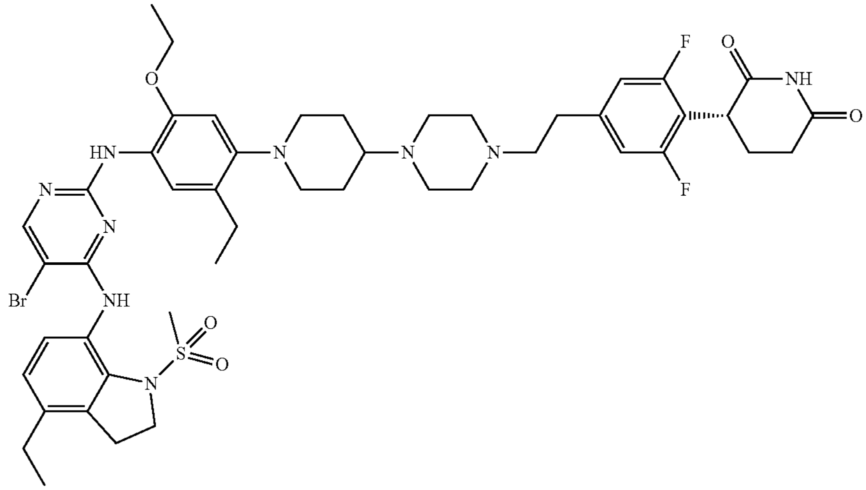

or an N-oxide thereof, or a pharmaceutically acceptable salt thereof, or a stereoisomer thereof, or a tautomer or a prodrug thereof.

Aspect 35. A pharmaceutical composition comprising a compound of any one of Aspects 1-34 or an N-oxide thereof, or a pharmaceutically acceptable salt thereof, or a stereoisomer thereof, or a tautomer or a prodrug thereof, together with a pharmaceutically acceptable excipient.

Aspect 36. A method of treating a disease in which EGFR modulation is involved, comprising administrating a subject in need thereof a therapeutically effective amount of a compound of any one of Aspects 1-34 or an N-oxide thereof, or a pharmaceutically acceptable salt thereof, or a stereoisomer thereof, or a tautomer or a prodrug thereof.

Aspect 37. The method of Aspect 36, wherein the disease is selected from cancer, preferred pancreatic cancer, breast cancer, glioblastoma multiforme, head and neck cancer, or non-small cell lung cancer.

Aspect 38. Use of a compound of any one of Aspects 1-34 or an N-oxide thereof, or a pharmaceutically acceptable salt thereof, or a stereoisomer thereof, or a tautomer or a prodrug thereof in the preparation of a medicament for treating a disease in which EGFR modulation is involved.

Aspect 39. The use of Aspect 37, wherein the disease is cancer, preferred pancreatic cancer, breast cancer, glioblastoma multiforme, head and neck cancer, or non-small cell lung cancer.

DETAILED DESCRIPTION OF THE INVENTION

The following terms have the indicated meanings throughout the specification:

Unless specifically defined elsewhere in this document, all other technical and scientific terms used herein have the meaning commonly understood by one of ordinary skill in the art to which this invention belongs.

The following terms have the indicated meanings throughout the specification:

As used herein, including the appended claims, the singular forms of words such as "a", "an", and "the", include their corresponding plural references unless the context clearly indicates otherwise.

The term "or" is used to mean, and is used interchangeably with, the term "and/or" unless the context clearly dictates otherwise.

The term "alkyl" includes a hydrocarbon group selected from linear and branched, saturated hydrocarbon groups comprising from 1 to 18, such as from 1 to 12, further such as from 1 to 10, more further such as from 1 to 8, or from 1 to 6, or from 1 to 4, carbon atoms. Examples of alkyl groups comprising from 1 to 6 carbon atoms (i.e., $C_{1-6}$ alkyl) include, but not limited to, methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu"), 1-pentyl, 2-pentyl, 3-pentyl, 2-methyl-2- butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups.

The term "propyl" includes 1-propyl or n-propyl ("n-Pr"), 2-propyl or isopropyl ("i-Pr").

The term "butyl" includes 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu").

The term "pentyl" includes 1-pentyl, 2-pentyl, 3-pentyl, 2-methyl-2-butyl, 3-methyl-2-butyl, 3-methyl-1-butyl, 2-methyl-1-butyl.

The term "hexyl" includes 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl.

The term "alkylene" refers to a divalent alkyl group by removing two hydrogens from alkane. Alkylene includes but not limited to methylene, ethylene, propylene, and so on.

The term "halogen" includes fluoro (F), chloro (Cl), bromo (Br) and iodo (I).

The term "alkenyl" includes a hydrocarbon group selected from linear and branched hydrocarbon groups comprising at least one C═C double bond and from 2 to 18, such as from 2 to 8, further such as from 2 to 6, carbon atoms. Examples of the alkenyl group, e.g., $C_{2-6}$ alkenyl, include, but not limited to ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-dienyl, hex-1-enyl, hex-2-enyl, hex-3-enyl, hex-4-enyl, and hexa-1,3-dienyl groups.

The term "alkenylene" refers to a divalent alkenyl group by removing two hydrogens from alkene. Alkenylene includes but not limited to, vinylidene, butenylene, and so on.

The term "alkynyl" includes a hydrocarbon group selected from linear and branched hydrocarbon group, comprising at least one C≡C triple bond and from 2 to 18, such as 2 to 8, further such as from 2 to 6, carbon atoms. Examples of the alkynyl group, e.g., $C_{2-6}$ alkynyl, include, but not limited to ethynyl, 1-propynyl, 2-propynyl (propargyl), 1-butynyl, 2-butynyl, and 3-butynyl groups.

The term "alkynylene" refers to a divalent alkynyl group by removing two hydrogens from alkyne. Alkenylene includes but not limited to ethynylene and so on.

The term "cycloalkyl" includes a hydrocarbon group selected from saturated cyclic hydrocarbon groups, comprising monocyclic and polycyclic (e.g., bicyclic and tricyclic) groups including fused, bridged or spiro cycloalkyl.

For example, the cycloalkyl group may comprise from 3 to 12, such as from 3 to 10, further such as 3 to 8, further such as 3 to 6, 3 to 5, or 3 to 4 carbon atoms. Even further for example, the cycloalkyl group may be selected from monocyclic group comprising from 3 to 12, such as from 3 to 10, further such as 3 to 8, 3 to 6 carbon atoms. Examples of the monocyclic cycloalkyl group include cyclopropyl, cyclobutyl, cyclopentyl, cyclohexyl, cycloheptyl, cyclooctyl, cyclononyl, cyclodecyl, cycloundecyl, and cyclododecyl groups. In particular, examples of the saturated monocyclic cycloalkyl group, e.g., $C_{3-8}$cycloalkyl, include, but not limited to cyclopropyl, cyclobutyl, cyclopentyl, cyclohexyl, cycloheptyl, and cyclooctyl groups. In a preferred embodiment, the cycloalkyl is a monocyclic ring comprising 3 to 6 carbon atoms (abbreviated as $C_{3-6}$ cycloalkyl), including but not limited to, cyclopropyl, cyclobutyl, cyclopentyl, and cyclohexyl. Examples of the bicyclic cycloalkyl groups include those having from 7 to 12 ring atoms arranged as a fused bicyclic ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. Further Examples of the bicyclic cycloalkyl groups include those arranged as a bicyclic ring selected from [5,6] and [6,6] ring systems.

The term "spiro cycloalkyl" includes a cyclic structure which contains carbon atoms and is formed by at least two rings sharing one atom.

The term "fused cycloalkyl" includes a bicyclic cycloalkyl group as defined herein which is saturated and is formed by two or more rings sharing two adjacent atoms.

The term "bridged cycloalkyl" includes a cyclic structure which contains carbon atoms and is formed by two rings sharing two atoms which are not adjacent to each other. The term "7 to 10 membered bridged cycloalkyl" includes a cyclic structure which contains 7 to 12 carbon atoms and is formed by two rings sharing two atoms which are not adjacent to each other.

Examples of fused cycloalkyl, fused cycloalkenyl, or fused cycloalkynyl include but are not limited to bicyclo[1.1.0]butyl, bicyclo[2.1.0]pentyl, bicyclo[3.1.0]hexyl, bicyclo[4.1.0]heptyl, bicyclo[3.3.0]octyl, bicyclo[4.2.0]octyl, decalin, as well as benzo 3 to 8 membered cycloalkyl, benzo $C_{4-6}$ cycloalkenyl, 2,3-dihydro-1H-indenyl, 1H-indenyl, 1, 2, 3,4-tetralyl, 1,4-dihydronaphthyl, etc. Preferred embodiments are 8 to 9 membered fused rings, which refer to cyclic structures containing 8 to 9 ring atoms within the above examples.

The term "aryl" used alone or in combination with other terms includes a group selected from:

- 5- and 6-membered carbocyclic aromatic rings, e.g., phenyl;
- bicyclic ring systems such as 7 to 12 membered bicyclic ring systems, wherein at least one ring is carbocyclic and aromatic, e.g., naphthyl and indanyl; and,
- tricyclic ring systems such as 10 to 15 membered tricyclic ring systems wherein at least one ring is carbocyclic and aromatic, e.g., fluorenyl.

The terms "aromatic hydrocarbon ring" and "aryl" are used interchangeably throughout the disclosure herein. In some embodiments, a monocyclic or bicyclic aromatic hydrocarbon ring has 5 to 10 ring-forming carbon atoms (i.e., $C_{5-10}$ aryl). Examples of a monocyclic or bicyclic aromatic hydrocarbon ring includes, but not limited to, phenyl, naphth-1-yl, naphth-2-yl, anthracenyl, phenanthrenyl, and the like. In some embodiments, the aromatic hydrocarbon ring is a naphthalene ring (naphth-1-yl or naphth-2-yl) or phenyl ring. In some embodiments, the aromatic hydrocarbon ring is a phenyl ring.

Specifically, the term "bicyclic fused aryl" includes a bicyclic aryl ring as defined herein. The typical bicyclic fused aryl is naphthalene.

The term "heteroaryl" includes a group selected from:

- 5-, 6- or 7-membered aromatic, monocyclic rings comprising at least one heteroatom, for example, from 1 to 4, or, in some embodiments, from 1 to 3, in some embodiments, from 1 to 2, heteroatoms, selected from nitrogen (N), sulfur (S) and oxygen (O), with the remaining ring atoms being carbon;
- 7- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and 11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. When the heteroaryl group contains more than one heteroatom ring member, the heteroatoms may be the same or different. The nitrogen atoms in the ring(s) of the heteroaryl group can be oxidized to form N-oxides.

Specifically, the term "bicyclic fused heteroaryl" includes a 7- to 12-membered, preferably 7- to 10-membered, more preferably 9- or 10-membered fused bicyclic heteroaryl ring as defined herein. Typically, a bicyclic fused heteroaryl is 5-membered/5-membered, 5-membered/6-membered, 6-membered/6-membered, or 6-membered/7-membered bicyclic. The group can be attached to the remainder of the molecule through either ring.

"Heterocyclyl", "heterocycle" or "heterocyclic" are interchangeable and include a non-aromatic heterocyclyl group comprising one or more heteroatoms selected from nitrogen, oxygen or optionally oxidized sulfur as ring members, with the remaining ring members being carbon, including monocyclic, fused, bridged, and spiro ring, i.e., containing monocyclic heterocyclyl, bridged heterocyclyl, spiro heterocyclyl, and fused heterocyclic groups.

The term "at least one substituent" disclosed herein includes, for example, from 1 to 4, such as from 1 to 3, further as 1 or 2, substituents, provided that the theory of valence is met. For example, "at least one substituent F" disclosed herein includes from 1 to 4, such as from 1 to 3, further as 1 or 2, substituents F.

The term "divalent" refers to a linking group capable of forming covalent bonds with two other moieties. For example, "a divalent cycloalkyl group" refers to a cycloalkyl group obtained by removing two hydrogen from the corresponding cycloalkane to form a linking group. the term "divalent aryl group", "divalent heterocyclyl group" or "divalent heteroaryl group" should be understood in a similar manner.

Compounds disclosed herein may contain an asymmetric center and may thus exist as enantiomers. "Enantiomers" refer to two stereoisomers of a compound which are non-superimposable mirror images of one another. Where the compounds disclosed herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

When compounds disclosed herein contain olefinic double bonds, unless specified otherwise, such double bonds are meant to include both E and Z geometric isomers.

When compounds disclosed herein contain a di-substituted cyclic ring system, substituents found on such ring system may adopt cis and trans formations. Cis formation means that both substituents are found on the upper side of the 2 substituent placements on the carbon, while trans would mean that they were on opposing sides. For example, the di-substituted cyclic ring system may be cyclohexyl or cyclobutyl ring.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art could select and apply the techniques most likely to achieve the desired separation.

"Diastereomers" refer to stereoisomers of a compound with two or more chiral centers but which are not mirror images of one another. Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. *Stereochemistry of Organic Compounds*. New York: John Wiley & Sons, Inc., 1994; Lochmuller, C. H, et al. "*Chromatographic resolution of enantiomers: Selective review.*" *J. Chromatogr.,* 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. *Drug Stereochemistry: Analytical Methods and Pharmacology*. New York: Marcel Dekker, Inc., 1993.

Some of the compounds disclosed herein may exist with different points of attachment of hydrogen, referred to as tautomers. For example, compounds including carbonyl $—CH_2C(O)—$ groups (keto forms) may undergo tautomerism to form hydroxyl $—CH{=}C(OH)—$ groups (enol forms). Both keto and enol forms, individually as well as mixtures thereof, are also intended to be included where applicable.

"Prodrug" refers to a derivative of an active agent that requires a transformation within the body to release the active agent. In some embodiments, the transformation is an enzymatic transformation. Prodrugs are frequently, although not necessarily, pharmacologically inactive until converted to the active agent.

"Pharmaceutically acceptable salts" refer to those salts which are, within the scope of sound medical judgment, suitable for use in contact with the tissues of humans and lower animals without undue toxicity, irritation, allergic response and the like, and are commensurate with a reasonable benefit/risk ratio. A pharmaceutically acceptable salt may be prepared in situ during the final isolation and purification of the compounds disclosed herein, or separately by reacting the free base function with a suitable organic acid or by reacting the acidic group with a suitable base. The term also includes salts of the stereoisomers (such as enantiomers and/or diastereomers), tautomers and prodrugs of the compound of the invention.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

The terms "administration", "administering", "treating" and "treatment" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" and "treatment" also means in vitro and ex vivo treatments, e.g., of a cell, by a reagent, diagnostic, binding compound, or by another cell. The term "subject" herein includes any organism, preferably an animal, more preferably a mammal (e.g., rat, mouse, dog, cat, and rabbit) and most preferably a human.

The term "effective amount" or "therapeutically effective amount" refers to an amount of the active ingredient, such as compound that, when administered to a subject for treating a disease, or at least one of the clinical symptoms of a disease or disorder, is sufficient to affect such treatment for the disease, disorder, or symptom. The term "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In some embodiments, "therapeutically effective amount" is an amount of at least one compound and/or at least one stereoisomer, tautomer or prodrug thereof, and/or at least one pharmaceutically acceptable salt thereof disclosed herein effective to "treat" as defined herein, a disease or disorder in a subject. In the case of combination therapy, the term "therapeutically effective amount" refers to the total amount of the combination objects for the effective treatment of a disease, a disorder or a condition.

The term "disease" refers to any disease, discomfort, illness, symptoms or indications, and can be interchangeable with the term "disorder" or "condition".

Throughout this specification and the claims which follow, unless the context requires otherwise, the term "comprise", and variations such as "comprises" and "comprising" are intended to specify the presence of the features thereafter, but do not exclude the presence or addition of one or more other features. When used herein the term "comprising" can be substituted with the term "containing", "including" or sometimes "having".

Throughout this specification and the claims which follow, the term "Cn-m" indicates a range which includes the endpoints, wherein n and m are integers and indicate the number of carbons. Examples include $C_{1-8}$, $C_{1-6}$, and the like.

Unless specifically defined elsewhere in this document, all other technical and scientific terms used herein have the meaning commonly understood by one of ordinary skill in the art to which this invention belongs.

General Reaction Scheme for Compound Preparation

The subject compounds and pharmaceutically acceptable salts thereof, can be prepared from (a) commercially available starting materials (b) known starting materials which may be prepared as described in literature procedures (c) new intermediates described in the schemes and experimental procedures herein. In making the compounds of the invention, the order of synthetic steps may be varied to increase the yield of the desired product. Some of the compounds in this invention may be generated by the methods as shown in the following reaction schemes and the description thereof.

Scheme A

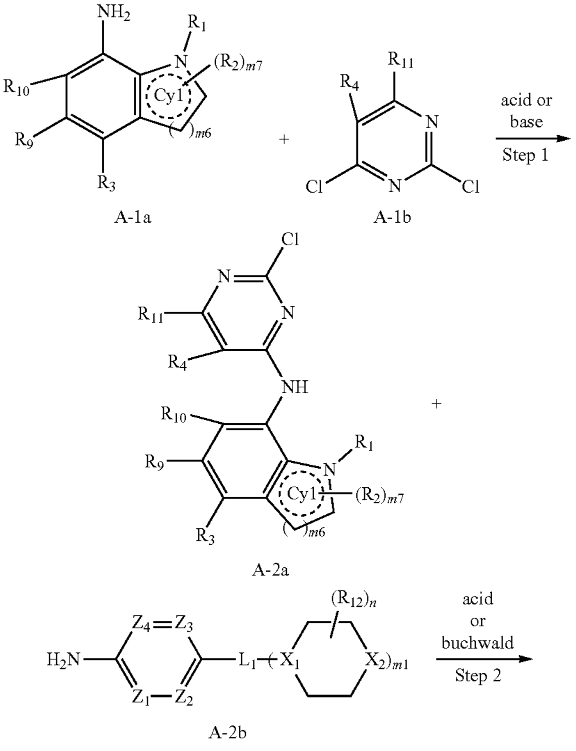

A-1a A-1b

A-2a

A-2b

-continued
-continued
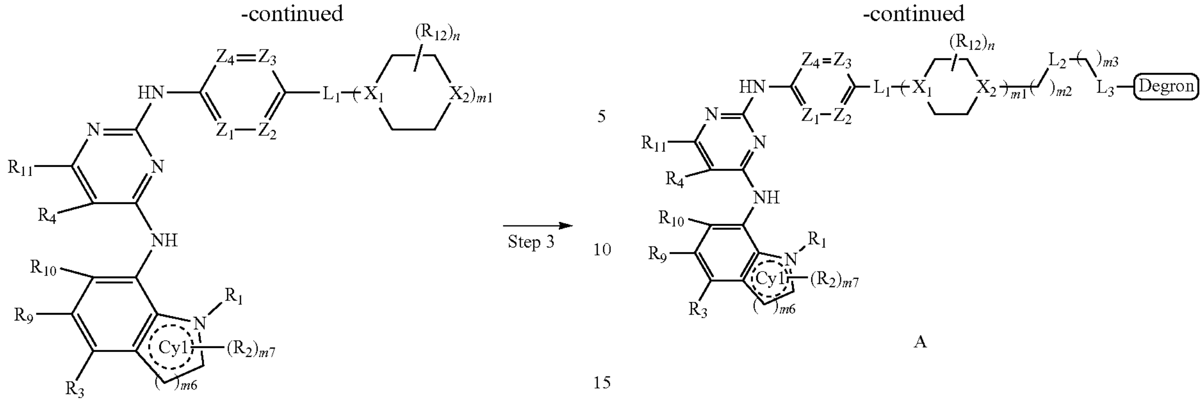
A-3
A
Scheme B
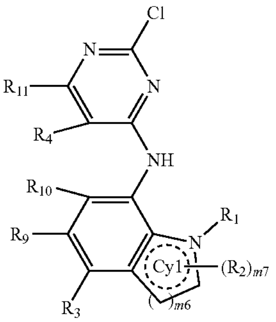
B-1a
+
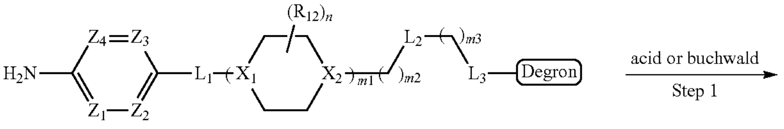
B-1b
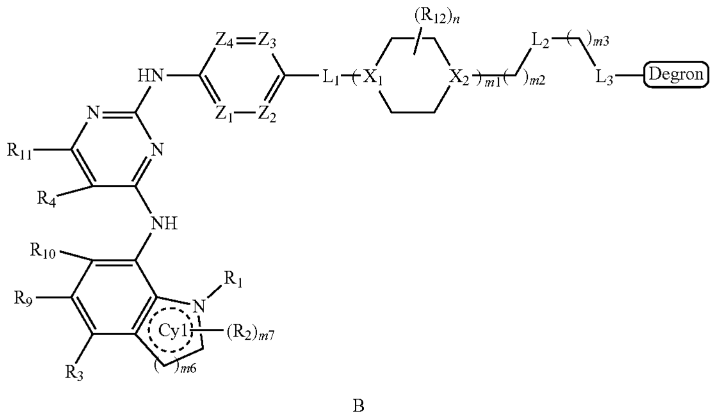
B Scheme C
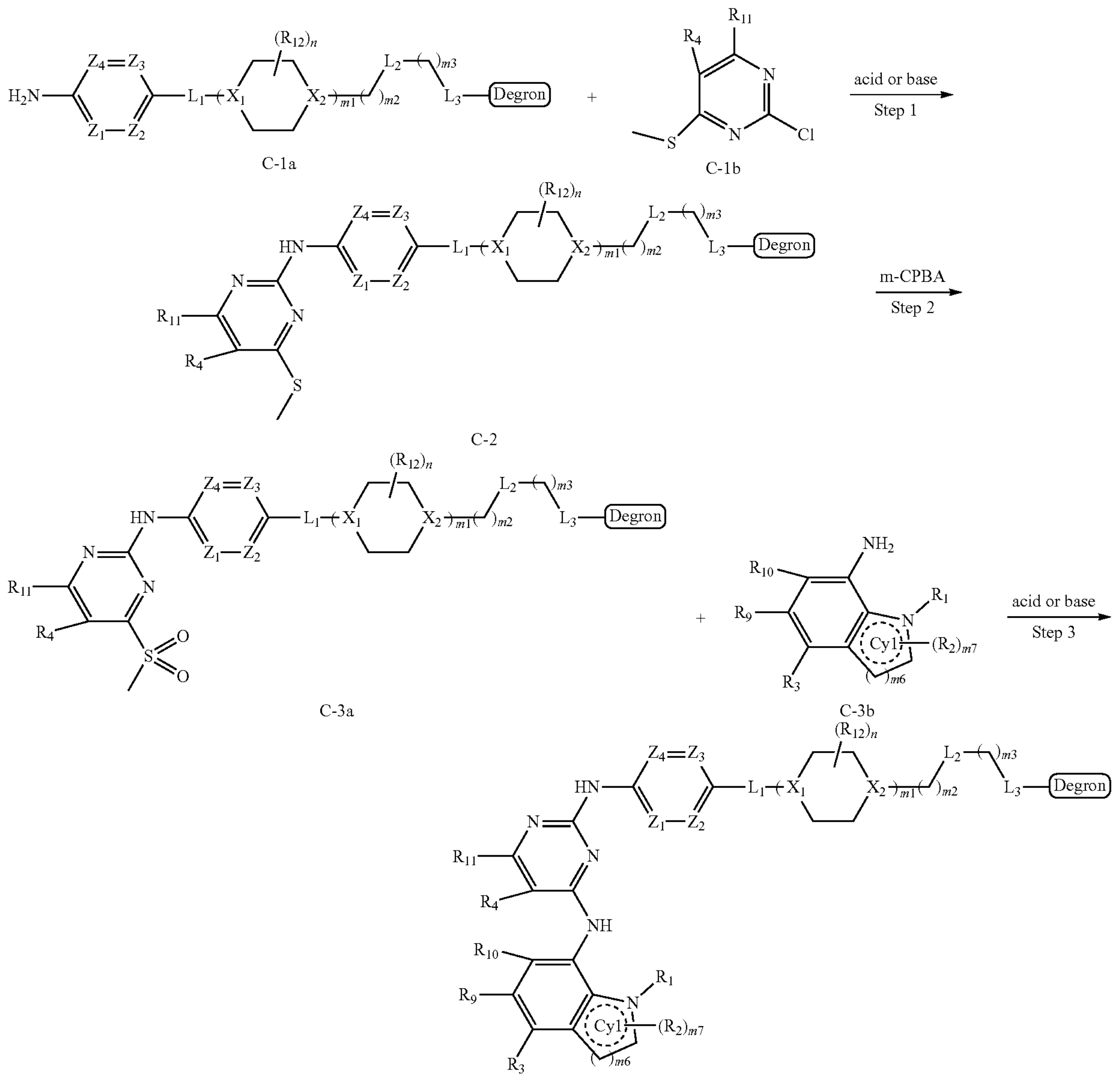
C-1a C-1b C-2 C-3a C-3b C
Scheme D
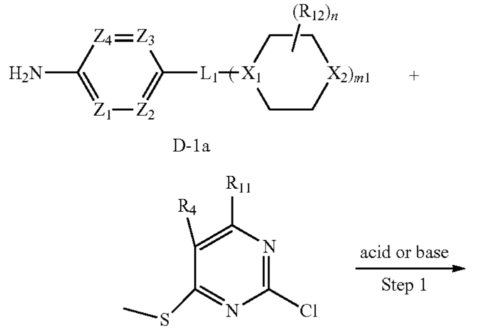
D-1a D-1b
-continued
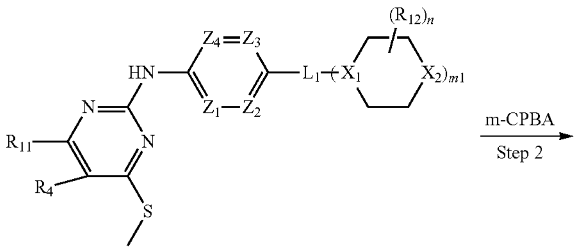
D-2

-continued

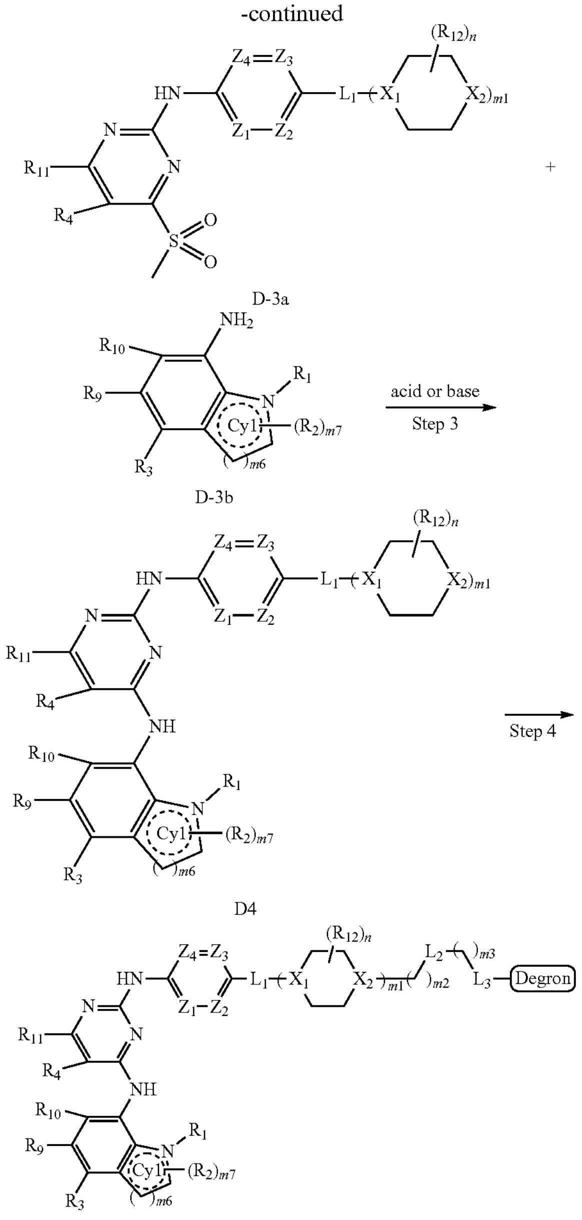

D-3a

D-3b

D4

D

EXAMPLES

The examples below are intended to be purely exemplary and should not be considered to be limiting in any way. Efforts have been made to ensure accuracy with respect to numbers used (for example, amounts, temperature, etc.), but some experimental errors and deviations should be accounted for. Unless indicated otherwise, the temperature is in degrees Centigrade. Reagents were purchased from commercial suppliers such as Sigma-Aldrich, Alfa Aesar, or TCI, and were used without further purification unless indicated otherwise. Unless indicated otherwise, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and/or heat dried.

$^1$H NMR spectra were recorded on an Agilent instrument operating at 400 MHz. $^1$HNMR spectra were obtained using $CDCl_3$, $CD_2Cl_2$, $CD_3OD$, $D_2O$, $d_6$-DMSO, $d_6$-acetone or $(CD_3)_2CO$ as solvent and tetramethylsilane (0.00 ppm) or residual solvent ($CDCl_3$: 7.25 ppm; $CD_3OD$: 3.31 ppm; $D_2O$: 4.79 ppm; $d_6$-DMSO: 2.50 ppm; $d_6$-acetone: 2.05; $(CD_3)_3CO$: 2.05) as the reference standard. When peak multiplicities are reported, the following abbreviations are used: s (singlet), d (doublet), t (triplet), q (quartet), qn (quintuplet), sx (sextuplet), m (multiplet), br (broadened), dd (doublet of doublets), dt (doublet of triplets). Coupling constants, when given, are reported in Hertz (Hz).

LCMS-1: LC-MS spectrometer (Agilent 1260 Infinity) Detector: MWD (190-400 nm), Mass detector: 6120 SQ Mobile phase: A: water with 0.1% Formic acid, B: acetonitrile with 0.1% Formic acid Column: Poroshell 120 EC-C18, 4.6x50 mm, 2.7 pm Gradient method: Flow: 1.8 mL/min Time (min) A % B %

| Time (min) | A(%) | B(%) |
|---|---|---|
| 0.00 | 95 | 5 |
| 1.5 | 5 | 95 |
| 2.0 | 5 | 95 |
| 2.1 | 95 | 5 |
| 3.0 | 95 | 5 |

LCMS, LCMS-3: LC-MS spectrometer (Agilent 1260 Infinity II) Detector: MWD (190-400 nm), Mass detector: G6125C SQ Mobile phase: A: water with 0.1% Formic acid, B: acetonitrile with 0.1% Formic acid Column: Poroshell 120 EC-C18, 4.6x50 mm, 2.7 pm Gradient method: Flow: 1.8 mL/min Time min) A((%) B (0%

| Time (min) | A(%) | B(%) |
|---|---|---|
| 0.00 | 95 | 5 |
| 1.5 | 5 | 95 |
| 2.0 | 5 | 95 |
| 2.1 | 95 | 5 |
| 3.0 | 95 | 5 |

LCMS-2: LC-MS spectrometer (Agilent 1290 Infinity II) Detector: MWD (190-400 nm), Mass detector: G6125C SQ Mobile phase: A: water with 0.1% Formic acid, B: acetonitrile with 0.1% Formic acid Column: Poroshell 120 EC-C18, 4.6x50 mm, 2.7 pm Gradient method: Flow: 1.2 mL/min Time (min) A %) B)

| Time (min) | A(%) | B(%) |
|---|---|---|
| 0.00 | 90 | 10 |
| 1.5 | 5 | 95 |
| 2.0 | 5 | 95 |
| 2.1 | 90 | 10 |
| 3.0 | 90 | 10 |

Preparative HPLC was conducted on a column (150x21.2 mm ID, 5 pm, Gemini NXC 18) at a flow rate of 20 ml/min, injection volume 2 ml, at room temperature and UV Detection at 214 nm and 254 nm.

In the following examples, the abbreviations below are used:

| | |
|---|---|
| $(BPin)_2$ | 4,4,4',4',5,5,5',5'-Octamethyl-2,2'-bi-1,3,2-dioxaborolane |
| $Ac_2O$ | acetic anhydride |
| AcCl | Acetyl chloride |
| ACN | Acetonitrile |
| AcOH or HOAc | Acetic acid |
| AcONa or NaOAc | Sodium acetate |
| Aq | Aqueous |
| BINAP | (±)-2,2'-Bis(diphenylphosphino)-1,1'-BINAPhthyl |
| Bn | benzyl |
| BnBr | Benzyl Bromide |
| Boc | t-Butyloxy carbonyl |
| C:40691-33-6 | dichlorobis(tri-o-tolylphosphine)palladium(II) |
| Cbz | Benzyloxycarbonyl |
| DCM | Dichloromethane |
| Con. | Concentrated |
| DavePhos | 2'-(Dicyclohexylphosphino)-N,N-dimethyl-2-biphenylamine |
| DBU | 1, 8-diazabicyclo[5.4.0]undec-7-ene |
| DCE | dichloroethane |
| DHP | 3,4-Dihydro-2H-pyran |
| DIBAL-H | Diisobutylaluminium hydride |
| DIEA or DIPEA | N, N-diisopropylethylamine |
| DMAP | 4-N, N-dimethylaminopyridine |
| DMF | N,N-Dimethylformamide |
| DMSO | Dimethyl sulfoxide |
| Dppf | 1, 1''-bis(diphenylphosphino)ferrocene |
| EA or EtOAc | Ethyl acetate |
| EtOH | ethanol |
| FA | Formic acid |
| h or hr | Hour |
| HATU | 2-(7-Azabenzotriazol-1-yl)-N,N,N',N'-tetramethyluronium hexafluorophosphate |
| HBTU | O-(7- Benzotriazole-1-yl)-N, N, N', N'-tetramethyluronium hexafluorophosphate |
| Hex | Hexane |
| HPLC | High Performance Liquid Chromatography |
| hrs | hours |
| IBX | 2-Iodoxybenzoic acid |
| IPA | 2-propanol |
| i-PrOH | Isopropyl alcohol |
| KHMDS | Potassium bis(trimethylsilyl)amide |
| KOAc | Potassium Acetate |
| MeCN or ACN | Acetonitrile |
| MeOH | Methanol |
| Min | Minutes |
| ms or MS | Mass spectrum |
| MsCl | Methanesulfonyl chloride |
| MsOH | Methanesulfonic acid |
| MTBE | Methyl tert-butyl ether |
| o/n | overnight |
| $Pd(dppf)Cl_2$ | [1,1'-Bis(diphenylphosphino)ferrocene]di-chloropalladium(II) |
| G3 BrettPhos Pd | Methanesulfonato(2-dicyclohexylphosphino-3,6-dimethoxy-2',4',6'-tri-i-propyl-1,1'-biphenyl)(2'-amino-1,1'-biphenyl-2-yl)palladium(II) |
| $Pd_2(dba)_2$ | |
| PE | Petroleum ether |
| PhMe | Toluene |
| PPA | Polyphosphoric acid |
| R.T. or r.t. | Room temperature |
| Rt | Retention time |
| SEMCl | 2-(Trimethylsilyl)ethoxymethyl chloride |
| STAB | Sodium Triacetoxyborohydride; Sodium triacetoborohydride |
| TBAF | Tetra-butyl ammonium fluoride |
| TBDPS | tert-Butyldiphenylsilyl |
| TBS | tert-Butyldimethylsilyl |
| TBSCl | tert-Butyldimethylsilyl chloride |
| t-Bu | tert-butyl |
| t-BuOH | tert-Butanol |
| t-BuONa | Sodium tert-butoxide |
| TEA | Triethylamine |

-continued

| | |
|---|---|
| $Tf_2O$ | Triflic anhydride |
| TFA | Trifluoroacetic acid |
| THF | Tetrahydrofuran |
| TLC | Thin layer chromatography |
| TMSOK | Potassium trimethylsilanolate |
| Ts | para-Toluenesulfonyl |
| TsCl | 4-Toluenesulfonyl chloride |
| TsOH | p-toluenesulfonic acid |
| TsOH, Py | Pyridinium toluene-4-sulphonate |
| Xphos | 2-Dicyclohexylphosphino-2',4',6'-triisopropylbiphenyl |
| XantPhos | 4,5-Bis(diphenylphosphino)-9,9-dimethylxanthene |

Example 3: 3-(2-fluoro-4-(2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)ethyl)phenyl)piperidine-2,6-dione

Step 1: 2-(4-bromo-3-fluorophenyl)ethan-1-ol

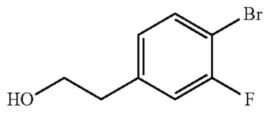 [SMILES: OCCc1ccc(Br)c(F)c1]

To a solution of 2-(4-bromo-3-fluorophenyl)acetic acid (45.0 g, 193 mmol) in THF (270 mL) was added $BH_3$-THF (1 M, 386 mL) at 0° C. Then the mixture was stirred at 20° C. for 2 hrs. Under cooling with ice, MeOH (250 mL) was added dropwise until there was no foaming in the system and the solvent was distilled off under reduced pressure. To the resulting residue, water (50 mL) was added for extraction with EtOAc (1000.0 mL). The combined organic phase was washed with brine (40.0 mL), dried over $Na_2SO_4$, filtered and concentrated in vacuum. 2-(4-bromo-3-fluorophenyl) ethan-1-ol (38.0 g, 89.8%) was obtained. $^1$HNMR (400 MHz, $CDCl_3$-d) δ ppm 7.45 (t, J=7.72 Hz, 1H), 7.00 (dd, J=9.48, 1.76 Hz, 1H), 6.86-6.92 (m, 1H), 3.82 (t, J=6.50 Hz, 2H), 2.80 (t, J=6.50 Hz, 2H), 2.03 (s, 1H); $[M+H]^+$=219.1.

Step 2: (4-bromo-3-fluorophenethoxy)(tert-butyl) dimethylsilane

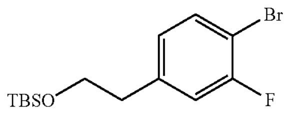 [SMILES: CC(C)(C)[Si](C)(C)OCCc1ccc(Br)c(F)c1]

To a solution of 2-(4-bromo-3-fluorophenyl)ethan-1-ol (38.0 g, 173 mmol) in DCM (210 mL) was added imidazole (17.7 g, 260 mmol) at 20° C. TBSCl (36.6 g, 242 mmol, 29.7 mL) was added to the reaction mixture at 0° C. Then the mixture was stirred at 20° C. for 3 hrs. Then the mixture was adjusted to pH=6 with 5% citric acid (180 mL), and extracted with DCM (150 mL). The organic phase was adjusted to pH=8 with $NaHCO_3$ and then aqueous phase was extracted with DCM (100 mL). The combined organic phase was washed with brine (150 mL), dried over $Na_2SO_4$, filtered and concentrated in vacuum. (4-bromo-3-fluoro-phenethoxy)(tert-butyl)dimethylsilane (52.0 g, 156 mmol) was obtained. $^1$HNMR (400 MHz, $CDCl_3$-d) 6 ppm 7.43 (t, J=7.72 Hz, 1H), 7.00 (dd, J=9.56, 1.87 Hz, 1H), 6.89 (dd, J=8.00, 1.87 Hz, 1H), 3.80 (t, J=6.48 Hz, 2H), 2.78 (t, J=6.48 Hz, 2H), 0.84-0.89 (m, 9H), - 0.05-0.01 (m, 6H); $[M+H]^+$=333.2.

Step 3: 2,6-bis(benzyloxy)-3-(4-(2-((tert-butyldimethylsilyl)oxy)ethyl)-2-fluorophenyl)pyridine

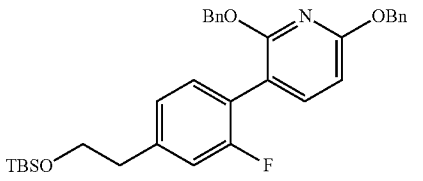 [SMILES: CC(C)(C)[Si](C)(C)OCCc1ccc(-c2ccc(OCc3ccccc3)nc2OCc2ccccc2)c(F)c1]

To a solution of (4-bromo-3-fluorophenethoxy)(tert-butyl)dimethylsilane (52.0 g, 156 mmol) and 2,6-bis(benzyloxy)-3-(4,4,5,5-tetramethyl-1,3,2-dioxaborolan-2-yl) pyridine (65.1 g, 156 mmol) in dioxane (320 mL) was added KOAc (45.9 g, 468 mmol) at 20° C. Pd(dppf)$Cl_2$ (11.4 g, 15.6 mmol) was added to the mixture at 20° C. The suspension was degassed under vacuum and purged with $N_2$ three times. Then the mixture was stirred at 90° C. for 16 hrs. Water (160 mL) was poured into the mixture, extracted with EtOAc (100 mL). The combined organic phase was washed with brine (100 mL), dried over $Na_2SO_4$, filtered and concentrated in vacuum. The residue was purified by column chromatography. 2,6-bis(benzyloxy)-3-(4-(2-((tert-butyldimethylsilyl)oxy)ethyl)-2-fluorophenyl)pyridine (32.0 g, 37.8%) was obtained.

$^1$HNMR (400 MHz, $CDCl_3$-d) δ ppm 7.55 (dd, J=8.04, 0.99 Hz, 1H), 7.43-7.47 (m, 2H), 7.33-7.42 (m, 7H), 7.25-7.33 (m, 3H), 6.98-7.05 (m, 2H), 5.40 (d, J=18.4 Hz, 4H), 3.87 (t, J=6.84 Hz, 1H), 3.84-3.89 (m, 1H), 2.86 (t, J=6.84 Hz, 2H), 0.88-0.92 (m, 9H), 0.01-0.03 (m, 6H); $[M+H]^+$=544.2.

Step 4: 3-(4-(2-((tert-butyldimethylsilyl)oxy)ethyl)-2-fluorophenyl)piperidine-2,6-dione

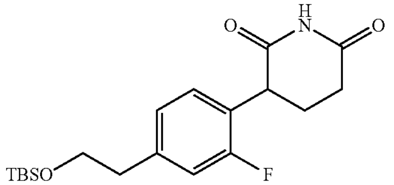 [SMILES: CC(C)(C)[Si](C)(C)OCCc1ccc(C2CCC(=O)NC2=O)c(F)c1]

To a solution of2,6-bis(benzyloxy)-3-(4-(2-((tert-butyldimethylsilyl)oxy)ethyl)-2-fluorophenyl)pyridine (32.0 g, 58.8 mmol) in THF (50.0 mL) was added Pd/C (0.800 g, 10.0% purity) under Ar at 20° C. The suspension was degassed and purged with $H_2$ for 3 times. The mixture was stirred under $H_2$ (50 Psi) at 50° C. for 16 hrs. The suspension was filtered through a pad of celite and the filter cake was washed with THF (200 mL×3). The combined filtrates were concentrated to dryness to give crude product. The crude product was triturated with petroleum ether (50.0 mL) at 20° C. for 1 hrs. 3-(4-(2-((tert-butyldimethylsilyl)oxy)ethyl)-2-fluorophenyl)piperidine-2,6-dione (12.0 g, 55.7%) was obtained. $^1$H NMR (400 MHz, $CDCl_3$-d) δ ppm 7.06-7.12 (m, 1H) 7.93 (br s, 1H), 6.96-7.04 (m, 2H), 3.91 (dd, J=11.2, 5.04 Hz, 1H), 3.81 (t, J=6.80 Hz, 2H), 2.82 (t, J=6.80 Hz, 2H), 2.58-2.73 (m, 2H), 2.18-2.34 (m, 2H), 0.87 (s, 9H), 0.00 (s, 6H); $[M+H]^+$=366.3.

Step 5: 3-(2-fluoro-4-(2-hydroxyethyl)phenyl)piperidine-2,6-dione

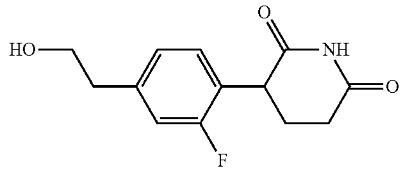 [SMILES: O=C1CCC(c2ccc(CCO)cc2F)C(=O)N1]

To a solution of 3-(4-(2-((tert-butyldimethylsilyl)oxy)ethyl)-2-fluorophenyl)piperidine-2,6-dione (12.0 g, 32.8 mmol) in MeOH (60 mL) was added HCl (12 M, 6 mL) at 20° C. Then the mixture was stirred at 20° C. for 3 hrs. Water (60 mL) was poured into the mixture, extracted with EtOAc (40 mL). The combined organic phase was washed with brine (40 mL), dried over $Na_2SO_4$, filtered and concentrated in vacuum. The combined crude product was purified by re-crystallization from toluene (32.0 mL) at 100° C. 3-(2-fluoro-4-(2-hydroxyethyl)phenyl)piperidine-2,6-dione (6.50 g, 78.8%) was obtained. $^1$HNMR (400 MHz, DMSO-$d_6$)$_6$ ppm 10.8 (s, 1H), 7.19 (t, J=7.84 Hz, 1H), 6.99-7.08 (m, 2H), 4.67 (t, J=5.18 Hz, 1H), 3.99 (dd, J=12.6, 4.74 Hz, 1H), 3.55-3.66 (m, 2H), 2.68-2.75 (m, 3H), 2.18 (qd, J=12.8, 3.86 Hz, 1H), 1.93-2.03 (m, 1H); $[M+H]^+$=252.2.

Step 6: 2-(4-(2,6-dioxopiperidin-3-yl)-3-fluorophenyl)acetaldehyde

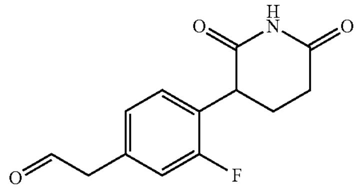 [SMILES: O=CCc1ccc(C2CCC(=O)NC2=O)c(F)c1]

To a solution of 3-(2-fluoro-4-(2-hydroxyethyl)phenyl) piperidine-2,6-dione (200 mg, 0.8 mmol) in DMSO (10 mL) was added IBX (338 mg, 1.2 mmol). The mixture was stirred in a flask at rt overnight. After being determined the reaction to be completed by LCMS, the mixture was extracted with EA (30 mL*3). The combined organic phase was dried over anhydrous $Na_2SO_4$, and evaporated in vacuum to afford the crude product (100 mg, crude), which was used for next step without further purification. $[M+H]^+$=250.4.

Step 7: tert-butyl 4-(1-(2-fluoro-4-nitrophenyl)piperidin-4-yl)piperazine-1-carboxylate

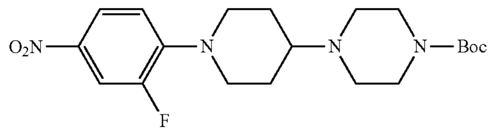 [SMILES: CC(C)(C)OC(=O)N1CCN(C2CCN(c3ccc([N+](=O)[O-])cc3F)CC2)CC1]

A mixture of 1,2-difluoro-4-nitrobenzene (500 mg, 3.1 mmol), tert-butyl 4-(piperidin-4-yl)piperazine-1-carboxylate (915 mg, 3.4 mmol) and $K_2CO_3$ (855 mg, 6.2 mmol) in DMF (15 mL) was stirred in a round bottom flask at 80° C. overnight. The reaction was cooled to room temperature, the mixture was poured into water (50 mL) and stirred for 10 mins. The solid was filtered and washed with water (30 mL×2), dried to give the product (750 mg, 58%). $[M+H]^+$=409.4.

Step 8: tert-butyl 4-(1-(4-amino-2-fluorophenyl) piperidin-4-yl)piperazine-1-carboxylate

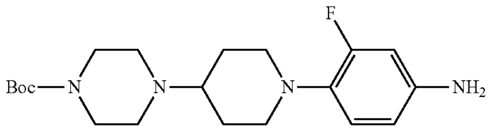 [SMILES: CC(C)(C)OC(=O)N1CCN(C2CCN(c3ccc(N)cc3F)CC2)CC1]

To a solution of tert-butyl 4-(1-(2-fluoro-4-nitrophenyl) piperidin-4-yl)piperazine-1-carboxylate (220 mg, 0.54 mmol) in MeOH (20 mL) was added 10% Pd/C (50 mg) at 25° C. And then the mixture was exchanged with $H_2$ two times and stirred under $H_2$ atmosphere at 25° C. for 2 h. The mixture was filtered through a pad of celite and washed with MeOH (20 mL). The filtrate was concentrated under vacuum to obtain the product (190 mg, 95%). $[M+H]^+$=378.2.

Step 9: 1-(methylsulfonyl)-7-nitroindoline

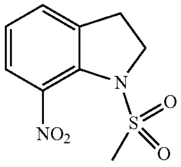 [SMILES: CS(=O)(=O)N1CCc2cccc([N+](=O)[O-])c21]

To a stirred solution of 7-nitroindoline (300 mg, 1.8 mmol) and NaH (146 mg, 3.6 mmol) in DMF (5 mL) was added methanesulfonyl chloride dropwise (315 mg, 2.7 mmol). The resulting mixture was stirred at room temperature for 1 hour. The reaction was quenched with saturated $NH_4C_1$ (aq.) solution and extracted with EtOAc (2×50 mL). The combined organic layer was washed with brine (2×50 mL), dried over $Na_2SO_4$ and concentrated under vacuum to afford the crude residue, which was purified with silica gel column chromatography (PE:EA=100:0~2:1 gradient elution) to give the title product (390 mg, 88%). $[M+H]^+$=243.1.

Step 10: 1-(methylsulfonyl)indolin-7-amine

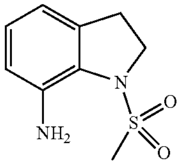

Under $N_2$, to a solution of 1-(methylsulfonyl)-7-nitroindoline (390 mg, 1.6 mmol) in MeOH (20 mL) was added 10% Pd/C (50 mg) at room temperature. And then the mixture was exchanged with $H_2$ two times and stirred under $H_2$ atmosphere at room temperature for 2 h. Reaction was monitored by LC-MS. The mixture was filtered through a pad of Celite and washed with MeOH (20 mL). The filtrate was concentrated under vacuum to obtain the title product (340 mg, 99%). $[M+H]^+$=213.1.

Step 11: 2-chloro-N-(1-(methylsulfonyl)indolin-7-yl)-7H-pyrrolo[2,3-d]pyrimidin-4-amine

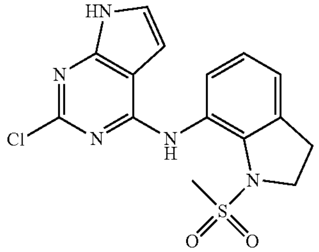 [SMILES: CS(=O)(=O)N1CCc2cccc(Nc3nc(Cl)nc4[nH]ccc34)c21]

To a solution of 1-(methylsulfonyl)indolin-7-amine (60 mg, 0.28 mmol) and 2,4-dichloro-5H-pyrrolo[3,2-d]pyrimidine (79 mg, 0.42 mmol) in i-PrOH (8 mL) was added conc. HCl (0.2 mL. The resulting mixture was heated at 80° C. overnight. The organic solvent was removed under reduced pressure, the residue was basified with saturated $NaHCO_3$ (aq.) solution and extracted with DCM (2×30 mL). The combined organic layer was dried over $Na_2SO_4$ and concentrated under vacuum to afford the crude residue, which was purified with silica gel column chromatography (PE: EA=100:0~1:1 gradient elution) to give the title product (100 mg, 97%). $[M+H]^+$=364.2.

Step 12: tert-butyl 4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazine-1-carboxylate

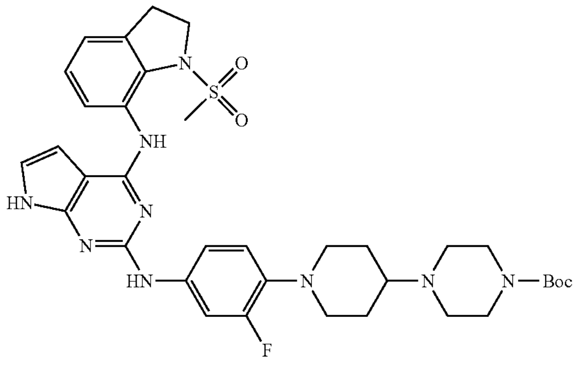 [SMILES: CC(C)(C)OC(=O)N1CCN(C2CCN(c3ccc(Nc4nc(Nc5cccc6c5N(S(C)(=O)=O)CC6)c5cc[nH]c5n4)cc3F)CC2)CC1]

A mixture of2-chloro-N-(1-(methylsulfonyl)indolin-7-yl)-7H-pyrrolo[2,3-d]pyrimidin-4-amine (40 mg, 0.11 mmol), tert-butyl 4-(1-(4-amino-2-fluorophenyl)piperidin-4-yl)piperazine-1-carboxylate (45 mg, 0.12 mmol), G3 BrettPhos Pd (10 mg, 0.011 mmol) and $Cs_2CO_3$ (72 mg, 0.22 mmol) in 1,4-dioxane (6 mL) was stirred in a round bottom flask at 100° C. overnight under $N_2$ atmosphere. The mixture was evaporated in vacuum to afford the crude product, which was purified by silica gel column chromatography (DCM:MeOH=100:0~5:1 gradient elution) to give the title product (60 mg, 78%). $[M+H]^+$=706.2.

Step 13: $N^2$-(3-fluoro-4-(4-(piperazin-1-yl)piperidin-1-yl)phenyl)-$N^4$-(1-(methylsulfonyl)indolin-7-yl)-7H-pyrrolo[2,3-d]pyrimidine-2,4-diamine

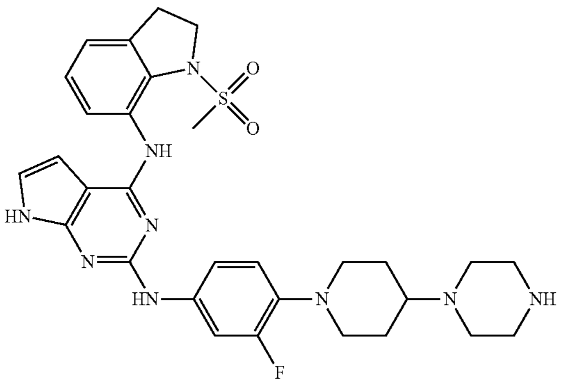 [SMILES: CS(=O)(=O)N1CCc2cccc(Nc3nc(Nc4ccc(N5CCC(N6CCNCC6)CC5)c(F)c4)nc4[nH]ccc34)c21]

A solution of tert-butyl 4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazine-1-carboxylate (750 mg, 1.06 mmol) in TFA/DCM=1/4 (5 mL) was stirred in a round bottom flask at room temperature for 2 h. The mixture was evaporated in vacuum to afford the crude product (610 mg, 95%), which was used for next step without further purification. $[M+H]^+$=606.4.

Step 14: 3-(2-fluoro-4-(2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)ethyl)phenyl)piperidine-2,6-dione

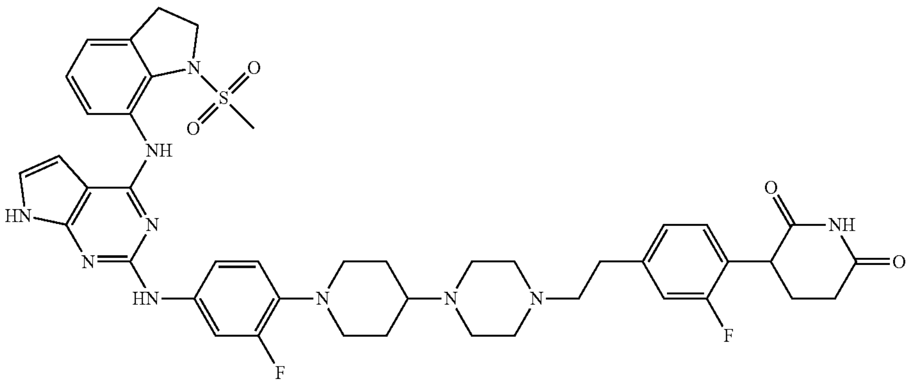 [SMILES: CS(=O)(=O)N1CCc2cccc(Nc3nc(Nc4ccc(N5CCC(N6CCN(CCc7ccc(C8CCC(=O)NC8=O)c(F)c7)CC6)CC5)c(F)c4)nc4[nH]ccc34)c21]

A mixture of $N^2$-(3-fluoro-4-(4-(piperazin-1-yl)piperidin-1-yl)phenyl)-$N^4$-(1-(methylsulfonyl)indolin-7-yl)-7H-pyrrolo[2,3-d]pyrimidine-2,4-diamine (40 mg, 0.066 mmol), 2-(4-(2,6-dioxopiperidin-3-yl)-3-fluorophenyl)acetaldehyde (17 mg, 0.069 mmol) and NaOAc (14 mg, 0.17 mmol) in chloromethane (4 mL) and EtOH (0.5 mL) was stirred in a flask at room temperature for 2 hour. The mixture was added $NaBH_3CN$ (10 mg, 0.17 mmol) and stirred in a flask at room temperature for another 2 h. Then the mixture was evaporated in vacuum to afford the crude product, which was purified with HPLC chromatography (0.1% FA in water: acetonitrile=90:10~50:50 gradient elution) to give the product (15 mg, 27%). $^1$H NMR (400 MHz, $CD_3OD$) δ 7.64 (s, 1H), 7.53 (s, 1H), 7.37 (s, 1H), 7.29 (s, 2H), 7.19-7.07 (m, 4H), 7.03 (s, 1H), 4.12 (s, 2H), 4.03 (d, J=7.9 Hz, 1H), 3.59 (d, 3H), 3.47 (s, 4H), 3.14-3.20 (m, 4H), 2.95 (s, 3H), 2.85-2.90 (m, 2H), 2.61-2.68 (s, 4H), 2.29 (s, 4H), 2.10-2.16 (m, 2H), 2.02-2.04 (m, 2H), 1.28 (s, 3H); $[M+H]^+$=839.4.

Example 1: 3-(4-(2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)ethyl)phenyl)piperidine-2,6-dione

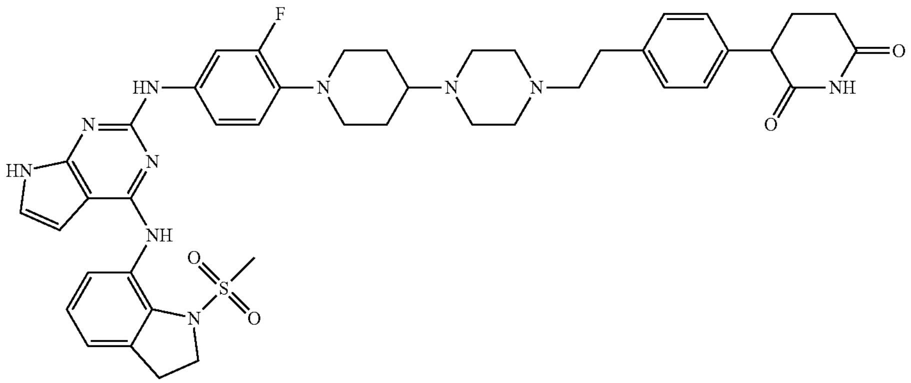 [SMILES: CS(=O)(=O)N1CCc2cccc(Nc3nc(Nc4ccc(N5CCC(N6CCN(CCc7ccc(C8CCC(=O)NC8=O)cc7)CC6)CC5)c(F)c4)nc4[nH]ccc34)c21]

The titled compound was prepared in a manner similar to that in Example 3. 1H NMR (400 MHz, DMSO) δ 11.60 (s, 1H), 10.84 (s, 1H), 9.44 (s, 1H), 8.09-7.72 (m, 2H), 7.24 (d, J=18.1 Hz, 6H), 7.02 (s, 2H), 6.34 (s, 1H), 4.10 (s, 2H), 3.84 (d, J=11.5 Hz, 6H), 3.61 (s, 2H), 3.30-3.21 (m, 2H), 3.12-3.18 (m, 3H), 3.10-2.88 (m, 7H), 2.68 (d, J=8.4 Hz, 4H), 2.54 (s, 1H), 2.19 (d, J=8.7 Hz, 3H), 2.03 (s, 1H), 1.90 (s, 2H), 1.23 (s, 2H); $[M+H]^+$=821.3.

Example 2: 3-(4-(2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)ethyl)-2-methoxyphenyl)piperidine-2,6-dione

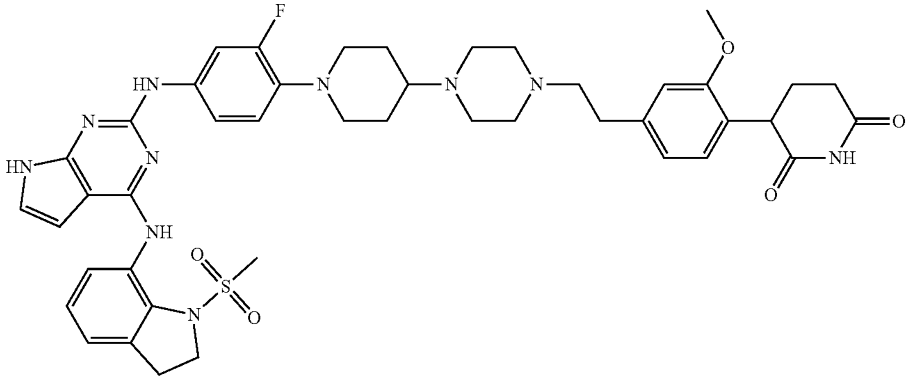 [SMILES: COc1cc(CCN2CCN(C3CCN(c4ccc(Nc5nc(Nc6cccc7c6N(S(C)(=O)=O)CC7)c6cc[nH]c6n5)cc4F)CC3)CC2)ccc1C1CCC(=O)NC1=O]

The titled compound was prepared in a manner similar to that in Example 3. $^1$H NMR (400 MHz, DMSO) δ 11.34 (s, 1H), 10.73 (s, 1H), 9.04 (s, 1H), 8.94 (s, 1H), 8.30 (d, J=6.7 Hz, 1H), 7.87 (d, J=15.1 Hz, 1H), 7.31 (d, J=9.1 Hz, 1H), 7.25 (s, 1H), 7.14 (s, 1H), 7.04-6.94 (m, 2H), 6.92 (d, J=14.8 Hz, 2H), 6.77 (d, J=7.4 Hz, 1H), 6.21 (s, 1H), 4.11 (s, 2H), 3.86 (s, 1H), 3.73 (s, 3H), 3.16-3.07 (m, 6H), 3.03-2.91 (m, 2H), 2.76-2.54 (m, 13H), 2.43-2.45 (m, 1H), 2.31-2.33 (m, 2H), 2.23-2.10 (m, 1H), 1.93-1.81 (m, 3H), 1.64-1.49 (m, 2H); $[M+H]^+$=851.2.

Example 4: 3-(4-(3-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)propoxy)phenoxy)piperidine-2,6-dione Step 1: 4-(3-((tert-butyldimethylsilyl)oxy)propoxy)phenol

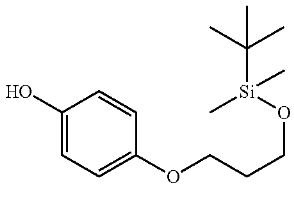 [SMILES: CC(C)(C)[Si](C)(C)OCCCOc1ccc(O)cc1]

Hydroquinone (10.6 g, 96.1 mmol) was dissolved in DMF (100 mL). The solution was added (3-bromopropoxy)(tert-butyl)dimethylsilane (23.0 g, 91 mmol) and $Cs_2CO_3$ (45.0 g, 138.1 mmol). The mixture was stirred at 50° C. for 2 h. The mixture was diluted with water (100 mL), extracted with EA (150 mL×2). The combined organic lays were washed with water (50 mL×3) and brine (50 mL×2), dried over $Na_2SO_4$ and concentrated under reduced pressure, the residue was purified by column chromatography to obtain the product (8.5 g, 31.3%). $[M+H]^+$=283.2.

Step 2: 3-bromopiperidine-2,6-dione

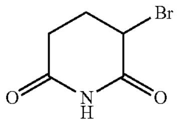

$Br_2$ (25.4 g, 158 mmol) was added to a solution of piperidine-2,6-dione (15.0 g, 132 mmol) in $CHCl_3$ (30 mL), the mixture is stirred for 4 h at 110° C. After cooling, the mixture was added water (200 mL), extracted with EA (200 mL×2). The combined organic lays were washed with water (100 mL) and brine (100 mL), dried over $Na_2SO_4$ and concentrated under reduced pressure. The residue was purified by column chromatography to give the product (7.9 g, 31%). $[M+H]^+$=192.2.

Step 3: 3-(4-(3-((tert-butyldimethylsilyl)oxy)propoxy)phenoxy)piperidine-2,6-dione

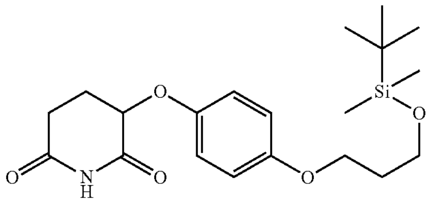 [SMILES: CC(C)(C)[Si](C)(C)OCCCOc1ccc(OC2CCC(=O)NC2=O)cc1]

4-(3-((Tert-butyldimethylsilyl)oxy)propoxy)phenol (22.1 g, 78.1 mmol) was dissolved in THF (100 mL). The solution was added NaH (4.7 g, 60%, 117.2 mmol) at 0° C., the resulting mixture was stirred for 1 h. Then the mixture was dropped into a solution of 3-bromopiperidine-2,6-dione (15.0 g, 78.1 mmol) in THF (100 mL). The mixture was stirred at 60° C. for 2 h, then added saturated aqueous solution of $NH_4Cl$ (100 mL) at 0° C., extracted with EA (100 mL×4). The combined organic phases were washed with water (50 mL×2) and brine (50 mL×2), dried over $Na_2SO_4$ and concentrated under reduced pressure. The residue was purified by column chromatography to give the product (14.5 g, 47%). $[M+H]^+$=394.2.

Step 4: 3-(4-(3-hydroxypropoxy)phenoxy)piperidine-2,6-dione

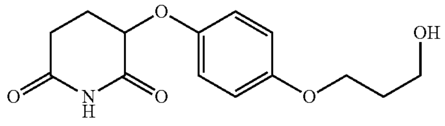 [SMILES: O=C1CCC(Oc2ccc(OCCCO)cc2)C(=O)N1]

3-(4-(3-((Tert-butyldimethylsilyl)oxy)propoxy)phenoxy)piperidine-2,6-dione (19.0 g, 48.3 mmol) was dissolved in THF (200 mL), was added TBAF (1M in THF) (72.5 mL, 72.5 mmol), the mixture was stirred at 25° C. for 5 h. The mixture was added water (100 mL), extracted with EA (150 mL×2). The combined organic phases were washed with water (100 mL) and brine (100 mL), dried over $Na_2SO_4$ and concentrated under reduced pressure. The residue was purified by column chromatography) to give the product (5.3 g, 39.3%). $^1H$ NMR (400 MHz, DMSO) $\delta_H$ 10.89 (s, 1H), 6.94 (d, J=9.1 Hz, 2H), 6.84 (d, J=9.1 Hz, 2H), 5.02 (dd, J=10.5, 4.9 Hz, 1H), 4.51 (t, J=5.1 Hz, 1H), 3.97 (t, J=6.4 Hz, 2H), 3.56-3.52 (m, 2H), 2.76-2.54 (m, 2H), 2.23-2.02 (m, 2H), 1.88-1.79 (m, 2H); $[M+H]^+$=280.2.

Step 5: 3-(4-((2,6-dioxopiperidin-3-yl)oxy)phenoxy)propyl methanesulfonate

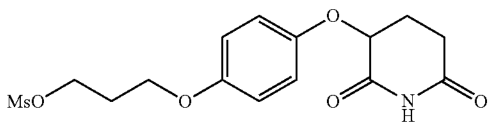 [SMILES: CS(=O)(=O)OCCCOc1ccc(OC2CCC(=O)NC2=O)cc1]

3-(4-(3-hydroxypropoxy)phenoxy)piperidine-2,6-dione (279 mg, 1.0 mmol), triethylamine (202 mg, 2.0 mmol) were dissolved in THF (5 mL), was added methanesulfonyl chloride (136.1.25 mg, 1.2 mmol), the mixture was stirred at 25° C. for 2 h. The mixture was added water (10 mL), extracted with EA (15 mL×2). The combined organic phases were washed with water (10 mL) and brine (10 mL), dried over $Na_2SO_4$ and concentrated under reduced pressure. The residue was purified by column chromatography) to give the product (200 mg, 56%). $[M+H]^+$=358.2.

Step 6: 3-(4-(3-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)propoxy)phenoxy)piperidine-2,6-dione

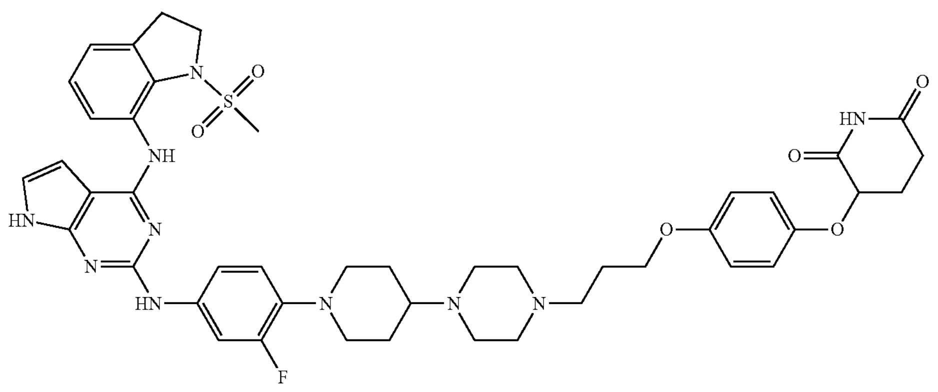 [SMILES: CS(=O)(=O)N1CCc2cccc(Nc3nc(Nc4ccc(N5CCC(N6CCN(CCCOc7ccc(OC8CCC(=O)NC8=O)cc7)CC6)CC5)c(F)c4)nc4[nH]ccc34)c21]

A mixture of $N^2$-(3-fluoro-4-(4-(piperazin-1-yl)piperidin-1-yl)phenyl)-$N^4$-(1-(methylsulfonyl)indolin-7-yl)-7H-pyrrolo[2,3-d]pyrimidine-2,4-diamine (34 mg, 0.057 mmol), 3-(4-((2,6-dioxopiperidin-3-yl)oxy)phenoxy)propyl methanesulfonate (24 mg, 0.069 mmol), KI (11.6 mg, 0.069 mmol) and DIEA (14.7 mg, 0.114 mmol) in acetonitrile (4 mL) was stirred in a round bottom flask at 75° C. for 12 hours. The reaction was quenched with water and the mixture was extracted with DCM, washed triple times with saturated brine, dried over anhydrous $Na_2SO_4$. After filtration, the filtrate was concentrated under reduced pressure. The residue was purified by HPLC chromatography to give the product (10 mg, 20%). $^1H$ NMR (400 MHz, DMSO) δ 11.32 (s, 1H), 10.90 (s, 1H), 9.03 (s, 1H), 8.92 (s, 1H), 8.30 (d, J=8.0 Hz, 1H), 7.86 (d, J=15.5 Hz, 1H), 7.35-7.20 (m, 2H), 7.12 (d, J=7.2 Hz, 1H), 7.02-6.77 (m, 5H), 6.21 (s, 1H), 5.10-4.96 (m, 1H), 4.11 (s, 2H), 3.94 (s, 2H), 3.18-2.83 (m, 8H), 2.75-2.54 (m, 8H), 2.45-2.24 (m, 5H), 2.23-2.00 (m, 2H), 1.95-1.76 (m, 4H), 1.65-1.47 (m, 2H); $[M+H]^+$=867.5.

Example 5: 3-(3-(2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)ethoxy)phenyl)piperidine-2,6-dione

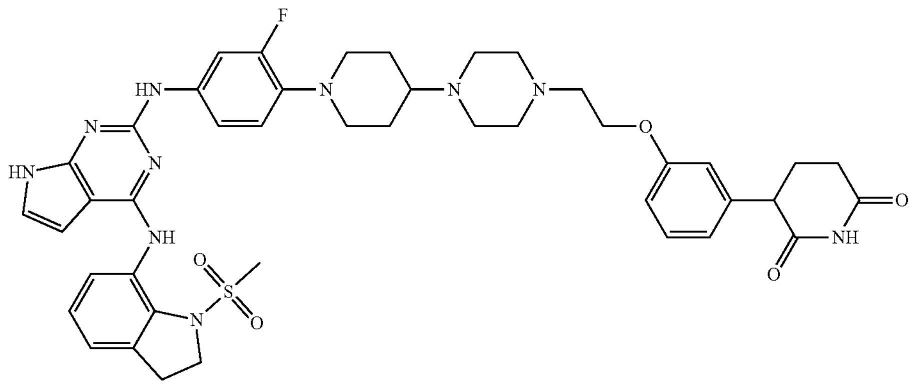 [SMILES: CS(=O)(=O)N1CCc2cccc(Nc3nc(Nc4ccc(N5CCC(N6CCN(CCOc7cccc(C8CCC(=O)NC8=O)c7)CC6)CC5)c(F)c4)nc4[nH]ccc34)c21]

The titled compound was prepared in a manner similar to that in Example 1. $^1$H NMR (400 MHz, DMSO) δ 11.32 (s, 1H), 10.83 (s, 1H), 9.03 (s, 1H), 8.92 (s, 1H), 8.30 (d, J=7.8 Hz, 1H), 7.86 (d, J=14.8 Hz, 1H), 7.27-7.81 (m, 3H), 7.12 (d, J=6.8 Hz, 1H), 7.01-6.75 (m, 5H), 6.21 (s, 1H), 4.08-4.11 (m, 4H), 3.81 (s, 1H), 3.28-3.21 (m, 3H), 3.17-3.07 (m, 6H), 3.04-2.87 (m, 2H), 2.74-2.52 (m, 10H), 2.32-2.14 (m, 2H), 2.10-1.92 (m, 1H), 1.95-1.75 (m, 2H), 1.65-1.47 (m, 2H); $[M+H]^+$=837.

Example 6: 3-(3-((2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)ethyl)(methyl)amino)phenyl)piperidine-2,6-dione

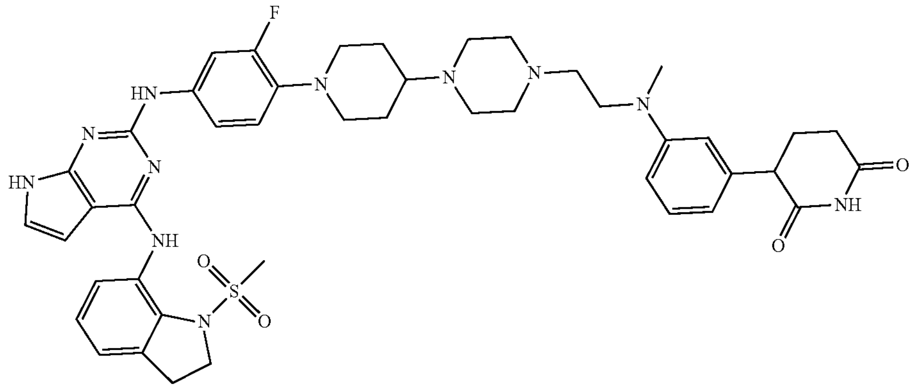 [SMILES: CN(CCN1CCN(C2CCN(c3ccc(Nc4nc(Nc5cccc6c5N(S(C)(=O)=O)CC6)c5cc[nH]c5n4)cc3F)CC2)CC1)c1cccc(C2CCC(=O)NC2=O)c1]

The titled compound was prepared in a manner similar to that in Example 1. $^1$H NMR (400 MHz, DMSO) δ 11.32 (s, 1H), 10.80 (s, 1H), 9.02 (s, 1H), 8.92 (s, 1H), 8.30 (d, J=8.0 Hz, 1H), 7.86 (d, J=15.8 Hz, 1H), 7.35-7.20 (m, 2H), 7.16-7.05 (m, 2H), 6.92-6.95 (m, 2H), 6.61-6.50 (m, 2H), 6.44 (d, J=7.1 Hz, 1H), 6.21 (s, 1H), 4.11 (s, 2H), 3.74 (s, 1H), 3.42 (s, 3H), 3.11 (m, 6H), 3.05-2.92 (m, 2H), 2.88 (s, 3H), 2.62-2.65 (m, 4H), 2.44-2.48 (m, 5H), 2.35-1.95 (m, 4H), 1.83-1.86 (m, 2H), 1.56-1.58 (m, 2H), 1.24 (s, 2H); $[M+H]^+$=850.

Example 8: 3-(4-(4-(2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)ethyl)piperidin-1-yl)phenyl)piperidine-2,6-dione Step 1: 2,6-bis(benzyloxy)-3-(4-bromophenyl)pyridine

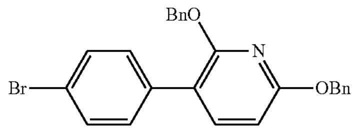 [SMILES: Brc1ccc(-c2ccc(OCc3ccccc3)nc2OCc2ccccc2)cc1]

To a stirred mixture of 2,6-bis(benzyloxy)-3-(4,4,5,5-tetramethyl-1,3,2-dioxaborolan-2-yl)pyridine (The intermediate can be prepared according to the way described in WO2017197046) (25 g, 59.9 mmol) and 4-bromoiodobenzene (20.3 g, 71.9 mmol) in dioxane (250 mL) and $H_2O$ (50 mL) were added $K_2CO_3$ (16.6 g, 120 mmol) and Pd(dppf)$Cl_2$ (4.4 g, 6.0 mmol) at room temperature under nitrogen atmosphere. The resulting mixture was stirred for 16 h at 80° C. under nitrogen atmosphere. The reaction mixture was allowed to cool down to room temperature. The resulting mixture was extracted with EtOAc (3x500 mL). The combined organic layers were washed with brine (500 mL), dried over anhydrous $Na_2SO_4$. After filtration, the filtrate was concentrated under reduced pressure. The residue was purified by silica gel column chromatography, eluted with PE/EtOAc (10:1) to afford the product (23 g, 86%); $[M+H]^+$=446.2.

Step 2: ethyl 2-(1-[4-[2,6-bis(benzyloxy)pyridin-3-yl]phenyl]piperidin-4-yl)acetate

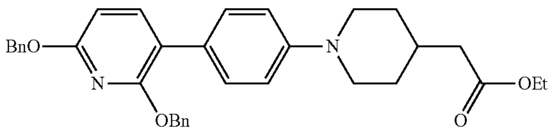 [SMILES: CCOC(=O)CC1CCN(c2ccc(-c3ccc(OCc4ccccc4)nc3OCc3ccccc3)cc2)CC1]

To a stirred solution of 2,6-bis(benzyloxy)-3-(4-bromophenyl)pyridine (15 g, 33.6 mmol) and ethyl 2-(piperidin-4-yl)acetate (8.6 g, 50.4 mmol) in 2-methyl-THF (150 mL) and $H_2O$ (15 mL) were added $Cs_2CO_3$ (32.9 g, 100.8 mmol), DavePhos (2.7 g, 6.7 mmol) and Pd2(dba)$_3$ (3.1 g, 3.4 mmol) at room temperature under nitrogen atmosphere. The resulting mixture was stirred for 16 h at 100° C. under nitrogen atmosphere. The mixture was allowed to cool down to room temperature. The resulting mixture was concentrated under reduced pressure. The residue was diluted with EtOAc (500 mL), washed with water (3x200 mL) and brine (200 mL). The organic layer was dried over anhydrous $Na_2SO_4$. After filtration, the filtrate was concentrated under reduced pressure. The residue was purified by silica gel column chromatography, eluted with PE/EtOAc (1:1) to afford the product (14 g, 78%); $[M+H]^+$=537.3.

Step 3: 2-(1-(4-(2,6-bis(benzyloxy)pyridin-3-yl)phenyl)piperidin-4-yl)ethan-1-ol

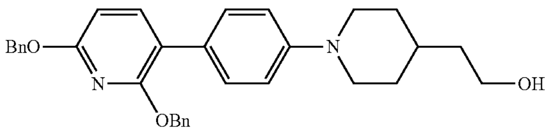 [SMILES: OCCC1CCN(c2ccc(-c3ccc(OCc4ccccc4)nc3OCc3ccccc3)cc2)CC1]

To a stirred solution of ethyl 2-(1-[4-[2,6-bis(benzyloxy)pyridin-3-yl]phenyl]piperidin-4-yl)acetate (13 g, 24.2 mmol) in THF (130 mL) was added $LiAlH_4$ (1 g, 26.6 mmol) in portions at 0° C. The resulting mixture was stirred for 2 h at room temperature. The reaction was quenched by the addition of water/ice (50 mL) at 0° C. The resulting mixture was extracted with EtOAc (3×50 mL). The combined organic layers were washed with brine (50 mL), dried over anhydrous $Na_2SO_4$. After filtration, the filtrate was concentrated under reduced pressure. The residue was purified by silica gel column chromatography, eluted with PE/EtOAc (1:1) to afford the product (11 g, 92%); $[M+H]^+$=495.3.

Step 4: 3-(4-(4-(2-hydroxyethyl)piperidin-1-yl)phenyl)piperidine-2,6-dione

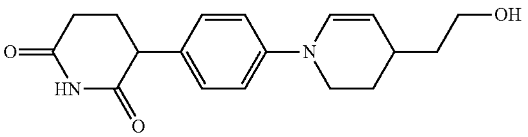 [SMILES: O=C1CCC(c2ccc(N3C=CC(CCO)CC3)cc2)C(=O)N1]

To a stirred solution of 2-(1-(4-(2,6-bis(benzyloxy)pyridin-3-yl)phenyl)piperidin-4-yl)ethan-1-ol (10.5 g, 21.2 mmol) in EtOH (100 mL), EtOAc (100 mL) and DCM (20 mL) was added Pd/C (wet, 10%) (5 g) under nitrogen atmosphere. The resulting mixture was stirred for 16 h at room temperature under hydrogen atmosphere. The resulting mixture was filtered, the filter cake was washed with DCM/$CH_{30}H$ (10:1, 200 mL). The filtrate was concentrated under reduced pressure. The residue was purified by silica gel column chromatography, eluted with MeOH/DCM (1:10) to afford the product (5.1 g, 76%). $[M+H]^+$=317.1.

Step 5: 2-(1-(4-(2,6-dioxopiperidin-3-yl)phenyl)piperidin-4-yl)acetaldehyde

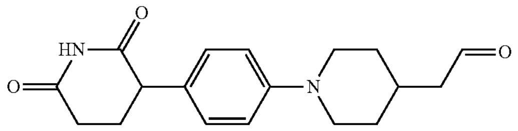 [SMILES: O=CCC1CCN(c2ccc(C3CCC(=O)NC3=O)cc2)CC1]

A mixture of 3-(4-(4-(2-hydroxyethyl)piperidin-1-yl)phenyl)piperidine-2,6-dione (100 mg, 0.32 mmol) and IBX (132 mg, 0.47 mmol) in DMSO (10 mL) was stirred in a flask at room temperature overnight. The reaction was quenched with water and the mixture was extracted with EtOAc, washed three times with saturated aqueous NaCl and twice with saturated aqueous $NaHCO_3$. The organic layer was dried over anhydrous $Na_2SO_4$ and evaporated in vacuum to afford the product (70 mg, 70%). $[M+H]^+$=315.2.

Step 6: 3-(4-(4-(2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)ethyl)piperidin-1-yl)phenyl)piperidine-2,6-dione

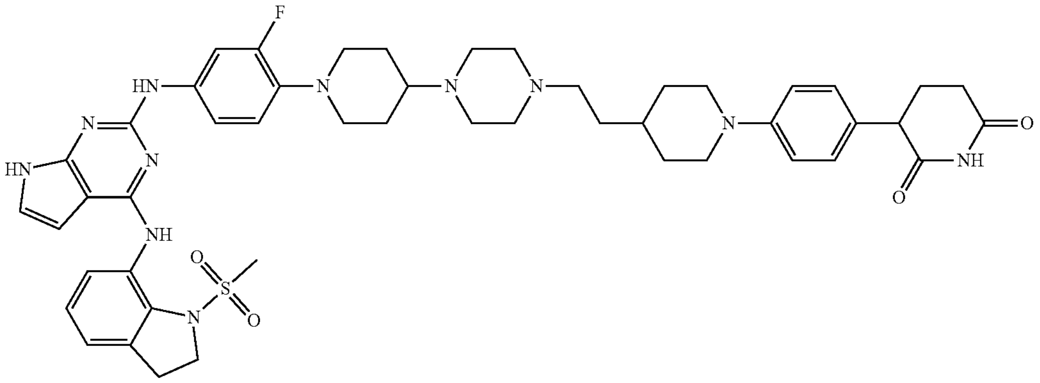

The titled compound was prepared in a manner similar to that in Example 3. $^1H$ NMR (400 MHz, DMSO) δ 11.32 (s, 1H), 10.77 (s, 1H), 9.03 (s, 1H), 8.92 (s, 1H), 8.30 (d, J=8.3 Hz, 1H), 7.86 (d, J=14.7 Hz, 1H), 7.28-7.30 (m, 2H), 7.13 (s, 1H), 7.03 (d, J=8.7 Hz, 2H), 6.91-6.95 (m, 4H), 6.21 (s, 1H), 4.16-4.06 (m, 2H), 3.75-3.61 (m, 3H), 3.20-3.03 (m, 6H), 2.73-2.54 (m, 10H), 2.49-2.21 (m, 7H), 2.20-2.06 (m, 1H), 2.05-1.95 (m, 1H), 1.89-1.80 (m, 2H), 1.79-1.68 (m, 2H), 1.63-1.51 (m, 2H), 1.47-1.35 (m, 3H), 1.30-1.17 (m, 3H); $[M+H]^+$=904.2.

Example 9: 3-(2-fluoro-4-(4-(2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)ethyl)piperidin-1-yl)phenyl)piperidine-2,6-dione

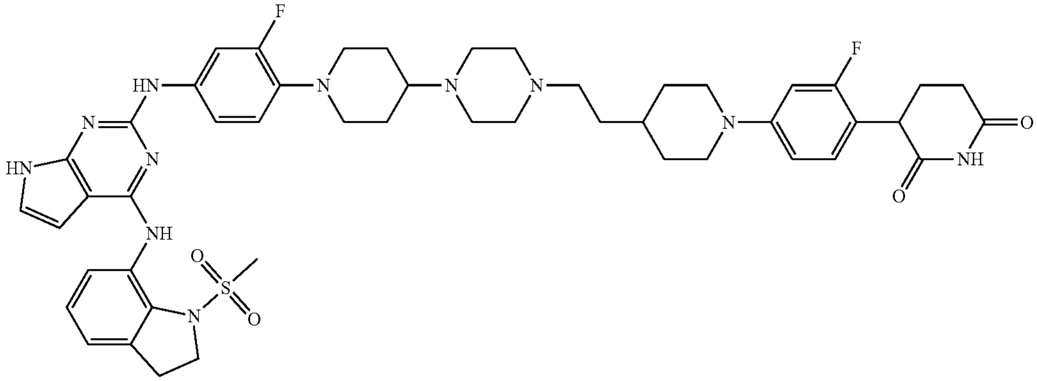 [SMILES: CS(=O)(=O)N1CCc2cccc(Nc3nc(Nc4ccc(N5CCC(N6CCN(CCC7CCN(c8ccc(C9CCC(=O)NC9=O)c(F)c8)CC7)CC6)CC5)c(F)c4)nc4[nH]ccc34)c21]

The titled compound was prepared in a manner similar to that in Example 3. $^1$H NMR (400 MHz, DMSO) δ 11.31 (s, 1H), 10.79 (s, 1H), 9.02 (s, 1H), 8.90 (s, 1H), 8.29 (d, J=7.3 Hz, 1H), 7.86 (d, J=16.9 Hz, 1H), 7.31 (d, J=7.7 Hz, 1H), 7.24 (t, J=7.8 Hz, 1H), 7.12 (d, J=7.0 Hz, 1H), 7.04 (d, J=8.5 Hz, 1H), 6.92 (m, 2H), 6.70 (d, J=10.8 Hz, 2H), 6.21 (s, 1H), 4.10 (s, 2H), 3.87 (d, J=7.8 Hz, 1H), 3.69 (d, J=11.7 Hz, 2H), 3.17-3.06 (m, 6H), 2.73-2.55 (m, 8H), 2.43-2.25 (m, 6H), 2.22-2.05 (m, 2H), 2.00-1.90 (m, 1H), 1.83 (s, 2H), 1.73 (d, J=11.5 Hz, 2H), 1.61-1.51 (m, 2H), 1.48-1.32 (m, 4H), 1.29-1.14 (m, 4H); $[M+H]^+$=922.3.

Example 10: 2-(2,6-dioxopiperidin-3-yl)-5-(4-(2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)ethyl)piperidin-1-yl)benzonitrile

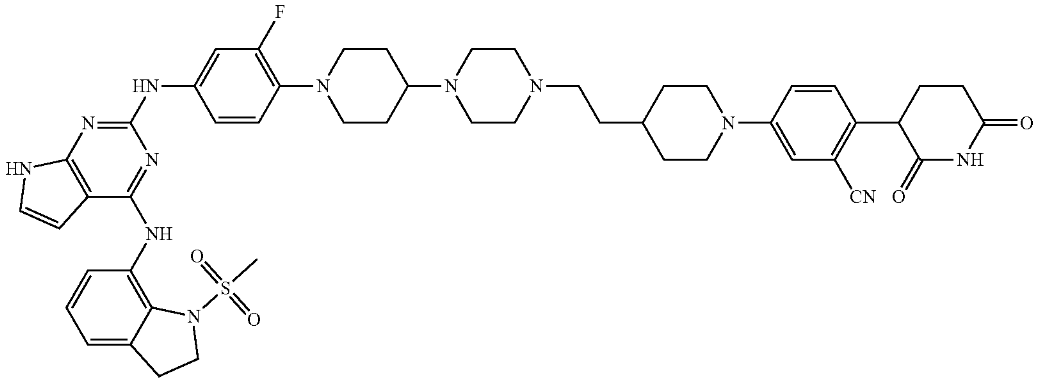 [SMILES: CS(=O)(=O)N1CCc2cccc(Nc3nc(Nc4ccc(N5CCC(N6CCN(CCC7CCN(c8ccc(C9CCC(=O)NC9=O)c(C#N)c8)CC7)CC6)CC5)c(F)c4)nc4[nH]ccc34)c21]

The titled compound was prepared in a manner similar to that in Example 3. $^1$H NMR (400 MHz, DMSO) δ 11.33 (s, 1H), 10.92 (s, 1H), 9.03 (s, 1H), 8.92 (s, 1H), 8.30 (d, J=8.1 Hz, 1H), 7.86 (d, J=15.3 Hz, 1H), 7.35-7.19 (m, 5H), 7.12 (d, J=7.2 Hz, 1H), 6.92-6.95 (m, 2H), 6.21 (s, 1H), 4.10 (d, J=7.2 Hz, 2H), 3.99 (dd, J=12.5, 4.6 Hz, 1H), 3.77 (d, J=12.1 Hz, 2H), 3.18-3.07 (m, 6H), 2.85-2.53 (m, 10H), 2.44-2.22 (m, 8H), 2.01-2.05 (m, 1H), 1.88-1.80 (m, 2H), 1.78-1.70 (m, 2H), 1.63-1.34 (m, 5H), 1.27-1.15 (m, 3H); $[M+H]^+$=929.2.

Example 11: 3-(4-(1-(3-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)-3-oxopropyl)piperidin-4-yl)phenyl)piperidine-2,6-dione

Step 1: tert-butyl 4-(4-(2,6-bis(benzyloxy)pyridin-3-yl)phenyl)piperidine-1-carboxylate

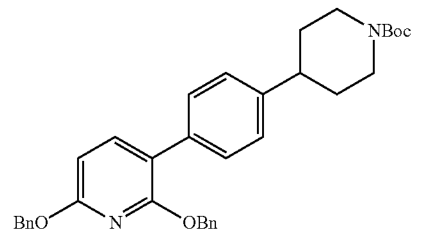 [SMILES: CC(C)(C)OC(=O)N1CCC(c2ccc(-c3ccc(OCc4ccccc4)nc3OCc3ccccc3)cc2)CC1]

Tert-butyl 4-(4-(4,4,5,5-tetramethyl-1,3,2-dioxaborolan-2-yl)phenyl)piperidine-1-carboxylate (17 g, 44 mmol), Pd(dppf)$Cl_2$ (3.2 g, 4.4 mmol), 2,6-bis(benzyloxy)-3-bromopyridine (16.2 g, 44.0 mmol), $Cs_2CO_3$ (28.7 g, 88 mmol) were placed in dioxane/water (300 mL, 10:1). The mixture was stirred at 100° C. for overnight until LC-MS indicated all the starting material was consumed. The resulting solution was filtered and the filtrate was concentrated to afford the crude residue which was purified by $SiO_2$-gel column (eluted with EtOAc/Hexane=1:1) to give the desired product (5 g, 21%). $[M+H]^+$=551.3.

Step 2: tert-butyl 4-(4-(2,6-dioxopiperidin-3-yl)phenyl)piperidine-1-carboxylate

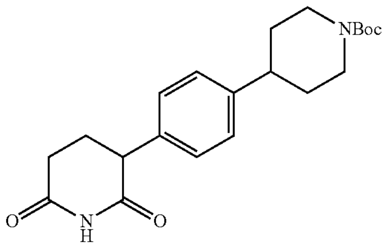 [SMILES: CC(C)(C)OC(=O)N1CCC(c2ccc(C3CCC(=O)NC3=O)cc2)CC1]

Tert-butyl 4-(4-(2,6-bis(benzyloxy)pyridin-3-yl)phenyl)piperidine-1-carboxylate (5 g, 9.1 mmol) was dissolved in MeOH (50 mL), Pd/C (10%, w/w, 0.5 g) was added to the solution in one portion. The resulting mixture was stirred under $H_2$ atmosphere overnight until LC-MS indicated all the starting material was consumed. The resulting solution was filtered and the filtrate was concentrated to give the desired product (1.9 g, 56.1%). $[M+H]^+$=373.

Step 3: 3-(4-(piperidin-4-yl)phenyl)piperidine-2,6-dione hydrochloride

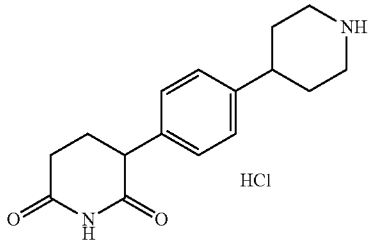 [SMILES: O=C1CCC(c2ccc(C3CCNCC3)cc2)C(=O)N1 ; Cl]

Tert-butyl 4-(4-(2,6-dioxopiperidin-3-yl)phenyl)piperidine-1-carboxylate (1.9 g, 5.1 mmol) was placed in HCl-dixoane (4M, 20 mL), the mixture was stirred at room temperature for 2 h until LC-MS indicated all the starting material was consumed. The resulting solution was concentrated to afford the crude residue which was triturated with MTBE (5 mL) to afford the desired product (1.38 g, 88%). $[M+H]^+$=273.2.

Step 4: tert-butyl 3-(4-(4-(2,6-dioxopiperidin-3-yl)phenyl)piperidin-1-yl)propanoate

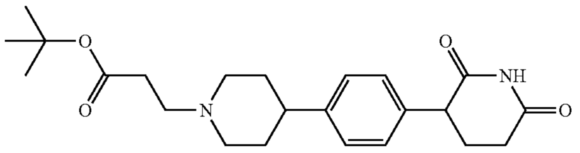 [SMILES: CC(C)(C)OC(=O)CCN1CCC(c2ccc(C3CCC(=O)NC3=O)cc2)CC1]

A mixture of 3-(4-(piperidin-4-yl)phenyl)piperidine-2,6-dione hydrochloride (228 mg, 0.74 mmol), tert-butyl acrylate (189 mg, 1.48 mmol) and DIEA (189 mg, 1.48 mmol) in MeCN (8 mL) was stirred in a flask at 80° C. overnight. The mixture was evaporated in vacuum to afford the crude product, which was further purified with silica gel column chromatography (DCM:MeOH=100:0~10:1 gradient elution) to give the product (178 mg, 60%); $[M+H]^+$=401.2.

Step 5: 3-(4-(4-(2,6-dioxopiperidin-3-yl)phenyl)piperidin-1-yl)propanoic acid

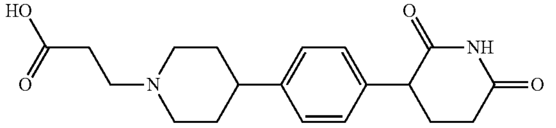 [SMILES: O=C(O)CCN1CCC(c2ccc(C3CCC(=O)NC3=O)cc2)CC1]

A solution of tert-butyl 3-(4-(4-(2,6-dioxopiperidin-3-yl)phenyl)piperidin-1-yl)propanoate (178 mg, 0.45 mmol) in HCl/1,4-dioxane (8 mL) was stirred in a flask at room temperature overnight. The mixture was evaporated in vacuum to afford the crude product (150 mg, 97%), which was used for next step without further purification. $[M+H]^+$=345.4.

Step 6: 3-(4-(1-(3-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)-3-oxopropyl)piperidin-4-yl)phenyl)piperidine-2,6-dione

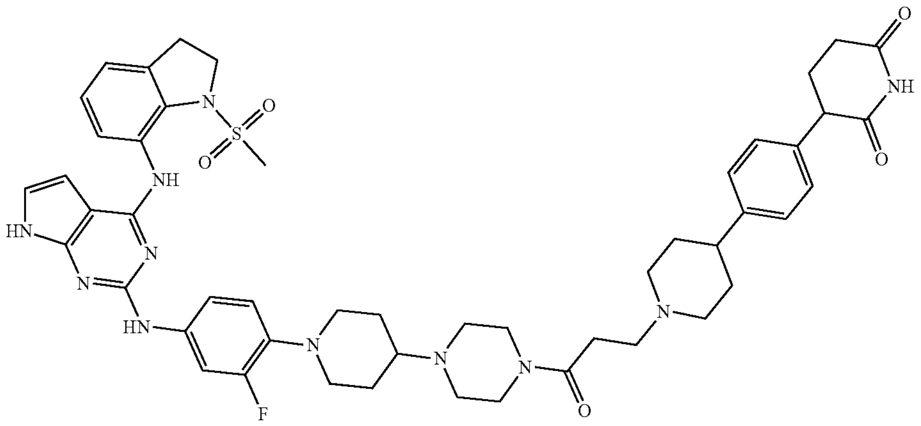 [SMILES: CS(=O)(=O)N1CCc2cccc(Nc3nc(Nc4ccc(N5CCC(N6CCN(C(=O)CCN7CCC(c8ccc(C9CCC(=O)NC9=O)cc8)CC7)CC6)CC5)c(F)c4)nc4[nH]ccc34)c21]

To a solution of 3-(4-(4-(2,6-dioxopiperidin-3-yl)phenyl) piperidin-1-yl)propanoic acid (24 mg, 0.069 mmol), HATU (27 mg, 0.073 mmol) and DIEA (34 mg, 0.264 mmol) in DMF (4 mL) was added $N^2$-(3-fluoro-4-(4-(piperazin-1-yl) piperidin-1-yl)phenyl)-$N^4$-(1-(methylsulfonyl)indolin-7-yl)-7H-pyrrolo[2,3-d]pyrimidine-2,4-diamine (40 mg, 0.066 mmol). The resulting mixture was stirred at room temperature for 5 h. The reaction was quenched with water and the mixture was extracted with DCM. The organic phase was washed with saturated brine, dried over anhydrous $Na_2SO_4$. After filtration, the filtrate was concentrated under reduced pressure, the residue was purified by Pre-HPLC (0.1% FA in water:acetonitrile=90:10~50:50 gradient elution) to give the title product (13.6 mg, 22%). 1H NMR (400 MHz, DMSO) δ 11.32 (s, 1H), 10.81 (s, 1H), 9.02 (s, 1H), 8.92 (s, 1H), 8.30 (d, J=7.9 Hz, 1H), 8.23 (s, 1H), 7.86 (d, J=15.7 Hz, 1H), 7.32 (d, J=8.5 Hz, 1H), 7.28-7.18 (m, 3H), 7.13 (d, J=7.7 Hz, 3H), 6.98-6.87 (m, 2H), 6.21 (s, 1H), 4.11 (s, 2H), 3.80 (d, J=6.8 Hz, 1H), 3.45 (s, 6H), 3.31-3.25 (m, 5H), 3.13 (s, 3H), 3.09 (s, 3H), 2.99 (d, J=10.7 Hz, 2H), 2.59 m, 3H), 2.48-2.42 (m, 3H), 2.35 (s, 1H), 2.16 (d, J=10.5 Hz, 1H), 2.10-2.00 (m, 3H), 1.83 (d, J=11.2 Hz, 2H), 1.74 (d, J=11.3 Hz, 2H), 1.62 (m, 4H); $[M+H]^+$=932.8.

Example 12: 3-(4-(4-(2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl) piperazin-1-yl)-2-oxoethyl)piperidin-1-yl)phenyl) piperidine-2,6-dione Step 1: 4-(2,6-bis(benzyloxy)pyridin-3-yl)aniline

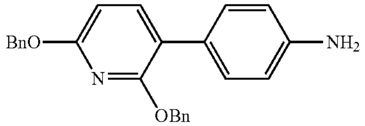 [SMILES: Nc1ccc(-c2ccc(OCc3ccccc3)nc2OCc2ccccc2)cc1]

2,6-bis(benzyloxy)-3-bromopyridine (58.0 g, 156.7 mmol), 4-aminophenylboronic acid pinacol ester (44.6 g, 203.7 mmol), $K_2CO_3$ (65.0 g, 470.0 mmol) and Pd(dppf)$Cl_2$ (11.5 g, 15.7 mmol) were added to the reaction flask, the mixture was degassed and purged with nitrogen for three times. Next 1.4-dioxane (1 L) and water (300 mL) were added to the reaction flask, and nitrogen was recharged three times again, the reaction was heated to reflux. After stirring for three hours, the reaction was cooled to room temperature, extracted with EtOAc (500 mL×3), the combined organic phases were washed with water and brine, dried and concentrated. 4-(2,6-bis(benzyloxy)pyridin-3-yl)aniline (57.3 g, 95.6%) was obtained after column separation (petroleum ether:ethyl acetate=10:1). $^1$H NMR (400 MHz, $CDCl_3$) δ 7.57 (d, J=8.0 Hz, 1H), 7.50-7.27 (m, 12H), 6.72 (d, J=8.5 Hz, 2H), 6.45 (d, J=8.0 Hz, 1H), 5.43 (s, 2H), 5.36 (s, 2H), 3.68 (s, 2H); $[M+H]^+$=383.2.

Step 2: 2,6-bis(benzyloxy)-3-(4-iodophenyl)pyridine

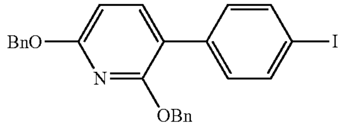 [SMILES: Ic1ccc(-c2ccc(OCc3ccccc3)nc2OCc2ccccc2)cc1]

p-Toluenesulfonic acid monohydrate (106.0 g, 557 mmol) was added to tert-Butanol (800 mL). 4-(2,6-bis(benzyloxy) pyridin-3-yl)aniline (78.5 g, 205 mmol) was dissolved in MeCN (400 mL) and added to the system, and the mixture was stirred at room temperature. $NaNO_2$ (28.3 g, 404 mmol) and KI (85.2 g, 513.1 mmol) in water (400 mL) was added. Then system was stirred at room temperature. After stirred for 1.5 h, the mixture was diluted with water (1.5 L), and pH was adjusted to 10 with 2M sodium hydroxide solution. 2M sodium thiosulfate solution (1 L) was added to the mixture, extracted with DCM (1 L×3). The combined organic phases were washed with water and brine, dried and concentrated. The residue was purified with silica gel column (petroleum ether:ethyl acetate=100:1) to obtain 2,6-bis(benzyloxy)-3-(4-iodophenyl)pyridine (31.2 g, 30.8%). $^1$H NMR (400

MHz, $CDCl_3$) δ 7.70 (d, J=8.4 Hz, 2H), 7.57 (d, J=8.1 Hz, 1H), 7.47-7.28 (m, 12H), 6.48 (d, J=8.1 Hz, 1H), 5.41 (s, 2H), 5.37 (s, 2H); $[M+H]^+$=494.1.

Step 3: tert-butyl 2-(1-(4-(2,6-bis(benzyloxy)pyridin-3-yl)phenyl)piperidin-4-yl)acetate

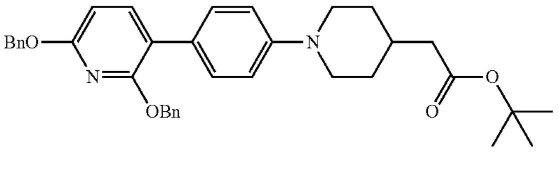 [SMILES: CC(C)(C)OC(=O)CC1CCN(c2ccc(-c3ccc(OCc4ccccc4)nc3OCc3ccccc3)cc2)CC1]

Under the atmosphere of nitrogen, add 2,6-bis(benzyloxy)-3-(4-iodophenyl)pyridine (45.4 g, 92.0 mmol), tert-butyl 2-(piperidin-4-yl)acetate (27.5 g, 138 mmol) and t-BuONa (13.3 g, 138 mmol) to 1.4-dioxane (450 mL). After pumping nitrogen three times, $Pd2(dba)_3$ (4.2 g, 4.6 mmol) and X-Phos (4.4 g, 9.2 mmol) were added to the system, and then nitrogen was pumped for three times again, then temperature was raised to reflux. After 1.5 h, the reaction was cooled to room temperature, water (250 mL) was added, extracted with DCM (3×250 mL). The combined organic phases were washed with water and brine, dried and concentrated. The residue was purified with silica gel column (petroleum ether:ethyl acetate=20:1) to obtain tert-butyl 2-(1-(4-(2,6-bis(benzyloxy)pyridin-3-yl)phenyl)piperidin-4-yl)acetate (31.1 g, 60.2%). $^1$H NMR (400 MHz, $CDCl_3$) δ 7.59 (d, J=8.1 Hz, 1H), 7.50-7.28 (m, 12H), 6.96 (d, J=8.8 Hz, 2H), 6.46 (d, J=8.0 Hz, 1H), 5.43 (s, 2H), 5.36 (s, 2H), 3.73-3.70 (m, 2H), 2.80-2.74 (m, 2H), 2.21 (d, J=7.0 Hz, 2H), 2.00-1.89 (m, 1H), 1.86-1.82 (m, 2H), 1.53-1.35 (m, 11H). $[M+H]^+$=565.3.

Step 4: tert-butyl 2-(1-(4-(2,6-dioxopiperidin-3-yl)phenyl)piperidin-4-yl)acetate

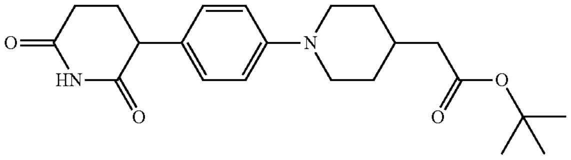 [SMILES: CC(C)(C)OC(=O)CC1CCN(c2ccc(C3CCC(=O)NC3=O)cc2)CC1]

Tert-butyl 2-(1-(4-(2,6-bis(benzyloxy)pyridin-3-yl)phenyl)piperidin-4-yl)acetate (28.6 g, 50.6 mmol) and Pd/C (7.5 g) were added to DMF (500 mL), the mixture was stirred at 50° C. under hydrogen atmosphere for 16 h, cooled to room temperature, filtered through a pad of Celite and washed with DCM. The filtrate was concentrated to get tert-butyl 2-(1-(4-(2,6-dioxopiperidin-3-yl)phenyl)piperidin-4-yl)acetate (17.4 g, 89%). $^1$H NMR (400 MHz, $CDCl_3$) δ 7.97 (s, 1H), 7.07 (d, J=8.5 Hz, 2H), 6.91 (d, J=8.4 Hz, 2H), 3.79-3.49 (m, 3H), 2.82-2.54 (m, 4H), 2.27-2.18 (m, 4H), 1.91-1.87 (m, 1H), 1.83-1.80 (m, 2H), 1.50-1.25 (m, 11H). $[M+H]^+$=387.2.

Step 5: 2-(1-(4-(2,6-dioxopiperidin-3-yl)phenyl)piperidin-4-yl)acetic acid trifluoroacetate

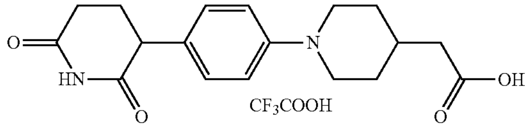

Tert-butyl 2-(1-(4-(2,6-dioxopiperidin-3-yl)phenyl)piperidin-4-yl)acetate (16.2 g, 41.9 mmol) and TFA (95.5 g, 838 mmol) were added to DCM (100 mL). The temperature was raised to 40° C. and stirred for 1.5 h. After cooling to room temperature, the mixture was concentrated, then recrystallized in MTBE (150 mL) to give the product (14.5 g, 77.9%). $^1$H NMR (400 MHz, MeOD) δ 7.57 (d, J=8.6 Hz, 2H), 7.47 (d, J=8.6 Hz, 2H), 3.96 (dd, J=11.7, 5.0 Hz, 1H), 3.71-3.68 (m, 2H), 3.61-3.56 (m, 2H), 2.78-2.63 (m, 2H), 2.39-2.38 (m, 2H), 2.27-2.13 (m, 6H), 1.79-1.69 (m, 2H). $[M+H]^+$=331.2.

Step 6: 3-(4-(4-(2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)-2-oxoethyl)piperidin-1-yl)phenyl)piperidine-2,6-dione

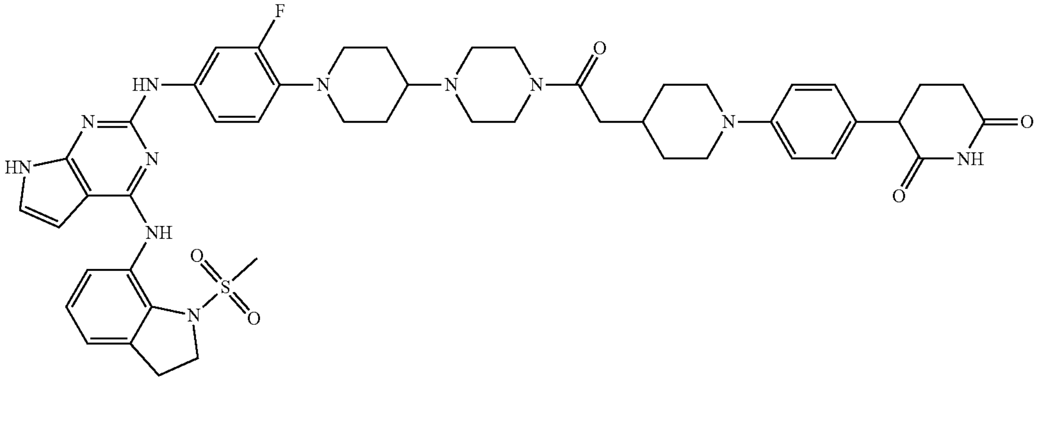 [SMILES: CS(=O)(=O)N1CCc2cccc(Nc3nc(Nc4ccc(N5CCC(N6CCN(C(=O)CC7CCN(c8ccc(C9CCC(=O)NC9=O)cc8)CC7)CC6)CC5)c(F)c4)nc4[nH]ccc34)c21]

The titled compound was prepared in a manner similar to that in Example 11. 1H NMR (400 MHz, DMSO) δ 11.38 (s, 1H), 10.77 (s, 1H), 10.37 (s, 1H), 9.07 (s, 2H), 7.82 (d, J=15.3 Hz, 1H), 7.20 (m, 6H), 6.94 (s, 3H), 6.22 (s, 1H), 4.47 (s, 1H), 4.06 (s, 4H), 3.77 (s, 2H), 3.56 (s, 3H), 3.47 (s, 4H), 3.10 (s, 3H), 3.03 (s, 4H), 2.98 (s, 1H), 2.63 (s, 4H), 2.35 (s, 2H), 2.11 (s, 3H), 1.98 (s, 2H), 1.82 (s, 4H), 1.45 (s, 2H), 1.19 (s, 1H); $[M+H]^+$=918.8.

Example 13: 3-(4-((S)-3-(2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)ethyl)pyrrolidin-1-yl)phenyl)piperidine-2,6-dione Step 1: tert-butyl (S)-3-(2-hydroxyethyl)pyrrolidine-1-carboxylate

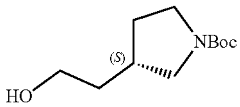

To a stirred solution of ((3S)-1-(tert-butoxycarbonyl)pyrrolidin-3-yl)acetic acid (5 g, 21.81 mmol) in THE (10 mL) was added $BH_3$-THF (20 mL) dropwise at 0° C. The resulting mixture was stirred overnight at room temperature. The reaction was quenched with MeOH at 0° C. The solvent was removed and the residue was purified by silica gel column chromatography, eluted with PE/EtOAc (1:1) to afford the product (3 g, 64%). $[M+H]^+$- 216.2.

Step 2: (S)-2-(pyrrolidin-3-yl)ethan-1-ol hydrochloride

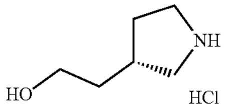

To a stirred solution of tert-butyl (3S)-3-(2-hydroxyethyl)pyrrolidine-1-carboxylate (3 g, 13.934 mmol) was added 4 M HCl in 1,4-dioxane (30 ml) dropwise at ° C. The resulting mixture was stirred for 3 h at room temperature which was concentrated under vacuum. The crude product was used in the next step directly without further purification. $[M+H]^+$=116.3.

Step 3: 3-(4-((S)-3-(2-hydroxyethyl)pyrrolidin-1-yl)phenyl)piperidine-2,6-dione

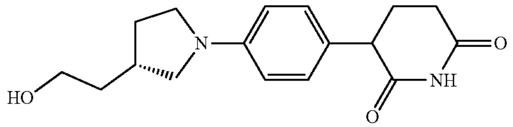 [SMILES: O=C1CCC(c2ccc(N3CC[C@@H](CCO)C3)cc2)C(=O)N1]

To a stirred solution of (S)-2-(pyrrolidin-3-yl)ethan-1-ol hydrochloride (1.99 g, 13.02 mmol) and 3-(4-bromophenyl)piperidine-2,6-dione (3.12 g, 11.72 mmol) in dioxane (30 mL) was added $Cs_2CO_3$ (12.73 g, 39.07 mmol) and Pd-PEPPSI-IPentCl 2-methylpyridine (o-picoline) (cas: 1612891-29-8, 413 mg, 0.49 mmol) at room temperature under nitrogen atmosphere. The resulting mixture was stirred overnight at 90° C. under nitrogen atmosphere. The mixture was acidified to pH 6 with citric acid. The aqueous layer was extracted with $CH_2C_2$ (2×100 mL). The resulting mixture was concentrated under vacuum. The residue was purified by prep-TLC ($CH_2Cl_2$/MeOH=10:1) to the product (212 mg, 6%). $[M+H]^+$=303.1.

Step 4: 2-((3S)-1-(4-(2,6-dioxopiperidin-3-yl)phenyl)pyrrolidin-3-yl)ethyl methanesulfonate

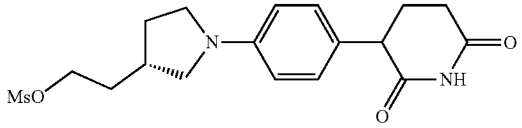 [SMILES: CS(=O)(=O)OCC[C@@H]1CCN(c2ccc(C3CCC(=O)NC3=O)cc2)C1]

The titled compound (140 mg, 62%) was prepared in a manner similar to that in Example 1 step 5 from 3-(4-((S)-3-(2-hydroxyethyl)pyrrolidin-1-yl)phenyl)piperidine-2,6-dione and sulfurous dichloride. $[M+H]^+$=381.2.

Step 5: 3-(4-((S)-3-(2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)ethyl)pyrrolidin-1-yl)phenyl)piperidine-2,6-dione

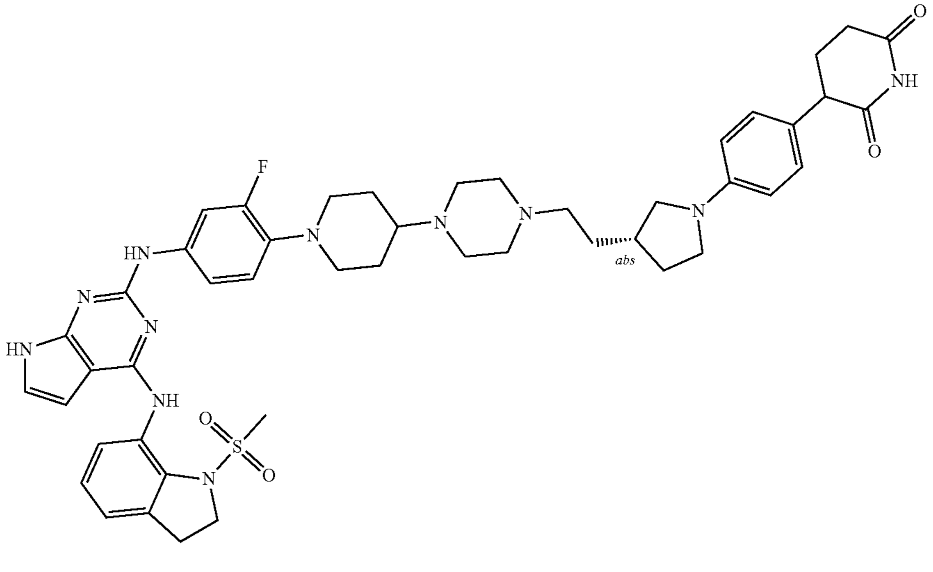 [SMILES: CS(=O)(=O)N1CCc2cccc(Nc3nc(Nc4ccc(N5CCC(N6CCN(CC[C@H]7CCN(c8ccc(C9CCC(=O)NC9=O)cc8)C7)CC6)CC5)c(F)c4)nc4[nH]ccc34)c21]

The titled compound was prepared in a manner similar to that in Example 1. $^1$H NMR (400 MHz, DMSO) δ 11.32 (s, 1H), 10.74 (s, 1H), 9.03 (s, 1H), 8.92 (s, 1H), 8.30 (d, J=8.3 Hz, 1H), 7.86 (d, J=15.3 Hz, 1H), 7.36-7.19 (m, 2H), 7.12 (d, J=7.2 Hz, 1H), 7.04-6.84 (m, 4H), 6.46 (d, J=8.6 Hz, 2H), 6.21 (s, 1H), 4.10 (s, 2H), 3.67 (d, J=5.8 Hz, 1H), 3.45-3.35 (m, 3H), 3.22-3.05 (m, 7H), 2.88-2.79 (m, 1H), 2.70-2.52 (m, 7H), 2.47-2.20 (m, 9H), 2.18-1.94 (m, 3H), 1.89-1.79 (m, 2H), 1.67-1.48 (m, 5H); $[M+H]^+$=890.2.

Example 14: 2-(2,6-dioxopiperidin-3-yl)-5-(4-((4-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazine-1-carbonyl)piperidin-1-yl)methyl)piperidin-1-yl)isoindoline-1,3-dione Step 1: benzyl 4-((4-(tert-butoxycarbonyl)piperidin-1-yl)methyl)piperidine-1-carboxylate

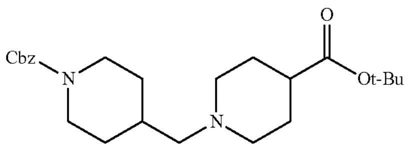 [SMILES: CC(C)(C)OC(=O)C1CCN(CC2CCN(C(=O)OCc3ccccc3)CC2)CC1]

To a stirred solution of benzyl 4-formylpiperidine-1-carboxylate (1.01 g, 4.044 mmol), tert-butyl piperidine-4-carboxylate hydrochloride (897 mg, 4.044 mmol), AcONa (3.31 g, 40.4 mmol,) and DCM (20 mL) was added STAB (5.14 g, 24.263 mmol) in portions at 0° C. The resulting mixture was stirred overnight at room temperature. The reaction was quenched with water at room temperature. The resulting mixture was extracted with $CH_2Cl_2$. The combined organic layers were washed with brine, dried over anhydrous $Na_2SO_4$. After filtration, the filtrate was concentrated under reduced pressure to afford the crude product (1.20 g) which was used in the next step directly without further purification. $[M+H]^+$=417.3.

Step 2: tert-butyl 1-(piperidin-4-ylmethyl)piperidine-4-carboxylate

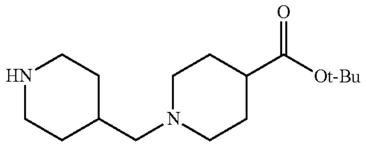 [SMILES: CC(C)(C)OC(=O)C1CCN(CC2CCNCC2)CC1]

A suspension of benzyl 4-((4-(tert-butoxycarbonyl)piperidin-1-yl)methyl)piperidine-1-carboxylate (1.20 g, crude), AcOH (20 mL) and Pd/C (1.20 g, 10% wt) in MeOH (20 mL) was stirred for 1 h at room temperature under hydrogen atmosphere. The resulting mixture was filtered, the filter cake was washed with MeOH. The filtrate was concentrated under reduced pressure to afford the crude product (900 mg) which was used in the next step directly without further purification. $[M+H]^+$=283.2.

Step 3: tert-butyl 1-((1-(2-(2,6-dioxopiperidin-3-yl)-1,3-dioxoisoindolin-5-yl)piperidin-4-yl)methyl)piperidine-4-carboxylate

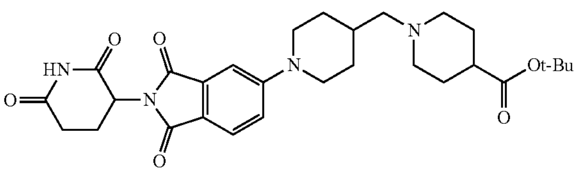 [SMILES: CC(C)(C)OC(=O)C1CCN(CC2CCN(c3ccc4c(c3)C(=O)N(C3CCC(=O)NC3=O)C4=O)CC2)CC1]

A solution of tert-butyl 1-(piperidin-4-ylmethyl)piperidine-4-carboxylate (500 mg, crude) and 2-(2,6-dioxopiperidin-3-yl)-5-fluoroisoindoline-1,3-dione (489 mg, 1.770 mmol), DIEA (1.14 g, 8.852 mmol) in DMSO (6 mL) was stirred for 1 h at 80° C. The resulting mixture was extracted with EtOAc. The combined organic layers were washed with brine, dried over anhydrous $Na_2SO_4$. After filtration, the filtrate was concentrated under reduced pressure to afford the crude product (830 mg) which was used in the next step directly without further purification. $[M+H]^+$=539.3.

Step 4: 1-((1-(2-(2,6-dioxopiperidin-3-yl)-1,3-dioxoisoindolin-5-yl)piperidin-4-yl)methyl)piperidine-4-carboxylic acid

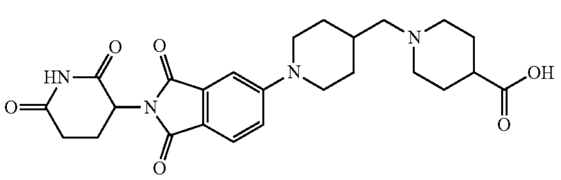 [SMILES: O=C1CCC(N2C(=O)c3ccc(N4CCC(CN5CCC(C(=O)O)CC5)CC4)cc3C2=O)C(=O)N1]

A solution of tert-butyl 1-((1-(2-(2,6-dioxopiperidin-3-yl)-1,3-dioxoisoindolin-5-yl)piperidin-4-yl)methyl)piperidine-4-carboxylate (810.00 mg, crude) and TFA (8 mL) in DCM (8 mL) was stirred for 1 h at room temperature. The resulting mixture was concentrated under vacuum. The resulting mixture was diluted with water. The resulting mixture was concentrated under vacuum to afford the crude product (725 mg) which was used in the next step directly without further purification. $[M+H]^+$=483.2.

Step 5: 2-(2,6-dioxopiperidin-3-yl)-5-(4-((4-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazine-1-carbonyl)piperidin-1-yl)methyl)piperidin-1-yl)isoindoline-1,3-dione

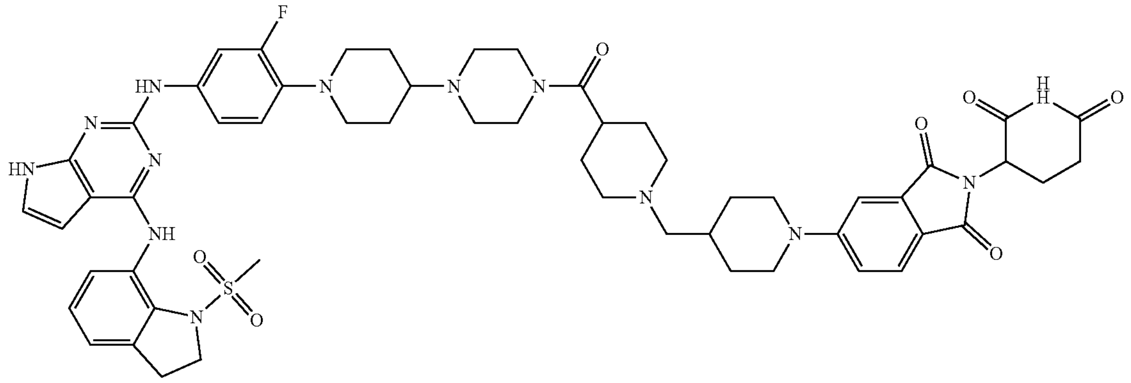

The titled compound was prepared in a manner similar to that in Example 11. 1H NMR (400 MHz, DMSO) δ 11.39 (s, 1H), 11.08 (s, 1H), 10.88 (s, 1H), 9.21 (s, 2H), 8.21 (s, 1H), 7.89 (d, J=15.4 Hz, 1H), 7.69 (d, J=8.2 Hz, 1H), 7.37 (s, 1H), 7.26 (s, 3H), 7.17 (s, 1H), 6.99 (s, 2H), 6.25 (s, 1H), 5.06 (s, 1H), 4.10 (s, 3H), 3.56 (s, 1H), 3.14 (s, 5H), 3.09 (s, 3H), 3.00 (s, 9H), 2.67 (s, 2H), 2.54 (s, 1H), 2.33 (s, 1H), 2.16 (s, 3H), 1.99 (s, 4H), 1.87 (s, 6H), 1.24 (s, 8H), 0.85 (s, 1H); $[M+H]^+$=1070.2.

Example 15: 2-(2,6-dioxopiperidin-3-yl)-5-(4-(3-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)-3-oxopropyl)piperazin-1-yl)isoindoline-1,3-dione

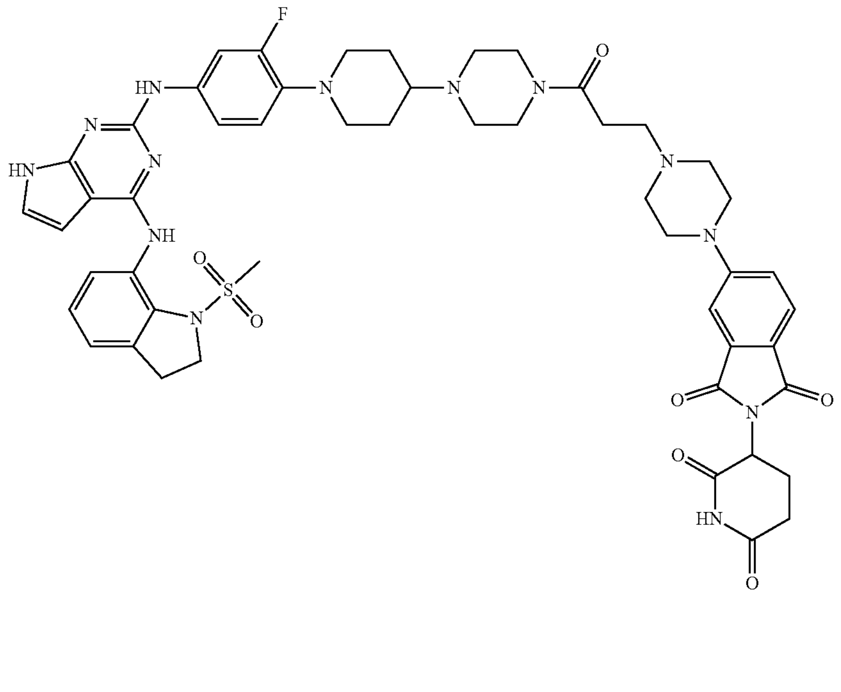 [SMILES: CS(=O)(=O)N1CCc2cccc(Nc3nc(Nc4ccc(N5CCC(N6CCN(C(=O)CCN7CCN(c8ccc9c(c8)C(=O)N(C8CCC(=O)NC8=O)C9=O)CC7)CC6)CC5)c(F)c4)nc4[nH]ccc34)c21]

The titled compound was prepared in a manner similar to that in Example 11. 1H NMR (400 MHz, DMSO) δ 11.42 (s, 1H), 11.09 (s, 1H), 10.95 (s, 1H), 10.50 (s, 1H), 9.12 (s, 1H), 8.17 (s, 1H), 7.77 (d, J=8.4 Hz, 1H), 7.51 (s, 1H), 7.38 (d, J=7.0 Hz, 1H), 7.28 (d, J=15.5 Hz, 2H), 7.18 (s, 1H), 6.99 (s, 2H), 6.26 (s, 1H), 5.10 (d, J=7.9 Hz, 1H), 4.48 (s, 1H), 4.25 (d, J=12.2 Hz, 2H), 4.10 (s, 3H), 3.61 (s, 5H), 3.14 (s, 7H), 3.08 (s, 3H), 3.01 (s, 5H), 2.65 (m, 4H), 2.18 (s, 2H), 2.01 (s, 2H), 1.89 (s, 2H), 1.24 (s, 4H); $[M+H]^+$=1002.7.

Example 16: 2-(2,6-dioxopiperidin-3-yl)-5-(4-((4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)methyl)piperidin-1-yl)isoindoline-1,3-dione

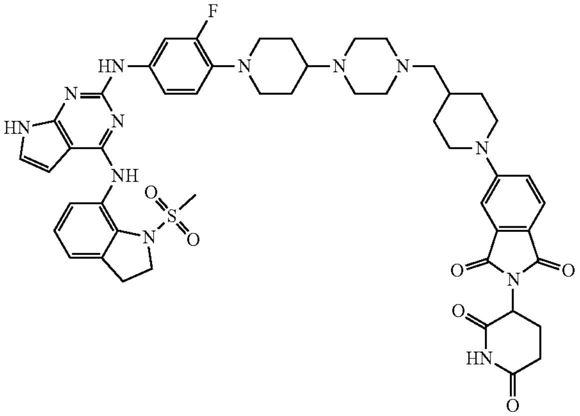 [SMILES: CS(=O)(=O)N1CCc2cccc(Nc3nc(Nc4ccc(N5CCC(N6CCN(CC7CCN(c8ccc9c(c8)C(=O)N(C8CCC(=O)NC8=O)C9=O)CC7)CC6)CC5)c(F)c4)nc4[nH]ccc34)c21]

The titled compound was prepared in a manner similar to that in Example 1. $^1$H NMR (400 MHz, DMSO) δ 11.32 (s, 1H), 11.07 (s, 1H), 9.03 (s, 1H), 8.92 (s, 1H), 8.29 (d, J=14.3 Hz, 2H), 7.86 (d, J=16.2 Hz, 1H), 7.64 (d, J=8.4 Hz, 1H), 7.35-7.20 (m, 2H), 7.12 (d, J=7.3 Hz, 1H), 6.93 (m, 3H), 6.80 (d, J=9.0 Hz, 1H), 6.21 (s, 1H), 5.04 (s, 1H), 4.11 (s, 2H), 3.60 (dd, J=16.3, 5.6 Hz, 2H), 3.15-2.84 (m, 11H), 2.60-2.62 (m, 4H), 2.43-2.10 (m, 7H), 2.05-1.93 (m, 2H), 1.85-1.88 (m, 2H), 1.72-1.51 (m, 5H), 1.24 (s, 3H); $[M+H]^+$=959.

Example 17: 2-(2,6-dioxopiperidin-3-yl)-5-(4-(2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)ethyl)piperidin-1-yl)isoindoline-1,3-dione

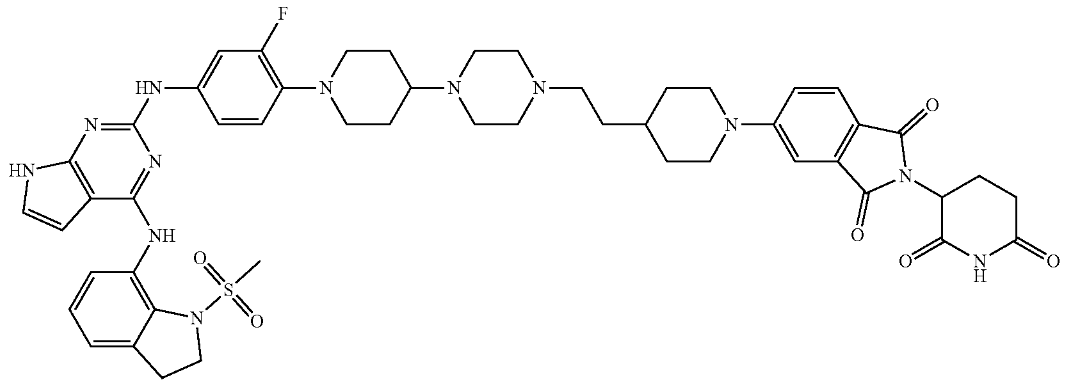 [SMILES: CS(=O)(=O)N1CCc2cccc(Nc3nc(Nc4ccc(N5CCC(N6CCN(CCC7CCN(c8ccc9c(c8)C(=O)N(C8CCC(=O)NC8=O)C9=O)CC7)CC6)CC5)c(F)c4)nc4[nH]ccc34)c21]

The titled compound was prepared in a manner similar to that in Example 1. $^1$H NMR (400 MHz, DMSO) δ 11.31 (s, 1H), 11.06 (s, 1H), 9.02 (s, 1H), 8.90 (s, 1H), 8.30 (d, J=8.2 Hz, 1H), 8.20 (s, 1H), 7.86 (d, J=15.5 Hz, 1H), 7.64 (d, J=8.5 Hz, 1H), 7.30 (s, 2H), 7.25 (d, J=7.5 Hz, 2H), 7.12 (d, J=7.5 Hz, 1H), 6.93 (m, 2H), 6.21 (s, 1H), 5.06 (d, J=7.7 Hz, 1H), 4.16-3.94 (m, 4H), 3.14-3.08 (m, 9H), 3.00-2.83 (m, 7H), 2.61 (d, J=10.8 Hz, 1H), 2.42-2.21 (m, 5H), 2.05-1.97 (m, 2H), 1.84-1.86 (m, 1H), 1.75-1.78 (m, 1H), 1.66-1.48 (m, 4H), 1.42-1.31 (m, 2H), 1.30-1.12 (m, 4H); $[M+H]^+$=973.

Example 18: 3-(5-(4-(2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)ethyl)piperidin-1-yl)-1-oxoisoindolin-2-yl)piperidine-2,6-dione Step 1: 3-(5-(4-(2-hydroxyethyl)piperidin-1-yl)-1-oxoisoindolin-2-yl)piperidine-2,6-dione

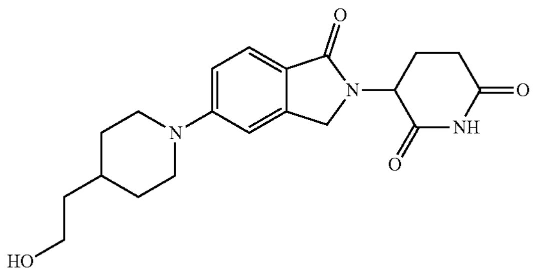 [SMILES: O=C1CCC(N2Cc3cc(N4CCC(CCO)CC4)ccc3C2=O)C(=O)N1]

To a stirred solution/mixture of 3-(5-bromo-1-oxo-3H-isoindol-2-yl)piperidine-2,6-dione (1.5 g, 4.642 mmol) and 4-piperidineethanol (0.63 g, 4.874 mmol) in dioxane (20 mL) was added $Cs_2CO_3$ (4.54 g, 13.926 mmol) and Pd-PEPPSI-IPentCl 2-methylpyridine (o-picoline) (cas: 1612891-29-8, 148.9 mg, 0.18 mmol) at room temperature under nitrogen atmosphere. The resulting mixture was stirred overnight at 90° C. under nitrogen atmosphere. The mixture was acidified to pH=6 with citric acid (2 mL). The resulting mixture was concentrated under vacuum to afford the crude residue which was purified by prep-TLC ($CH_2Cl_2$/MeOH=10:1) to afford the product (650 mg, 38%). $[M+H]^+$=372.2.

Step 2: 2-(1-(2-(2,6-dioxopiperidin-3-yl)-1-oxoisoindolin-5-yl)piperidin-4-yl)ethyl methanesulfonate

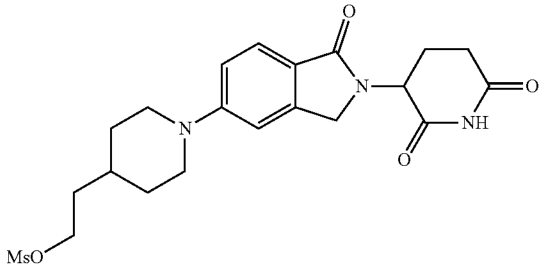 [SMILES: CS(=O)(=O)OCCC1CCN(c2ccc3c(c2)CN(C2CCC(=O)NC2=O)C3=O)CC1]

The titled compound (210 mg, 34%) was prepared in a manner similar to that in Example 1 step 5 from 3-(5-(4-(2-hydroxyethyl)piperidin-1-yl)-1-oxoisoindolin-2-yl)piperidine-2,6-dione_ and sulfurous dichloride. $[M+H]^+$=450.2.

Step 3: 3-(5-(4-(2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)ethyl)piperidin-1-yl)-1-oxoisoindolin-2-yl)piperidine-2,6-dione

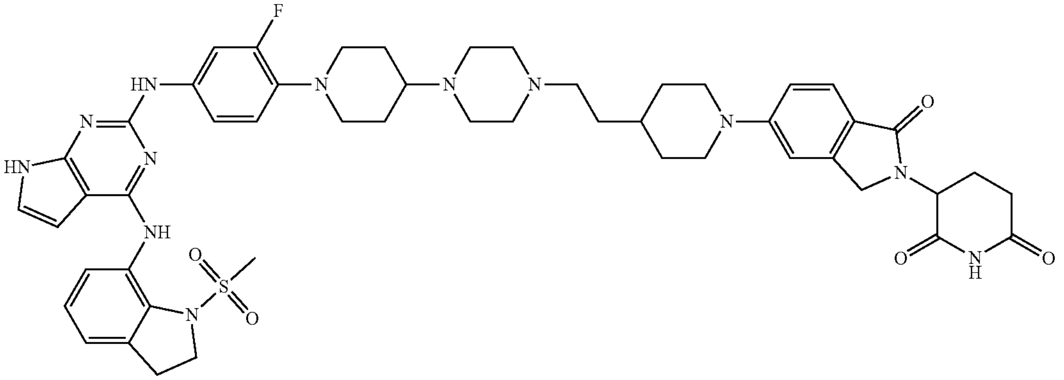 [SMILES: CS(=O)(=O)N1CCc2cccc(Nc3nc(Nc4ccc(N5CCC(N6CCN(CCC7CCN(c8ccc9c(c8)CN(C8CCC(=O)NC8=O)C9=O)CC7)CC6)CC5)c(F)c4)nc4[nH]ccc34)c21]

The titled compound was prepared in a manner similar to that in Example 1. $^1$H NMR (400 MHz, DMSO) δ 11.32 (s, 1H), 10.94 (s, 1H), 9.03 (s, 1H), 8.92 (s, 1H), 8.30 (d, J=8.2 Hz, 1H), 7.86 (d, J=17.1 Hz, 1H), 7.49 (d, J=8.2 Hz, 1H), 7.31 (d, J=8.9 Hz, 1H), 7.24 (d, J=8.0 Hz, 1H), 7.12 (d, J=7.4 Hz, 1H), 7.05 (s, 2H), 6.96 (s, 1H), 6.92 (d, J=8.9 Hz, 1H), 6.21 (s, 1H), 5.04 (d, J=8.1 Hz, 1H), 4.25 (m, 2H), 4.11 (s, 2H), 3.86 (d, J=11.3 Hz, 2H), 3.15-3.05 (m, 6H), 2.89 (m, 6H), 2.70-2.57 (m, 4H), 2.45-2.19 (m, 8H), 1.99-1.91 (m, 1H), 1.83 (s, 2H), 1.75 (d, J=10.2 Hz, 2H), 1.64-1.46 (m, 3H), 1.45-1.34 (m, 2H), 1.29-1.15 (m, 3H); $[M+H]^+$=959.2.

Example 19: 2-(2,6-dioxopiperidin-3-yl)-5-(3-(3-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)propyl)azetidin-1-yl)isoindoline-1,3-dione Step 1: 3-(azetidin-3-yl)propan-1-ol

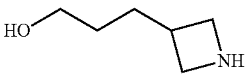

Into a 25-mL flask, was placed tert-butyl 3-(3-hydroxypropyl)azetidine-1-carboxylate (950 mg, 4.413 mmol), DCM (4.0 mL), TFA (2.0 mL, 2.693 mmol). The resulting solution was stirred for 1 hour at room temperature. The resulting mixture was concentrated under vacuum to afford 1.4 g crude product. $[M+H]^+$=116.2.

Step 2: 2-(2,6-dioxopiperidin-3-yl)-5-(3-(3-hydroxypropyl)azetidin-1-yl)isoindoline-1,3-dione

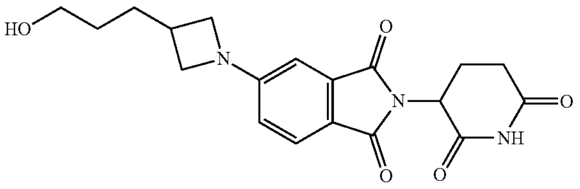 [SMILES: O=C1CCC(N2C(=O)c3ccc(N4CC(CCCO)C4)cc3C2=O)C(=O)N1]

Into a 50-mL flask, was placed 3-(azetidin-3-yl)propan-1-ol (1.40 g, crude), DMSO (10 mL), 2-(2,6-dioxopiperidin-3-yl)-5-fluoroisoindole-1,3-dione (1.21 g, 4.38 mmol), DIEA (2.83 g, 21.9 mmol). The resulting solution was stirred for 1 hour at 80° C. The reaction mixture was cooled to room temperature. The resulting solution was diluted with EA. The resulting solution was extracted with $H_2O$ and the organic layers were combined and dried over anhydrous sodium sulfate and concentrated under vacuum. The residue was applied onto a silica gel column with dichloromethane/methanol (8:1) to afford the product (550 mg, 33.6% for two steps). $[M+H]^+$=372.3.

Step 3: 3-(1-(2-(2,6-dioxopiperidin-3-yl)-1,3-dioxoisoindolin-5-yl)azetidin-3-yl)propyl 4-methylbenzenesulfonate

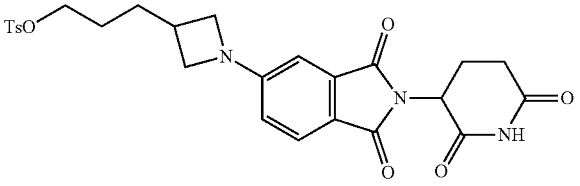 [SMILES: Cc1ccc(S(=O)(=O)OCCCC2CN(c3ccc4c(c3)C(=O)N(C3CCC(=O)NC3=O)C4=O)C2)cc1]

Into a 25-mL flask, was placed 2-(2,6-dioxopiperidin-3-yl)-5-(3-(3-hydroxypropyl)azetidin-1-yl)isoindoline-1,3-dione (480 mg, 1.29 mmol), DCM (10 mL), TEA (262 mg, 2.59 mmol), TsCl (493 mg, 2.59 mmol). The resulting solution was stirred overnight at room temperature. The resulting mixture was concentrated under vacuum. The residue was applied onto a silica gel column with dichloromethane/methanol (7:1) to afford the product (400 mg, 58.89%). $[M+H]^+$=526.2.

Step 4: 2-(2,6-dioxopiperidin-3-yl)-5-(3-(3-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)propyl)azetidin-1-yl)isoindoline-1,3-dione

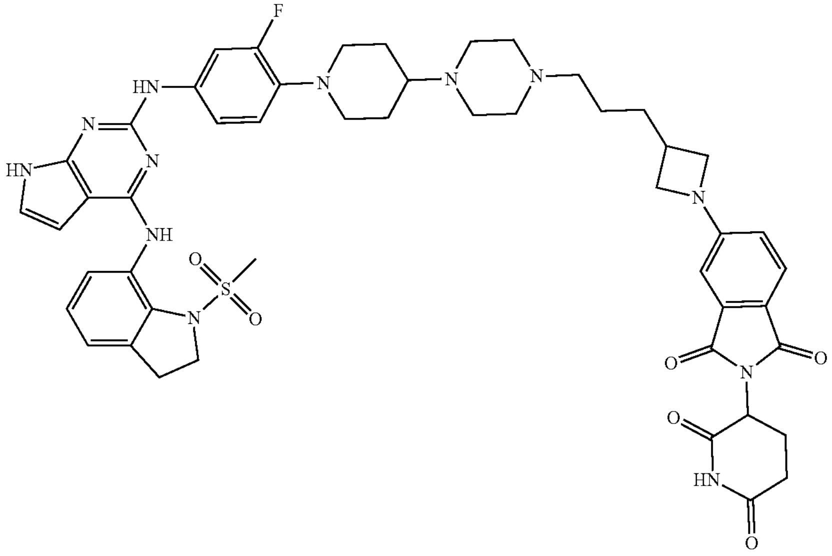 [SMILES: CS(=O)(=O)N1CCc2cccc(Nc3nc(Nc4ccc(N5CCC(N6CCN(CCCC7CN(c8ccc9c(c8)C(=O)N(C8CCC(=O)NC8=O)C9=O)C7)CC6)CC5)c(F)c4)nc4[nH]ccc34)c21]

The titled compound was prepared in a manner similar to that in Example 1. 1H NMR (400 MHz, DMSO) δ 11.32 (s, 1H), 11.07 (s, 1H), 9.02 (s, 1H), 8.92 (s, 1H), 8.29 (s, 1H), 7.84 (s, 1H), 7.63 (d, J=8.3 Hz, 1H), 7.30 (s, 1H), 7.24 (s, 1H), 7.13 (s, 1H), 6.96 (s, 1H), 6.90 (s, 1H), 6.76 (s, 1H), 6.62 (d, J=8.6 Hz, 1H), 6.21 (s, 1H), 5.04 (s, 1H), 4.12 (d, J=8.3 Hz, 4H), 3.65 (s, 2H), 3.28-3.24 (m, 3H), 3.13 (s, 2H), 3.09 (s, 3H), 2.76 (s, 4H), 2.63 (m, 6H), 2.35 (d, J=13.5 Hz, 3H), 2.27 (s, 3H), 2.01 (s, 1H), 1.82 (s, 2H), 1.60 (m, 4H), 1.43 (s, 2H); $[M+H]^+$=959.8.

Example 20: 3-(4-(2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)ethoxy)-1-oxoisoindolin-2-yl)piperidine-2,6-dione Step 1: methyl 2-formyl-3-hydroxybenzoate

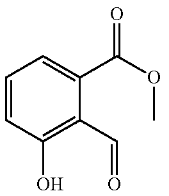

A solution of methyl 3-hydroxybenzoate (40.00 g, 262.90 mmol) in TFA (1.00 L) was stirred at room temperature. To the above mixture was added hexamethylenetetraamine (44.17 g, 315.48 mmol) in portions at room temperature. The resulting mixture was stirred for additional 4 h at 80° C. The resulting mixture was extracted with EtOAc. The combined organic layers were washed with ice water, dried over anhydrous $Na_2SO_4$. After filtration, the filtrate was concentrated under reduced pressure. The residue was purified by silica gel column chromatography, eluted with PE/EtOAc (10:1) to afford methyl 2-formyl-3-hydroxybenzoate (20 g, 42%). m/z $[M+H]^+$=181.1.

Step 2: methyl 3-(2-(benzyloxy)ethoxy)-2-formylbenzoate

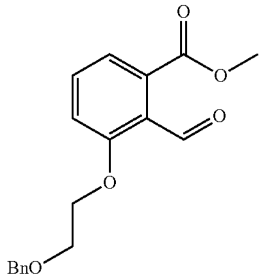 [SMILES: COC(=O)c1cccc(OCCOCc2ccccc2)c1C=O]

A mixture of methyl 2-formyl-3-hydroxybenzoate (20.00 g, 111.01 mmol) and [(2-bromoethoxy)methyl]benzene (71.63 g, 333.03 mmol), $K_2CO_3$ (30.69 g, 222.02 mmol), KI (9.21 g, 55.50 mmol) in DMF (300 mL) was stirred overnight at 70° C. The resulting mixture was extracted with EtOAc. The combined organic layers were washed with brine, dried over anhydrous $Na_2SO_4$. After filtration, the filtrate was concentrated under reduced pressure. The residue was purified by silica gel column chromatography, eluted with PE/EtOAc (2:1) to afford the product (10 g, 29%). $[M+H]^+$=315.1.

Step 3: 3-(4-(2-(benzyloxy)ethoxy)-1-oxoisoindolin-2-yl)piperidine-2,6-dione

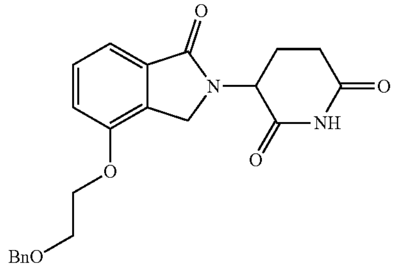 [SMILES: O=C1CCC(N2Cc3c(OCCOCc4ccccc4)cccc3C2=O)C(=O)N1]

A mixture of 3-aminopiperidine-2,6-dione hydrochloride (6.26 g, 38.17 mmol) and DIEA (8.22 g, 63.62 mmol) in DCE (100 mL) and DMF (5 mL) was stirred for 2 h at room temperature. The mixture was acidified to pH=6 with AcOH. To the resulting solution was added methyl 3-(2-(benzyloxy) ethoxy)-2-formylbenzoate (10.00 g, 31.81 mmol). Then it was stirred overnight at room temperature. And then $NaBH_3CN$ (6.00 g, 95.43 mmol) was added to the mixture in portions at room temperature. The resulting mixture was stirred for additional 5 h at room temperature. The reaction was quenched by the addition of water. The resulting mixture was extracted with $CH_2Cl_2$. The combined organic layers were washed with brine, dried over anhydrous $Na_2SO_4$. After filtration, the filtrate was concentrated under reduced pressure. The residue was purified by silica gel column chromatography, eluted with $CH_2Cl_2$/MeOH (5:1) to afford crude product. The residue was purified by reverse phase flash chromatography (0 to 50% MeCN in $H_2O$) to afford the product (4.1 g, 33%), [M+1]=395.3.

Step 4: 3-(4-(2-hydroxyethoxy)-1-oxoisoindolin-2-yl)piperidine-2,6-dione

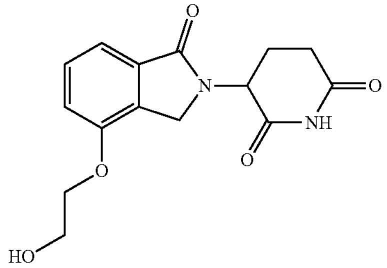 [SMILES: O=C1CCC(N2Cc3c(OCCO)cccc3C2=O)C(=O)N1]

A mixture of 3-(4-(2-(benzyloxy)ethoxy)-1-oxoisoindolin-2-yl)piperidine-2,6-dione (4.10 g, 10.39 mmol), Pd/C (2.00 g, 10% wt), AcOH (4 mL), THF (30 mL) and DCM (30 mL) was stirred overnight at 40° C. under hydrogen atmosphere. The resulting mixture was filtered, the filter cake was washed with MeOH and DCM. The filtrate was concentrated under reduced pressure to afford the product (2.13 g, 67%). $[M+1]^+$=305.3.

Step 5: 2-((2-(2,6-dioxopiperidin-3-yl)-1-oxoisoindolin-4-yl)oxy)ethyl methanesulfonate

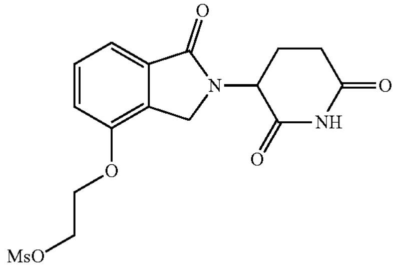

The titled compound (310 mg, 34%) was prepared in a manner similar to that in Example 1 step 5 from 3-(4-(2-hydroxyethoxy)-1-oxoisoindolin-2-yl)piperidine-2,6-dione and sulfurous dichloride.

Step 6: 3-(4-(2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)ethoxy)-1-oxoisoindolin-2-yl)piperidine-2,6-dione

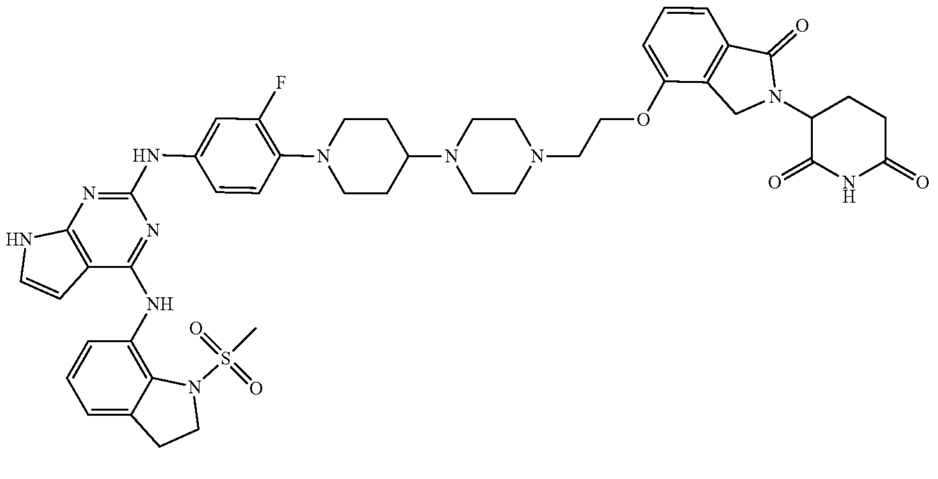 [SMILES: CS(=O)(=O)N1CCc2cccc(Nc3nc(Nc4ccc(N5CCC(N6CCN(CCOc7cccc8c7CN(C7CCC(=O)NC7=O)C8=O)CC6)CC5)c(F)c4)nc4[nH]ccc34)c21]

The titled compound was prepared in a manner similar to that in Example 1. $^{1}$H NMR (400 MHz, DMSO) δ 11.32 (s, 1H), 10.98 (s, 1H), 9.02 (s, 1H), 8.92 (s, 1H), 8.29 (d, J=8.2 Hz, 1H), 7.86 (d, J=15.5 Hz, 1H), 7.47 (d, J=7.6 Hz, 1H), 7.36-7.18 (m, 4H), 7.12 (d, J=6.7 Hz, 1H), 6.99-6.82 (m, 2H), 6.21 (s, 1H), 5.10-5.12 (m, 1H), 4.37-4.39 (m, 1H), 4.25 (s, 3H), 4.10 (s, 2H), 3.92 (s, 1H), 3.46-3.50 (m, 3H), 3.26-2.60 (m, 17H), 2.46-2.40 (m, 1H), 2.36-2.24 (m, 1H), 2.04-1.93 (m, 1H), 1.80-1.83 (m, 2H), 1.66-1.49 (m, 2H). $[M+H]^+$=892.1.

Example 21: 3-(4-(2-(4-(1-(3-methoxy-4-((4-((1-(methylsulfonyl)indolin-7-yl)amino)-7H-pyrrolo[2,3-d]pyrimidin-2-yl)amino)phenyl)piperidin-4-yl)piperazin-1-yl)ethyl)phenyl)piperidine-2,6-dione

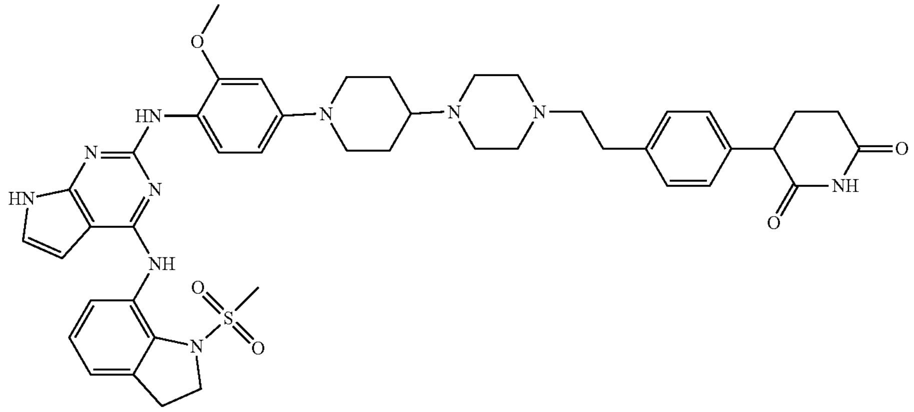 [SMILES: COc1cc(N2CCC(N3CCN(CCc4ccc(C5CCC(=O)NC5=O)cc4)CC3)CC2)ccc1Nc1nc(Nc2cccc3c2N(S(C)(=O)=O)CC3)c2cc[nH]c2n1]

The titled compound was prepared in a manner similar to that in Example 3. 1H NMR (400 MHz, DMSO) δ 11.25 (s, 1H), 10.82 (s, 1H), 8.99 (s, 1H), 8.24-8.17 (m, 1H), 7.97 (d, J=8.5 Hz, 1H), 7.25-7.15 (m, 4H), 7.12 (d, J=8.2 Hz, 3H), 6.92 (s, 1H), 6.63 (s, 1H), 6.44 (s, 1H), 6.19 (s, 1H), 4.09 (s, 2H), 3.82 (s, 4H), 3.65 (s, 2H), 3.11 (d, J=14.1 Hz, 5H), 3.04-2.87 (m, 2H), 2.76-2.52 (m, 11H), 2.48-2.40 (m, 3H), 2.32 (s, 1H), 2.21-2.12 (m, 1H), 2.03 (s, 1H), 1.85 (s, 2H), 1.55 (s, 2H); $[M+H]^+$=833.7.

Example 27: 3-(4-(4-(2-(4-(2-fluoro-4-((4-((1-(methylsulfonyl)indolin-7-yl)amino)-7H-pyrrolo[2,3-d]pyrimidin-2-yl)amino)phenyl)piperazin-1-yl)ethyl)piperidin-1-yl)phenyl)piperidine-2,6-dione

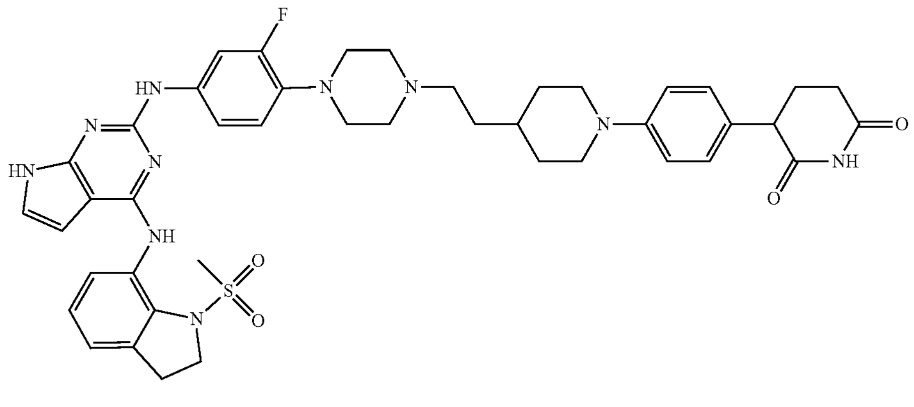 [SMILES: CS(=O)(=O)N1CCc2cccc(Nc3nc(Nc4ccc(N5CCN(CCC6CCN(c7ccc(C8CCC(=O)NC8=O)cc7)CC6)CC5)c(F)c4)nc4[nH]ccc34)c21]

The titled compound was prepared in a manner similar to that in Example 3. $^1$H NMR (400 MHz, DMSO) δ 11.33 (s, 1H), 10.77 (s, 1H), 9.03 (s, 1H), 8.93 (s, 1H), 8.29 (s, 1H), 7.87 (d, J=15.5 Hz, 1H), 7.32 (s, 1H), 7.25 (s, 1H), 7.13 (s, 1H), 7.02 (s, 2H), 6.92-6.94 (d, 4H), 6.21 (s, 1H), 4.11 (s, 2H), 3.75-3.56 (m, 4H), 3.17-3.05 (m, 6H), 2.93 (s, 4H), 2.61 (s, 4H), 2.39 (s, 3H), 2.11 (s, 1H), 2.01 (s, 1H), 1.76 (d, J=10.2 Hz, 2H), 1.43 (s, 3H), 1.24 (s, 3H); $[M+H]^+$=821.

Example 34: 3-(4-(2-(4-(1-(4-((5-chloro-4-((1-(methylsulfonyl)indolin-7-yl)amino)pyrimidin-2-yl)amino)-3-methoxyphenyl)piperidin-4-yl)piperazin-1-yl)ethyl)phenyl)piperidine-2,6-dione

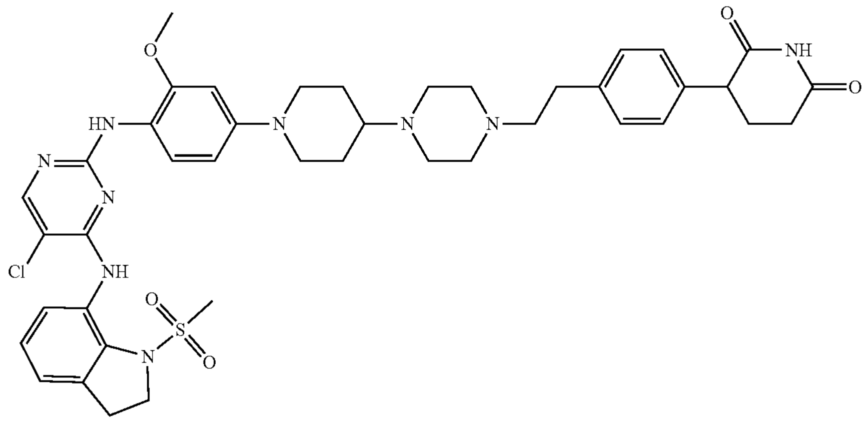 [SMILES: COc1cc(N2CCC(N3CCN(CCc4ccc(C5CCC(=O)NC5=O)cc4)CC3)CC2)ccc1Nc1ncc(Cl)c(Nc2cccc3c2N(S(C)(=O)=O)CC3)n1]

The titled compound was prepared in a manner similar to that in Example 3. $^1$H NMR (400 MHz, DMSO) δ 10.83 (s, 1H), 8.93 (s, 1H), 8.08 (s, 1H), 7.89 (s, 2H), 7.44 (s, 1H), 7.17 (d, J=16.8 Hz, 6H), 6.42 (s, 1H), 4.09-4.00 (m, 2H), 3.88-3.65 (m, 6H), 3.14-2.98 (m, 6H), 2.84-2.55 (m, 11H), 2.45-2.28 (m, 4H), 2.18-2.20 (m, 2H), 2.08-1.98 (m, 2H), 1.96-1.84 (m, 2H), 1.63-1.45 (m, 2H); $[M+H]^+$=828.

Example 35: 3-(4-(4-(2-(4-(1-(4-((5-chloro-4-((1-(methylsulfonyl)indolin-7-yl)amino)pyrimidin-2-yl)amino)-3-methoxyphenyl)piperidin-4-yl)piperazin-1-yl)ethyl)piperidin-1-yl)phenyl)piperidine-2,6-dione

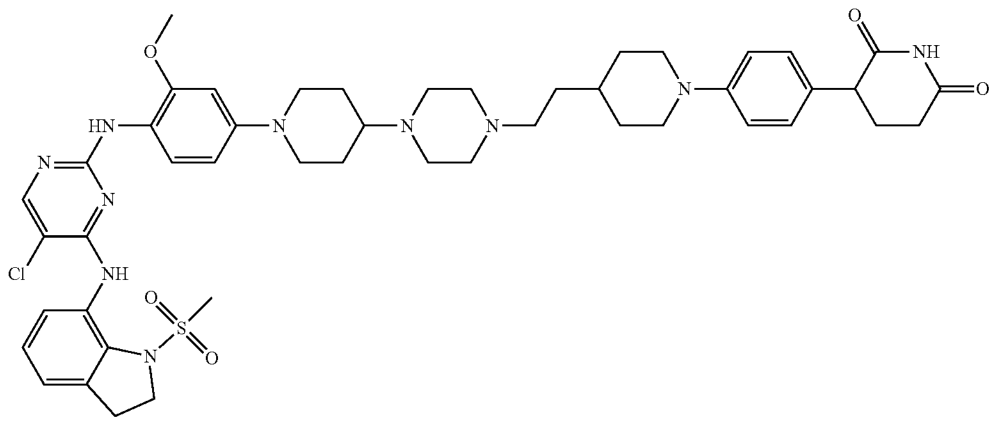 [SMILES: COc1cc(N2CCC(N3CCN(CCC4CCN(c5ccc(C6CCC(=O)NC6=O)cc5)CC4)CC3)CC2)ccc1Nc1ncc(Cl)c(Nc2cccc3c2N(S(C)(=O)=O)CC3)n1]

The titled compound was prepared in a manner similar to that in Example 3. $^1$H NMR (400 MHz, DMSO) δ 10.78 (s, 1H), 8.92 (s, 1H), 8.08 (s, 1H), 7.89 (s, 2H), 7.43 (s, 1H), 7.15 (s, 2H), 7.01 (s, 2H), 6.89 (s, 2H), 6.60 (s, 1H), 6.41 (s, 1H), 4.05 (s, 2H), 3.60-3.80 (m, 8H), 2.80-3.10 (m, 7H), 2.70-2.60 (m, 6H), 1.70-2.35 (m, 12H), 1.83 (m, 2H), 1.73 (m, 2H), 1.34-1.60 (m, 4H), 1.25 (m, 2H); $[M+H]^+$=911.2.

Example 36: 3-(4-(4-(2-(4-(1-(4-((5-chloro-4-((1-(methylsulfonyl)indolin-7-yl)amino)pyrimidin-2-yl)amino)-3-methoxyphenyl)piperidin-4-yl)piperazin-1-yl)ethyl)piperidin-1-yl)-2-fluorophenyl)piperidine-2,6-dione

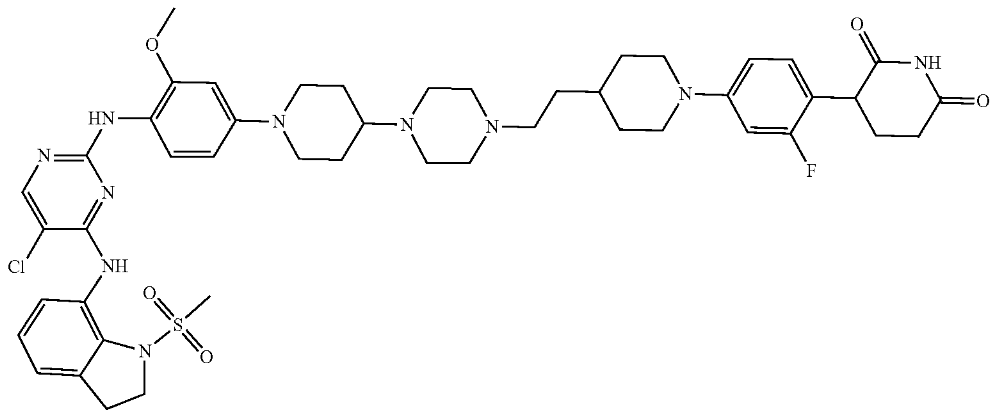 [SMILES: COc1cc(N2CCC(N3CCN(CCC4CCN(c5ccc(C6CCC(=O)NC6=O)c(F)c5)CC4)CC3)CC2)ccc1Nc1ncc(Cl)c(Nc2cccc3c2N(S(C)(=O)=O)CC3)n1]

The titled compound was prepared in a manner similar to that in Example 3. $^1$H NMR (400 MHz, DMSO) δ 10.78 (s, 1H), 8.91 (s, 1H), 8.08 (s, 1H), 7.86 (s, 2H), 7.45 (d, J=8.7 Hz, 1H), 7.14 (s, 2H), 7.04 (d, J=8.8 Hz, 1H), 6.69 (d, J=12.5 Hz, 2H), 6.59 (s, 1H), 6.40 (d, J=6.8 Hz, 1H), 4.05 (s, 2H), 3.87 (d, J=7.6 Hz, 1H), 3.76 (s, 3H), 3.68 (d, J=11.6 Hz, 4H), 3.10 (s, 3H), 3.04 (s, 4H), 2.75-2.59 (m, 6H), 2.48-2.25 (m, 8H), 2.19-2.07 (m, 1H), 2.02-1.89 (m, 1H), 1.85 (d, J=10.0 Hz, 2H), 1.73 (d, J=11.9 Hz, 2H), 1.58-1.43 (m, 3H), 1.41-1.33 (m, 2H), 1.28-1.13 (m, 3H); $[M+H]^+$=929.3.

Example 37: 5-(4-(2-(4-(1-(4-((5-chloro-4-((1-(methylsulfonyl)indolin-7-yl)amino)pyrimidin-2-yl)amino)-3-methoxyphenyl)piperidin-4-yl)piperazin-1-yl)ethyl)piperidin-1-yl)-2-(2,6-dioxopiperidin-3-yl)isoindoline-1,3-dione

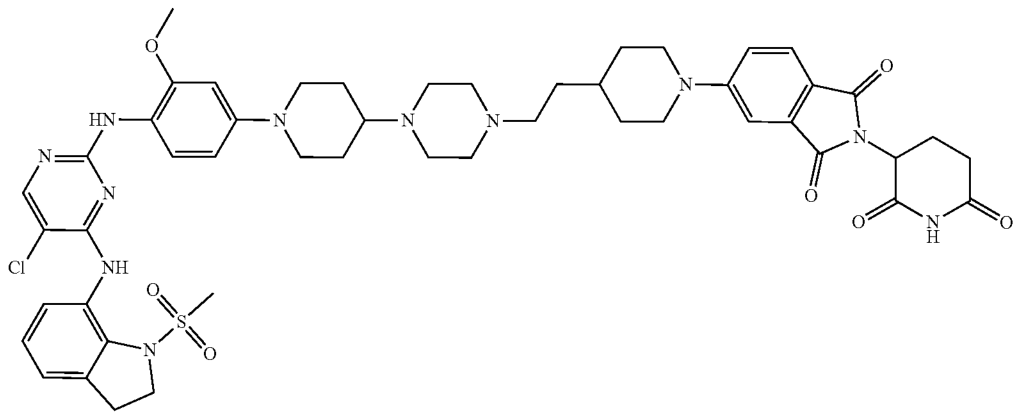 [SMILES: COc1cc(N2CCC(N3CCN(CCC4CCN(c5ccc6c(c5)C(=O)N(C5CCC(=O)NC5=O)C6=O)CC4)CC3)CC2)ccc1Nc1ncc(Cl)c(Nc2cccc3c2N(S(C)(=O)=O)CC3)n1]

The titled compound was prepared in a manner similar to that in Example 1. $^1$H NMR (400 MHz, DMSO) δ 11.06 (s, 1H), 8.92 (s, 1H), 8.08 (s, 1H), 7.86 (s, 2H), 7.64 (d, J=8.4 Hz, 1H), 7.45 (d, J=8.5 Hz, 1H), 7.30 (s, 1H), 7.23 (d, J=8.1 Hz, 1H), 7.14 (s, 2H), 6.59 (s, 1H), 6.40 (d, J=8.4 Hz, 1H), 5.06 (d, J=12.7 Hz, 1H), 4.05 (s, 4H), 3.76 (s, 3H), 3.68 (d, J=11.4 Hz, 2H), 3.16-2.82 (m, 12H), 2.70-2.54 (m, 5H), 2.43-2.25 (m, 6H), 2.08-1.95 (m, 1H), 1.85 (d, J=12.1 Hz, 2H), 1.75 (d, J=12.6 Hz, 2H), 1.62-1.46 (m, 3H), 1.41-1.32 (m, 2H), 1.26-1.12 (m, 2H); $[M+H]^+$=980.2.

Example 38: 3-(4-(2-(4-(4-(4-((5-chloro-4-((1-(methylsulfonyl)indolin-7-yl)amino)pyrimidin-2-yl)amino)-3-methoxyphenyl)piperazin-1-yl)piperidin-1-yl)ethyl)phenyl)piperidine-2,6-dione

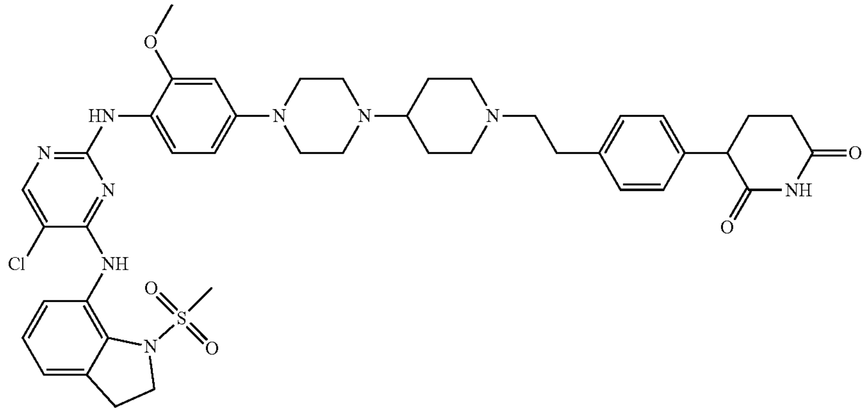 [SMILES: COc1cc(N2CCN(C3CCN(CCc4ccc(C5CCC(=O)NC5=O)cc4)CC3)CC2)ccc1Nc1ncc(Cl)c(Nc2cccc3c2N(S(C)(=O)=O)CC3)n1]

The titled compound was prepared in a manner similar to that in Example 3. 1H NMR (400 MHz, DMSO) δ 10.82 (s, 1H), 8.92 (s, 1H), 8.08 (s, 1H), 7.88 (s, 2H), 7.46 (d, J=8.6 Hz, 1H), 7.15 (dt, J=14.2, 8.0 Hz, 6H), 6.60 (s, 1H), 6.39 (d, J=8.6 Hz, 1H), 4.05 (s, 2H), 3.81 (dd, J=11.5, 4.7 Hz, 1H), 3.76 (s, 3H), 3.10 (s, 6H), 3.02 (d, J=13.7 Hz, 6H), 2.71 (d, J=8.1 Hz, 2H), 2.64 (s, 5H), 2.54 (s, 1H), 2.46 (s, 1H), 2.19 (m, 2H), 1.99 (t, J=11.0 Hz, 3H), 1.80 (d, J=10.7 Hz, 2H), 1.46 (d, J=10.5 Hz, 2H); $[M+H]^+$=828.7.

Example 39: 3-(4-(2-(4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)ethyl)phenyl)piperidine-2,6-dione

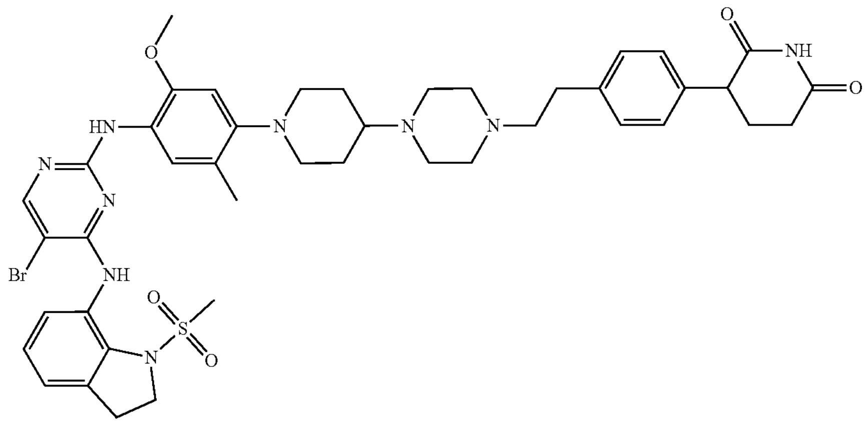 [SMILES: COc1cc(N2CCC(N3CCN(CCc4ccc(C5CCC(=O)NC5=O)cc4)CC3)CC2)c(C)cc1Nc1ncc(Br)c(Nc2cccc3c2N(S(C)(=O)=O)CC3)n1]

The titled compound was prepared in a manner similar to that in Example 3. $^{1}H$ NMR (400 MHz, DMSO) δ 10.83 (s, 1H), 8.80 (s, 1H), 8.18 (s, 1H), 7.88 (s, 2H), 7.44 (s, 1H), 7.16 (m, 6H), 6.68 (s, 1H), 4.05 (s, 2H), 3.76 (s, 4H), 3.07 (m, 8H), 2.51-2.80 (m, 12H), 2.33-2.48 (m, 3H), 1.80-2.28 (m, 6H), 1.89 (m, 2H), 1.61 (m, 2H); $[M+H]^{+}$=886.2.

Example 40: 3-(4-(4-((4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)methyl)piperidin-1-yl)phenyl)piperidine-2,6-dione

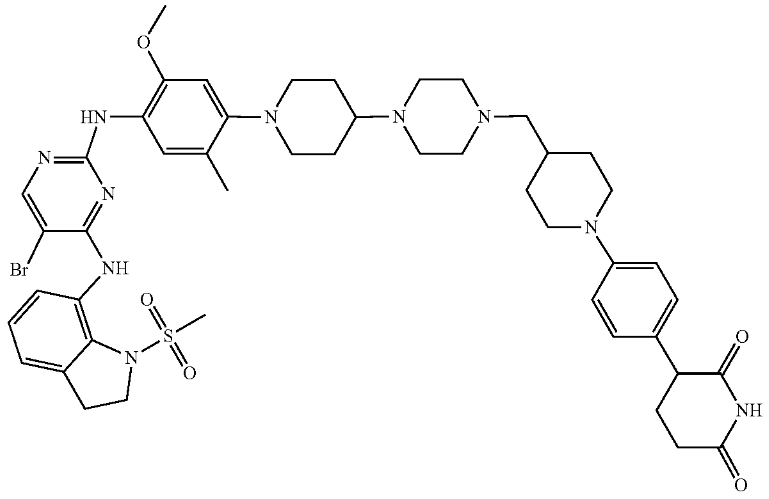 [SMILES: COc1cc(N2CCC(N3CCN(CC4CCN(c5ccc(C6CCC(=O)NC6=O)cc5)CC4)CC3)CC2)c(C)cc1Nc1ncc(Br)c(Nc2cccc3c2N(S(C)(=O)=O)CC3)n1]

The titled compound was prepared in a manner similar to that in Example 3. $^{1}H$ NMR (400 MHz, DMSO) δ 10.76 (s, 1H), 8.79 (s, 1H), 8.17 (s, 1H), 7.86 (s, 2H), 7.44 (s, 1H), 7.15 (s, 2H), 7.03 (d, J=8.5 Hz, 2H), 6.88 (d, J=8.5 Hz, 2H), 6.68 (s, 1H), 4.05 (s, 2H), 3.70 (m, 6H), 3.07 (m, 7H), 2.61 (m, 9H), 2.38 (s, 6H), 2.11 (m, 7H), 1.76 (s, 4H), 1.57 (d, J=10.4 Hz, 3H), 1.19 (d, J=11.3 Hz, 2H); $[M+H]^{+}$=955.2.

Example 41: 3-(4-(4-(2-(4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)ethyl)piperidin-1-yl)phenyl)piperidine-2,6-dione

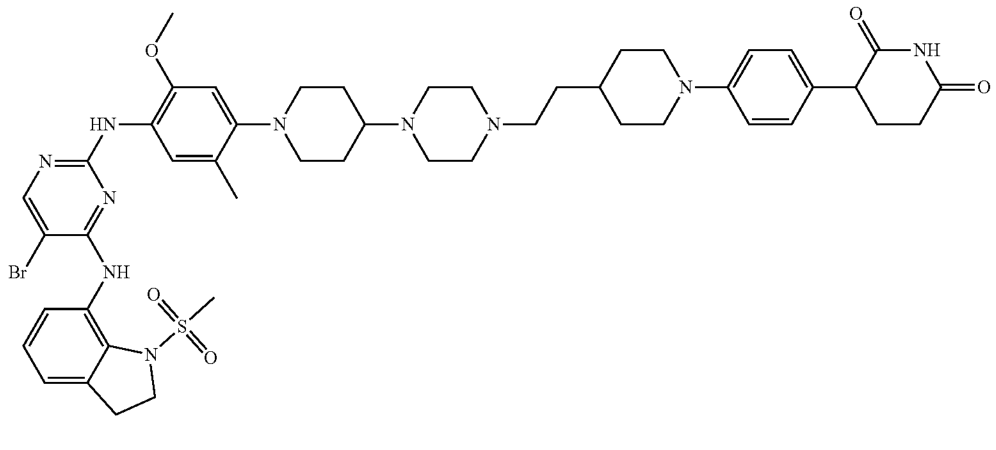 [SMILES: COc1cc(N2CCC(N3CCN(CCC4CCN(c5ccc(C6CCC(=O)NC6=O)cc5)CC4)CC3)CC2)c(C)cc1Nc1ncc(Br)c(Nc2cccc3c2N(S(C)(=O)=O)CC3)n1]

The titled compound was prepared in a manner similar to that in Example 3. 1H NMR (400 MHz, DMSO) δ 10.77 (s, 1H), 8.78 (s, 1H), 8.16 (s, 1H), 7.87 (s, 1H), 7.78 (s, 1H), 7.40 (s, 1H), 7.13 (s, 2H), 7.01 (d, J=8.8 Hz, 2H), 6.86 (d, J=8.8 Hz, 2H), 6.65 (s, 1H), 4.02 (d, J=7.7 Hz, 2H), 3.73 (s, 3H), 3.71-3.66 (m, 1H), 3.62 (d, J=11.0 Hz, 2H), 3.05-3.11 (m, 9H), 2.58 (m, 4H), 2.31 (m, 5H), 2.09 (m, 2H), 2.05 (s, 3H), 1.99 (m, 2H), 1.82-1.85 (m, 3H), 1.72-175 (m, 3H), 1.55-1.60 (m, 3H), 1.38-1.42 (m, 3H), 1.18-1.21 (m, 3H); $[M+H]^+$=969.3.

Example 42: 5-(4-(3-(4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)-3-oxopropyl)piperazin-1-yl)-2-(2,6-dioxopiperidin-3-yl)isoindoline-1,3-dione

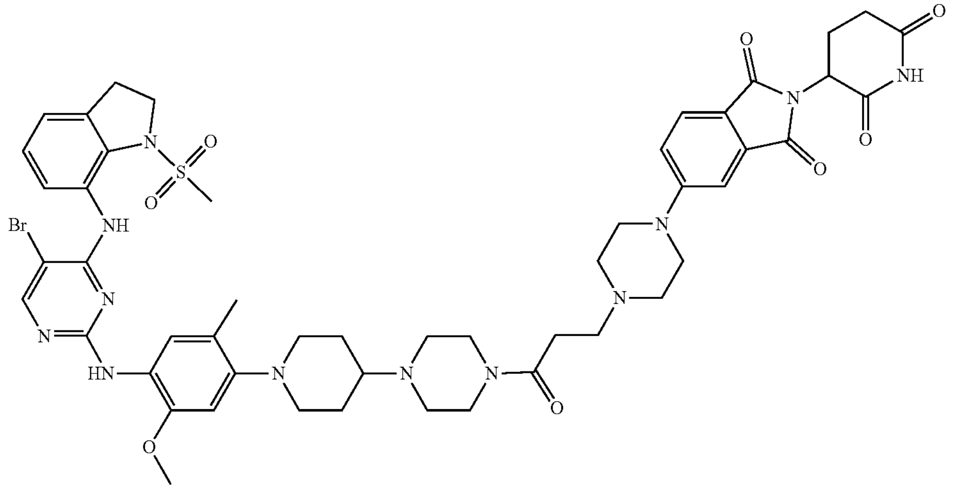 [SMILES: COc1cc(N2CCC(N3CCN(C(=O)CCN4CCN(c5ccc6c(c5)C(=O)N(C5CCC(=O)NC5=O)C6=O)CC4)CC3)CC2)c(C)cc1Nc1ncc(Br)c(Nc2cccc3c2N(S(C)(=O)=O)CC3)n1]

The titled compound was prepared in a manner similar to that in Example 11. 1H NMR (400 MHz, DMSO) δ 11.08 (s, 1H), 8.80 (s, 1H), 8.17 (d, J=4.1 Hz, 1H), 7.87 (s, 1H), 7.80 (s, 1H), 7.68 (d, J=8.3 Hz, 1H), 7.43 (s, 1H), 7.35 (s, 1H), 7.27 (d, J=8.9 Hz, 1H), 7.15 (s, 2H), 6.68 (s, 1H), 5.07 (d, J=7.8 Hz, 1H), 4.05 (s, 2H), 3.76 (s, 3H), 3.44 (s, 10H), 3.14-3.02 (m, 8H), 2.86 (d, J=12.1 Hz, 1H), 2.60 (s, 4H), 2.54 (s, 9H), 2.37 (s, 1H), 2.07 (s, 3H), 2.02 (s, 1H), 1.83 (s, 2H), 1.58 (d, J=11.0 Hz, 2H); $[M+H]^+$=1067.3.

Example 43: 5-(4-((4-(4-(1-(4-((5-bromo-4-((1-(methylsulfonyl)indolin-7-yl)amino)pyrimidin-2-yl)amino)-5-methoxy-2-methylphenyl)piperidin-4-yl)piperazine-1-carbonyl)piperidin-1-yl)methyl)piperidin-1-yl)-2-(2,6-dioxopiperidin-3-yl)isoindoline-1,3-dione Step 1: 1-(methylsulfonyl)-7-nitroindoline

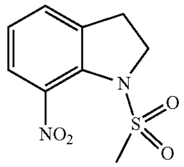 [SMILES: CS(=O)(=O)N1CCc2cccc([N+](=O)[O-])c21]

To a stirred solution of 7-nitroindoline (300 mg, 1.8 mmol) and NaH (146 mg, 3.6 mmol) in DMF (5 mL) was added methanesulfonyl chloride dropwise (315 mg, 2.7 mmol). The resulting mixture was stirred at room temperature for 1 hour. The reaction was quenched with saturated $NH_4Cl$ (aq.) solution and extracted with EtOAc (2×50 mL). The combined organic layer was washed with brine (2×50 mL), dried over $Na_2SO_4$ and concentrated under vacuum to afford the crude residue, which was purified with silica gel column chromatography (PE:EA=100:0~2:1 gradient elution) to give the title product (390 mg, 88%). $[M+H]^+$=243.1.

Step 2: 1-(methylsulfonyl)indolin-7-amine

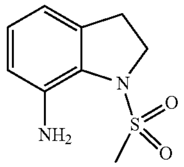

Under $N_2$, to a solution of 1-(methylsulfonyl)-7-nitroindoline (390 mg, 1.6 mmol) in MeOH (20 mL) was added 10% Pd/C (50 mg) at room temperature. And then the mixture was exchanged with $H_2$ two times and stirred under $H_2$ atmosphere at room temperature for 2 h. Reaction was monitored by LC-MS. The mixture was filtered through a pad of Celite and washed with MeOH (20 mL). The filtrate was concentrated under vacuum to obtain the title product (340 mg, 99%). $[M+H]^+$=213.1.

Step 3: N-(5-bromo-2-chloropyrimidin-4-yl)-1-(methylsulfonyl)indolin-7-amine

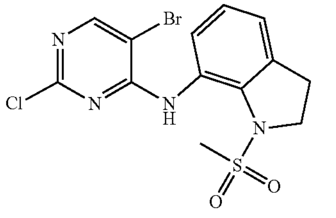 [SMILES: CS(=O)(=O)N1CCc2cccc(Nc3nc(Cl)ncc3Br)c21]

A mixture of 1-(methylsulfonyl)indolin-7-amine (340 mg, 1.6 mmol), 5-bromo-2,4-dichloropyrimidine (729 mg, 3.2 mmol) and DIEA (412 mg, 3.2 mmol) in i-PrOH (20 mL) was stirred in a round bottom flask at 100° C. for 16 h. The mixture was evaporated in vacuum to afford the crude product, which was purified with silica gel column chromatography (PE:EA=100:0~2:1 gradient elution) to give the title product (550 mg, 85%). $[M+H]^+$=402.8, 404.7.

Step 4: 5-bromo-$N^2$-(2-methoxy-5-methyl-4-(4-(piperazin-1-yl)piperidin-1-yl)phenyl)-$N^4$-(1-(methylsulfonyl)indolin-7-yl)pyrimidine-2,4-diamine

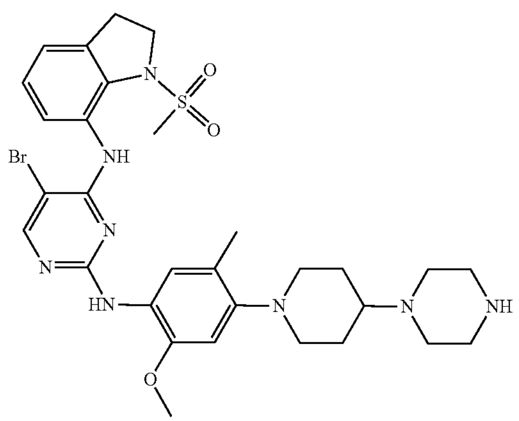 [SMILES: COc1cc(N2CCC(N3CCNCC3)CC2)c(C)cc1Nc1ncc(Br)c(Nc2cccc3c2N(S(C)(=O)=O)CC3)n1]

A mixture of N-(5-bromo-2-chloropyrimidin-4-yl)-1-(methylsulfonyl)indolin-7-amine (500 mg, 1.24 mmol), tert-butyl 4-(1-(4-amino-5-methoxy-2-methylphenyl)piperidin-4-yl)piperazine-1-carboxylate (637 mg, 1.57 mmol) and MsOH (476 mg, 4.96 mmol) in t-BuOH (10 mL) was stirred in a round bottom flask at 100° C. for 16 hours. The mixture was evaporated in vacuum to afford the crude product which was diluted with water and extracted with DCM (2×30 mL). The organic layer was combined and washed with brine (2×50 mL), dried over $Na_2SO_4$ and concentrated under vacuum to afford the crude title product (560 mg, 67%); $[M+H]^+$=671.3, 673.3.

Step 5: 5-(4-((4-(4-(1-(4-((5-bromo-4-((1-(methylsulfonyl)indolin-7-yl)amino)pyrimidin-2-yl)amino)-5-methoxy-2-methylphenyl)piperidin-4-yl)piperazine-1-carbonyl)piperidin-1-yl)methyl)piperidin-1-yl)-2-(2,6-dioxopiperidin-3-yl)isoindoline-1,3-dione

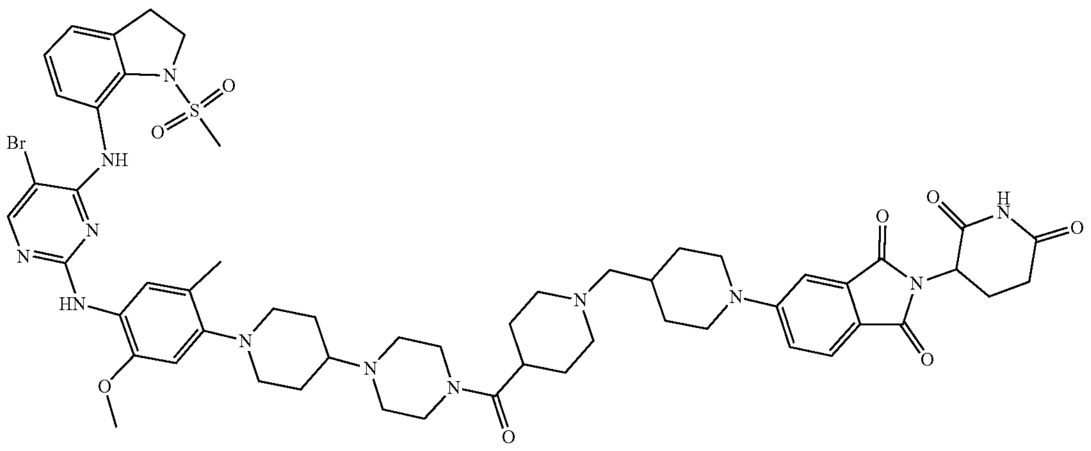 [SMILES: COc1cc(N2CCC(N3CCN(C(=O)C4CCN(CC5CCN(c6ccc7c(c6)C(=O)N(C6CCC(=O)NC6=O)C7=O)CC5)CC4)CC3)CC2)c(C)cc1Nc1ncc(Br)c(Nc2cccc3c2N(S(C)(=O)=O)CC3)n1]

To a solution of 1-((1-(2-(2,6-dioxopiperidin-3-yl)-1,3-dioxoisoindolin-5-yl)piperidin-4-yl)methyl)piperidine-4-carboxylic acid (37.6 mg, 0.078 mmol), HATU (30.9 mg, 0.081 mmol) and DIEA (38 mg, 0.296 mmol) in DMF (5 mL) was added 5-bromo-$N^2$-(2-methoxy-5-methyl-4-(4-(piperazin-1-yl)piperidin-1-yl)phenyl)-$N^4$-(1-(methylsulfonyl)indolin-7-yl)pyrimidine-2,4-diamine (50 mg, 0.074 mmol). The resulting mixture was stirred at room temperature for 4 h. The reaction was quenched with water and the mixture was extracted with DCM, washed with saturated brine. dried over anhydrous $Na_2SO_4$. After filtration, the filtrate was concentrated under reduced pressure, the residue was purified by Pre-HPLC to give the title product (23.4 mg, 27%). $^1H$ NMR (400 MHz, DMSO) δ 11.08 (s, 1H), 8.80 (s, 1H), 8.17 (s, 1H), 7.87 (s, 1H), 7.80 (s, 1H), 7.65 (d, J=8.4 Hz, 1H), 7.43 (s, 1H), 7.30 (s, 1H), 7.23 (d, J=8.6 Hz, 1H), 7.15 (s, 2H), 6.68 (s, 1H), 5.06 (d, J=7.2 Hz, 1H), 4.05 (s, 4H), 3.76 (s, 3H), 3.47 (s, 4H), 3.07 (m, 8H), 3.01-2.90 (m, 3H), 2.84 (s, 3H), 2.61 (s, 3H), 2.53 (s, 3H), 2.47-2.45 (m, 1H), 2.36 (s, 1H), 2.10 (d, J=18.9 Hz, 5H), 1.96 (m, 3H), 1.87-1.75 (m, 5H), 1.58 (s, 6H), 1.14 (s, 2H); $[M+H]^+$=1135.4.

Example 44: 5-(3-(3-(4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)propyl)azetidin-1-yl)-2-(2,6-dioxopiperidin-3-yl)isoindoline-1,3-done

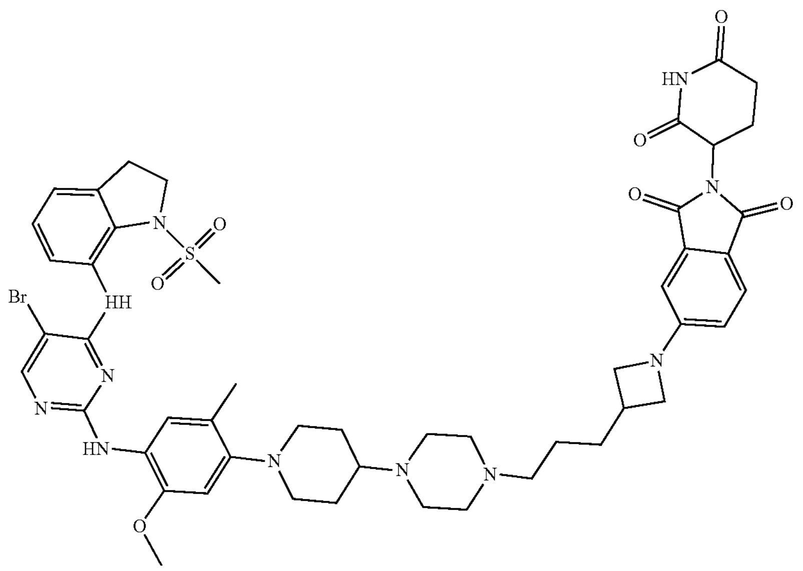

The titled compound was prepared in a manner similar to that in Example 1. 1H NMR (400 MHz, DMSO) δ 11.07 (s, 1H), 8.79 (s, 1H), 8.17 (s, 1H), 7.87 (s, 1H), 7.80 (s, 1H), 7.64 (d, J=8.3 Hz, 1H), 7.43 (s, 1H), 7.15 (s, 2H), 6.76 (s, 1H), 6.67 (s, 1H), 6.63 (d, J=8.6 Hz, 1H), 5.05 (d, J=8.0 Hz, 1H), 4.12 (d, J=8.3 Hz, 2H), 4.05 (s, 2H), 3.76 (s, 3H), 3.65 (s, 3H), 3.10 (s, 3H), 3.05 (s, 5H), 2.86 (d, J=11.4 Hz, 2H), 2.77 (s, 1H), 2.57 (m, 8H), 2.40 (s, 3H), 2.29 (s, 3H), 2.07 (s, 3H), 2.01 (s, 1H), 1.84 (s, 2H), 1.62 (s, 2H), 1.56 (d, J=10.4 Hz, 1H), 1.44 (s, 2H); $[M+H]^+$=1024.3.

Example 45: 3-(4-(2-(4-(1-(4-((5-chloro-4-((1-(methylsulfonyl)indolin-7-yl)amino)pyrimidin-2-yl)amino)-2-fluorophenyl)piperidin-4-yl)piperazin-1-yl)ethyl)phenyl)piperidine-2,6-dione

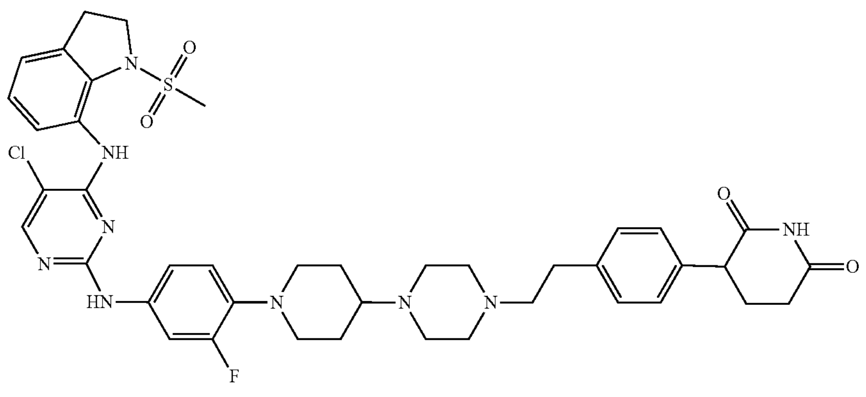 [SMILES: CS(=O)(=O)N1CCc2cccc(Nc3nc(Nc4ccc(N5CCC(N6CCN(CCc7ccc(C8CCC(=O)NC8=O)cc7)CC6)CC5)c(F)c4)ncc3Cl)c21]

The titled compound was prepared in a manner similar to that in Example 3. 1H NMR (400 MHz, DMSO) δ 10.81 (s, 1H), 9.40 (s, 1H), 9.02 (s, 1H), 8.18 (s, 1H), 7.86 (s, 1H), 7.55 (d, J=15.2 Hz, 1H), 7.32-7.22 (m, 2H), 7.18 (d, J=8.0 Hz, 3H), 7.12 (d, J=8.0 Hz, 2H), 6.87 (t, J=9.4 Hz, 1H), 4.07 (s, 2H), 3.81 (d, J=6.8 Hz, 1H), 3.29-3.23 (m, 3H), 3.10 (m, 6H), 2.71 (s, 2H), 2.60 (m, 7H), 2.48-2.39 (m, 4H), 2.27 (s, 2H), 2.17 (d, J=10.6 Hz, 1H), 2.03 (s, 1H), 1.82 (s, 2H), 1.55 (d, J=11.7 Hz, 2H); $[M+H]^+$=816.6.

Example 46: 3-(4-(4-(2-((1-(7-((5-chloro-4-((1-(methylsulfonyl)indolin-7-yl)amino)pyrimidin-2-yl)amino)-2,3-dihydrobenzofuran-4-yl)piperidin-4-yl)(methyl)amino)ethyl)piperidin-1-yl)-2-fluorophenyl)piperidine-2,6-dione

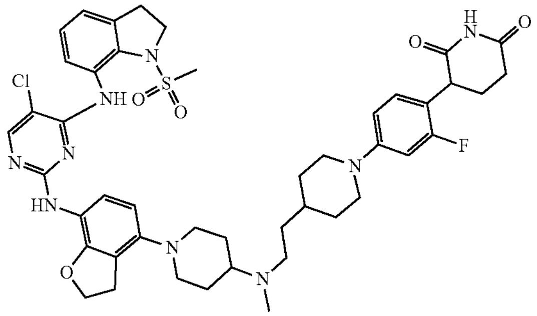 [SMILES: CN(CCC1CCN(c2ccc(C3CCC(=O)NC3=O)c(F)c2)CC1)C1CCN(c2ccc(Nc3ncc(Cl)c(Nc4cccc5c4N(S(C)(=O)=O)CC5)n3)c3c2CCO3)CC1]

The titled compound was prepared in a manner similar to that in Example 3. $^1$H NMR (400 MHz, DMSO) $\delta_H$ 10.80 (s, 1H), 8.89 (s, 1H), 8.28 (s, 1H), 8.20 (s, 1H), 8.07 (s, 1H), 7.91 (d, J=7.5 Hz, 1H), 7.11 (d, J=6.2 Hz, 2H), 7.06 (t, J=8.6 Hz, 2H), 6.70 (d, J=10.8 Hz, 2H), 6.36 (d, J=8.5 Hz, 1H), 4.45 (t, J=8.4 Hz, 2H), 4.04 (t, J=6.6 Hz, 2H), 3.87 (dd, J=12.1, 4.2 Hz, 1H), 3.70 (d, J=12.6 Hz, 3H), 3.17-3.06 (m, 6H), 3.03 (s, 3H), 2.72-2.57 (m, 4H), 2.54 (s, 3H), 2.24 (s, 3H), 2.14 (d, J=12.5 Hz, 1H), 1.99-1.89 (m, 1H), 1.78 (dd, J=24.1, 12.5 Hz, 4H), 1.64-1.45 (m, 3H), 1.43-1.34 (m, 2H), 1.22 (dd, J=20.3, 10.9 Hz, 2H); $[M+H]^+$=886.4.

Example 47: 5-(4-(2-((1-(7-((5-chloro-4-((1-(methylsulfonyl)indolin-7-yl)amino)pyrimidin-2-yl)amino)-2,3-dihydrobenzofuran-4-yl)piperidin-4-yl)(methyl)amino)ethyl)piperidin-1-yl)-2-(2,6-dioxopiperidin-3-yl)isoindoline-1,3-dione

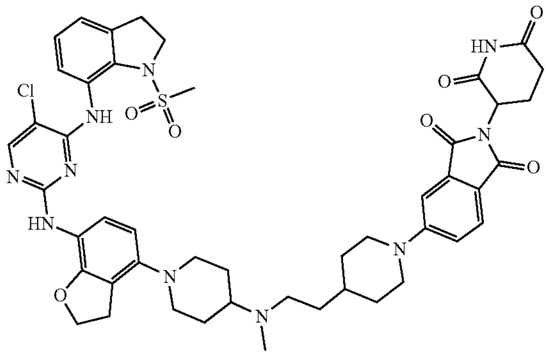 [SMILES: CN(CCC1CCN(c2ccc3c(c2)C(=O)N(C2CCC(=O)NC2=O)C3=O)CC1)C1CCN(c2ccc(Nc3ncc(Cl)c(Nc4cccc5c4N(S(C)(=O)=O)CC5)n3)c3c2CCO3)CC1]

The titled compound was prepared in a manner similar to that in Example 3. $^1$H NMR (400 MHz, DMSO) $\delta_H$ 11.08 (s, 1H), 8.93-8.84 (m, 1H), 8.28 (s, 1H), 8.07 (s, 1H), 7.92 (d, J=7.9 Hz, 1H), 7.65 (d, J=8.4 Hz, 1H), 7.31 (s, 1H), 7.24 (d, J=8.2 Hz, 1H), 7.11 (d, J=7.5 Hz, 2H), 7.06 (t, J=8.2 Hz, 1H), 6.36 (d, J=8.4 Hz, 1H), 5.06 (dd, J=13.5, 4.8 Hz, 1H), 4.46 (t, J=8.1 Hz, 2H), 4.11-3.99 (m, 4H), 3.17-3.07 (m, 5H), 3.04 (s, 3H), 2.99-2.92 (m, 3H), 2.92-2.80 (m, 2H), 2.64-2.54 (m, 6H), 2.27 (s, 3H), 2.01 (dt, J=19.0, 7.9 Hz, 1H), 1.86-1.73 (m, 4H), 1.67-1.55 (m, 3H), 1.46-1.34 (m, 2H), 1.20 (m, 2H); $[M+H]^+$=937.4.

Example 48: 3-(4-(2-((1-(7-((5-chloro-4-((1-(methylsulfonyl)indolin-7-yl)amino)pyrimidin-2-yl)amino)-2,3-dihydrobenzofuran-4-yl)piperidin-4-yl)(methyl)amino)ethyl)-2-fluorophenyl)piperidine-2,6-dione

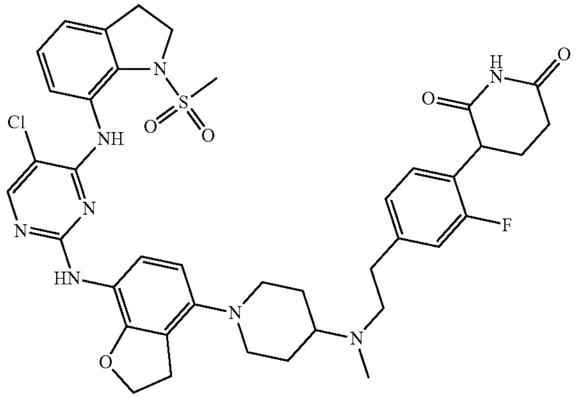 [SMILES: CN(CCc1ccc(C2CCC(=O)NC2=O)c(F)c1)C1CCN(c2ccc(Nc3ncc(Cl)c(Nc4cccc5c4N(S(C)(=O)=O)CC5)n3)c3c2CCO3)CC1]

The titled compound was prepared in a manner similar to that in Example 3. $^1$H NMR (400 MHz, DMSO) $\delta_H$ 10.86 (s, 1H), 8.93-8.85 (m, 1H), 8.27 (s, 1H), 8.07 (s, 1H), 7.96-7.87 (m, 1H), 7.21 (m, 1H), 7.08 (m, 5H), 6.35 (d, J=8.6 Hz, 1H), 4.45 (t, J=8.6 Hz, 2H), 4.08-3.96 (m, 4H), 3.30 (s, 2H), 3.17-3.06 (m, 4H), 3.03 (s, 3H), 2.73 (s, 5H), 2.60 (m, 3H), 2.31 (s, 3H), 2.17 (t, J=11.8 Hz, 1H), 1.98 (dd, J=14.0, 6.0 Hz, 1H), 1.80 (d, J=12.7 Hz, 2H), 1.57 (m, 2H); $[M+H]^+$=803.3.

Example 49: 3-(4-(4-(2-((1-(7-((5-chloro-4-((1-(methylsulfonyl)indolin-7-yl)amino)pyrimidin-2-yl)amino)-2,3-dihydrobenzofuran-4-yl)piperidin-4-yl)(methyl)amino)ethyl)piperidin-1-yl)phenyl)piperidine-2,6-dione

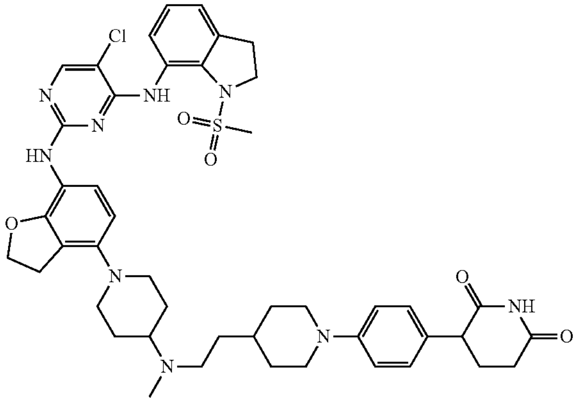 [SMILES: CN(CCC1CCN(c2ccc(C3CCC(=O)NC3=O)cc2)CC1)C1CCN(c2ccc(Nc3ncc(Cl)c(Nc4cccc5c4N(S(C)(=O)=O)CC5)n3)c3c2CCO3)CC1]

The titled compound was prepared in a manner similar to that in Example 3. $^1$H NMR (400 MHz, DMSO) $\delta_H$ 10.76 (s, 1H), 8.94-8.84 (m, 1H), 8.26 (s, 1H), 8.07 (s, 1H), 7.92 (d, J=8.5 Hz, 1H), 7.15-6.99 (m, 5H), 6.88 (d, J=8.7 Hz, 2H), 6.36 (d, J=8.9 Hz, 1H), 4.45 (t, J=8.7 Hz, 2H), 4.04 (t, J=7.2 Hz, 2H), 3.71 (dd, J=10.5, 4.6 Hz, 1H), 3.65 (d, J=11.7 Hz, 2H), 3.30-3.27 (m, 4H), 3.12 (dt, J=14.7, 5.1 Hz, 4H), 3.03 (s, 3H), 2.61 (t, J=11.1 Hz, 5H), 2.49-2.40 (m, 2H), 2.22 (s, 3H), 2.12 (d, J=11.0 Hz, 1H), 2.01 (dd, J=13.2, 9.1 Hz, 1H), 1.76 (d, J=13.7 Hz, 4H), 1.58 (dd, J=21.1, 9.5 Hz, 2H), 1.49-1.36 (m, 3H), 1.25 (m, 2H); $[M+H]^+$=868.4.

Example 50: 5-(3-(3-((1-(7-((5-chloro-4-((1-(methylsulfonyl)indolin-7-yl)amino)pyrimidin-2-yl)amino)-2,3-dihydrobenzofuran-4-yl)piperidin-4-yl)(methyl)amino)propyl)azetidin-1-yl)-2-(2,6-dioxopiperidin-3-yl)isoindoline-1,3-dione

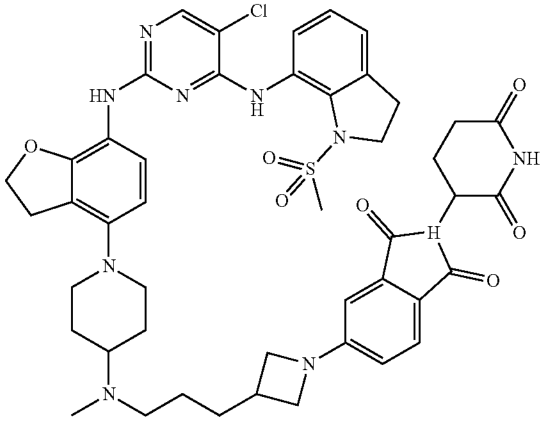

The titled compound was prepared in a manner similar to that in Example 1. $^1$H NMR (400 MHz, DMSO) $\delta_H$ 11.07 (s, 1H), 8.89 (s, 1H), 8.27 (s, 1H), 8.17 (s, 1H), 8.07 (s, 1H), 7.91 (d, J=9.0 Hz, 1H), 7.64 (d, J=8.4 Hz, 1H), 7.15-7.03 (m, 3H), 6.77 (s, 1H), 6.63 (d, J=7.7 Hz, 1H), 6.36 (d, J=8.7 Hz, 1H), 5.05 (dd, J=12.9, 5.7 Hz, 1H), 4.45 (t, J=9.0 Hz, 2H), 4.15 (d, J=7.8 Hz, 2H), 4.04 (t, J=6.5 Hz, 2H), 3.69-3.62 (m, 4H), 3.50 (s, 8H), 3.19-3.06 (m, 3H), 3.03 (s, 3H), 2.93-2.73 (m, 1H), 2.69-2.52 (m, 5H), 2.25 (s, 2H), 2.01 (s, 1H), 1.81 (d, J=9.3 Hz, 1H), 1.69-1.52 (m, 3H), 1.50-1.37 (m, 2H); $[M+H]^+$=923.4.

Example 51: 3-(4-(4-(2-(4-(1-(7-((5-chloro-4-((1-(methylsulfonyl)indolin-7-yl)amino)pyrimidin-2-yl)amino)-2,3-dihydrobenzofuran-4-yl)piperidin-4-yl)piperazin-1-yl)ethyl)piperidin-1-yl)-2-fluorophenyl)piperidine-2,6-dione

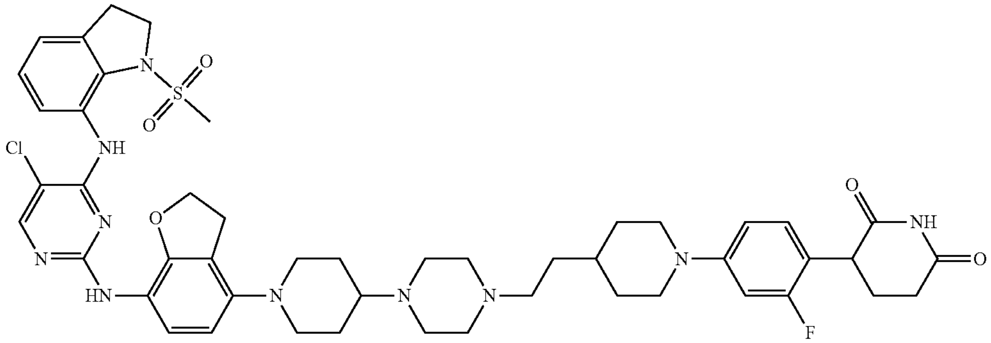 [SMILES: CS(=O)(=O)N1CCc2cccc(Nc3nc(Nc4ccc(N5CCC(N6CCN(CCC7CCN(c8ccc(C9CCC(=O)NC9=O)c(F)c8)CC7)CC6)CC5)c5c4OCC5)ncc3Cl)c21]

The titled compound was prepared in a manner similar to that in Example 3. 1H NMR (400 MHz, DMSO) δ 10.80 (s, 1H), 8.89 (s, 1H), 8.27 (s, 1H), 8.07 (s, 1H), 7.90 (s, 1H), 7.08 (m, 4H), 6.70 (d, J=11.3 Hz, 2H), 6.35 (d, J=8.3 Hz, 1H), 4.45 (s, 2H), 4.04 (s, 2H), 3.85 (s, 1H), 3.69 (d, J=10.2 Hz, 2H), 3.09 (s, 5H), 3.03 (s, 4H), 2.73-2.58 (m, 6H), 2.52 (s, 4H), 2.39 (s, 3H), 2.32 (s, 4H), 2.13 (d, J=12.9 Hz, 1H), 1.96 (s, 1H), 1.85 (s, 2H), 1.73 (d, J=11.8 Hz, 2H), 1.54 (s, 2H), 1.40 (s, 3H), 1.22 (s, 2H); $[M+H]^+$=941.7.

Example 52: 5-(4-(2-(4-(1-(7-((5-chloro-4-((1-(methylsulfonyl)indolin-7-yl)amino)pyrimidin-2-yl)amino)-2,3-dihydrobenzofuran-4-yl)piperidin-4-yl)piperazin-1-yl)ethyl)piperidin-1-yl)-2-(2,6-dioxopiperidin-3-yl)isoindoline-1,3-dione

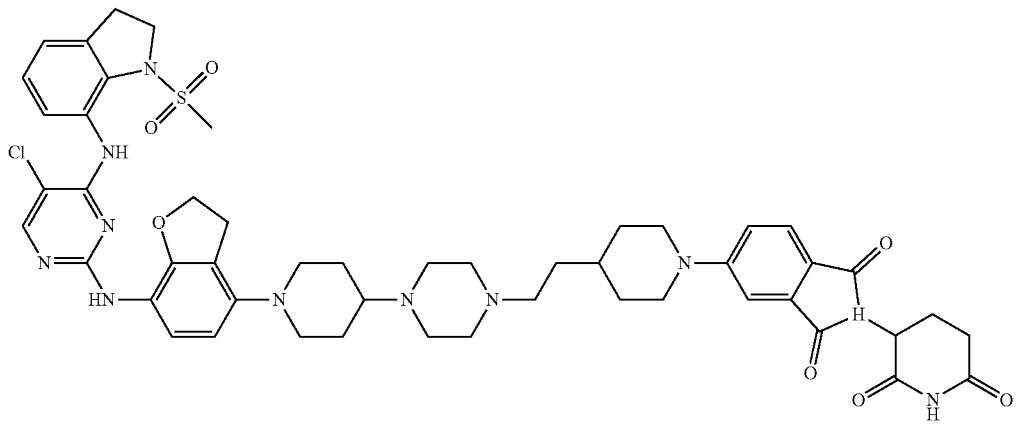

The titled compound was prepared in a manner similar to that in Example 1.1H NMR (400 MHz, DMSO) δ 11.08 (s, 1H), 8.89 (s, 1H), 8.27 (s, 1H), 8.07 (s, 1H), 7.90 (s, 1H), 7.65 (d, J=8.5 Hz, 1H), 7.30 (s, 1H), 7.23 (d, J=8.3 Hz, 1H), 7.09 (t, J=13.2 Hz, 3H), 6.35 (d, J=8.5 Hz, 1H), 5.06 (d, J=7.6 Hz, 1H), 4.45 (s, 2H), 4.03 (d, J=7.9 Hz, 4H), 3.10 (d, J=11.8 Hz, 5H), 3.04 (s, 4H), 2.92 (m, 5H), 2.60 (s, 6H), 2.39 (s, 2H), 2.31 (s, 5H), 2.02 (s, 1H), 1.85 (s, 2H), 1.75 (d, J=10.7 Hz, 2H), 1.52 (d, J=10.9 Hz, 3H), 1.39 (s, 2H), 1.18 (d, J=10.8 Hz, 2H); $[M+H]^+$=992.8.

Example 53: 3-(4-(2-(4-(1-(7-((5-chloro-4-((1-(methylsulfonyl)indolin-7-yl)amino)pyrimidin-2-yl)amino)-2,3-dihydrobenzofuran-4-yl)piperidin-4-yl)piperazin-1-yl)ethyl)-2-fluorophenyl)piperidine-2,6-dione

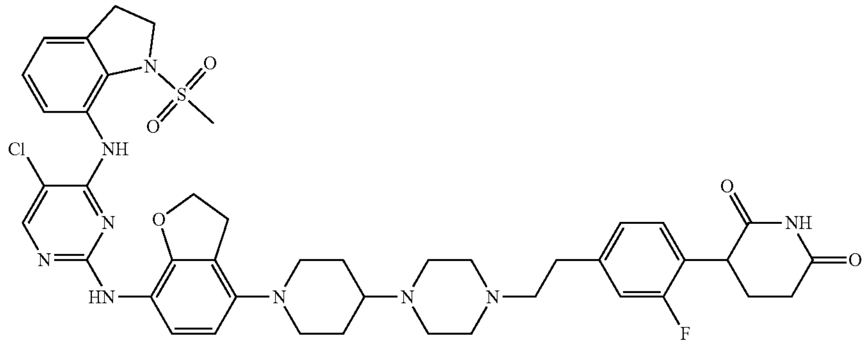 [SMILES: CS(=O)(=O)N1CCc2cccc(Nc3nc(Nc4ccc(N5CCC(N6CCN(CCc7ccc(C8CCC(=O)NC8=O)c(F)c7)CC6)CC5)c5c4OCC5)ncc3Cl)c21]

The titled compound was prepared in a manner similar to that in Example 3. 1H NMR (400 MHz, DMSO) δ 10.86 (s, 1H), 8.89 (s, 1H), 8.27 (s, 1H), 8.07 (s, 1H), 7.90 (s, 1H), 7.20 (t, J=7.6 Hz, 1H), 7.15-7.01 (m, 5H), 6.36 (d, J=8.4 Hz, 1H), 4.45 (s, 2H), 4.09-3.98 (m, 3H), 3.09 (m, 8H), 2.74 (s, 3H), 2.62 (d, J=11.4 Hz, 10H), 2.49-2.42 (m, 4H), 2.33 (s, 1H), 2.18 (d, J=10.8 Hz, 1H), 1.99 (s, 1H), 1.87 (d, J=10.6 Hz, 2H), 1.54 (d, J=10.5 Hz, 2H); $[M+H]^+$=858.7.

Example 54: 3-(4-(4-(2-(4-(1-(7-((5-chloro-4-((1-(methylsulfonyl)indolin-7-yl)amino)pyrimidin-2-yl)amino)-2,3-dihydrobenzofuran-4-yl)piperidin-4-yl)piperazin-1-yl)ethyl)piperidin-1-yl)phenyl)piperidine-2,6-dione

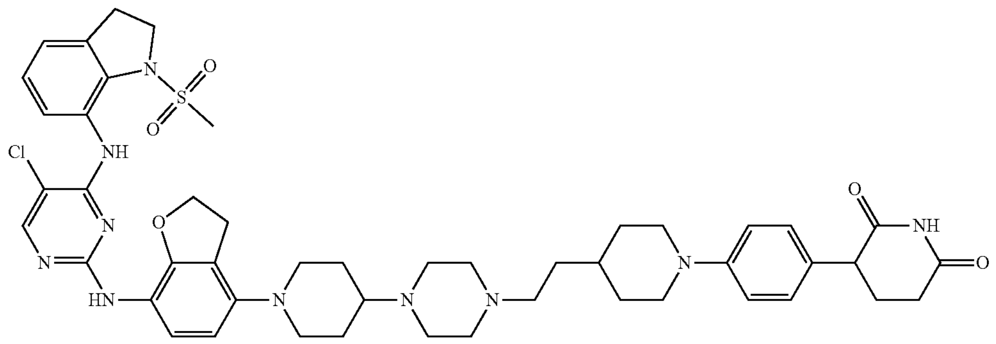 [SMILES: CS(=O)(=O)N1CCc2cccc(Nc3nc(Nc4ccc(N5CCC(N6CCN(CCC7CCN(c8ccc(C9CCC(=O)NC9=O)cc8)CC7)CC6)CC5)c5c4OCC5)ncc3Cl)c21]

The titled compound was prepared in a manner similar to that in Example 3. 1H NMR (400 MHz, DMSO) δ 11.07 (s, 1H), 8.89 (s, 1H), 8.27 (s, 1H), 8.07 (s, 1H), 7.94-7.87 (m, 1H), 7.64 (d, J=8.2 Hz, 1H), 7.10 (s, 2H), 7.08-7.02 (m, 1H), 6.76 (s, 1H), 6.63 (s, 1H), 6.34 (s, 1H), 5.04 (s, 1H), 4.45 (s, 2H), 4.13 (s, 2H), 4.04 (s, 2H), 3.66 (s, 3H), 3.46-3.41 (m, 2H), 3.06 (m, 8H), 2.91-2.73 (m, 3H), 2.57 (m, 9H), 2.40-2.24 (m, 4H), 2.04-1.96 (m, 1H), 1.86 (s, 2H), 1.62 (s, 2H), 1.57-1.49 (m, 2H), 1.47-1.39 (m, 2H), 1.24 (s, 2H); $[M+H]^+$=923.8.

Example 55: 5-(3-(3-(4-(1-(7-((5-chloro-4-((1-(methylsulfonyl)indolin-7-yl)amino)pyrimidin-2-yl)amino)-2,3-dihydrobenzofuran-4-yl)piperidin-4-yl)piperazin-1-yl)propyl)azetidin-1-yl)-2-(2,6-dioxopiperidin-3-yl)isoindoline-1,3-dione Step 1: tert-butyl 4-(1-(7-nitro-2,3-dihydrobenzofuran-4-yl)piperidin-4-yl)piperazine-1-carboxylate

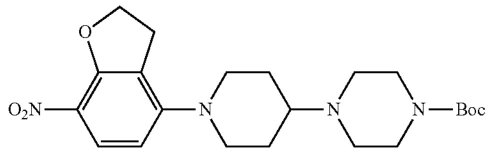 [SMILES: CC(C)(C)OC(=O)N1CCN(C2CCN(c3ccc([N+](=O)[O-])c4c3CCO4)CC2)CC1]

A mixture of 4-bromo-7-nitro-2,3-dihydrobenzofuran (1.0 g, 4.098 mmol), tert-butyl 4-(piperidin-4-yl)piperazine-1-carboxylate (1.32 g, 4.917 mmol), Pd2(dba)$_3$ (375 mg, 0.409 mmol), BINAP (254 mg, 0.409 mmol) and $K_3PO_4$ (2.6 g, 12.29 mmol) in toluene (30 mL) was stirred in a round bottom flask at 100° C. overnight under $N_2$. The mixture was evaporated in vacuum to afford the crude product, which was further purified with silica gel column chromatography (DCM:MeOH=100:0~50:1 gradient elution) to give the product (350 mg, 19%). $[M+H]^+$=433.5.

Step 2: tert-butyl 4-(1-(7-amino-2,3-dihydrobenzofuran-4-yl)piperidin-4-yl)piperazine-1-carboxylate

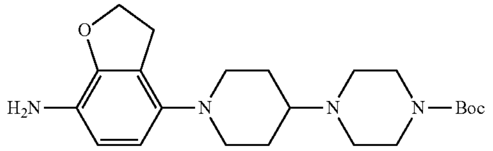 [SMILES: CC(C)(C)OC(=O)N1CCN(C2CCN(c3ccc(N)c4c3CCO4)CC2)CC1]

To a solution of tert-butyl 4-(1-(7-nitro-2,3-dihydrobenzofuran-4-yl)piperidin-4-yl)piperazine-1-carboxylate (350 mg, 0.809 mmol) in MeOH (5 mL) and DCM (5 mL) was added 10% Pd/C (100 mg) at 25° C. And then the mixture was exchanged with $H_2$ three times and stirred under $H_2$ atmosphere at 25° C. for 12 h. Reaction was monitored by LCMS. The mixture was filtered through a pad of Celite and washed with MeOH (20 mL). The filtrate was concentrated under vacuum to obtain the product (280 mg, 86%). $[M+H]^+$=403.4.

Step 3: tert-butyl 4-(1-(7-((5-chloro-4-((1-(methylsulfonyl)indolin-7-yl)amino)pyrimidin-2-yl)amino)-2,3-dihydrobenzofuran-4-yl)piperidin-4-yl)piperazine-1-carboxylate

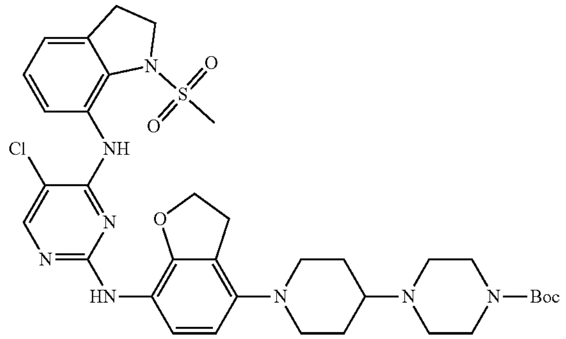 [SMILES: CC(C)(C)OC(=O)N1CCN(C2CCN(c3ccc(Nc4ncc(Cl)c(Nc5cccc6c5N(S(C)(=O)=O)CC6)n4)c4c3CCO4)CC2)CC1]

A mixture of N-(2,5-dichloropyrimidin-4-yl)-1-(methylsulfonyl)indolin-7-amine (210 mg, 0.588 mmol) (The intermediate was prepared according to the same procedure as step 3 in example 43 from 2,4,5-trichloropyrimidine), tert-butyl 4-(1-(7-amino-2,3-dihydrobenzofuran-4-yl)piperidin-4-yl)piperazine-1-carboxylate (260 mg, 0.647 mmol), Pd2 $(dba)_3$ (54 mg, 0.059 mmol), BINAP (37 mg, 0.059 mmol) and $K_3PO_4$ (373 mg, 1.764 mmol) in toluene (15 mL) was stirred in a round bottom flask at 100° C. overnight under $N_2$. The mixture was evaporated in vacuum to afford the crude product, which was further purified with silica gel column chromatography (DCM:MeOH=100:0~50:1 gradient elution) to give the product (240 mg, 56%). $[M+H]^+$=725.6.

Step 4: 5-chloro-$N^4$-(1-(methylsulfonyl)indolin-7-yl)-$N^2$-(4-(4-(piperazin-1-yl)piperidin-1-yl)-2,3-dihydrobenzofuran-7-yl)pyrimidine-2,4-diamine hydrochloride

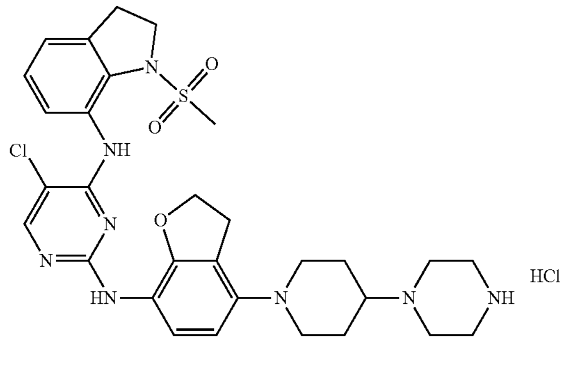 [SMILES: CS(=O)(=O)N1CCc2cccc(Nc3nc(Nc4ccc(N5CCC(N6CCNCC6)CC5)c5c4OCC5)ncc3Cl)c21 ; Cl]

A solution of tert-butyl 4-(1-(7-((5-chloro-4-((1-(methylsulfonyl)indolin-7-yl)amino)pyrimidin-2-yl)amino)-2,3-dihydrobenzofuran-4-yl)piperidin-4-yl)piperazine-1-carboxylate (230 mg, 0.317 mmol) in HCl/1,4-dioxane (4 mL) was stirred in a round bottom flask at room temperature for 2 h. The mixture was evaporated in vacuum to afford the crude product (180 mg, 86%), which was used for next step without further purification. $[M+H]^+$=625.5.

Step 5: 5-(3-(3-(4-(1-(7-((5-chloro-4-((1-(methylsulfonyl)indolin-7-yl)amino)pyrimidin-2-yl)amino)-2,3-dihydrobenzofuran-4-yl)piperidin-4-yl)piperazin-1-yl)propyl)azetidin-1-yl)-2-(2,6-dioxopiperidin-3-yl)isoindoline-1,3-dione

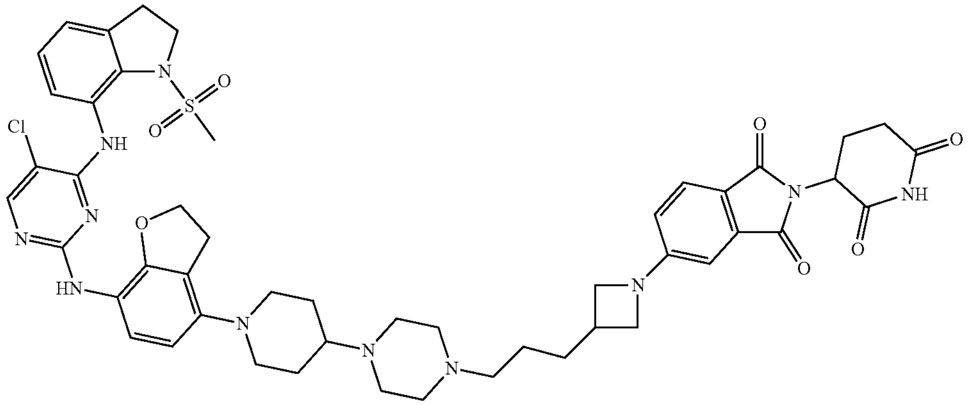 [SMILES: CS(=O)(=O)N1CCc2cccc(Nc3nc(Nc4ccc(N5CCC(N6CCN(CCCC7CN(c8ccc9c(c8)C(=O)N(C8CCC(=O)NC8=O)C9=O)C7)CC6)CC5)c5c4OCC5)ncc3Cl)c21]

The titled compound was synthesized in the procedures similar to Example 1. 1H NMR (400 MHz, DMSO) δ 11.07 (s, 1H), 8.89 (s, 1H), 8.27 (s, 1H), 8.07 (s, 1H), 7.90 (s, 1H), 7.65 (s, 1H), 7.10 (s, 3H), 6.76 (s, 1H), 6.61 (s, 1H), 6.37 (s, 1H), 5.04 (s, 1H), 4.45 (s, 2H), 4.13 (s, 2H), 4.04 (s, 2H), 3.66 (s, 3H), 3.42 (s, 2H), 3.06 (m, 7H), 2.92-2.72 (m, 3H), 2.57 (m, 7H), 2.29 (s, 4H), 2.05-1.96 (m, 1H), 1.86 (s, 2H), 1.63 (s, 2H), 1.57-1.48 (m, 2H), 1.48-1.40 (m, 2H), 1.24 (s, 2H); $[M+H]^+$=978.4.

Example 56: 3-(4-(4-(2-(4-(4-((5-chloro-4-((1-(methylsulfonyl)indolin-7-yl)amino)pyrimidin-2-yl)amino)-3-methoxyphenyl)piperazin-1-yl)ethyl)piperidin-1-yl)phenyl)piperidine-2,6-dione

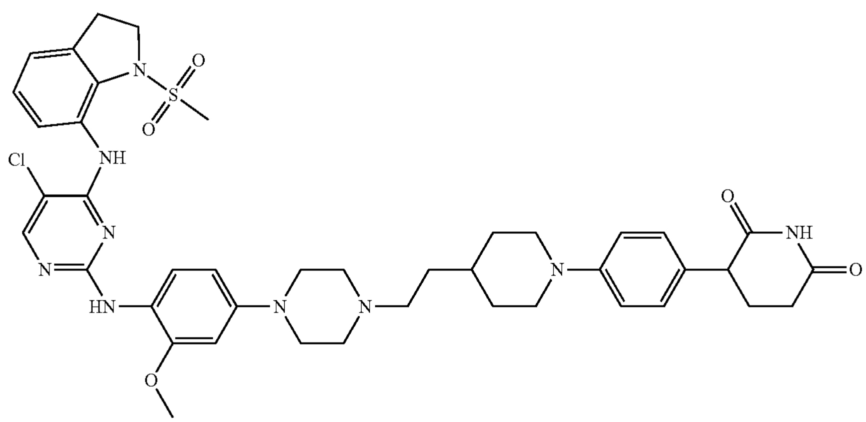 [SMILES: COc1cc(N2CCN(CCC3CCN(c4ccc(C5CCC(=O)NC5=O)cc4)CC3)CC2)ccc1Nc1ncc(Cl)c(Nc2cccc3c2N(S(C)(=O)=O)CC3)n1]

The titled compound was prepared in a manner similar to that in Example 3. 1H NMR (400 MHz, DMSO) δ 10.77 (s, 1H), 8.92 (s, 1H), 8.08 (s, 1H), 7.89 (s, 2H), 7.47 (s, 1H), 7.15 (s, 2H), 7.03 (d, J=8.3 Hz, 2H), 6.88 (d, J=8.7 Hz, 2H), 6.61 (s, 1H), 6.41 (s, 1H), 4.05 (s, 2H), 3.77 (s, 3H), 3.64 (s, 4H), 3.12 (s, 6H), 3.04 (s, 3H), 2.62 (s, 4H), 2.53 (s, 3H), 2.41 (s, 2H), 2.17-2.07 (m, 1H), 2.05-1.96 (m, 1H), 1.76 (s, 2H), 1.46 (s, 3H), 1.29 (s, 2H); $[M+H]^+$=828.3.

Example 58: 3-(4-(3-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazine-1-carbonyl)azetidin-1-yl)phenyl)piperidine-2,6-dione Step 1: methyl 1-(4-(2,6-bis(benzyloxy)pyridin-3-yl)phenyl)azetidine-3-carboxylate

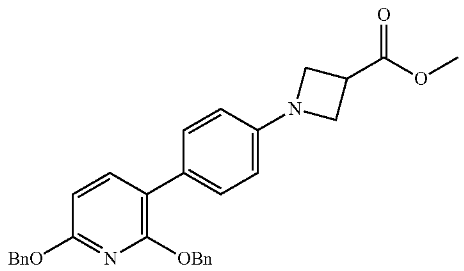 [SMILES: COC(=O)C1CN(c2ccc(-c3ccc(OCc4ccccc4)nc3OCc3ccccc3)cc2)C1]

To the solution of 2,6-bis(benzyloxy)-3-(4-bromophenyl)pyridine (4 g, 9 mmol), methyl azetidine-3-carboxylate hydrochloride (1.5 g, 9.9 mmol) and $Cs_2CO_3$ (7.3 g, 22.5 mmol) in 50 mL dioxane, $Pd2(dba)_3$ (824 mg, 0.9 mmol) and Xantphos (780 mg, 1.35 mmol) were added. The mixture was stirred at 100° C. for 16 hours under $N_2$ atmosphere. After LCMS showed the reaction was completed. The mixture was evaporated and purified by silica column chromatography (PE:EA=10:1-1:1) to afford the product (2.3 g, 53.2% yield). $[M+H]^+$=481.4.

Step 2: 1-(4-(2,6-bis(benzyloxy)pyridin-3-yl)phenyl)azetidine-3-carboxylic acid

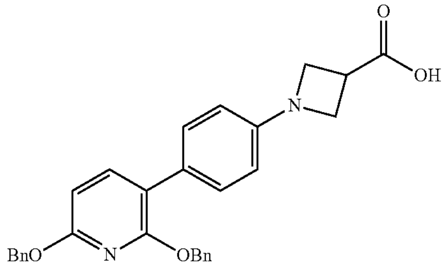 [SMILES: O=C(O)C1CN(c2ccc(-c3ccc(OCc4ccccc4)nc3OCc3ccccc3)cc2)C1]

To the solution of methyl 1-(4-(2,6-bis(benzyloxy)pyridin-3-yl)phenyl)azetidine-3-carboxylate (1.3 g, 2.7 mmol) in 10 mL THF and 10 mL MeOH, LiOH $H_2O$ (340 mg, 8.1 mmol) in 5 mL water was added. The mixture was stirred at room temperature for 2 hours. Then the mixture was concentrated in vacuum to afford the residue which was diluted with water (50 mL) and adjust pH=3 with 1N aqueous HCl solution. The mixture was extracted with EtOAc (50 mL×2) and separated. The organic phase was dried over $Na_2SO_4$ and filtered. The filtrate was concentrated to afford the product (1.26 g, 100% yield). $[M+H]^+$=467.4.

Step 3: 1-(4-(2,6-dioxopiperidin-3-yl)phenyl)azetidine-3-carboxylic acid

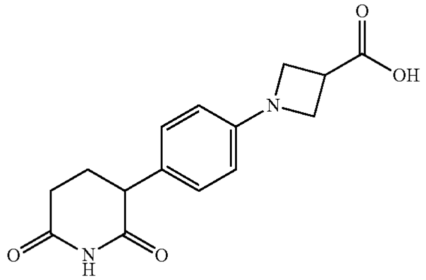 [SMILES: O=C1CCC(c2ccc(N3CC(C(=O)O)C3)cc2)C(=O)N1]

To the solution of 1-(4-(2,6-bis(benzyloxy)pyridin-3-yl)phenyl)azetidine-3-carboxylic acid (1.3 g, 2.79 mmol) in 50 mL MeOH, 130 mg Pd/C was added. The mixture was stirred at room temperature for 16 hours at $H_2$ atmosphere. After LCMS showed the reaction was completed. The mixture was filtered through a pad of celite. The filtrate was concentrated to afford the product (240 mg, 29.8% yield). $[M+H]^+$=289.2.

Step 4: 3-(4-(3-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazine-1-carbonyl)azetidin-1-yl)phenyl)piperidine-2,6-dione

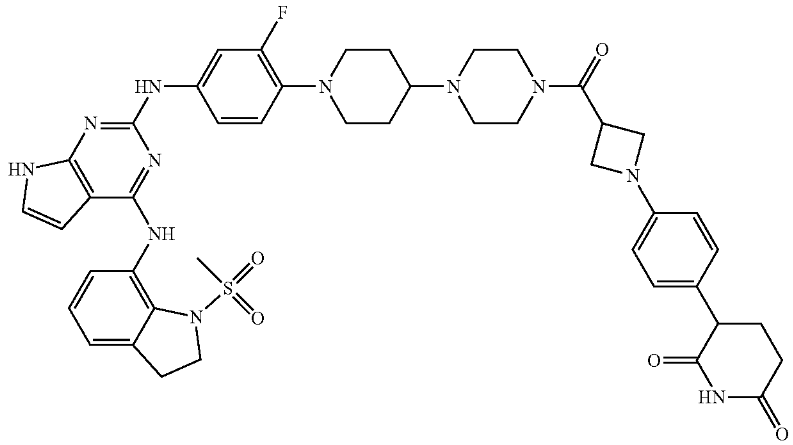 [SMILES: CS(=O)(=O)N1CCc2cccc(Nc3nc(Nc4ccc(N5CCC(N6CCN(C(=O)C7CN(c8ccc(C9CCC(=O)NC9=O)cc8)C7)CC6)CC5)c(F)c4)nc4[nH]ccc34)c21]

The titled compound was prepared in a manner similar to that in Example 11. $^1$H NMR (400 MHz, DMSO) δ 11.32 (s, 1H), 10.76 (s, 1H), 9.03 (s, 1H), 8.93 (s, 1H), 8.30 (d, J=8.1 Hz, 1H), 7.87 (d, J=17.7 Hz, 1H), 7.32 (d, J=7.7 Hz, 1H), 7.24 (d, J=7.9 Hz, 1H), 7.12 (d, J=7.2 Hz, 1H), 7.01 (d, J=8.4 Hz, 2H), 6.98-6.86 (m, 2H), 6.42 (d, J=8.6 Hz, 2H), 6.21 (s, 1H), 4.11 (t, J=7.4 Hz, 2H), 4.00 (s, 2H), 3.90-3.78 (m, 3H), 3.70-3.73 (m, 1H), 3.52-3.44 (m, 2H), 3.31-3.23 (m, 3H), 3.18-3.11 (m, 2H), 3.09 (s, 3H), 2.62-2.68 (m, 7H), 2.39-2.41 (m, 3H), 2.16-2.04 (m, 1H), 2.03-1.95 (m, 1H), 1.88-1.77 (m, 2H), 1.65-1.53 (m, 2H); $[M+H]^+$=876.6.

Example 59: 3-(5-(3-((4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)methyl)azetidin-1-yl)-1-oxoisoindolin-2-yl)piperidine-2,6-dione

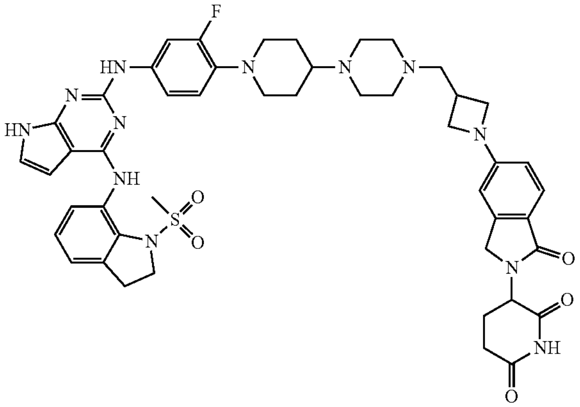 [SMILES: CS(=O)(=O)N1CCc2cccc(Nc3nc(Nc4ccc(N5CCC(N6CCN(CC7CN(c8ccc9c(c8)CN(C8CCC(=O)NC8=O)C9=O)C7)CC6)CC5)c(F)c4)nc4[nH]ccc34)c21]

The titled compound was prepared in a manner similar to that in Example 1 (The key intermediate (1-(2-(2,6-dioxopiperidin-3-yl)-1-oxoisoindolin-5-yl)azetidin-3-yl)methyl 4-methylbenzenesulfonate was prepared according to the way described in WO2020038415A1). $^1$H NMR (400 MHz, DMSO) δ 11.32 (s, 1H), 10.94 (s, 1H), 9.03 (s, 1H), 8.93 (s, 1H), 8.30 (d, J=7.9 Hz, 1H), 7.87 (d, J=15.5 Hz, 1H), 7.48 (d, J=8.3 Hz, 1H), 7.30 (t, J=8.6 Hz, 1H), 7.25 (t, J=7.7 Hz, 1H), 7.13 (d, J=7.2 Hz, 1H), 6.98-6.87 (m, 2H), 6.53-6.44 (m, 2H), 6.21 (s, 1H), 5.03 (dd, J=13.2, 5.0 Hz, 1H), 4.30 (d, J=17.1 Hz, 1H), 4.17 (d, J=17.0 Hz, 1H), 4.11 (t, J=7.4 Hz, 2H), 4.02 (t, J=7.3 Hz, 2H), 3.59-3.52 (m, 2H), 3.17-3.05 (m, 6H), 3.00-2.84 (m, 3H), 2.68-2.54 (m, 9H), 2.44-2.26 (m, 5H), 2.00-1.90 (m, 1H), 1.91-1.80 (m, 2H), 1.63-1.47 (m, 3H); $[M+H]^+$=917.5.

Example 60: 2-(2,6-dioxopiperidin-3-yl)-5-(3-((4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)methyl)azetidin-1-yl)isoindoline-1,3-dione Step 1: 2-(2,6-dioxopiperidin-3-yl)-5-(3-(hydroxymethyl)azetidin-1-yl)isoindoline-1,3-dione

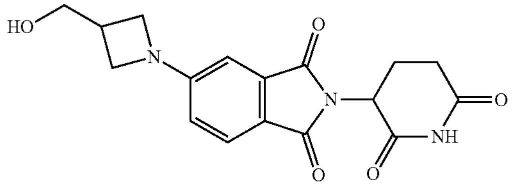 [SMILES: O=C1CCC(N2C(=O)c3ccc(N4CC(CO)C4)cc3C2=O)C(=O)N1]

Into a 100-mL flask, was placed azetidin-3-ylmethanol hydrochloride (500 mg, 4.05 mmol), DMSO (8 mL), 2-(2,6-dioxopiperidin-3-yl)-5-fluoroisoindole-1,3-dione (1.23 g, 4.45 mmol), DIEA (2.61 g, 20.25 mmol). The resulting solution was stirred for 3 hours at 80° C. The reaction mixture was cooled to room temperature. The reaction was quenched with water and extracted with DCM (2×50 mL). The combined organic layers were washed with brine, dried over anhydrous $Na_2SO_4$, and evaporated in vacuum to afford the crude product, which was further purified with silica gel column chromatography (DCM:MeOH=100:0~90:10 gradient elution) to give the product (600 mg, 43%). $[M+H]^+$ =344.1.

Step 2: (1-(2-(2,6-dioxopiperidin-3-yl)-1,3-dioxoisoindolin-5-yl)azetidin-3-yl)methyl methanesulfonate

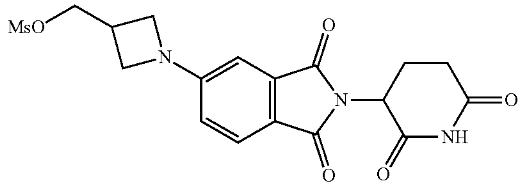 [SMILES: CS(=O)(=O)OCC1CN(c2ccc3c(c2)C(=O)N(C2CCC(=O)NC2=O)C3=O)C1]

To a solution of2-(2,6-dioxopiperidin-3-yl)-5-(3-(hydroxymethyl)azetidin-1-yl)isoindoline-1,3-dione (300 mg, 0.875 mmol) in DCM (10 mL) was added TEA (353 mg, 3.498 mmol). The reaction mixture was cool down to 0° C., then MsCl (152 mg, 1.313 mmol) was added. The mixture was stirred at 25° C. for 3 hrs. The reaction was quenched with water and extracted with DCM (2×30 mL). The combined organic layers were washed with brine, dried over anhydrous $Na_2SO_4$, and evaporated in vacuum to afford the crude product, which was further purified with silica gel column chromatography (DCM:MeOH=100:0-20:1 gradient elution) to give the product (180 mg, 49%). $[M+H]^+$ =422.3.

Step 3: 2-(2,6-dioxopiperidin-3-yl)-5-(3-((4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)methyl)azetidin-1-yl)isoindoline-1,3-dione

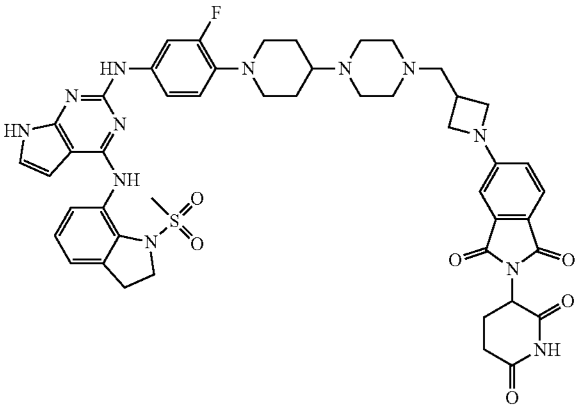 [SMILES: CS(=O)(=O)N1CCc2cccc(Nc3nc(Nc4ccc(N5CCC(N6CCN(CC7CN(c8ccc9c(c8)C(=O)N(C8CCC(=O)NC8=O)C9=O)C7)CC6)CC5)c(F)c4)nc4[nH]ccc34)c21]

The titled compound was prepared in a manner similar to that in Example 1. $^1$H NMR (400 MHz, DMSO) δ 11.33 (s, 1H), 11.07 (s, 1H), 9.03 (s, 1H), 8.93 (s, 1H), 8.32-8.25 (m, 2H), 7.86 (d, J=14.5 Hz, 1H), 7.63 (d, J=8.1 Hz, 1H), 7.35-7.21 (m, 2H), 7.13 (d, J=6.8 Hz, 1H), 6.94 m, 2H), 6.77 (s, 1H), 6.64 (d, J=6.7 Hz, 1H), 6.21 (s, 1H), 5.04 (s, 1H), 4.12 (d, J=8.2 Hz, 4H), 3.68 (s, 2H), 3.15-3.06 (m, 6H), 3.02-2.85 (m, 5H), 2.64-2.54 (m, 6H), 2.46-2.23 (m, 6H), 2.05-1.96 (m, 1H), 1.88-1.79 (m, 2H), 1.62-1.50 (m, 2H); $[M+H]^+$=931.7.

Example 61: 2-(2,6-dioxopiperidin-3-yl)-5-(3-(2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)-2-oxoethyl)azetidin-1-yl)isoindoline-1,3-dione Step 1: 2-(1-(2-(2,6-dioxopiperidin-3-yl)-1,3-dioxoisoindolin-5-yl)azetidin-3-yl)acetic acid

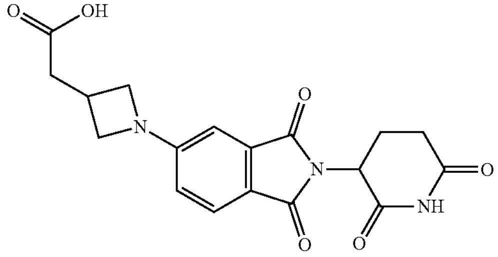 [SMILES: O=C(O)CC1CN(c2ccc3c(c2)C(=O)N(C2CCC(=O)NC2=O)C3=O)C1]

To the solution of 2-(azetidin-3-yl)acetic acid hydrochloride (1 g, 6.6 mmol), 2-(2,6-dioxopiperidin-3-yl)-5-fluoroisoindoline-1,3-dione (1.66 g, 6 mmol) and DIEA (3.1 g, 24 mmol) in 10 mL DMSO. The mixture was stirred at 80° C. for 16 hours. After LCMS showed the reaction was completed, the mixture was poured into water (50 mL) and extracted with DCM (50 mL×2). The combined organic layers were washed with brine (50 mL) and dried over $Na_2SO_4$. The mixture was filtered and the filtrate was evaporated to afford the product (100 mg, 4.5% yield). $[M+H]^+$=372.2.

Step 2: 2-(2,6-dioxopiperidin-3-yl)-5-(3-(2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)-2-oxoethyl)azetidin-1-yl)isoindoline-1,3-dione

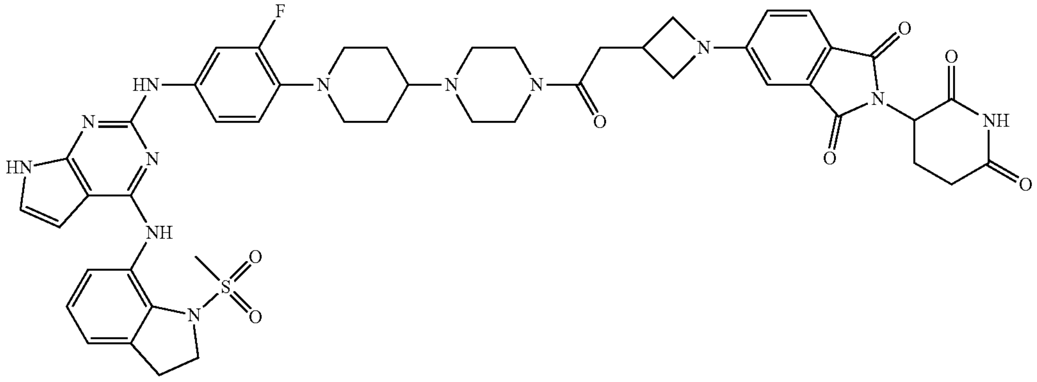 [SMILES: CS(=O)(=O)N1CCc2cccc(Nc3nc(Nc4ccc(N5CCC(N6CCN(C(=O)CC7CN(c8ccc9c(c8)C(=O)N(C8CCC(=O)NC8=O)C9=O)C7)CC6)CC5)c(F)c4)nc4[nH]ccc34)c21]

The titled compound was prepared in a manner similar to that in Example 11. $^1$H NMR (400 MHz, DMSO) δ 11.60 (s, 1H), 10.84 (s, 1H), 9.44 (s, 1H), 8.09-7.72 (m, 2H), 7.24 (m, 6H), 7.02 (s, 2H), 6.34 (s, 1H), 4.10 (s, 2H), 3.84 (d, J=11.5 Hz, 6H), 3.61 (s, 2H), 3.30-3.21 (m, 2H), 3.12-3.16 (m, 3H), 3.10-2.88 (m, 6H), 2.68-2.70 (m, 4H), 2.54 (m, 4H), 2.19-2.20 (m, 3H), 2.03-2.06 (m, 1H), 1.90-2.00 (m, 2H), 1.23-1.26 (m, 2H); $[M+H]^+$=959.7.

Example 62: 2-(2,6-dioxopiperidin-3-yl)-5-((R)-3-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazine-1-carbonyl)pyrrolidin-1-yl)isoindoline-1,3-dione

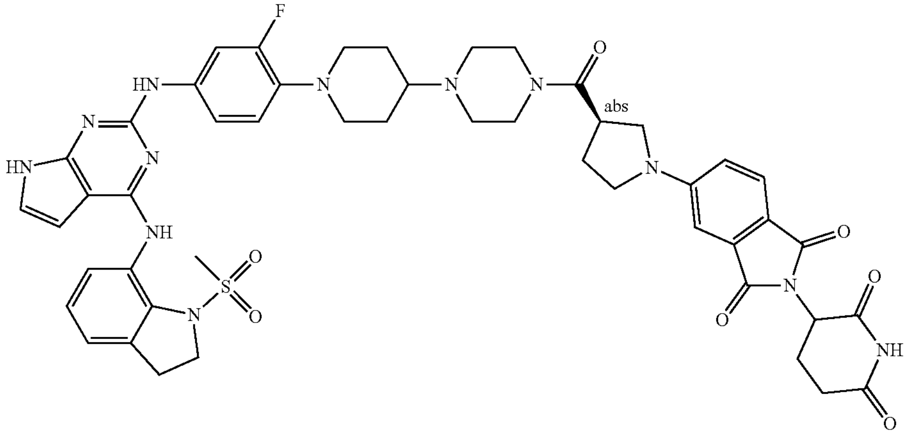 [SMILES: CS(=O)(=O)N1CCc2cccc(Nc3nc(Nc4ccc(N5CCC(N6CCN(C(=O)[C@@H]7CCN(c8ccc9c(c8)C(=O)N(C8CCC(=O)NC8=O)C9=O)C7)CC6)CC5)c(F)c4)nc4[nH]ccc34)c21]

The titled compound was prepared in a manner similar to that in Example 11. $^1$H NMR (400 MHz, DMSO) δ 11.32 (s, 1H), 11.07 (s, 1H), 9.03 (s, 1H), 8.93 (s, 1H), 8.30 (d, J=8.1 Hz, 1H), 7.87 (d, J=17.6 Hz, 1H), 7.65 (d, J=8.3 Hz, 1H), 7.26 (dd, J=19.5, 12.1 Hz, 2H), 7.13 (d, J=7.2 Hz, 1H), 6.93 (t, J=13.7 Hz, 3H), 6.84 (d, J=8.7 Hz, 1H), 6.21 (s, 1H), 5.06 (d, J=12.7 Hz, 1H), 4.11 (s, 2H), 3.69-3.41 (m, 10H), 3.12 (d, J=16.4 Hz, 6H), 2.95-2.82 (m, 2H), 2.69-2.54 (m, 7H), 2.44-2.28 (m, 1H), 2.23 (m, 1H), 2.16-2.06 (m, 1H), 2.06-1.95 (m, 1H), 1.92-1.80 (m, 2H), 1.69-1.53 (m, 2H); $[M+H]^+$=959.6.

Example 63: 2-(2,6-dioxopiperidin-3-yl)-5-((S)-3-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazine-1-carbonyl)pyrrolidin-1-yl)isoindoline-1,3-dione Step 1: (3S)-1-(2-(2,6-dioxopiperidin-3-yl)-1,3-dioxoisoindolin-5-yl)pyrrolidine-3-carboxylic acid

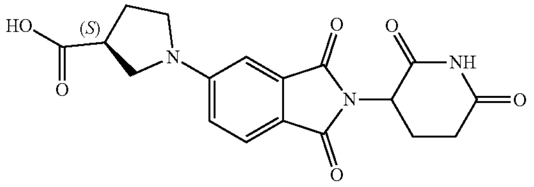

To a stirred mixture of 2-(2,6-dioxopiperidin-3-yl)-5-fluoroisoindole-1,3-dione (3.00 g, 10.86 mmol) in DMSO (50 mL) was added (3S)-pyrrolidine-3-carboxylic acid (1.50 g, 13.03 mmol) and DIEA (9.5 mL, 54.31 mmol), which was stirred overnight at 120° C. The mixture was allowed to cool down to room temperature and neutralized to pH=5 with 1 N HCl (5 mL). The resulting mixture was extracted with EtOAc. The combined organic layers were washed with brine, dried over anhydrous $Na_2SO_4$. After filtration, the filtrate was concentrated under reduced pressure to afford the product (3.37 g, 84%). $[M+H]^+$=372.2.

Step 2: 2-(2,6-dioxopiperidin-3-yl)-5-((S)-3-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazine-1-carbonyl)pyrrolidin-1-yl)isoindoline-1, 3-dione

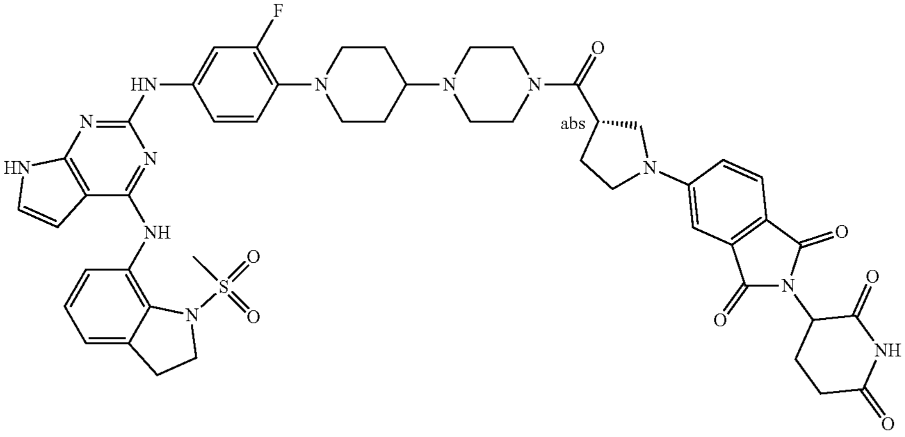 [SMILES: CS(=O)(=O)N1CCc2cccc(Nc3nc(Nc4ccc(N5CCC(N6CCN(C(=O)[C@H]7CCN(c8ccc9c(c8)C(=O)N(C8CCC(=O)NC8=O)C9=O)C7)CC6)CC5)c(F)c4)nc4[nH]ccc34)c21]

The titled compound was prepared in a manner similar to that in Example 11. $^1$H NMR (400 MHz, DMSO) δ 11.32 (s, 1H), 11.07 (s, 1H), 9.03 (s, 1H), 8.93 (s, 1H), 8.30 (d, J=8.0 Hz, 1H), 7.87 (d, J=15.7 Hz, 1H), 7.65 (d, J=8.5 Hz, 1H), 7.32 (d, J=7.1 Hz, 1H), 7.25 (t, J=7.8 Hz, 1H), 7.13 (d, J=7.3 Hz, 1H), 6.99-6.88 (m, 3H), 6.84 (d, J=8.7 Hz, 1H), 6.21 (s, 1H), 5.06 (dd, J=13.0, 5.3 Hz, 1H), 4.11 (t, J=7.4 Hz, 2H), 3.71-3.39 (m, 10H), 3.14 (t, J=7.6 Hz, 2H), 3.10 (s, 3H), 2.89-2.91 (m, 2H), 2.69-2.51 (m, 8H), 2.41-2.28 (m, 1H), 2.27-2.18 (m, 1H), 2.13-2.16 (m, 1H), 2.02-2.05 (m, 1H), 1.89-1.77 (m, 2H), 1.68-1.51 (m, 2H); $[M+H]^+$=959.6.

Example 64: 3-(4-((R)-3-(2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)ethyl)pyrrolidin-1-yl)phenyl)piperidine-2,6-dione

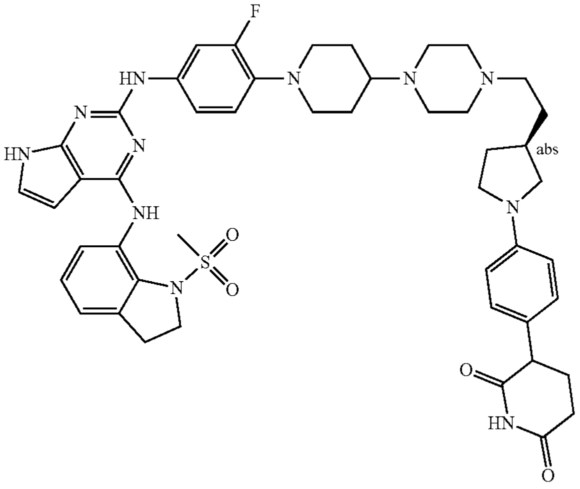 [SMILES: CS(=O)(=O)N1CCc2cccc(Nc3nc(Nc4ccc(N5CCC(N6CCN(CC[C@@H]7CCN(c8ccc(C9CCC(=O)NC9=O)cc8)C7)CC6)CC5)c(F)c4)nc4[nH]ccc34)c21]

The titled compound was prepared in a manner similar to that in Example 3. $^1$H NMR (400 MHz, DMSO) δ 11.32 (s, 1H), 10.74 (s, 1H), 9.03 (s, 1H), 8.92 (s, 1H), 8.30 (d, J=8.1 Hz, 1H), 7.86 (d, J=15.7 Hz, 1H), 7.31 (d, J=8.7 Hz, 1H), 7.25 (t, J=7.8 Hz, 1H), 7.12 (d, J=7.4 Hz, 1H), 7.04-6.94 (m, 3H), 6.91 (t, J=9.4 Hz, 1H), 6.46 (d, J=8.6 Hz, 2H), 6.21 (s, 1H), 4.11 (t, J=7.6 Hz, 2H), 3.67 (dd, J=10.5, 5.0 Hz, 1H), 3.38 (dd, J=16.6, 8.4 Hz, 3H), 3.21-3.07 (m, 7H), 2.83 (t, J=8.4 Hz, 1H), 2.66-2.53 (m, 7H), 2.47-2.20 (m, 9H), 2.11-2.15 (m, 2H), 2.04-1.95 (m, 1H), 1.90-1.80 (m, 2H), 1.66-1.50 (m, 5H); $[M+H]^+$=890.6.

Example 66: 3-((4-(2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)ethyl)phenyl)amino)piperidine-2,6-dione Step 1: 4-(2-((tert-butyldimethylsilyl)oxy)ethyl)aniline

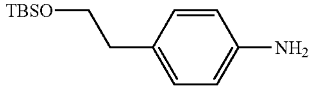 [SMILES: CC(C)(C)[Si](C)(C)OCCc1ccc(N)cc1]

2-(4-aminophenyl)ethan-1-ol (13.7 g, 100 mmol), TEA (20.0 g, 200 mmol) and DMAP (1.2 g, 10 mmol) were placed in DCM (150 mL). TBSCl (17.0 g, 110 mmol) was added to the solution in dropwise at 0° C. The resulting mixture was stirred at room temperature for 1 h. The mixture was diluted with ice-water, extracted with DCM, the combined organic phases were washed with 0.5 M HCl solution for 3 times and Brine for once. The resulting organic phase was dried over $Na_2SO_4$, concentrated to give the desired product (16.9 g, 67.3%), which was used directly without further purification. $[M+H]^+$=252.2.

Step 2: 3-((4-(2-((tert-butyldimethylsilyl)oxy)ethyl)phenyl)amino)piperidine-2,6-dione

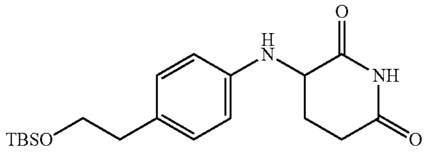 [SMILES: CC(C)(C)[Si](C)(C)OCCc1ccc(NC2CCC(=O)NC2=O)cc1]

4-(2-((tert-butyldimethylsilyl)oxy)ethyl)aniline (9.4 g, 37.5 mmol), 3-bromopiperidine-2,6-dione (10.8 g, 56 mmol) and DIEA (9.7 g, 75 mmol) were placed in MeCN (200 mL). The mixture was stirred at 80° C. for 8 h. Cooling the reaction to room temperature, concentrated and purified with $SiO_2$-gel column to give the desired product (4.8 g, 35.2%). $[M+H]^+$=363.2.

Step 3: 3-((4-(2-hydroxyethyl)phenyl)amino)piperidine-2,6-dione hydrochloride

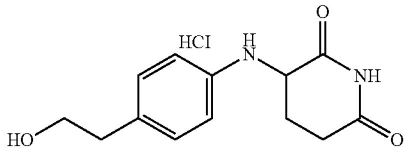

3-((4-(2-((tert-butyldimethylsilyl)oxy)ethyl)phenyl)amino)piperidine-2,6-dione (4.8 g, 13.2 mmol) was placed in HCl-dixoane (4M, 30 mL), the mixture was stirred at room temperature for 2 h. Concentrated and triturated with MTBE to afford desired product (3.1 g, 95%). $[M+H]^+$=249.1.

Step 4: 4-((2,6-dioxopiperidin-3-yl)amino)phenethyl 4-methylbenzenesulfonate

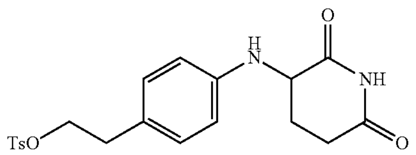 [SMILES: Cc1ccc(S(=O)(=O)OCCc2ccc(NC3CCC(=O)NC3=O)cc2)cc1]

Into a 25-mL flask, 3-((4-(2-hydroxyethyl)phenyl)amino)piperidine-2,6-dione hydrochloride was placed (170.0 mg, 0.6 mmol) was dissolved in pyridine (4.0 mL), TsCl (230.0 mg, 1.2 mmol) was added. The resulting solution was stirred overnight at room temperature. The resulting mixture was concentrated under vacuum. The residue was applied onto a silica gel column with dichloromethane/methanol (7:1) to afford the product (100 mg, 41.7%). $[M+H]^+$=403.2.

Step 5: 3-((4-(2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)ethyl)phenyl)amino)piperidine-2,6-dione

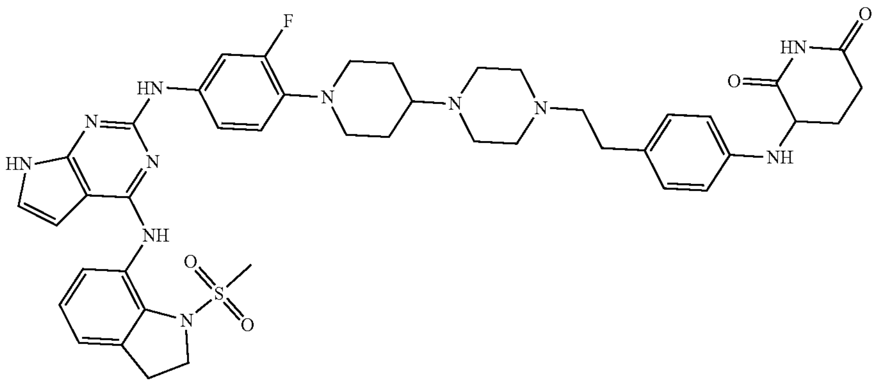 [SMILES: CS(=O)(=O)N1CCc2cccc(Nc3nc(Nc4ccc(N5CCC(N6CCN(CCc7ccc(NC8CCC(=O)NC8=O)cc7)CC6)CC5)c(F)c4)nc4[nH]ccc34)c21]

The titled compound was prepared in a manner similar to that in Example 1. $^1$H NMR (400 MHz, DMSO) δ 11.32 (s, 1H), 10.77 (s, 1H), 9.03 (s, 1H), 8.92 (s, 1H), 8.30 (d, J=8.1 Hz, 1H), 7.87 (d, J=15.4 Hz, 1H), 7.37-7.18 (m, 2H), 7.13

(d, J=7.3 Hz, 1H), 6.94 (d, J=8.4 Hz, 4H), 6.60 (d, J=7.8 Hz, 2H), 6.21 (s, 1H), 5.65 (d, J=7.4 Hz, 1H), 4.26 (s, 1H), 4.11 (s, 2H), 3.14 (ddd, J=11.7, 6.1, 2.0 Hz, 5H), 3.06-2.86 (m, 2H), 2.78-2.51 (m, 16H), 2.36-2.26 (m, 1H), 2.17-2.05 (m, 1H), 1.92-1.79 (m, 3H), 1.63-1.50 (m, 2H); $[M+H]^+$=836.6.

Example 67: 3-(2,6-difluoro-4-(4-(2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)ethyl)piperidin-1-yl)phenyl) piperidine-2,6-dione Step 1: 2,6-bis(benzyloxy)-3-(4,4,5,5-tetramethyl-1,3,2-dioxaborolan-2-yl)pyridine

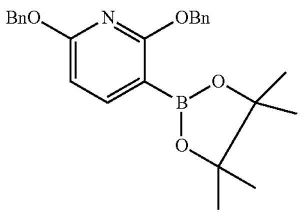 [SMILES: CC1(C)OB(c2ccc(OCc3ccccc3)nc2OCc2ccccc2)OC1(C)C]

A mixture of 2,6-bis(benzyloxy)-3-bromopyridine (15 g, 40.65 mmol) and 4,4,4',4',5,5,5',5'-octamethyl-2,2'-bi(1,3,2-dioxaborolane) (12.6 g, 49.61 mmol), $Pd(dppf)Cl_2$ (3.32 g, 4.07 mmol), KOAc (12 g, 122.45 mmol) in dioxane (200 mL) was stirred at 100° C. for 16 h under nitrogen atmosphere. The resulting mixture was filtered, the filter cake was washed with MeOH and DCM. The filtrate was concentrated under reduced pressure to afford the residue, which was purified by silica gel column chromatography eluted with PE/EtOAc (8:1) to afford the product (9.00 g, 53%). $[M+H]^+$ =418.2.

Step 2: 2,6-bis(benzyloxy)-3-(4-bromo-2,6-difluoro-phenll)pyridine

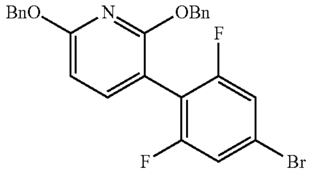 [SMILES: Fc1cc(Br)cc(F)c1-c1ccc(OCc2ccccc2)nc1OCc1ccccc1]

A mixture of2,6-bis(benzyloxy)-3-(4,4,5,5-tetramethyl-1,3,2-dioxaborolan-2-yl)pyridine (9.00 g, 21.56 mmol) and 5-bromo-1,3-difluoro-2-iodobenzene (6.88 g, 21.57 mmol), $K_2CO_3$ (10.43 g, 75.48 mmol), $Pd(dppf)Cl_2$ (789 mg, 1.078 mmol) in dioxane (90 mL) and $H_2O$ (30 mL) was stirred overnight at 100° C. under nitrogen atmosphere. The resulting mixture was extracted with EtOAc. The combined organic layers were washed with brine, dried over anhydrous $Na_2SO_4$. After filtration, the filtrate was concentrated under reduced pressure. The residue was purified by silica gel column chromatography, eluted with PE/EtOAc (5:1) to afford the product (4 g, 38%). $[M+H]^+$=482.2, 484.3.

Step 3: ethyl 2-(1-(4-(2,6-bis(benzyloxy)pyridin-3-yl)-3,5-difluorophenyl)piperidin-4-yl)acetate

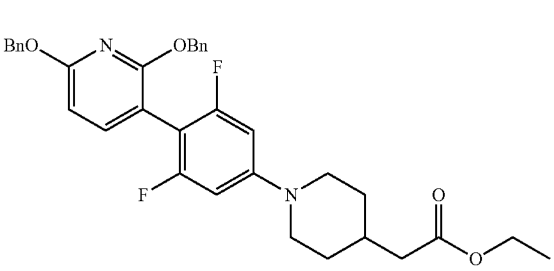 [SMILES: CCOC(=O)CC1CCN(c2cc(F)c(-c3ccc(OCc4ccccc4)nc3OCc3ccccc3)c(F)c2)CC1]

A mixture of 2,6-bis(benzyloxy)-3-(4-bromo-2,6-difluorophenyl)pyridine (4.00 g, 8.29 mmol), ethyl 2-(piperidin-4-yl)acetate (2.13 g, 12.43 mmol), $Cs_2CO_3$ (8.11 g, 24.89 mmol), DavePhos (652.7 mg, 1.659 mmol), $Pd2(dba)_3$ (759.4 mg, 0.829 mmol) in 2-methyl-THF (50 mL) and $H_2O$ (5 mL) was stirred overnight at 100° C. under nitrogen atmosphere. The resulting mixture was extracted with EtOAc. The combined organic layers were washed with brine, dried over anhydrous $Na_2SO_4$. After filtration, the filtrate was concentrated under reduced pressure. The residue was purified by silica gel column chromatography, eluted with PE/EtOAc (1:1) to afford the product (2 g, 42%). $[M+H]^+$=573.5.

Step 4: 2-(1-(4-(2,6-bis(benzyloxy)pyridin-3-yl)-3,5-difluorophenyl)piperidin-4-yl)ethan-1-ol

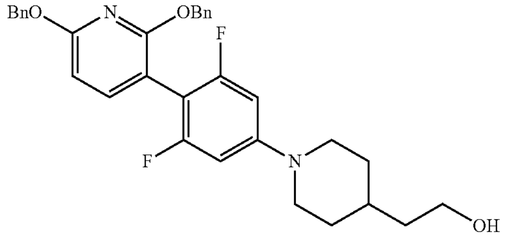 [SMILES: OCCC1CCN(c2cc(F)c(-c3ccc(OCc4ccccc4)nc3OCc3ccccc3)c(F)c2)CC1]

To a stirred mixture of ethyl 2-(1-(4-(2,6-bis(benzyloxy) pyridin-3-yl)-3,5-difluorophenyl)piperidin-4-yl)acetate (2.00 g, 3.49 mmol) in THF (50 mL) was added $LiBH_4$ (1.52 g, 69.77 mmol) in portions at room temperature overnight. The reaction was quenched with water at room temperature. The resulting mixture was extracted with EtOAc. The combined organic layers were washed with brine, dried over anhydrous $Na_2SO_4$. After filtration, the filtrate was concentrated under reduced pressure to afford the product (1.8 g, 97%). $[M+H]^+$=531.4.

Step 5: 3-(2,6-difluoro-4-(4-(2-hydroxyethyl)piperidin-1-yl)phenyl)piperidine-2,6-dione

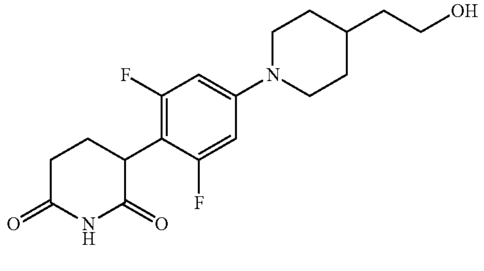 [SMILES: O=C1CCC(c2c(F)cc(N3CCC(CCO)CC3)cc2F)C(=O)N1]

To a stirred mixture of 2-(1-(4-(2,6-bis(benzyloxy)pyridin-3-yl)-3,5-difluorophenyl)piperidin-4-yl)ethan-1-ol (1.80 g, 3.39 mmol) and Pd/C (1 g, 10% wt) in EtOH (20 mL) and DCM (20 mL) were added AcOH (20 mL) at rt and stirred at 40° C. under hydrogen atmosphere overnight. The resulting mixture was filtered, the filter cake was washed with MeOH. The filtrate was concentrated under reduced pressure to afford the product (1.2 g, 100%). $[M+H]^+$=353.1.

Step 6: 2-(1-(4-(2,6-dioxopiperidin-3-yl)-3,5-difluorophenyl)piperidin-4-yl)ethyl methanesulfonate

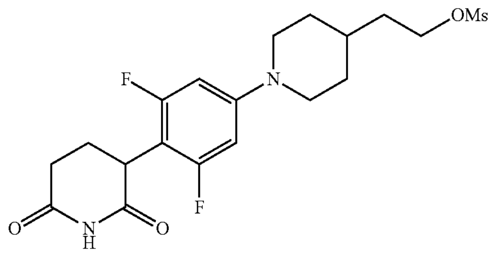 [SMILES: CS(=O)(=O)OCCC1CCN(c2cc(F)c(C3CCC(=O)NC3=O)c(F)c2)CC1]

The titled compound (210 mg, 52%) was prepared in a manner similar to that in Example 1 step 5 from 3-(2,6-difluoro-4-(4-(2-hydroxyethyl)piperidin-1-yl)phenyl)piperidine-2,6-dione and sulfurous dichloride. $[M+H]^+$=431.1.

Step 7: 3-(2,6-difluoro-4-(4-(2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)ethyl)piperidin-1-yl)phenyl)piperidine-2,6-dione

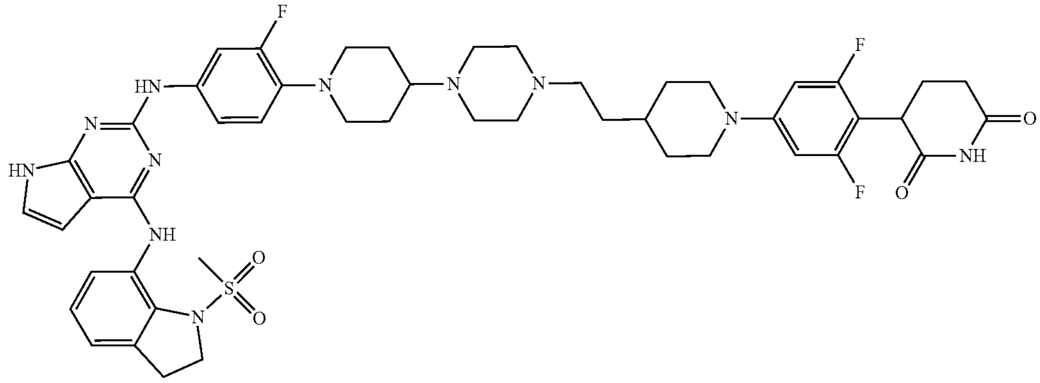 [SMILES: CS(=O)(=O)N1CCc2cccc(Nc3nc(Nc4ccc(N5CCC(N6CCN(CCC7CCN(c8cc(F)c(C9CCC(=O)NC9=O)c(F)c8)CC7)CC6)CC5)c(F)c4)nc4[nH]ccc34)c21]

The titled compound was prepared in a manner similar to that in Example 3. $^1$H NMR (400 MHz, DMSO) δ 11.32 (s, 1H), 10.86 (s, 1H), 9.02 (s, 1H), 8.92 (s, 1H), 8.30 (d, J=7.9 Hz, 1H), 8.18 (s, 1H), 7.86 (d, J=17.4 Hz, 1H), 7.27 (dd, J=29.6, 7.6 Hz, 2H), 7.12 (d, J=7.6 Hz, 1H), 6.99-6.87 (m, 2H), 6.60 (d, J=12.9 Hz, 2H), 6.21 (s, 1H), 4.08 (d, J=19.0 Hz, 3H), 3.73 (d, J=12.3 Hz, 2H), 3.17-3.06 (m, 6H), 2.82-2.53 (m, 8H), 2.31-2.45 (m, 9H), 2.14-2.01 (m, 1H), 1.99-1.89 (m, 1H), 1.88-1.80 (m, 2H), 1.75-1.66 (m, 2H), 1.62-1.34 (m, 5H), 1.25-1.11 (m, 2H); $[M+H]^+$=940.5.

Example 68: 3-(2,6-difluoro-4-(2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)ethyl)phenyl)piperidine-2,6-dione

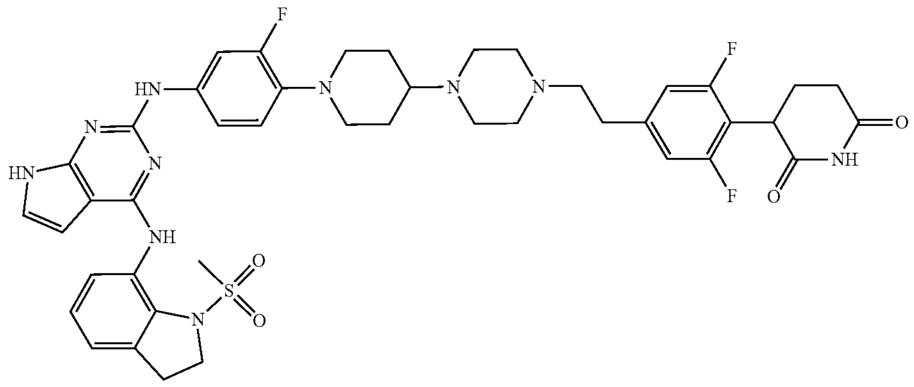 [SMILES: CS(=O)(=O)N1CCc2cccc(Nc3nc(Nc4ccc(N5CCC(N6CCN(CCc7cc(F)c(C8CCC(=O)NC8=O)c(F)c7)CC6)CC5)c(F)c4)nc4[nH]ccc34)c21]

The titled compound was prepared in a manner similar to that in Example 3. $^1$H NMR (400 MHz, DMSO) δ 11.32 (s, 1H), 10.96 (s, 1H), 9.03 (s, 1H), 8.96 (s, 1H), 8.29 (d, J=8.0 Hz, 1H), 7.90 (d, J=15.4 Hz, 1H), 7.33 (d, J=8.5 Hz, 1H), 7.25 (t, J=7.7 Hz, 1H), 7.10 (dd, J=23.0, 8.4 Hz, 3H), 6.95 (d, J=13.1 Hz, 2H), 6.21 (s, 1H), 4.28-4.17 (m, 1H), 4.15-4.06 (m, 2H), 3.60-3.38 (m, 6H), 3.19-2.89 (m, 10H), 2.90-2.74 (m, 3H), 2.71-2.58 (m, 4H), 2.57-2.53 (m, 1H), 2.46-2.31 (m, 1H), 2.22-2.06 (m, 2H), 2.04-1.95 (m, 1H), 1.90-1.54 (m, 2H); [M+H]$^+$=857.5.

Example 69: 3-(2,3-difluoro-4-(2-(4-(1-(2-fluoro-4-((4-((1-(methylsulfonyl)indolin-7-yl)amino)-7H-pyrrolo[2,3-d]pyrimidin-2-yl)amino)phenyl)piperidin-4-yl)piperazin-1-yl)ethyl)phenyl)piperidine-2,6-dione

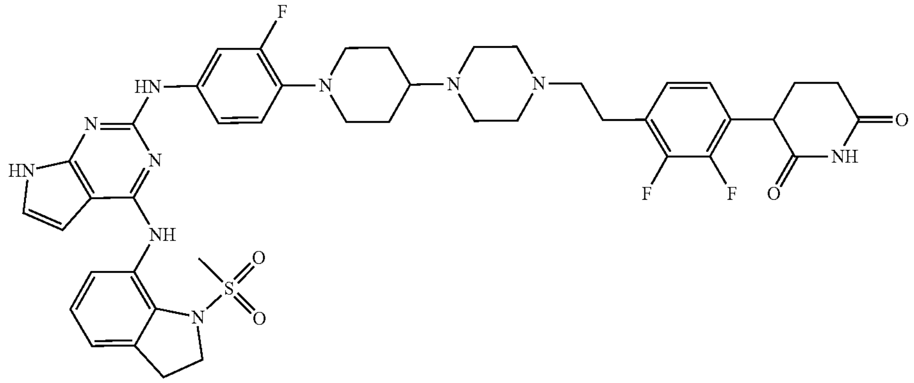 [SMILES: CS(=O)(=O)N1CCc2cccc(Nc3nc(Nc4ccc(N5CCC(N6CCN(CCc7ccc(C8CCC(=O)NC8=O)c(F)c7F)CC6)CC5)c(F)c4)nc4[nH]ccc34)c21]

The titled compound was prepared in a manner similar to that in Example 3. $^1$H NMR (400 MHz, DMSO) δ 11.32 (s, 1H), 10.92 (s, 1H), 9.03 (s, 1H), 8.92 (s, 1H), 8.30 (d, J=8.0 Hz, 1H), 8.21 (s, 1H), 7.86 (d, J=15.6 Hz, 1H), 7.34-7.20 (m, 2H), 7.17-7.00 (m, 3H), 6.92 (dd, J=19.8, 10.5 Hz, 2H), 6.21 (s, 1H), 4.17-4.05 (m, 3H), 3.20-3.05 (m, 8H), 3.05-2.90 (m, 2H), 2.85-2.68 (m, 4H), 2.66-2.52 (m, 7H), 2.38-2.13 (m, 3H), 2.07-1.96 (m, 1H), 1.89-1.79 (m, 2H), 1.63-1.49 (m, 2H); [M+H]$^+$=857.5.

Example 73: 2-(2,6-dioxopiperidin-3-yl)-5-(3-(4-(1-(2-methoxy-4-((4-((1-(methylsulfonyl)indolin-7-yl)amino)-7H-pyrrolo[2,3-d]pyrimidin-2-yl)amino)phenyl)piperidin-4-yl)piperazine-1-carbonyl)azetidin-1-yl)isoindoline-1,3-dione

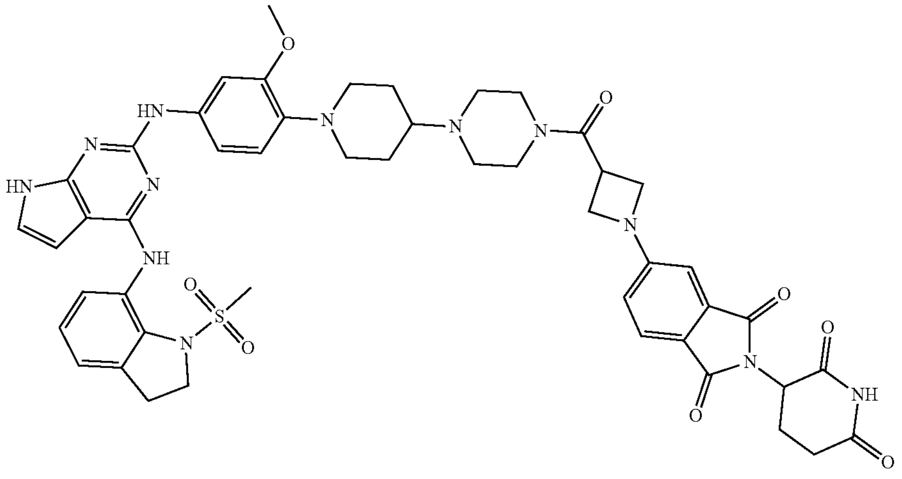 [SMILES: COc1cc(Nc2nc(Nc3cccc4c3N(S(C)(=O)=O)CC4)c3cc[nH]c3n2)ccc1N1CCC(N2CCN(C(=O)C3CN(c4ccc5c(c4)C(=O)N(C4CCC(=O)NC4=O)C5=O)C3)CC2)CC1]

The titled compound was prepared in a manner similar to that in Example 11. 1H NMR (400 MHz, DMSO) δ 11.25 (s, 1H), 11.07 (s, 1H), 8.98 (s, 1H), 8.68 (s, 1H), 8.39 (d, J=7.9 Hz, 1H), 8.21 (s, 1H), 7.66 (d, J=8.3 Hz, 1H), 7.45 (s, 1H), 7.34 (d, J=8.3 Hz, 1H), 7.22 (t, J=7.8 Hz, 1H), 7.10 (d, J=7.0 Hz, 1H), 6.97-6.92 (m, 1H), 6.84 (d, J=1.7 Hz, 1H), 6.77 (d, J=8.7 Hz, 1H), 6.70 (d, J=8.4 Hz, 1H), 6.19 (s, 1H), 5.06 (dd, J=12.9, 5.2 Hz, 1H), 4.24 (t, J=8.4 Hz, 2H), 4.12 (dd, J=18.8, 7.1 Hz, 4H), 3.92 (s, 1H), 3.73 (s, 3H), 3.51 (s, 3H), 3.39 (s, 3H), 3.29-3.25 (m, 2H), 3.16-3.08 (m, 5H), 2.92-2.84 (m, 1H), 2.57 (m, 4H), 2.48-2.45 (m, 1H), 2.35 (s, 1H), 2.03 (s, 1H), 1.81 (d, J=10.4 Hz, 2H), 1.58 (d, J=9.9 Hz, 2H); $[M+H]^+$=957.7.

Example 74: 2-(2,6-dioxopiperidin-3-yl)-5-((S)-3-(4-(1-(2-methoxy-4-((4-((1-(methylsulfonyl)indolin-7-yl)amino)-7H-pyrrolo[2,3-d]pyrimidin-2-yl)amino)phenyl)piperidin-4-yl)piperazine-1-carbonyl)pyrrolidin-1-yl)isoindoline-1,3-dione

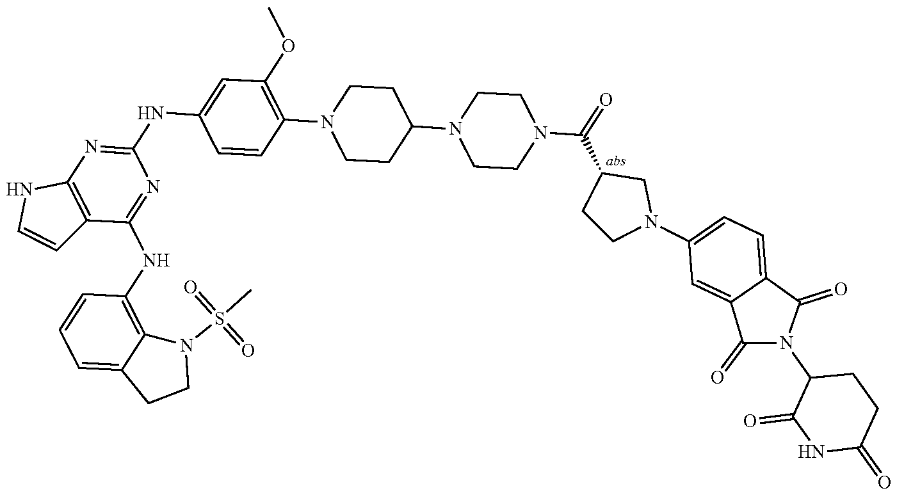 [SMILES: COc1cc(Nc2nc(Nc3cccc4c3N(S(C)(=O)=O)CC4)c3cc[nH]c3n2)ccc1N1CCC(N2CCN(C(=O)[C@H]3CCN(c4ccc5c(c4)C(=O)N(C4CCC(=O)NC4=O)C5=O)C3)CC2)CC1]

The titled compound was prepared in a manner similar to that in Example 11. 1H NMR (400 MHz, DMSO) δ 11.25 (s, 1H), 11.07 (s, 1H), 8.98 (s, 1H), 8.68 (s, 1H), 8.39 (d, J=7.9 Hz, 1H), 7.65 (d, J=8.4 Hz, 1H), 7.46 (s, 1H), 7.34 (d, J=8.4 Hz, 1H), 7.22 (t, J=7.7 Hz, 1H), 7.10 (d, J=7.6 Hz, 1H), 6.94 (s, 2H), 6.84 (d, J=8.6 Hz, 1H), 6.77 (d, J=8.8 Hz, 1H), 6.19 (s, 1H), 5.06 (dd, J=12.9, 5.4 Hz, 1H), 4.10 (t, J=7.5 Hz, 2H), 3.73 (s, 3H), 3.61 (d, J=17.8 Hz, 5H), 3.48 (d, J=15.0 Hz, 8H), 3.15-3.08 (m, 5H), 2.87 (d, J=13.0 Hz, 1H), 2.56 (d, J=12.9 Hz, 5H), 2.48-2.45 (m, 1H), 2.36 (s, 1H), 2.23 (s, 1H), 2.13 (s, 1H), 2.03 (s, 1H), 1.80 (s, 2H), 1.58 (d, J=10.2 Hz, 2H); $[M+H]^+$=971.8.

Example 75: 2-(2,6-dioxopiperidin-3-yl)-5-((R)-3-(4-(1-(2-methoxy-4-((4-((1-(methylsulfonyl)indolin-7-yl)amino)-7H-pyrrolo[2,3-d]pyrimidin-2-yl)amino)phenyl)piperidin-4-yl)piperazine-1-carbonyl)pyrrolidin-1-yl)isoindoline-1,3-dione

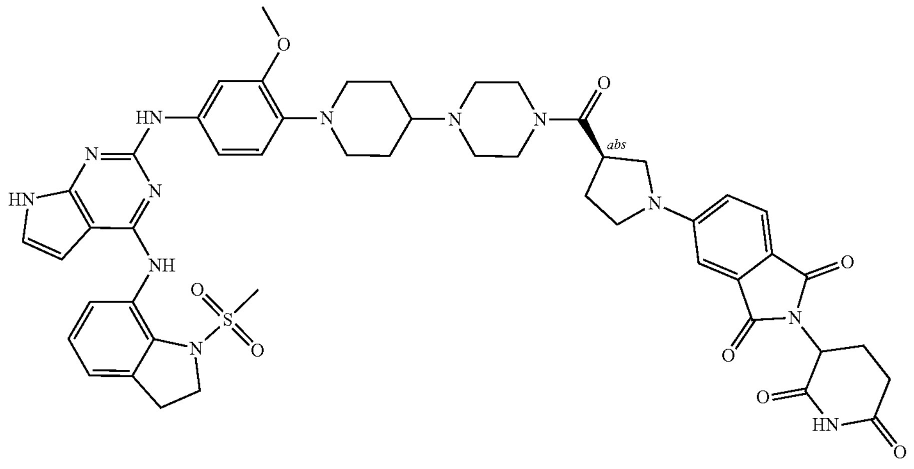 [SMILES: COc1cc(Nc2nc(Nc3cccc4c3N(S(C)(=O)=O)CC4)c3cc[nH]c3n2)ccc1N1CCC(N2CCN(C(=O)[C@@H]3CCN(c4ccc5c(c4)C(=O)N(C4CCC(=O)NC4=O)C5=O)C3)CC2)CC1]

The titled compound was prepared in a manner similar to that in Example 11. 1H NMR (400 MHz, DMSO) δ 11.21 (s, 1H), 11.02 (s, 1H), 8.93 (s, 1H), 8.64 (s, 1H), 8.34 (d, J=8.3 Hz, 1H), 7.61 (d, J=8.5 Hz, 1H), 7.42 (s, 1H), 7.29 (d, J=8.3 Hz, 1H), 7.18 (t, J=7.9 Hz, 1H), 7.06 (d, J=7.6 Hz, 1H), 6.90 (s, 2H), 6.80 (d, J=8.7 Hz, 1H), 6.73 (d, J=8.7 Hz, 1H), 6.15 (s, 1H), 5.02 (dd, J=12.6, 5.6 Hz, 1H), 4.06 (s, 2H), 3.69 (s, 3H), 3.51 (d, J=32.6 Hz, 9H), 3.41 (d, J=7.5 Hz, 1H), 3.29 (s, 3H), 3.07 (d, J=14.5 Hz, 5H), 2.83 (d, J=13.3 Hz, 1H), 2.58-2.49 (m, 5H), 2.45-2.42 (m, 1H), 2.32 (s, 1H), 2.19 (s, 1H), 2.09 (s, 1H), 1.98 (s, 1H), 1.76 (s, 2H), 1.54 (d, J=10.7 Hz, 2H); $[M+H]^+$=971.8.-

Example 76: 5-(3-((4-(1-(4-((5-chloro-4-((1-(methylsulfonyl)indolin-7-yl)amino)pyrimidin-2-yl)amino)-2-fluorophenyl)piperidin-4-yl)piperazin-1-yl)methyl)azetidin-1-yl)-2-(2,6-dioxopiperidin-3-yl)isoindoline-1,3-dione

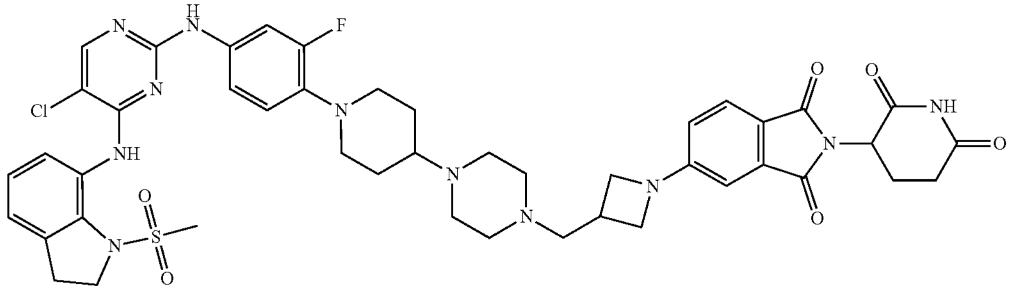 [SMILES: CS(=O)(=O)N1CCc2cccc(Nc3nc(Nc4ccc(N5CCC(N6CCN(CC7CN(c8ccc9c(c8)C(=O)N(C8CCC(=O)NC8=O)C9=O)C7)CC6)CC5)c(F)c4)ncc3Cl)c21]

The titled compound was prepared in a manner similar to that in Example 1. 1H NMR (400 MHz, DMSO) δ 11.07 (s, 1H), 9.41 (s, 1H), 9.03 (s, 1H), 8.18 (s, 1H), 7.87 (d, J=6.9 Hz, 1H), 7.63 (d, J=8.2 Hz, 1H), 7.55 (d, J=15.3 Hz, 1H), 7.28 (dd, J=14.9, 7.1 Hz, 2H), 7.19 (d, J=9.0 Hz, 1H), 6.88 (t, J=9.4 Hz, 1H), 6.77 (s, 1H), 6.64 (d, J=8.3 Hz, 1H), 5.05 (dd, J=12.7, 5.3 Hz, 1H), 4.16-4.03 (m, 4H), 3.68 (s, 2H), 3.28-3.24 (m, 4H), 3.14 (s, 3H), 3.06 (s, 3H), 2.99 (s, 2H), 2.86 (d, J=11.7 Hz, 1H), 2.58 (s, 7H), 2.42 (s, 3H), 2.28 (s, 1H), 2.02 (s, 1H), 1.84 (d, J=10.6 Hz, 2H), 1.55 (d, J=9.8 Hz, 2H); $[M+H]^+$=926.7.

Example 77: 5-(3-(4-(1-(4-((5-chloro-4-((1-(methylsulfonyl)indolin-7-yl)amino)pyrimidin-2-yl)amino)-2-fluorophenyl)piperidin-4-yl)piperazine-1-carbonyl)azetidin-1-yl)-2-(2,6-dioxopiperidin-3-yl)isoindoline-1,3-dione

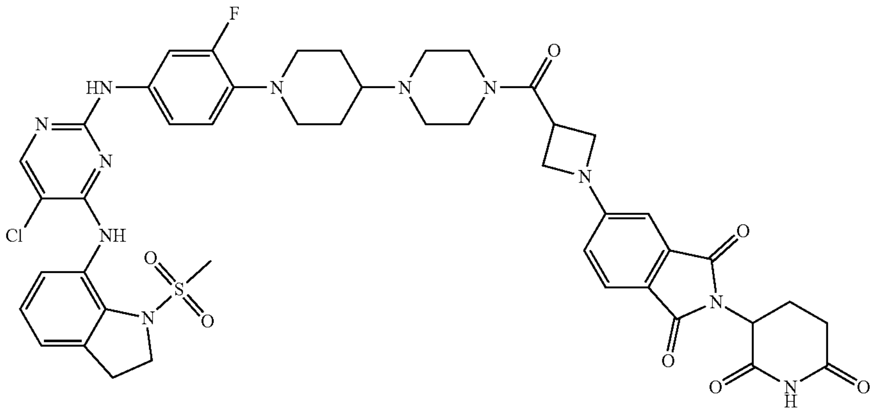 [SMILES: CS(=O)(=O)N1CCc2cccc(Nc3nc(Nc4ccc(N5CCC(N6CCN(C(=O)C7CN(c8ccc9c(c8)C(=O)N(C8CCC(=O)NC8=O)C9=O)C7)CC6)CC5)c(F)c4)ncc3Cl)c21]

The titled compound was prepared in a manner similar to that in Example 11. 1H NMR (400 MHz, DMSO) δ 11.07 (s, 1H), 9.41 (s, 1H), 9.03 (s, 1H), 8.19 (s, 1H), 7.87 (s, 1H), 7.66 (d, J=8.3 Hz, 1H), 7.55 (d, J=13.2 Hz, 1H), 7.31-7.22 (m, 2H), 7.18 (s, 1H), 6.89 (d, J=9.5 Hz, 1H), 6.83 (s, 1H), 6.70 (d, J=7.8 Hz, 1H), 5.07 (d, J=12.4 Hz, 1H), 4.22 (d, J=8.3 Hz, 2H), 4.10 (d, J=23.3 Hz, 4H), 3.92 (s, 1H), 3.50 (s, 2H), 3.30-3.25 (m, 3H), 3.14 (s, 2H), 3.06 (s, 3H), 2.88 (s, 1H), 2.57 (d, J=22.9 Hz, 9H), 2.37 (s, 1H), 2.03 (s, 1H), 1.82 (s, 2H), 1.58 (d, J=11.7 Hz, 2H); $[M+H]^+$=940.7.

Example 78: 5-(3-(3-(4-(1-(4-((5-chloro-4-((1-(methylsulfonyl)indolin-7-yl)amino)pyrimidin-2-yl)amino)-2-fluorophenyl)piperidin-4-yl)piperazin-1-yl)propyl)azetidin-1-yl)-2-(2,6-dioxopiperidin-3-yl)isoindoline-1,3-dione

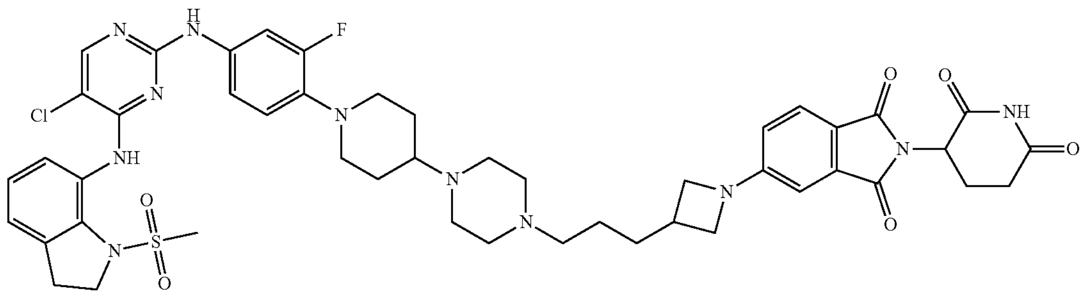 [SMILES: CS(=O)(=O)N1CCc2cccc(Nc3nc(Nc4ccc(N5CCC(N6CCN(CCCC7CN(c8ccc9c(c8)C(=O)N(C8CCC(=O)NC8=O)C9=O)C7)CC6)CC5)c(F)c4)ncc3Cl)c21]

The titled compound was prepared in a manner similar to that in Example 1. 1H NMR (400 MHz, DMSO) δ 11.07 (s, 1H), 9.40 (s, 1H), 9.03 (s, 1H), 8.17 (d, J=12.6 Hz, 1H), 7.86 (s, 1H), 7.64 (d, J=8.7 Hz, 1H), 7.55 (d, J=14.5 Hz, 1H), 7.27 (d, J=15.0 Hz, 2H), 7.17 (s, 1H), 6.87 (s, 1H), 6.76 (s, 1H), 6.62 (d, J=7.9 Hz, 1H), 5.04 (s, 1H), 4.10 (d, J=22.9 Hz, 4H), 3.65 (s, 2H), 3.26-3.23 (m, 2H), 3.14 (s, 3H), 3.06 (s, 3H), 2.82 (d, J=46.0 Hz, 4H), 2.67 (s, 1H), 2.55 (s, 4H), 2.44-2.23 (m, 7H), 2.02 (s, 1H), 1.82 (s, 2H), 1.59 (d, J=25.1 Hz, 4H), 1.43 (s, 2H); $[M+H]^+$=954.8.

Example 79: 3-(4-(4-(2-(4-(1-(4-((5-chloro-4-((1-(methylsulfonyl)indolin-7-yl)amino)pyrimidin-2-yl)amino)-2-fluorophenyl)piperidin-4-yl)piperazin-1-yl)ethyl)piperidin-1-yl)phenyl)piperidine-2,6-dione

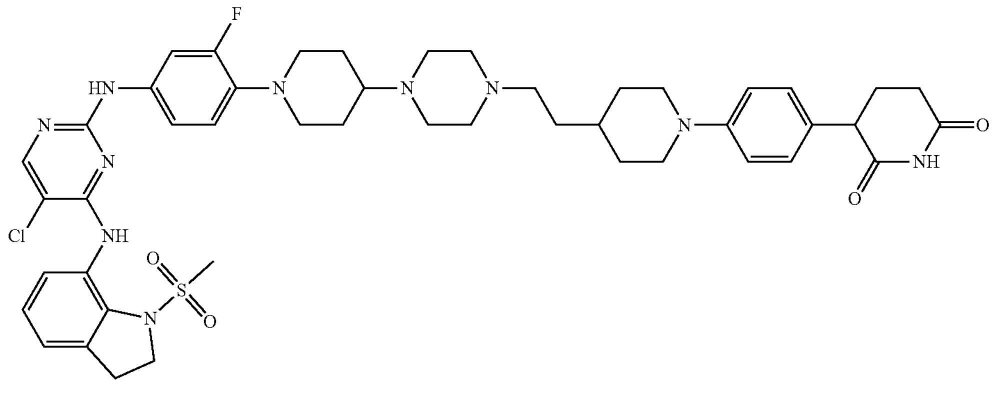 [SMILES: CS(=O)(=O)N1CCc2cccc(Nc3nc(Nc4ccc(N5CCC(N6CCN(CCC7CCN(c8ccc(C9CCC(=O)NC9=O)cc8)CC7)CC6)CC5)c(F)c4)ncc3Cl)c21]

The titled compound was prepared in a manner similar to that in Example 3. 1H NMR (400 MHz, DMSO) δ 10.77 (s, 1H), 9.40 (s, 1H), 9.03 (s, 1H), 8.18 (s, 1H), 7.86 (s, 1H), 7.55 (d, J=15.1 Hz, 1H), 7.32-7.21 (m, 2H), 7.18 (s, 1H), 7.02 (d, J=8.4 Hz, 2H), 6.88 (d, J=6.5 Hz, 3H), 4.07 (s, 2H), 3.72 (s, 1H), 3.63 (d, J=11.9 Hz, 2H), 3.29-3.22 (m, 3H), 3.14 (s, 2H), 3.06 (s, 3H), 2.59 (dd, J=21.8, 13.0 Hz, 8H), 2.37 (d, J=53.1 Hz, 8H), 2.11 (s, 1H), 2.01 (s, 1H), 1.81 (s, 2H), 1.74 (d, J=12.9 Hz, 2H), 1.54 (d, J=10.5 Hz, 2H), 1.39 (s, 3H), 1.24 (s, 2H); $[M+H]^+$=899.8.

Example 80: 3-(4-(4-(2-(4-(1-(4-((5-chloro-4-((1-(methylsulfonyl)indolin-7-yl)amino)pyrimidin-2-yl)amino)-2-fluorophenyl)piperidin-4-yl)piperazin-1-yl)ethyl)piperidin-1-yl)-2-fluorophenyl)piperidine-2,6-dione

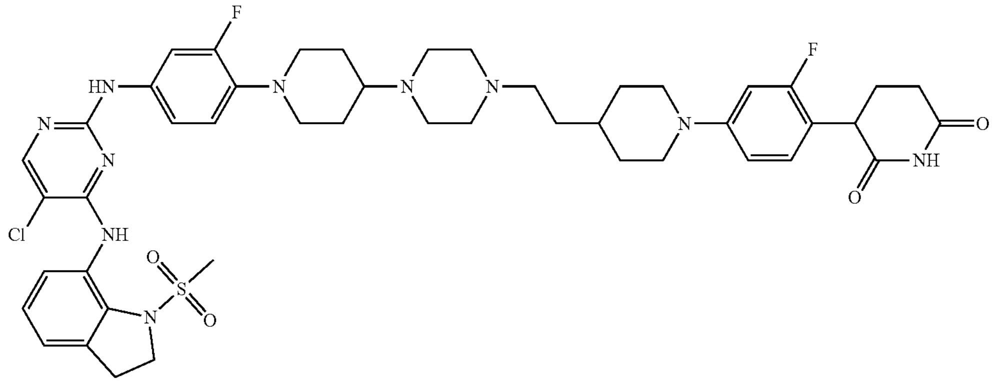 [SMILES: CS(=O)(=O)N1CCc2cccc(Nc3nc(Nc4ccc(N5CCC(N6CCN(CCC7CCN(c8ccc(C9CCC(=O)NC9=O)c(F)c8)CC7)CC6)CC5)c(F)c4)ncc3Cl)c21]

The titled compound was prepared in a manner similar to that in Example 3. 1H NMR (400 MHz, DMSO) δ 10.80 (s, 1H), 9.41 (s, 1H), 9.03 (s, 1H), 8.18 (s, 1H), 7.86 (s, 1H), 7.55 (d, J=15.6 Hz, 1H), 7.28 (dd, J=15.2, 7.2 Hz, 2H), 7.18 (d, J=7.3 Hz, 1H), 7.05 (t, J=8.6 Hz, 1H), 6.88 (d, J=8.7 Hz, 1H), 6.70 (d, J=11.2 Hz, 2H), 4.07 (s, 2H), 3.87 (d, J=7.3 Hz, 1H), 3.69 (d, J=11.9 Hz, 2H), 3.26 (s, 4H), 3.14 (s, 2H), 3.06 (s, 3H), 2.63 (dd, J=27.2, 13.1 Hz, 8H), 2.35 (d, J=30.3 Hz, 7H), 2.14 (d, J=12.7 Hz, 1H), 1.96 (s, 1H), 1.83 (d, J=10.6 Hz, 2H), 1.73 (d, J=11.2 Hz, 2H), 1.54 (d, J=10.9 Hz, 2H), 1.39 (s, 3H), 1.21 (d, J=11.0 Hz, 2H); $[M+H]^+$=917.8.

Example 81: 5-(4-(2-(4-(1-(4-((5-chloro-4-((1-(methylsulfonyl)indolin-7-yl)amino)pyrimidin-2-yl)amino)-2-fluorophenyl)piperidin-4-yl)piperazin-1-yl)ethyl)piperidin-1-yl)-2-(2,6-dioxopiperidin-3-yl)isoindoline-1,3-dione

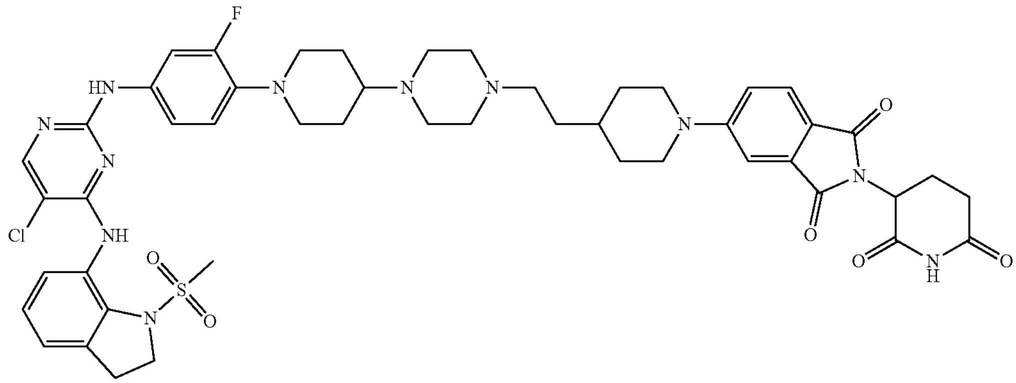 [SMILES: CS(=O)(=O)N1CCc2cccc(Nc3nc(Nc4ccc(N5CCC(N6CCN(CCC7CCN(c8ccc9c(c8)C(=O)N(C8CCC(=O)NC8=O)C9=O)CC7)CC6)CC5)c(F)c4)ncc3Cl)c21]

The titled compound was prepared in a manner similar to that in Example 1. 1H NMR (400 MHz, DMSO) δ 11.08 (s, 1H), 9.41 (s, 1H), 9.03 (s, 1H), 8.18 (s, 1H), 7.86 (s, 1H), 7.65 (d, J=8.6 Hz, 1H), 7.55 (d, J=14.7 Hz, 1H), 7.36-7.14 (m, 5H), 6.87 (s, 1H), 5.06 (d, J=7.3 Hz, 1H), 4.12-3.98 (m, 4H), 3.29-3.23 (m, 3H), 3.14 (s, 2H), 3.06 (s, 3H), 3.00-2.81 (m, 4H), 2.57 (d, J=25.4 Hz, 6H), 2.33 (s, 7H), 2.01 (s, 1H), 1.88-1.71 (m, 4H), 1.56 (s, 3H), 1.39 (s, 2H), 1.18 (d, J=10.6 Hz, 2H); $[M+H]^+$=968.8.

Example 82: 5-((S)-3-(4-(1-(4-((5-chloro-4-((1-(methylsulfonyl)indolin-7-yl)amino)pyrimidin-2-yl)amino)-2-fluorophenyl)piperidin-4-yl)piperazine-1-carbonyl)pyrrolidin-1-yl)-2-(2,6-dioxopiperidin-3-yl)isoindoline-1,3-dione

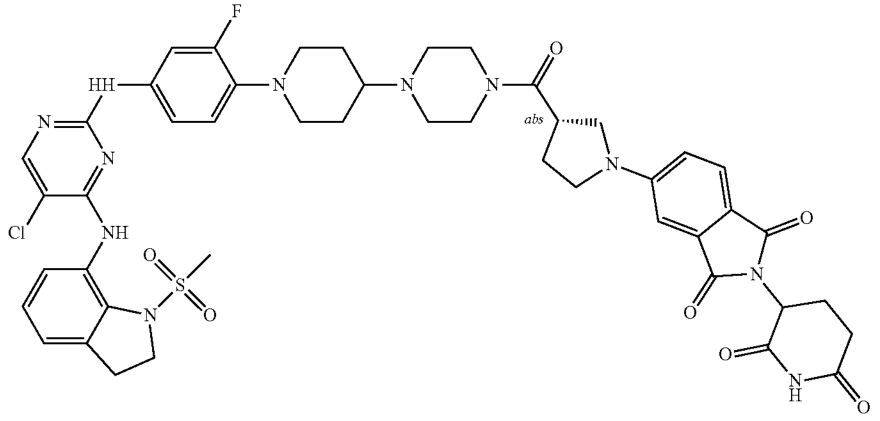

The titled compound was prepared in a manner similar to that in Example 11. 1H NMR (400 MHz, DMSO) δ 11.07 (s, 1H), 9.41 (s, 1H), 9.03 (s, 1H), 8.18 (s, 1H), 7.87 (d, J=7.6 Hz, 1H), 7.65 (d, J=8.4 Hz, 1H), 7.56 (d, J=15.6 Hz, 1H), 7.27 (dt, J=14.6, 7.2 Hz, 2H), 7.19 (d, J=8.2 Hz, 1H), 6.93 (s, 1H), 6.87 (dd, J=21.9, 9.0 Hz, 2H), 5.06 (dd, J=12.9, 5.4 Hz, 1H), 4.07 (t, J=7.1 Hz, 2H), 3.68-3.42 (m, 10H), 3.28 (s, 3H), 3.14 (t, J=7.2 Hz, 2H), 3.06 (s, 3H), 2.93-2.84 (m, 1H), 2.64-2.53 (m, 6H), 2.37 (s, 1H), 2.22 (s, 1H), 2.14 (d, J=7.4 Hz, 1H), 2.02 (s, 1H), 1.84 (d, J=10.5 Hz, 2H), 1.59 (d, J=11.3 Hz, 2H); $[M+H]^+$=954.7.

Example 83: 5-((R)-3-(4-(1-(4-((5-chloro-4-((1-(methylsulfonyl)indolin-7-yl)amino)pyrimidin-2-yl)amino)-2-fluorophenyl)piperidin-4-yl)piperazine-1-carbonyl)pyrrolidin-1-yl)-2-(2,6-dioxopiperidin-3-yl)isoindoline-1,3-dione

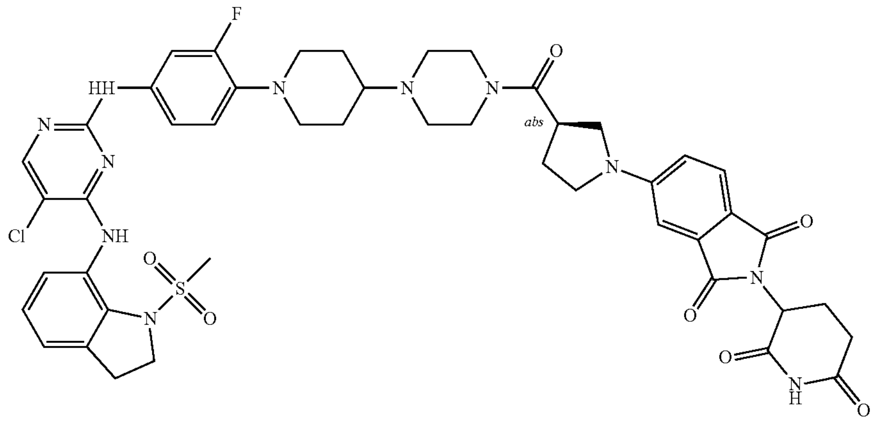

The titled compound was prepared in a manner similar to that in Example 11. 1H NMR (400 MHz, DMSO) δ 11.07 (s, 1H), 9.41 (s, 1H), 9.03 (s, 1H), 8.19 (s, 1H), 7.87 (d, J=7.5 Hz, 1H), 7.65 (d, J=8.4 Hz, 1H), 7.55 (d, J=15.6 Hz, 1H), 7.27 (dt, J=14.7, 7.3 Hz, 2H), 7.19 (d, J=8.4 Hz, 1H), 6.93 (s, 1H), 6.87 (dd, J=21.9, 8.9 Hz, 2H), 5.06 (dd, J=12.9, 5.4 Hz, 1H), 4.07 (t, J=7.5 Hz, 2H), 3.67-3.42 (m, 10H), 3.28 (s, 3H), 3.14 (t, J=7.3 Hz, 2H), 3.06 (s, 3H), 2.89 (t, J=12.7 Hz, 1H), 2.65-2.54 (m, 6H), 2.37 (s, 1H), 2.23 (s, 1H), 2.14 (d, J=6.5 Hz, 1H), 2.03 (s, 1H), 1.84 (d, J=10.4 Hz, 2H), 1.59 (d, J=9.5 Hz, 2H); $[M+H]^+$=954.7.

Example 84: 3-(4-(3-(2-(4-(1-(4-((5-chloro-4-((1-(methylsulfonyl)indolin-7-yl)amino)pyrimidin-2-yl)amino)-3-methoxyphenyl)piperidin-4-yl)piperazin-1-yl)ethyl)azetidin-1-yl)phenyl)piperidine-2,6-dione The titled compound was prepared in a manner similar to that in Example 1. $^1H$ NMR (400 MHz, DMSO) δ 10.93 (s, 1H), 8.92 (s, 1H), 8.08 (s, 1H), 7.88 (s, 2H), 7.46 (dd, J=12.7, 8.5 Hz, 2H), 7.16 (d, J=6.6 Hz, 2H), 6.60 (s, 1H), 6.53-6.44 (m, 2H), 6.40 (d, J=8.6 Hz, 1H), 5.03 (dd, J=13.3, 5.2 Hz, 1H), 4.30 (d, J=17.0 Hz, 1H), 4.17 (d, J=17.0 Hz, 1H), 4.12-3.96 (m, 4H), 3.76 (s, 3H), 3.69 (d, J=11.8 Hz, 2H), 3.60-3.50 (m, 2H), 3.10 (t, J=7.5 Hz, 2H), 3.04 (s, 3H), 3.00-2.83 (m, 3H), 2.71-2.53 (m, 8H), 2.45-2.27 (m, 6H), 1.94-2.01 (m, 1H), 1.85 (ddt, J=9.6, 4.7, 1.9 Hz, 2H), 1.61-1.46 (m, 2H); $[M+H]^+$=924.5.

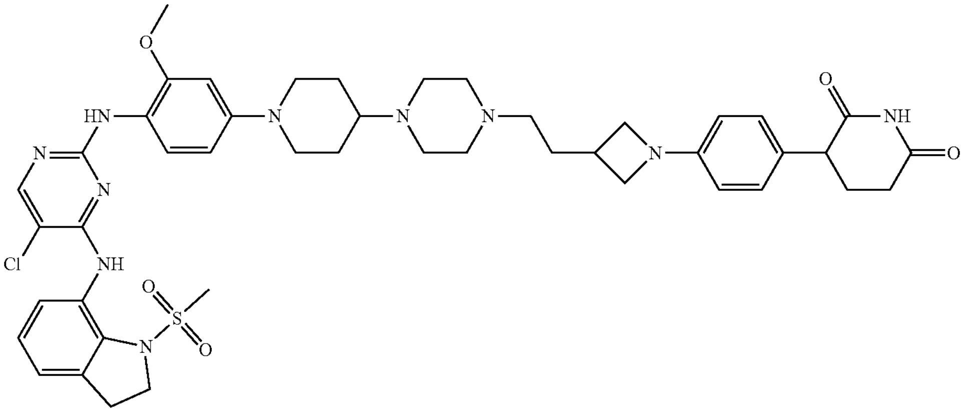 [SMILES: COc1cc(N2CCC(N3CCN(CCC4CN(c5ccc(C6CCC(=O)NC6=O)cc5)C4)CC3)CC2)ccc1Nc1ncc(Cl)c(Nc2cccc3c2N(S(C)(=O)=O)CC3)n1]

The titled compound was prepared in a manner similar to that in Example 1. $^1H$ NMR (400 MHz, $CD_3OD$) δ 8.16 (s, 1H), 7.63 (s, 2H), 7.40 (d, J=7.0 Hz, 1H), 7.32 (t, J=7.7 Hz, 1H), 7.19 (d, J=8.4 Hz, 3H), 6.97 (d, J=8.0 Hz, 2H), 6.90 (s, 1H), 4.09 (t, J=7.4 Hz, 2H), 4.03 (s, 1H), 3.94 (s, 3H), 3.83 (tt, J=24.1, 11.9 Hz, 10H), 3.52-3.40 (m, 7H), 3.20 (t, J=7.3 Hz, 2H), 3.08-2.99 (m, 1H), 2.95 (s, 3H), 2.73-2.57 (m, 3H), 2.45-2.50 (m, 1H), 2.36-2.27 (m, 2H), 2.25-2.07 (m, 6H); $[M+H]^+$=883.5.

Example 85: 3-(5-(3-((4-(1-(4-((5-chloro-4-((1-(methylsulfonyl)indolin-7-yl)amino)pyrimidin-2-yl)amino)-3-methoxyphenyl)piperidin-4-yl)piperazin-1-yl)methyl)azetidin-1-yl)-1-oxoisoindolin-2-yl)piperidine-2,6-dione

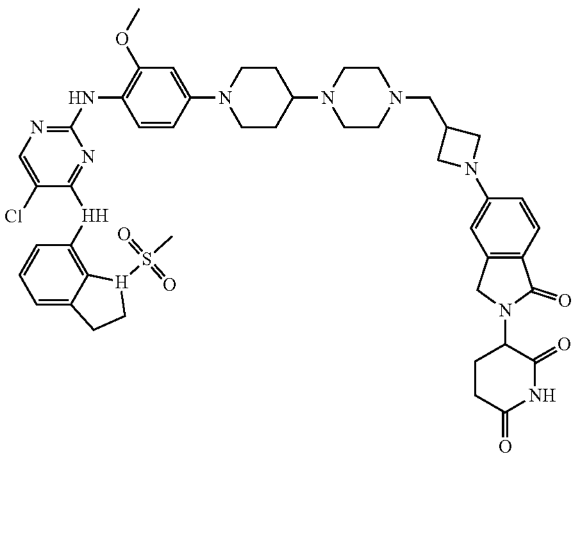

Example 86: 5-(3-((4-(1-(4-((5-chloro-4-((1-(methylsulfonyl)indolin-7-yl)amino)pyrimidin-2-yl)amino)-3-methoxyphenyl)piperidin-4-yl)piperazin-1-yl)methyl)azetidin-1-yl)-2-(2,6-dioxopiperidin-3-yl)isoindoline-1,3-dione Step 1: N-(2,5-dichloropyrimidin-4-yl)-1-(methylsulfonyl)indolin-7-amine

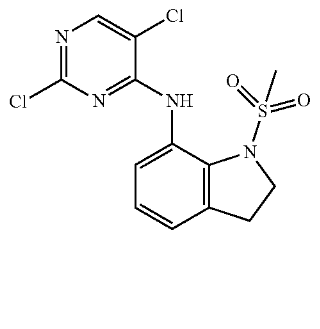 [SMILES: CS(=O)(=O)N1CCc2cccc(Nc3nc(Cl)ncc3Cl)c21]

A mixture of 1-(methylsulfonyl)indolin-7-amine (340 mg, 1.6 mmol), 2,4,5-trichloropyrimidine (584 mg, 3.2 mmol) and DIEA (412 mg, 3.2 mmol) in i-PrOH (20 mL) was stirred in a round bottom flask at 100° C. for 16 h. The mixture was evaporated in vacuum to afford the crude product, which was purified with silica gel column chromatography (PE:EA=100:0~2:1 gradient elution) to give the title product (540 mg, 94%). $[M+H]^+$=359.2.

Step 2: 5-chloro-$N^2$-(2-methoxy-4-(4-(piperazin-1-yl)piperidin-1-yl)phenyl)-$N^4$-(1-(methylsulfonyl)indolin-7-yl)pyrimidine-2,4-diamine

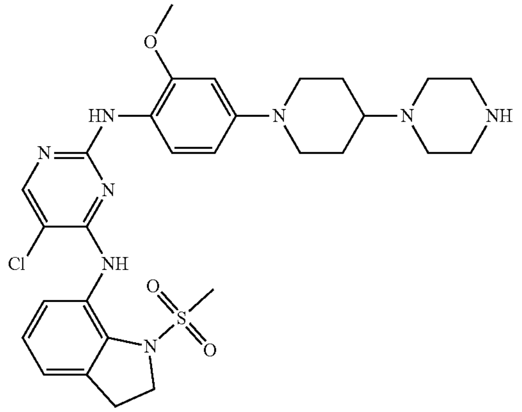 [SMILES: COc1cc(N2CCC(N3CCNCC3)CC2)ccc1Nc1ncc(Cl)c(Nc2cccc3c2N(S(C)(=O)=O)CC3)n1]

The titled compound (170 mg, 44%) was prepared in a manner similar to that in Example 43 step 4 from N-(2,5-dichloropyrimidin-4-yl)-1-(methylsulfonyl)indolin-7-amine and tert-butyl 4-(1-(4-amino-3-methoxyphenyl)piperidin-4-yl)piperazine-1-carboxylate. $[M+H]^+$=613.2.

Step 3: 5-(3-((4-(1-(4-((5-chloro-4-((1-(methylsulfonyl)indolin-7-yl)amino)pyrimidin-2-yl)amino)-3-methoxyphenyl)piperidin-4-yl)piperazin-1-yl)methyl)azetidin-1-yl)-2-(2,6-dioxopiperidin-3-yl)isoindoline-1,3-dione

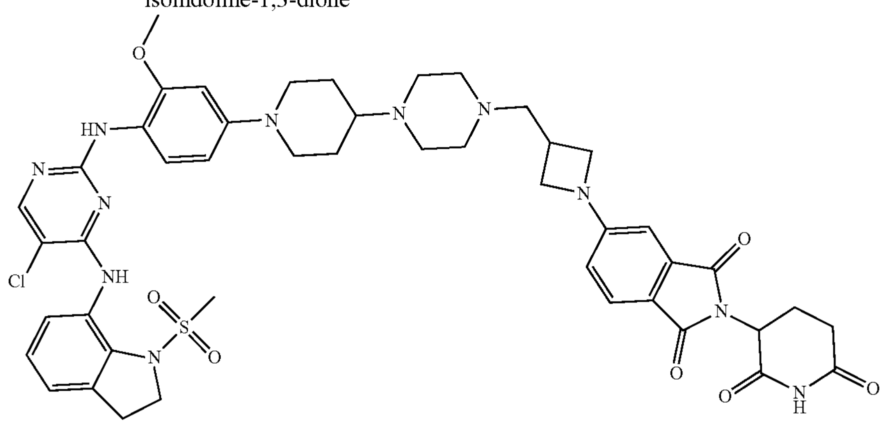

A mixture of 5-chloro-$N^2$-(2-methoxy-4-(4-(piperazin-1-yl)piperidin-1-yl)phenyl)-$N^4$-(1-(methylsulfonyl)indolin-7-yl)pyrimidine-2,4-diamine (35 mg, 0.057 mmol) and (1-(2-(2,6-dioxopiperidin-3-yl)-1,3-dioxoisoindolin-5-yl)azetidin-3-yl)methyl methanesulfonate (30 mg, 0.069 mmol), KI (11.6 mg, 0.069 mmol) and DIEA (14.7 mg, 0.114 mmol) in acetonitrile (4 mL) was stirred in a round bottom flask at 75° C. for 12 hours. The reaction was quenched with water and the mixture was extracted with DCM, washed with saturated brine and dried over anhydrous $Na_2SO_4$. After filtration, the filtrate was concentrated under reduced pressure to afford the residue which was purified by HPLC chromatography to give the product (5 mg, 10%). $^1$H NMR (400 MHz, DMSO) δ 11.07 (s, 1H), 8.92 (s, 1H), 8.08 (s, 1H), 7.88 (s, 2H), 7.63 (d, J=8.4 Hz, 1H), 7.44 (s, 1H), 7.15 (s, 2H), 6.77 (s, 1H), 6.61 (d, J=12.5 Hz, 2H), 6.41 (s, 1H), 5.04 (s, 1H), 4.18-4.10 (m, 2H), 4.09-4.00 (m, 2H), 3.76 (s, 3H), 3.69 (tt, J=6.3, 3.2 Hz, 4H), 3.00 (s, 9H), 2.71-2.54 (m, 9H), 2.38-2.50 (m, 4H), 2.06-1.96 (m, 1H), 1.92-1.80 (m, 2H), 1.60-1.45 (m, 2H); $[M+H]^+$=938.5.

Example 87: 5-((S)-3-(4-(1-(4-((5-chloro-4-((1-(methylsulfonyl)indolin-7-yl)amino)pyrimidin-2-yl)amino)-3-methoxyphenyl)piperidin-4-yl)piperazine-1-carbonyl)pyrrolidin-1-yl)-2-(26-dioxopiperidin-3-yl)isoindoline-1,3-dione

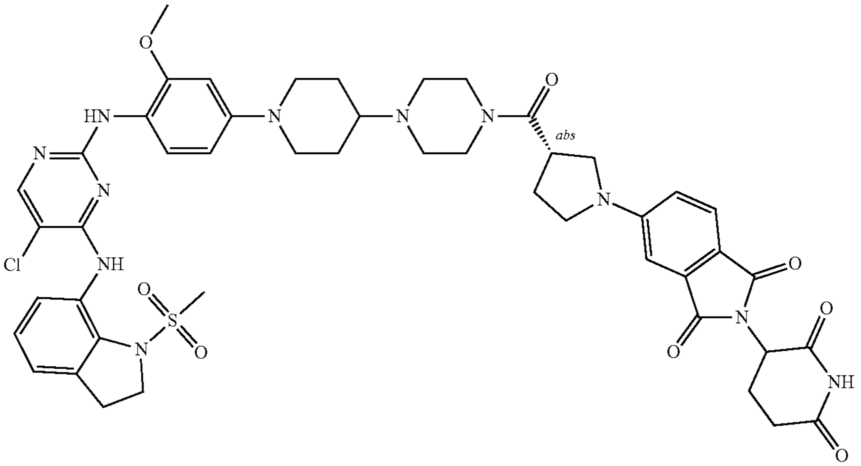 [SMILES: COc1cc(N2CCC(N3CCN(C(=O)[C@H]4CCN(c5ccc6c(c5)C(=O)N(C5CCC(=O)NC5=O)C6=O)C4)CC3)CC2)ccc1Nc1ncc(Cl)c(Nc2cccc3c2N(S(C)(=O)=O)CC3)n1]

The titled compound was prepared in a manner similar to that in Example 11. $^1$H NMR (400 MHz, DMSO) δ 11.07 (s, 1H), 8.92 (s, 1H), 8.08 (s, 1H), 7.88 (s, 2H), 7.65 (d, J=8.4 Hz, 1H), 7.45 (d, J=8.7 Hz, 1H), 7.16 (d, J=6.9 Hz, 2H), 6.93 (s, 1H), 6.84 (d, J=8.6 Hz, 1H), 6.60 (s, 1H), 6.41 (d, J=9.3 Hz, 1H), 5.06 (dd, J=12.8, 5.2 Hz, 1H), 4.05 (t, J=7.3 Hz, 2H), 3.77 (s, 3H), 3.71 (d, J=12.1 Hz, 2H), 3.66-3.41 (m, 9H), 3.10 (t, J=7.2 Hz, 2H), 3.04 (s, 3H), 2.93-2.82 (m, 1H), 2.71-2.52 (m, 7H), 2.47-2.32 (m, 2H), 2.27-2.19 (m, 1H), 2.12-2.16 (m, 1H), 2.04-1.97 (m, 1H), 1.91-1.80 (m, 2H), 1.62-1.48 (m, 2H); $[M+H]^+$=966.5.

Example 88: 5-((R)-3-(4-(1-(4-((5-chloro-4-((1-(methylsulfonyl)indolin-7-yl)amino)pyrimidin-2-yl)amino)-3-methoxyphenyl)piperidin-4-yl)piperazine-1-carbonyl)pyrrolidin-1-yl)-2-(2,6-dioxopiperidin-3-yl)isoindoline-1,3-dione

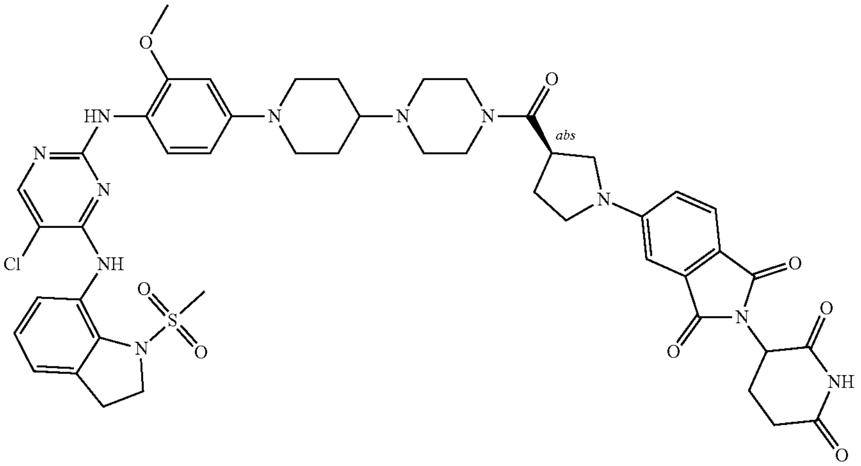 [SMILES: COc1cc(N2CCC(N3CCN(C(=O)[C@@H]4CCN(c5ccc6c(c5)C(=O)N(C5CCC(=O)NC5=O)C6=O)C4)CC3)CC2)ccc1Nc1ncc(Cl)c(Nc2cccc3c2N(S(C)(=O)=O)CC3)n1]

The titled compound was prepared in a manner similar to that in Example 11. $^1$H NMR (400 MHz, DMSO) δ 11.06 (s, 1H), 8.92 (s, 1H), 8.08 (s, 1H), 7.88 (s, 2H), 7.65 (d, J=8.4 Hz, 1H), 7.45 (d, J=8.7 Hz, 1H), 7.16 (d, J=6.9 Hz, 2H), 6.93 (s, 1H), 6.84 (d, J=8.6 Hz, 1H), 6.60 (s, 1H), 6.41 (d, J=9.3 Hz, 1H), 5.07 (dd, J=12.8, 5.2 Hz, 1H), 4.05 (t, J=7.3 Hz, 2H), 3.77 (s, 3H), 3.71 (d, J=12.1 Hz, 2H), 3.66-3.41 (m, 9H), 3.10 (t, J=7.2 Hz, 2H), 3.04 (s, 3H), 2.93-2.82 (m, 1H), 2.71-2.52 (m, 7H), 2.47-2.32 (m, 2H), 2.27-2.19 (m, 1H), 2.12-2.16 (m, 1H), 2.04-1.97 (m, 1H), 1.91-1.80 (m, 2H), 1.62-1.47 (m, 2H); $[M+H]^+$=966.5.

Example 90: 3-(4-(4-(2-(4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)ethyl)piperidin-1-yl)-2-fluorophenyl)piperidine-2,6-dione

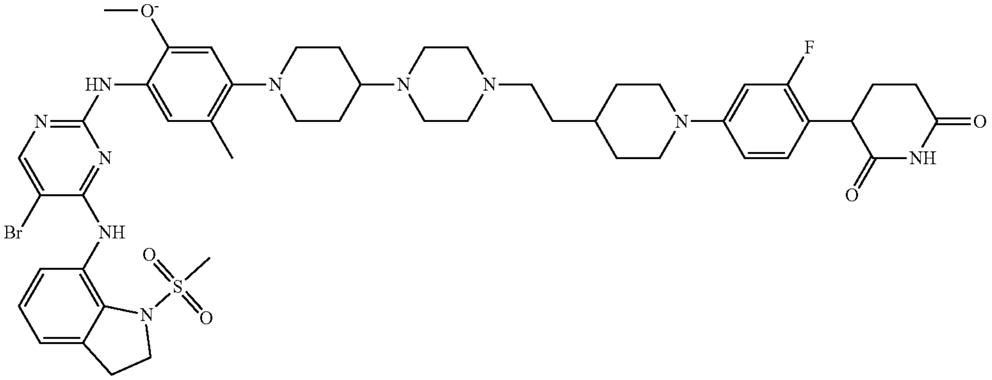

The titled compound was prepared in a manner similar to that in Example 3. 1H NMR (400 MHz, DMSO) δ 10.80 (s, 1H), 8.79 (s, 1H), 8.17 (s, 1H), 7.86 (s, 1H), 7.81 (d, J=6.0 Hz, 1H), 7.43 (s, 1H), 7.18-7.11 (m, 2H), 7.06 (t, J=8.7 Hz, 1H), 6.69 (d, J=14.9 Hz, 3H), 4.05 (t, J=7.3 Hz, 2H), 3.90-3.85 (m, 1H), 3.76 (s, 3H), 3.69 (d, J=12.7 Hz, 2H), 3.13-3.00 (m, 8H), 2.75-2.57 (m, 6H), 2.51 (s, 3H), 2.37 (s, 3H), 2.30 (s, 4H), 2.14 (d, J=12.1 Hz, 1H), 2.07 (s, 3H), 1.96 (s, 1H), 1.85 (d, J=11.6 Hz, 2H), 1.73 (d, J=11.4 Hz, 2H), 1.56 (d, J=9.0 Hz, 2H), 1.39 (s, 3H), 1.21 (d, J=12.1 Hz, 2H); $[M+H]^+$=987.5, 989.7.

Example 91: 5-(4-(2-(4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)ethyl)piperidin-1-yl)-2-(2,6-dioxopiperidin-3-yl)isoindoline-1,3-dione

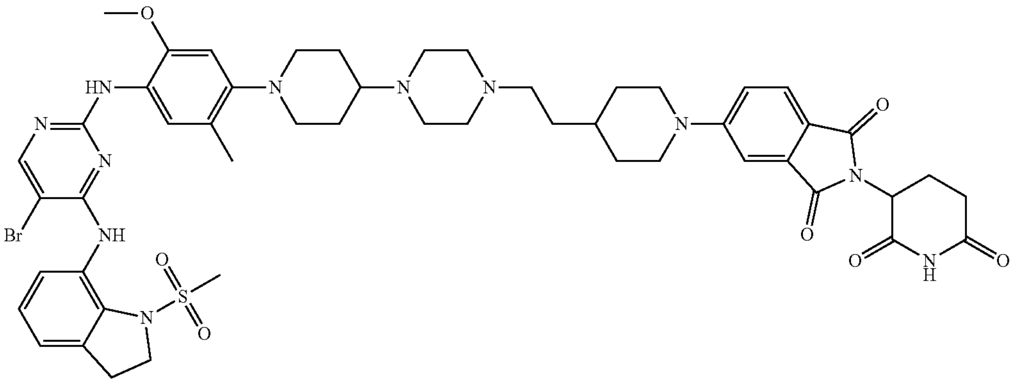 [SMILES: COc1cc(N2CCC(N3CCN(CCC4CCN(c5ccc6c(c5)C(=O)N(C5CCC(=O)NC5=O)C6=O)CC4)CC3)CC2)c(C)cc1Nc1ncc(Br)c(Nc2cccc3c2N(S(C)(=O)=O)CC3)n1]

The titled compound was prepared in a manner similar to that in Example 1. 1H NMR (400 MHz, DMSO) δ 11.07 (s, 1H), 8.79 (s, 1H), 8.17 (s, 1H), 7.87 (s, 1H), 7.81 (d, J=7.0 Hz, 1H), 7.65 (d, J=8.6 Hz, 1H), 7.43 (s, 1H), 7.30 (s, 1H), 7.23 (d, J=8.6 Hz, 1H), 7.14 (d, J=7.5 Hz, 2H), 6.67 (s, 1H), 5.06 (dd, J=12.7, 5.2 Hz, 1H), 4.04 (d, J=7.8 Hz, 4H), 3.76 (s, 3H), 3.10 (t, J=7.4 Hz, 3H), 3.05 (s, 4H), 2.93 (dd, J=24.5, 12.4 Hz, 4H), 2.65-2.52 (m, 7H), 2.41 (s, 3H), 2.33 (s, 4H), 2.07 (s, 3H), 2.02 (s, 1H), 1.85 (d, J=10.6 Hz, 2H), 1.76 (d, J=12.4 Hz, 2H), 1.57 (s, 3H), 1.40 (s, 2H), 1.19 (d, J=11.1 Hz, 2H); $[M+H]^+$=1038.7, 1040.9.

Example 151: 5-(3-((4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)methyl)azetidin-1-yl)-2-(2,6-dioxopiperidin-3-yl)isoindoline-1,3-dione

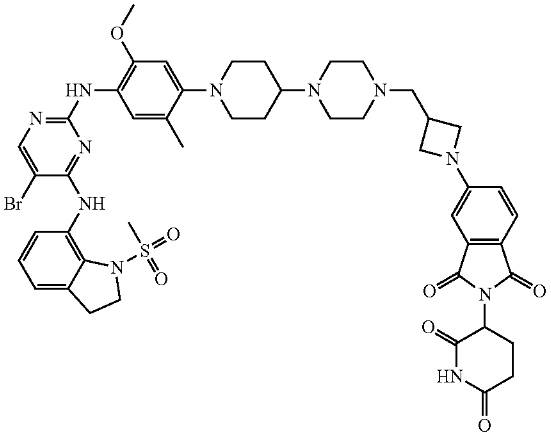 [SMILES: COc1cc(N2CCC(N3CCN(CC4CN(c5ccc6c(c5)C(=O)N(C5CCC(=O)NC5=O)C6=O)C4)CC3)CC2)c(C)cc1Nc1ncc(Br)c(Nc2cccc3c2N(S(C)(=O)=O)CC3)n1]

The title compound was prepared in a procedure similar to that in Example 3.

$^1$H NMR (500 MHz, DMSO) δ 11.07 (s, 1H), 8.80 (s, 1H), 8.17 (d, J=5.8 Hz, 1H), 7.87 (s, 1H), 7.81 (d, J=7.2 Hz, 1H), 7.63 (d, J=8.3 Hz, 1H), 7.43 (s, 1H), 7.15 (t, J=8.0 Hz, 2H), 6.77 (s, 1H), 6.65 (dd, J=15.8, 7.5 Hz, 2H), 5.05 (dd, J=12.9, 5.4 Hz, 1H), 4.13 (t, J=8.0 Hz, 2H), 4.05 (t, J=7.4 Hz, 2H), 3.76 (s, 3H), 3.70-3.63 (m, 2H), 3.13-2.96 (m, 8H), 2.88 (s, 1H), 2.66-2.51 (m, 10H), 2.43 (s, 4H), 2.30 (s, 1H), 2.08 (s, 3H), 2.04-1.96 (m, 1H), 1.86 (d, J=11.2 Hz, 2H), 1.56 (d, J=9.7 Hz, 2H); $[M+H]^+$=996.3.

Example 152: 3-((4-(2-(4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)ethyl)phenyl)amino)piperidine-2,6-dione

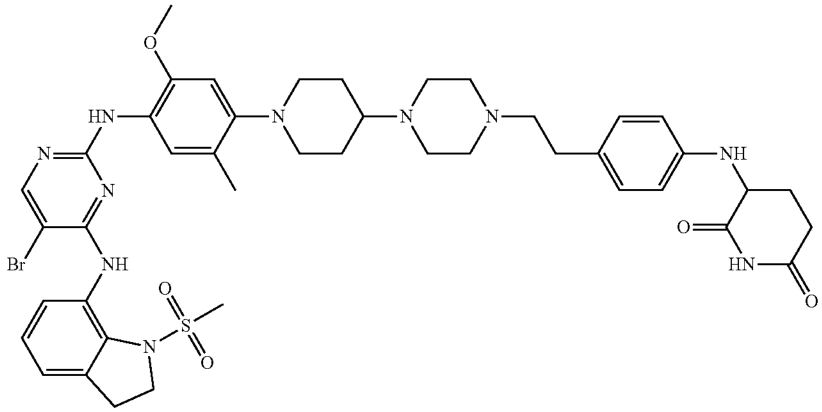 [SMILES: COc1cc(N2CCC(N3CCN(CCc4ccc(NC5CCC(=O)NC5=O)cc4)CC3)CC2)c(C)cc1Nc1ncc(Br)c(Nc2cccc3c2N(S(C)(=O)=O)CC3)n1]

The title compound was prepared in a procedure similar to that in Example 3.

$^1$H NMR (500 MHz, DMSO) δ 10.78 (s, 1H), 8.80 (s, 1H), 8.18 (s, 1H), 7.87 (s, 1H), 7.81 (d, J=8.1 Hz, 1H), 7.43 (s, 1H), 7.15 (s, 2H), 6.93 (d, J=8.3 Hz, 2H), 6.68 (s, 1H), 6.59 (d, J=8.4 Hz, 2H), 5.65 (d, J=7.2 Hz, 1H), 4.27 (s, 1H), 4.05 (s, 2H), 3.76 (s, 3H), 3.08 (d, J=28.0 Hz, 7H), 2.79-2.69 (m, 1H), 2.66-2.52 (m, 10H), 2.42 (d, J=8.1 Hz, 5H), 2.29 (s, 1H), 2.08 (s, 4H), 1.86 (d, J=11.7 Hz, 3H), 1.56 (d, J=9.1 Hz, 2H); $[M+H]^+$=901.2.

Example 153: 3-((4-(2-(4-(1-(4-((5-chloro-4-((1-(methylsulfonyl)indolin-7-yl)amino)pyrimidin-2-yl)amino)-3-methoxyphenyl)piperidin-4-yl)piperazin-1-yl)ethyl)phenyl)amino)piperidine-2,6-dione

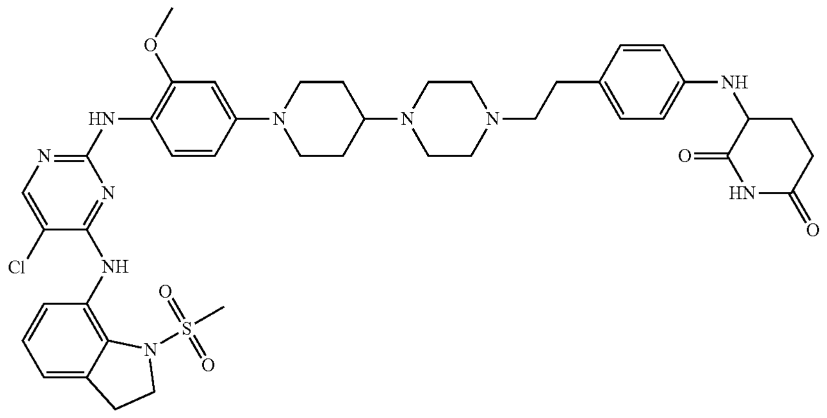 [SMILES: COc1cc(N2CCC(N3CCN(CCc4ccc(NC5CCC(=O)NC5=O)cc4)CC3)CC2)ccc1Nc1ncc(Cl)c(Nc2cccc3c2N(S(C)(=O)=O)CC3)n1]

The title compound was prepared in a procedure similar to that in Example 3.

$^1$H NMR (500 MHz, DMSO) δ 10.78 (s, 1H), 8.92 (s, 1H), 8.08 (s, 1H), 7.88 (s, 2H), 7.44 (d, J=8.7 Hz, 1H), 7.15 (d, J=6.9 Hz, 2H), 6.93 (d, J=8.4 Hz, 2H), 6.59 (d, J=8.0 Hz, 3H), 6.40 (d, J=8.8 Hz, 1H), 5.65 (d, J=7.4 Hz, 1H), 4.29-4.23 (m, 1H), 4.05 (t, J=7.4 Hz, 2H), 3.76 (s, 3H), 3.69 (d, J=12.0 Hz, 2H), 3.10 (t, J=7.4 Hz, 2H), 3.04 (s, 3H), 2.78-2.53 (m, 10H), 2.44-2.40 (m, 7H), 2.14-2.05 (m, 1H), 1.86-1.83 (m, 3H), 1.53-1.51 (m, 2H); $[M+H]^+$=843.2.

Example 154: 3-(5-((S)-3-((4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)methyl)pyrrolidin-1-yl)-1-oxoisoindolin-2-yl)piperidine-2,6-dione

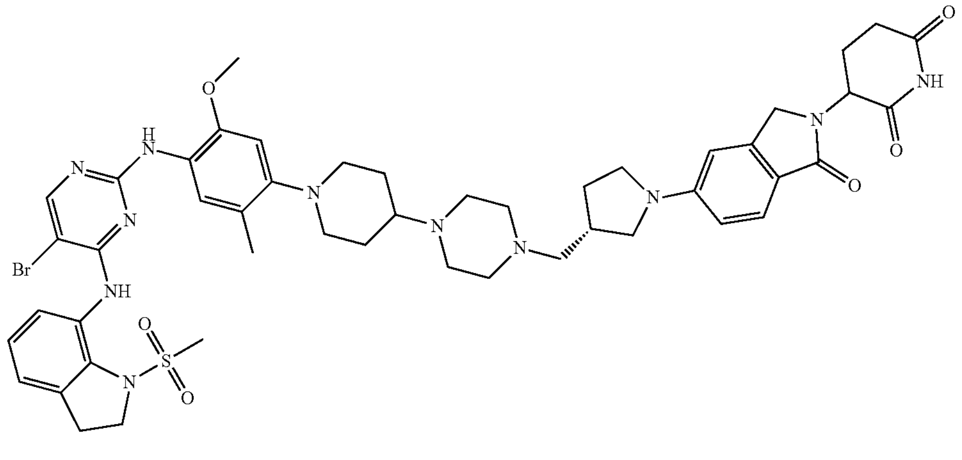 [SMILES: COc1cc(N2CCC(N3CCN(C[C@@H]4CCN(c5ccc6c(c5)CN(C5CCC(=O)NC5=O)C6=O)C4)CC3)CC2)c(C)cc1Nc1ncc(Br)c(Nc2cccc3c2N(S(C)(=O)=O)CC3)n1]

The title compound was prepared in a procedure similar to that in Example 3.

$^1$H NMR (500 MHz, DMSO) δ 10.93 (s, 1H), 8.80 (s, 1H), 8.18 (s, 1H), 7.87 (s, 1H), 7.82 (s, 1H), 7.52-7.42 (m, 2H), 7.15 (s, 2H), 6.68 (s, 1H), 6.63 (s, 2H), 5.03 (d, J=9.2 Hz, 1H), 4.30 (d, J=15.8 Hz, 1H), 4.19 (d, J=16.4 Hz, 1H), 4.05 (s, 2H), 3.76 (s, 3H), 3.43-3.41 (m, 2H), 3.17-3.02 (m, 10H), 2.91-2.89 (m, 1H), 2.63-2.59 (m, 10H), 2.46-2.28 (m, 5H), 2.13-2.11 (m, 4H), 2.00-1.83 (m, 3H), 1.79-1.70 (m, 1H), 1.68-1.53 (m, 2H); $[M+H]^+$=996.3.

Example 155: 3-(4-(2-(4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)ethyl)-2,5-difluorophenyl)piperidine-2,6-dione

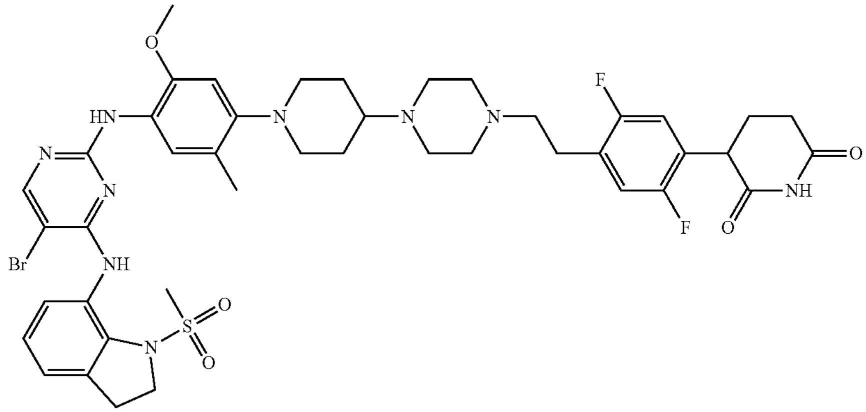 [SMILES: COc1cc(N2CCC(N3CCN(CCc4cc(F)c(C5CCC(=O)NC5=O)cc4F)CC3)CC2)c(C)cc1Nc1ncc(Br)c(Nc2cccc3c2N(S(C)(=O)=O)CC3)n1]

The title compound was prepared in a procedure similar to that in Example 3.

$^1$H NMR (500 MHz, DMSO) δ 10.90 (s, 1H), 8.79 (s, 1H), 8.16 (d, J=12.5 Hz, 1H), 7.86 (s, 1H), 7.80 (s, 1H), 7.43 (s, 1H), 7.22 (s, 1H), 7.15 (s, 3H), 6.68 (s, 1H), 4.05 (s, 3H), 3.76 (s, 3H), 3.15-3.00 (m, 7H), 2.80-2.68 (m, 3H), 2.66-2.52 (m, 11H), 2.40-2.17 (m, 3H), 2.08 (s, 3H), 2.00-1.97 (m, 1H), 1.91-1.81 (m, 2H), 1.57-1.54 (m, 2H), 1.06 (s, 1H); $[M+H]^+$=922.2.

Example 156: 5-((R)-3-((4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)methyl)pyrrolidin-1-yl)-2-(2,6-dioxopiperidin-3-yl)isoindoline-1,3-dione

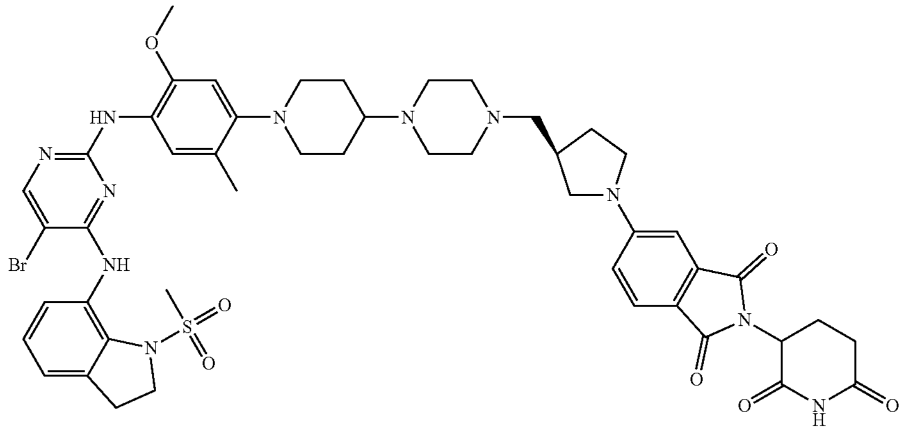 [SMILES: COc1cc(N2CCC(N3CCN(C[C@H]4CCN(c5ccc6c(c5)C(=O)N(C5CCC(=O)NC5=O)C6=O)C4)CC3)CC2)c(C)cc1Nc1ncc(Br)c(Nc2cccc3c2N(S(C)(=O)=O)CC3)n1]

The title compound was prepared in a procedure similar to that in Example 3.

$^1$H NMR (500 MHz, DMSO) δ 11.06 (s, 1H), 8.79 (s, 1H), 8.18 (s, 1H), 7.87 (s, 1H), 7.81 (s, 1H), 7.65 (d, J=8.0 Hz, 1H), 7.44 (s, 1H), 7.15 (s, 2H), 6.90 (s, 1H), 6.82 (d, J=8.0 Hz, 1H), 6.68 (s, 1H), 5.05 (d, J=7.7 Hz, 1H), 4.05 (s, 2H), 3.76 (s, 3H), 3.53 (d, J=29.6 Hz, 2H), 3.37 (s, 2H), 3.17-3.01 (m, 9H), 2.94-2.82 (m, 1H), 2.69-2.53 (m, 10H), 2.41-2.30 (m, 4H), 2.18-2.06 (m, 4H), 2.04-1.97 (m, 1H), 1.93-1.83

(m, 2H), 1.81-1.71 (m, 1H), 1.66-1.52 (m, 2H); $[M+H]^+$=1010.3.

Example 157: 3-((4-(1-(2-(4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)ethyl)piperidin-4-yl)phenyl)amino)piperidine-2,6-dione

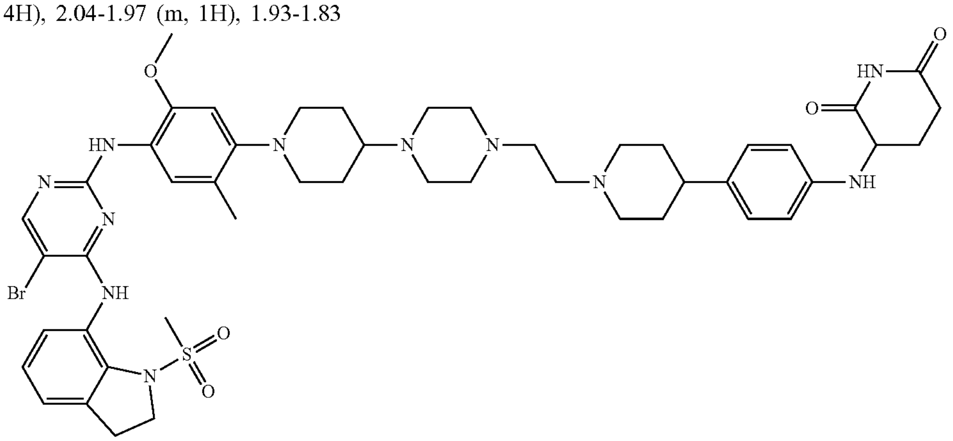

The title compound was prepared in a procedure similar to that in Example 3.

$^1$H NMR (500 MHz, DMSO) δ 10.77 (s, 1H), 8.79 (s, 1H), 8.16 (d, J=9.0 Hz, 1H), 7.83 (d, J=28.7 Hz, 2H), 7.43 (s, 1H), 7.15 (s, 2H), 6.95 (d, J=6.7 Hz, 2H), 6.68 (s, 1H), 6.61 (d, J=6.6 Hz, 2H), 5.65 (d, J=5.9 Hz, 1H), 4.30 (d, J=40.6 Hz, 1H), 4.05 (s, 2H), 3.76 (s, 3H), 3.48-3.39 (m, 2H), 3.14-2.97 (m, 10H), 2.79-2.68 (m, 1H), 2.66-2.56 (m, 5H), 2.48-2.39 (m, 5H), 2.39-2.26 (m, 3H), 2.14-2.03 (m, 6H), 1.91-1.81 (m, 3H), 1.73-1.64 (m, 2H), 1.63-1.51 (m, 4H), 1.08-1.03 (m, 1H); $[M+H]^+$=984.2.

Example 158: 5-(((1r,3r)-3-(4-(1-(4-((5-bromo-4-((1-(methylsulfonyl)indolin-7-yl)amino)pyrimidin-2-yl)amino)-5-methoxy-2-methylphenyl)piperidin-4-yl)piperazine-1-carbonyl)cyclobutyl)(methyl)amino)-2-(2,6-dioxopiperidin-3-yl)isoindoline-1,3-dione

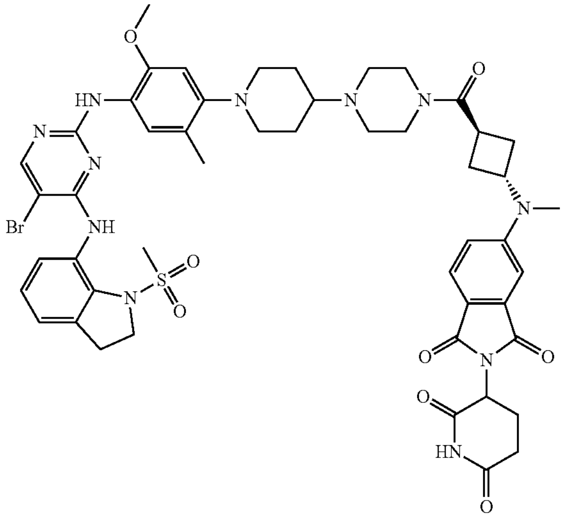 [SMILES: COc1cc(N2CCC(N3CCN(C(=O)[C@H]4C[C@H](N(C)c5ccc6c(c5)C(=O)N(C5CCC(=O)NC5=O)C6=O)C4)CC3)CC2)c(C)cc1Nc1ncc(Br)c(Nc2cccc3c2N(S(C)(=O)=O)CC3)n1]

The title compound was prepared in a procedure similar to that in Example 11.

$^1$H NMR (500 MHz, DMSO) δ 11.07 (s, 1H), 8.79 (s, 1H), 8.17 (s, 1H), 7.86 (s, 1H), 7.82 (s, 1H), 7.67 (d, J=7.7 Hz, 1H), 7.44 (s, 1H), 7.15 (s, 2H), 7.03-6.91 (m, 2H), 6.68 (s, 1H), 5.06 (d, J=8.0 Hz, 1H), 4.35 (s, 1H), 4.05 (s, 2H), 3.76 (s, 3H), 3.48-3.41 (m, 4H), 3.26-3.21 (m, 1H), 3.10-2.91 (m, 12H), 2.88-2.71 (m, 1H), 2.68-2.54 (m, 7H), 2.44-2.28 (m, 1H), 2.36 (t, J=7.9 Hz, 1H), 2.32-2.22 (m, 1H), 2.08 (s, 3H), 2.04-1.96 (m, 1H), 1.92-1.79 (m, 2H), 1.66-1.52 (m, 2H), 1.09-1.01 (m, 1H); $[M+H]^+$=1038.4.

Example 159: 3-(5-((1r,3r)-3-((4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)methyl)cyclobutyl)-1-oxoisoindolin-2-yl)piperidine-2,6-dione

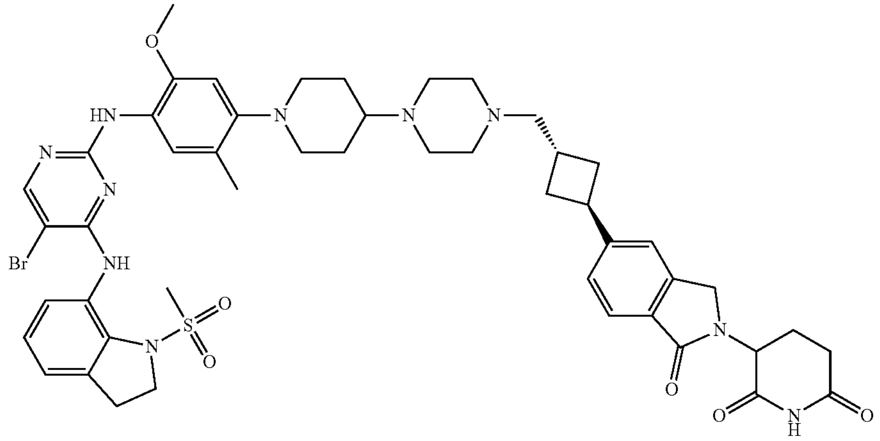 [SMILES: COc1cc(N2CCC(N3CCN(C[C@H]4C[C@H](c5ccc6c(c5)CN(C5CCC(=O)NC5=O)C6=O)C4)CC3)CC2)c(C)cc1Nc1ncc(Br)c(Nc2cccc3c2N(S(C)(=O)=O)CC3)n1]

The title compound was prepared in a procedure similar to that in Example 3.

$^1$H NMR (500 MHz, DMSO) δ 10.98 (s, 1H), 8.79 (s, 1H), 8.17 (s, 1H), 7.86 (s, 1H), 7.81 (s, 1H), 7.65 (s, 1H), 7.51 (s, 1H), 7.42 (d, J=19.1 Hz, 2H), 7.15 (s, 2H), 6.68 (s, 1H), 5.09 (s, 1H), 4.43-4.40 (m, 1H), 4.38-4.25 (m, 2H), 4.10-3.99 (m, 2H), 3.78-3.66 (m, 4H), 3.49-3.40 (m, 3H), 3.15-2.99 (m, 7H), 2.97-2.86 (m, 1H), 2.60-2.55 (m, 8H), 2.43-2.31 (m, 4H), 2.28-2.13 (m, 4H), 2.08 (s, 3H), 2.02-1.94 (m, 1H), 1.91-1.81 (m, 2H), 1.57-1.52 (m, 2H).

$[M+H]^+$=981.2.

Example 160: 3-(4-(4-(2-(4-(1-(4-((5-bromo-4-((1-(methylsulfonyl)indolin-7-yl)amino)pyrimidin-2-yl)amino)-2-ethyl-5-methoxyphenyl)piperidin-4-yl)piperazin-1-yl)ethyl)piperidin-1-yl)-2,6-difluorophenyl)piperidine-2,6-dione

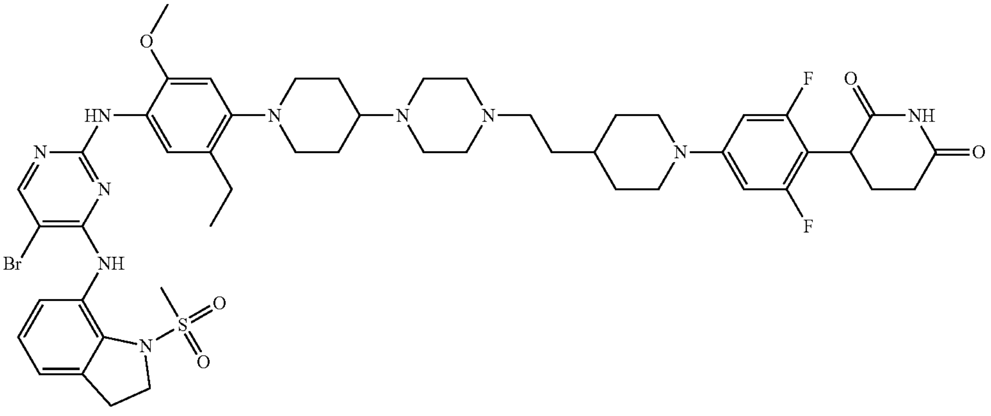 [SMILES: CCc1cc(Nc2ncc(Br)c(Nc3cccc4c3N(S(C)(=O)=O)CC4)n2)c(OC)cc1N1CCC(N2CCN(CCC3CCN(c4cc(F)c(C5CCC(=O)NC5=O)c(F)c4)CC3)CC2)CC1]

The titled compound was prepared in a manner similar to that in Example 3. $^1$H NMR (500 MHz, DMSO) δ 10.86 (s, 1H), 8.76 (s, 1H), 8.18 (s, 1H), 7.90 (s, 1H), 7.77 (d, J=8.0 Hz, 1H), 7.45 (s, 1H), 7.15 (d, J=7.0 Hz, 1H), 7.10 (t, J=7.7 Hz, 1H), 6.73 (s, 1H), 6.60 (d, J=12.8 Hz, 2H), 4.04 (t, J=7.1 Hz, 3H), 3.75 (s, 3H), 3.72 (s, 2H), 3.10 (t, J=7.4 Hz, 2H), 3.05 (s, 3H), 2.97 (d, J=10.9 Hz, 2H), 2.82-2.62 (m, 6H), 2.54 (s, 4H), 2.49-2.25 (m, 9H), 2.14-2.03 (m, 1H), 1.98-1.92 (m, 1H), 1.88-1.82 (m, 2H), 1.77-1.73 (m, 2H), 1.61-1.52 (m, 2H), 1.50-1.45 (m, 1H), 1.42-1.35 (m, 2H), 1.23-1.13 (m, 2H), 0.99 (t, J=7.4 Hz, 3H); $[M+H]^+$=1021.7.

Example 161: 5-(4-(4-(1-(4-((5-chloro-4-((1-(methylsulfonyl)indolin-7-yl)amino)pyrimidin-2-yl)amino)-3-methoxyphenyl)piperidin-4-yl)piperazine-1-carbonyl)piperidin-1-yl)-2-(2,6-dioxopiperidin-3-yl)isoindoline-1,3-dione

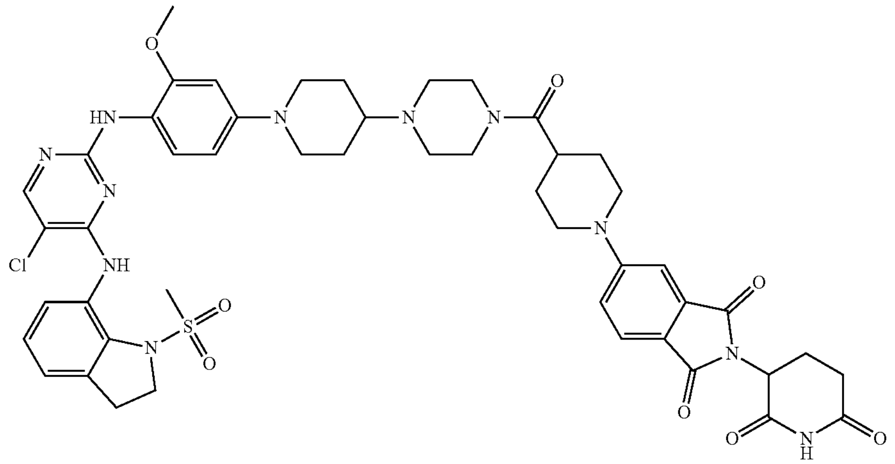 [SMILES: COc1cc(N2CCC(N3CCN(C(=O)C4CCN(c5ccc6c(c5)C(=O)N(C5CCC(=O)NC5=O)C6=O)CC4)CC3)CC2)ccc1Nc1ncc(Cl)c(Nc2cccc3c2N(S(C)(=O)=O)CC3)n1]

The titled compound was prepared in a manner similar to that in Example 11. $^1$H NMR (500 MHz, DMSO) δ 11.07 (s, 1H), 8.92 (s, 1H), 8.08 (s, 1H), 7.87 (s, 2H), 7.66 (d, J=8.5 Hz, 1H), 7.45 (d, J=8.7 Hz, 1H), 7.33 (d, J=1.9 Hz, 1H), 7.24 (dd, J=8.7, 2.1 Hz, 1H), 7.19-7.12 (m, 2H), 6.60 (d, J=2.3 Hz, 1H), 6.41 (dd, J=8.8, 2.2 Hz, 1H), 5.07 (dd, J=12.8, 5.4 Hz, 1H), 4.11-4.03 (m, 4H), 3.77 (s, 3H), 3.71 (d, J=11.5 Hz, 2H), 3.55 (s, 2H), 3.46 (s, 2H), 3.13-3.05 (m, 4H), 3.04 (s, 3H), 3.03-2.93 (m, 1H), 2.90-2.84 (m, 1H), 2.69-2.59 (m, 3H), 2.57-2.52 (m, 3H), 2.47 (s, 2H), 2.44-2.35 (m, 1H), 2.05-1.97 (m, 1H), 1.88-1.81 (m, 2H), 1.73-1.67 (m, 2H), 1.66-1.49 (m, 4H); $[M+H]^+$=980.7.

Example 162: 3-(2-fluoro-4-(2-(4-(1-(5-methoxy-2-methyl-4-((4-((1-(methylsulfonyl)indolin-7-yl)amino)-7H-pyrrolo[2,3-d]pyrimidin-2-yl)amino)phenyl)piperidin-4-yl)piperazin-1-yl)ethyl)phenyl)piperidine-2,6-dione

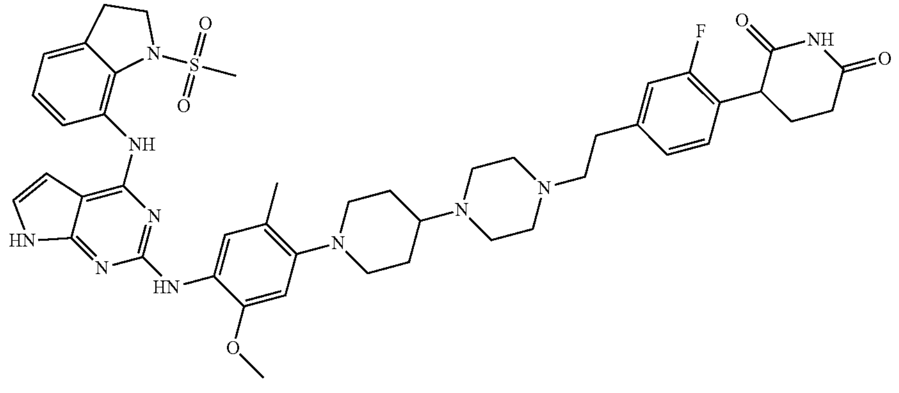 [SMILES: COc1cc(N2CCC(N3CCN(CCc4ccc(C5CCC(=O)NC5=O)c(F)c4)CC3)CC2)c(C)cc1Nc1nc(Nc2cccc3c2N(S(C)(=O)=O)CC3)c2cc[nH]c2n1]

The title compound was prepared in a procedure similar to that in Example 3. 1H NMR (400 MHz, DMSO) δ 11.25 (s, 1H), 10.86 (s, 1H), 9.04 (s, 1H), 8.20 (d, J=8.1 Hz, 1H), 8.01 (s, 1H), 7.25 (s, 1H), 7.23-7.19 (m, 2H), 7.12-7.03 (m, 3H), 6.96-6.92 (m, 1H), 6.70 (s, 1H), 6.21 (s, 1H), 4.10 (t, J=7.5 Hz, 2H), 4.00 (dd, J=12.4, 5.0 Hz, 1H), 3.82 (s, 3H), 3.13 (t, J=7.5 Hz, 2H), 3.09 (s, 3H), 3.06 (d, J=11.0 Hz, 2H), 2.80-2.68 (m, 4H), 2.64-2.54 (m, 11H), 2.36 (s, 2H), 2.20 (d, J=4.1 Hz, 1H), 2.16 (s, 3H), 2.02-1.97 (m, 1H), 1.88-1.86 (m, 2H), 1.58 (d, J=8.7 Hz, 2H); $[M+H]^+$=865.7.

Example 163: 3-(2,6-difluoro-4-(2-(4-(1-(5-methoxy-2-methyl-4-((4-((1-(methylsulfonyl)indolin-7-yl)amino)-7H-pyrrolo[2,3-d]pyrimidin-2-yl)amino)phenyl)piperidin-4-yl)piperazin-1-yl)ethyl)phenyl)piperidine-2,6-dione

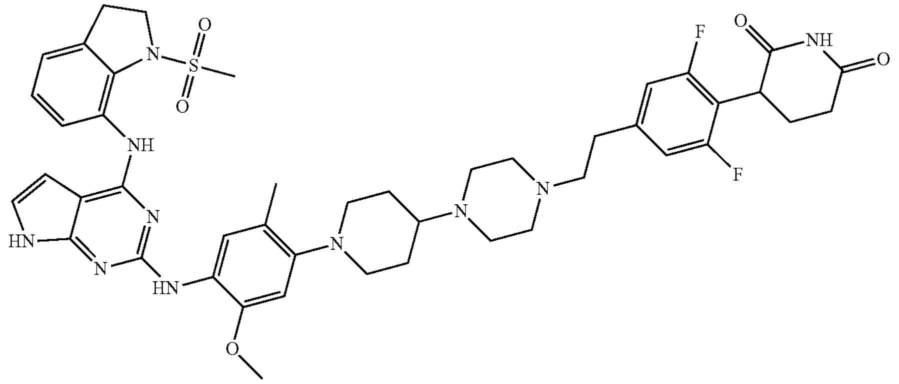 [SMILES: COc1cc(N2CCC(N3CCN(CCc4cc(F)c(C5CCC(=O)NC5=O)c(F)c4)CC3)CC2)c(C)cc1Nc1nc(Nc2cccc3c2N(S(C)(=O)=O)CC3)c2cc[nH]c2n1]

The title compound was prepared in a procedure similar to that in Example 3. 1H NMR (400 MHz, DMSO) δ 11.25 (s, 1H), 10.95 (s, 1H), 9.04 (s, 1H), 8.20 (d, J=8.4 Hz, 1H), 8.01 (s, 1H), 7.25 (s, 1H), 7.21 (t, J=10.0 Hz, 2H), 7.10 (d, J=7.4 Hz, 1H), 7.03 (d, J=10.0 Hz, 2H), 6.97-6.93 (m, 1H), 6.70 (s, 1H), 6.21 (dd, J=3.3, 1.9 Hz, 1H), 4.20 (dd, J=13.0, 5.1 Hz, 1H), 4.10 (t, J=7.5 Hz, 2H), 3.82 (s, 3H), 3.13 (t, J=7.3 Hz, 2H), 3.09 (s, 3H), 3.06 (d, J=11.3 Hz, 2H), 2.85-2.75 (m, 4H), 2.64-2.54 (m, 11H), 2.36 (s, 1H), 2.15-2.12 (m, 4H), 2.04-1.96 (m, 1H), 1.88 (d, J=9.2 Hz, 2H), 1.58 (d, J=9.8 Hz, 2H); $[M+H]^+$=883.6.

Example 164: 5-((S)-3-((4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)methyl)pyrrolidin-1-yl)-2-(2,6-dioxopiperidin-3-yl)isoindoline-1,3-dione

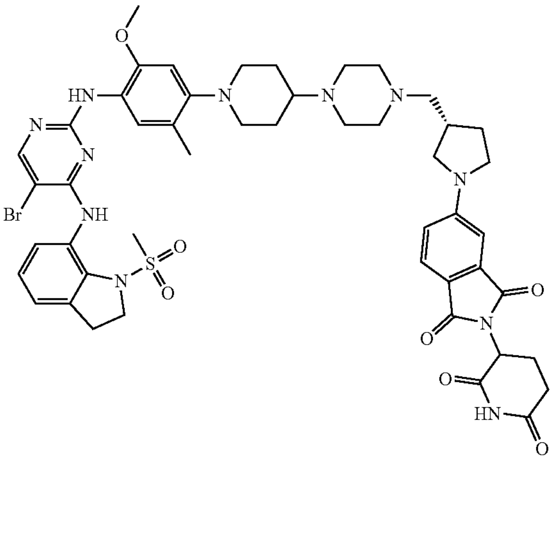 [SMILES: COc1cc(N2CCC(N3CCN(C[C@@H]4CCN(c5ccc6c(c5)C(=O)N(C5CCC(=O)NC5=O)C6=O)C4)CC3)CC2)c(C)cc1Nc1ncc(Br)c(Nc2cccc3c2N(S(C)(=O)=O)CC3)n1]

The title compound was prepared in a procedure similar to that in Example 3.

$^1$H NMR (500 MHz, DMSO) δ 11.06 (s, 1H), 8.79 (s, 1H), 8.18 (s, 1H), 7.86 (s, 1H), 7.81 (d, J=7.9 Hz, 1H), 7.64 (d, J=8.5 Hz, 1H), 7.44 (s, 1H), 7.14 (q, J=7.4 Hz, 2H), 6.90 (s, 1H), 6.82 (d, J=8.6 Hz, 1H), 6.68 (s, 1H), 5.05 (dd, J=12.9, 5.3 Hz, 1H), 4.05 (t, J=7.3 Hz, 2H), 3.76 (s, 3H), 3.54-3.52 (m, 2H), 3.43-3.36 (m, 2H), 3.05-3.01 (m, 8H), 2.94-2.81 (m, 1H), 2.68-2.53 (m, 9H), 2.35 (d, J=7.6 Hz, 6H), 2.08 (s, 4H), 2.05-1.97 (m, 1H), 1.87-1.84 (m, 2H), 1.77-1.75 (m, 1H), 1.57-1.54 (m, 2H). $[M+H]^+$=1010.2.

Example 165: 5-(((1r,3r)-3-((4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)methyl)cyclobutyl)(methyl)amino)-2-(2,6-dioxopiperidin-3-yl)isoindoline-1,3-dione

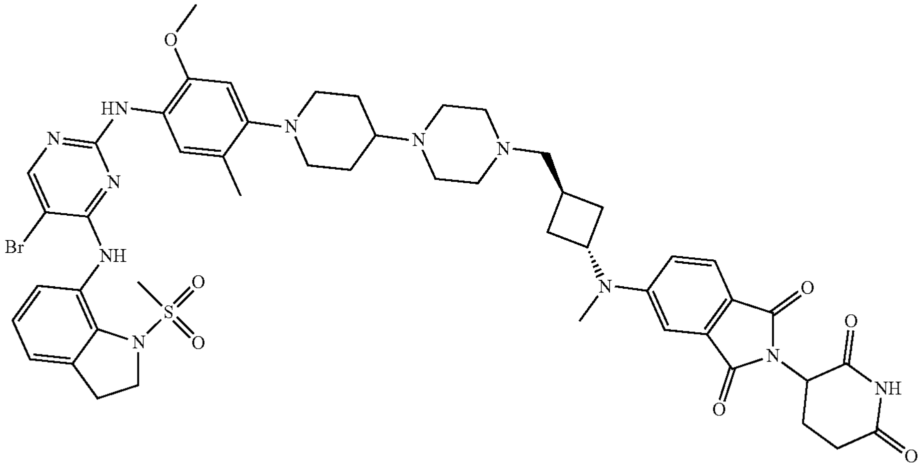 [SMILES: COc1cc(N2CCC(N3CCN(C[C@H]4C[C@H](N(C)c5ccc6c(c5)C(=O)N(C5CCC(=O)NC5=O)C6=O)C4)CC3)CC2)c(C)cc1Nc1ncc(Br)c(Nc2cccc3c2N(S(C)(=O)=O)CC3)n1]

The title compound was prepared in a procedure similar to that in Example 3.

$^1$H NMR (500 MHz, DMSO) δ 11.07 (s, 1H), 8.79 (s, 1H), 8.22 (s, 1H), 8.17 (s, 1H), 7.86 (s, 1H), 7.81 (d, J=7.2 Hz, 1H), 7.65 (d, J=8.5 Hz, 1H), 7.43 (s, 1H), 7.13 (dt, J=7.6, 4.9 Hz, 3H), 7.05-6.98 (m, 1H), 6.68 (s, 1H), 5.06 (dd, J=13.0, 5.3 Hz, 1H), 4.58-4.47 (m, 1H), 4.05 (t, J=7.4 Hz, 2H), 3.76 (s, 3H), 3.03-2.98 (m, 8H), 2.88-2.86 (m, 1H), 2.54-2.51 (m, 7H), 2.33-2.29 (m, 8H), 2.08-2.06 (m, 5H), 2.03-1.97 (m, 1H), 1.86-1.83 (m, 2H), 1.56-1.53 (m, 2H), 1.24-122 (m, 4H); $[M+H]^+$=1024.3.

Example 166: 4-(2-(4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)ethoxy)-2-(2,6-dioxopiperidin-3-yl)isoindoline-1,3-dione

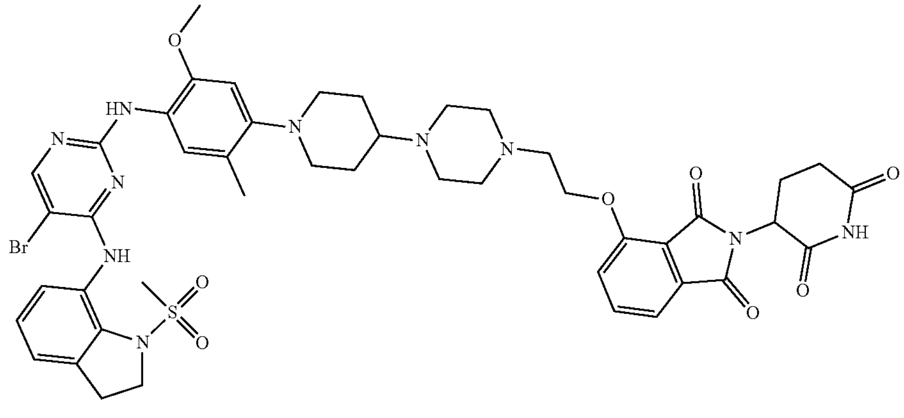 [SMILES: COc1cc(N2CCC(N3CCN(CCOc4cccc5c4C(=O)N(C4CCC(=O)NC4=O)C5=O)CC3)CC2)c(C)cc1Nc1ncc(Br)c(Nc2cccc3c2N(S(C)(=O)=O)CC3)n1]

The title compound was prepared in a procedure similar to that in Example 3.

$^1$H NMR (500 MHz, DMSO) δ 11.10 (s, 1H), 8.79 (s, 1H), 8.17 (s, 1H), 7.83-7.81 (m, 3H), 7.55 (d, J=8.4 Hz, 1H), 7.48-7.43 (m, 2H), 7.14 (q, J=7.5 Hz, 2H), 6.67 (s, 1H), 5.09 (dd, J=12.7, 5.5 Hz, 1H), 4.33 (t, J=5.3 Hz, 2H), 4.05 (t, J=7.3 Hz, 2H), 3.76 (s, 3H), 3.09-3.07 (m, 3H), 3.05-3.02 (m, 5H), 2.87-2.85 (m, 1H), 2.75 (s, 2H), 2.67-2.52 (m, 11H), 2.29 (s, 1H), 2.07-2.03 (m, 4H), 1.85-1.83 (m, 2H), 1.61-1.49 (m, 2H); $[M+H]^+$=971.2.

Example 167: 5-(4-(4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)piperidin-1-yl)-2-(2,6-dioxopiperidin-3-yl)isoindoline-1,3-dione

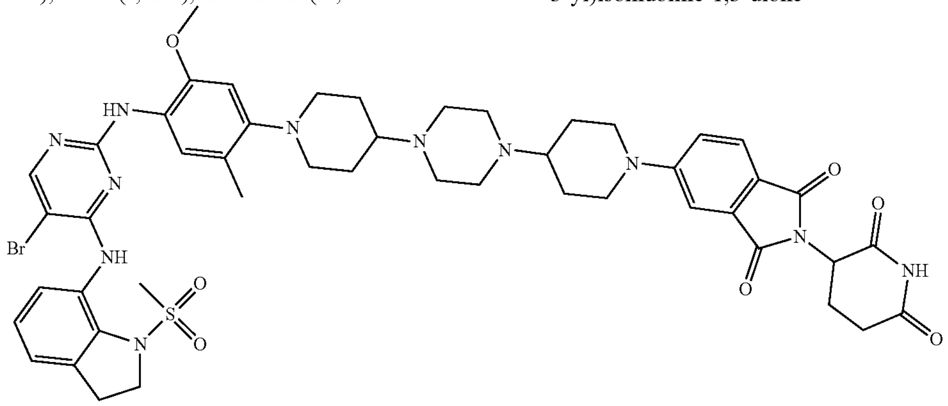

The title compound was prepared in a procedure similar to that in Example 3.

$^1$H NMR (500 MHz, DMSO) δ 11.12 (s, 1H), 8.79 (s, 1H), 8.18 (s, 1H), 7.87 (d, J=7.6 Hz, 2H), 7.81 (d, J=7.4 Hz, 1H), 7.74 (s, 2H), 7.44 (s, 1H), 7.15 (s, 2H), 6.68 (s, 1H), 5.14 (dd, J=12.8, 5.4 Hz, 1H), 4.05 (s, 2H), 3.76 (s, 3H), 3.08-3.06 (m, 7H), 2.94-2.85 (m, 2H), 2.71-2.51 (m, 10H), 2.37-2.19 (m, 3H), 2.08-2.06 (m, 6H), 1.89-1.86 (m, 4H), 1.56-1.52 (m, 6H); $[M+H]^+$=1010.4.

Example 168: 3-(5-((R)-3-((4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)methyl)pyrrolidin-1-yl)-1-oxoisoindolin-2-yl)piperidine-2,6-dione

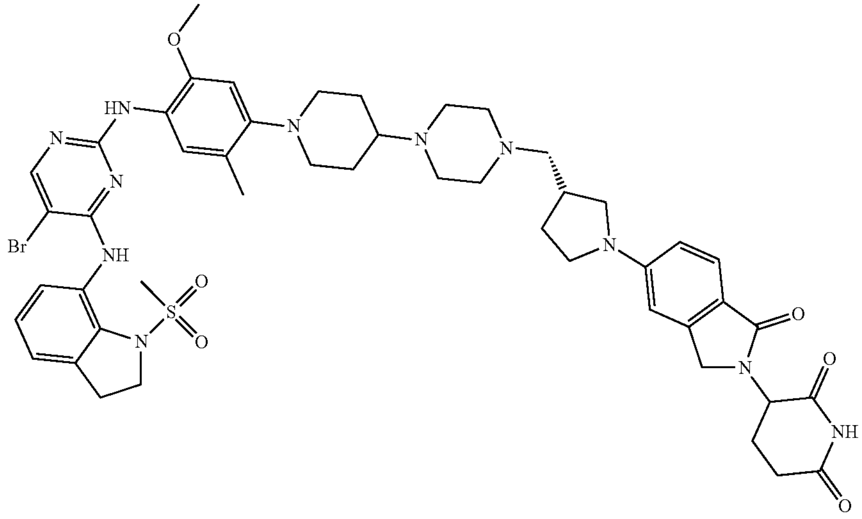

The title compound was prepared in a procedure similar to that in Example 3.

$^1$H NMR (500 MHz, DMSO) δ 10.93 (s, 1H), 8.79 (s, 1H), 8.18 (s, 2H), 7.86 (s, 1H), 7.81 (d, J=7.7 Hz, 1H), 7.51-7.42 (m, 2H), 7.14 (d, J=7.9 Hz, 2H), 6.68 (s, 1H), 6.63 (s, 2H), 5.03 (dd, J=13.3, 5.0 Hz, 1H), 4.30 (dd, J=16.9, 3.5 Hz, 1H), 4.18 (dd, J=16.9, 2.8 Hz, 1H), 4.05 (s, 2H), 3.76 (s, 3H), 3.45 (t, J=8.0 Hz, 2H), 3.14-3.00 (m, 9H), 2.94-2.84 (m, 1H), 2.58-2.55 (m, 8H), 2.34-2.31 (m, 7H), 2.08 (s, 4H), 1.97-1.91 (m, 1H), 1.86-1.84 (m, 2H), 1.73-1.71 (m, 1H), 1.57-1.55 (m, 2H); $[M+H]^+$=996.2.

Example 169: 3-(4-(3-((4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)methyl)azetidin-1-yl)-2-fluorophenyl)piperidine-2,6-dione

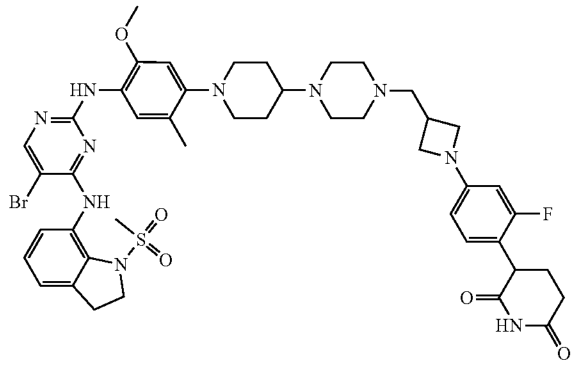 [SMILES: COc1cc(N2CCC(N3CCN(CC4CN(c5ccc(C6CCC(=O)NC6=O)c(F)c5)C4)CC3)CC2)c(C)cc1Nc1ncc(Br)c(Nc2cccc3c2N(S(C)(=O)=O)CC3)n1]

The title compound was prepared in a procedure similar to that in Example 3.

$^1$H NMR (500 MHz, DMSO) δ 10.78 (s, 1H), 8.79 (s, 1H), 8.17 (s, 1H), 7.86 (s, 2H), 7.44 (s, 1H), 7.15 (s, 2H), 7.03 (t, J=8.6 Hz, 1H), 6.68 (s, 1H), 6.19 (s, 2H), 4.05 (s, 2H), 3.92 (s, 2H), 3.85 (dd, J=12.3, 4.9 Hz, 1H), 3.76 (s, 3H), 3.45 (s, 2H), 3.08-3.05 (m, 7H), 2.95-2.85 (m, 1H), 2.75-2.53 (m, 10H), 2.46-2.24 (m, 5H), 2.08-2.06 (m, 4H), 1.98-1.90 (m, 1H), 1.86 (d, J=11.7 Hz, 2H), 1.56 (d, J=8.8 Hz, 2H); $[M+H]^+$=945.2.

Example 170: 3-(4-(((1r,3r)-3-(4-(1-(4-((5-bromo-4-((1-(methylsulfonyl)indolin-7-yl)amino)pyrimidin-2-yl)amino)-5-methoxy-2-methylphenyl)piperidin-4-yl)piperazine-1-carbonyl)cyclobutyl)(methyl)amino)phenyl)piperidine-2,6-dione

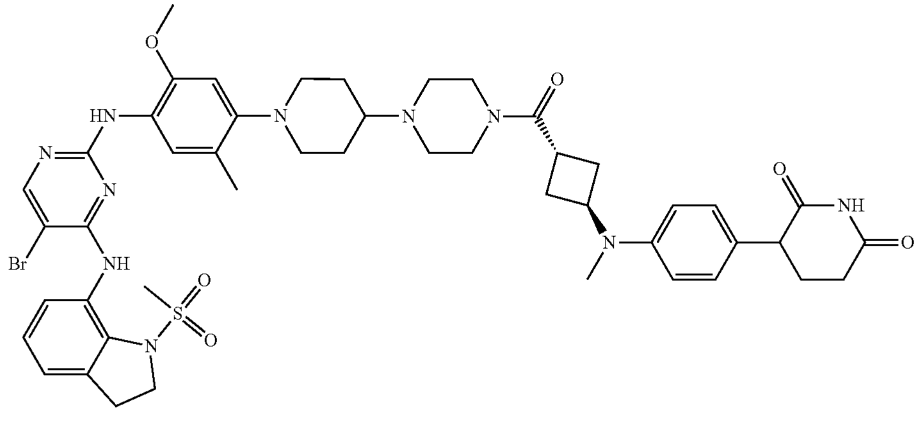 [SMILES: COc1cc(N2CCC(N3CCN(C(=O)[C@H]4C[C@H](N(C)c5ccc(C6CCC(=O)NC6=O)cc5)C4)CC3)CC2)c(C)cc1Nc1ncc(Br)c(Nc2cccc3c2N(S(C)(=O)=O)CC3)n1]

The title compound was prepared in a procedure similar to that in Example 11.

$^1$H NMR (500 MHz, DMSO) δ 10.76 (s, 1H), 8.79 (s, 1H), 8.17 (s, 1H), 7.88-7.78 (m, 2H), 7.43 (s, 1H), 7.14 (d, J=8.4 Hz, 2H), 7.02 (dd, J=8.7, 2.3 Hz, 2H), 6.76-6.65 (m, 3H), 4.05 (t, J=7.4 Hz, 2H), 3.94-3.91 (m, 1H), 3.78-3.64 (m, 5H), 3.43-3.41 (m, 4H), 3.19-3.17 (m, 1H), 3.13-2.96 (m, 8H), 2.77-2.75 (m, 3H), 2.67-2.55 (m, 4H), 2.42-2.40 (m, 6H), 2.22-1.96 (m, 8H), 1.83-1.81 (m, 2H), 1.58-1.56 (m, 2H); $[M+H]^+$=969.3.

Example 171: 3-(6-(3-(4-(1-(4-((5-bromo-4-((1-(methylsulfonyl)indolin-7-yl)amino)pyrimidin-2-yl)amino)-5-methoxy-2-methylphenyl)piperidin-4-yl)piperazine-1-carbonyl)azetidin-1-yl)-1-oxoisoindolin-2-yl)piperidine-2,6-dione

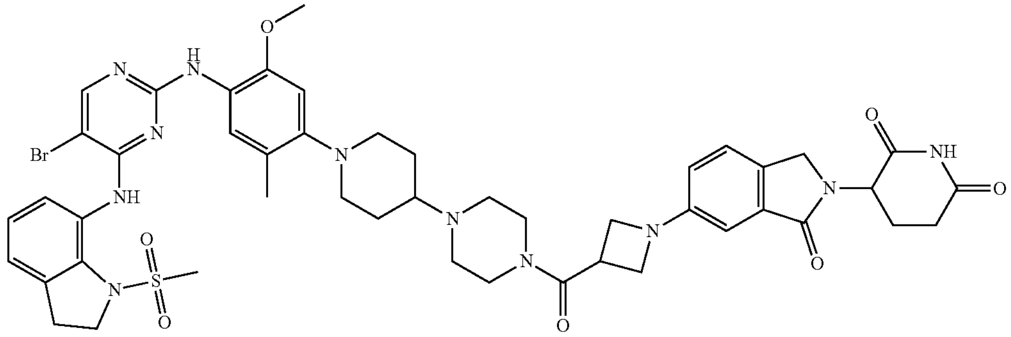 [SMILES: COc1cc(N2CCC(N3CCN(C(=O)C4CN(c5ccc6c(c5)C(=O)N(C5CCC(=O)NC5=O)C6)C4)CC3)CC2)c(C)cc1Nc1ncc(Br)c(Nc2cccc3c2N(S(C)(=O)=O)CC3)n1]

The title compound was prepared in a procedure similar to that in Example 11.

$^1$H NMR (500 MHz, DMSO) δ 10.96 (s, 1H), 8.79 (s, 1H), 8.18 (s, 1H), 7.89-7.75 (m, 2H), 7.44 (s, 2H), 7.15 (s, 2H), 6.70-6.68 (m, 3H), 5.09 (dd, J=13.3, 5.2 Hz, 1H), 4.32 (d, J=16.7 Hz, 1H), 4.20 (d, J=16.7 Hz, 1H), 4.13-3.99 (m, 4H), 3.93 (s, 3H), 3.76 (s, 3H), 3.50 (s, 2H), 3.08-3.05 (m, 7H), 2.89-2.87 (m, 1H), 2.58-2.56 (m, 6H), 2.46-2.30 (m, 5H), 2.08-2.06 (m, 3H), 2.00-1.98 (m, 1H), 1.85 (m, 2H), 1.59-1.57 (m, 2H); $[M+H]^+$=996.3.

Example 172: 3-(5-(3-(4-(1-(4-((5-bromo-4-((1-(methylsulfonyl)indolin-7-yl)amino)pyrimidin-2-yl)amino)-5-methoxy-2-methylphenyl)piperidin-4-yl)piperazine-1-carbonyl)azetidin-1-yl)-1-oxoisoindolin-2-yl)piperidine-2,6-dione

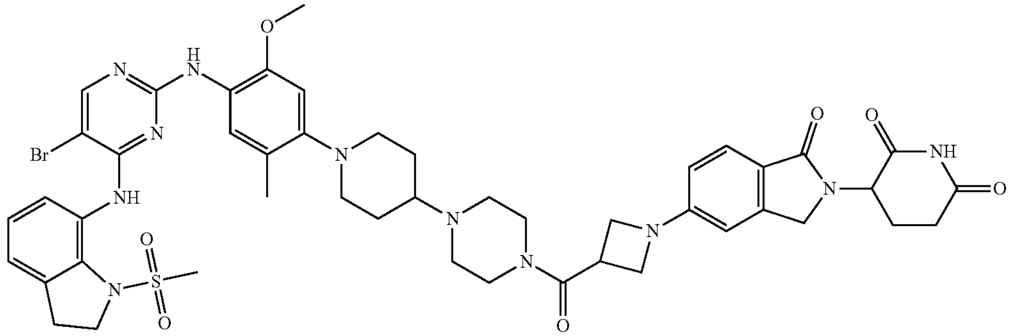 [SMILES: COc1cc(N2CCC(N3CCN(C(=O)C4CN(c5ccc6c(c5)CN(C5CCC(=O)NC5=O)C6=O)C4)CC3)CC2)c(C)cc1Nc1ncc(Br)c(Nc2cccc3c2N(S(C)(=O)=O)CC3)n1]

The title compound was prepared in a procedure similar to that in Example 11.

$^1$H NMR (500 MHz, DMSO) δ 10.93 (s, 1H), 8.79 (s, 1H), 8.18 (s, 1H), 7.88-7.76 (m, 2H), 7.54-7.39 (m, 2H), 7.14 (d, J=7.9 Hz, 2H), 6.68 (s, 1H), 6.59-6.46 (m, 2H), 5.04 (dd, J=13.3, 5.0 Hz, 1H), 4.31-4.29 (m, 1H), 4.17 (s, 1H), 4.13 (t, J=7.8 Hz, 2H), 4.02-3.99 (m, 4H), 3.88-3.86 (m, 1H), 3.76-3.74 (m, 3H), 3.50-3.48 (m, 2H), 3.35-3.32 (m, 2H), 3.14-3.00 (m, 7H), 2.95-2.83 (m, 1H), 2.67-2.51 (m, 7H), 2.43-2.30 (m, 2H), 2.08-2.06 (m, 3H), 2.00-1.91 (m, 1H), 1.85-1.83 (m, 2H), 1.59-1.57 (m, 2H); $[M+H]^+$=996.3.

Example 173: 3-(4-((2-(4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)ethyl)amino)-1-oxoisoindolin-2-yl)piperidine-2,6-dione

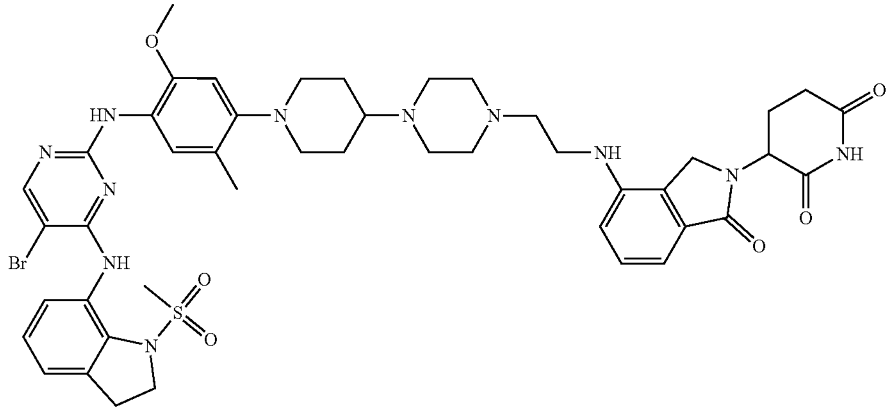 [SMILES: COc1cc(N2CCC(N3CCN(CCNc4cccc5c4CN(C4CCC(=O)NC4=O)C5=O)CC3)CC2)c(C)cc1Nc1ncc(Br)c(Nc2cccc3c2N(S(C)(=O)=O)CC3)n1]

The title compound was prepared in a procedure similar to that in Example 3.

$^1$H NMR (500 MHz, DMSO) δ 11.01 (s, 1H), 8.79 (s, 1H), 8.18 (s, 1H), 7.87 (s, 1H), 7.82 (s, 1H), 7.44 (s, 1H), 7.30 (t, J=7.7 Hz, 1H), 7.16 (s, 2H), 6.96 (d, J=7.3 Hz, 1H), 6.80 (d, J=7.9 Hz, 1H), 6.68 (s, 1H), 5.46 (s, 1H), 5.12-5.10 (m, 1H), 4.24-4.22 (m, 1H), 4.13-4.15 (d, 1H), 4.05-4.03 (m, 2H), 3.76-3.74 (m, 3H), 3.28-3.26 (m, 3H), 3.16-3.02 (m, 7H), 2.93-2.91 (m, 1H), 2.61-2.59 (m, 12H), 2.41-2.26 (m, 2H), 2.08-2.06 (m, 4H), 1.87-1.85 (m, 2H), 1.58-1.56 (m, 2H); $[M+H]^+$=956.2.

Example 174: 3-(4-(2-(4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)ethyl)-2-chloro-5-fluorophenyl)piperidine-2,6-dione

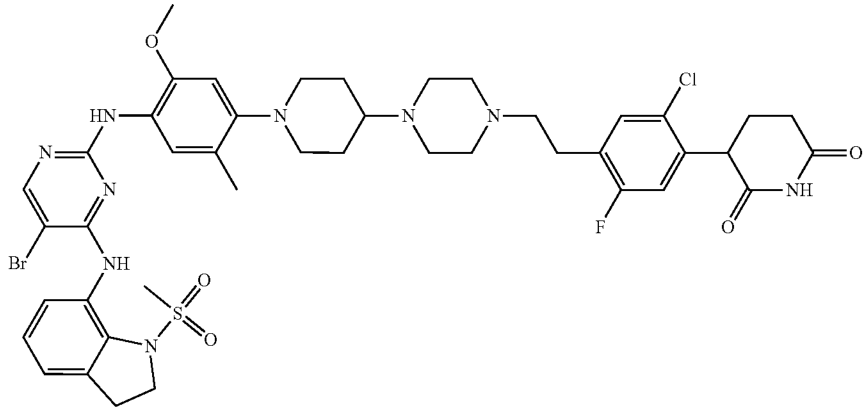 [SMILES: COc1cc(N2CCC(N3CCN(CCc4cc(Cl)c(C5CCC(=O)NC5=O)cc4F)CC3)CC2)c(C)cc1Nc1ncc(Br)c(Nc2cccc3c2N(S(C)(=O)=O)CC3)n1]

The title compound was prepared in a procedure similar to that in Example 3.

$^1$H NMR (500 MHz, DMSO) δ 10.91 (s, 1H), 8.79 (s, 1H), 8.17 (s, 1H), 7.86 (s, 1H), 7.81 (d, J=7.2 Hz, 1H), 7.49-7.40 (m, 2H), 7.22 (d, J=10.8 Hz, 1H), 7.15 (t, J=8.2 Hz, 2H), 6.68 (s, 1H), 4.18-4.16 (m, 1H), 4.05-4.03 (m, 2H), 3.76-3.74 (m, 3H), 3.29-3.27 (m, 3H), 3.05-3.03 (m, 8H), 2.75-2.73 (m, 3H), 2.67-2.53 (m, 7H), 2.38-2.25 (m, 4H), 2.08-2.06 (m, 3H), 1.96-1.94 (m, 1H), 1.85-1.83 (m, 2H), 1.57-1.55 (m, 2H); $[M+H]^+$=938.2.

Example 175: 3-(5-(4-((4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)methyl)piperidin-1-yl)-1-oxoisoindolin-2-yl)piperidine-2,6-dione

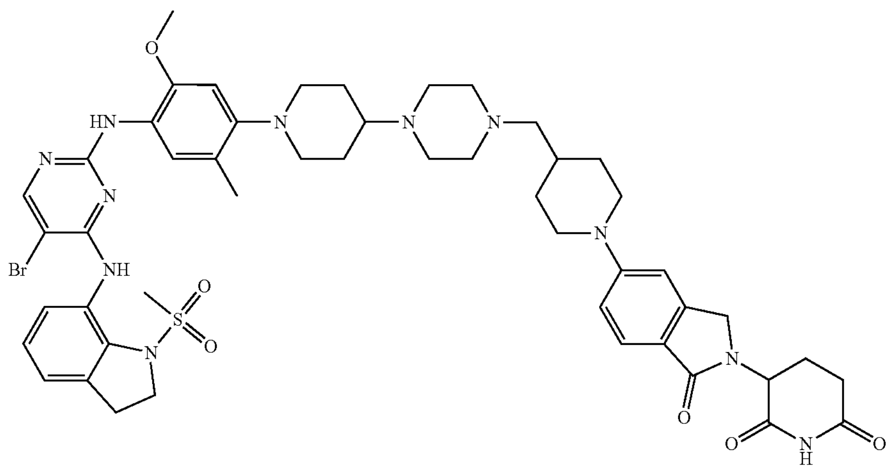 [SMILES: COc1cc(N2CCC(N3CCN(CC4CCN(c5ccc6c(c5)CN(C5CCC(=O)NC5=O)C6=O)CC4)CC3)CC2)c(C)cc1Nc1ncc(Br)c(Nc2cccc3c2N(S(C)(=O)=O)CC3)n1]

The title compound was prepared in a procedure similar to that in Example 3.

$^1$H NMR (500 MHz, DMSO) δ 10.92 (s, 1H), 8.79 (s, 1H), 8.16-8.14 (m, 1H), 7.88-7.78 (m, 2H), 7.50-7.41 (m, 2H), 7.14-7.12 (m, 2H), 6.68 (s, 1H), 6.61 (d, J=7.4 Hz, 2H), 5.05-4.98 (m, 1H), 4.30 (d, J=16.6 Hz, 1H), 4.18 (d, J=16.4 Hz, 1H), 4.05 (t, J=7.4 Hz, 2H), 3.76-3.74 (m, 3H), 3.50-3.48 (m, 1H), 3.38-3.36 (m, 3H), 3.12-3.00 (m, 7H), 2.94-2.92 (m, 2H), 2.67-2.52 (m, 7H), 2.34-2.32 (m, 8H), 2.15-2.13 (m, 1H), 2.07-2.05 (m, 3H), 1.98-1.92 (m, 1H), 1.86-1.84 (m, 2H), 1.59-1.57 (m, 5H); $[M+H]^+$=1010.4.

Example 176: 3-(4-(((1r,3r)-3-((4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)methyl)cyclobutyl)(methyl)amino)phenyl)piperidine-2,6-dione

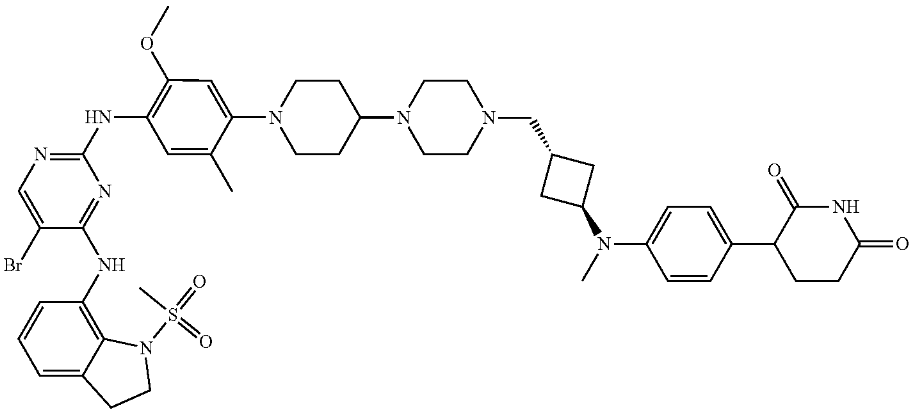 [SMILES: COc1cc(N2CCC(N3CCN(C[C@H]4C[C@H](N(C)c5ccc(C6CCC(=O)NC6=O)cc5)C4)CC3)CC2)c(C)cc1Nc1ncc(Br)c(Nc2cccc3c2N(S(C)(=O)=O)CC3)n1]

The title compound was prepared in a procedure similar to that in Example 3.

$^1$H NMR (500 MHz, DMSO) δ 10.75 (s, 1H), 8.79 (s, 1H), 8.17 (s, 3H), 7.88-7.71 (m, 2H), 7.43 (s, 1H), 7.14 (d, J=8.6 Hz, 2H), 7.00 (d, J=8.6 Hz, 2H), 6.76-6.61 (m, 3H), 4.34-4.31 (m, 1H), 4.04-4.02 (m, 2H), 3.76-3.73 (m, 6H), 3.04-2.98 (m, 7H), 2.74-2.71 (m, 2H), 2.66-2.57 (m, 4H), 2.35-2.33 (m, 8H), 2.11-2.09 (m, 2H), 2.07-2.05 (m, 2H), 2.01-1.98 (m, 2H), 1.84-1.82 (m, 2H), 1.60-1.57 (m, 4H), 1.06-1.04 (m, 2H); $[M+H]^+$=955.2.

Example 177: 3-(3-(4-(4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)piperidin-1-yl)phenyl)piperidine-2,6-dione

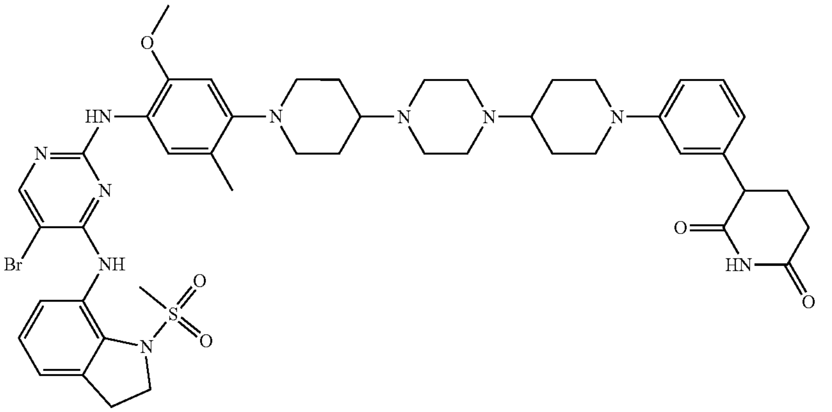 [SMILES: COc1cc(N2CCC(N3CCN(C4CCN(c5cccc(C6CCC(=O)NC6=O)c5)CC4)CC3)CC2)c(C)cc1Nc1ncc(Br)c(Nc2cccc3c2N(S(C)(=O)=O)CC3)n1]

The title compound was prepared in a procedure similar to that in Example 3.

$^1$H NMR (500 MHz, DMSO) δ 10.79 (s, 1H), 8.79 (s, 1H), 8.17 (s, 1H), 7.86 (s, 2H), 7.43 (s, 1H), 7.15 (d, J=7.9 Hz, 3H), 6.79 (s, 2H), 6.68-6.66 (m, 1H), 6.59-6.57 (m, 1H), 4.05-4.02 (m, 2H), 3.76-3.73 (m, 6H), 3.07-3.04 (m, 7H), 2.61-2.59 (m, 14H), 2.33-2.15 (m, 3H), 2.07-2.05 (m, 4H), 1.86-1.83 (m, 4H), 1.60-1.43 (m, 4H); $[M+H]^+$=941.2.

Example 178: 5-(4-(4-(1-(4-((5-chloro-4-((1-(methylsulfonyl)indolin-7-yl)amino)pyrimidin-2-yl)amino)-5-methoxy-2-methylphenyl)piperidin-4-yl)piperazine-1-carbonyl)piperidin-1-yl)-2-(2,6-dioxopiperidin-3-yl)isoindoline-1,3-dione

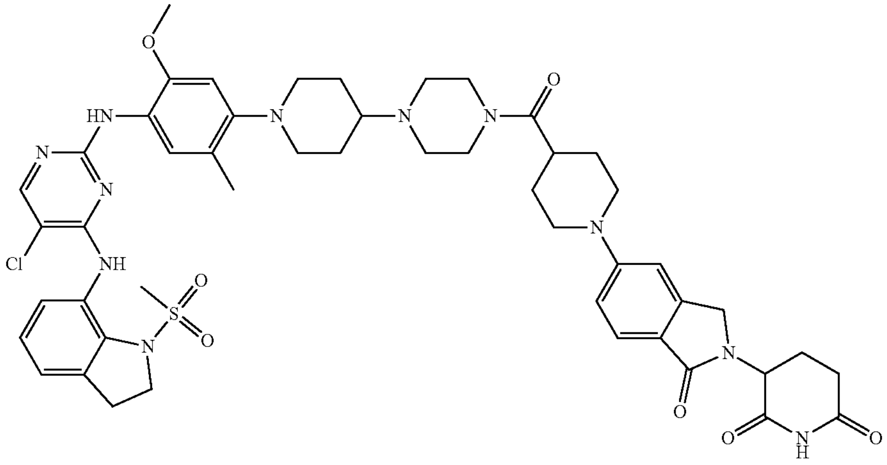 [SMILES: COc1cc(N2CCC(N3CCN(C(=O)C4CCN(c5ccc6c(c5)CN(C5CCC(=O)NC5=O)C6=O)CC4)CC3)CC2)c(C)cc1Nc1ncc(Cl)c(Nc2cccc3c2N(S(C)(=O)=O)CC3)n1]

The titled compound was prepared in a manner similar to that in Example 11. $^1$H NMR (500 MHz, DMSO) δ 11.07 (s, 1H), 8.95 (s, 1H), 8.12 (d, J=1.1 Hz, 1H), 7.86 (d, J=7.6 Hz, 2H), 7.67 (d, J=8.5 Hz, 1H), 7.47 (s, 1H), 7.33 (s, 1H), 7.25 (d, J=8.5 Hz, 1H), 7.18-7.13 (m, 2H), 6.69 (s, 1H), 5.07 (dd, J=12.4, 5.3 Hz, 1H), 4.10-4.01 (m, 4H), 3.77 (s, 3H), 3.56 (s, 2H), 3.47 (s, 2H), 3.12-3.05 (m, 10H), 3.01-2.95 (m, 1H), 2.93-2.84 (m, 1H), 2.66-2.54 (m, 6H), 2.39-2.34 (m, 2H), 2.09 (s, 3H), 2.04-2.00 (m, 1H), 1.88-1.83 (m, 2H), 1.75-1.67 (m, 2H), 1.67-1.55 (m, 4H); $[M+H]^+$=994.5.

Example 180: 3-(6-(3-((4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)methyl)azetidin-1-yl)-1-oxoisoindolin-2-yl)piperidine-2,6-dione

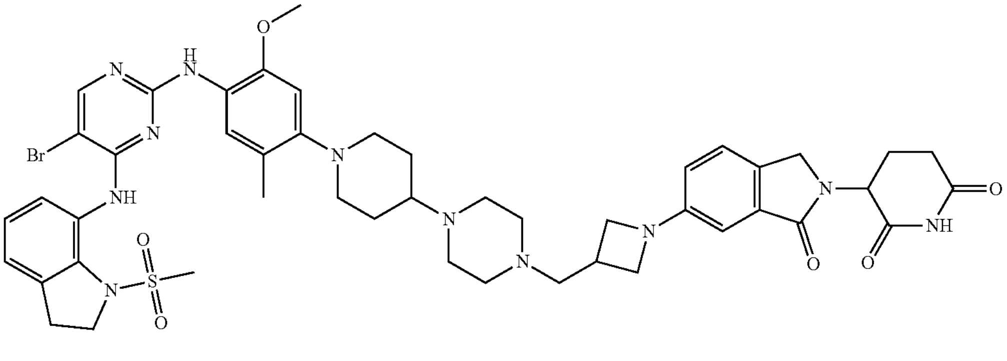 [SMILES: COc1cc(N2CCC(N3CCN(CC4CN(c5ccc6c(c5)C(=O)N(C5CCC(=O)NC5=O)C6)C4)CC3)CC2)c(C)cc1Nc1ncc(Br)c(Nc2cccc3c2N(S(C)(=O)=O)CC3)n1]

The title compound was prepared in a procedure similar to that in Example 3.

$^1$H NMR (500 MHz, DMSO) δ 10.96 (s, 1H), 8.79 (s, 1H), 8.18 (s, 1H), 7.86 (s, 1H), 7.81 (d, J=7.6 Hz, 1H), 7.44 (s, 1H), 7.37 (d, J=8.0 Hz, 1H), 7.15 (s, 2H), 6.68 (d, J=3.1 Hz, 3H), 5.08-1.05 (m, 1H), 4.31-4.29 (m, 1H), 4.19-4.16 (m, 1H), 4.05-4.02 (m, 2H), 3.98-3.97 (m, 2H), 3.76-3.73 (m, 3H), 3.50-3.48 (m, 2H), 3.08-3.05 (m, 8H), 2.98-2.84 (m, 2H), 2.61-2.59 (m, 10H), 2.36-2.33 (m, 4H), 2.08-2.06 (m, 3H), 2.03-1.93 (m, 1H), 1.86-1.84 (m, 2H), 1.57-1.55 (m, 2H); $[M+H]^+$=982.2.

Example 181: 3-(4-(4-((4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)methyl)piperidin-1-yl)-2,6-difluorophenyl)piperidine-2,6-dione

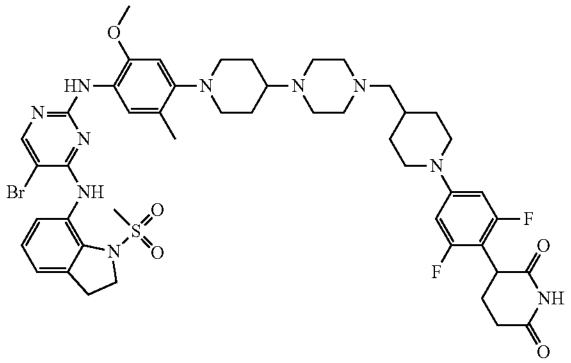 [SMILES: COc1cc(N2CCC(N3CCN(CC4CCN(c5cc(F)c(C6CCC(=O)NC6=O)c(F)c5)CC4)CC3)CC2)c(C)cc1Nc1ncc(Br)c(Nc2cccc3c2N(S(C)(=O)=O)CC3)n1]

The title compound was prepared in a procedure similar to that in Example 3.

$^1$H NMR (500 MHz, DMSO) δ 10.86 (s, 1H), 8.79 (s, 1H), 8.33 (s, 1H), 8.17 (s, 1H), 7.86 (s, 1H), 7.81 (d, J=7.2 Hz, 1H), 7.43 (s, 1H), 7.14 (q, J=7.9 Hz, 2H), 6.68 (s, 1H), 6.60-6.58 (m, 2H), 4.35 (s, 2H), 4.04-4.01 (m, 3H), 3.76-3.72 (m, 5H), 3.05-3.01 (m, 8H), 2.74-2.71 (m, 3H), 2.60-2.56 (m, 3H), 2.32-2.29 (m, 5H), 2.13-2.09 (m, 2H), 2.07-2.04 (m, 4H), 1.96-1.93 (m, 1H), 1.86-1.83 (m, 2H), 1.74-1.71 (m, 3H), 1.56-1.52 (m, 2H), 1.18-1.08 (m, 2H); $[M+H]^+$=991.3.

Example 182: 3-((4-(3-(4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)cyclobutyl)phenyl)amino)piperidine-2,6-dione

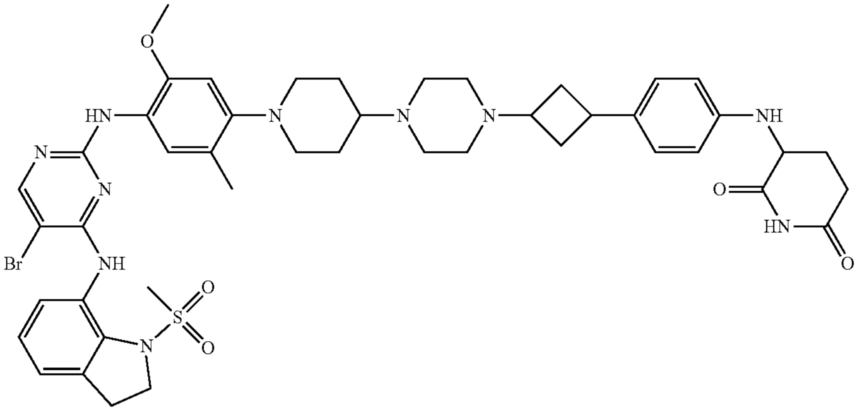 [SMILES: COc1cc(N2CCC(N3CCN(C4CC(c5ccc(NC6CCC(=O)NC6=O)cc5)C4)CC3)CC2)c(C)cc1Nc1ncc(Br)c(Nc2cccc3c2N(S(C)(=O)=O)CC3)n1]

The title compound was prepared in a procedure similar to that in Example 3.

$^1$H NMR (500 MHz, DMSO) δ 10.76 (s, 1H), 8.79 (s, 1H), 8.17 (s, 2H), 7.86 (s, 1H), 7.81 (d, J=7.3 Hz, 1H), 7.43 (s, 1H), 7.20-7.10 (m, 2H), 6.95 (d, J=8.4 Hz, 2H), 6.68 (s, 1H), 6.62 (t, J=9.4 Hz, 2H), 5.67 (d, J=7.6 Hz, 1H), 4.26 (d, J=11.8 Hz, 1H), 4.05 (t, J=7.6 Hz, 2H), 3.76 (s, 3H), 3.05-3.02 (m, 7H), 2.95 (s, 1H), 2.78-2.68 (m, 1H), 2.60-2.57 (m, 6H), 2.34-2.31 (m, 6H), 2.08 (m, 5H), 1.86-1.84 (m, 3H), 1.74-1.72 (m, 2H), 1.57-1.53 (m, 2H); $[M+H]^+$=927.2.

Example 183: 3-(4-(2-(4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)ethyl)phenyl)-3-methylpiperidine-2,6-dione

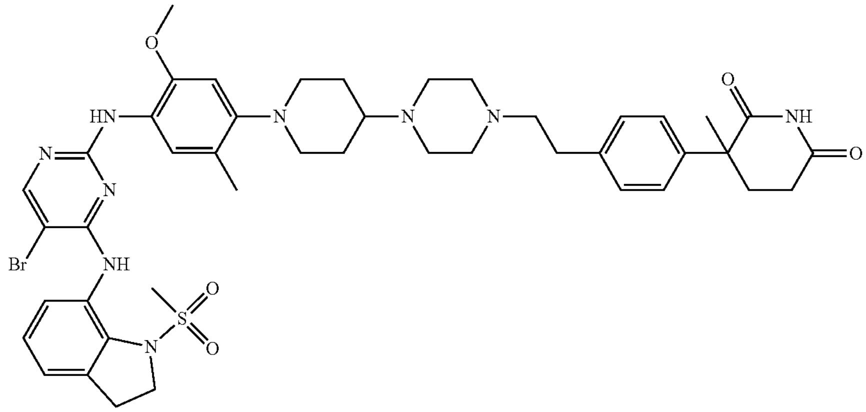 [SMILES: COc1cc(N2CCC(N3CCN(CCc4ccc(C5(C)CCC(=O)NC5=O)cc4)CC3)CC2)c(C)cc1Nc1ncc(Br)c(Nc2cccc3c2N(S(C)(=O)=O)CC3)n1]

The title compound was prepared in a procedure similar to that in Example 3.

$^1$H NMR (500 MHz, DMSO) δ 10.90 (s, 1H), 8.79 (s, 1H), 8.17 (s, 1H), 7.83-7.80 (m, 2H), 7.43 (s, 1H), 7.26-6.98 (m, 6H), 6.68 (s, 1H), 4.05 (t, J=7.3 Hz, 2H), 3.76 (s, 3H), 3.14-2.97 (m, 7H), 2.74-2.67 (m, 2H), 2.59-2.54 (m, 5H), 2.46-2.22 (m, 10H), 2.13-1.96 (m, 5H), 1.85-1.82 (m, 2H), 1.56-1.52 (m, 2H), 1.42 (s, 3H); $[M+H]^+$=900.2.

Example 184: 3-(4-(3-((4-(1-(4-((5-bromo-4-((1-(methylsulfonyl)indolin-7-yl)amino)pyrimidin-2-yl)amino)-5-methoxy-2-methylphenyl)piperidin-4-yl)piperazin-1-yl)methyl)azetidin-1-yl)-2,6-difluorophenyl)piperidine-2,6-dione

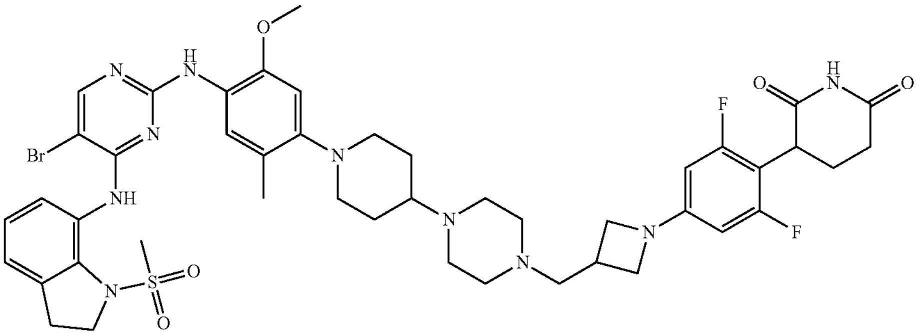 [SMILES: COc1cc(N2CCC(N3CCN(CC4CN(c5cc(F)c(C6CCC(=O)NC6=O)c(F)c5)C4)CC3)CC2)c(C)cc1Nc1ncc(Br)c(Nc2cccc3c2N(S(C)(=O)=O)CC3)n1]

The title compound was prepared in a procedure similar to that in Example 3.

$^1$H NMR (500 MHz, DMSO) δ 10.85 (s, 1H), 8.79 (s, 1H), 8.17 (s, 1H), 7.86 (s, 1H), 7.81 (d, J=7.6 Hz, 1H), 7.43 (s, 1H), 7.15 (t, J=8.3 Hz, 2H), 6.68 (s, 1H), 6.10 (d, J=11.6 Hz, 2H), 4.09-3.98 (m, 3H), 3.93 (t, J=7.5 Hz, 2H), 3.76 (s, 3H), 3.51-3.44 (m, 3H), 3.14-3.00 (m, 8H), 2.95-2.85 (m, 1H), 2.76-2.71 (m, 1H), 2.61-2.56 (m, 3H), 2.54-2.51 (m, 5H), 2.40 (s, 3H), 2.30-2.28 (m, 1H), 2.07-2.05 (m, 4H), 1.98-1.90 (m, 1H), 1.85-1.82 (m, 2H), 1.56-1.52 (m, 2H); $[M+H]^+$=963.2.

Example 185: 3-(4-(2-(4-(1-(4-((5-bromo-4-((1-(methylsulfonyl)indolin-7-yl)amino)pyrimidin-2-yl)amino)-5-methoxy-2-methylphenyl)piperidin-4-yl)-3-oxopiperazin-1-yl)ethyl)-2,6-difluorophenyl)piperidine-2,6-dione

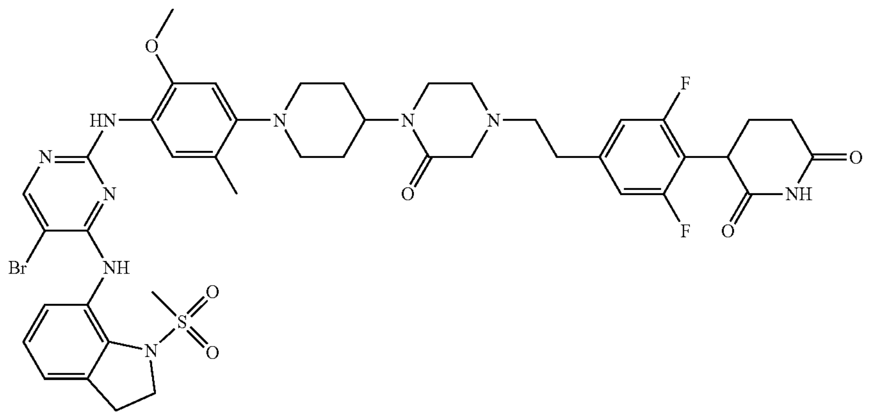 [SMILES: COc1cc(N2CCC(N3CCN(CCc4cc(F)c(C5CCC(=O)NC5=O)c(F)c4)CC3=O)CC2)c(C)cc1Nc1ncc(Br)c(Nc2cccc3c2N(S(C)(=O)=O)CC3)n1]

The title compound was prepared in a procedure similar to that in Example 3.

$^1$H NMR (500 MHz, DMSO) δ 10.95 (s, 1H), 8.79 (s, 1H), 8.18 (s, 1H), 7.88 (s, 1H), 7.81 (d, J=7.1 Hz, 1H), 7.44 (s, 1H), 7.15 (d, J=7.3 Hz, 2H), 7.05 (d, J=10.1 Hz, 2H), 6.73 (s, 1H), 4.38 (s, 1H), 4.20-4.18 (m, 1H), 4.05-4.01 (m, 2H), 3.77 (s, 3H), 3.29-3.23 (m, 3H), 3.09-3.04 (m, 9H), 2.85-2.68 (m, 7H), 2.62-2.58 (m, 2H), 2.18-2.04 (m, 4H), 2.00-1.95 (m, 1H), 1.87 (m, 2H), 1.61-1.58 (m, 2H); $[M+H]^+$=936.2.

Example 186: 3-(4-(4-(2-(4-(1-(4-((5-bromo-4-((1-(methylsulfonyl)indolin-7-yl)amino)pyrimidin-2-yl)amino)-5-methoxy-2-methylphenyl)piperidin-4-yl)-3-oxopiperazin-1-yl)ethyl)piperidin-1-yl)-2,6-difluorophenyl)piperidine-2,6-dione

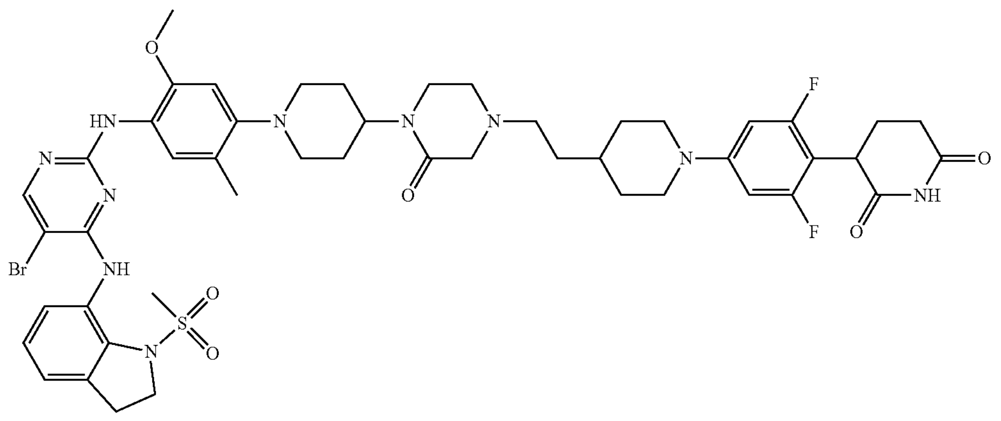 [SMILES: COc1cc(N2CCC(N3CCN(CCC4CCN(c5cc(F)c(C6CCC(=O)NC6=O)c(F)c5)CC4)CC3=O)CC2)c(C)cc1Nc1ncc(Br)c(Nc2cccc3c2N(S(C)(=O)=O)CC3)n1]

The title compound was prepared in a procedure similar to that in Example 3.

$^1$H NMR (500 MHz, DMSO) δ 10.86 (s, 1H), 8.79 (s, 1H), 8.18 (s, 1H), 7.88 (s, 1H), 7.80 (s, 1H), 7.44 (s, 1H), 7.15 (d, J=7.3 Hz, 2H), 6.73 (s, 1H), 6.61 (d, J=12.8 Hz, 2H), 4.38 (t, J=12.0 Hz, 1H), 4.05 (t, J=7.4 Hz, 3H), 3.81-3.67 (m, 5H), 3.29-3.22 (m, 3H), 3.14-2.97 (m, 9H), 2.72-2.68 (m, 5H), 2.66-2.59 (m, 2H), 2.42-2.33 (m, 2H), 2.09-2.05 (m, 4H), 1.86-1.82 (m, 3H), 1.72-1.68 (m, 2H), 1.61-1.56 (m, 2H), 1.50-1.46 (m, 1H), 1.40-1.37 (m, 2H), 1.18-1.09 (m, 2H); $[M+H]^+$=1019.3.

Example 187: 3-(4-(3-(4-(1-(4-((5-bromo-4-((1-(methylsulfonyl)indolin-7-yl)amino)pyrimidin-2-yl)amino)-5-methoxy-2-methylphenyl)piperidin-4-yl)piperazine-1-carbonyl)pyrrolidin-1-yl)-2,6-difluorophenyl)piperidine-2,6-dione

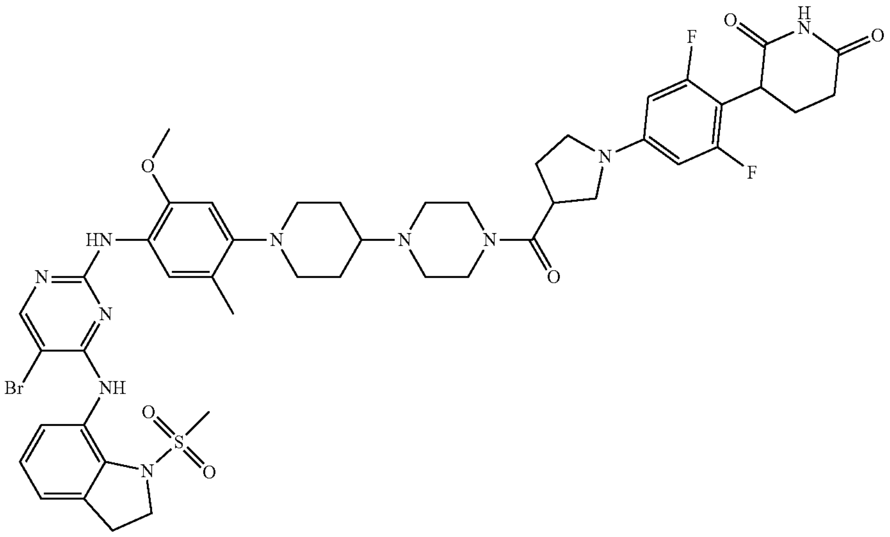 [SMILES: COc1cc(N2CCC(N3CCN(C(=O)C4CCN(c5cc(F)c(C6CCC(=O)NC6=O)c(F)c5)C4)CC3)CC2)c(C)cc1Nc1ncc(Br)c(Nc2cccc3c2N(S(C)(=O)=O)CC3)n1]

The title compound was prepared in a procedure similar to that in Example 11.

$^1$H NMR (500 MHz, DMSO) δ 10.84 (s, 1H), 8.79 (s, 1H), 8.18 (d, J=3.6 Hz, 1H), 7.87 (s, 1H), 7.82 (d, J=6.1 Hz, 1H), 7.44 (s, 1H), 7.15 (d, J=10.5 Hz, 2H), 6.68 (s, 1H), 6.23 (d, J=14.5 Hz, 2H), 4.10-3.98 (m, 3H), 3.76 (d, J=3.3 Hz, 3H), 3.62-3.40 (m, 7H), 3.32 (s, 3H), 3.26 (s, 2H), 3.07-3.01 (m, 7H), 2.78-2.74 (m, 1H), 2.62-2.56 (m, 4H), 2.39 (s, 1H), 2.12-2.09 (m, 6H), 1.96 (s, 1H), 1.86-1.82 (m, 2H), 1.60-1.56 (m, 2H); $[M+H]^+$=991.2.

Example 188: 3-(4-(3-(4-(1-(4-((5-bromo-4-((1-(methylsulfonyl)indolin-7-yl)amino)pyrimidin-2-yl)amino)-5-methoxy-2-methylphenyl)piperidin-4-yl)piperazine-1-carbonyl)azetidin-1-yl)-2,6-difluorophenyl)piperidine-2,6-dione

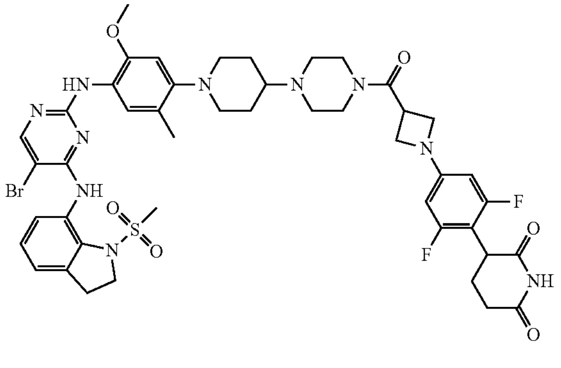 [SMILES: COc1cc(N2CCC(N3CCN(C(=O)C4CN(c5cc(F)c(C6CCC(=O)NC6=O)c(F)c5)C4)CC3)CC2)c(C)cc1Nc1ncc(Br)c(Nc2cccc3c2N(S(C)(=O)=O)CC3)n1]

The title compound was prepared in a procedure similar to that in Example 11.

$^1$H NMR (500 MHz, DMSO) δ 10.86 (s, 1H), 8.79 (s, 1H), 8.17 (s, 1H), 7.86 (s, 1H), 7.81 (d, J=6.9 Hz, 1H), 7.44 (s, 1H), 7.15 (s, 2H), 6.68 (s, 1H), 6.17 (d, J=11.1 Hz, 2H), 4.09-3.98 (m, 6H), 3.92 (s, 4H), 3.76 (s, 3H), 3.49 (s, 2H), 3.07-3.04 (m, 8H), 2.77-2.74 (m, 1H), 2.61-2.58 (m, 3H), 2.36-2.32 (m, 4H), 2.08-2.05 (m, 4H), 1.95-1.72 (m, 1H), 1.84-1.81 (m, 2H), 1.59-1.57 (m, 2H); $[M+H]^+$=977.2.

Example 192: 3-(4-(2-(4-(1-(4-((5-bromo-4-((4-ethyl-1-(methylsulfonyl)indolin-7-yl)amino)pyrimidin-2-yl)amino)-2-ethyl-5-methoxyphenyl)piperidin-4-yl)piperazin-1-yl)ethyl)-2,6-difluorophenyl)piperidine-2,6-dione

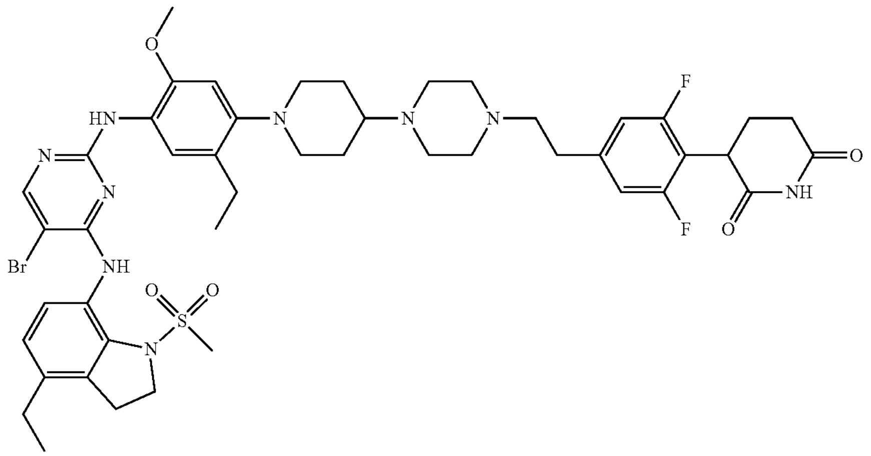 [SMILES: CCc1cc(Nc2ncc(Br)c(Nc3ccc(CC)c4c3N(S(C)(=O)=O)CC4)n2)c(OC)cc1N1CCC(N2CCN(CCc3cc(F)c(C4CCC(=O)NC4=O)c(F)c3)CC2)CC1]

The titled compound was prepared in a manner similar to that in Example 43.

$^1$H NMR (500 MHz, DMSO) δ 10.94 (s, 1H), 8.71 (s, 1H), 8.16 (s, 1H), 7.86 (s, 1H), 7.67 (d, J=8.2 Hz, 1H), 7.46 (s, 1H), 7.03 (d, J=10.1 Hz, 2H), 6.96 (d, J=8.3 Hz, 1H), 6.74 (s, 1H), 4.20 (dd, J=12.7, 4.9 Hz, 1H), 4.04 (t, J=7.3 Hz, 2H), 3.75 (s, 3H), 3.26-3.18 (m, 2H), 3.08-3.00 (m, 5H), 2.97 (d, J=11.1 Hz, 2H), 2.83-2.74 (m, 3H), 2.67 (t, J=11.0 Hz, 2H), 2.59-2.52 (m, 7H), 2.49-2.40 (m, 6H), 2.29 (t, J=11.2 Hz, 1H), 2.18-2.07 (m, 1H), 2.03-1.95 (m, 1H), 1.84 (d, J=11.5 Hz, 2H), 1.61-1.51 (m, 2H), 1.18 (t, J=7.6 Hz, 3H), 0.98 (t, J=7.4 Hz, 3H). $[M+H]^+$=964.7.

Example 193: 3-(4-(2-(4-(1-(4-((5-bromo-4-((4-cyclopropyl-1-(methylsulfonyl)indolin-7-yl)amino)pyrimidin-2-yl)amino)-2-ethyl-5-methoxyphenyl)piperidin-4-yl)piperazin-1-yl)ethyl)-2,6-difluorophenyl)piperidine-2,6-dione

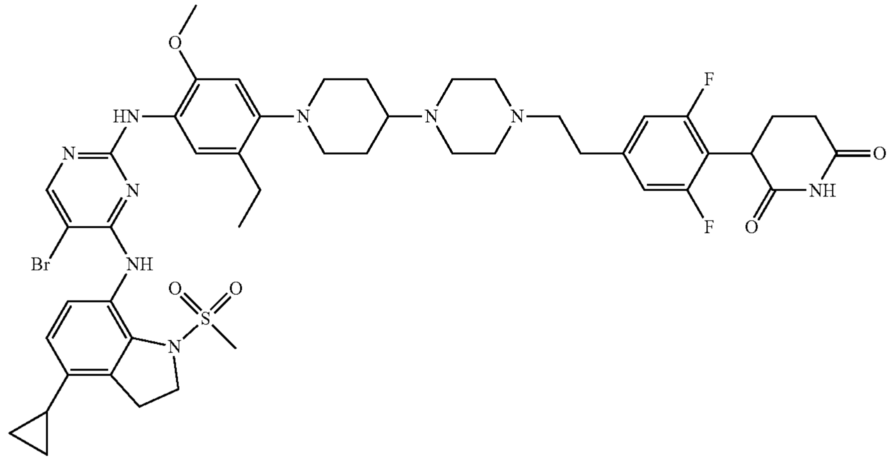 [SMILES: CCc1cc(Nc2ncc(Br)c(Nc3ccc(C4CC4)c4c3N(S(C)(=O)=O)CC4)n2)c(OC)cc1N1CCC(N2CCN(CCc3cc(F)c(C4CCC(=O)NC4=O)c(F)c3)CC2)CC1]

The titled compound was prepared in a manner similar to that in Example 43.

$^{1}$H NMR (500 MHz, DMSO) δ 10.94 (s, 1H), 8.70 (s, 1H), 8.15 (s, 1H), 7.88 (s, 1H), 7.62 (d, J=8.4 Hz, 1H), 7.41 (s, 1H), 7.03 (d, J=10.1 Hz, 2H), 6.74 (s, 1H), 6.61 (d, J=8.5 Hz, 1H), 4.20 (dd, J=12.6, 5.0 Hz, 1H), 4.06 (t, J=7.4 Hz, 2H), 3.75 (s, 3H), 3.29-3.22 (m, 2H), 3.14 (t, J=7.3 Hz, 2H), 3.04 (s, 3H), 2.98 (d, J=11.2 Hz, 2H), 2.85-2.73 (m, 3H), 2.67 (t, J=11.2 Hz, 2H), 2.59-2.52 (m, 7H), 2.49-2.39 (m, 6H), 2.31 (t, J=11.2 Hz, 1H), 2.12 (tt, J=17.0, 8.6 Hz, 1H), 2.04-1.97 (m, 1H), 1.84 (dd, J=17.7, 9.4 Hz, 3H), 1.63-1.53 (m, 2H), 1.02-0.92 (m, 5H), 0.65 (q, J=5.3 Hz, 2H). $[M+H]^+$=976.7.

Example 194: (R)-3-(4-((R)-3-(4-(1-(4-((5-bromo-4-((4-fluoro-1-(methylsulfonyl)indolin-7-yl)amino)pyrimidin-2-yl)amino)-2-ethyl-5-methoxyphenyl)piperidin-4-yl)piperazine-1-carbonyl)pyrrolidin-1-yl)-2,6-difluorophenyl)piperidine-2,6-dione

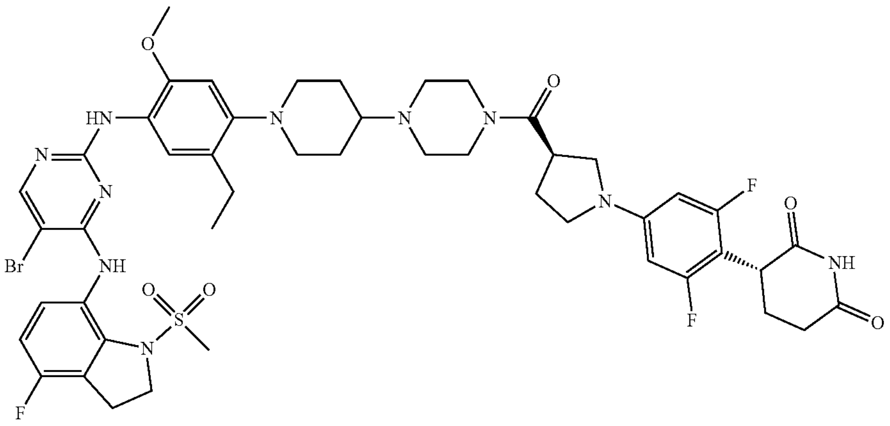 [SMILES: CCc1cc(Nc2ncc(Br)c(Nc3ccc(F)c4c3N(S(C)(=O)=O)CC4)n2)c(OC)cc1N1CCC(N2CCN(C(=O)[C@@H]3CCN(c4cc(F)c([C@H]5CCC(=O)NC5=O)c(F)c4)C3)CC2)CC1]

The titled compound (32 mg, 46%) was prepared in a manner similar to that in Example 11. $^{1}$H NMR (500 MHz, DMSO) δ 10.84 (s, 1H), 8.69 (s, 1H), 8.17 (s, 1H), 7.86 (s, 1H), 7.70 (s, 1H), 7.44 (s, 1H), 6.98 (t, J=8.5 Hz, 1H), 6.74 (s, 1H), 6.23 (d, J=12.0 Hz, 2H), 4.10 (t, J=7.5 Hz, 2H), 4.02 (dd, J=12.5, 5.0 Hz, 1H), 3.76 (s, 3H), 3.58-3.42 (m, 6H), 3.38-3.33 (m, 2H), 3.30-3.20 (m, 3H), 3.17-3.08 (m, 5H), 2.98 (d, J=11.0 Hz, 2H), 2.82-2.74 (m, 1H), 2.72-2.63 (m, 2H), 2.60-2.55 (m, 2H), 2.49-2.43 (m, 3H), 2.38 (t, J=10.5 Hz, 1H), 2.20-2.04 (m, 3H), 1.97-1.91 (m, 1H), 1.85 (d, J=11.1 Hz, 2H), 1.65-1.53 (m, 2H), 0.98 (t, J=7.4 Hz, 3H). $[M+H]^+$=1023.60.

Example 195: (R)-3-(4-(2-(4-(1-(4-((5-bromo-4-((4-fluoro-1-(methylsulfonyl)indolin-7-yl)amino)pyrimidin-2-yl)amino)-2-ethyl-5-methoxyphenyl)piperidin-4-yl)piperazin-1-yl)ethyl)-2,6-difluorophenyl)piperidine-2,6-dione

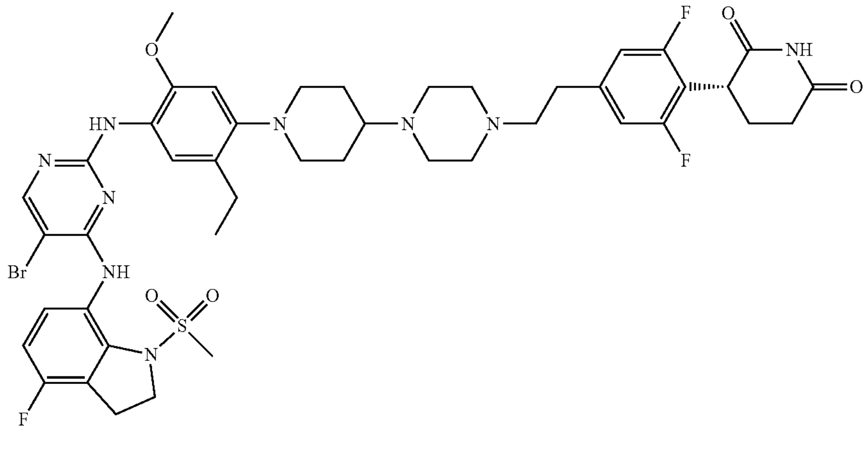 [SMILES: CCc1cc(Nc2ncc(Br)c(Nc3ccc(F)c4c3N(S(C)(=O)=O)CC4)n2)c(OC)cc1N1CCC(N2CCN(CCc3cc(F)c([C@H]4CCC(=O)NC4=O)c(F)c3)CC2)CC1]

The titled compound (29 mg, 40%) was prepared in a manner similar to that in Example 3. $^1$H NMR (500 MHz, DMSO) δ 10.95 (s, 1H), 8.69 (s, 1H), 8.17 (s, 1H), 7.86 (s, 1H), 7.71 (dd, J=8.0, 4.0 Hz, 1H), 7.44 (s, 1H), 7.06-6.95 (m, 3H), 6.74 (s, 1H), 4.20 (dd, J=12.6, 5.0 Hz, 1H), 4.10 (t, J=7.4 Hz, 2H), 3.76 (s, 3H), 3.18-3.09 (m, 5H), 2.97 (d, J=11.0 Hz, 2H), 2.85-2.74 (m, 3H), 2.66 (t, J=11.0 Hz, 2H), 2.60-2.52 (m, 6H), 2.49-2.40 (m, 5H), 2.34-2.26 (m, 1H), 2.17-2.07 (m, 1H), 2.03-1.96 (m, 1H), 1.85 (d, J=11.5 Hz, 2H), 1.56 (dd, J=20.0, 11.5 Hz, 2H), 0.97 (t, J=7.5 Hz, 3H). [M+H]$^+$=954.60.

Example 196: (R)-3-(4-(3-(4-(1-(4-((5-bromo-4-((1-(methylsulfonyl)-4-(trifluoromethyl)indolin-7-yl)amino)pyrimidin-2-yl)amino)-2-ethyl-5-methoxy-phenyl)piperidin-4-yl)piperazine-1-carbonyl)azetidin-1-yl)-2,6-difluorophenyl)piperidine-2,6-dione

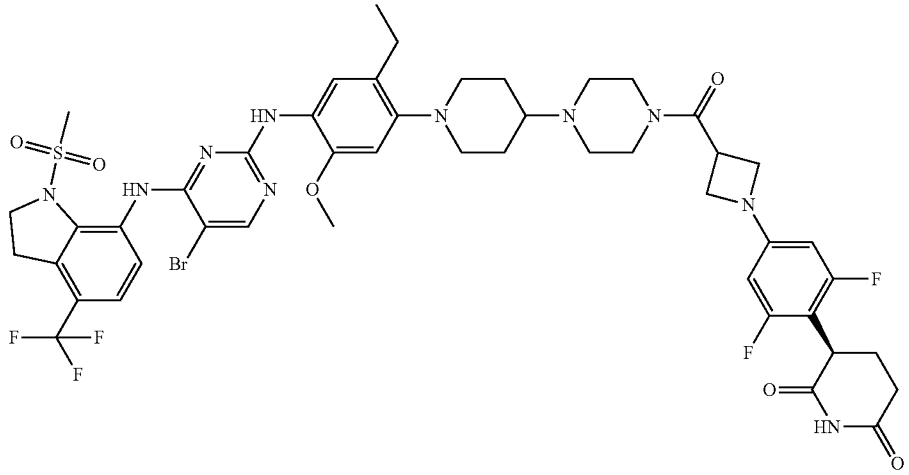 [SMILES: CCc1cc(Nc2ncc(Br)c(Nc3ccc(C(F)(F)F)c4c3N(S(C)(=O)=O)CC4)n2)c(OC)cc1N1CCC(N2CCN(C(=O)C3CN(c4cc(F)c([C@H]5CCC(=O)NC5=O)c(F)c4)C3)CC2)CC1]

The titled compound was prepared in a manner similar to that in Example 11. $^1$H NMR (500 MHz, DMSO-$d_6$) δ 10.86 (s, 1H), 8.90 (s, 1H), 8.24 (s, 1H), 8.20 (s, 1H), 7.99 (s, 1H), 7.36-7.26 (m, 2H), 6.78 (s, 1H), 6.17 (d, J=10 Hz, 2H), 4.13 (t, J=10 Hz, 2H), 4.06-4.01 (m, 3H), 3.95-3.90 (m, 2H), 3.86-3.81 (m, 1H), 3.75 (s, 3H), 3.53-3.46 (m, 2H), 3.31-3.29 (m, 1H), 3.22 (t, J=10 Hz, 2H), 3.14 (s, 3H), 3.02-2.97 (m, 2H), 2.82-2.66 (m, 3H), 2.62-2.51 (m, 5H), 2.49-2.45 (m, 2H), 2.44-2.35 (m, 1H), 2.12-2.03 (m, 1H), 1.96-1.81 (m, 3H), 1.66-1.55 (m, 2H), 1.00 (t, J=10 Hz, 3H); [M+H]$^+$=1059.7.

Example 197: (R)-3-(4-((R)-3-(4-(1-(4-((5-bromo-4-((1-(methylsulfonyl)-4-(trifluoromethyl)indolin-7-yl)amino)pyrimidin-2-yl)amino)-2-ethyl-5-methoxy-phenyl)piperidin-4-yl)piperazine-1-carbonyl)pyrrolidin-1-yl)-2,6-difluorophenyl)piperidine-2,6-dione

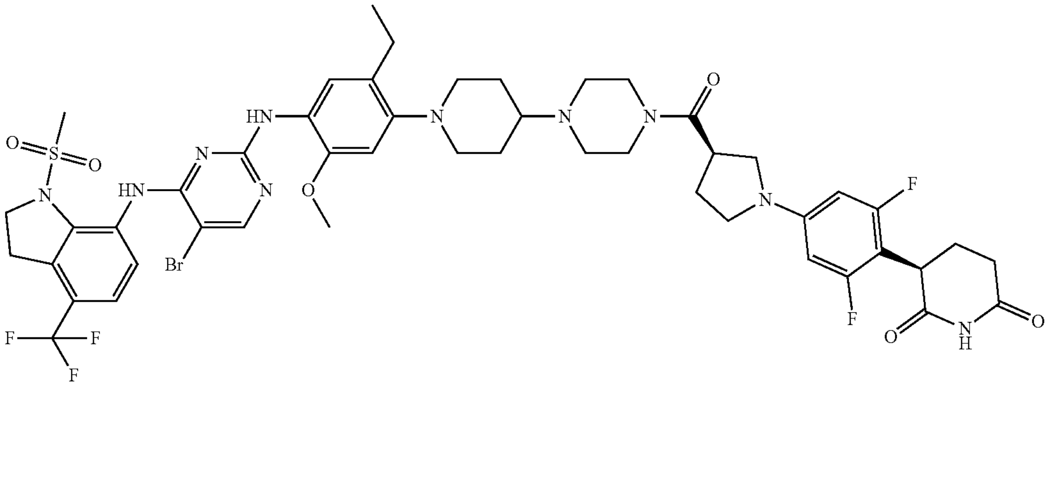 [SMILES: CCc1cc(Nc2ncc(Br)c(Nc3ccc(C(F)(F)F)c4c3N(S(C)(=O)=O)CC4)n2)c(OC)cc1N1CCC(N2CCN(C(=O)[C@@H]3CCN(c4cc(F)c([C@H]5CCC(=O)NC5=O)c(F)c4)C3)CC2)CC1]

The titled compound was prepared in a manner similar to that in Example 11. $^1$H NMR (500 MHz, DMSO-$d_6$) δ 10.84 (s, 1H), 8.90 (s, 1H), 8.24 (s, 1H), 8.20 (s, 1H), 7.99 (s, 1H), 7.36-7.26 (m, 2H), 6.78 (s, 1H), 6.23 (d, J=10 Hz, 2H), 4.13 (t, J=10 Hz, 2H), 4.02 (dd, J=15 Hz, 1H), 3.75 (s, 3H), 3.61-3.41 (m, 6H), 3.36-3.34 (m, 2H), 3.32-3.20 (m, 3H), 3.14 (s, 3H), 3.04-2.97 (m, 2H), 2.82-2.66 (m, 3H), 2.62-2.51 (m, 5H), 2.49-2.45 (m, 2H), 2.44-2.35 (m, 1H), 2.21-2.03 (m, 3H), 1.98-1.82 (m, 3H), 1.67-1.57 (m, 2H), 1.00 (t, J=10 Hz, 3H); [M+H]$^+$=1073.7.

Example 198: (R)-3-(4-((R)-3-(4-(1-(4-((5-bromo-4-((4-ethyl-1-(methylsulfonyl)indolin-7-yl)amino)pyrimidin-2-yl)amino)-2-ethyl-5-methoxyphenyl)piperidin-4-yl)piperazine-1-carbonyl)pyrrolidin-1-yl)-2,6-difluorophenyl)piperidine-2,6-dione

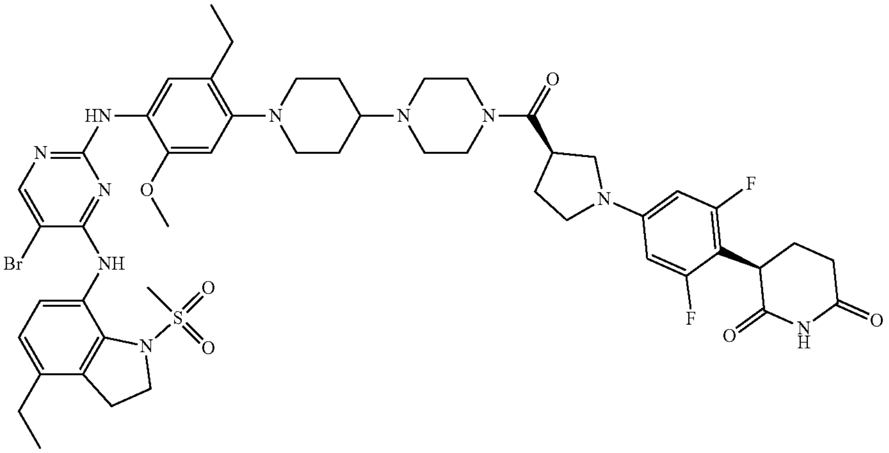 [SMILES: CCc1cc(Nc2ncc(Br)c(Nc3ccc(CC)c4c3N(S(C)(=O)=O)CC4)n2)c(OC)cc1N1CCC(N2CCN(C(=O)[C@@H]3CCN(c4cc(F)c([C@H]5CCC(=O)NC5=O)c(F)c4)C3)CC2)CC1]

The titled compound was prepared in a manner similar to that in Example 43.

$^1$H NMR (500 MHz, DMSO) δ 10.84 (s, 1H), 8.71 (s, 1H), 8.16 (s, 1H), 7.87 (s, 1H), 7.67 (d, J=8.2 Hz, 1H), 7.46 (s, 1H), 6.96 (d, J=8.4 Hz, 1H), 6.75 (s, 1H), 6.23 (d, J=12.2 Hz, 2H), 4.08-3.99 (m, 3H), 3.76 (s, 3H), 3.59-3.42 (m, 8H), 3.30-3.21 (m, 4H), 3.08-2.96 (m, 7H), 2.78 (ddd, J=17.6, 13.6, 5.5 Hz, 1H), 2.68 (t, J=11.1 Hz, 2H), 2.61-2.53 (m, 4H), 2.49-2.45 (m, 2H), 2.39 (t, J=11.2 Hz, 1H), 2.16 (dt, J=12.3, 6.1 Hz, 1H), 2.12-2.03 (m, 2H), 1.98-1.91 (m, 1H), 1.85 (d, J=10.7 Hz, 2H), 1.65-1.53 (m, 2H), 1.18 (t, J=7.6 Hz, 3H), 0.98 (t, J=7.4 Hz, 3H). [M+H]$^+$=1033.7.

Example 200: (R)-3-(4-(2-(4-(1-(4-((5-bromo-4-((4-(dimethylamino)-1-(methylsulfonyl)indolin-7-yl)amino)pyrimidin-2-yl)amino)-2-ethyl-5-methoxyphenyl)piperidin-4-yl)piperazin-1-yl)ethyl)-2,6-difluorophenyl)piperidine-2,6-dione

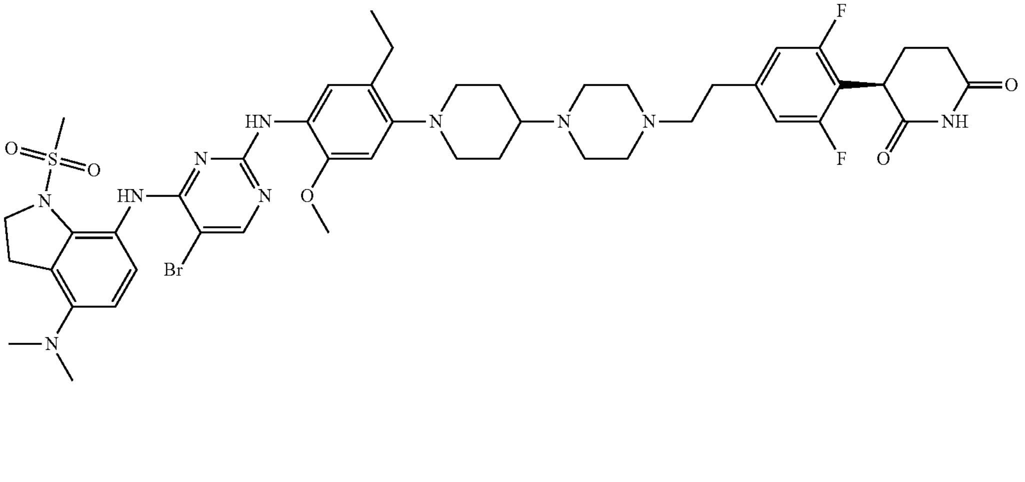 [SMILES: CCc1cc(Nc2ncc(Br)c(Nc3ccc(N(C)C)c4c3N(S(C)(=O)=O)CC4)n2)c(OC)cc1N1CCC(N2CCN(CCc3cc(F)c([C@H]4CCC(=O)NC4=O)c(F)c3)CC2)CC1]

The titled compound was prepared in a manner similar to that in Example 3. $^1H$ NMR (500 MHz, DMSO-$d_6$) δ 10.95 (s, 1H), 8.53 (s, 1H), 8.12 (s, 1H), 7.81 (s, 1H), 7.60 (d, J=8.5 Hz, 1H), 7.49 (s, 1H), 7.03 (d, J=10 Hz, 2H), 6.73 (s, 1H), 6.64 (d, J=8.5 Hz, 1H), 4.20 (dd, J=13 Hz, 1H), 4.00 (t, J=7 Hz, 2H), 3.76 (s, 3H), 3.08-3.01 (m, 5H), 3.00-2.94 (m, 2H), 2.86-2.51 (m, 18H), 2.49-2.26 (m, 7H), 2.17-2.07 (m, 1H), 2.03-1.95 (m, 1H), 1.88-1.81 (m, 2H), 1.61-1.51 (m, 2H), 0.98 (t, J=7 Hz, 3H); $[M+H]^+$=979.0.

Example 203: (R)-3-(4-(2-(4-(1-(4-((5-bromo-4-((4-ethyl-1-(methylsulfonyl)indolin-7-yl)amino)pyrimidin-2-yl)amino)-5-ethoxy-2-ethylphenyl)piperidin-4-yl)piperazin-1-yl)ethyl)-2,6-difluorophenyl)piperidine-2,6-dione

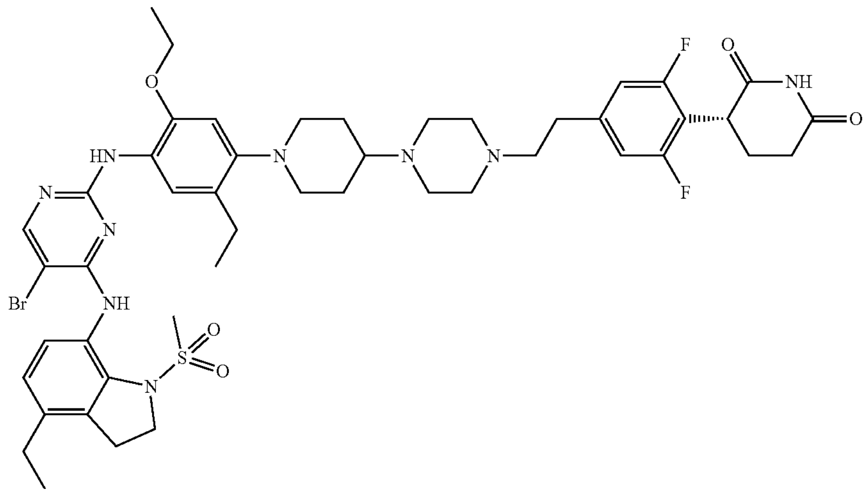 [SMILES: CCOc1cc(N2CCC(N3CCN(CCc4cc(F)c([C@H]5CCC(=O)NC5=O)c(F)c4)CC3)CC2)c(CC)cc1Nc1ncc(Br)c(Nc2ccc(CC)c3c2N(S(C)(=O)=O)CC3)n1]

The titled compound was prepared in a manner similar to that in Example 3. 6'H NMR (500 MHz, d-DMSO) δ 10.95 (s, 1H), 8.73 (s, 1H), 8.17 (s, 1H), 7.79 (s, 1H), 7.65 (d, J=8.5 Hz, 1H), 7.51 (s, 1H), 7.02 (d, J=10.0 Hz, 2H), 6.97 (d, J=8.5 Hz, 1H), 6.71 (s, 1H), 4.20 (dd, J=13.0, 5.5 Hz, 1H), 4.06-3.98 (m, 4H), 3.08-2.99 (m, 5H), 2.95 (d, J=11.0 Hz, 2H), 2.83-2.74 (m, 3H), 2.64 (t, J=11.0 Hz, 2H), 2.60-2.41 (m, 15H), 2.29 (t, J=11.0 Hz, 1H), 2.14-2.11 (m, 1H), 2.03-1.95 (m, 1H), 1.84 (d, J=11.0 Hz, 2H), 1.61-1.49 (m, 2H), 1.27 (t, J=7.0 Hz, 3H), 1.18 (t, J=7.5 Hz, 3H), 0.96 (t, J=7.5 Hz, 3H). $[M+H]^+$=978.2.

Cell Degradation 1

Cell Treatment

On day 1, $H_{1975}$ cells are seeded at 30000 cells/well at a volume of 90 μl/well in cell culture medium [RPMI1640 (Gibco, Cat #72400-047), 10% heat-inactive FBS, 1% PS(Gibco, Cat #10378)] in Corning 96 well plate (Cat #3599), $H_{1975}$ cells are treated with compounds diluted in 0.2% DMSO on day 2, dilution is done according to the following protocol: (1) make 1000× stock solution in DMSO from 10 mM by 4-fold dilution, total 8 doses were included; (2) make 10× solution in cell culture medium by transferring 1 μl 1000× stock solution into 99 μl medium; (3) 10 μl of 10× solution is added to cells and incubate for 16 h.

HTFR Assay

After 16 h treatment, add 100 μl 1×lysis buffer to each well; seal the plate and incubate 1 hour at room temperature on a plate shaker; Once the cells are lysed, 16 μL of cell lysate are transferred to a PE 384-well HTRF detection plate; 4 μL of pre-mixed HTRF antibodies are added to each well; Cover the plate with a plate sealer, spin 1000 rpm for 1 min, Incubate overnight at room temperature; Read on BMG PheraStar with HTRF protocol (337 nm-665 nm-620 nm).

The inhibition (degradation) percentage of the compound was calculated by the following equation: Inhibition percentage of Compound=100−100× (Signal−low control)/(High control−low control), wherein signal=each test compound group Low control=only lysis buffer without cells, indicating that EGFR is completely degraded;

High control=Cell group with added DMSO and without compound, indicating microplate readings without EGFR degradation;

Dmax is the maximum percentage of inhibition (degradation).

The $IC_{50}$ ($DC_{50}$) value of a compound can be obtained by fitting the following equation $$Y=\text{Bottom}+(\text{TOP}-\text{Bottom})/(1+((IC_{50}/X)^\wedge\text{hillslope}))$$

Wherein, X and Y are known values, and $IC_{50}$, Hillslope, Top and Bottom are the parameters obtained by fitting with software. Y is the inhibition percentage (calculated from the equation), X is the concentration of the compound; $IC_{50}$ is the concentration of the compound when the 50% inhibition is reached. The smaller the $IC_{50}$ value is, the stronger the inhibitory ability of the compound is. Vice versa, the higher the $IC_{50}$ value is, the weaker the ability the inhibitory ability of the compound is; Hillslope represents the slope of the fitted curve, generally around 1*; Bottom represents the minimum value of the curve obtained by data fitting, which is generally 0%±20%; Top represents the maximum value of the curve obtained by data fitting, which is generally 100%±20%. The experimental data were fitted by calculating and analyzing with Dotmatics data analysis software.

TABLE 1

| Degradation result | | | | | | | |
|---|---|---|---|---|---|---|---|
| Example | $DC_{50}$ (nM) | Example | $DC_{50}$ (nM) | Example | $DC_{50}$ (nM) | Example | $DC_{50}$ (nM) |
| 1 | 9.9 | 2 | 36.9 | 3 | 9.5 | 4 | 15.5 |
| 5 | 9 | 6 | 7.4 | 8 | 9.1 | 9 | 19.1 |
| 10 | 9.3 | 11 | 23.7 | 12 | 12.4 | 13 | 11.05 |
| 14 | 27.1 | 15 | 10 | 16 | 33.7 | 17 | 9.6 |
| 18 | 14.1 | 19 | 6.03 | 20 | 9.7 | 21 | 38.4 |
| 27 | 10.6 | 34 | 7 | 35 | 7.2 | 36 | 15.5 |
| 37 | 3.8 | 38 | 9.8 | 39 | 12.1 | 40 | 10.5 |
| 41 | 20.7 | 42 | 13.5 | 43 | 49.1 | 44 | 10.9 |
| 45 | 2.3 | 46 | 23.2 | 47 | 21.4 | 48 | >10000 |
| 49 | >10000 | 50 | 7.5 | 51 | 19.5 | 52 | 7 |
| 53 | 2.6 | 54 | 8.9 | 55 | 9.6 | 56 | 13.5 |
| 58 | 2.8 | 59 | 2.7 | 60 | 4.9 | 61 | 5.7 |
| 62 | 4.4 | 63 | 3.9 | 64 | 6.1 | 66 | 7.1 |
| 67 | 13.8 | 68 | 3.7 | 69 | 10.8 | 73 | 3.4 |
| 74 | 4.7 | 75 | 3.9 | 76 | 3.4 | 77 | 2.3 |
| 78 | 5.5 | 79 | 6 | 80 | 5.5 | 81 | 12.2 |
| 82 | 3.2 | 83 | 3.2 | 84 | >10000 | 85 | 3.0 |
| 86 | 1.8 | 87 | 3.5 | 88 | 4.2 | 90 | 96.4 |
| 91 | 3.5 | 154 | 16 | 159 | 3.0 | 163 | 3.0 |
| 168 | 7.0 | | | | | | |

The foregoing examples and description of certain embodiments should be taken as illustrating, rather than as limiting the present invention as defined by the claims. As will be readily appreciated, numerous variations and combinations of the features set forth above can be utilized without departing from the present invention as set forth in the claims. All such variations are intended to be included within the scope of the present invention. All references cited are incorporated herein by reference in their entireties.

It is to be understood that, if any prior art publication is referred to herein, such reference does not constitute an admission that the publication forms a part of the common general knowledge in the art in any country.

Cell Degradation 2

Cell Treatment

On day 1, HCC827 cells are seeded at 20000 cells/well at a volume of 90 μl/well in cell culture medium [RPMI1640 (Gibco, Cat #72400-047), 10% heat-inactive FBS, 1% PS(Gibco, Cat #10378)] in Corning 96 well plate (Cat #3599), HCC827 cells are treated with compounds diluted in 0.2% DMSO on day 2, dilution is done according to the following protocol: (1) make 1000× stock solution in DMSO from 10 mM by 4-fold dilution, total 8 doses were included; (2) make 10× solution in cell culture medium by transferring 1 μl 1000× stock solution into 99 μl medium; (3) 10 μl of 10× solution is added to cells and incubate for 16 h.

HTFR Assay

After 16 h treatment, add 100 μl 1×lysis buffer to each well; seal the plate and incubate 1 hour at room temperature on a plate shaker; Once the cells are lysed, 16 μl diluted (2 μL to 14 μl 1× lysisi buffer) cell lysate are transferred to a PE 384-well HTRF detection plate; 4 μL of pre-mixed HTRF antibodies are added to each well; Cover the plate with a plate sealer, spin 1000 rpm for 1 min, Incubate overnight at room temperature; Read on BMG PheraStar with HTRF protocol (337 nm-665 nm-620 nm).

The inhibition (degradation) percentage of the compound was calculated by the following equation: Inhibition percentage of Compound=100-100× (Signal-low control)/(High control-low control), wherein signal=each test compound group

- Low control=only lysis buffer without cells, indicating that EGFR is completely degraded;
- High control=Cell group with added DMSO and without compound, indicating microplate readings without EGFR degradation;
- Dmax is the maximum percentage of inhibition (degradation).

The $IC_{50}$ ($DC_{50}$) value of a compound can be obtained by fitting the following equation $$Y=\text{Bottom}+(\text{TOP}-\text{Bottom})/(1+((IC_{50}/X)\hat{}\,\text{hillslope}))$$

Wherein, X and Y are known values, and $IC_{50}$, Hillslope, Top and Bottom are the parameters obtained by fitting with software. Y is the inhibition percentage (calculated from the equation), X is the concentration of the compound; $IC_{50}$ is the concentration of the compound when the 50% inhibition is reached. The smaller the $IC_{50}$ value is, the stronger the inhibitory ability of the compound is. Vice versa, the higher the $IC_{50}$ value is, the weaker the ability the inhibitory ability of the compound is; Hillslope represents the slope of the fitted curve, generally around 1*; Bottom represents the minimum value of the curve obtained by data fitting, which is generally 0%±20%; Top represents the maximum value of the curve obtained by data fitting, which is generally 100%±20%. The experimental data were fitted by calculating and analyzing with Dotmatics data analysis software.

TABLE 2

| Degradation result | | | | | | | |
|---|---|---|---|---|---|---|---|
| Examplem | $DC_{50}$ (nM) | Example | $DC_{50}$ (nM) | Example | $DC_{50}$ (nM) | Example | $DC_{50}$ (nM) |
| 1 | 24.7 | 2 | 33.4 | 3 | 19.8 | 4 | >10000.0 |
| 5 | 62.6 | 6 | 29.3 | 8 | 12.7 | 9 | 16.7 |
| 10 | >10000.0 | 11 | 123 | 12 | 33.5 | 13 | 29.3 |

TABLE 2-continued

| Degradation result | | | | | | | |
|---|---|---|---|---|---|---|---|
| Examplem | $DC_{50}$ (nM) | Example | $DC_{50}$ (nM) | Example | $DC_{50}$ (nM) | Example | $DC_{50}$ (nM) |
| 14 | 92.2 | 15 | 9.2 | 16 | 32.6 | 17 | 30.8 |
| 18 | 10.8 | 19 | 10.8 | 20 | 14.7 | 21 | 113.3 |
| 27 | 33.6 | 34 | 6.7 | 35 | 8.4 | 36 | 8.6 |
| 37 | 3.5 | 38 | 9.7 | 39 | 13.6 | 40 | 8.2 |
| 41 | 16.7 | 42 | 4.9 | 43 | 11.1 | 44 | 4.6 |
| 45 | 6.7 | 46 | 32.2 | 47 | 13.8 | 48 | 51.8 |
| 49 | 138.3 | 50 | 36.9 | 51 | 12.4 | 52 | 3.5 |
| 53 | 3.7 | 54 | 8.9 | 55 | 11.9 | 56 | 5.8 |
| 58 | 17.7 | 59 | 3.1 | 60 | 14.6 | 61 | 19.4 |
| 62 | 22.1 | 63 | >10000.0 | 64 | 155.7 | 66 | 18 |
| 67 | 3.5 | 68 | 17.6 | 69 | 29.8 | 73 | 1173.9 |
| 74 | >10000.0 | 75 | >10000.0 | 76 | 3.3 | 77 | 1.7 |
| 78 | 4.6 | 79 | 5.5 | 80 | 4.3 | 81 | 3.4 |
| 82 | 2.8 | 83 | 3.0 | 84 | 1977.2 | 85 | 2.9 |
| 86 | 2.7 | 87 | 3.1 | 88 | 2.7 | 90 | 40.2 |
| 91 | 6.4 | 154 | 6 | 159 | 2.0 | 163 | 20 |
| 168 | 2.0 | 172 | 2.0 | | | | |

Cell Degradation 3

Cell Treatment

BaF3 cells are seeded at 100000 cells/well at a volume of 30 μl/well in cell culture medium [RPMI1640(Gibco, phenol red free, Cat #11835-030), 10% heat-inactive FBS, 1% PS(Gibco, Cat #10378)] in Corning 96 well plate (Cat #3799). BaF3 cells are treated with compounds diluted in 0.2% DMSO, dilution is done according to the following protocol: (1) make 500× stock solution in DMSO from 5 mM by 4-fold dilution, total 8 doses were included; (2) make 2× solution in cell culture medium by transferring 0.5 μl 500× stock solution into 125 μl medium; (3) 30 μl of 2× solution is added to cells and incubate for 16 h.

HTFR Assay

After 16 h treatment, add 20 μl 4×lysis buffer to each well; seal the plate and incubate 1 hour at room temperature on a plate shaker; Once the cells are lysed, 16 μL of cell lysate are transferred to a PE 384-well HTRF detection plate (for triple mutant cells, the lysate were diluted by the qual volume 1×lysis buffer before transfer); 4 μL of pre-mixed HTRF antibodies are added to each well; Cover the plate with a plate sealer, spin 1000 rpm for 1 min, Incubate overnight at room temperature; Read on BMG PheraStar with HTRF protocol (337 nm-665 nm-620 nm).

The inhibition (degradation) percentage of the compound was calculated by the following equation: Inhibition percentage of Compound=100-100× (Signal-low control)/(High control-low control), wherein signal=each test compound group Low control=only lysis buffer without cells, indicating that EGFR is completely degraded;

High control=Cell group with added DMSO and without compound, indicating microplate readings without EGFR degradation;

Dmax is the maximum percentage of inhibition (degradation).

The $IC_{50}$ ($DC_{50}$) value of a compound can be obtained by fitting the following equation $$Y=\text{Bottom}+(\text{TOP}-\text{Bottom})/(1+((IC_{50}/X)^\wedge\text{hillslope}))$$

Wherein, X and Y are known values, and $IC_{50}$, Hillslope, Top and Bottom are the parameters obtained by fitting with software. Y is the inhibition percentage (calculated from the equation), X is the concentration of the compound; $IC_{50}$ is the concentration of the compound when the 50% inhibition is reached. The smaller the $IC_{50}$ value is, the stronger the inhibitory ability of the compound is. Vice versa, the higher the $IC_{50}$ value is, the weaker the ability the inhibitory ability of the compound is; Hillslope represents the slope of the fitted curve, generally around 1*; Bottom represents the minimum value of the curve obtained by data fitting, which is generally 0%±20%; Top represents the maximum value of the curve obtained by data fitting, which is generally 100%±20%. The experimental data were fitted by calculating and analyzing with Dotmatics data analysis software.

TABLE 3

| Degradation result | | |
|---|---|---|
| Example | $DC_{50}$ (nM) DTC | $DC_{50}$ (nM) LTC |
| 3 | 11.6 | 19.9 |
| 8 | 13.4 | 8.4 |
| 15 | 35.8 | 68.3 |
| 19 | 16.7 | 24.2 |
| 34 | 38.2 | 276.1 |
| 35 | 48.1 | 202.8 |
| 36 | 26.3 | 42.6 |
| 37 | 16.7 | 43.1 |
| 38 | 176.3 | 230.2 |
| 39 | 33.7 | 157.2 |
| 45 | 9.9 | 17.3 |
| 53 | 21.8 | 35.7 |
| 54 | 120.5 | 442.8 |
| 56 | 23.6 | 232.7 |
| 62 | 3.0 | 4.7 |
| 67 | 11.7 | 15.7 |
| 68 | 3.0 | 4.4 |
| 76 | 4.8 | 8.0 |
| 77 | 1.8 | 2.7 |
| 79 | 49.6 | 84.6 |
| 80 | 6.5 | 12.2 |
| 82 | 3.5 | 15.1 |
| 83 | 5.9 | 14.6 |
| 85 | 1.8 | 2.8 |
| 86 | 13.0 | 16.2 |
| 87 | 2.4 | 16.5 |
| 88 | 15.6 | 43.3 |
| 91 | 14.9 | 39.9 |
| 151 | 14 | 17 |
| 152 | 66 | 27 |
| 154 | 11 | 13 |
| 155 | 19 | 56 |
| 156 | 21 | 33 |
| 157 | 300 | 396 |
| 158 | 19 | 41 |
| 159 | 11 | 19 |
| 160 | 150 | 162 |

TABLE 3-continued

| Degradation result | | |
|---|---|---|
| Example | $DC_{50}$ (nM) DTC | $DC_{50}$ (nM) LTC |
| 162 | 78 | >10000 |
| 163 | 49 | 40 |
| 164 | 52 | 60 |
| 165 | 91 | 100 |
| 166 | 175 | 247 |
| 167 | 225 | >10000 |
| 168 | 14 | 25 |
| 169 | 39 | 57 |
| 170 | 8 | 23 |
| 171 | 4 | 9 |
| 172 | 4 | 9 |
| 173 | 15 | 27 |
| 174 | 30 | 69 |
| 175 | 17 | 31 |
| 176 | 94 | 65 |
| 177 | >10000 | 123 |
| 178 | 8 | 23 |
| 180 | 14 | 30 |
| 181 | 43 | 64 |
| 182 | 77 | 70 |
| 184 | 27 | 33 |
| 185 | 4 | 18 |
| 186 | 6 | 27 |
| 187 | 14 | 19 |
| 188 | 6 | 15 |
| 192 | | 65 |
| 193 | | 74 |
| 194 | | 29 |
| 195 | | 24 |
| 196 | | 71 |
| 197 | | 83 |
| 198 | | 34 |
| 200 | | 513 |
| 203 | | 83 |

The foregoing examples and description of certain embodiments should be taken as illustrating, rather than as limiting the present invention as defined by the claims. As will be readily appreciated, numerous variations and combinations of the features set forth above can be utilized without departing from the present invention as set forth in the claims. All such variations are intended to be included within the scope of the present invention. All references cited are incorporated herein by reference in their entirety.

It is to be understood that, if any prior art publication is referred to herein, such reference does not constitute an admission that the publication forms a part of the common general knowledge in the art in any country.

What is claimed is:

1. A compound of Formula (I):

(I)

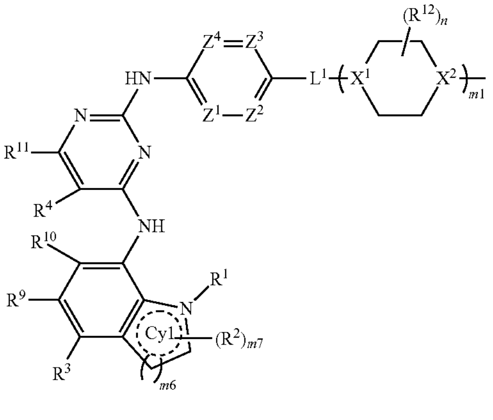

-continued

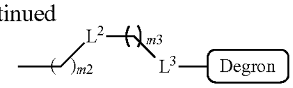

or an N-oxide thereof, or a pharmaceutically acceptable salt thereof, or a stereoisomer thereof, or a tautomer or a prodrug thereof, wherein:

Cy1 is an aromatic ring or non-aromatic ring;

$R^1$ is —$S(O)R^{1a}$, —$S(O)_2R^{1a}$, —$C(O)R^{1a}$ or —$P(O)R^{1a}R^{1b}$, wherein $R^{1a}$ and $R^{1b}$ are each independently —$C_{1-8}$alkyl, —$C_{2-8}$alkenyl, —$C_{2-8}$alkynyl, cycloalkyl, heterocyclyl, aryl, heteroaryl, —CN, —$OR^{1d}$, —$CH_2CONR^{1d}R^{1e}$, —$CH_2CH_2CONR^{1d}R^{1e}$, —$CH_2CH_2CH_2CONR^{1d}R^{1e}$, —$NR^{1d}R^{1e}$, —$CH_2NR^{1d}R^{1e}$, —$CH_2CH_2NR^{1d}R^{1e}$, —$CH_2CH_2CH_2NR^{1d}R^{1e}$ or —$NR^{1d}COR^{1e}$, wherein each of said —$C_{1-8}$alkyl, —$C_{2-8}$alkenyl, —$C_{2-8}$alkynyl, cycloalkyl, heterocyclyl, aryl and heteroaryl is optionally substituted with at least one substituent $R^{1f}$;

$R^{1d}$ and $R^{1e}$ are each independently hydrogen, —$C_{1-8}$alkyl, —$C_{1-8}$haloalkyl, —$C_{2-8}$alkenyl, —$C_{2-8}$alkynyl, cycloalkyl, heterocyclyl, aryl, or heteroaryl; or $R^{1d}$ and $R^{1e}$ together with the atom(s) to which they are attached, form a 3- to 12-membered ring, said ring comprising 0, 1 or 2 additional heteroatom(s) independently selected from nitrogen, oxygen and optionally oxidized sulfur as ring member(s), said ring is optionally substituted with at least one substituent $R^{1f}$;

$R^{1f}$, at each of its occurrences, is independently hydrogen, halogen, hydroxyl, —$C_{1-8}$alkyl, —$C_{1-8}$haloalkyl, —$C_{2-8}$alkenyl, —$C_{2-8}$alkynyl, cycloalkyl, heterocyclyl, aryl, heteroaryl, oxo, —CN, —$OR^{1g}$, —$COR^{1g}$, —$CO_2R^{1g}$, —$CONR^{1g}R^{1h}$, —$NR^{1g}R^{1h}$, —$NR^{1g}COR^{1h}$, or —$NR^{1g}CO_2R^{1h}$, wherein each of said cycloalkyl, heterocyclyl, aryl and heteroaryl is optionally substituted with 1, 2 or 3 substituents selected from halogen and —$C_{1-8}$alkyl;

$R^{1g}$ and $R^{1h}$ are each independently hydrogen, halogen, hydroxyl, —$C_{1-8}$alkyl, $C_{1-8}$alkoxy-$C_{1-8}$alkyl-, —$C_{1-8}$haloalkyl, —$C_{2-8}$alkenyl, —$C_{2-8}$alkynyl, cycloalkyl, heterocyclyl, aryl or heteroaryl;

$R^2$, at each of their occurrences, is hydrogen, halogen, oxo, —$C_{1-8}$alkyl, cycloalkyl, heterocyclyl, —$C_6$-$C_{12}$aryl, 5- to 12-membered heteroaryl, —CN, —$OR^{2a}$, —$COR^{2a}$, —$CO_2R^{2a}$, —$CONR^{2a}R^{2b}$, —$NR^{2a}R^{2b}$, —$NR^{2a}COR^{2b}$ or —$NR^{2a}CO_2R^{2b}$, wherein each of said —$C_{1-8}$alkyl, cycloalkyl, heterocyclyl, aryl and heteroaryl is optionally substituted with at least one substituent $R^{2c}$; or when m≥2, two $R^2$ together with the atom(s) to which they are attached, form a 3-to 12-membered ring, said ring comprising 0, 1 or 2 heteroatom(s) independently selected from nitrogen, oxygen, and optionally oxidized sulfur as ring member(s), said ring is optionally substituted with at least one substituent $R^{2c}$;

$R^{2a}$ and $R^{2b}$ are each independently hydrogen, —$C_{1-8}$alkyl, —$C_{2-8}$alkenyl, —$C_{2-8}$alkynyl, $C_{1-8}$alkoxy-$C_{1-8}$alkyl-, cycloalkyl, heterocyclyl, aryl or heteroaryl, wherein each of said —$C_{1-8}$alkyl, —$C_{2-8}$alkenyl, —$C_{2-8}$alkynyl, $C_{1-8}$alkoxy-$C_{1-8}$alkyl-, cycloalkyl, heterocyclyl, aryl and heteroaryl is optionally substituted with at least one substituent $R^{2c}$;

$R^{2c}$, at each of its occurrence, is independently halogen, hydroxyl, —$C_{1-8}$alkyl, -halo$C_{1-8}$alkyl, —$C_{2-8}$alkenyl, —$C_{2-8}$alkynyl, cycloalkyl, heterocyclyl, aryl, heteroaryl, oxo, —CN, —$OR^{2d}$, —$COR^{2d}$, —$CO_2R^{2d}$, —$CONR^{2d}R^{2e}$, —$NR^{2d}R^{2e}$, —$NR^{2d}COR^{2e}$, or —$NR^{2d}CO_2R^{2e}$;

$R^{2d}$ and $R^{2e}$ are each independently hydrogen, —$C_{1-8}$alkyl, -halo$C_{1-8}$alkyl, —$C_{2-8}$alkenyl, —$C_{2-8}$alkynyl, cycloalkyl, heterocyclyl, aryl or heteroaryl;

$R^3$, $R^9$ and $R^{10}$ are each independently hydrogen, halogen, —$C_{1-8}$alkyl, —$NR^{3a}R^{3b}$, —$OR^{3a}$, cycloalkyl, heterocyclyl, aryl, heteroaryl, —CN, —$COR^{3a}$ or —$CO_2R^{3a}$ wherein each of said —$C_{1-8}$alkyl, cycloalkyl, heterocyclyl, aryl, and heteroaryl is optionally substituted with at least one substituent $R^{3c}$;

$R^{3a}$ and $R^{3b}$ are each independently hydrogen, —$C_{1-8}$alkyl, —$C_{2-8}$alkenyl, —$C_{2-8}$alkynyl, $C_{1-8}$alkoxy-$C_{1-8}$alkyl-, cycloalkyl, heterocyclyl, aryl or heteroaryl, wherein each of said —$C_{1-8}$alkyl, —$C_{2-8}$alkenyl, —$C_{2-8}$alkynyl, cycloalkyl, heterocyclyl, aryl and heteroaryl is optionally substituted with at least one substituent $R^{3d}$; or $R^{3c}$ and $R^{3d}$ are each independently halogen, hydroxy, —$C_{1-8}$alkyl, -halo$C_{1-8}$alkyl, —$C_{1-8}$alkoxy, —$C_{2-8}$alkenyl, —$C_{2-8}$alkynyl, cycloalkyl, heterocyclyl, aryl or heteroaryl;

$R^4$ and $R^{11}$ are each independently hydrogen, halogen, —$C_{1-8}$alkyl, —$C_{2-8}$alkynyl, —$C_{1-8}$alkoxy, cycloalkyl, heterocyclyl, aryl, heteroaryl, —CN, —$OR^{4a}$, —$NR^{4a}R^{4b}$, —$NR^{4a}COR^{4b}$, or $CONR^{4a}R^{4b}$, wherein each of said —$C_{1-8}$alkyl, —$C_{2-8}$alkynyl, —$C_{1-8}$alkoxy, cycloalkyl, heterocyclyl, aryl, and heteroaryl is optionally substituted with at least one $R^{4c}$, or $R^{4a}$ and $R^{4b}$ are each independently hydrogen, —$C_{1-8}$alkyl, -halo$C_{1-8}$alkyl, —$C_{2-8}$alkenyl, —$C_{2-8}$alkynyl, cycloalkyl, heterocyclyl, aryl, or heteroaryl; or $R^4$ and $R^{11}$, together with the atom(s) to which they are attached, form a 3- to 12-membered ring, said ring comprising 0, 1 or 2 heteroatom(s) independently selected from nitrogen, oxygen, and optionally oxidized sulfur as ring member(s), said ring is optionally substituted with at least one substituent $R^{4e}$;

$R^{4e}$ is halogen, —$C_{1-8}$alkyl, -halo$C_{1-8}$alkyl, cycloalkyl, heterocyclyl, aryl, heteroaryl, oxo, —CN, —$OR^{4c}$, —$SO_2R^{4c}$, —$SO_2NR^{4c}R^{4d}$, —$COR^{4c}$, —$CO_2R^{4c}$, —$CONR^{4c}R^{4d}$; $NR^{4c}R^{4d}$, —$NR^{4c}COR^{4d}$, —$NR^{4c}CO_2R^{4d}$, or —$NR^{4c}SO_2R^{4d}$;

$R^{4c}$ and $R^{4d}$ are each independently hydrogen, —$C_{1-8}$alkyl, -halo$C_{1-8}$alkyl, —$C_{2-8}$alkenyl, —$C_{2-8}$alkynyl, cycloalkyl, heterocyclyl, aryl, or heteroaryl;

$R^{12}$ is independently hydrogen, halogen, —$C_{1-8}$alkyl, —$NR^{12a}R^{12b}$, —$OR^{12a}$, cycloalkyl, heterocyclyl, aryl, heteroaryl, oxo or —CN, wherein each of said —$C_{1-8}$alkyl, cycloalkyl, heterocyclyl, aryl, or heteroaryl is optionally substituted with at least one substituent $R^{12c}$; or two $R^{12}$ together with the atom(s) to which they are attached, form a 3- to 12-membered ring, said ring comprising 0, 1 or 2 heteroatom(s) independently selected from nitrogen, oxygen, and optionally oxidized sulfur as ring member(s), said ring is optionally substituted with at least one substituent $R^{12c}$;

$R^{12a}$ and $R^{12b}$ are each independently hydrogen, —$C_{1-8}$alkyl, —$C_{2-8}$alkenyl, —$C_{2-8}$alkynyl, cycloalkyl, heterocyclyl, aryl or heteroaryl, wherein each of said —$C_{1-8}$alkyl, —$C_{2-8}$alkenyl, —$C_{2-8}$alkynyl, cycloalkyl, heterocyclyl, aryl and heteroaryl is optionally substituted with at least one substituent $R^{12d}$; or $R^{12c}$ and $R^{12d}$ are each independently halogen, hydroxy, —$C_{1-8}$alkyl, -halo$C_{1-8}$alkyl, —$C_{1-8}$alkoxy, —$C_{2-8}$alkenyl, —$C_{2-8}$alkynyl, cycloalkyl, heterocyclyl, aryl or heteroaryl;

$Z^1$, $Z^2$, $Z^3$ and $Z^4$ are each independently —$CR^Z$, or N;

$R^Z$, at each of its occurrences, is independently hydrogen, halogen, —$C_{1-8}$alkyl, —$NR^{Za}R^{Zb}$, —$OR^{Za}$, cycloalkyl, heterocyclyl, aryl, heteroaryl, or CN, wherein each of said —$C_{1-8}$alkyl, cycloalkyl, heterocyclyl, aryl, and heteroaryl is optionally substituted with at least one $R^{Zc}$;

or two $R^Z$, when attached to adjacent carbon atoms of the ring, together with the two carbon atoms to which they are attached, form a 3- to 12-membered ring comprising 0, 1 or 2 heteroatom(s) independently selected from nitrogen, oxygen and optionally oxidized sulfur as ring member(s), said ring is optionally substituted with at least one substituent $R^{Ze}$;

$R^{Za}$ and $R^{Zb}$ are each independently hydrogen, —$C_{1-8}$alkyl, —$C_{2-8}$alkenyl, —$C_{2-8}$alkynyl, cycloalkyl, heterocyclyl, aryl, or heteroaryl, wherein each of said —$C_{1-8}$alkyl, —$C_{2-8}$alkenyl, —$C_{2-8}$alkynyl, cycloalkyl, heterocyclyl, aryl, or heteroaryl is optionally substituted with at least one substituent $R^{Zd}$;

$R^{Zc}$ is independently halogen, hydroxy, —$C_{1-8}$alkyl, -halo$C_{1-8}$alkyl, —$C_{1-8}$alkoxy, —$C_{2-8}$alkenyl, —$C_{2-8}$alkynyl, cycloalkyl, heterocyclyl, aryl, or heteroaryl; or two $R^{Zc}$, together with the atom(s) to which they are attached, form a 3- to 12-membered ring, said ring comprising 0, 1 or 2 heteroatom(s) independently selected from nitrogen, oxygen, and optionally oxidized sulfur as ring member(s), said ring is optionally substituted with at least one substituent $R^{Zd}$;

$R^{Zd}$ is independently halogen, hydroxy, —$C_{1-8}$alkyl, -halo$C_{1-8}$alkyl, —$C_{1-8}$alkoxy, —$C_{2-8}$alkenyl, —$C_{2-8}$alkynyl, cycloalkyl, heterocyclyl, aryl, or heteroaryl;

$L^1$ is a single bond, —O—, —$SO_2$—, —C(O)—, —$NR^{L1a}$—, —$C_3$-$C_8$cycloalkylene-, $*^{L1}$—O—$C_{1-8}$alkylene-$**^{L1}$, $*^{L1}$—$C_{1-8}$alkylene-O—$**^{L1}$, $*^{L1}$—$SO_2$—$C_{1-8}$alkylene-$**^{L1}$, $*^{L1}$—$C_{1-8}$alkylene-$SO_2$—$**^{L1}$, $*^{L1}$—C(O)—$C_{1-8}$alkylene-$**^{L1}$, $*^{L1}$—$C_{1-8}$alkylene-C(O)—$**^{L1}$, $*^{L1}$—$NR^{L1a}$—$C_{1-8}$alkylene-$**^{L1}$, $*^{L1}$—$C_{1-8}$alkylene-$NR^{L1a}$—$**^{L1}$, $*^{L1}$—$NR^{L1a}$C(O)—$**^{L1}$, $*^{L1}$—C(O)$NR^{L1a}$, —$**^{L1}$—$C_{1-8}$alkylene-, —$C_{2-8}$alkenylene-, —$C_{2-8}$alkynylene-, —$[O(CR^{L1a}R^{L1b})_{m4}]_{m5}$—,

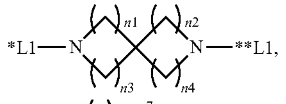

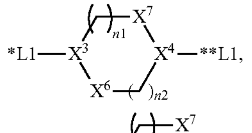

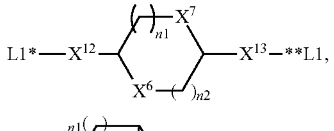

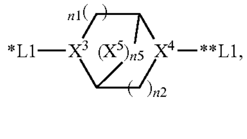
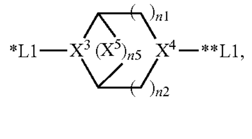

-continued
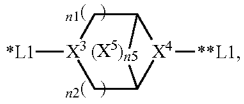
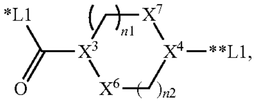
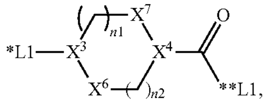
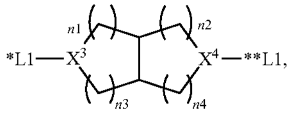
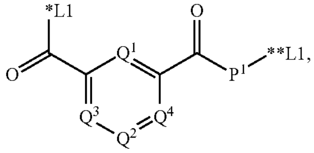
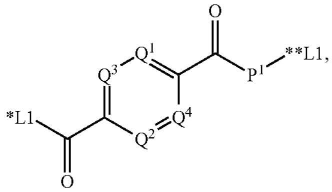
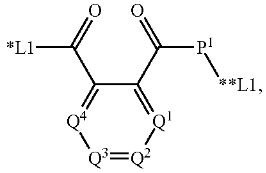
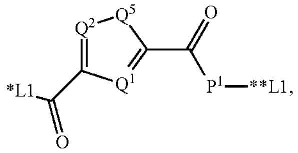
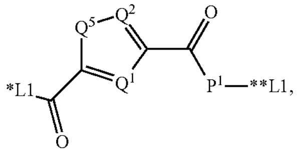
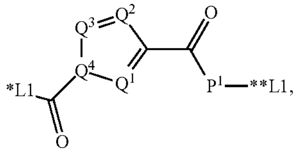
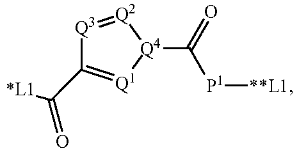
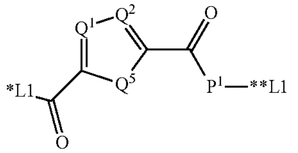 or
-continued
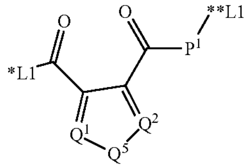
each of said —$C_3$-$C_8$cycloalkylene-, $*^{L1}$—O—$C_{1-8}$alkylene-$**^{L1}$, $*^{L1}$—$C_{1-8}$alkylene-O—$**^{L1}$, $*^{L1}$—S—$C_{1-8}$alkylene-$**^{L1}$, $*^{L1}$—$SO_2$—$C_{1-8}$alkylene-$**^{L1}$, $*^{L1}$—$C_{1-8}$alkylene-$SO_2$—$**^{L1}$, $*^{L1}$—$C_{1-8}$alkylene-$**^{L1}$, $*^{L1}$—$C_{1-8}$alkylene-CO—$**^{L1}$, $*^{L1}$—$NR^{L1a}$—$C_{1-8}$alkylene-$**^{L1}$, $*^{L1}$—$C_{1-8}$alkylene-$NR^{L1a}$—$**^{L1}$, —$C_{1-8}$alkylene-, —$C_{2-8}$alkenylene-, —$C_{2-8}$alkynylene-,
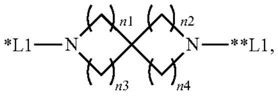
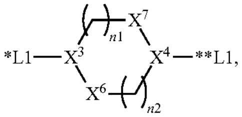
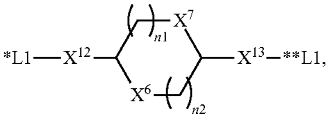
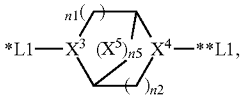
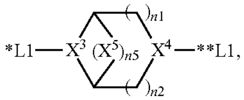
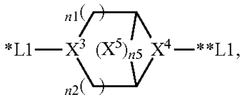
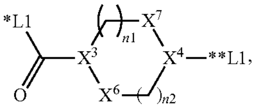
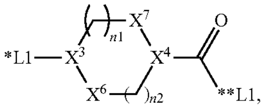
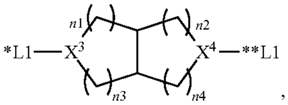,
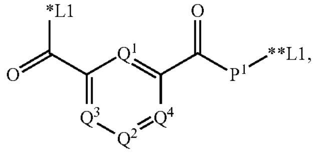
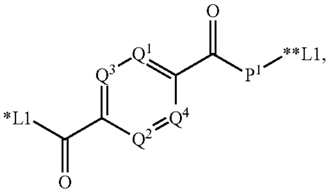
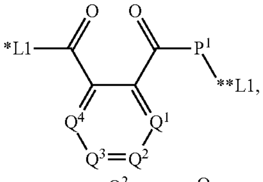
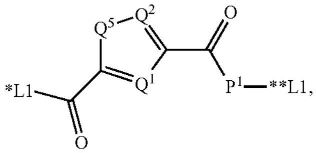

-continued

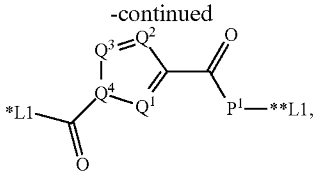

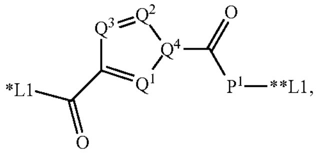

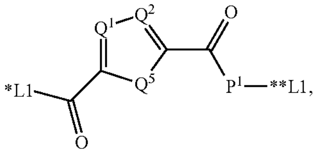

and

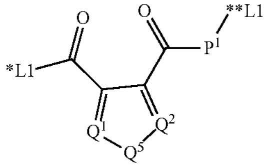

are optionally substituted with at least one $R^{L1c}$; wherein $*^{L1}$ refers to the position attached to the

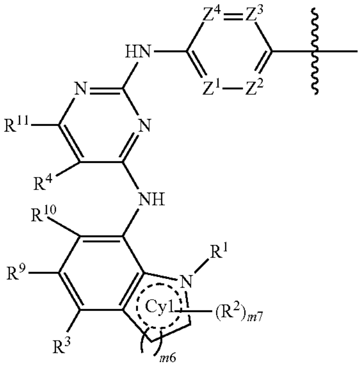

moiety, and $**^{L1}$ refers to the position attached to the

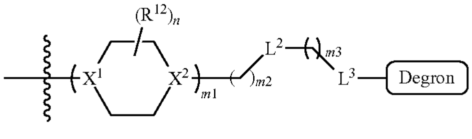

moiety;

$R^{L1a}$ and $R^{L1b}$ are each independently hydrogen, $—C_{1-8}$alkyl, $—C_{2-8}$alkenyl, $—C_{2-8}$alkynyl, cycloalkyl, heterocyclyl, aryl or heteroaryl, wherein each of said $—C_{1-8}$alkyl, $—C_{2-8}$alkenyl, $—C_{2-8}$alkynyl, cycloalkyl, heterocyclyl, aryl and heteroaryl is optionally substituted with at least one substituent $R^{L1d}$;

each of said $R^{L1c}$ and $R^{L1d}$ is independently halogen, hydroxy, $—C_{1-8}$alkyl, -halo$C_{1-8}$alkyl, $—C_{1-8}$alkoxy, $—C_{2-8}$alkenyl, $—C_{2-8}$alkynyl, cycloalkyl, heterocyclyl, aryl or heteroaryl;

$L_2$ is a single bond, —O—, $—SO_2—$, —CO—, $—NR^{L2a}—$, $—C_3$-$C_8$cycloalkylene-$*^{L2}$—O—$C_{1-8}$alkylene-$**^{L2}$, $*^{L2}—C_{1-8}$alkylene-O—$**^{L2}$, $*^{L2}—SO_2—C_{1-8}$alkylene-$**^{L2}$, $*^{L2}—C_{1-8}$alkylene-$SO_2—**^{L2}$, $*^{L2}—C_{1-8}$alkylene-$**^{L2}$, $*^{L2}—C_{1-8}$alkylene-CO—$**^{L2}$, $*^{L2}—NR^{L2a}—C_{1-8}$alkylene-$**^{L2}$$*^{L2}—C_{1-8}$alkylene-$NR^{L2a}—**^{L2}$, $*^{L2}—NR^{L2a}C(O)—**^{L2}$, $*^{L2}$-C(O)$NR^{L2a}—**^{L2}$, $—C_{1-8}$alkylene-, $—C_{2-8}$alkenylene-, $—C_{2-8}$alkynylene-, $—[O(CR^{L2a}R^{L2b})_{m4}]_{m5}—$,

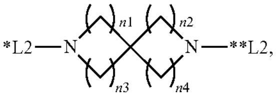

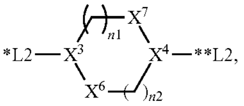

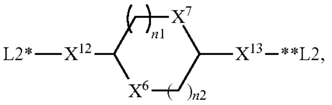

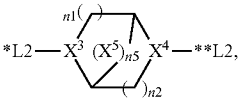

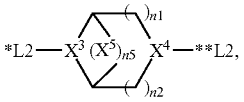

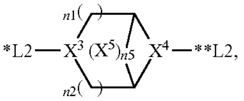

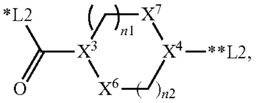

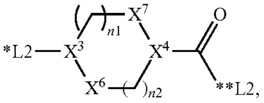

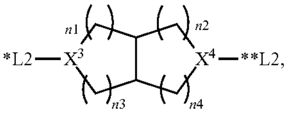

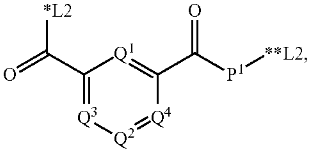

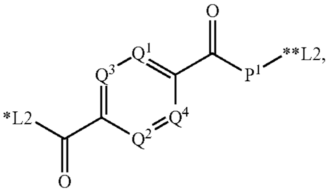

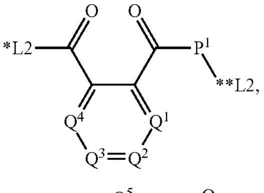

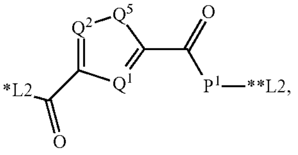

-continued

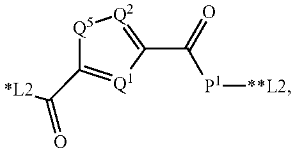

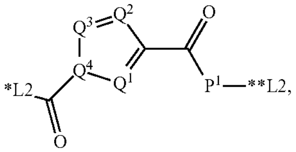

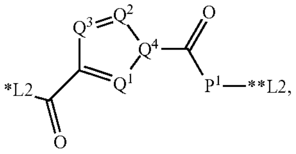

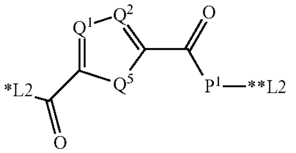

or

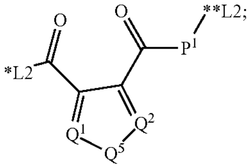

each of said $-C_3$-$C_8$cycloalkylene-, $*^{L2}$—O—$C_{1-8}$alkylene-$**^{L2}$, $*^{L2}$—$C_{1-8}$alkylene-O—$**^{L2}$, $*^{L2}$—$SO_2$—$C_{1-8}$alkylene-$**^{L2}$, $*^{L2}$—$C_{1-8}$alkylene-$SO_2$—$**^{L2}$, $*^{L2}$—$C_{1-8}$alkylene-$**^{L2}$, $*^{L2}$—$C_{1-8}$alkylene-CO—$**^{L2}$, $*^{L2}$—$NR^{L2a}$—$C_{1-8}$alkylene-$**^{L2}$, $*^{L2}$—$C_{1-8}$alkylene-$NR^{L2a}$—$**^{L2}$, —$C_{1-8}$alkylene-, —$C_{2-8}$alkenylene-, —$C_{2-8}$alkynylene-,

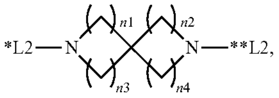

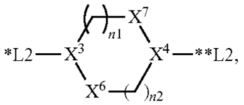

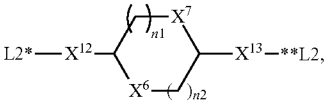

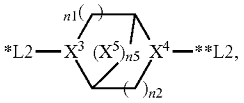

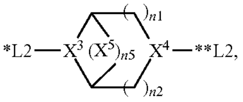

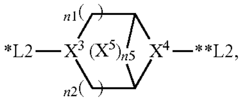

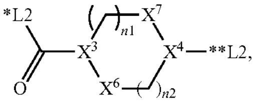

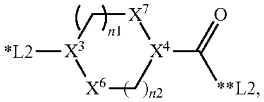

-continued

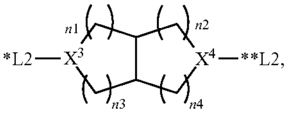

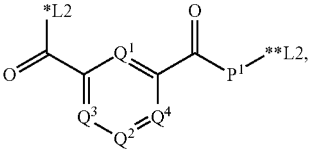

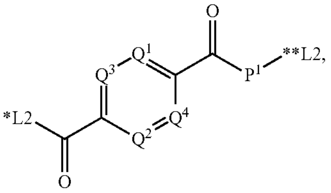

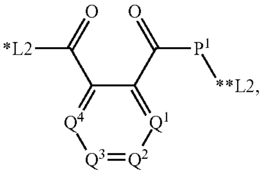

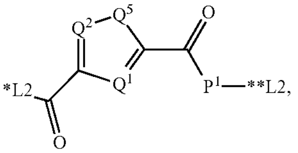

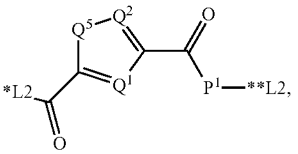

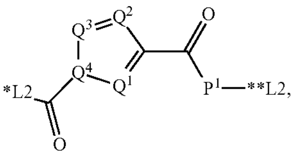

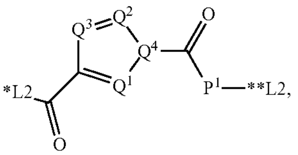

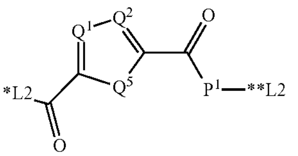

and

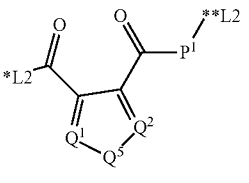

are optionally substituted with at least one substituent $R^{L2c}$;

wherein $*^{L2}$ refers to the position attached to the

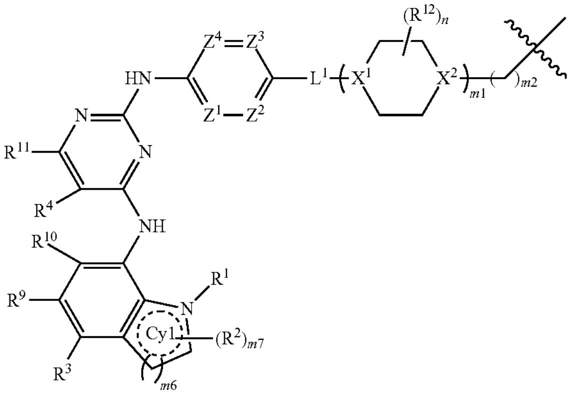

moiety, and $**^{L2}$ refers to the position attached to the

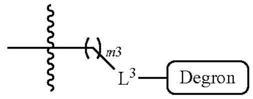

moiety;

$R^{L2a}$ and $R^{L2b}$ are each independently hydrogen, —$C_{1-8}$alkyl, —$C_{2-8}$alkenyl, —$C_{2-8}$alkynyl, cycloalkyl, heterocyclyl, aryl or heteroaryl, wherein each of said —$C_{1-8}$alkyl, —$C_{2-8}$alkenyl, —$C_{2-8}$alkynyl, cycloalkyl, heterocyclyl, aryl and heteroaryl is optionally substituted with at least one substituent $R^{L2d}$;

each of said $R^{L2c}$ and $R^{L2d}$ is independently halogen, hydroxy, —$C_{1-8}$alkyl, -halo$C_{1-8}$alkyl, —$C_{1-8}$alkoxy, —$C_{2-8}$alkenyl, —$C_{2-8}$alkynyl, cycloalkyl, heterocyclyl, aryl or heteroaryl;

$L^3$ is a single bond, —O—, —$SO_2$—, —CO—, —$NR^{L3a}$—, —$C_3$-$C_8$cycloalkylene-$*^{L3}$—O—$C_{1-8}$alkylene-$**^{L3}$, $*^{L3}$—$C_{1-8}$alkylene-O—$**^{L3}$, $*^{L3}$—$SO_2$—$C_{1-8}$alkylene-$**^{L3}$, $*^{L3}$—$C_{1-8}$alkylene-$SO_2$—$**^{L3}$, $*^{L3}$—CO—$C_{1-8}$alkylene-$**^{L3}$, $*^{L3}$—$C_{1-8}$alkylene-CO—$**^{L3}$, $*^{L3}$—$NR^{L3a}$—$C_{1-8}$alkylene-$**^{L3}$, $*^{L3}$—$C_{1-8}$alkylene-$NR^{L3a}$—$**^{L3}$, $*^{L3}NR^{L3a}C(O)$—$**^{L3}$, $*^{L3}$-C(O)$NR^{L3a}$—$**^{L3}$—$C_{1-8}$ alkylene-, —$C_{2-8}$alkenylene-, —$C_{2-8}$alkynylene-, —[O($CR^{L3a}R^{L3b}$)$_{m4}$]$_{m5}$-,

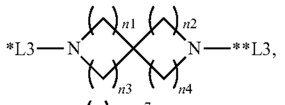

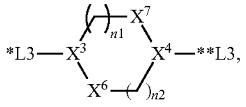

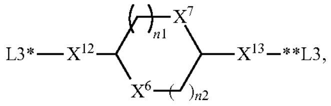

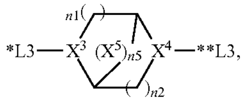

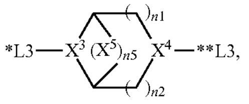

-continued

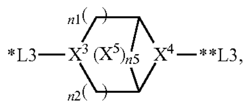

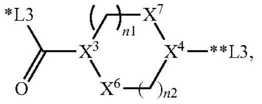

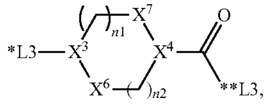

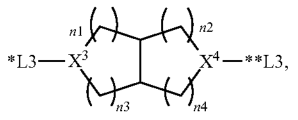

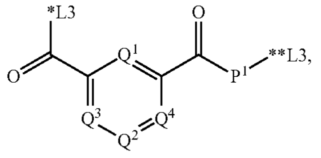

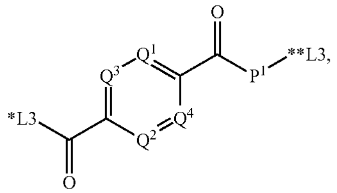

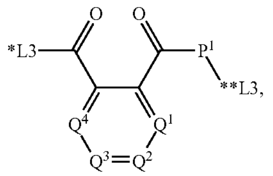

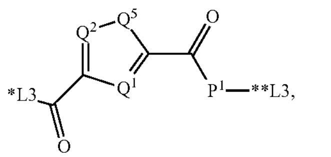

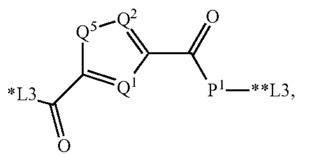

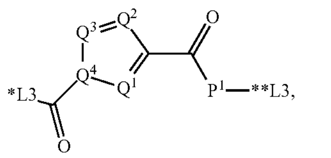

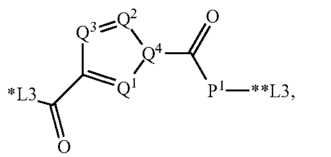

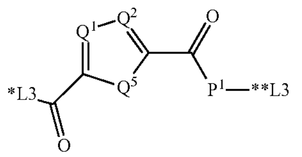

or

-continued

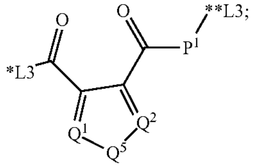

each of said- $C_3$-$C_8$cycloalkylene-, $*^{L3}$—O—$C_{1-8}$alkylene-$**^{L3}$, $*^{L3}$—$C_{1-8}$alkylene-O—$*^{L3}SO_2$—$C_{1-8}$alkylene-$^{L1}$, $*^{L3}C_{1-8}$alkylene-$SO_2$—$**^{L1}$, $*^{L3}COC_{1-8}$alkylene-$**^{L1}$, $*^{L3}$—$C_{1-8}$alkylene-CO—$**^{L3}$, $*^{L3}$—$NR^{L3a}$—$C_{1-8}$alkylene-$**^{L3}$, $*^{L3}$—$C_{1-8}$alkylene-$NR^{L3a}$—$**^{L3}$, —$C_{1-8}$alkylene-, —$C_{2-8}$alkenylene-, —$C_{2-8}$alkynylene-,

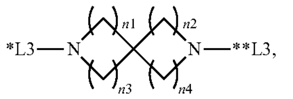

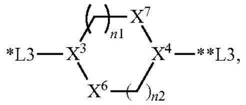

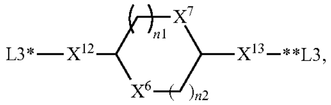

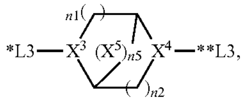

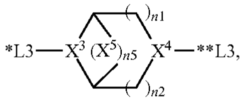

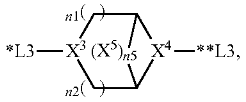

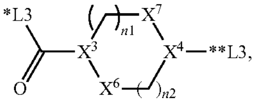

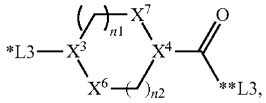

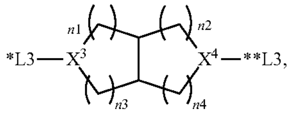

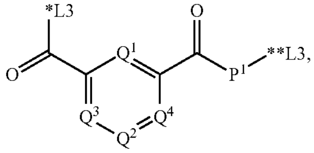

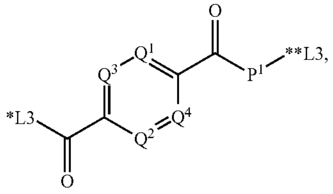

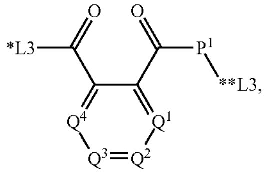

-continued

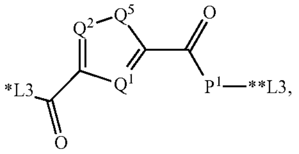

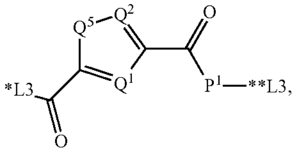

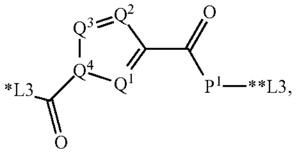

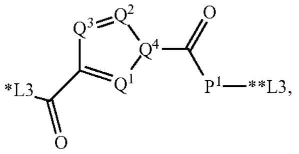

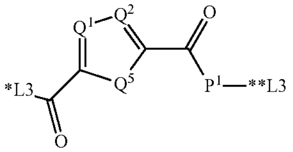

and

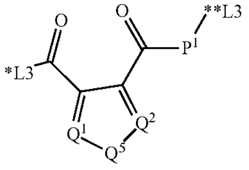

are optionally substituted with at least one substituent $R^{L3c}$;

wherein $*^{L3}$ refers to the position attached to the

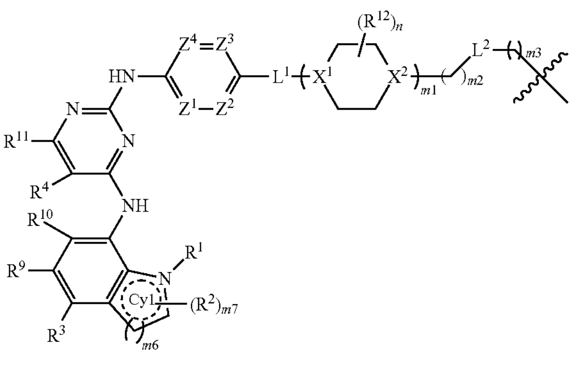

moiety, and $**^{L3}$ refers to the position attached to the

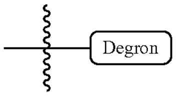

moiety;

$R^{L3a}$ and $R^{L3b}$ are each independently hydrogen, $-C_{1-8}$alkyl, $-C_{2-8}$alkenyl, $-C_{2-8}$alkynyl, cycloalkyl, heterocyclyl, aryl or heteroaryl, wherein each of said $-C_{1-8}$alkyl, $-C_{2-8}$alkenyl, $-C_{2-8}$alkynyl, cycloalkyl, heterocyclyl, aryl and heteroaryl is optionally substituted with at least one substituent $R^{L3d}$;

each of said $R^{L3c}$ and $R^{L3d}$ is independently halogen, hydroxy, $-C_{1-8}$alkyl, -halo$C_{1-8}$alkyl, $-C_{1-8}$alkoxy, $-C_{2-8}$alkenyl, $-C_{2-8}$alkynyl, cycloalkyl, heterocyclyl, aryl or heteroaryl;

Degron is

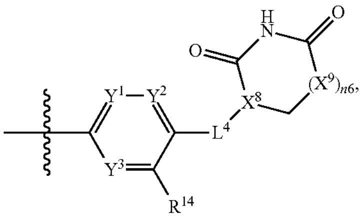

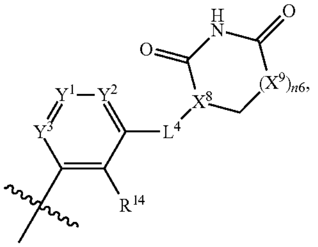

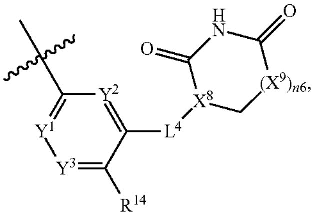

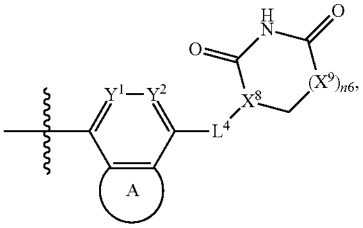

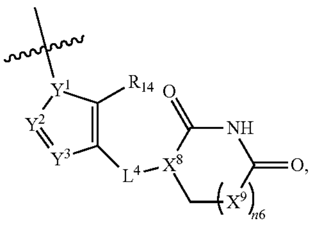

-continued

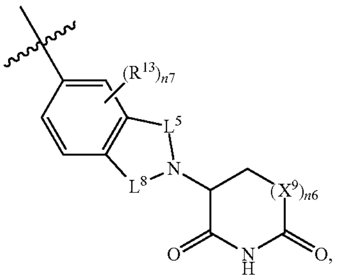

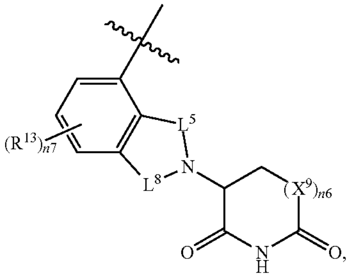

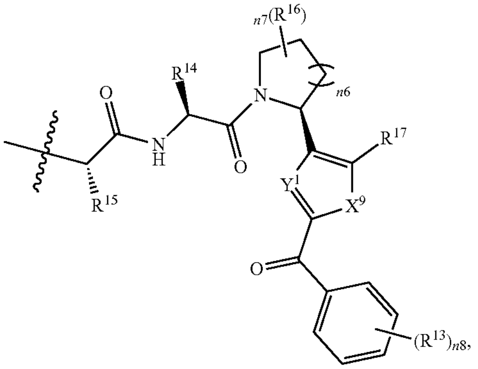

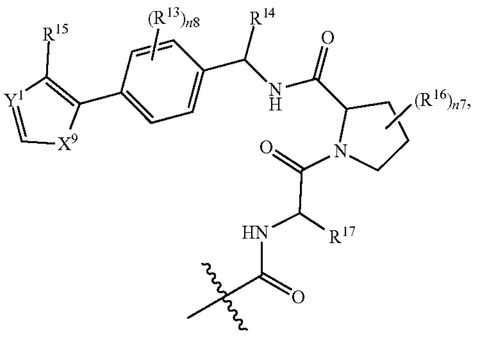

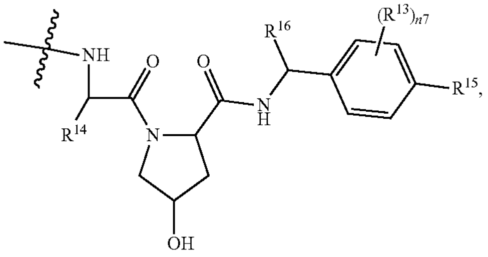

or

-continued

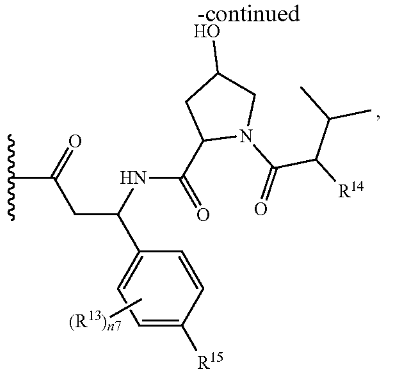

wherein Ring A is 3-12 membered cycloalkyl, 3-12 membered heterocyclyl, aryl, or heteroaryl;

$R^{13}$, $R^{14}$, $R^{15}$, $R^{16}$ and $R^{17}$ are each independently hydrogen, halogen, CN, —$C_{1-8}$alkyl, —$C_{1-8}$alkoxy, cycloalkyl, heterocyclyl, aryl, heteroaryl, —$OR^{13a}$, —$COR^{13a}$, —$CO_2R^{13a}$—$NR^{13a}R^{13b}$, —$NR^{13a}COR^{13b}$ or —$NR^{13a}CO_2R^{13b}$, wherein each of said —$C_{1-8}$alkyl, —$C_{1-8}$alkoxy, cycloalkyl, heterocyclyl, aryl and heteroaryl is optionally substituted with at least one substituent halogen, —$C_{1-8}$alkyl, -halo$C_{1-8}$alkyl, $C_{1-8}$alkoxy-$C_{1-8}$alkyl-, —$C_{2-8}$alkenyl, —$C_{2-8}$alkynyl, cycloalkyl, heterocyclyl, aryl or heteroaryl;

$R^{13a}$ and $R^{13b}$ are each independently hydrogen, —$C_{1-8}$alkyl, —$C_{2-8}$alkenyl, —$C_{2-8}$alkynyl, $C_{1-8}$alkoxy-$C_{1-8}$alkyl-, cycloalkyl, heterocyclyl, aryl or heteroaryl, wherein each of said —$C_{1-8}$alkyl, —$C_{2-8}$alkenyl, —$C_{2-8}$alkynyl, $C_{1-8}$alkoxy-$C_{1-8}$alkyl-, cycloalkyl, heterocyclyl, aryl and heteroaryl is optionally substituted with at least one substituent halogen, —$C_{1-8}$alkyl, -halo$C_{1-8}$alkyl, $C_{1-8}$alkoxy-$C_{1-8}$alkyl-, —$C_{2-8}$alkenyl, —$C_{2-8}$alkynyl, cycloalkyl, heterocyclyl, aryl or heteroaryl;

$X^1$, $X^2$, $X^3$, $X^4$ and $X^8$ are each independently —$CR^a$ or N;

$X^5$, $X^6$, $X^7$ and $X^9$ are each independently —$NR^a$—, —O—, —S— and —$CR^aR^b$—;

$X^{12}$ and $X^{13}$ are each independently a single bond, —$NR^a$— and —O—;

$L^4$ is each independently a single bond, —O—, —$NR^a$—, —$(CR^aR^b)_{n9}$—, —$O(CR^aR^b)_{n9}$—, —$NR^a(CR^aR^b)_{n9}$— or —C(O)—;

$L^5$ and $L^6$ are each independently —$CR^aR^b$— or —C(O)—;

$Q^1$, $Q^2$, $Q^3$, $Q^4$, $Y^1$, $Y^2$ and $Y^3$ are each independently $CR^a$ or N;

$Q^5$ is each independently —O—, —$NR^a$—, —$CR^aR^b$—, —S— or —C(O)—;

$P^1$ is a single bond, —O—, —NH—, —$CH_2$—, —S—, —SO— or —$SO_2$—;

$R^a$ and $R^b$ are each independently oxo, hydrogen, halogen, CN, —$C_{1-8}$alkyl, —$C_{1-8}$alkoxy, —$C_{2-8}$alkenyl, —$C_{2-8}$alkynyl, cycloalkyl, heterocyclyl, aryl or heteroaryl, wherein each of said —$C_{1-8}$alkyl, —$C_{1-8}$alkoxy, —$C_{2-8}$alkenyl, —$C_{2-8}$alkynyl, cycloalkyl, heterocyclyl, aryl and heteroaryl is optionally substituted with at least one substituent halogen, hydroxy, halogen, —$C_{1-8}$alkyl, —$C_{1-8}$alkoxy, —$C_{2-8}$alkenyl, —$C_{2-8}$alkynyl, cycloalkyl, heterocyclyl, aryl or heteroaryl;

m1 is 0, 1 or 2;

m2 and m3 are each independently 0, 1, 2, 3, 4, 5, 6, 7 or 8;

m4, m5 are each independently 0, 1, 2 or 3;

m6 is each independently 0, 1, 2 or 3;

m7 each independently 0, 1, 2, 3 or 4;

n, $n_1$, $n_2$, $n_3$, $n_4$ and $n_5$ are each independently 0, 1, 2 or 3; and $n_6$, $n_7$, $n_8$ and $n_9$ are each independently 0, 1, 2, 3 or 4.

2. The compound of claim 1, wherein $R^1$ is —$SO_2R^{1a}$, wherein $R^{1a}$ is each independently —$C_{1-8}$alkyl, —$C_{6-8}$aryl, —$C_{3-7}$cycloalkyl, or 4- to 7-membered heterocyclyl or —$NR^{1d}R^{1e}$, wherein each of said —$C_{1-8}$alkyl, —$C_{6-8}$aryl, —$C_{3-7}$cycloalkyl, and 4- to 7-membered heterocyclyl is optionally substituted with at least one substituent $R^{1f}$;

$R^{1d}$ and $R^{1c}$ are each independently hydrogen, —$C_{1-8}$alkyl, —$C_{1-8}$haloalkyl, —$C_{2-8}$alkenyl, —$C_{2-8}$alkynyl, cycloalkyl, heterocyclyl, aryl, or heteroaryl;

$R^{1f}$ at each of its occurrences, is independently hydrogen, halogen, —$C_{1-8}$alkyl, —$C_{1-8}$haloalkyl, —$C_{2-8}$alkenyl, —$C_{2-8}$alkynyl, cycloalkyl, halocycloalkyl, heterocyclyl, phenyl, heteroaryl, —CN, or —$OR^{1g}$, wherein each of said cycloalkyl, heterocyclyl, aryl and heteroaryl is optionally substituted with 1, 2 or 3 substituents selected from halogen and —$C_{1-8}$alkyl;

$R^{1g}$ is hydrogen, —$C_{1-8}$alkyl, —$C_{1-8}$haloalkyl, $C_{1-8}$alkoxy-$C_{1-8}$alkyl-, —$C_{2-8}$alkenyl, —$C_{2-8}$alkynyl, cycloalkyl, heterocyclyl, aryl, or heteroaryl.

3. The compound of claim 1, wherein $R^2$ is independently hydrogen, —F, —Cl, —Br, —I, methyl, ethyl, propyl, butyl, pentyl, hexyl, heptyl, octyl, cyclopropyl, cyclobutyl, cyclopentyl, cyclohexyl, cycloheptyl, cyclooctyl, —CN, —$OR^{2a}$ or —$COR^2$a, wherein each of said methyl, ethyl, propyl, butyl, pentyl, hexyl, heptyl, octyl, cyclopropyl, cyclobutyl, cyclopentyl, cyclohexyl, cycloheptyl, or cyclooctyl is optionally substituted with at least one substituent $R^{2c}$, or two germinal $R^2$ together with the atom to which they are attached, form a spiro 3-, 4-, 5- or 6-membered cycloalkyl, said cycloalkyl is optionally substituted with at least one substituent $R^{2c}$; or two $R^2$ on different atoms, together with the atoms to which they are attached, form a 3-, 4-, 5- or 6-membered cycloalkyl, said cycloalkyl is optionally substituted with at least one substituent $R^{2c}$;

$R^{2a}$ is hydrogen, —$C_{1-8}$alkyl, —$C_{2-8}$alkenyl, —$C_{2-8}$alkynyl, $C_{1-8}$alkoxy-$C_{1-8}$alkyl-, or $C_{3-8}$cycloalkyl;

$R^{2c}$, at each of its occurrences, is independently —F, —Cl, —Br, —I, —OH, —$C_{1-8}$alkyl, -halo$C_{1-8}$alkyl, —$C_{2-8}$alkenyl, —$C_{2-8}$alkynyl, or —$C_{3-8}$cycloalkyl.

4. The compound of claim 1, wherein $R^3$, $R^9$ and $R^{10}$ are independently hydrogen, —F, —Cl, —Br, —I, methyl, ethyl, propyl, butyl, pentyl, hexyl, heptyl, octyl, cyclopropyl, cyclobutyl, cyclopentyl, cyclohexyl, cycloheptyl, cyclooctyl, —$NR^{3a}R^{3b}$, —CN, —$OR^3$a, —$COR^3$a or —$CO_2R^{3a}$, wherein each of methyl, ethyl, propyl, butyl, pentyl, hexyl, h eptyl, octyl, cyclopropyl, cyclobutyl, cyclopentyl, cyclohexyl, cycloheptyl, and cyclooctyl is optionally substituted with at least one substituent $R^{3c}$, $R^{3a}$ is each independently hydrogen, —$C_{1-8}$alkyl, —$C_{2-8}$alkenyl, —$C_{2-8}$alkynyl, $C_{1-8}$alkoxy-$C_{1-8}$alkyl-, or $C_{3-8}$cycloalkyl, wherein each of said —$C_{1-8}$alkyl, —$C_{2-8}$alkenyl, —$C_{2-8}$alkynyl, $C_{1-8}$alkoxy-$C_{1-8}$alkyl-, and $C_{3-8}$cycloalkyl is optionally substituted with at least one substituent $R^{3d}$;

$R^{3c}$ and $R^{3d}$, at each of their occurrences, is independently halogen, —$C_{1-8}$alkyl, —$C_{2-8}$alkenyl, —$C_{2-8}$alkynyl, or —$C_{3-8}$cycloalkyl.

5. The compound of claim 1, wherein the

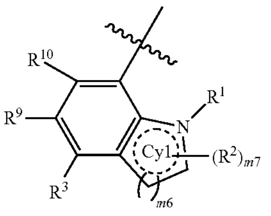

moiety is

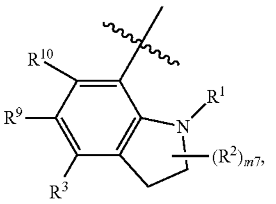

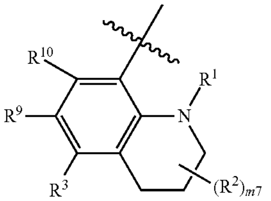 or

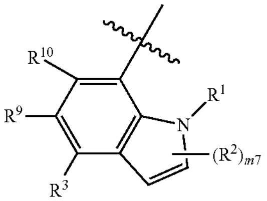

6. The compound of claim 1, wherein $R^4$ and $R^{11}$ are each independently hydrogen, F, Br, Cl, I, methyl, ethyl, propyl, butyl, pentyl, hexyl, heptyl, octyl, cyclopropyl, cyclobutyl, cyclopentyl, cyclohexyl, cycloheptyl, cyclooctyl, 3- to 8-membered heterocyclyl, —CN, —$OR^{4a}$, or —$NR^{4a}R^{4b}$, wherein each of said methyl, ethyl, propyl, butyl, pentyl, hexyl, heptyl, octyl, cyclopropyl, cyclobutyl, cyclopentyl, cyclohexyl, cycloheptyl, cyclooctyl and 3- to 8-membered heterocyclyl is optionally substituted with at least one $R^{4c}$;

$R^{4a}$ and $R^{4b}$ are each independently hydrogen, —$C_{1-8}$alkyl, -halo$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl, or 5- to 12-membered heteroaryl;

$R^{4c}$ is F, Br, Cl, I, methyl, ethyl, propyl, butyl, pentyl, hexyl, heptyl, octyl, cyclopropyl, cyclobutyl, cyclopentyl, cyclohexyl, cycloheptyl, cyclooctyl, 3- to 8-membered heterocyclyl, phenyl, 5- to 12-membered heteroaryl, oxo, —CN, or —$OR^{4c}$;

$R^{4c}$ is independently hydrogen, methyl, ethyl, propyl, butyl, pentyl, hexyl, heptyl, octyl, or phenyl.

7. The compound of claim 1, wherein

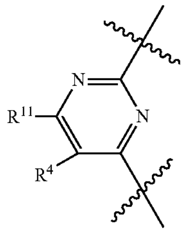

moiety is

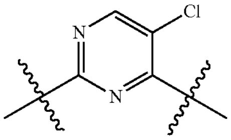, 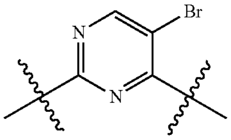,

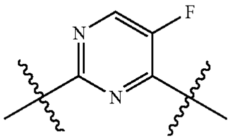, 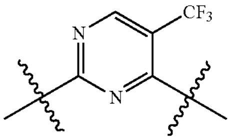,

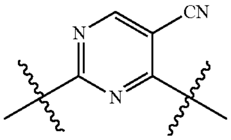, 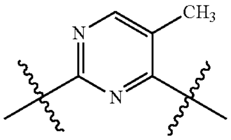,

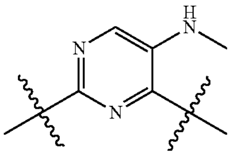, 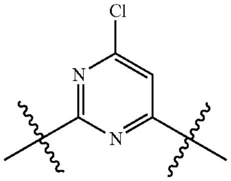,

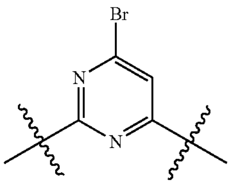, 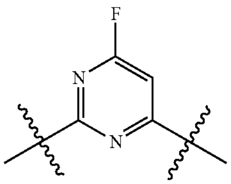,

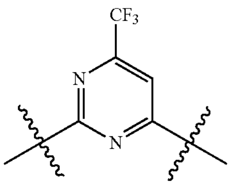, 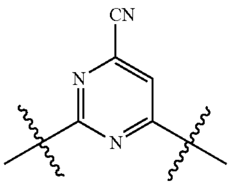,

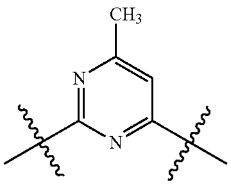, 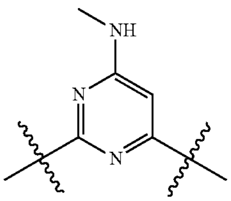,

-continued

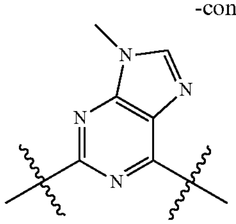,
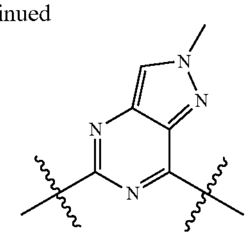,
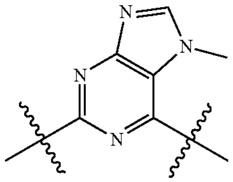,
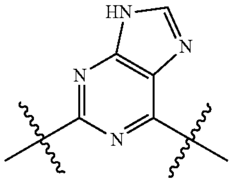,
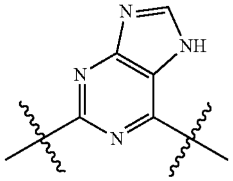,
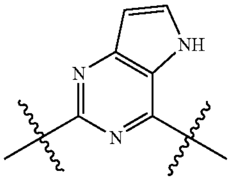,
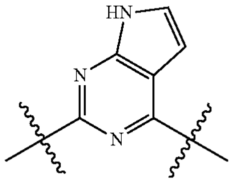,
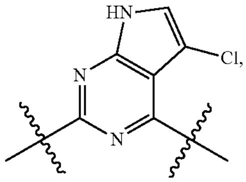Cl,
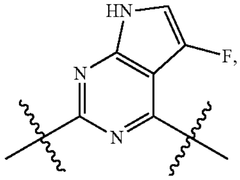F,
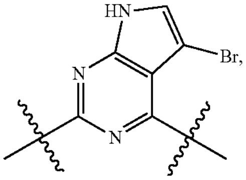Br,
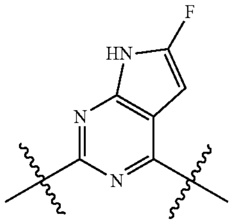,
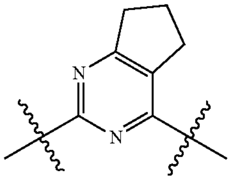,
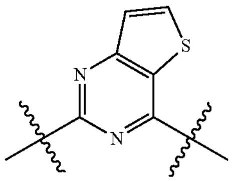,
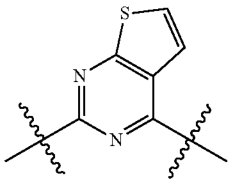or
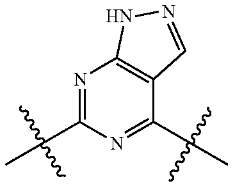.

8. The compound of claim 1, wherein $R^{12}$ independently hydrogen, F, Cl, Br, I, OH, methyl, ethyl, propyl, butyl, pentyl, hexyl, methoxy, ethoxy, propoxy, butoxy, pentoxy, hexoxy, phenyl, cyclopropyl, cyclobutyl, cyclopentyl, cyclohexyl, oxo or —CN; or two germinal $R^{12}$ together with the atom to which they are attached, form a spiro 3-, 4-, 5-, or 6-membered cycloalkyl, said cycloalkyl is optionally substituted with at least one substituent $R^{12c}$; or two $R^{12}$ on different atoms, together with the atoms to which they are attached, form a 3-, 4-, 5-, or 6-membered cycloalkyl, said cycloalkyl is optionally substituted with at least one substituent $R^{12c}$;

$R^{12c}$ is independently halogen, hydroxy, —$C_{1-8}$alkyl, -haloC$_{1-8}$alkyl, —$C_{1-8}$alkoxy, —$C_{2-8}$alkenyl, —$C_{2-8}$alkynyl, cycloalkyl, heterocyclyl, aryl or heteroaryl.

9. The compound of claim 1, wherein

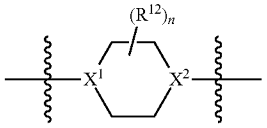

is

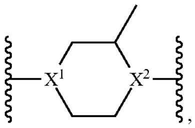,
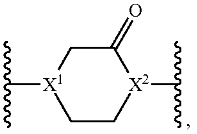,
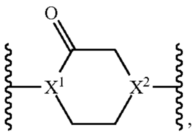,
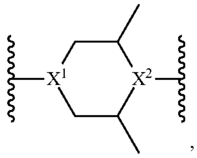,
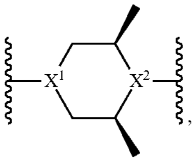,
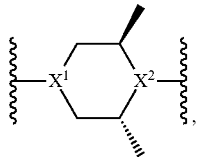,
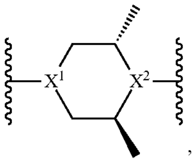,
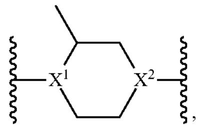,
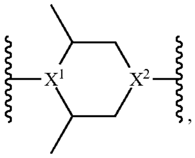,
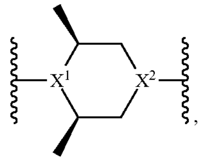,
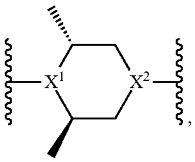,
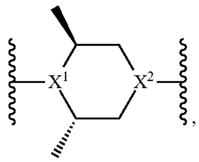,
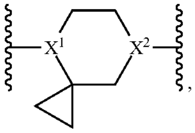,
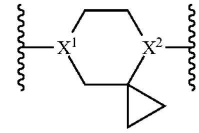,
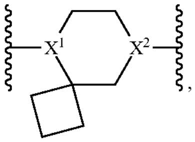,
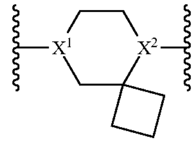

-continued

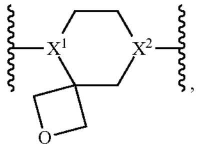

or

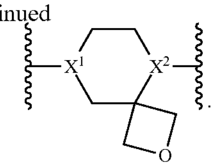

10. The compound of claim 1, wherein $Z^1$, $Z^2$, $Z^3$ and $Z^4$ are each independently —$CR^z$, or N;

$R^Z$, at each of its occurrences, is independently hydrogen, —F, —Cl, —Br, —I, methyl, ethyl, propyl, butyl, pentyl, hexyl, heptyl, octyl, —$NR^{Za}R^{Zb}$, —$OR^{Za}$, cyclopropyl, cyclobutyl, cyclopentyl, cyclohexyl, cycloheptyl, cyclooctyl, 3- to 8-membered heterocyclyl, phenyl, 5- to 12-membered heteroaryl, or CN, wherein each of said methyl, ethyl, propyl, butyl, pentyl, hexyl, heptyl, octyl, cyclopropyl, cyclobutyl, cyclopentyl, cyclohexyl, cycloheptyl, cyclooctyl, 3- to 8-membered heterocyclyl, phenyl, and 5- to 12-membered heteroaryl is optionally substituted with at least one $R^{Zc}$; or or two $R^Z$, when attached to adjacent carbon atoms of the ring, together with the two carbon atoms to which they are attached, form a 3- to 12-membered ring comprising 0, 1 or 2 heteroatom(s) independently selected from nitrogen, oxygen and optionally oxidized sulfur as ring member(s), said ring is optionally substituted with at least one substituent $R^{Ze}$;

$R^{Za}$ and $R^{Zb}$ are each independently hydrogen, methyl, ethyl, propyl, butyl, pentyl, hexyl, heptyl, octyl, cyclopropyl, cyclobutyl, cyclopentyl, cyclohexyl, cycloheptyl, cyclooctyl, or phenyl, wherein each of said methyl, ethyl, propyl, butyl, pentyl, hexyl, heptyl, octyl, cyclopropyl, cyclobutyl, cyclopentyl, cyclohexyl, cycloheptyl, cyclooctyl, and phenyl is optionally substituted with at least one substituent $R^{Zd}$;

$R^{Zc}$ and $R^{Zd}$ are each independently —F, —Cl, —Br, —I, —OH, methyl, ethyl, propyl, butyl, pentyl, hexyl, heptyl, octyl, —$OCH_3$, —$OC_2H_5$, —$OC_3H_7$, —$OC_4H_9$, —$OC_5H_{11}$, cyclopropyl, cyclobutyl, cyclopentyl, cyclohexyl, cycloheptyl, cyclooctyl, and phenyl, or two $R^{Zc}$, together with the atom(s) to which they are attached, form a 3- to 8-membered ring, said ring comprising 0, 1 or 2 heteroatom(s) independently nitrogen, oxygen, or optionally oxidized sulfur as ring member(s).

11. The compound of claim 1, wherein the

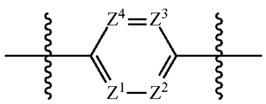

moiety is

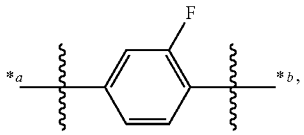

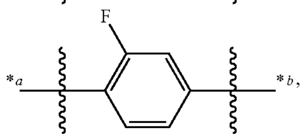

-continued

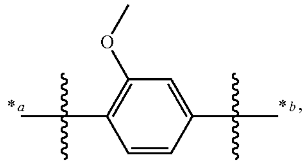

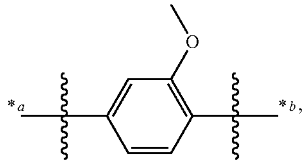

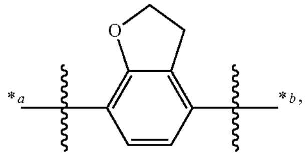

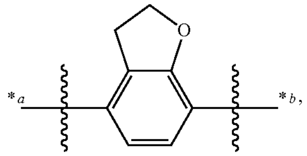

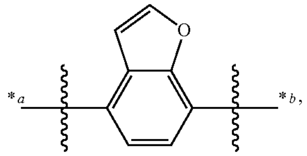

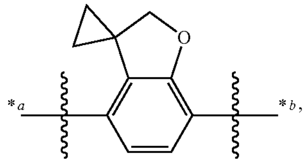

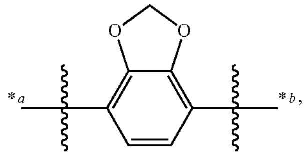

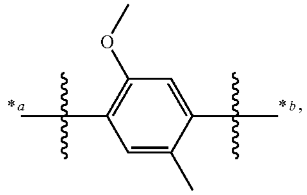

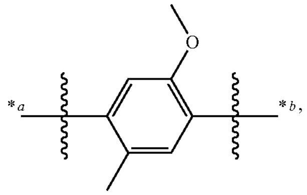

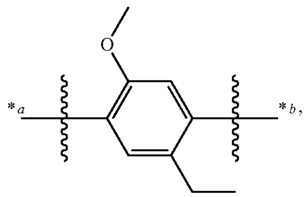

-continued

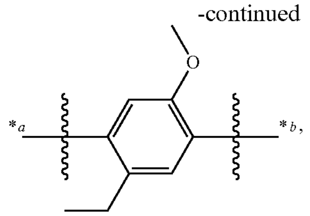

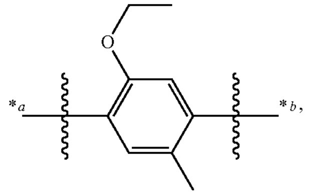

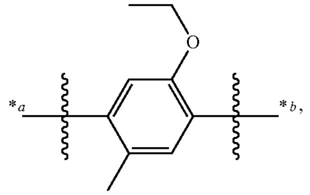

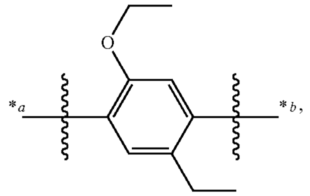

and

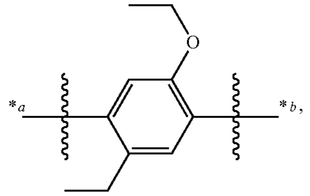

wherein *a refers to the position attached to

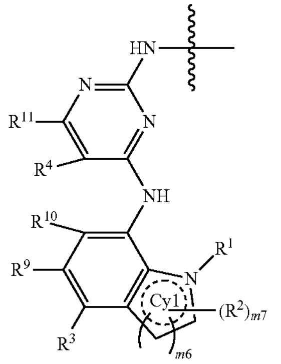

moiety, and *b refers to the position attached to the

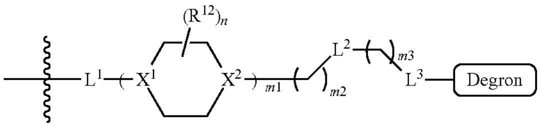

moiety.

12. The compound of claim 1, wherein $L_1$ is a single bond, —$C_{1-8}$alkylene-,

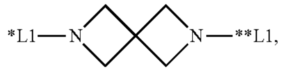

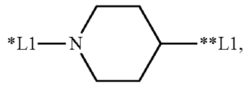 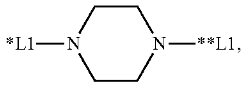

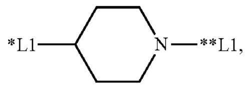 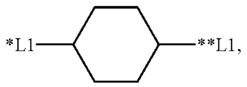

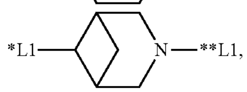 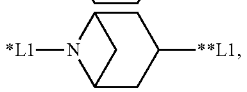

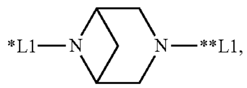 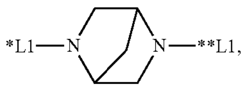

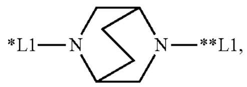 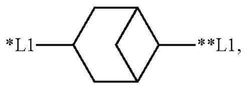

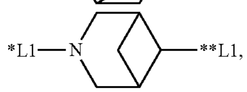 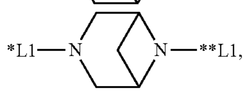

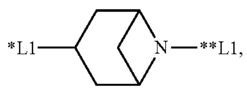 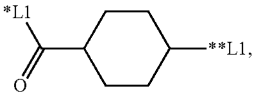

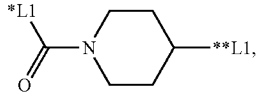 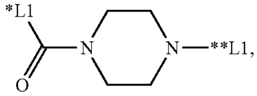

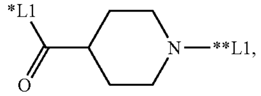

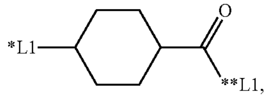

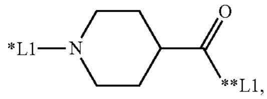

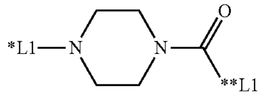

or

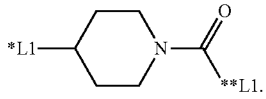

13. The compound of claim 1, wherein $X^1$ and $X^2$ are each independently CH or N; m1=1 or 0; and $R^{12}$ is hydrogen or —$CH_3$.

14. The compound of claim 1, wherein m2 and m3 are each independently 0, 1, 2, 3, 4 or 5.

15. The compound of claim 1, wherein L2 is a single bond, —CO—, —O—, —$NR^{L2a}$—, —$C_{1-8}$alkylene,

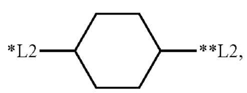 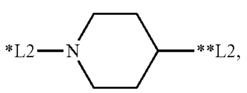

-continued
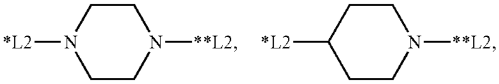
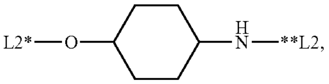
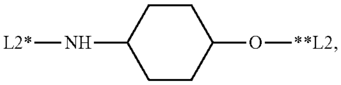
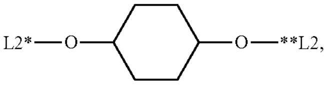
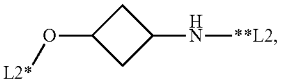
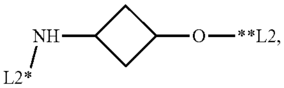
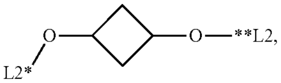
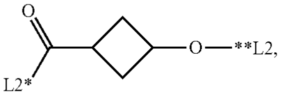
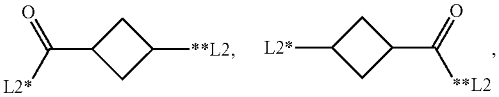
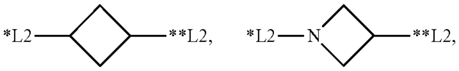
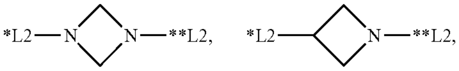
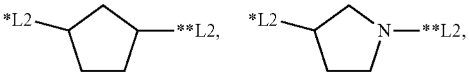
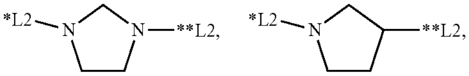
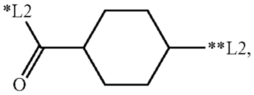
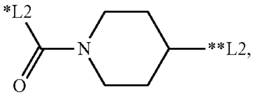
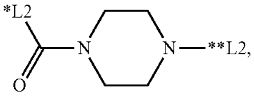
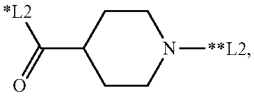
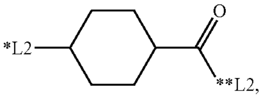
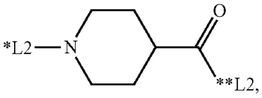
-continued
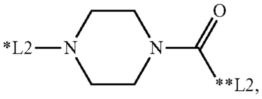
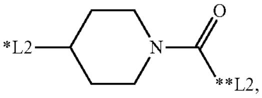
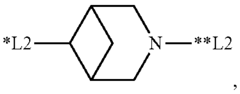
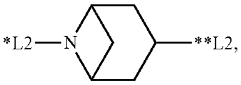
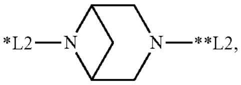
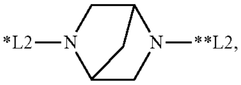
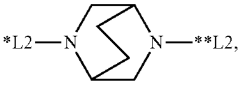
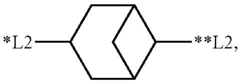
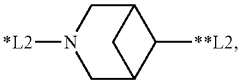
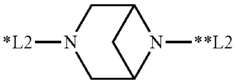
or
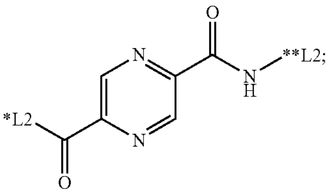
wherein $R^{L2a}$ is hydrogen, methyl, ethyl or propyl.
16. The compound of claim 1, wherein $L^3$ is a single bond, —O—, —$NR^{L3a}$—, —$C_{1-8}$alkylene
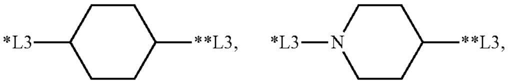
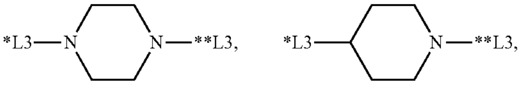
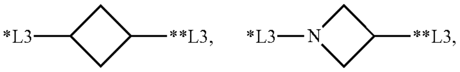
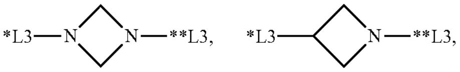
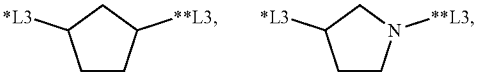
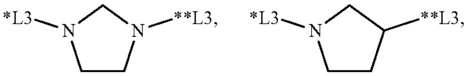
or
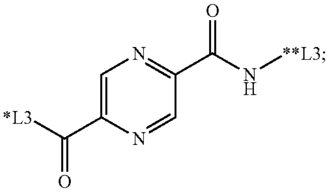
wherein $R^{L3a}$ is selected from hydrogen, methyl, ethyl or propyl.

17. The compound of claim 1, wherein
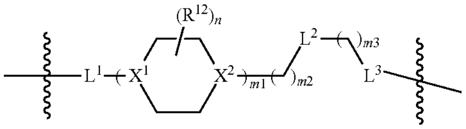
is
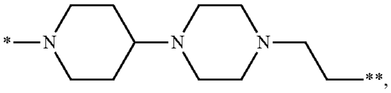
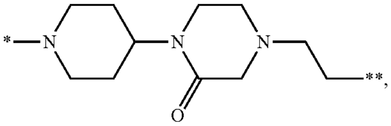
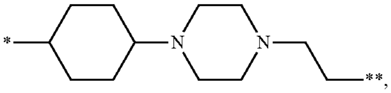
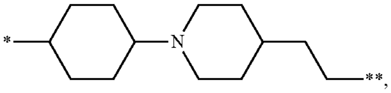
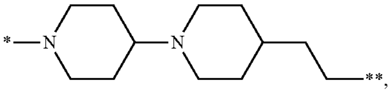
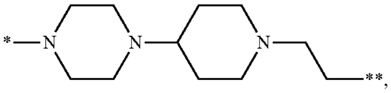
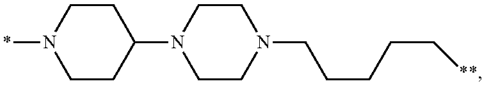
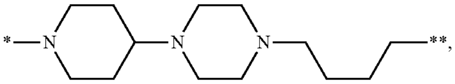
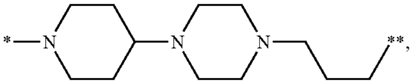
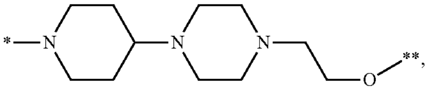
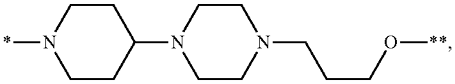
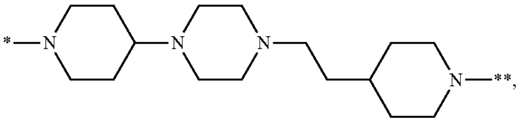
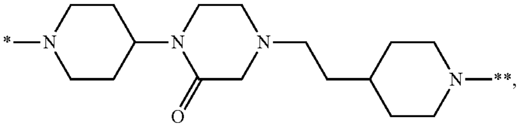
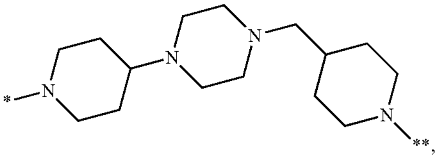
-continued
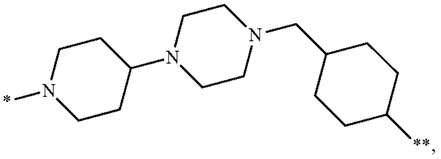
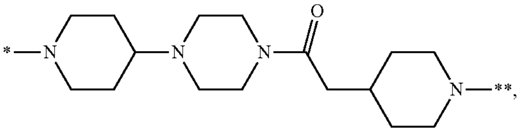
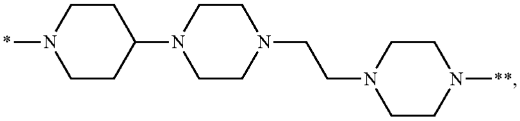
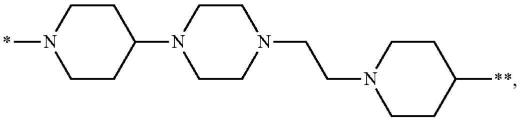
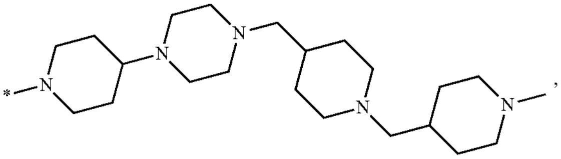
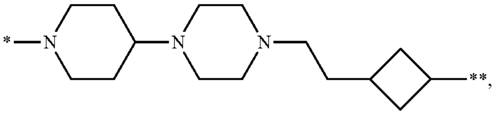
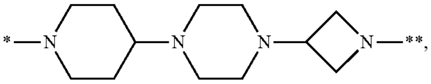
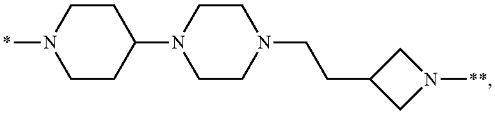
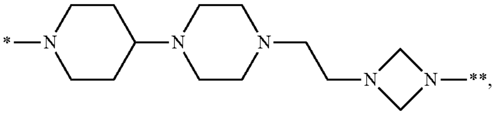
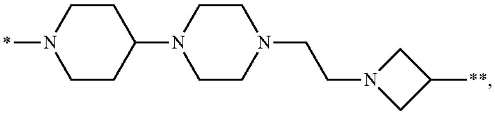
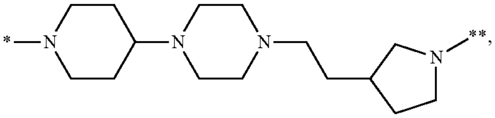
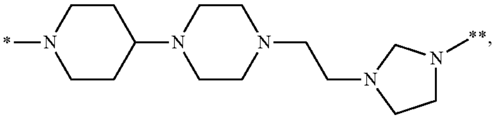
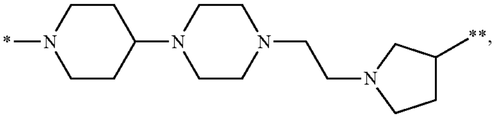

-continued
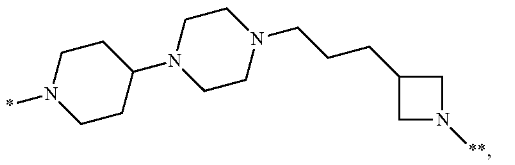
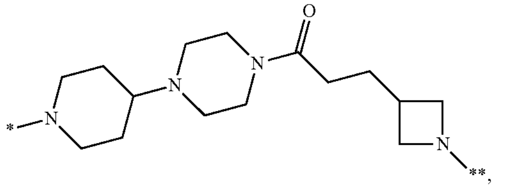
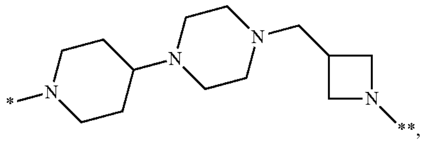
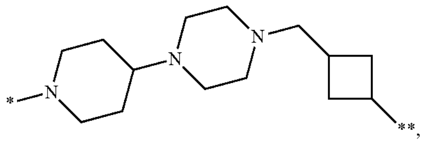
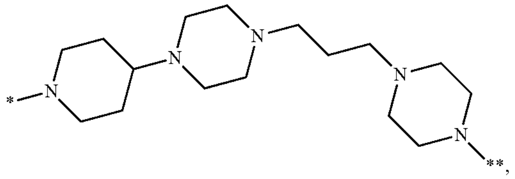
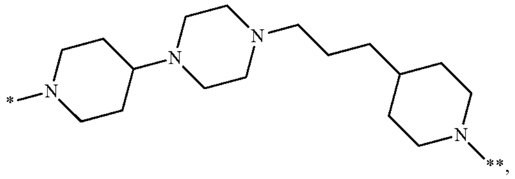
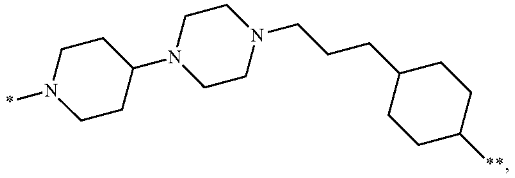
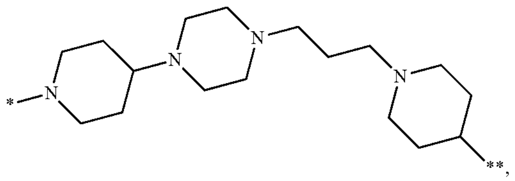
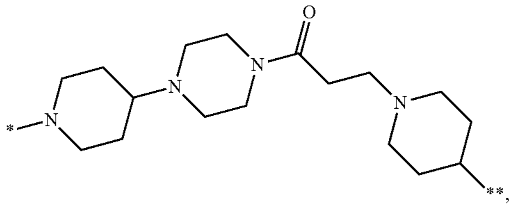
-continued
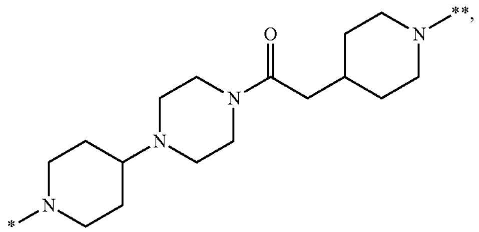
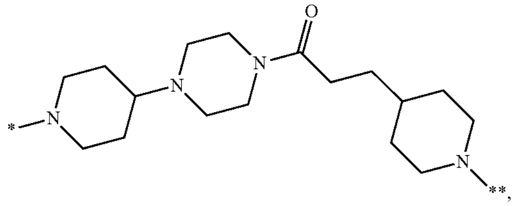
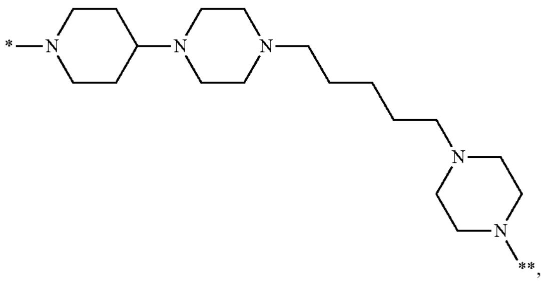
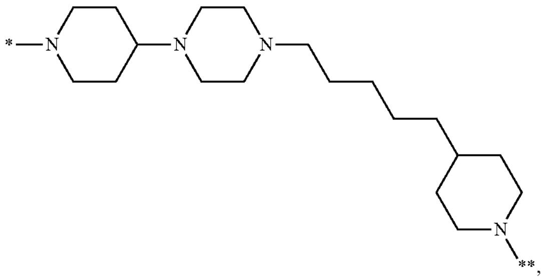
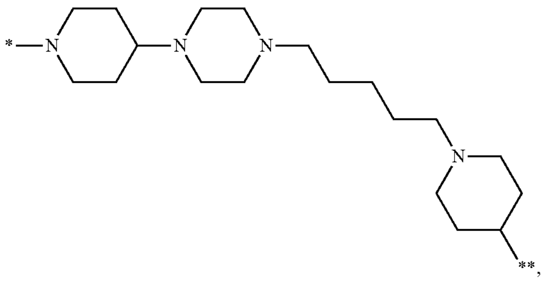
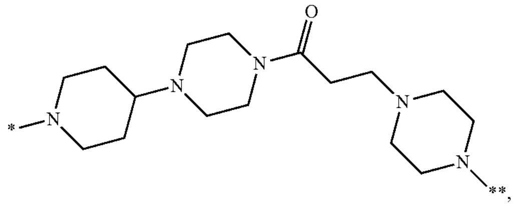
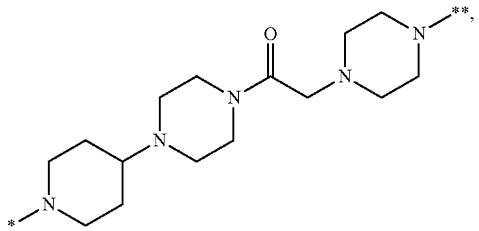

-continued
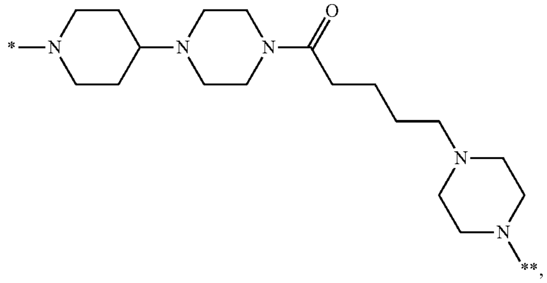
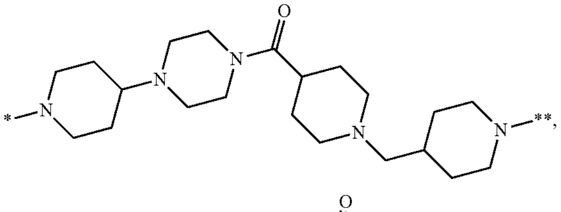
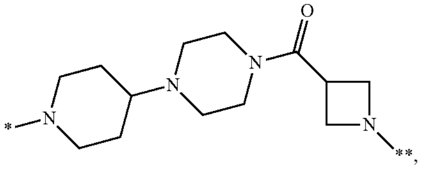
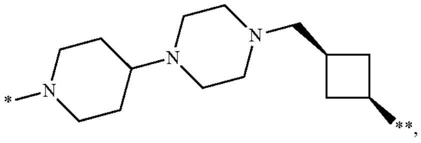
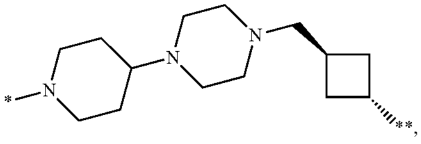
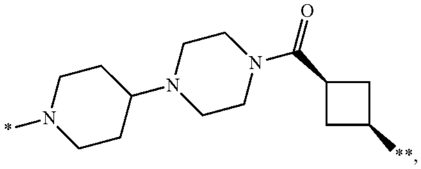
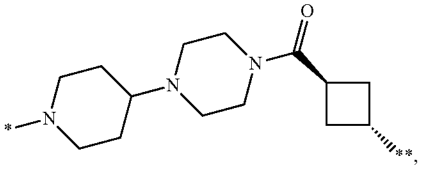
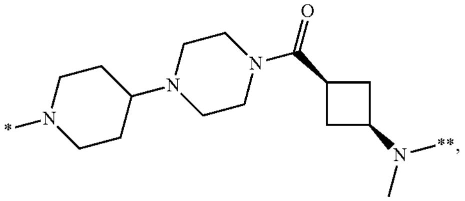
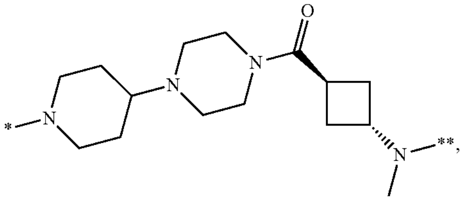
-continued
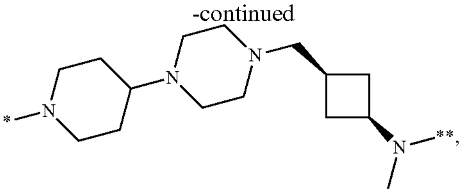
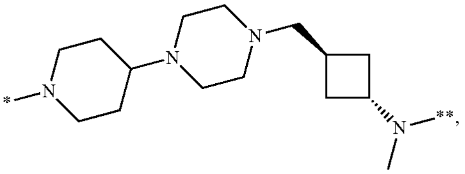
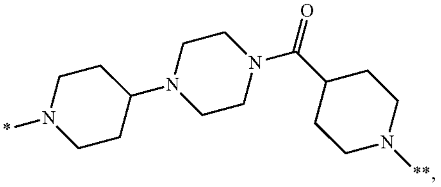
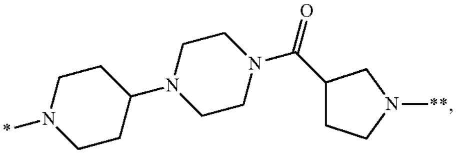
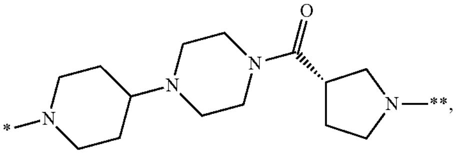
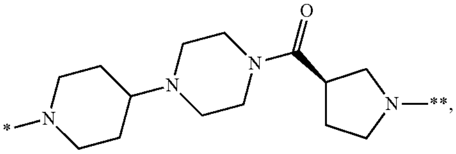
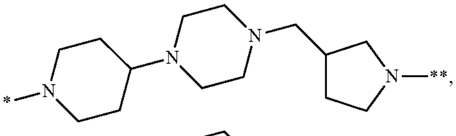
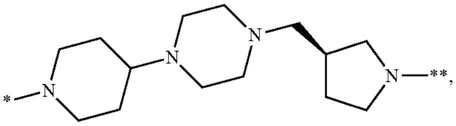
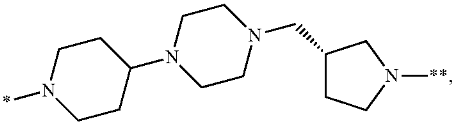
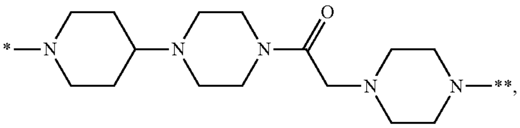
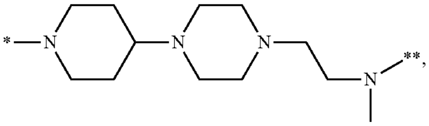
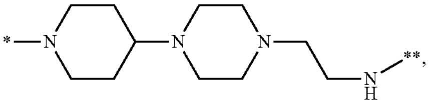

-continued
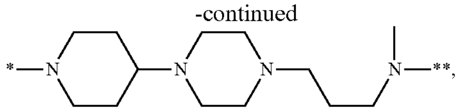
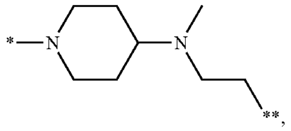
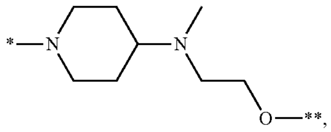
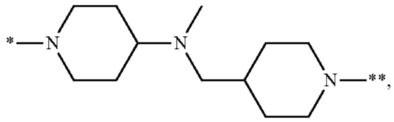
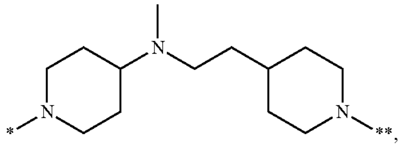
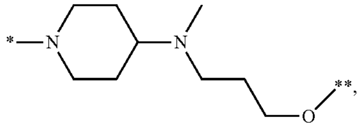
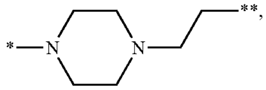
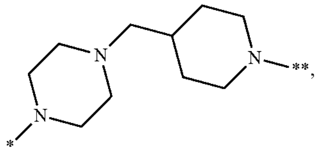
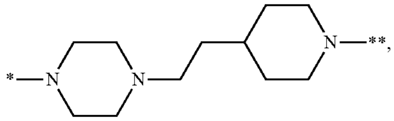
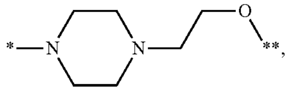
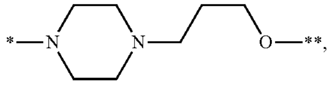
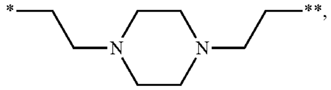
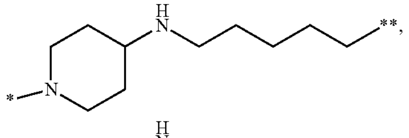
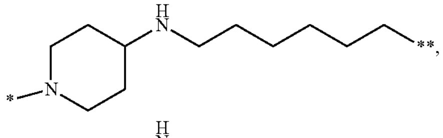
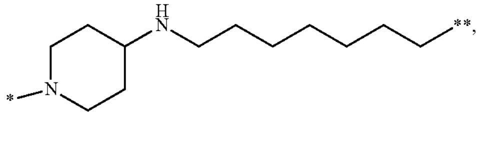
-continued
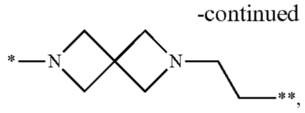
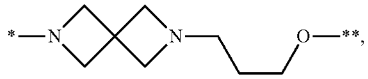
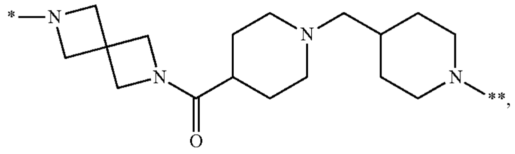
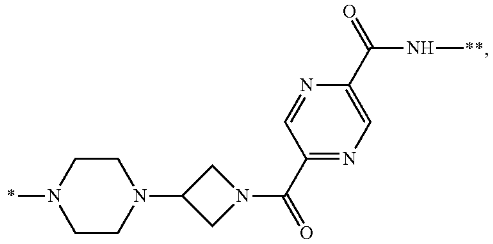
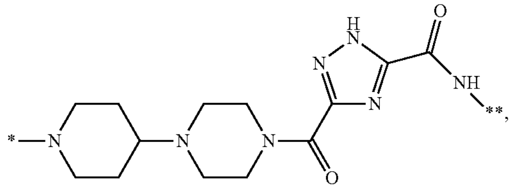
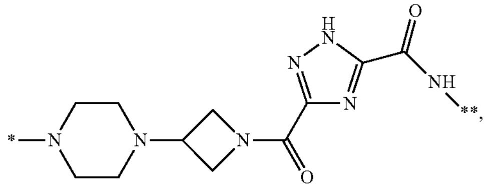
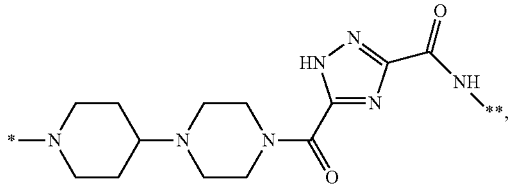
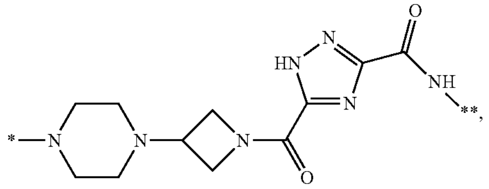
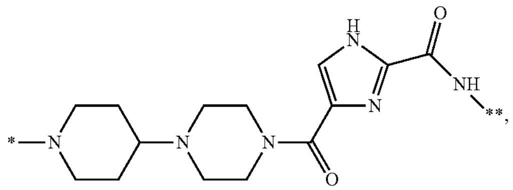
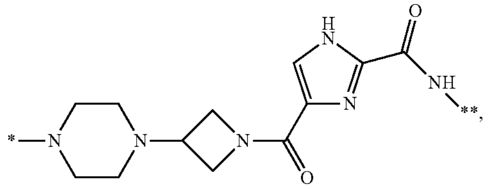

-continued
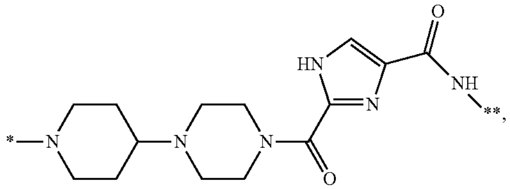
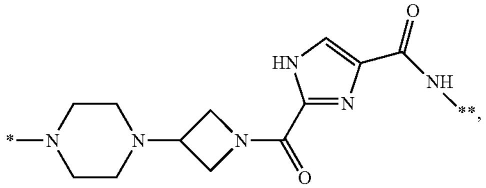
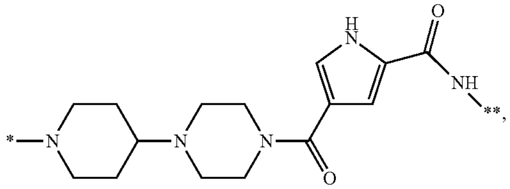
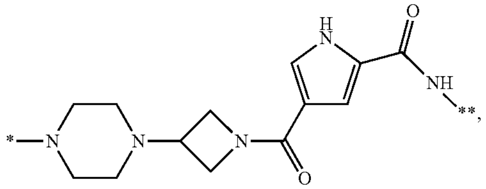
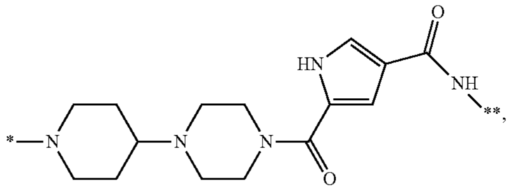
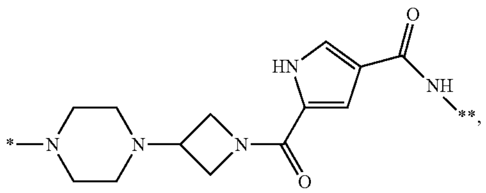
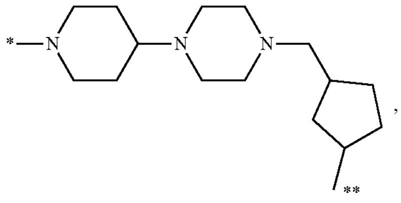
-continued
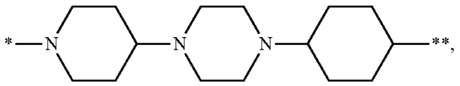
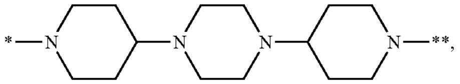
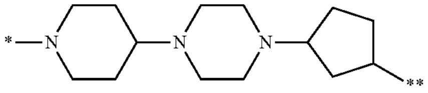
or
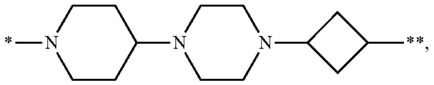
wherein * refers to the position attached to
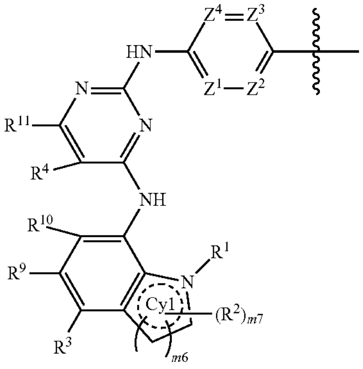
moiety, and ** refers to the position attached to the
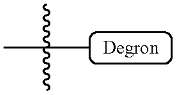
moiety.
18. The compound of claim 1, wherein the compound is Formula (II):

(II)

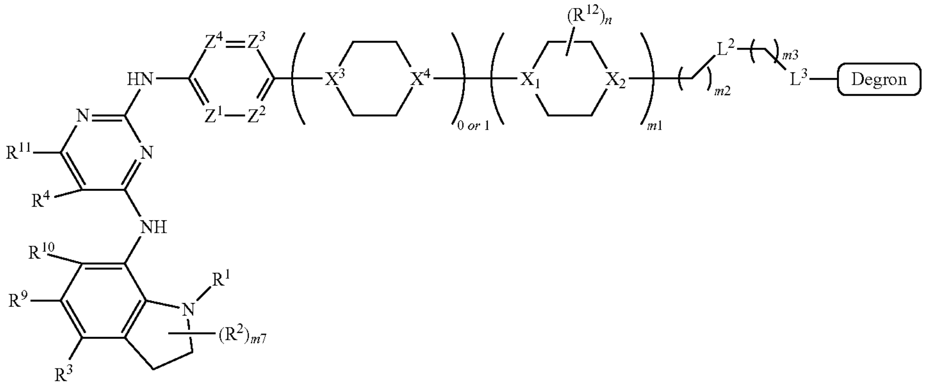

or an N-oxide thereof, or a pharmaceutically acceptable salt thereof, or a stereoisomer thereof, or a tautomer or a prodrug thereof, wherein: $R^1$, $R^2$, $R^3$, $R^4$, $R^9$, $R^{10}$, $R^{11}$, $R^{12}$, $Z_1$, $Z_2$, $Z_3$, $Z_4$, $X_1$, $X_2$, $X_3$, $X_4$, $L_2$, $L_3$, Degron, n, $m_1$, $m_2$, $m_3$ and $m_7$ have the same meaning with claim 1.

19. The compound of claim 1, wherein the compound is Formula (III):

(III)

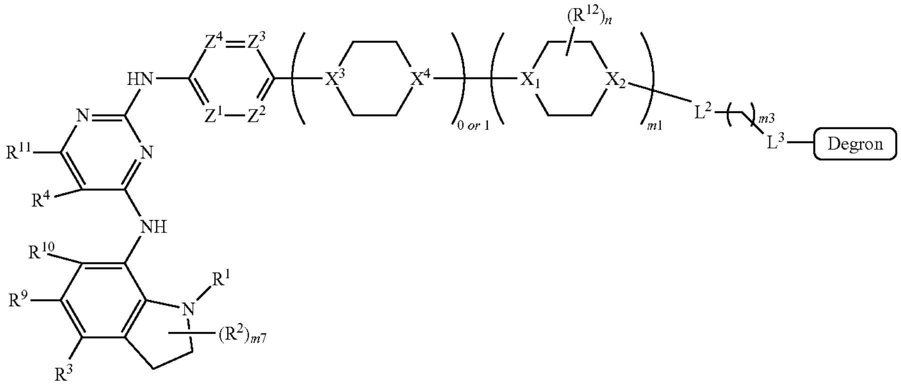

or an N-oxide thereof, or a pharmaceutically acceptable salt thereof, or a stereoisomer thereof, or a tautomer or a prodrug thereof, wherein: $R^1$, $R^2$, $R^3$, $R^4$, $R^9$, $R^{10}$, $R^{11}$, $R^{12}$, $Z_1$, $Z_2$, $Z_3$, $Z_4$, $X_1$, $X_2$, $X_3$, $X_4$, $L_2$, $L_3$, Degron, n, $m_1$, $m_3$ and $m_7$ have the same meaning with claim 1, optionally wherein m1 is 0 or 1.

20. The compound of claim 1, wherein

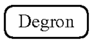

is

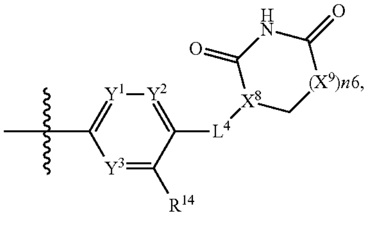

-continued

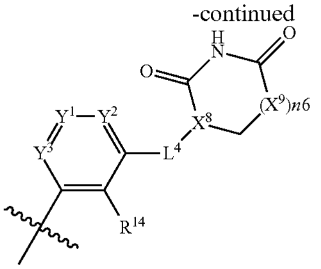

or

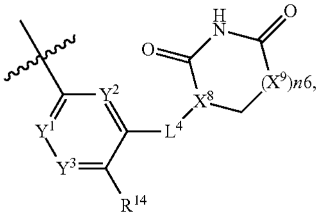

$R^{14}$ is independently hydrogen, halogen, —$C_{1-8}$alkyl, —$C_{1-8}$alkoxy, or CN, wherein each of said —$C_{1-8}$alkyl and —$C_{1-8}$alkoxy is optionally substituted by one or more halogen or —$C_{1-8}$alkyl.

21. The compound of claim 1, wherein

Degron is

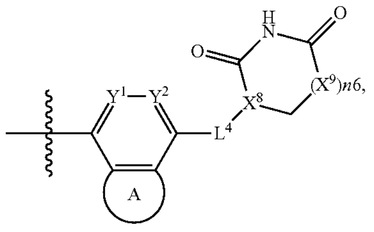

wherein Ring A is 5-7 membered cycloalkyl, 5-7 membered heterocyclyl, aryl, or heteroaryl;

$X^8$ is independently CF, CH, $C(CH_3)$, $C(C_2H_5)$, $C(C_3H_7)$, C(CN) or N;

$L^4$ is independently a single bond, —O—, —NH—, —$CH_2$—, —CHF—, or —$CF_2$—;

$Y^1$ and $Y^2$ are each independently $CR^a$ or N;

$R^a$ is each independently hydrogen, halogen, —$C_{1-8}$alkyl, or —$C_{1-8}$alkoxy, each of said —$C_{1-8}$alkyl and —$C_{1-8}$alkoxy is optionally substituted with at least one or more halogen, hydroxy, halogen, —$C_{1-8}$alkyl, or —$C_{1-8}$alkoxy;

$X^9$ is $CH_2$; and $n_6$ is independently 0, 1 or 2.

22. The compound of claim 1, wherein

Degron is

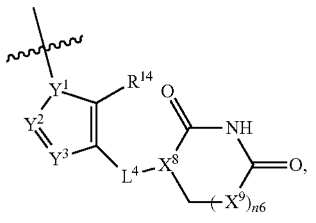

wherein $R^{14}$ is independently hydrogen, halogen, —$C_{1-8}$alkyl, or —$C_{1-8}$alkoxy, wherein each of said each —$C_{1-8}$alkyl and —$C_{1-8}$alkoxy is optionally substituted by one or more halogen, —$C_{1-8}$alkyl, or $C_{1-8}$alkoxy-$C_{1-8}$alkyl-;

$X^8$ is independently CH, $C(CH_3)$, $C(C_2H_5)$, $C(C_3H_7)$, C(CN) or N;

$L^4$ is independently a single bond, —O—, —NH—, —$CH_2$—, —CHF—, or —$CF_2$—;

$Y^1$, $Y^2$, and $Y^3$ are each independently $CR^a$, or N;

$R^a$ is each independently hydrogen, halogen, —$C_{1-8}$alkyl, or —$C_{1-8}$alkoxy, each of said —$C_{1-8}$alkyl, and —$C_{1-8}$alkoxy is optionally substituted with at least one or more halogen, hydroxy, halogen, —$C_{1-8}$alkyl, or —$C_{1-8}$alkoxy;

$X^9$ is $CH_2$; and $n_6$ is independently 0, 1 or 2.

23. The compound of claim 1, wherein

Degron is

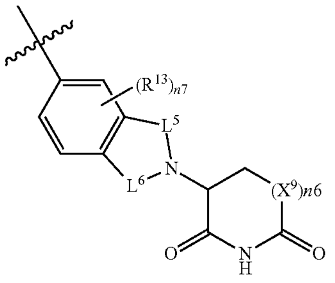

or

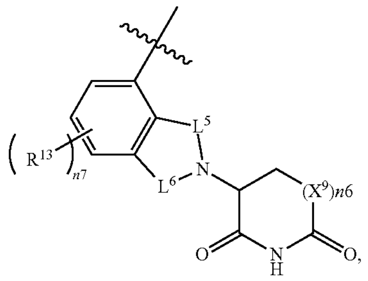

wherein $L^5$ and $L^6$ are each independently —$CH_2$ or —CO—;

$X^9$ is $CH_2$;

each $R^{13}$ is independently hydrogen, halogen, CN, —$C_{1-8}$alkyl, or —$C_{1-8}$alkoxy;

$n_6$ is 0 or 1; and $n_7$ is 0, 1 or 2.

24. The compound of claim 1, wherein

Degron is

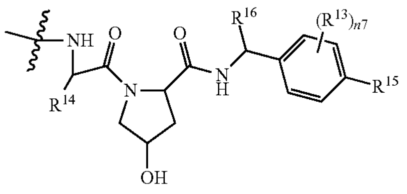

or

-continued

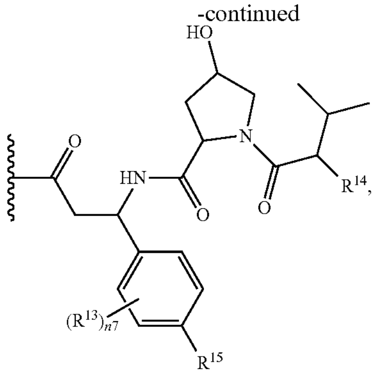

wherein $R_{13}$ and $R_{16}$ are independently hydrogen, halogen, —$C_{1-8}$alkyl, or —$C_{1-8}$alkoxy; said each —$C_{1-8}$alkyl and —$C_{1-8}$alkoxy is optionally substituted by one or more halogen, —$C_{1-8}$alkyl, or $C_{1-8}$alkoxy-$C_{1-8}$alkyl-;

$R_{15}$ and $R_{14}$ is selected from the group consisting of 5- to 12-membered heteroaryl, 3- to 8-membered heterocyclyl, and $C_6$-$C_{12}$aryl, and $R^{15}$ is optionally substituted by one or more halogen, —$C_{1-8}$alkyl, or $C_{1-8}$alkoxy-$C_{1-8}$alkyl-; and $n_7$ is independently 0, 1, 2, 3 or 4.

25. The compound of claim 1, wherein

Degron is

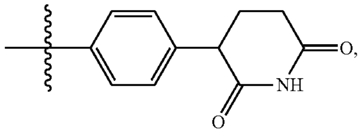

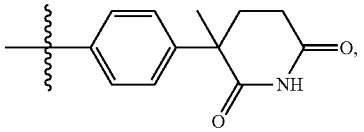

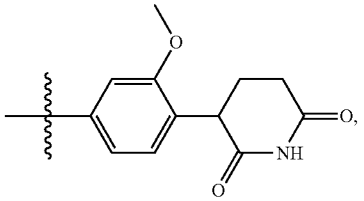

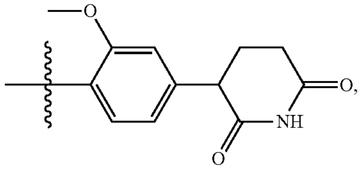

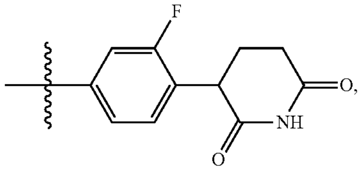

-continued

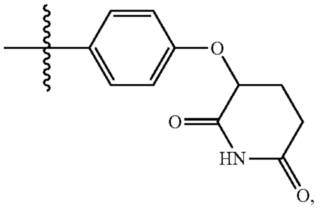

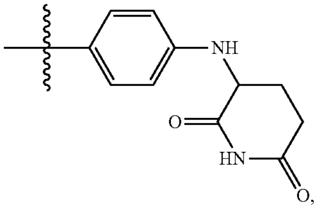

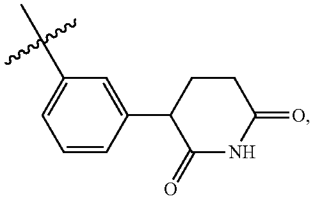

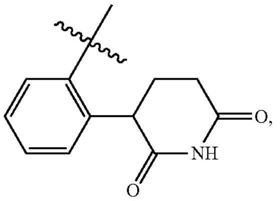

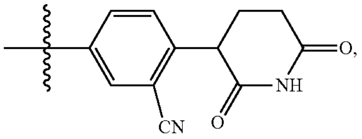

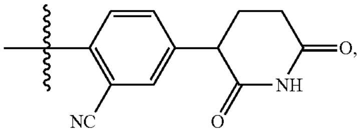

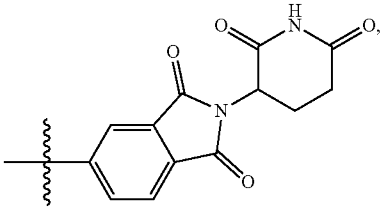

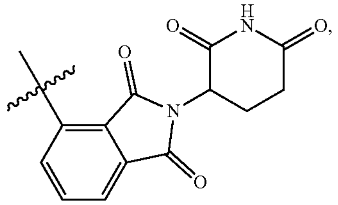

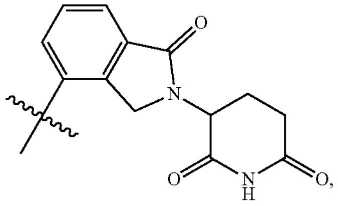

-continued
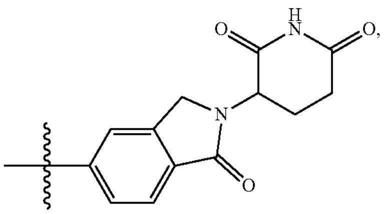
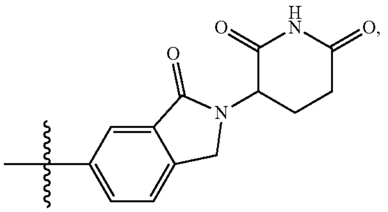
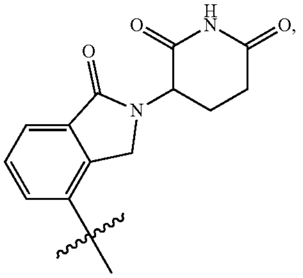
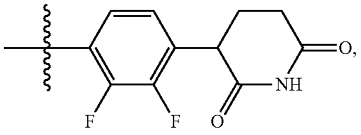
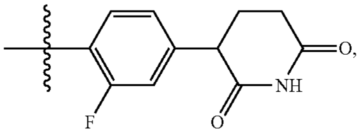
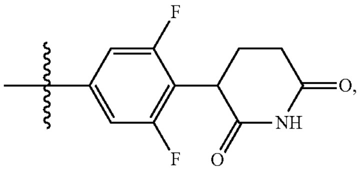
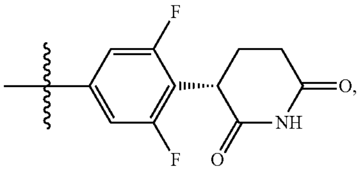
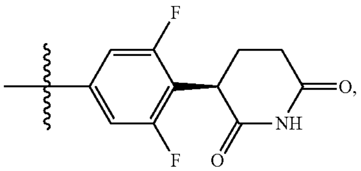
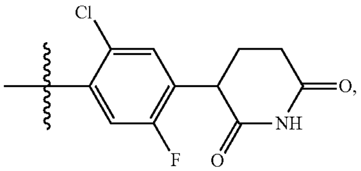
-continued
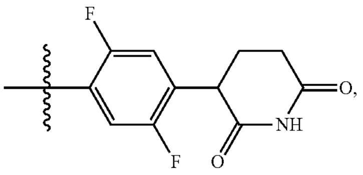
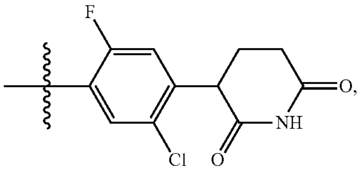
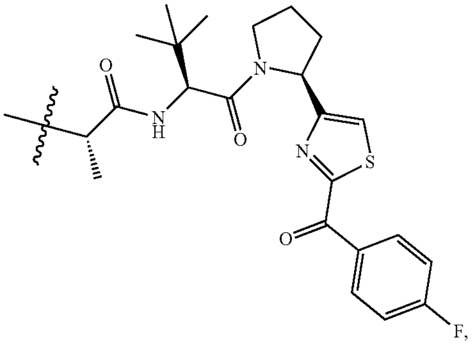
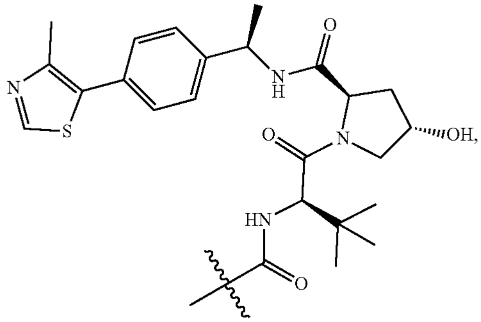
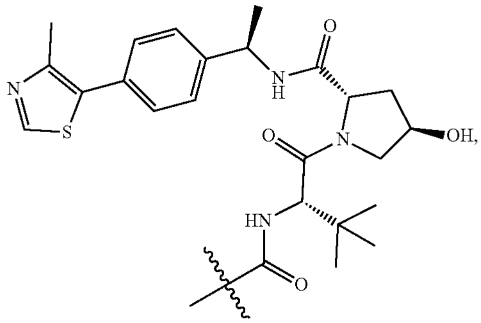
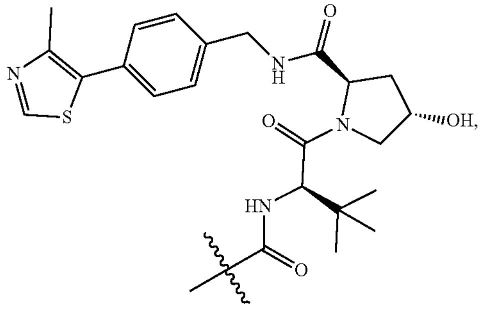

-continued
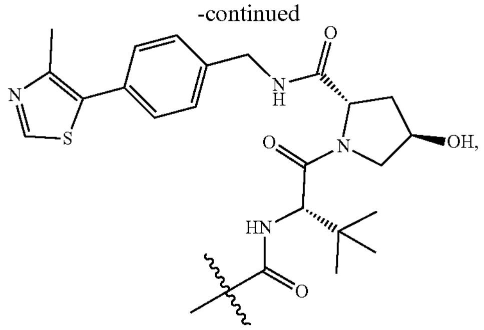
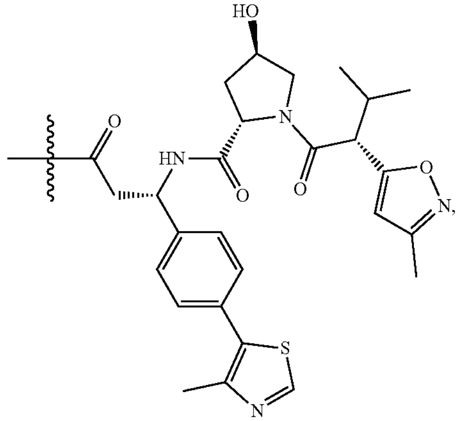
or
-continued
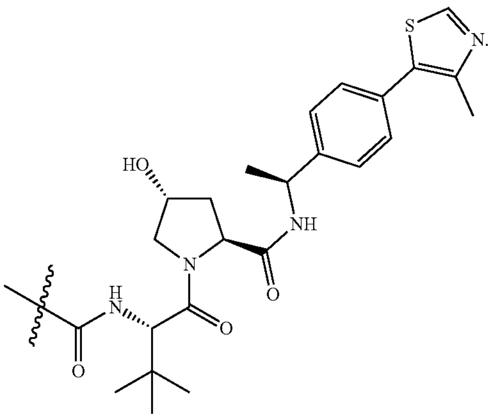
26. A compound selected from
1
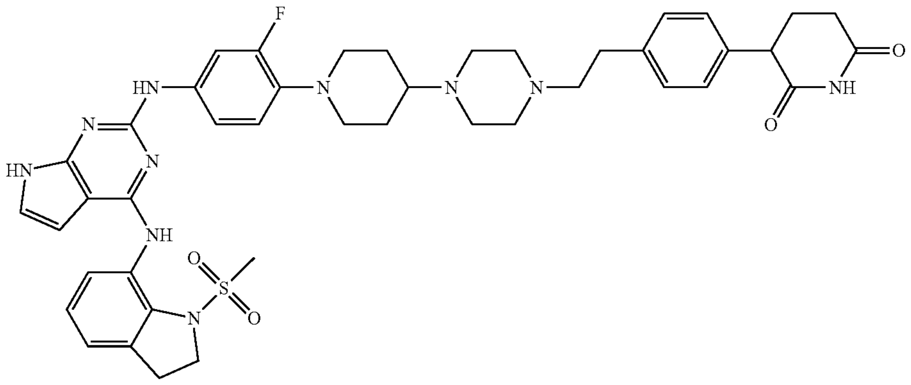
2
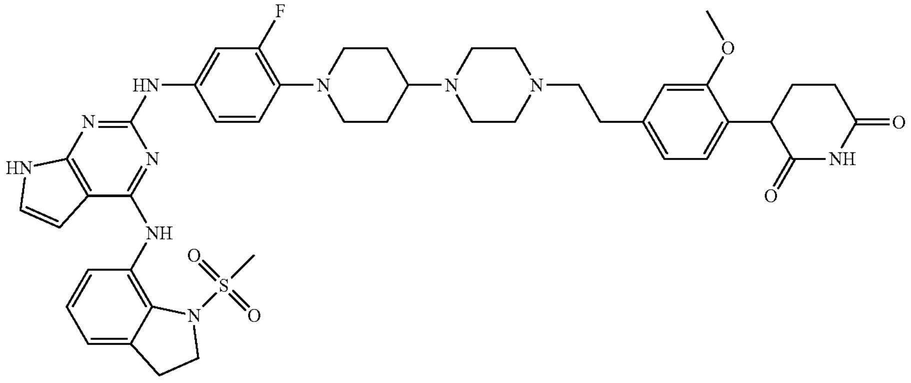

-continued
3
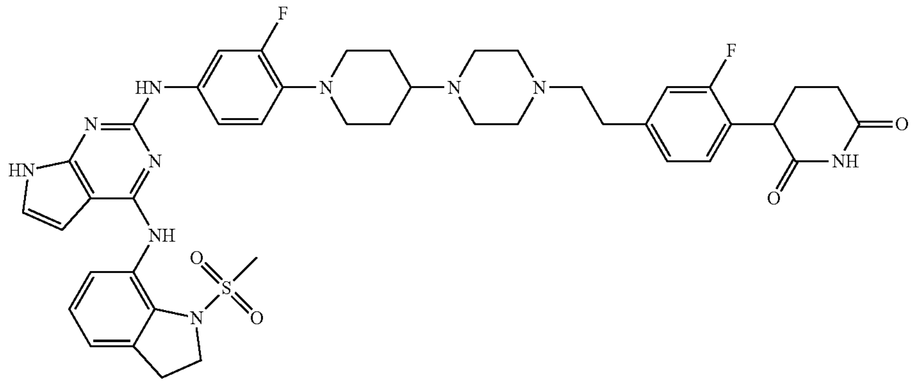
4
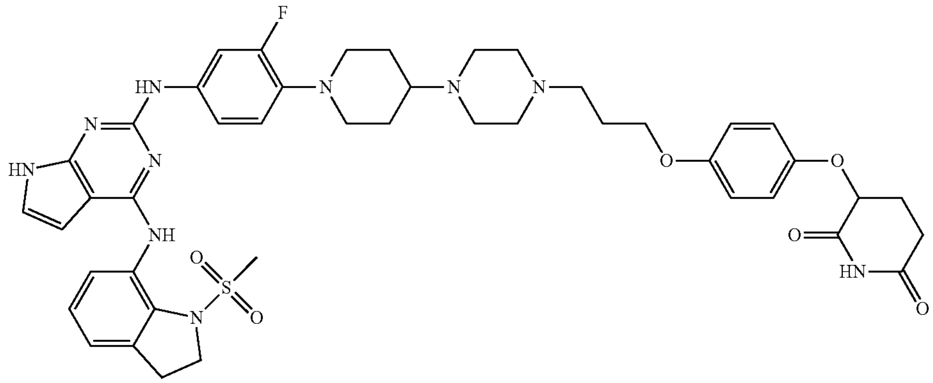
5
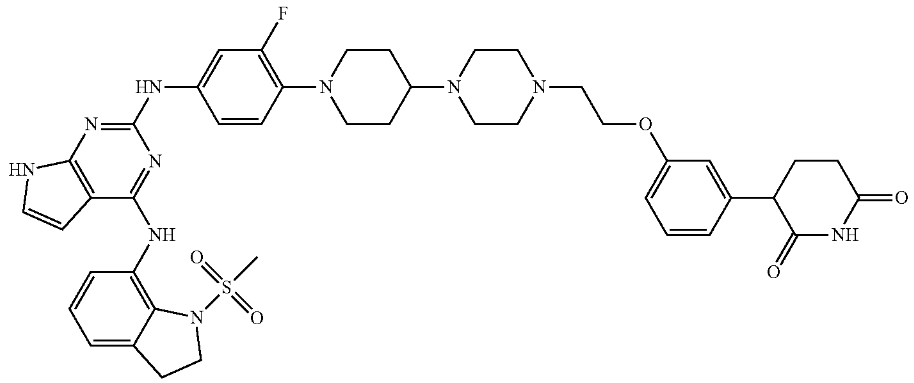
6
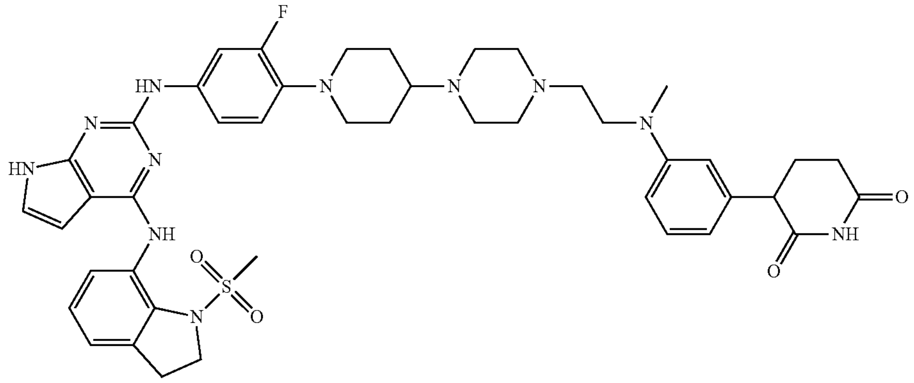

-continued
7
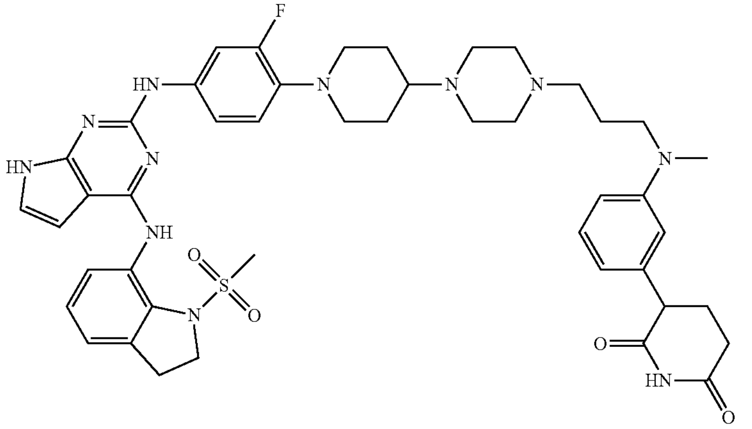
8
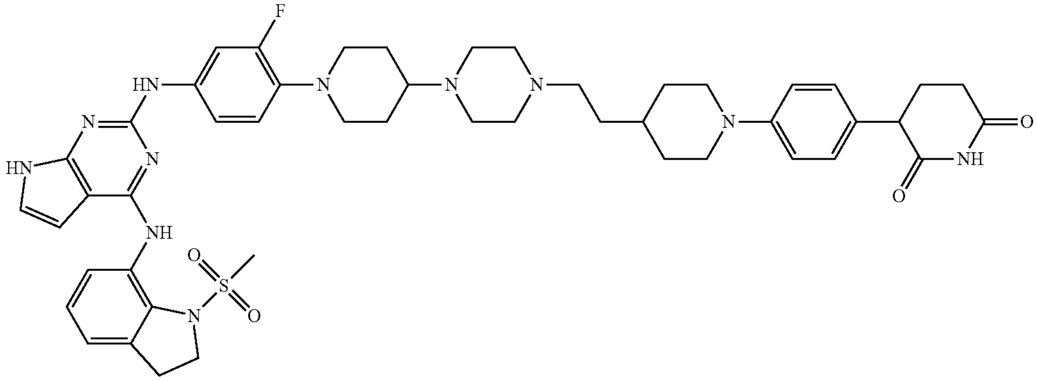
9
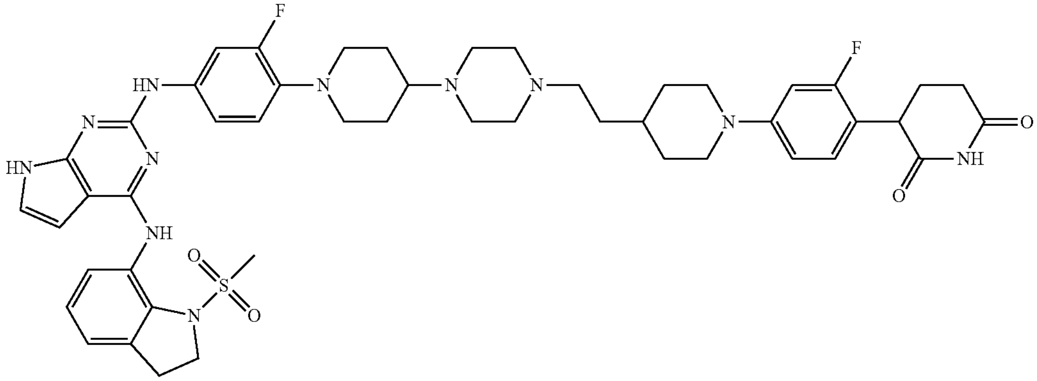
10
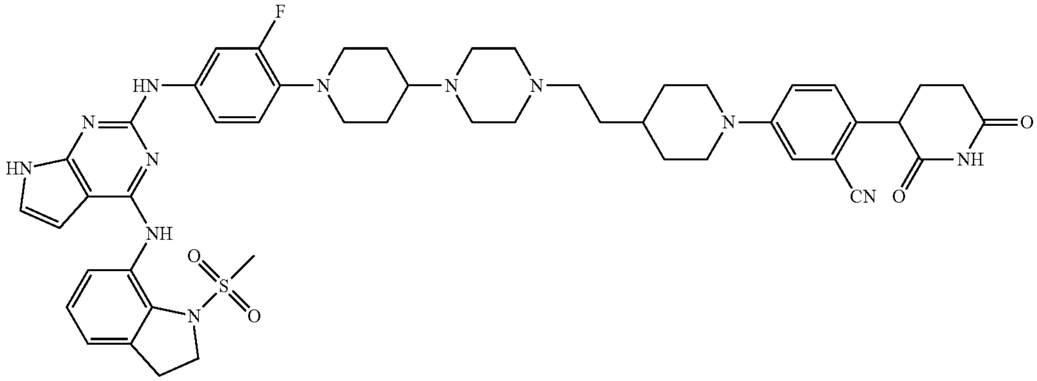

-continued
11
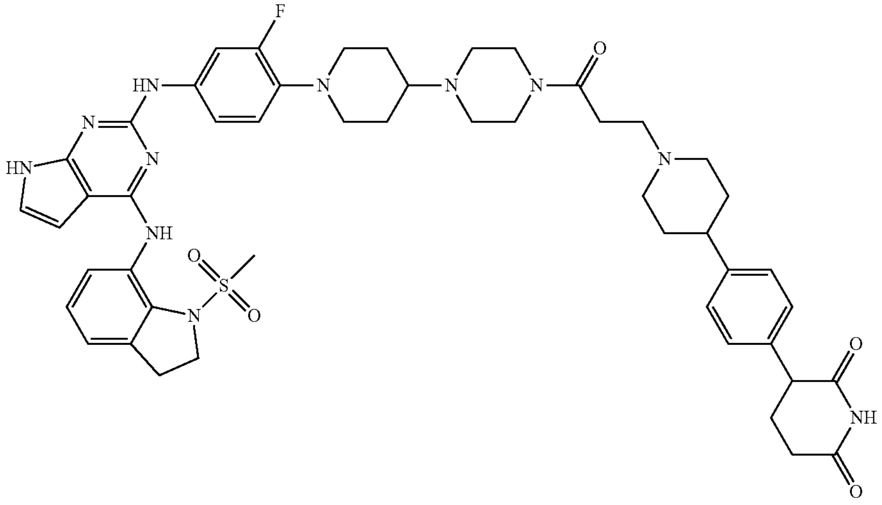
12
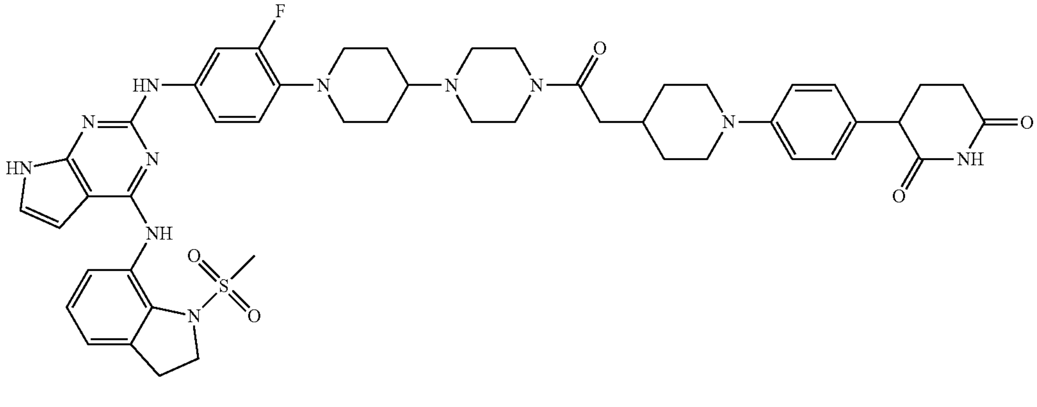
13
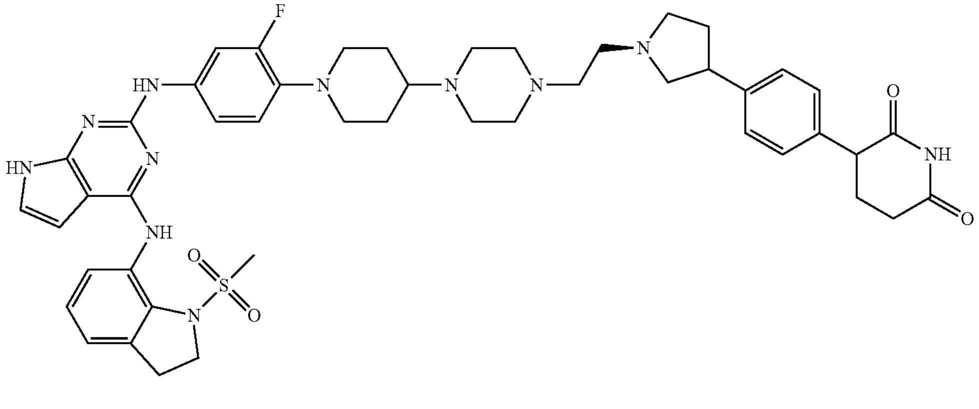

-continued
14
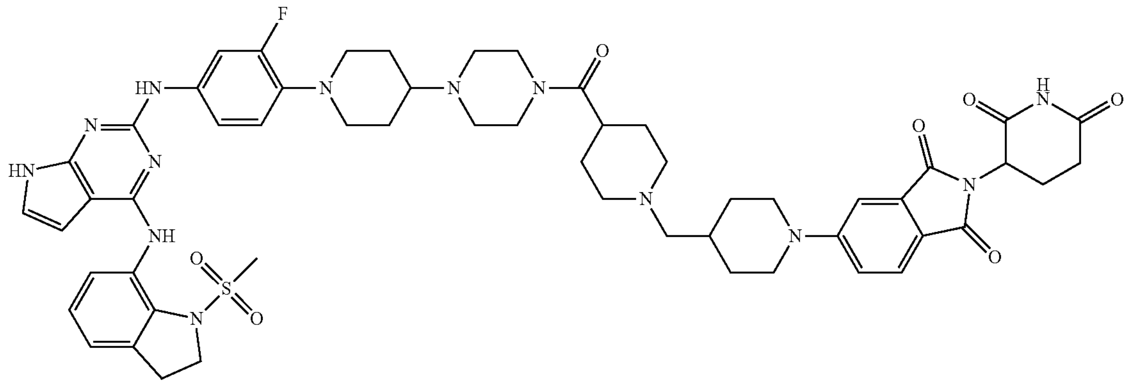
15
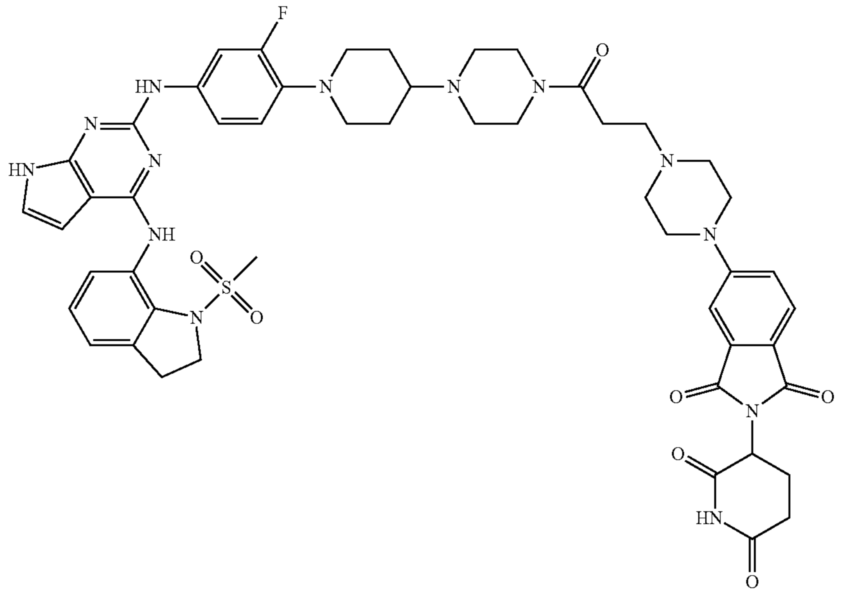
16
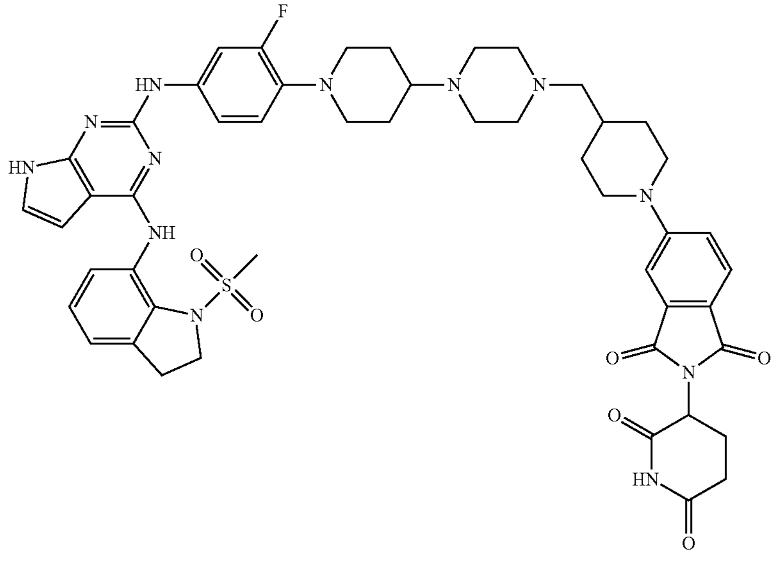

-continued
17
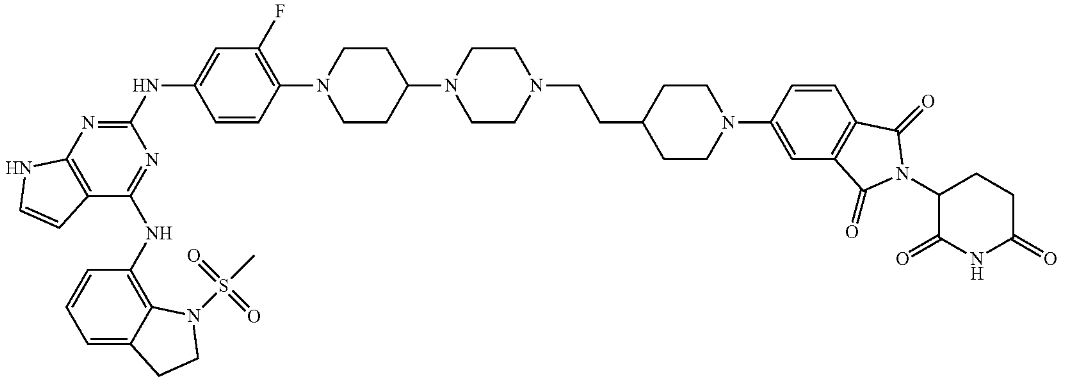
18
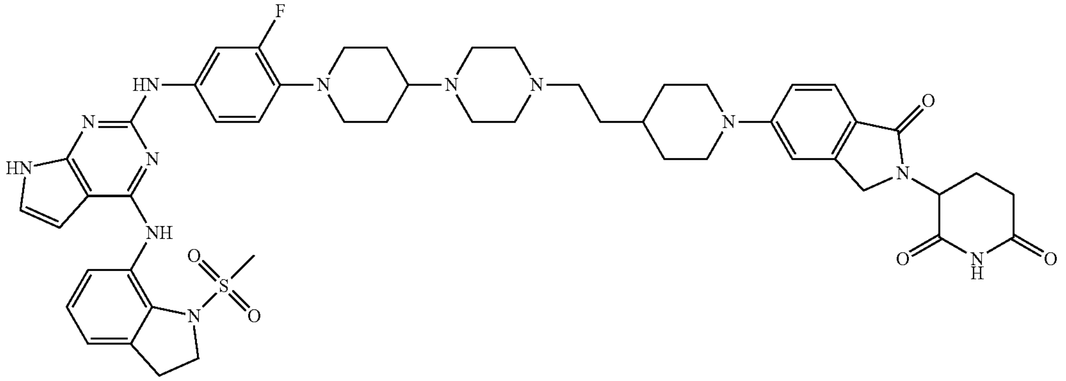
19
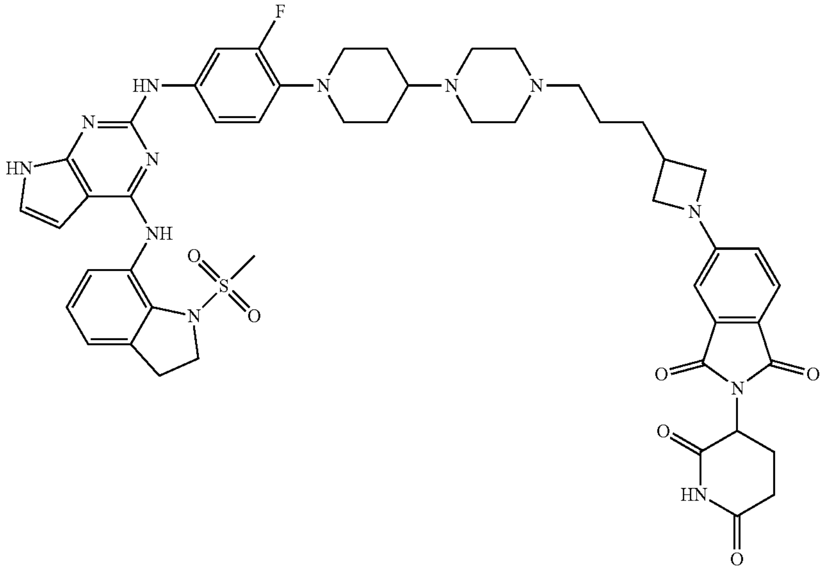

-continued
20
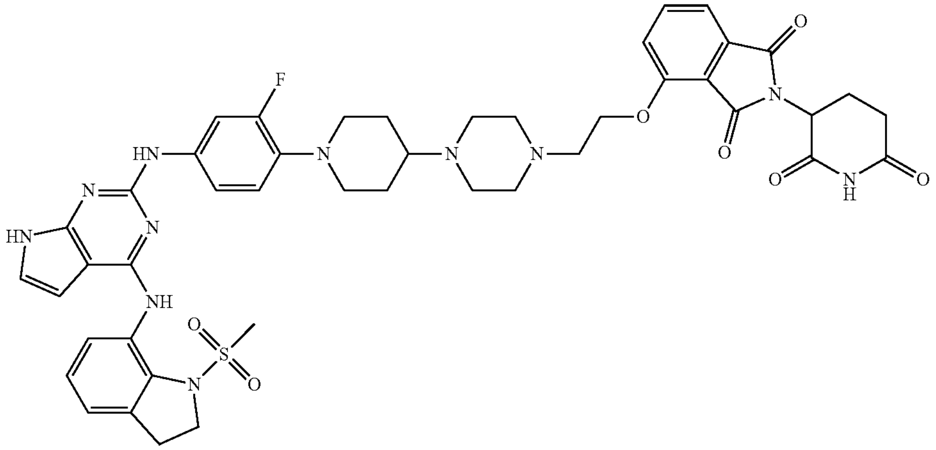
21
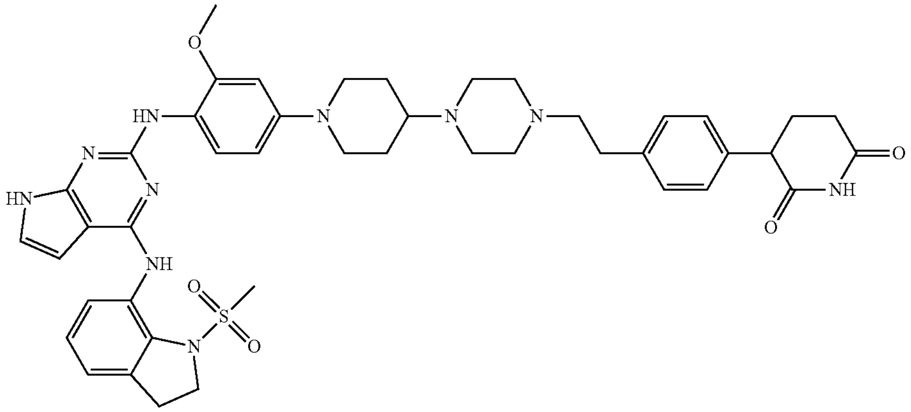
22
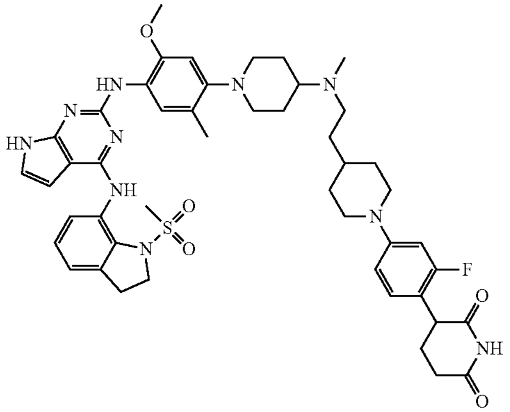
23
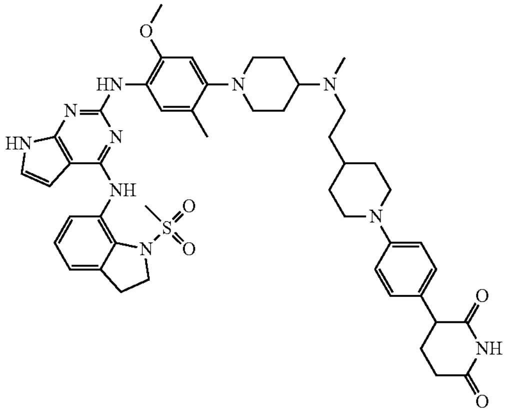

-continued
24
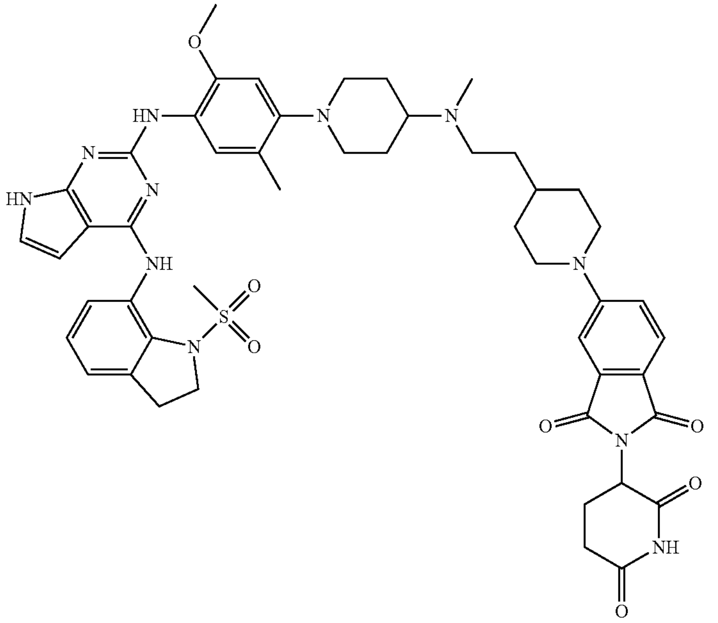
25
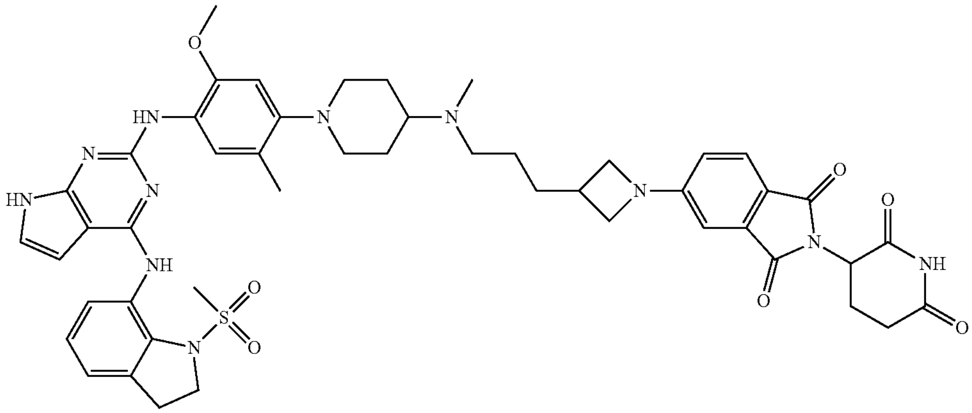
26
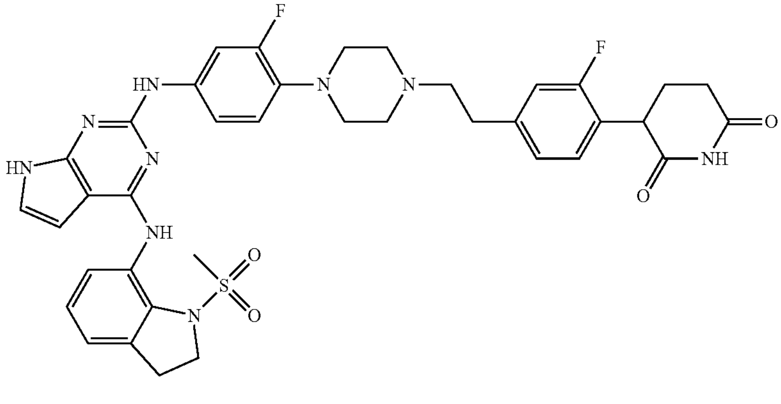

-continued
27
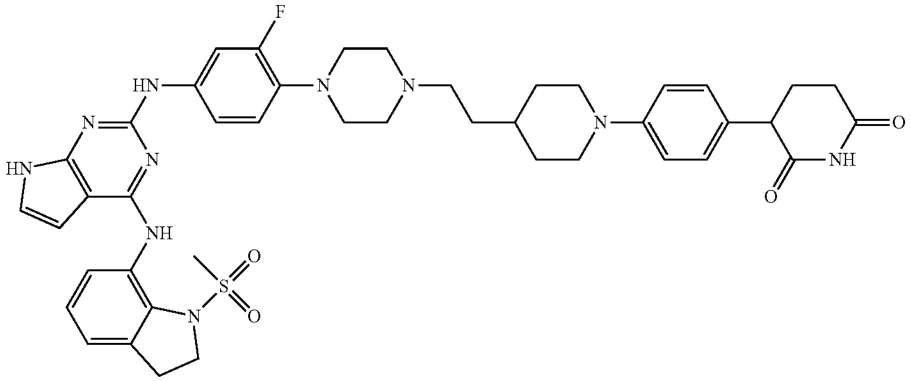
28
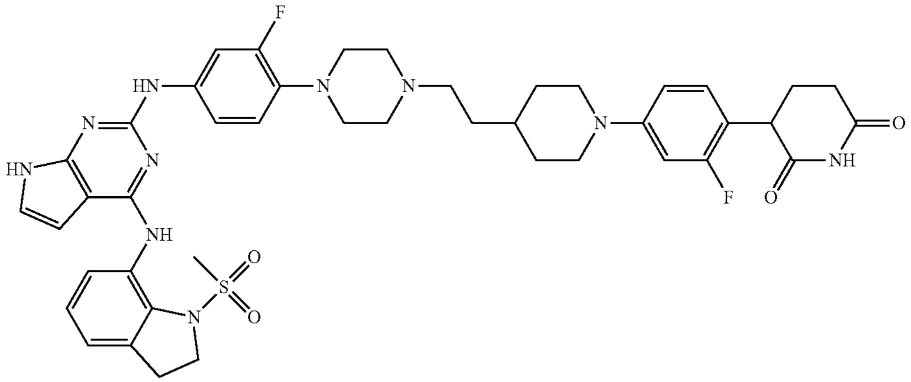
29
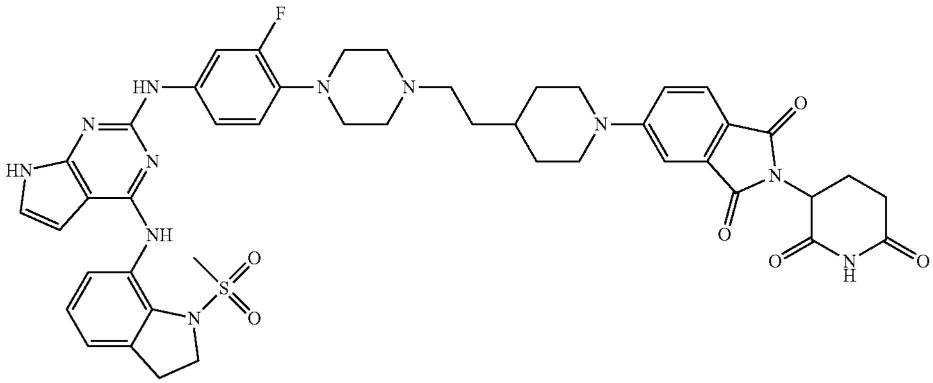

-continued
30
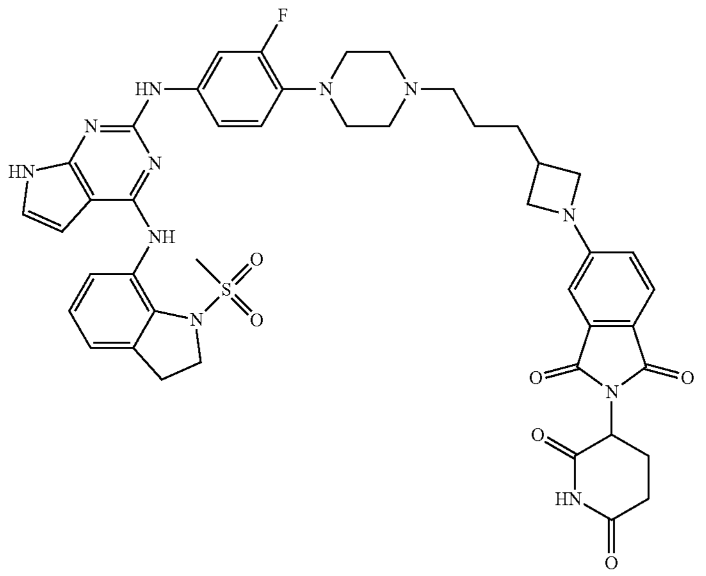
31
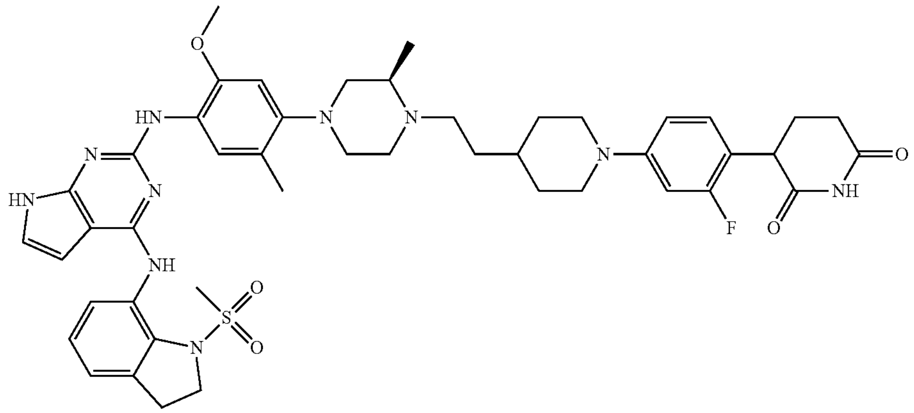
32
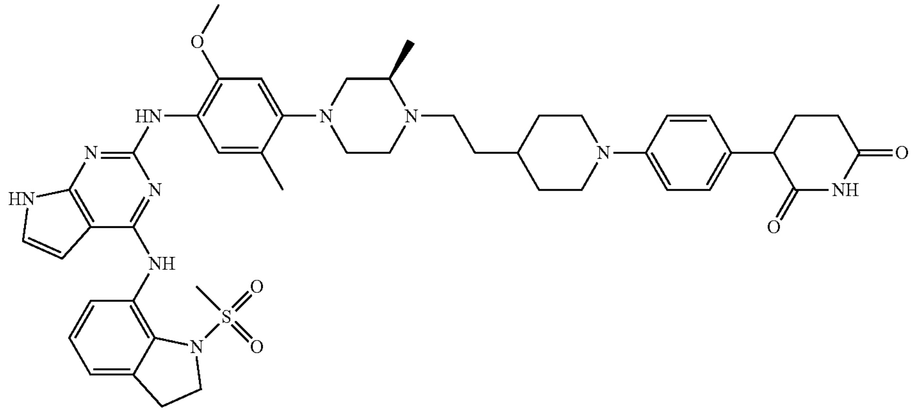

-continued
33
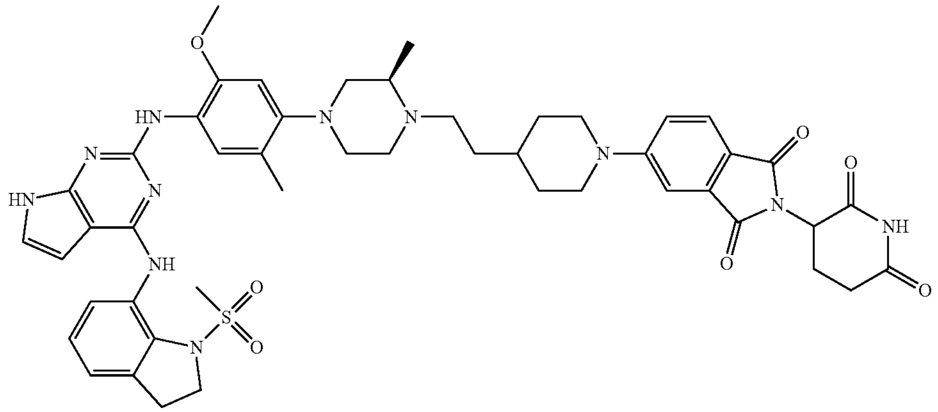
34
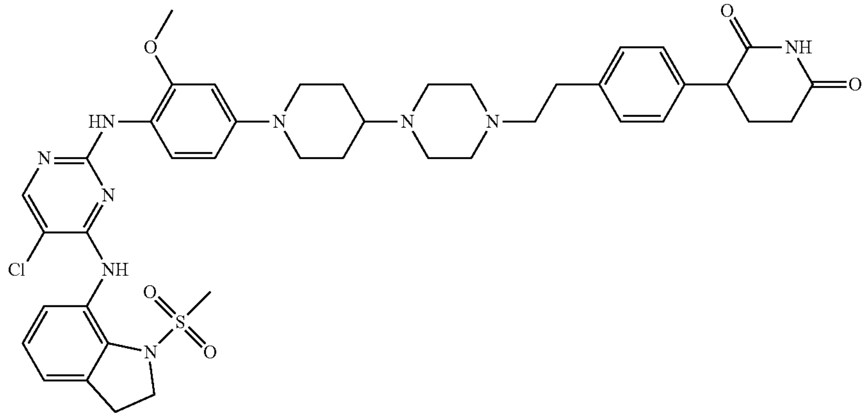
35
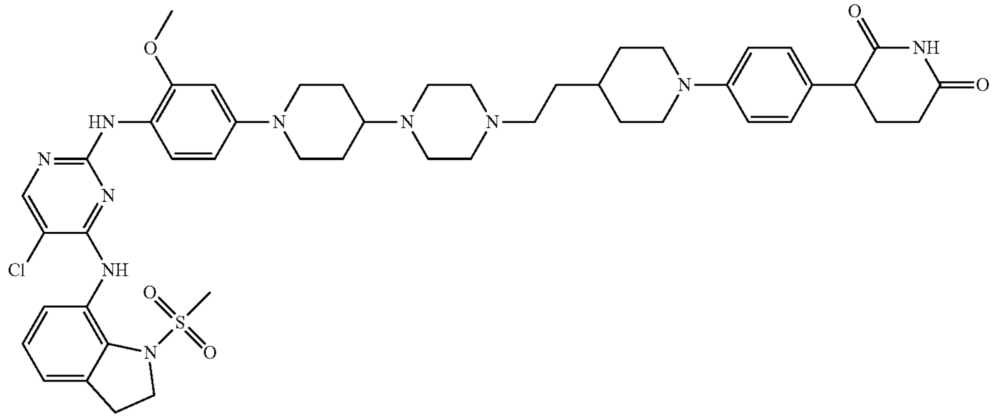

-continued
36
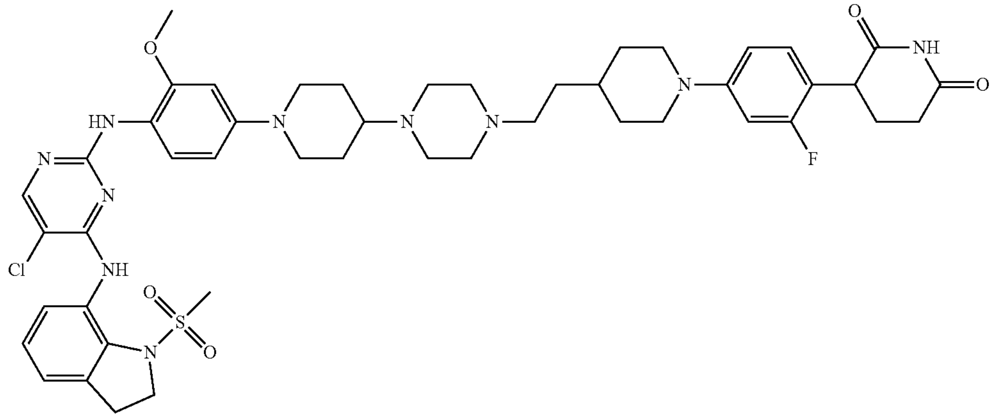
37
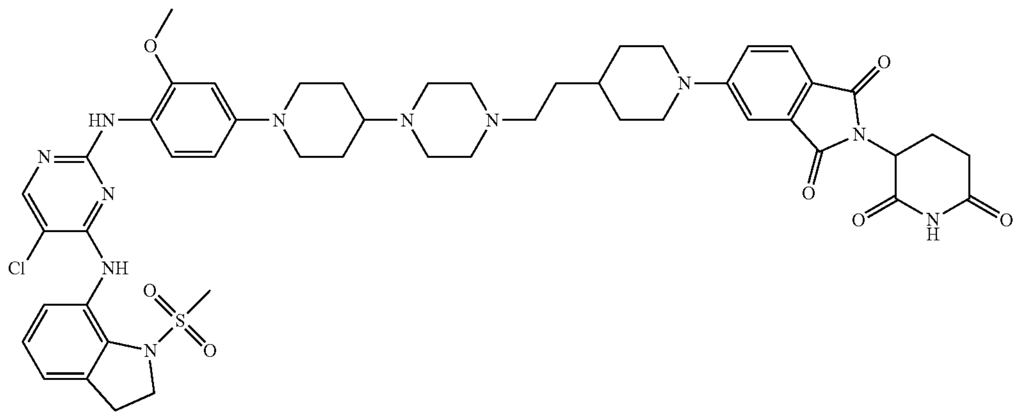
38
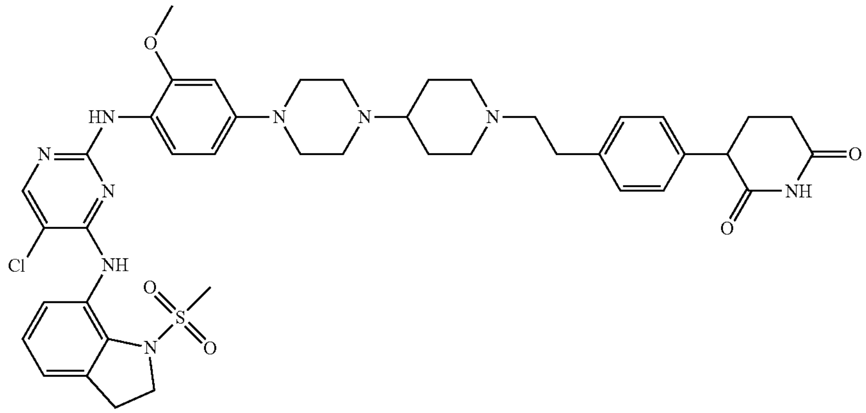

-continued
39
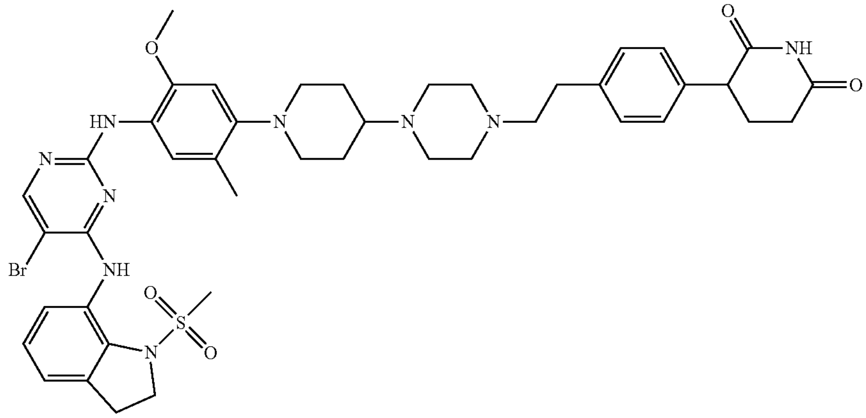
40
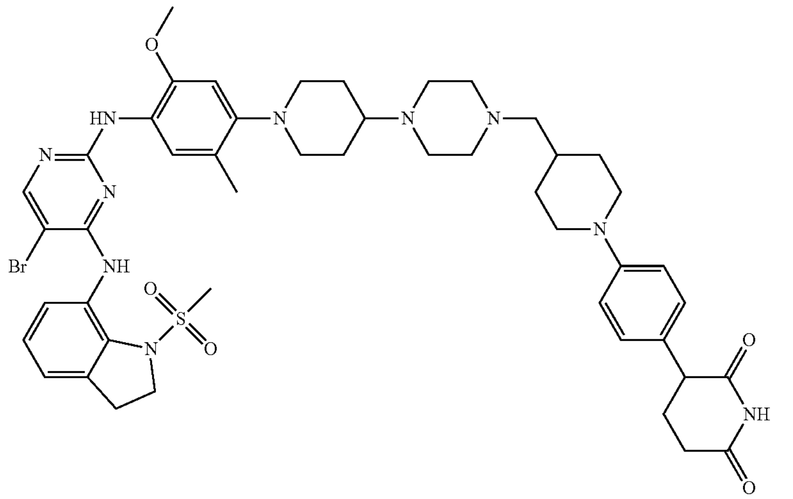
41
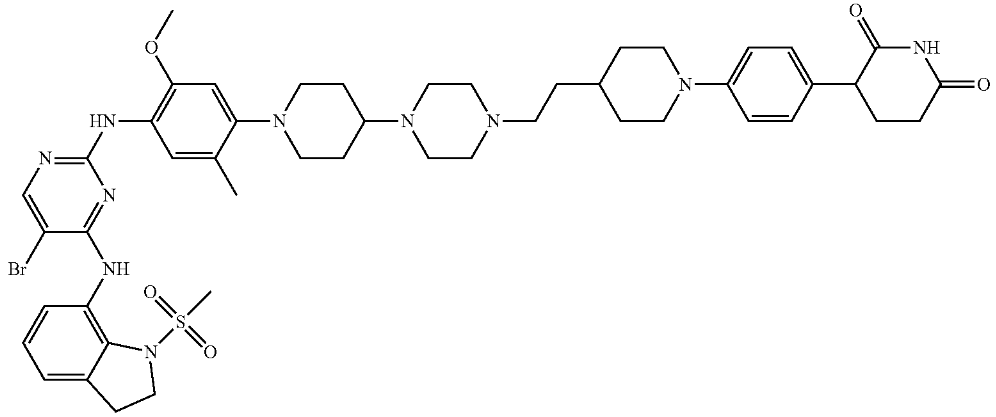

-continued
42
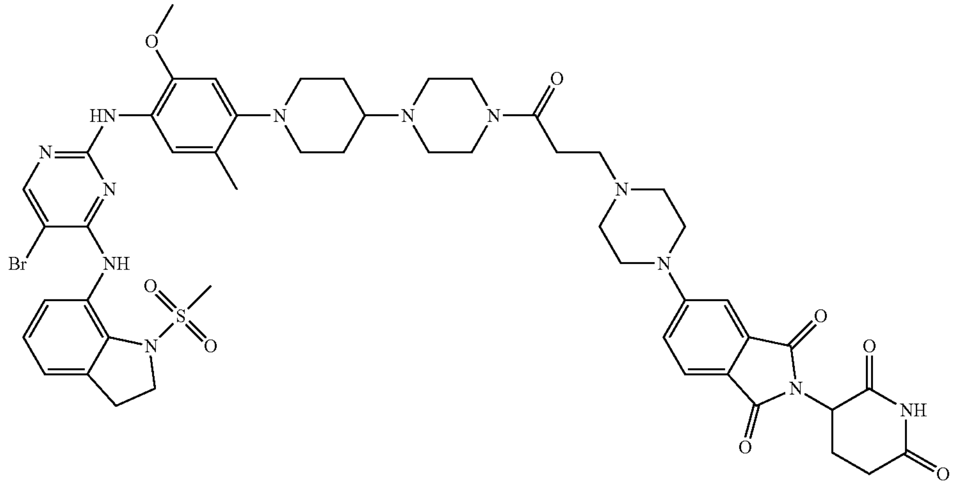
43
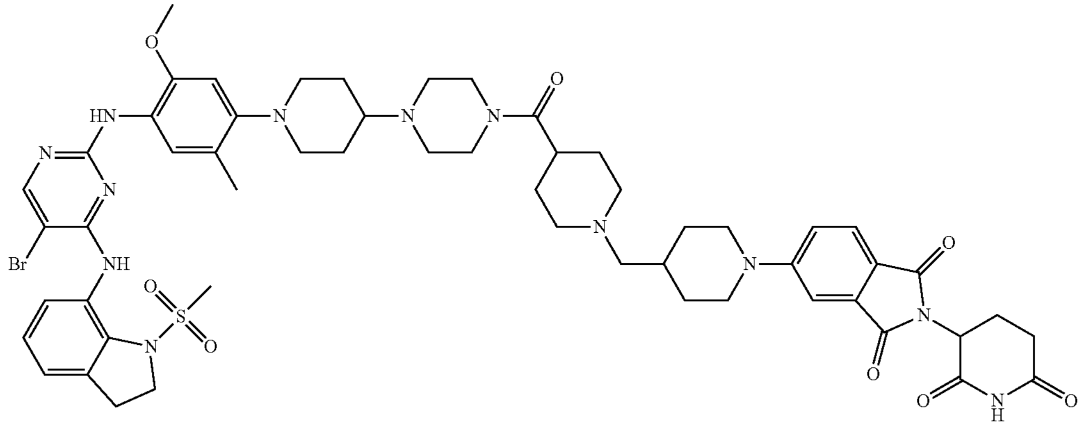
44
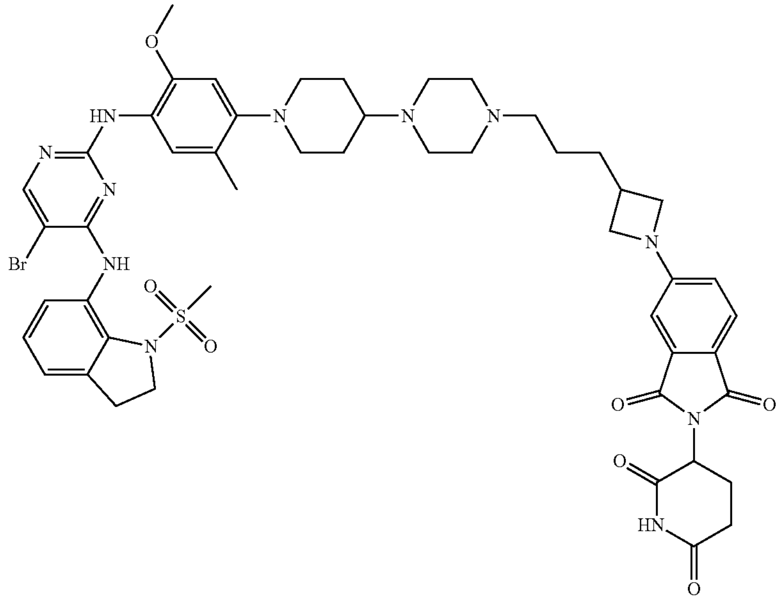

-continued
45
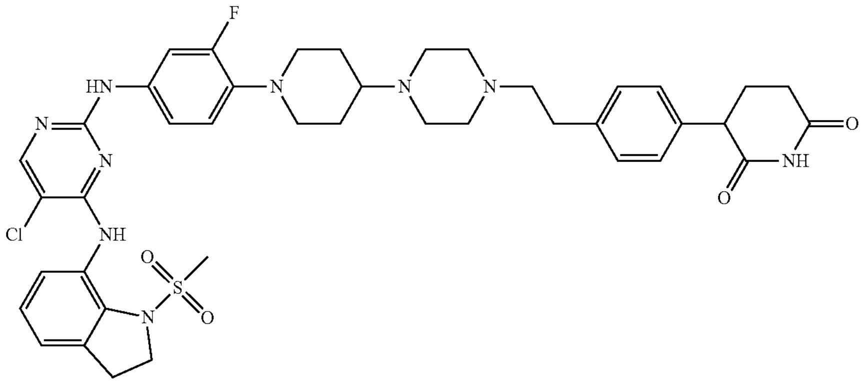
46
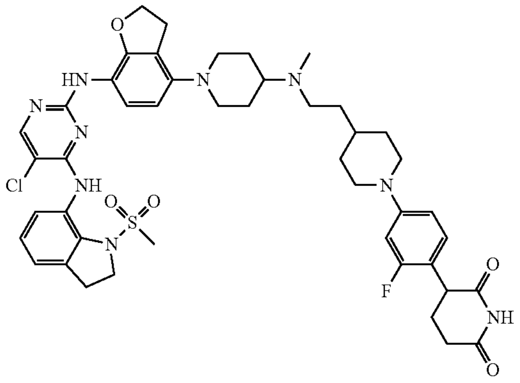
47
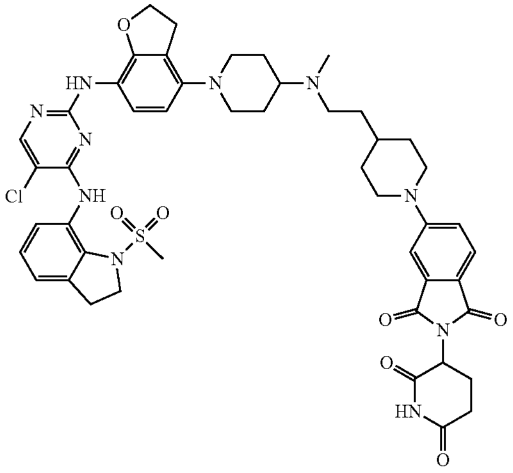
48
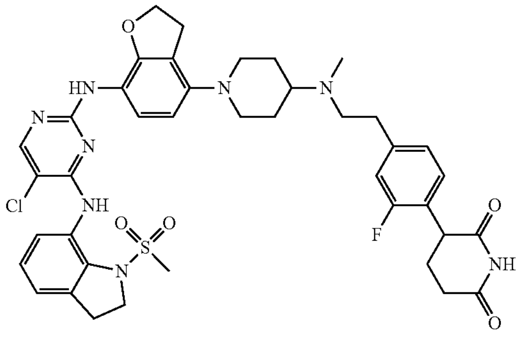
49
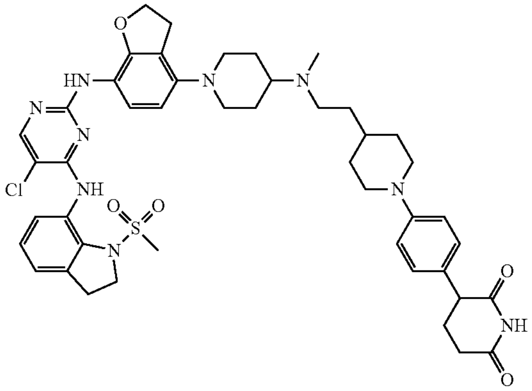

-continued
50
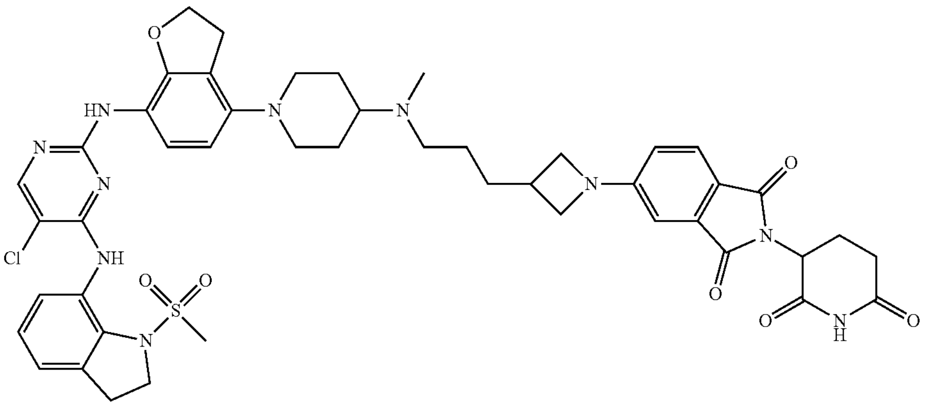
51
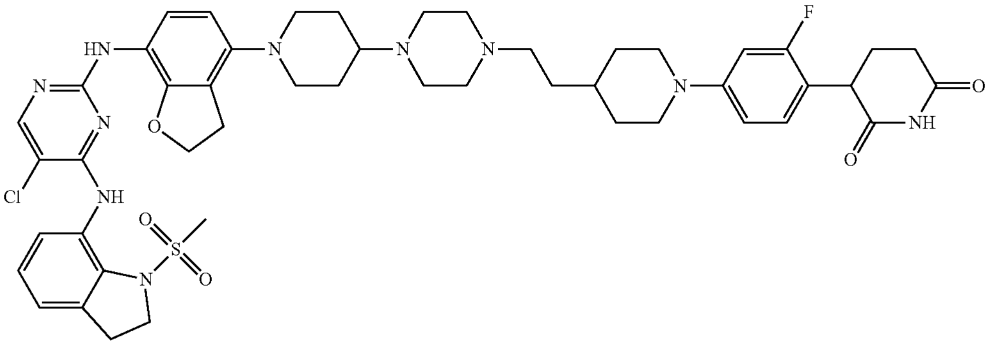
52
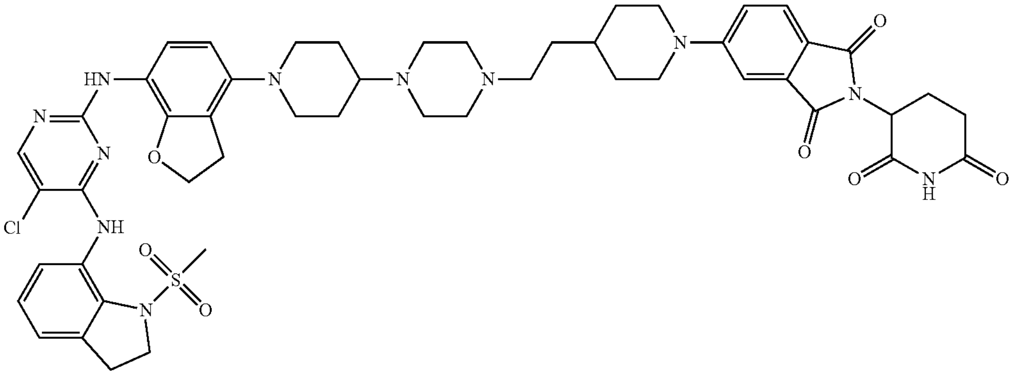
53
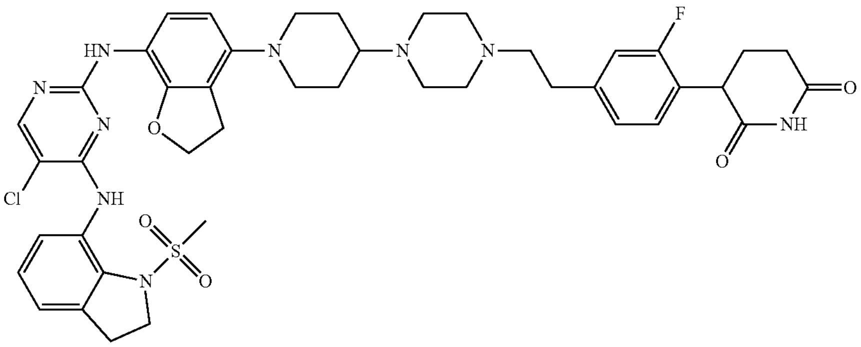

-continued
54
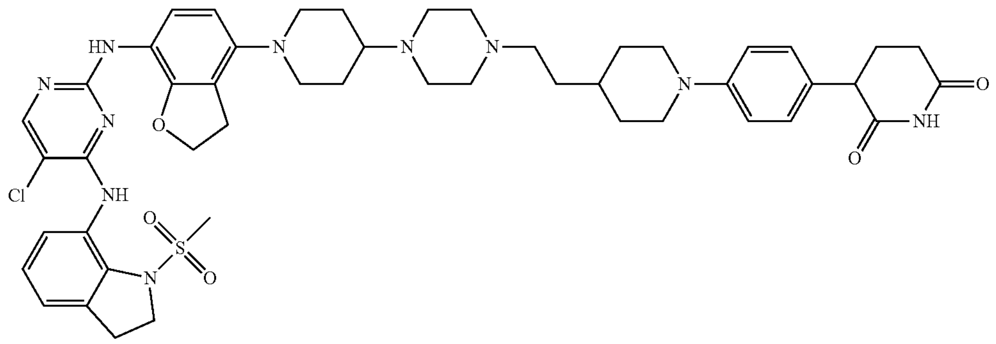
55
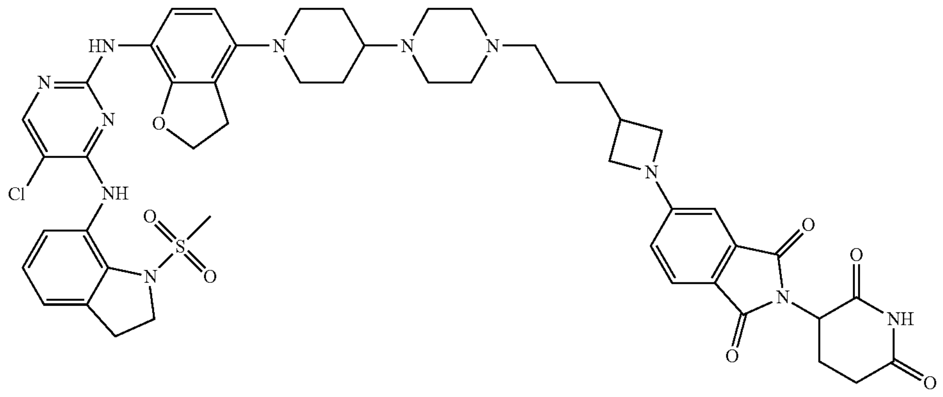
56
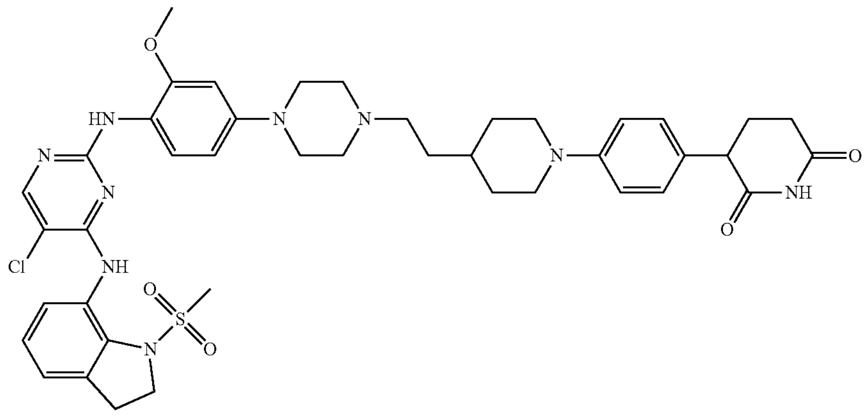
57
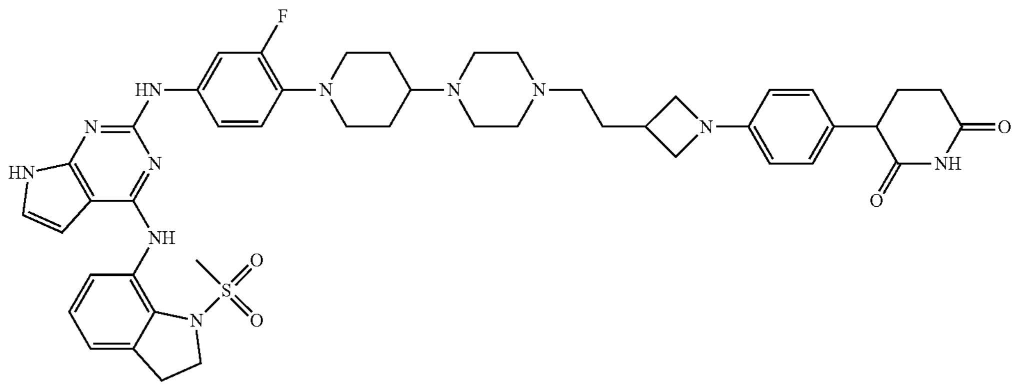

-continued
58
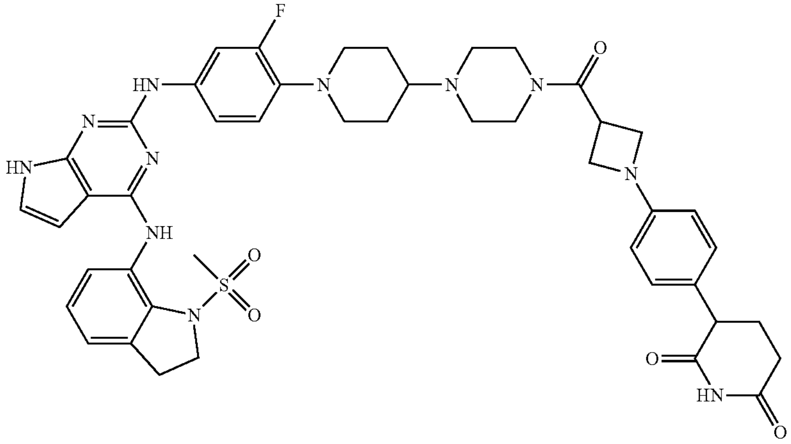
59
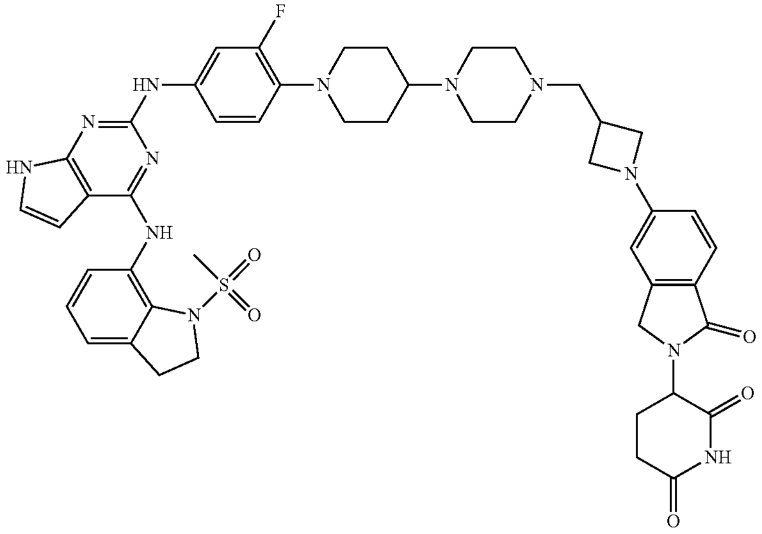
60
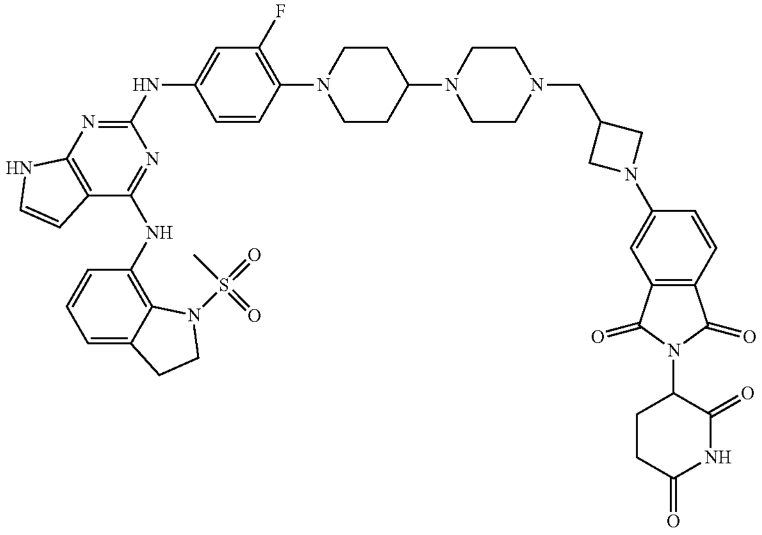

-continued
61
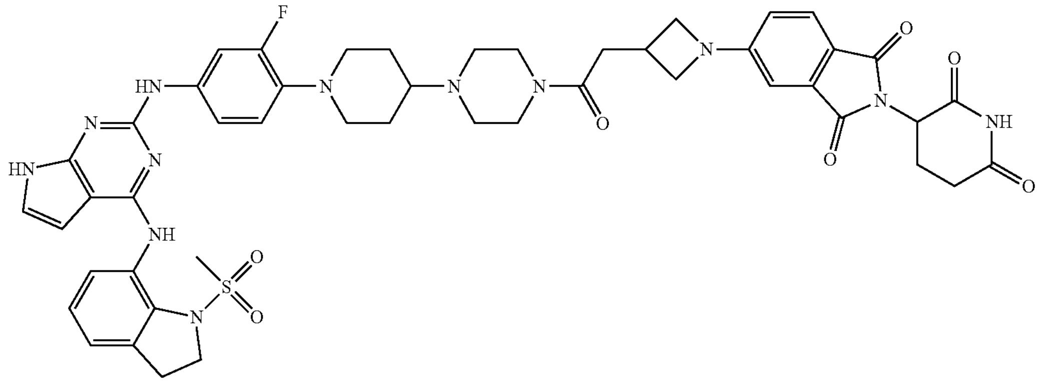
62
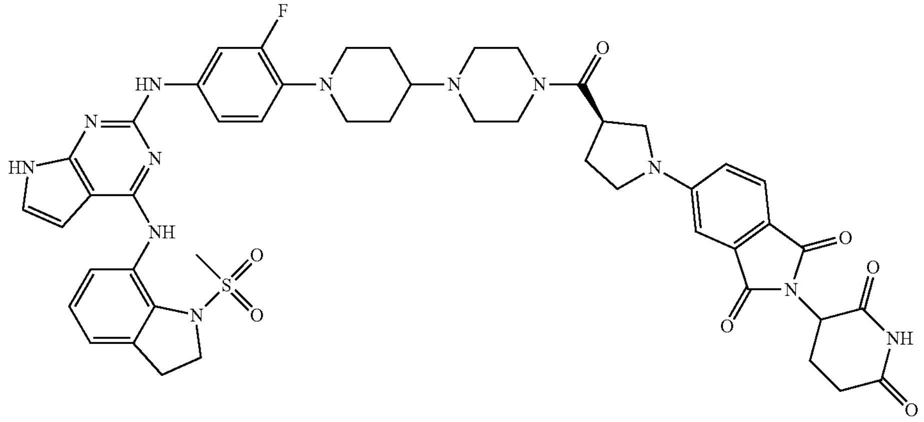
63
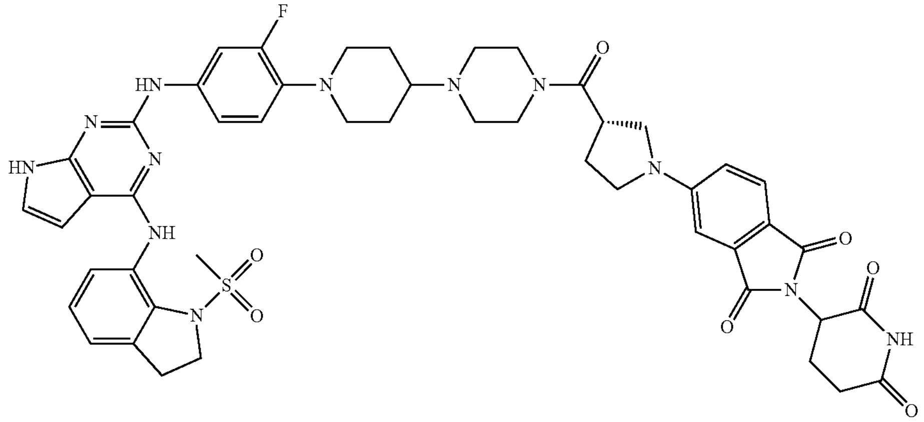

-continued
64
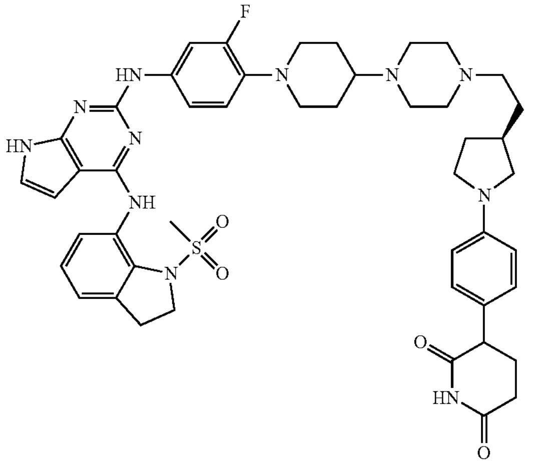
65
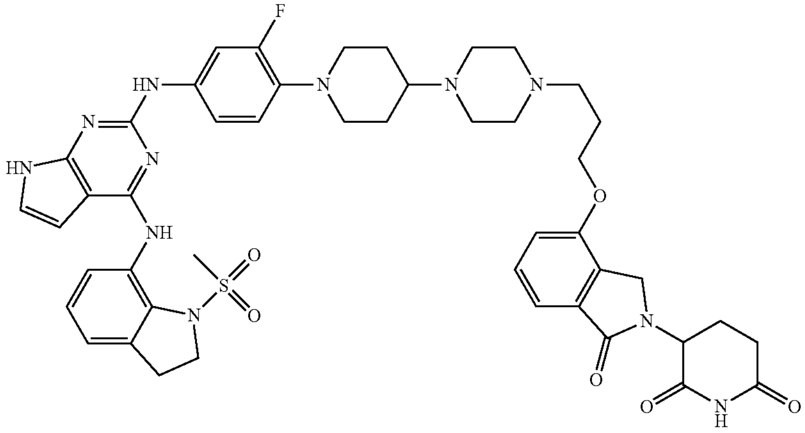
66
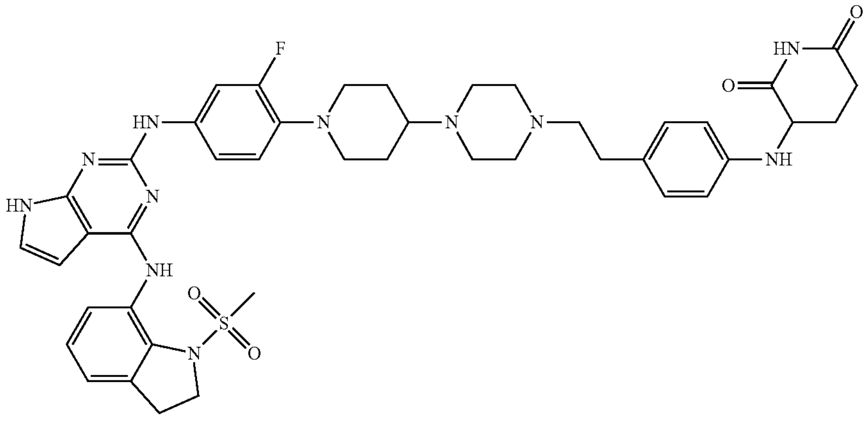

-continued
67
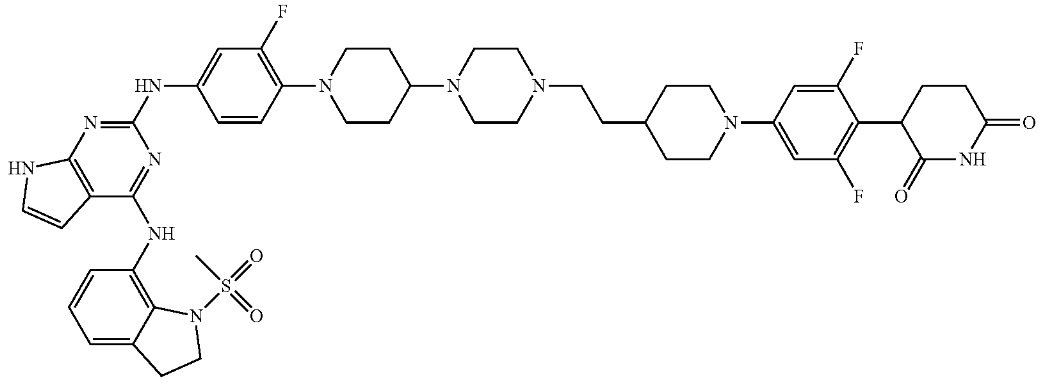
68
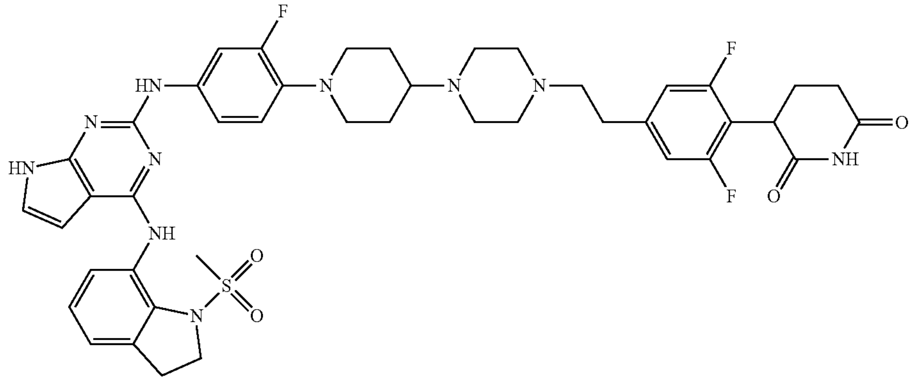
69
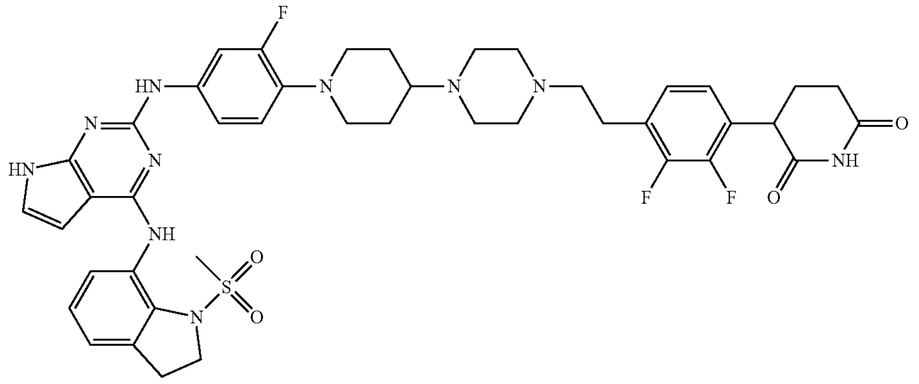
70
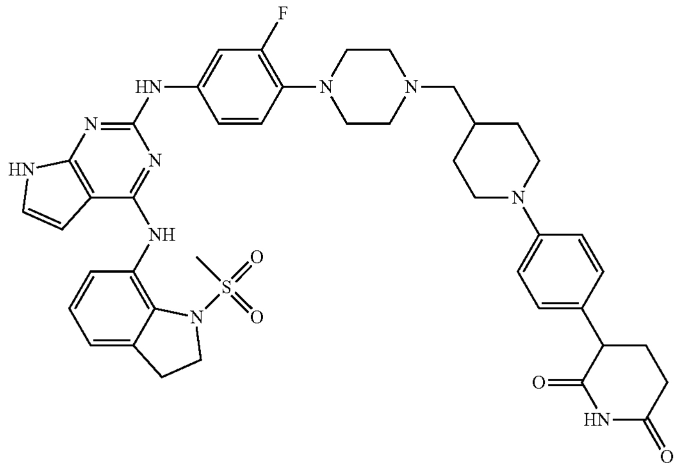

-continued
71
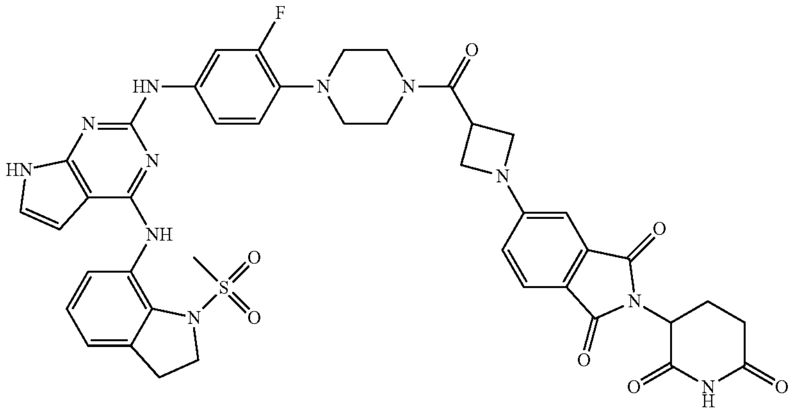
72
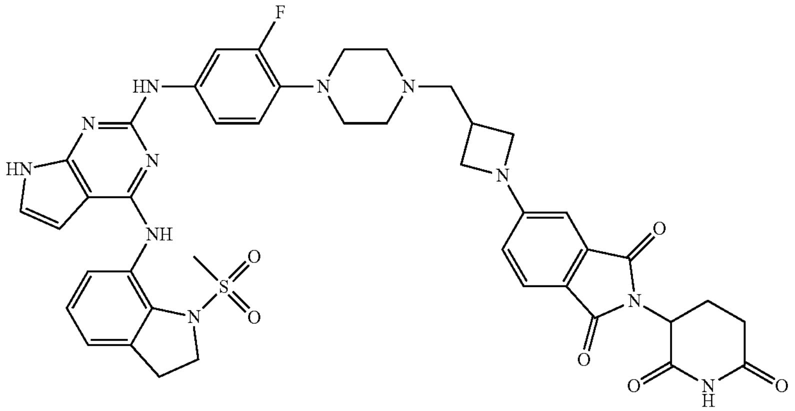
73
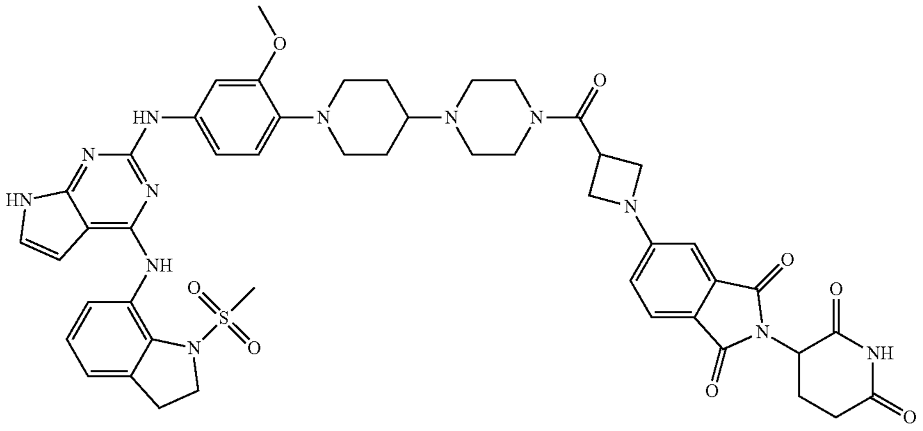

-continued
74
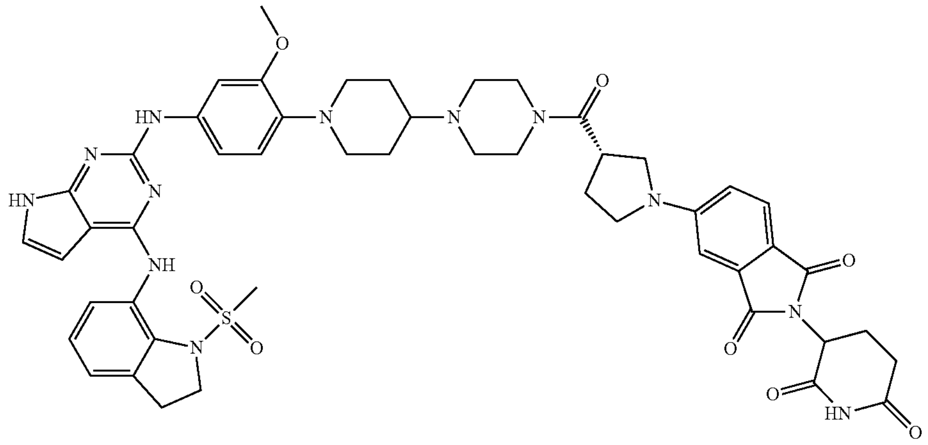
75
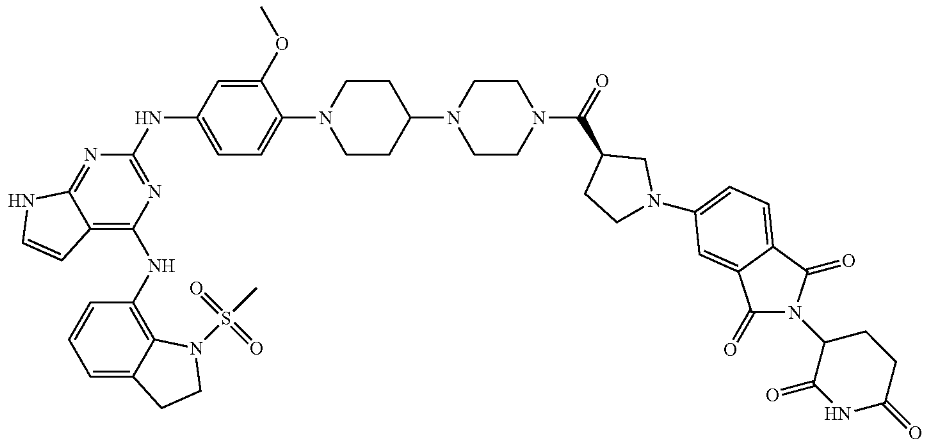
76
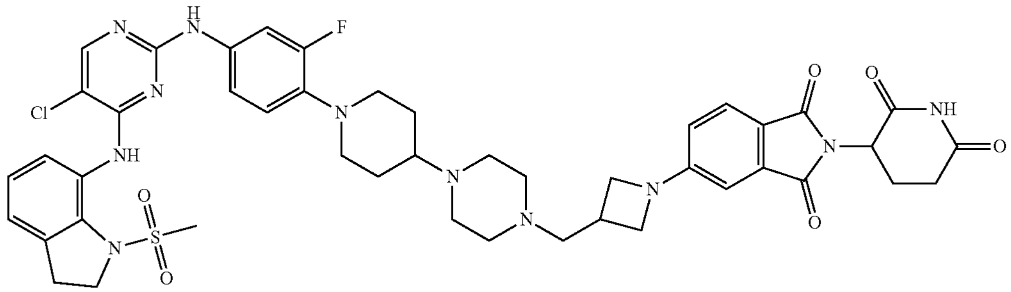
77
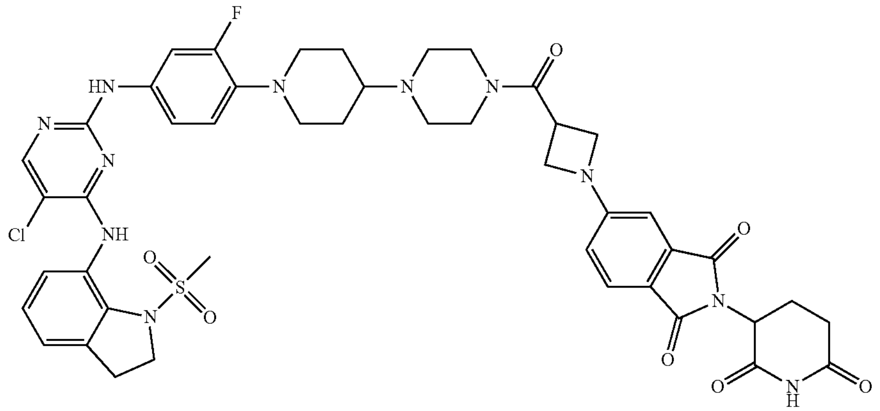

-continued
78
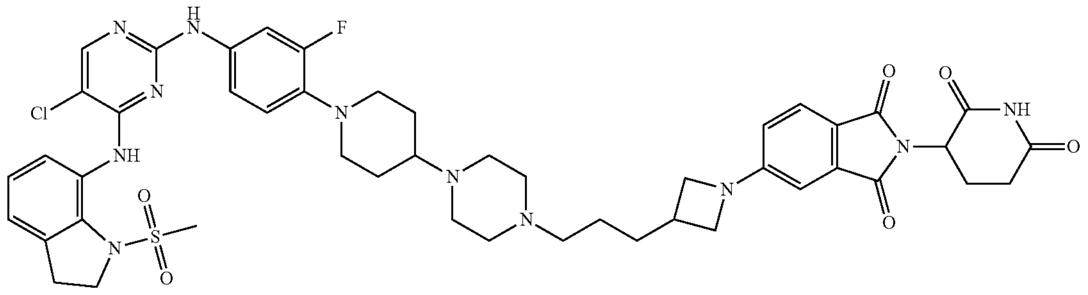
79
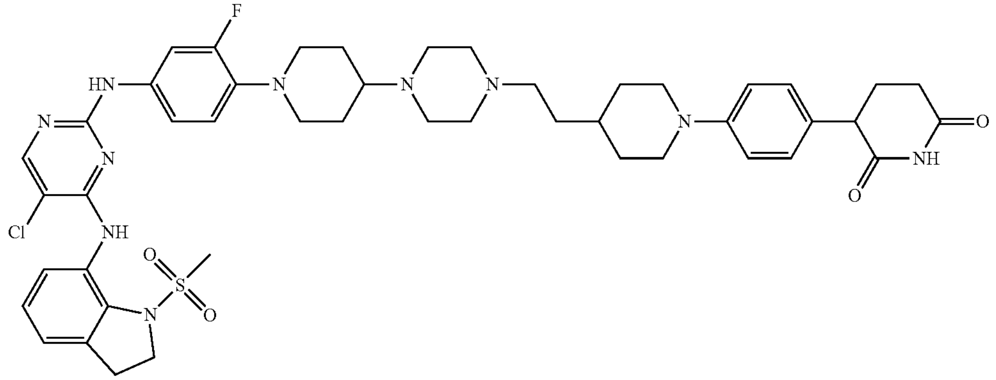
80
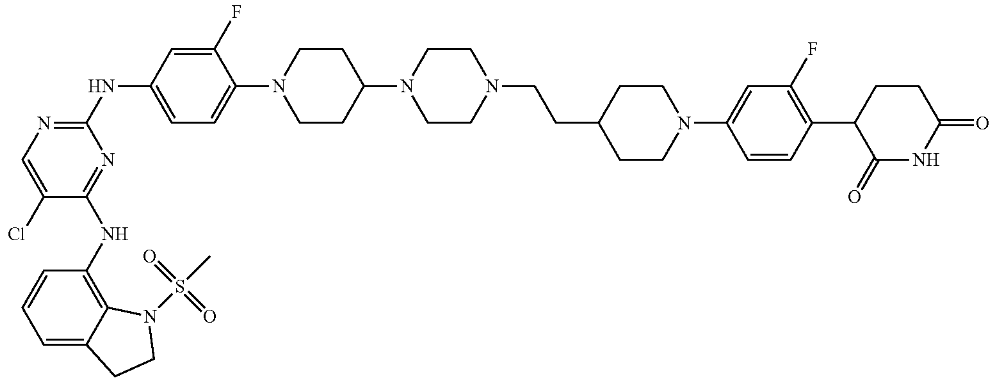
81
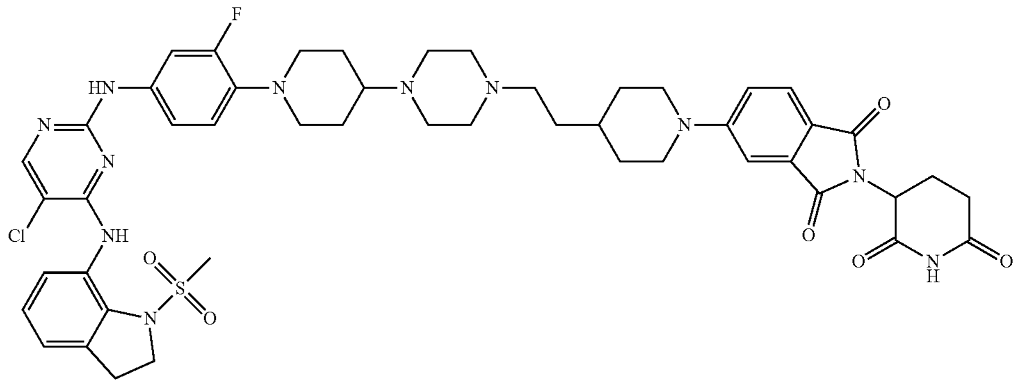

-continued
82
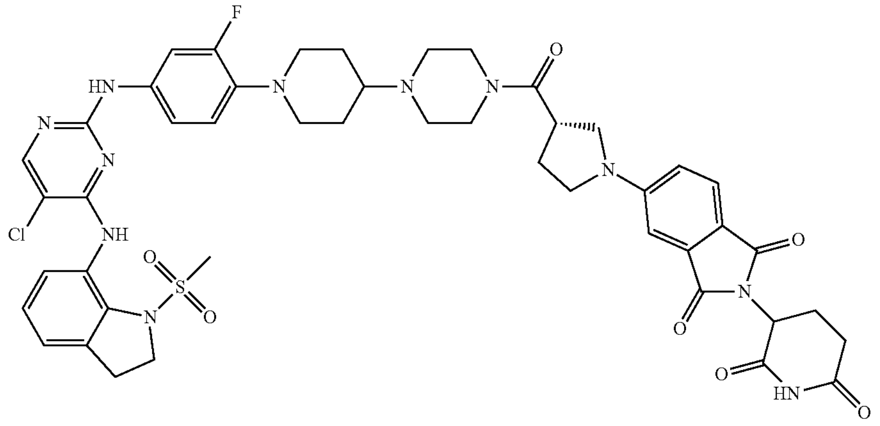
83
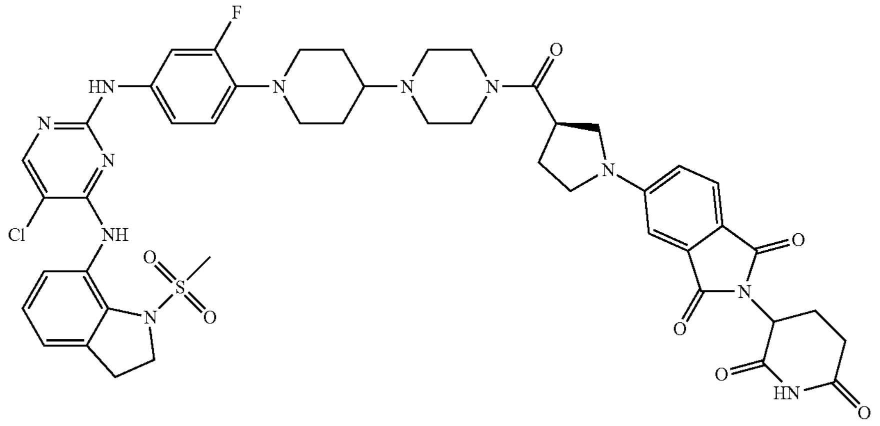
84
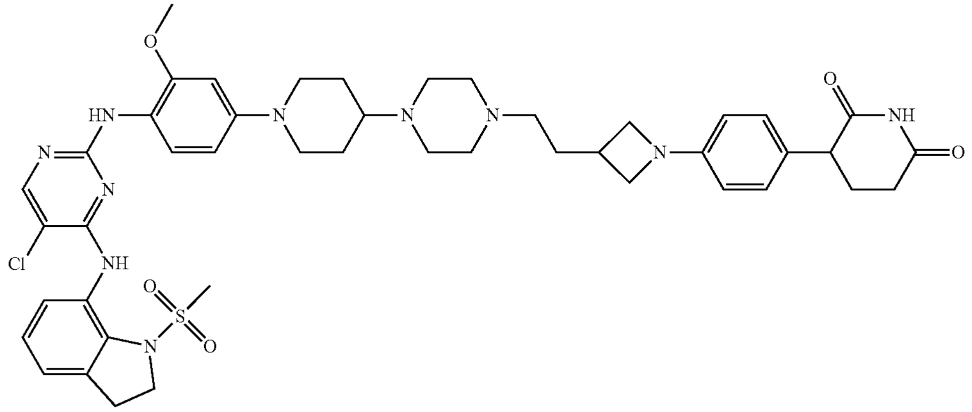

-continued
85
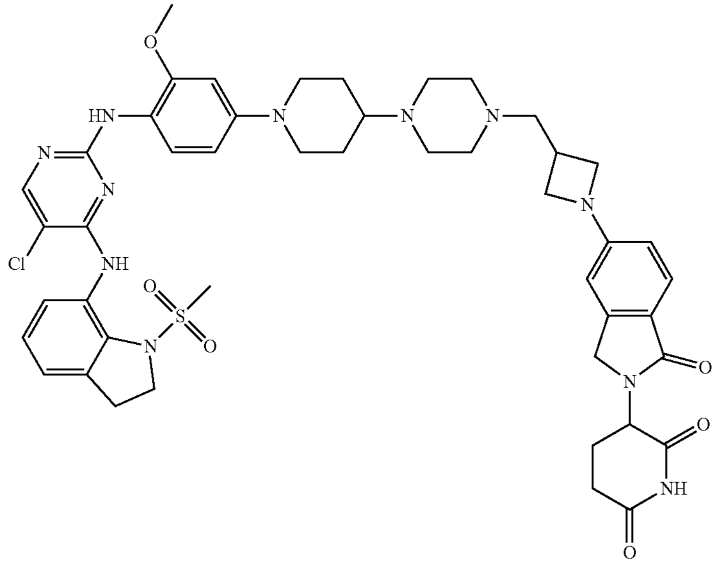
86
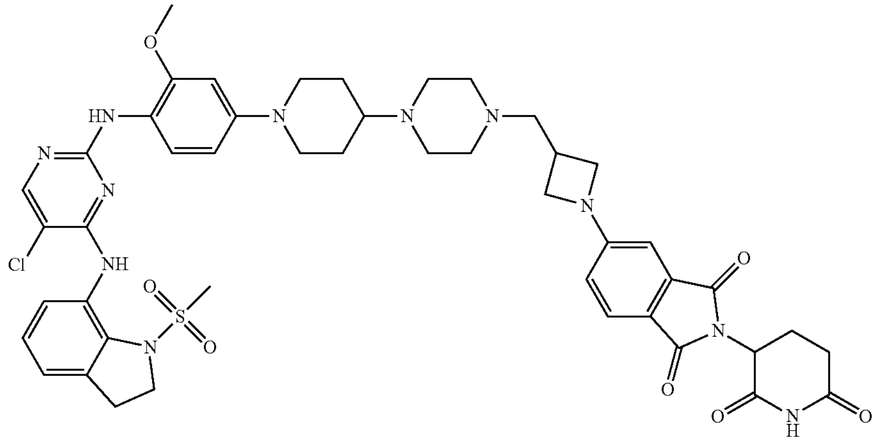
87
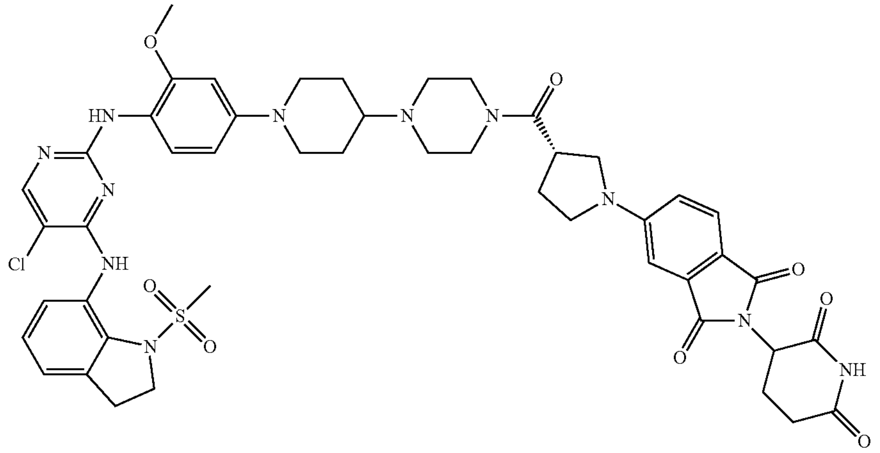

-continued
88
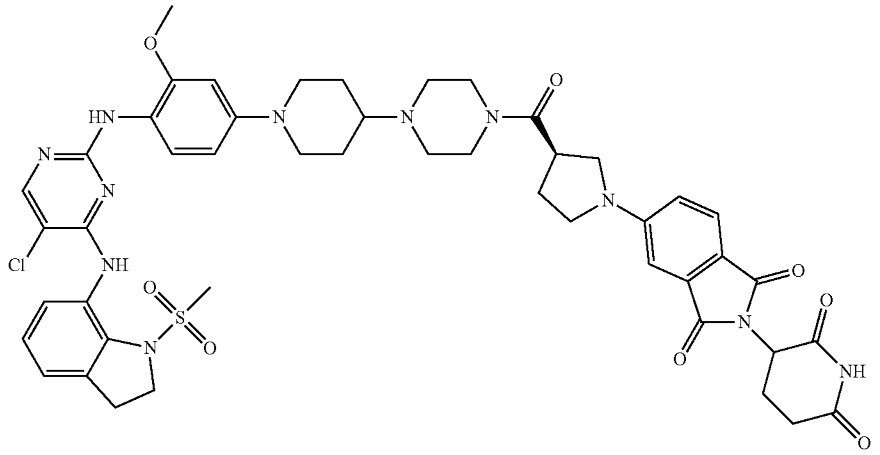
89
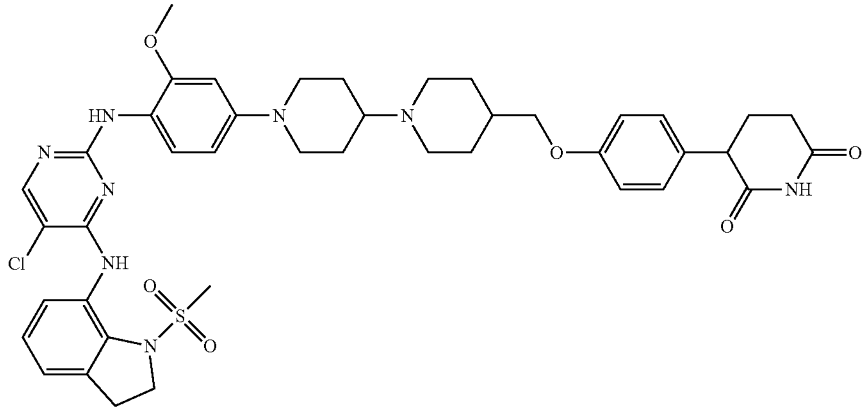
90
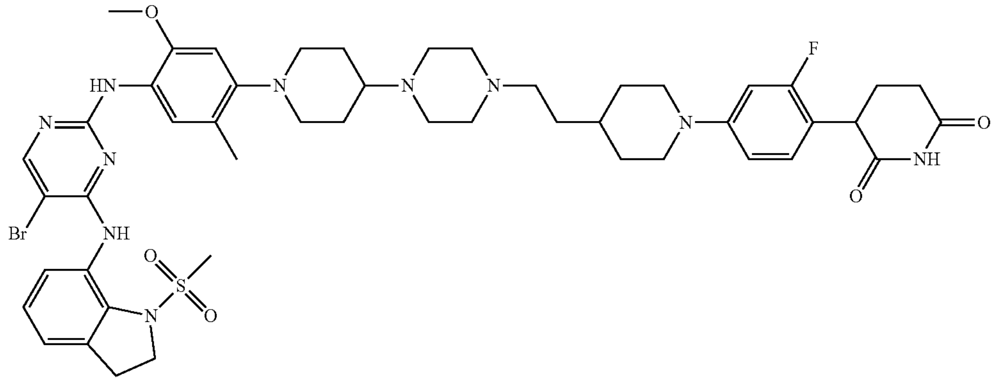
91
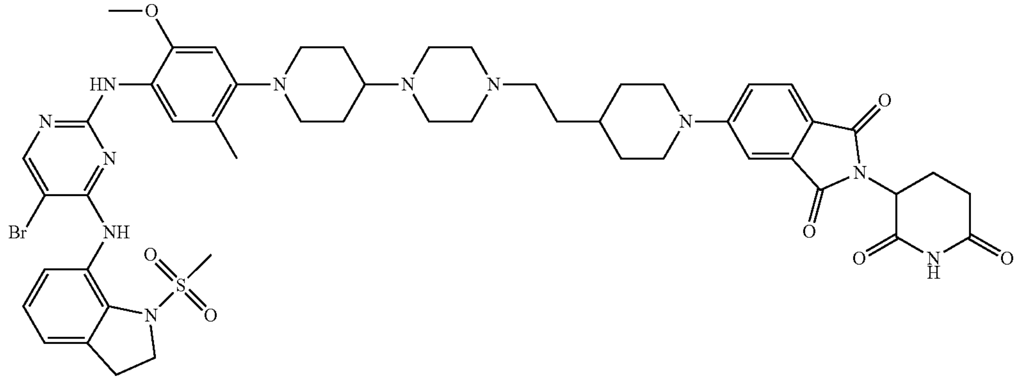

-continued
92
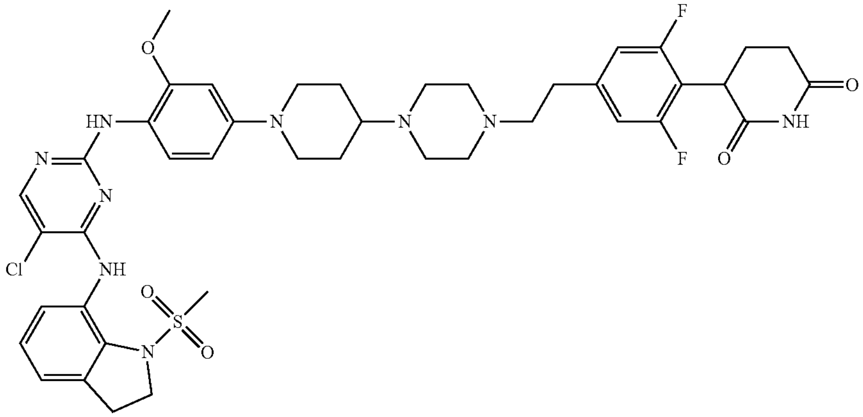
93
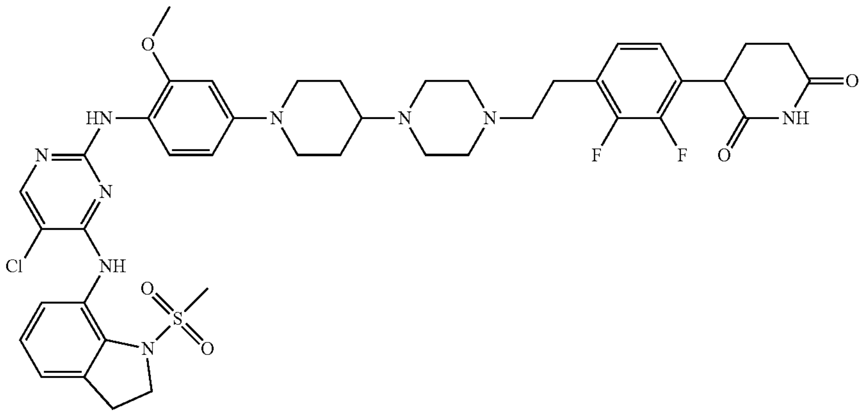
94
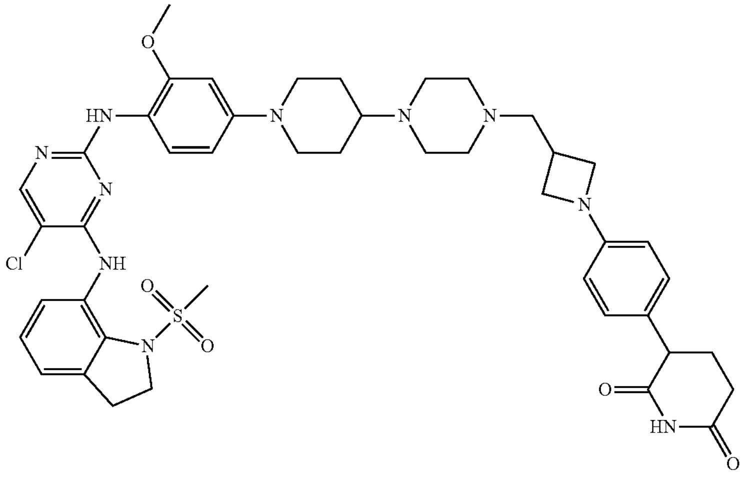

-continued
95
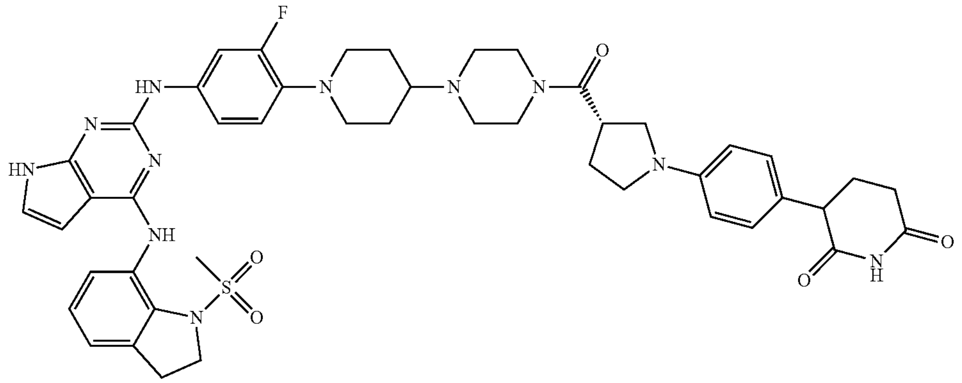
96
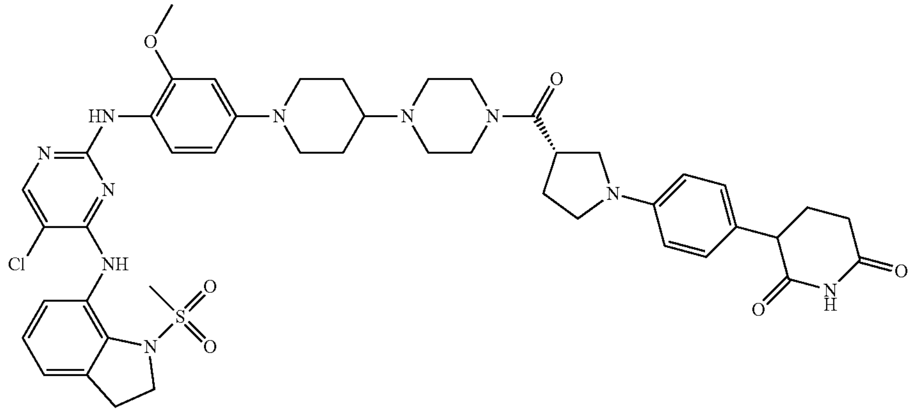
97
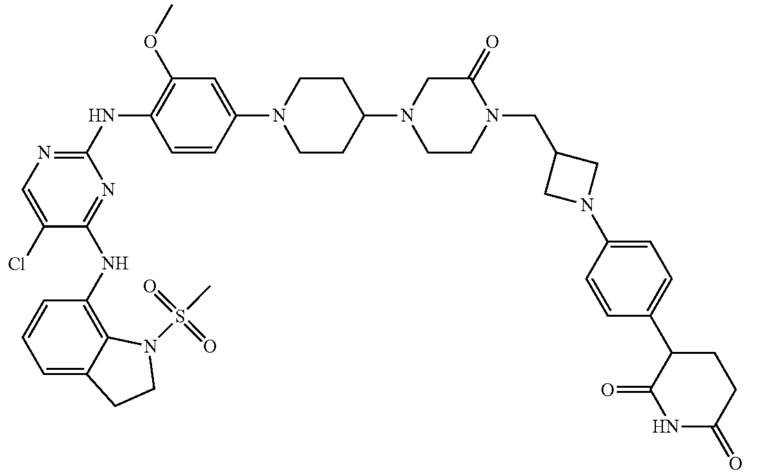
98
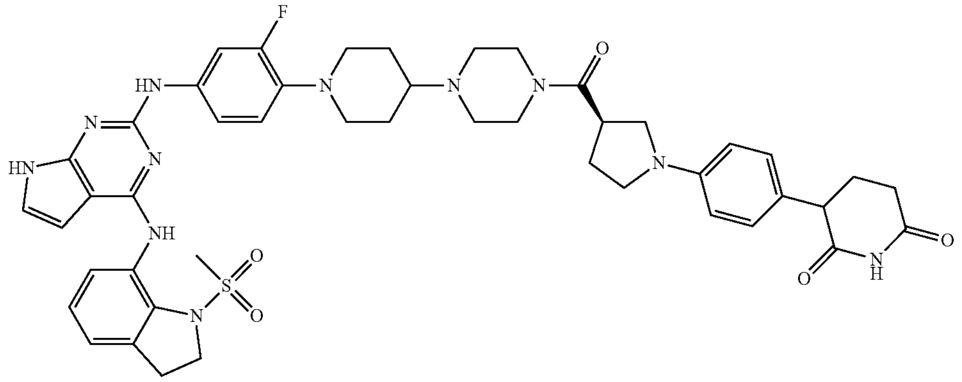

-continued
99
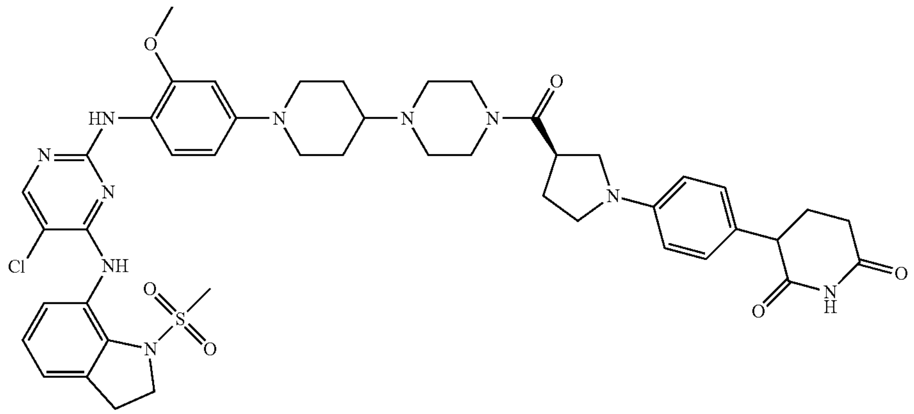
100
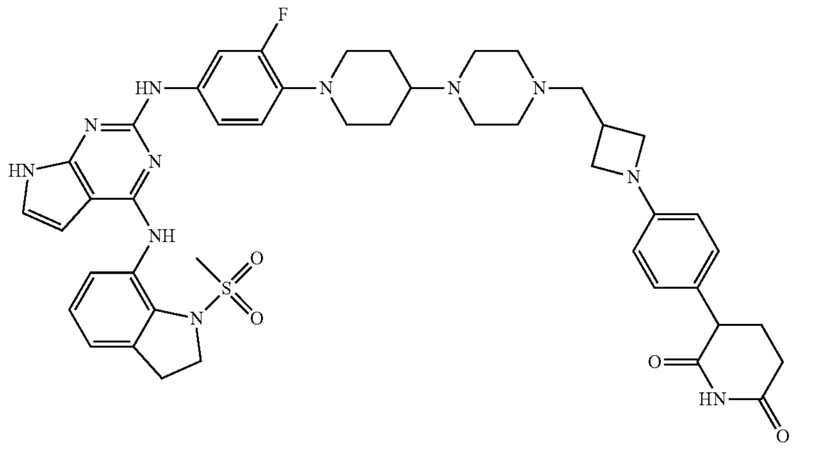
101
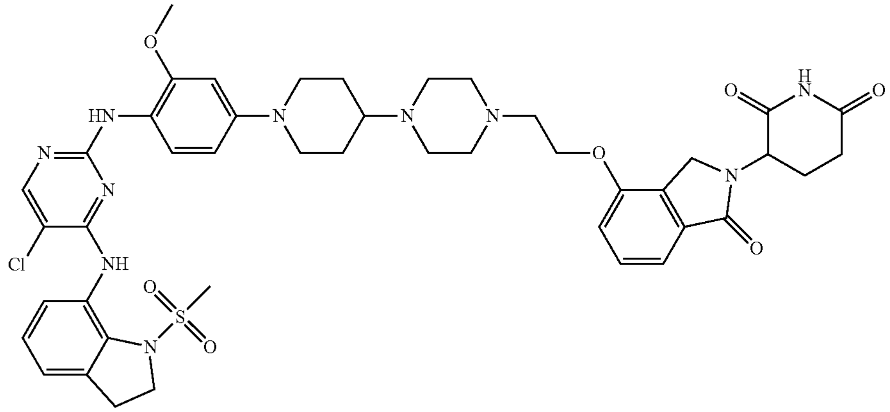

-continued
102
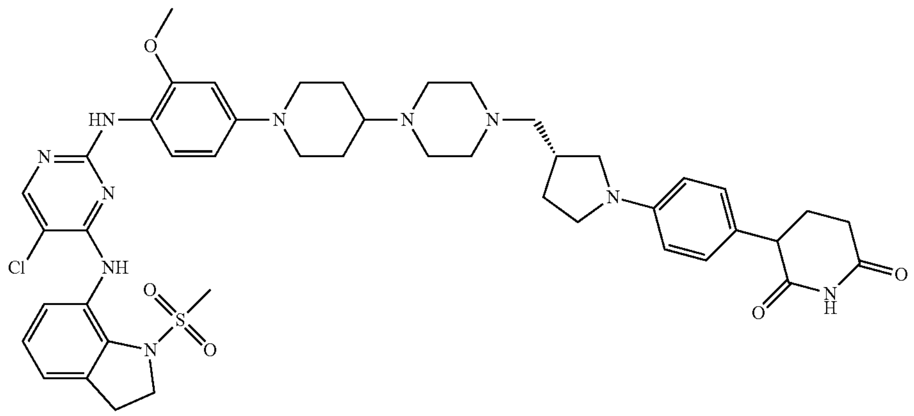
103
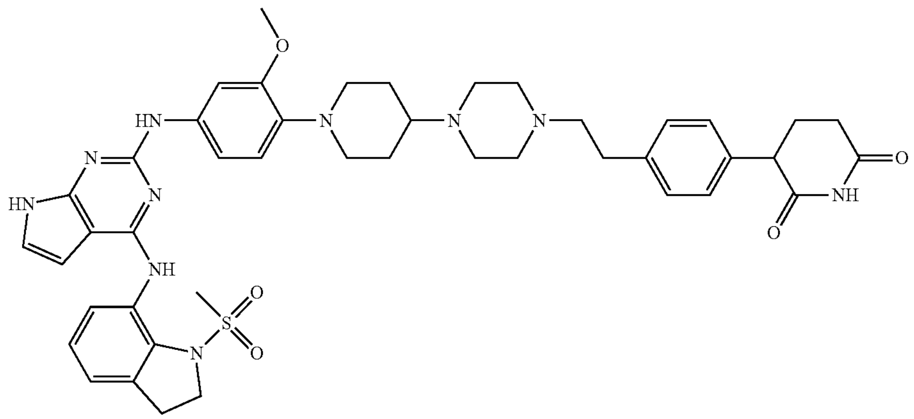
104
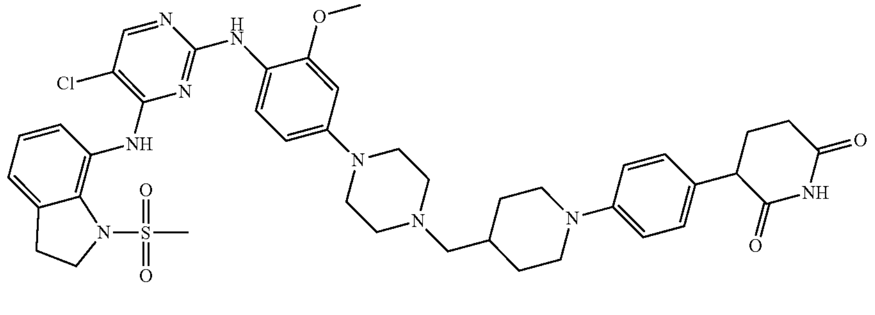
105
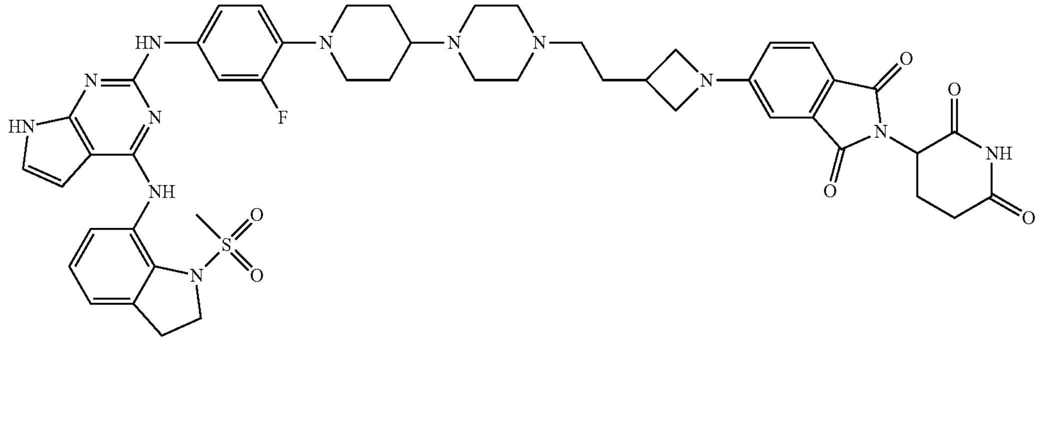

-continued
106
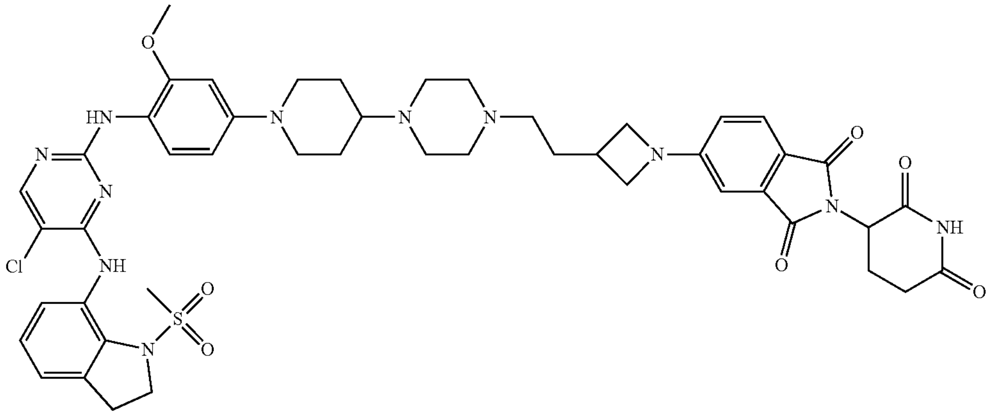
107
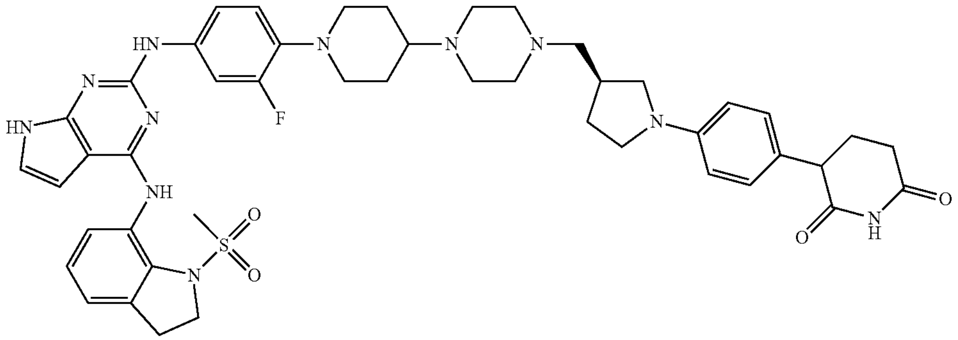
108
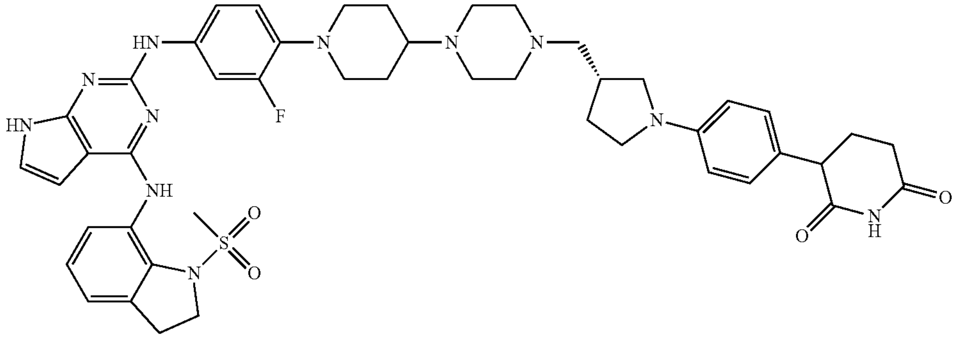
109
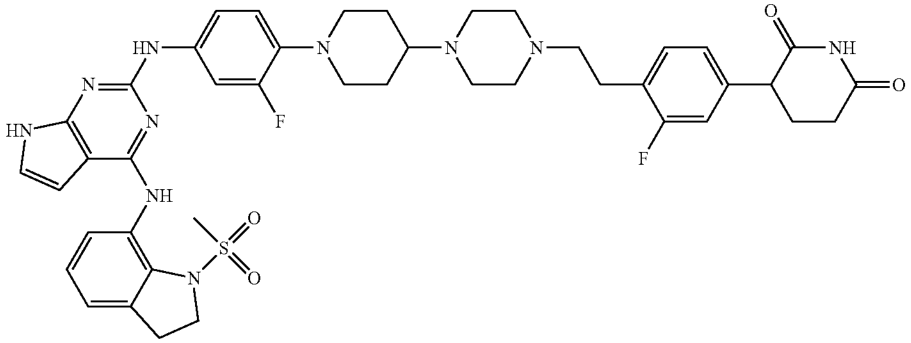

-continued
110
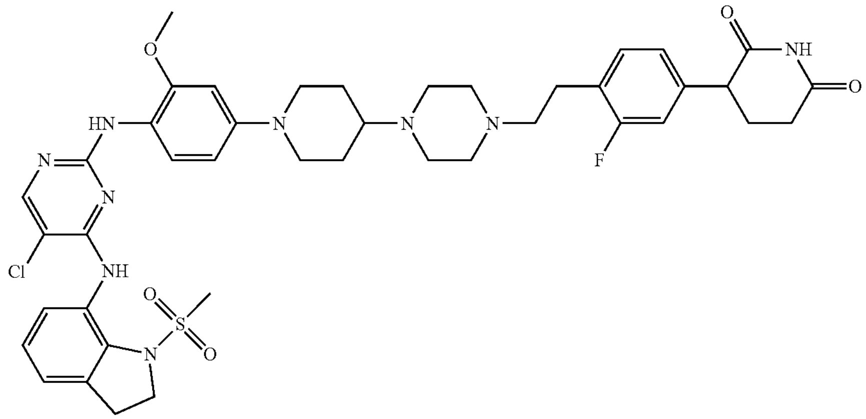
111
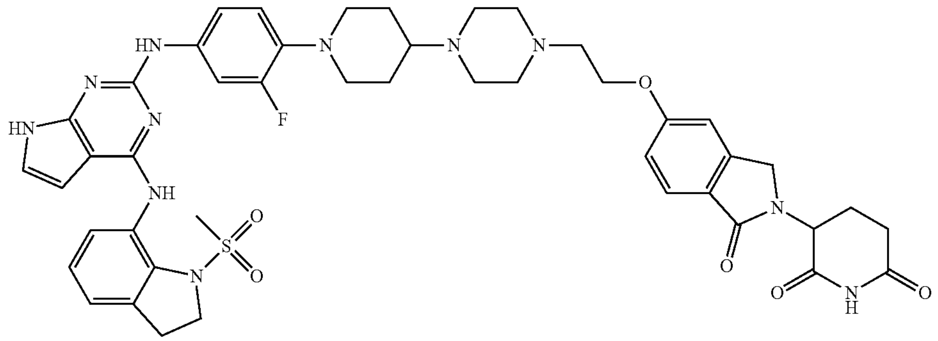
112
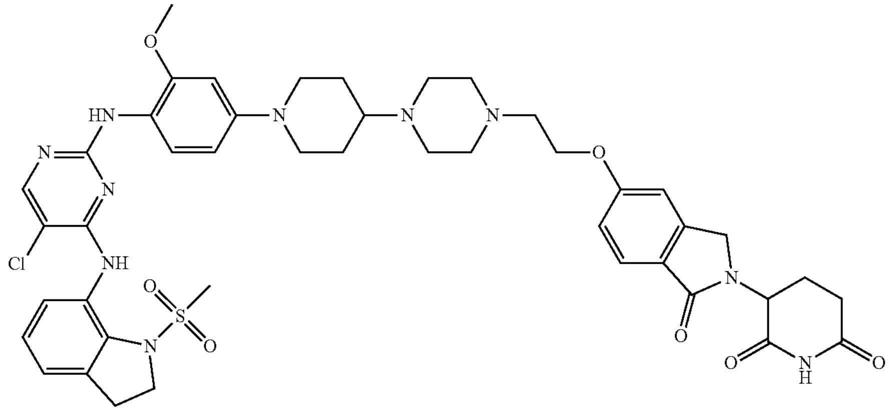
113
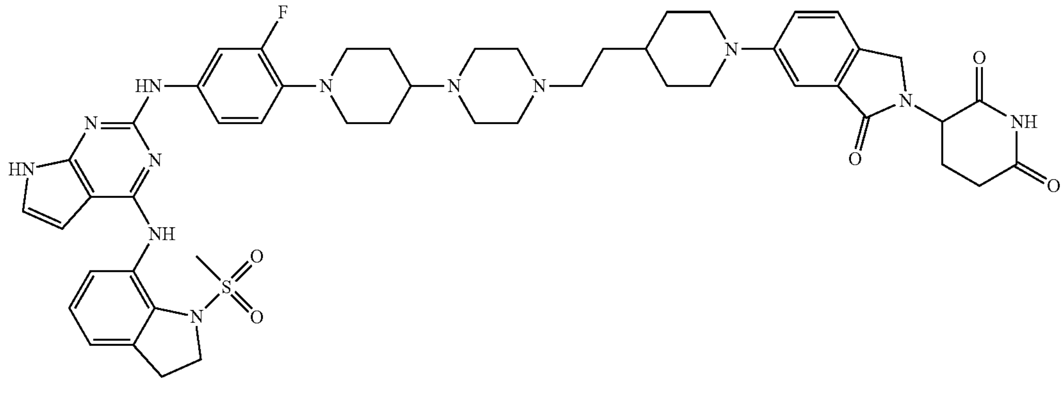

-continued
114
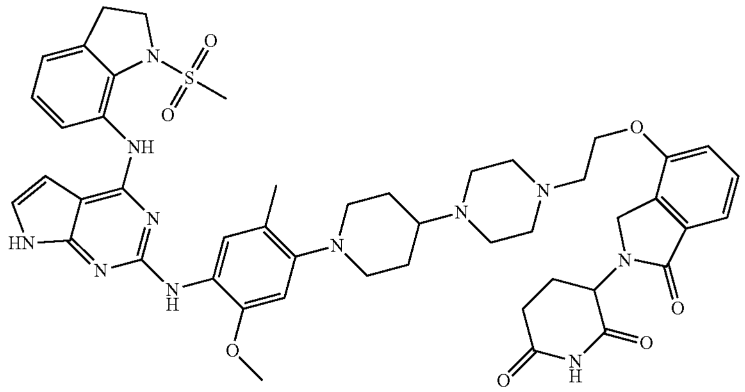
115
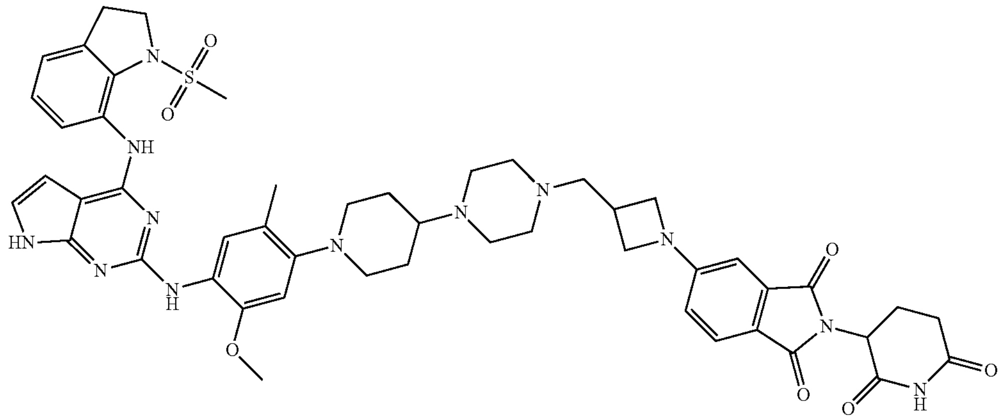
116
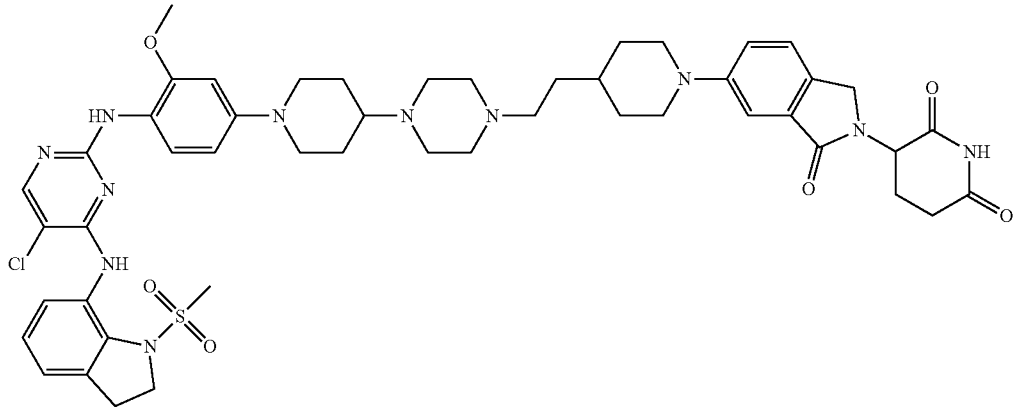
117
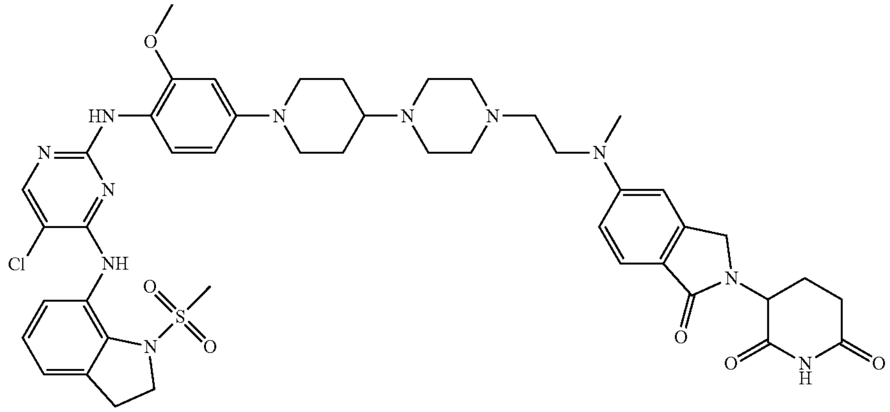

-continued
118
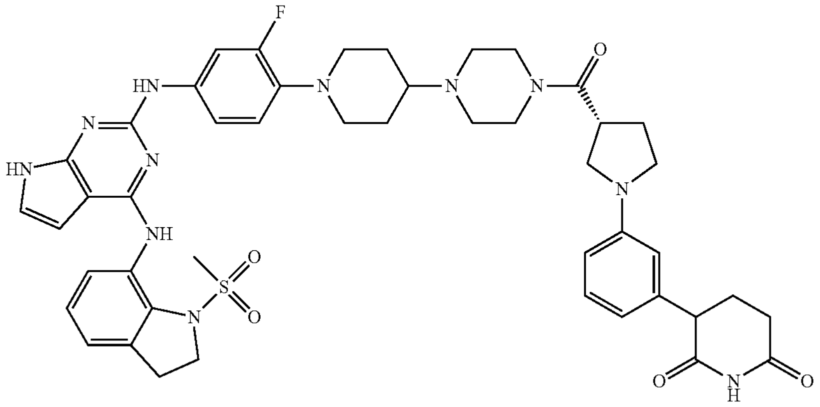
119
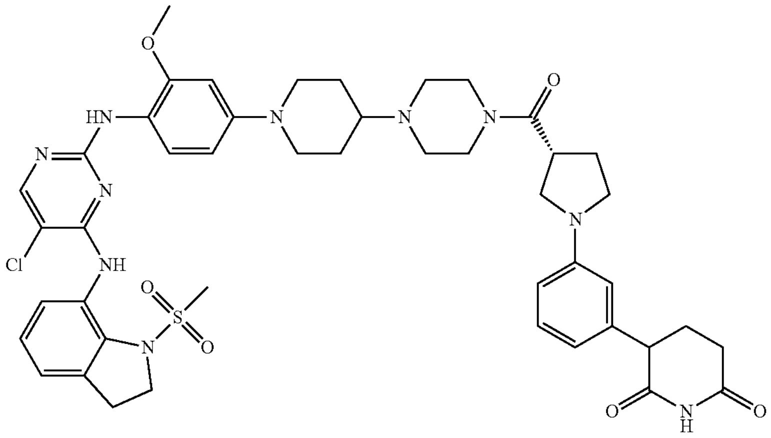
120
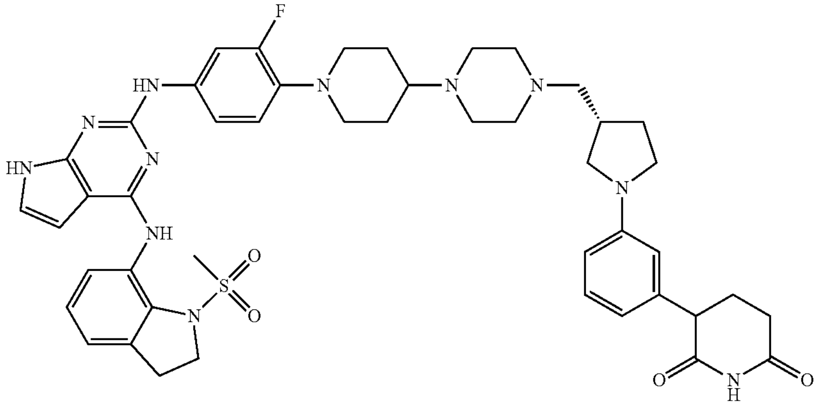

-continued
121
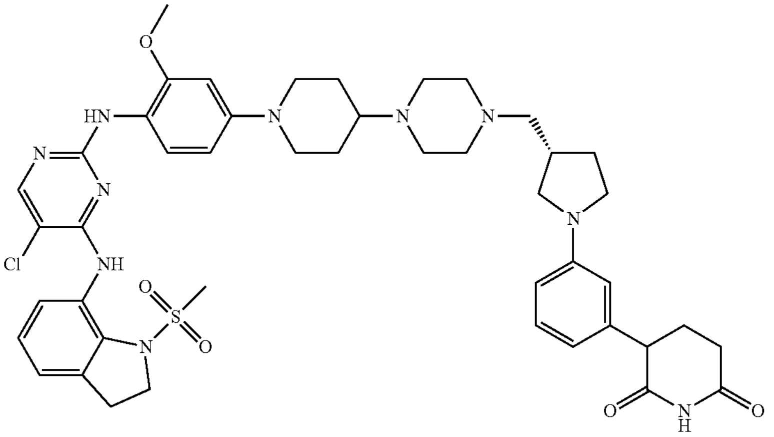
122
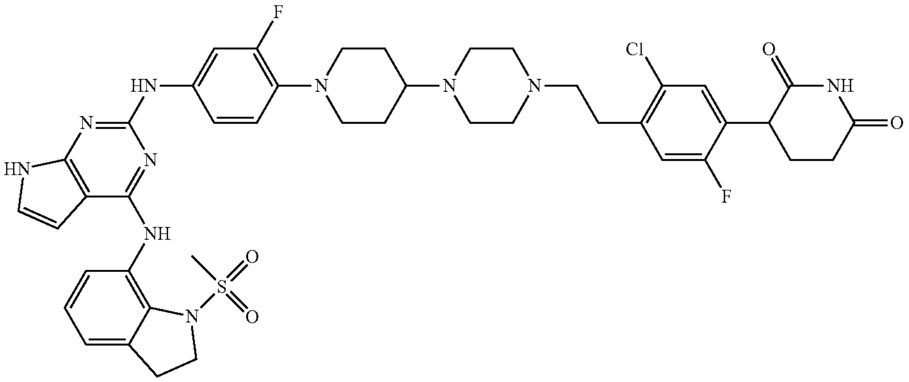
123
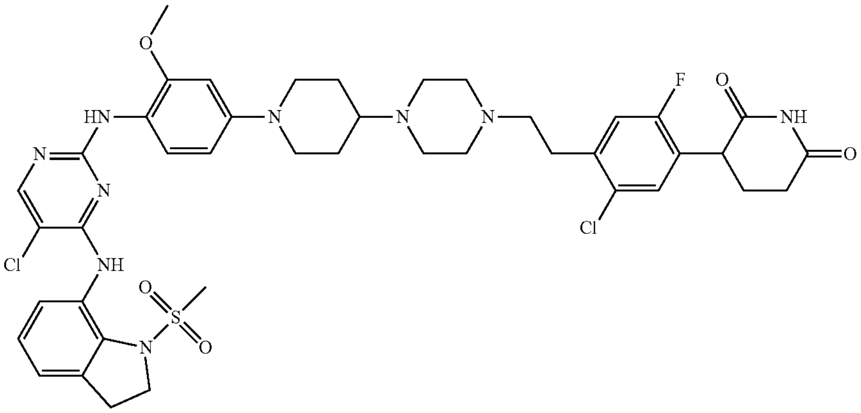
124
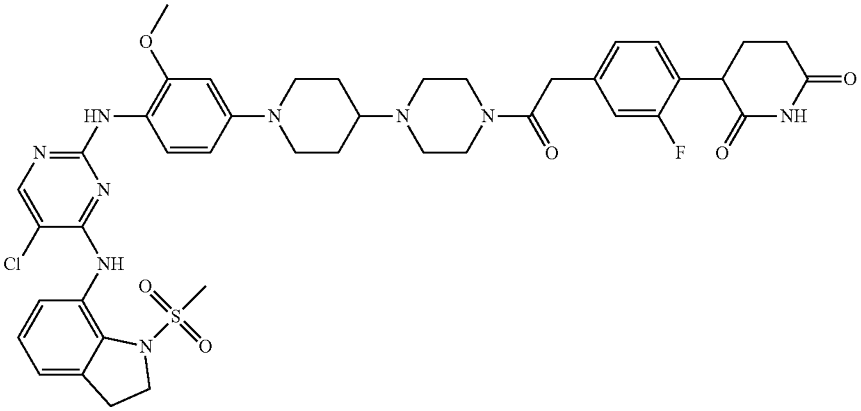

-continued
125
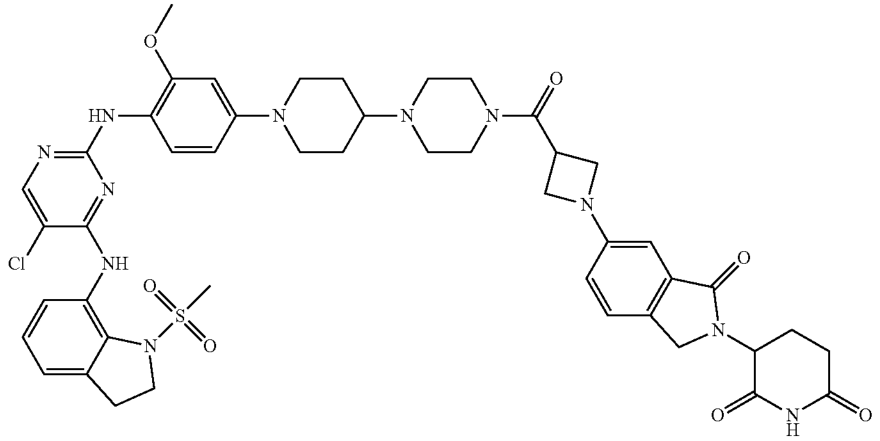
126
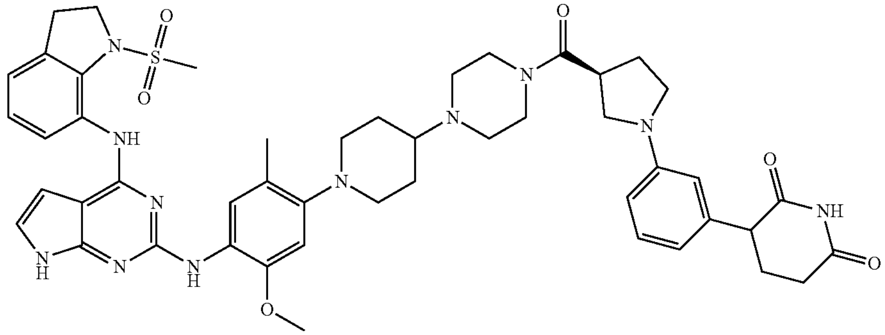
127
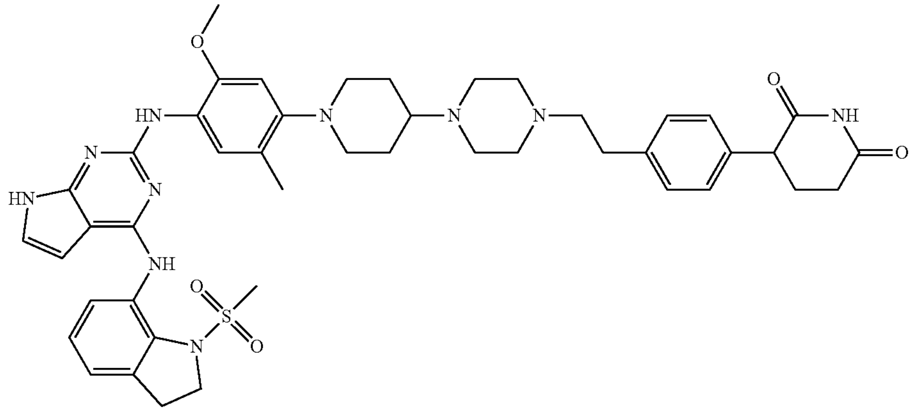
128
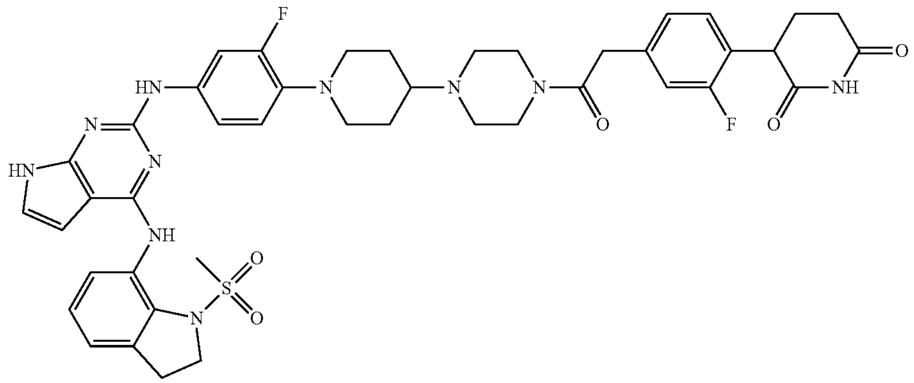

-continued
129
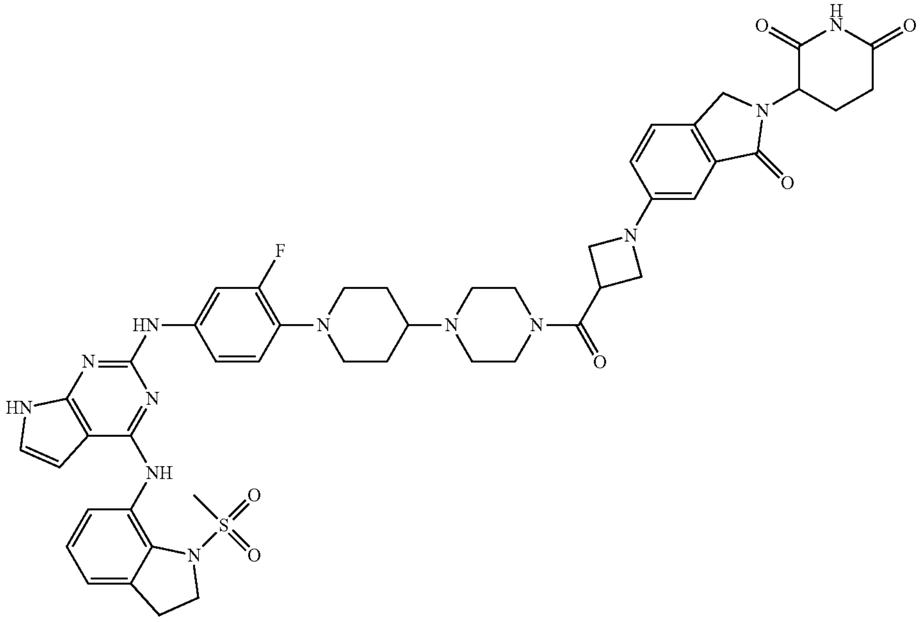
130
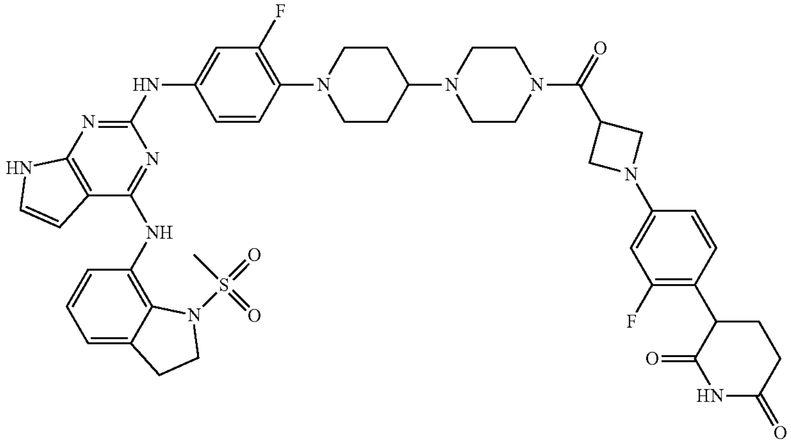
131
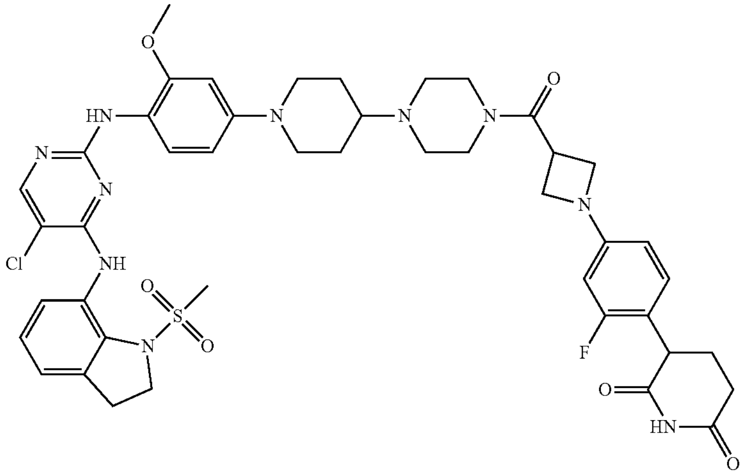

-continued
132
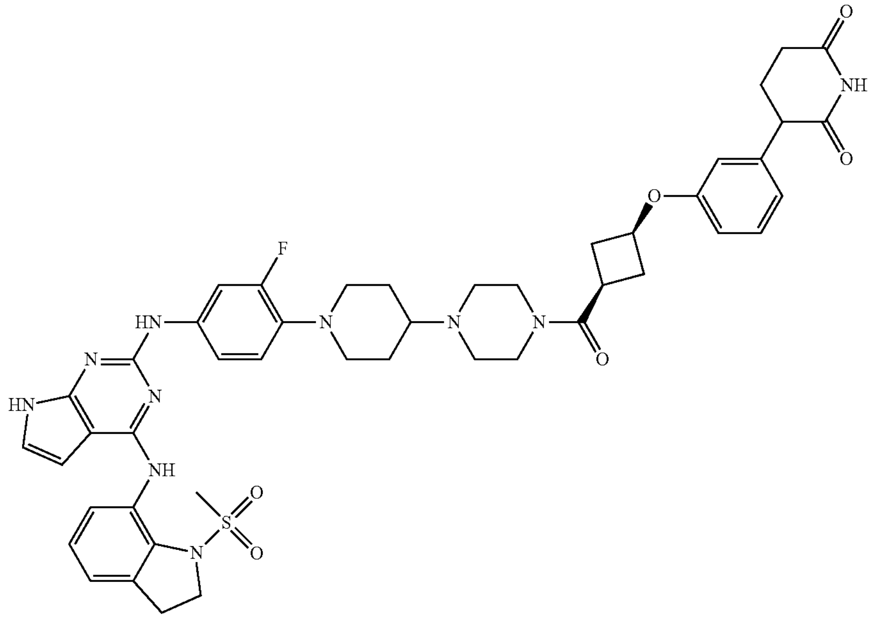
133
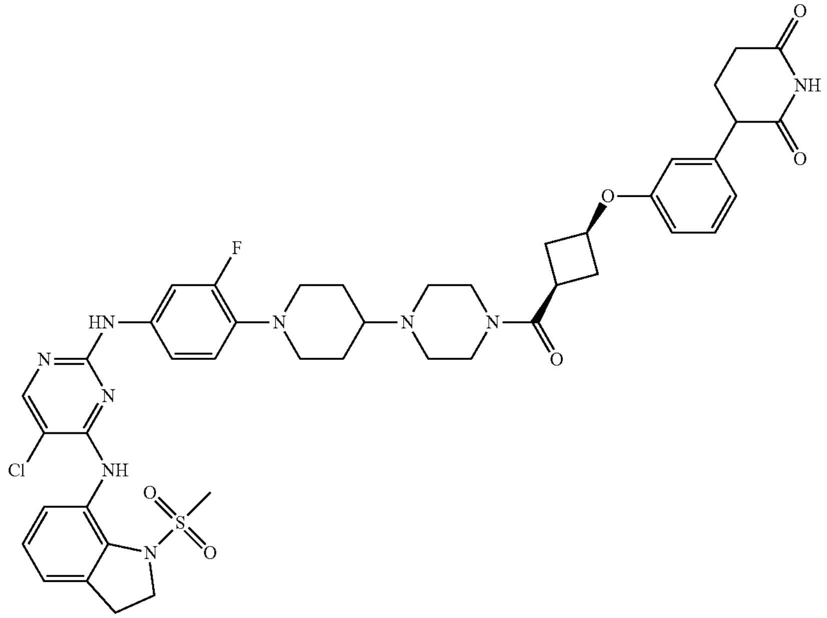
134
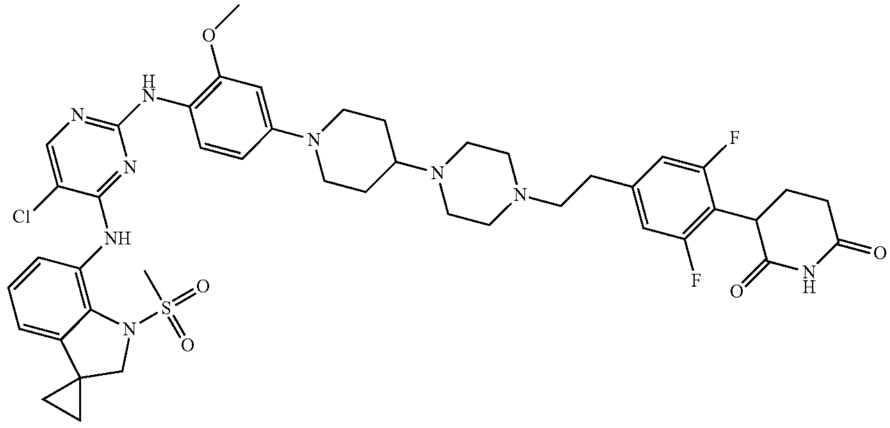

-continued
135
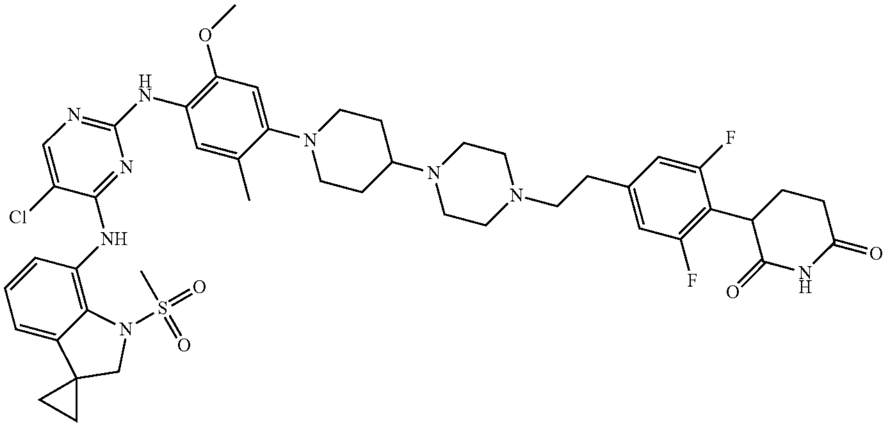
136
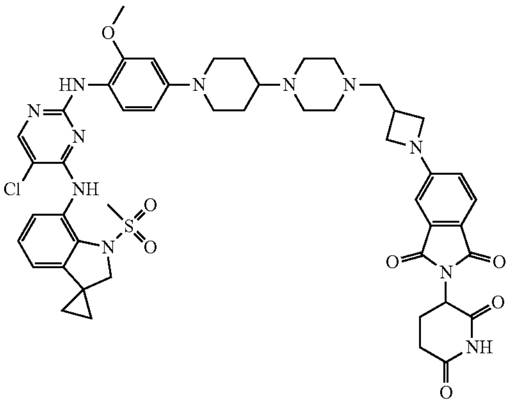
137
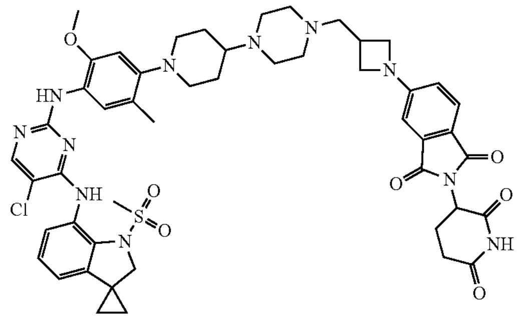
138
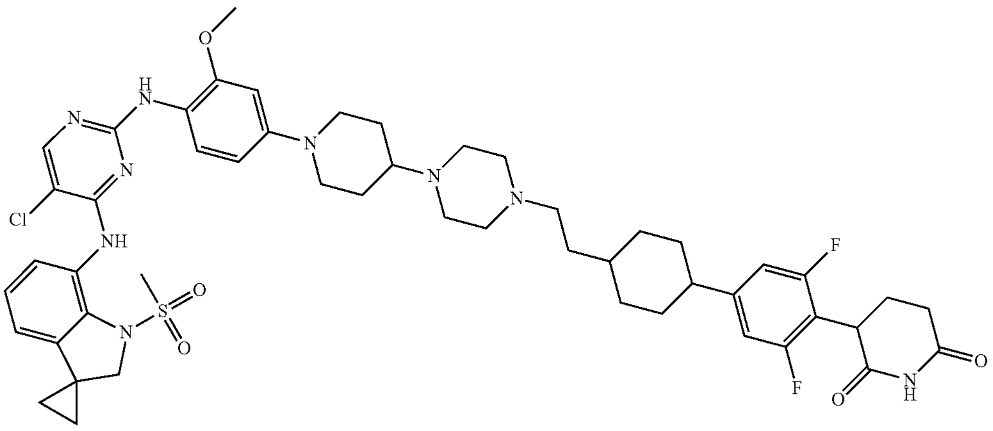

-continued
139
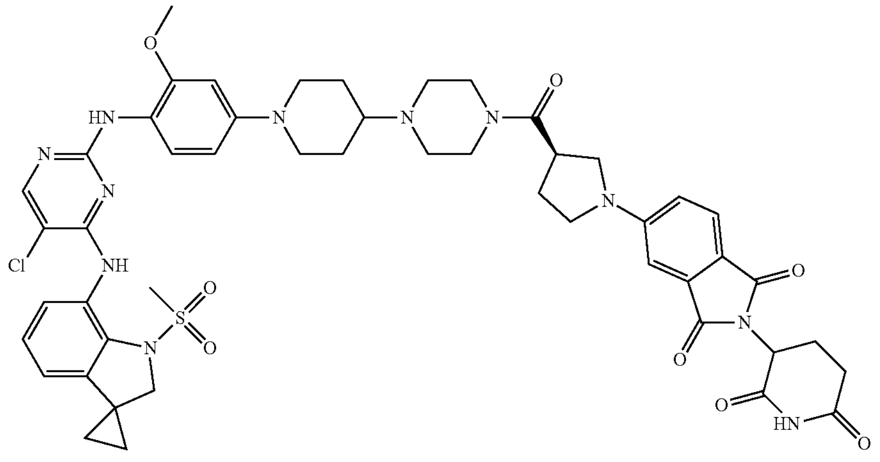
140
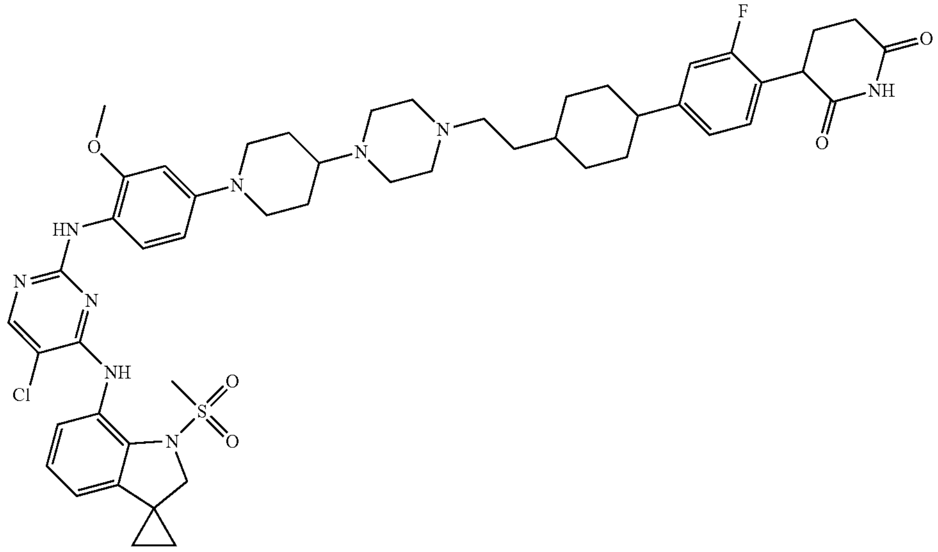
141
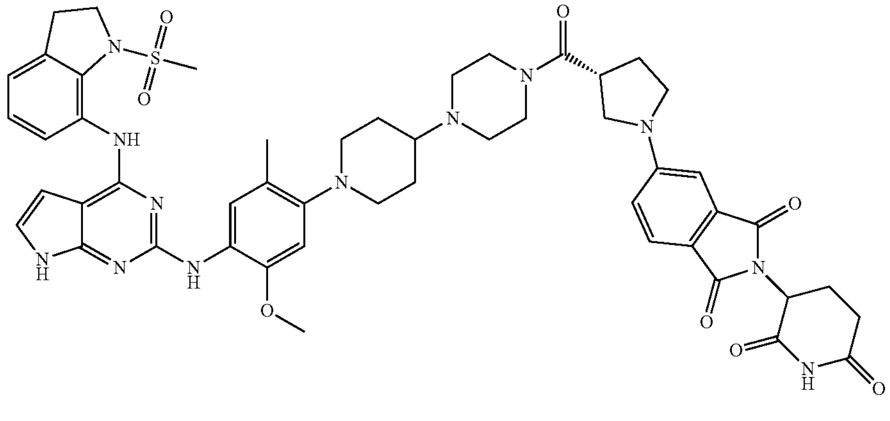

-continued
142
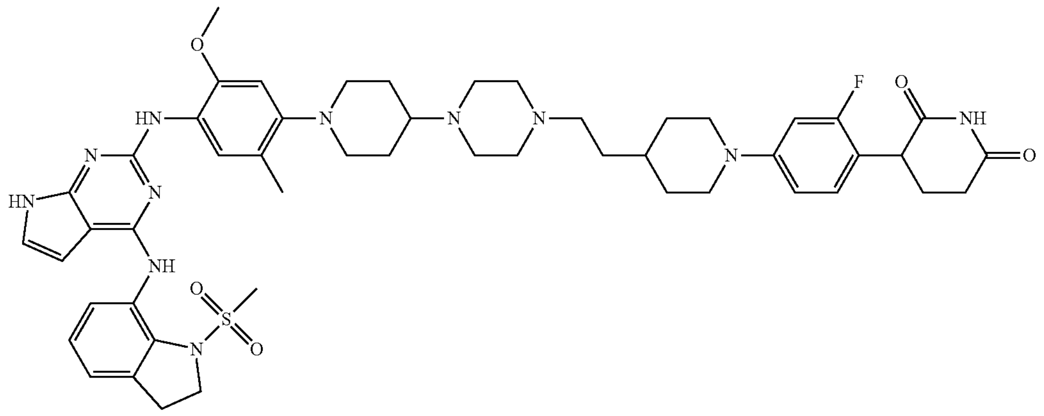
143
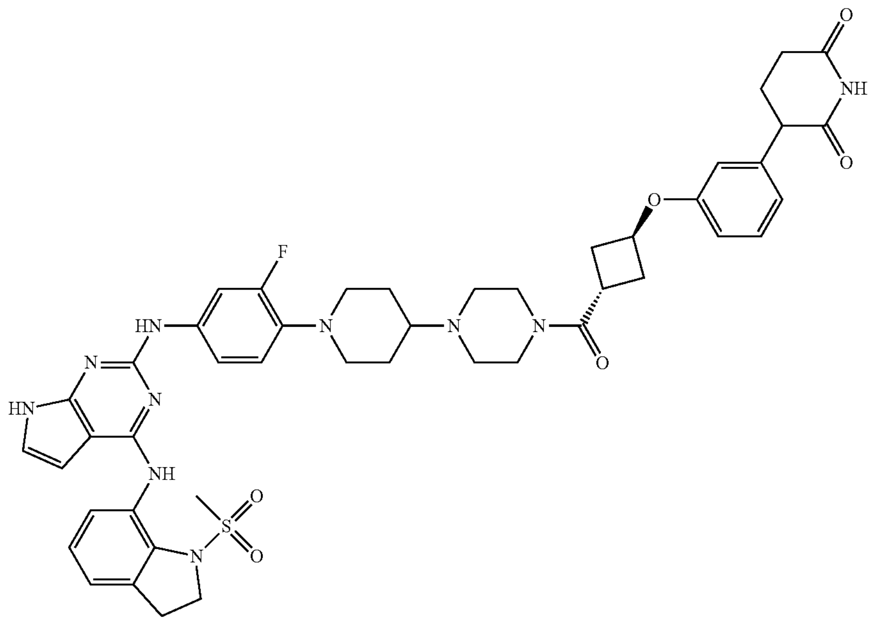
144
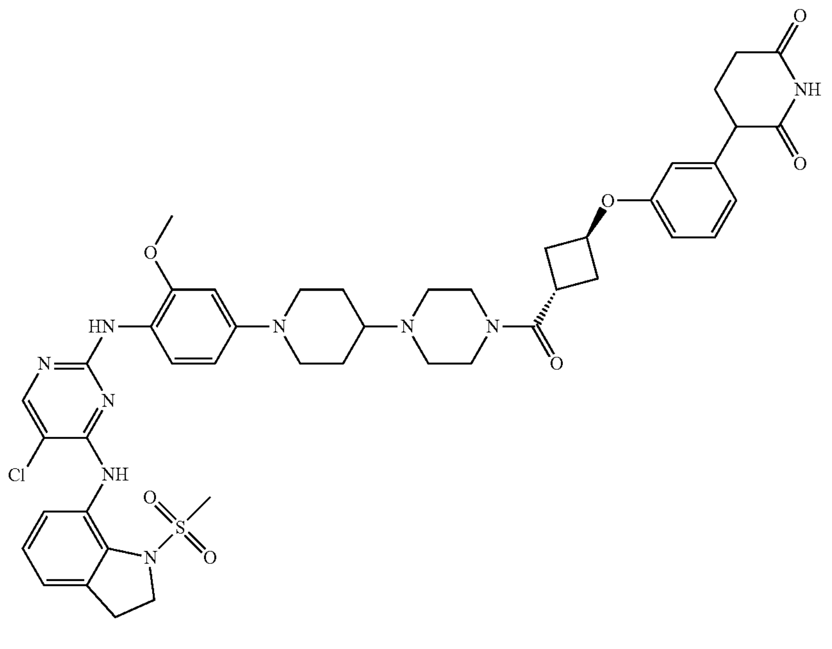

-continued
145
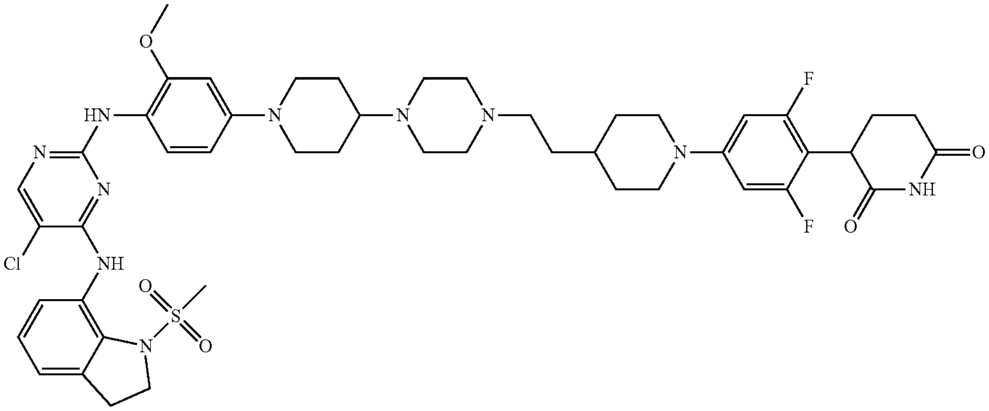
146
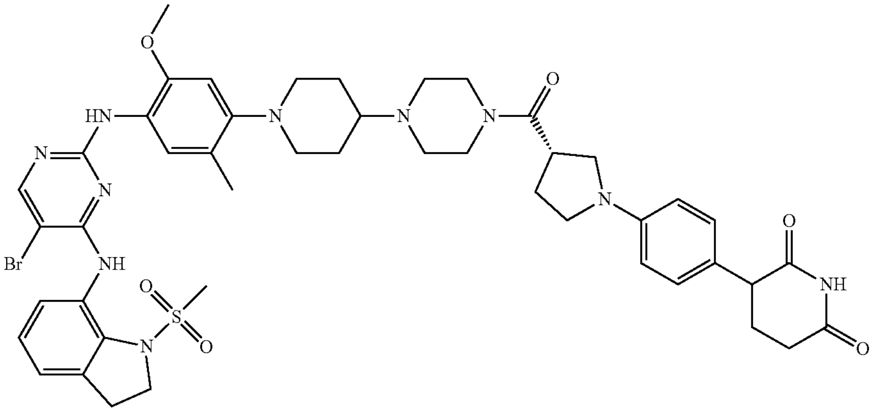
147
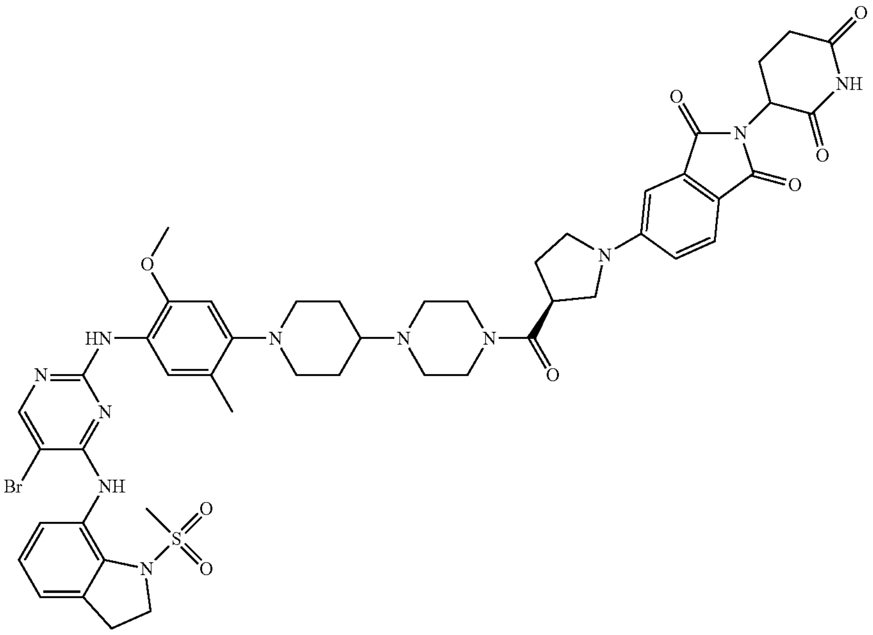

-continued
148
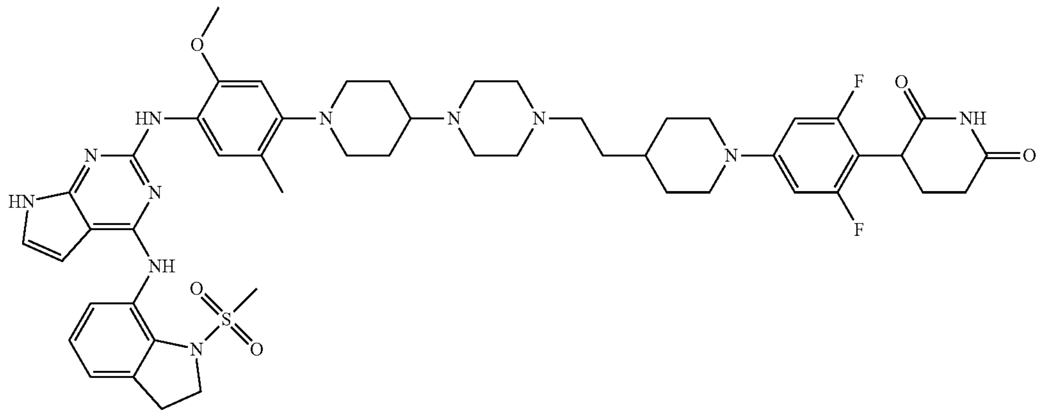
149
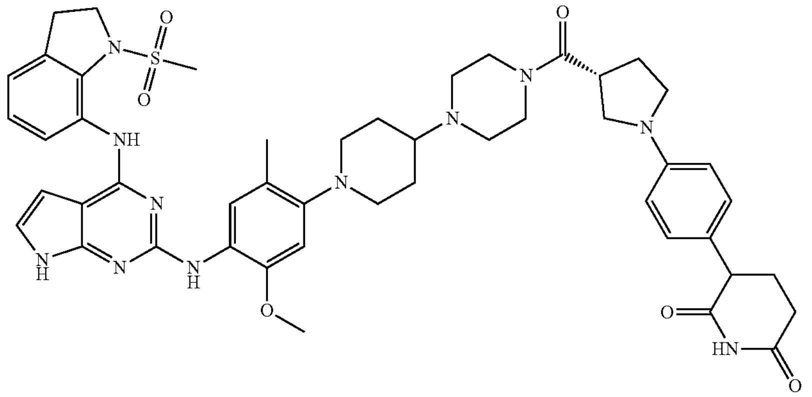
150
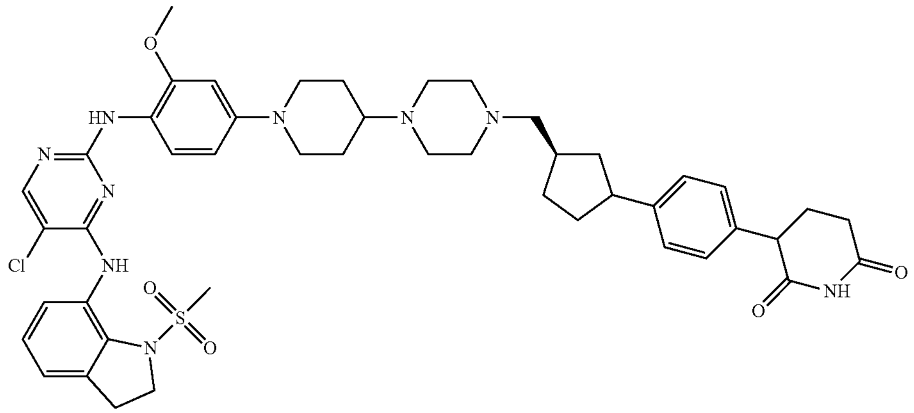

-continued
151
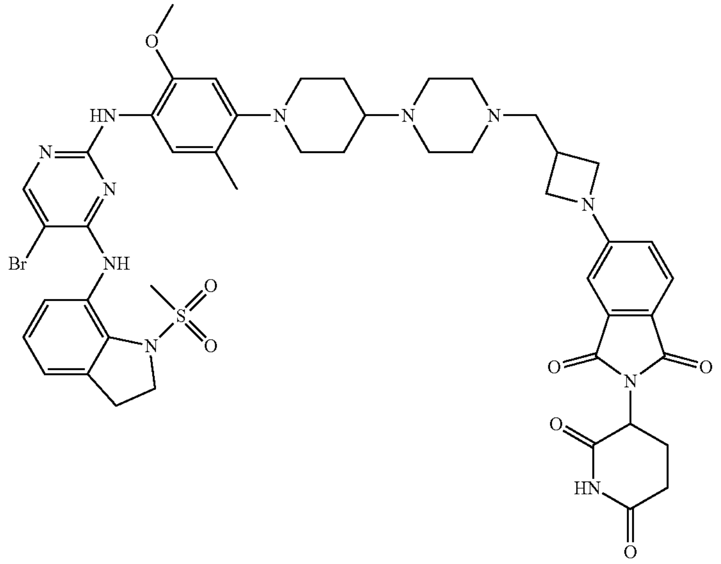
152
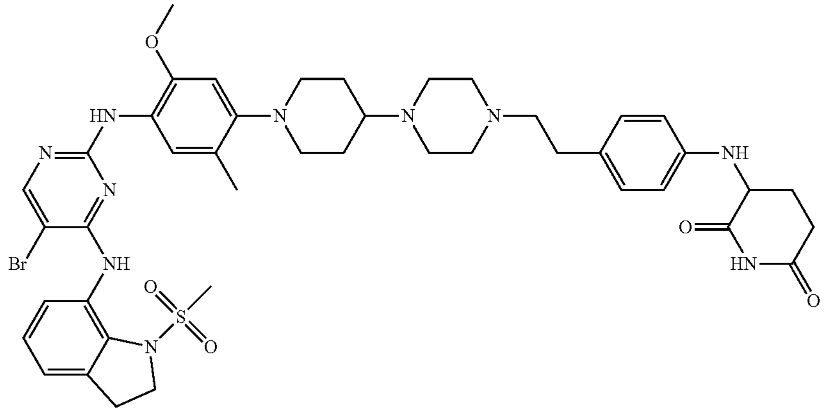
153
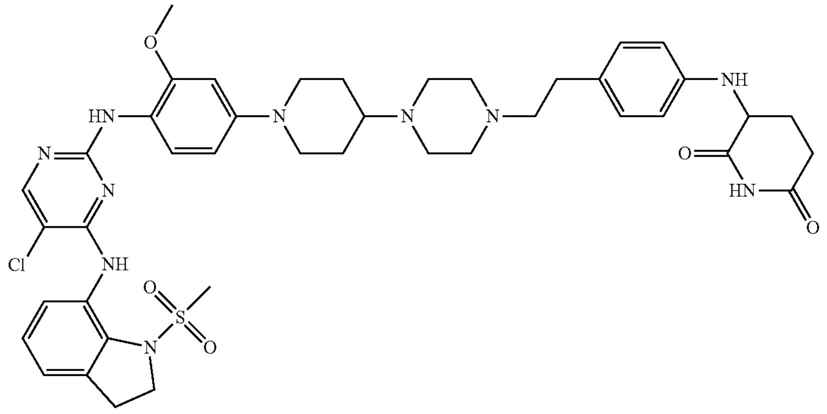

-continued
154
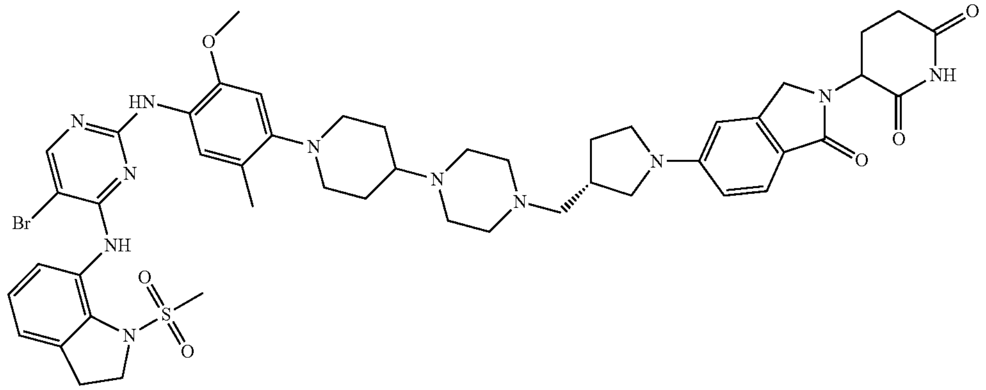
155
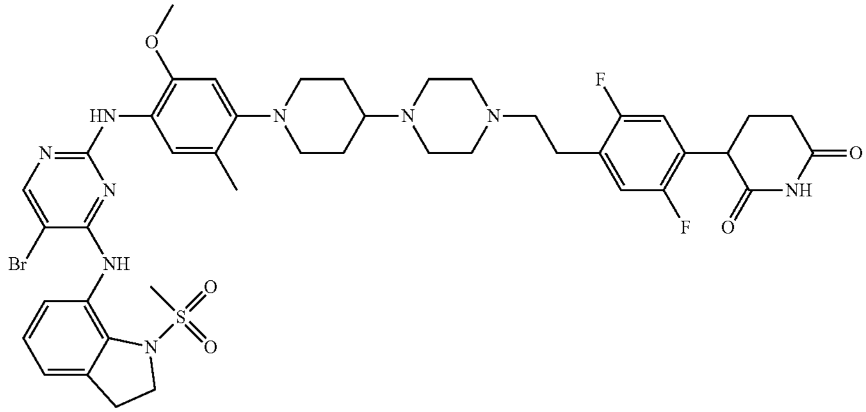
156
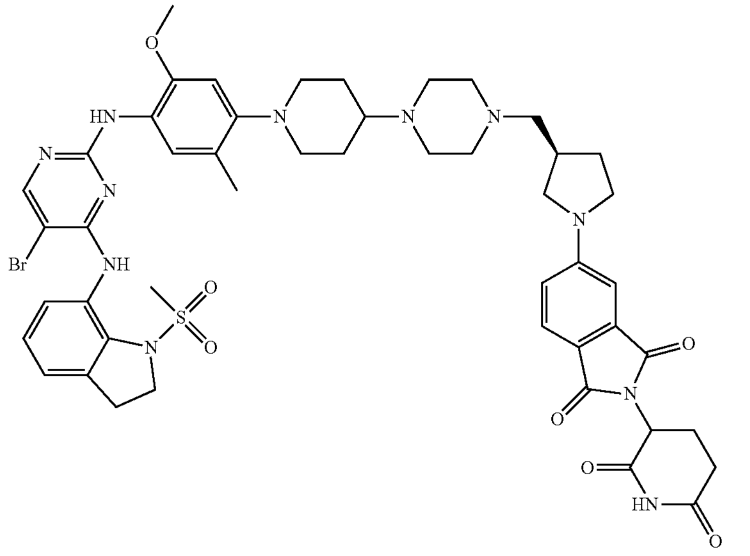

-continued
157
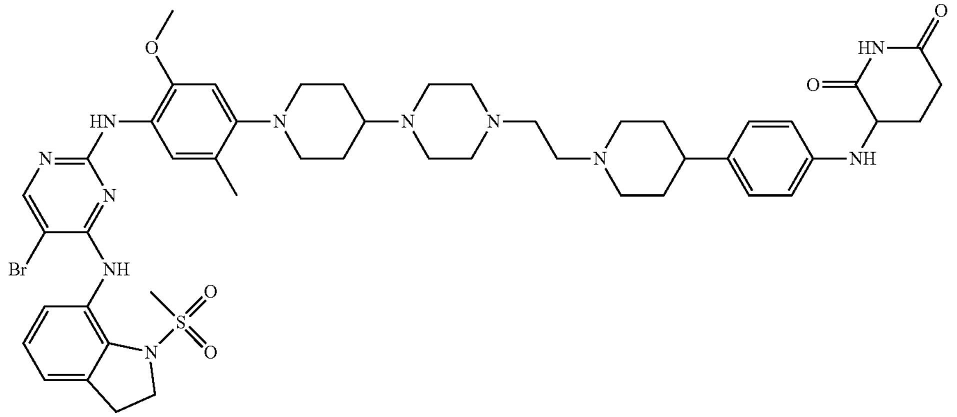
158
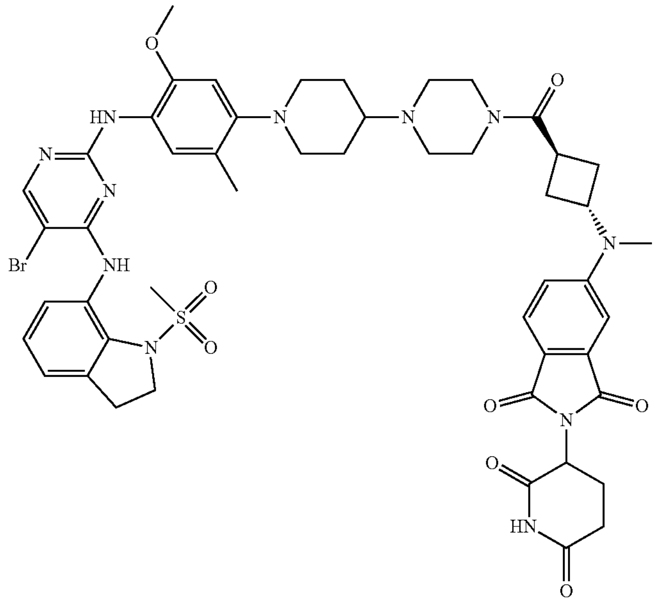
159
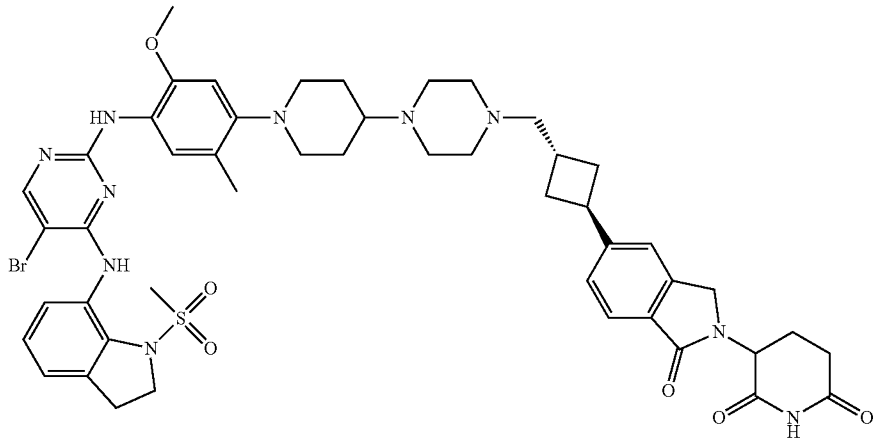

-continued
160
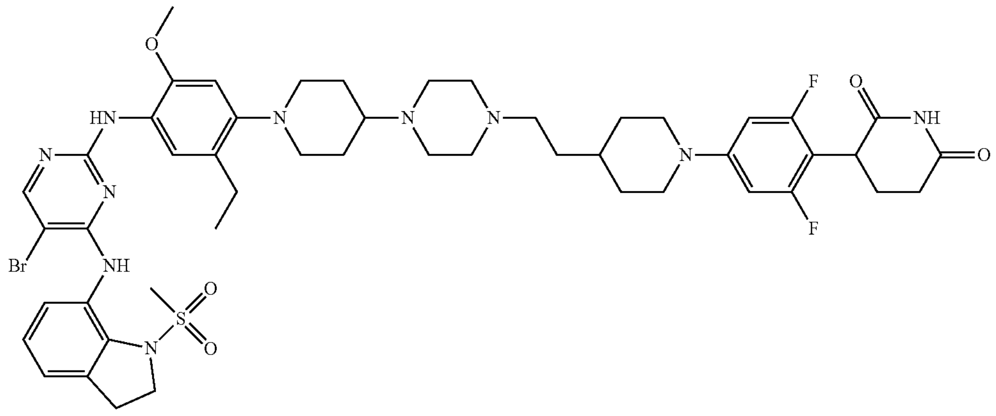
161
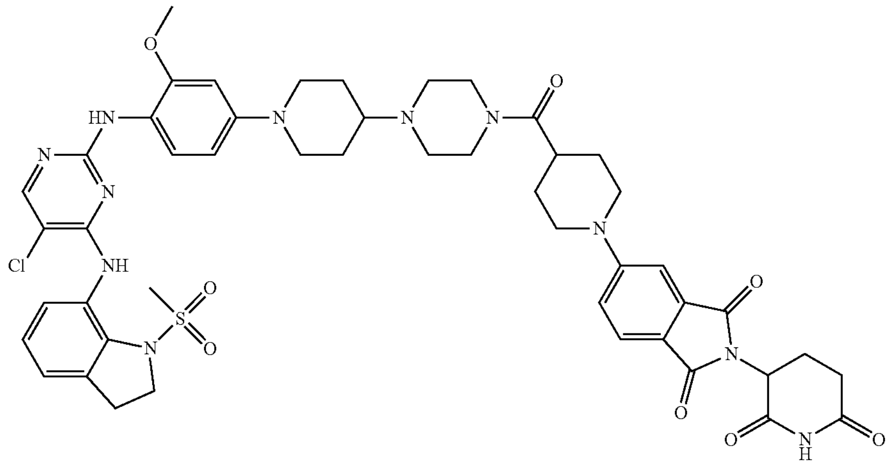
162
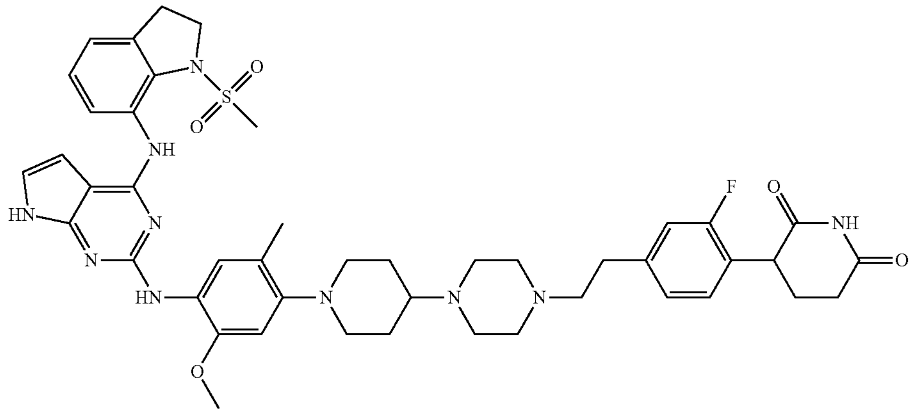

-continued
163
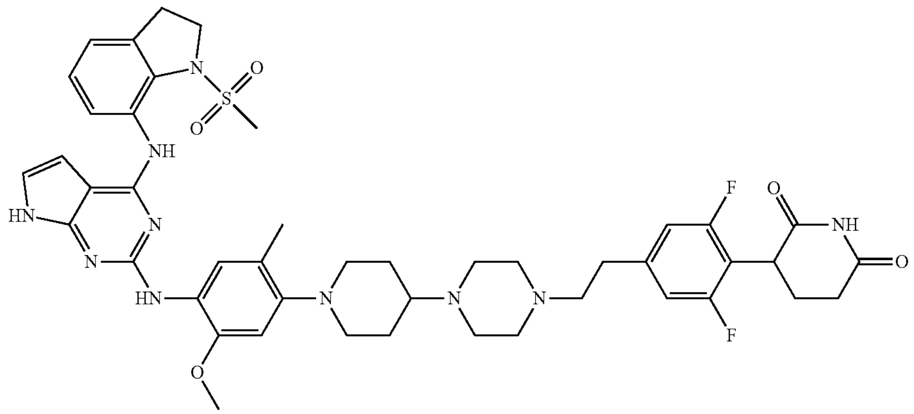
164
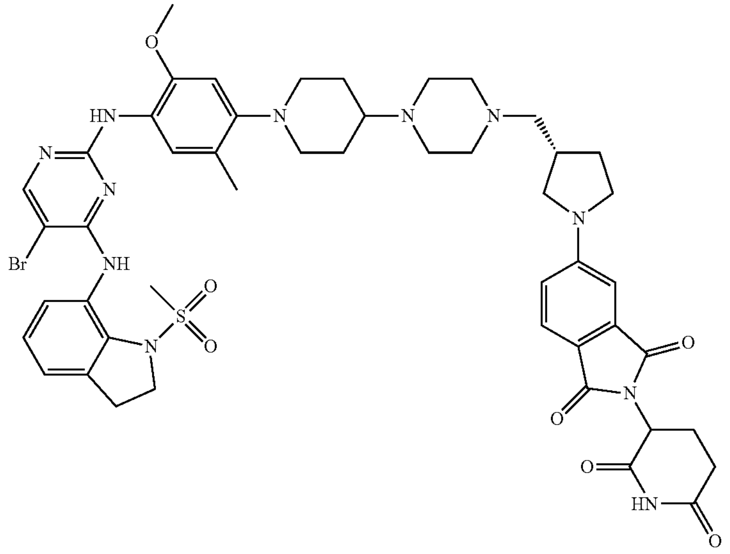
165
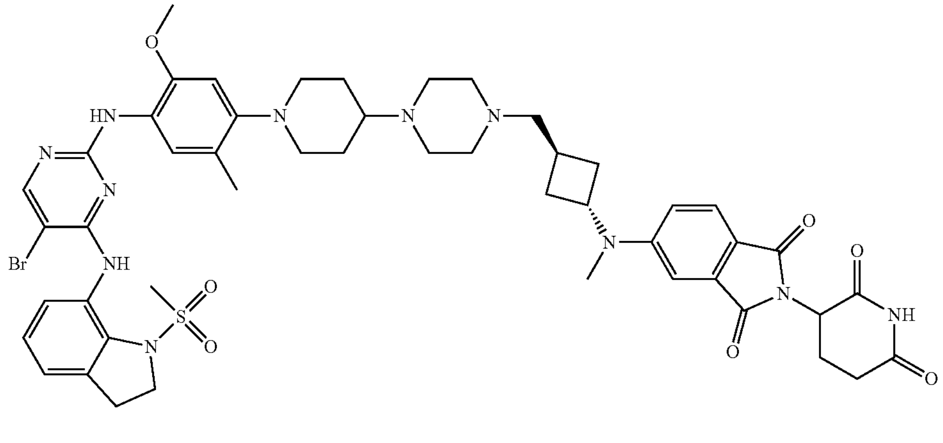

-continued
166
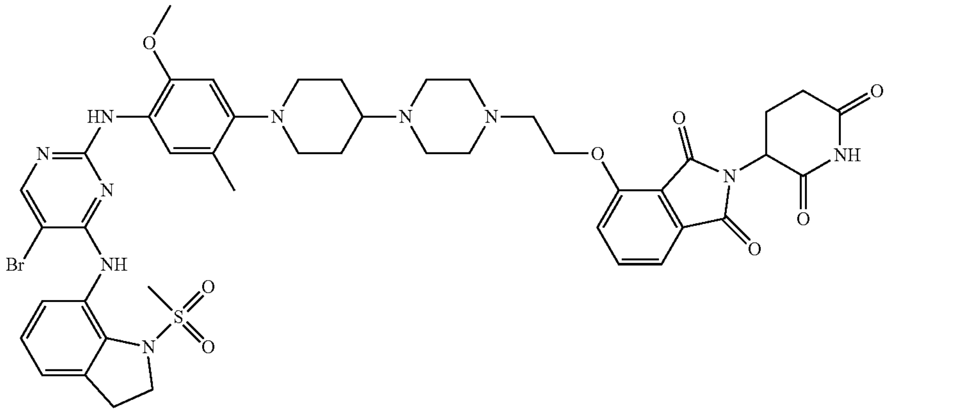
167
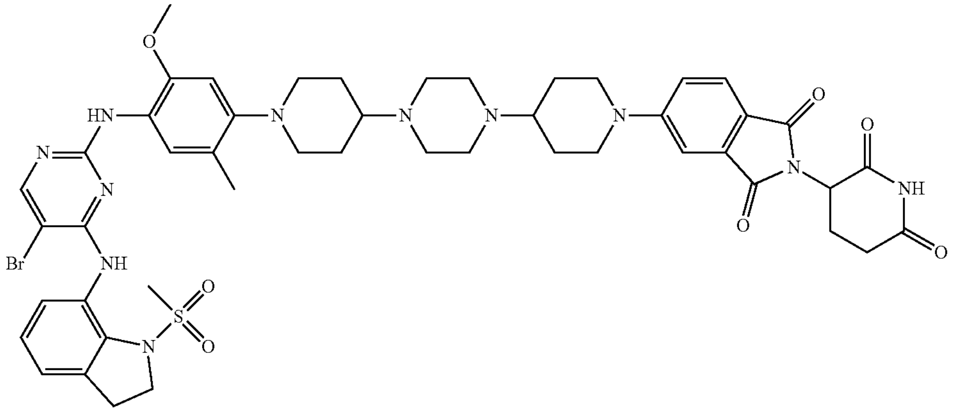
168
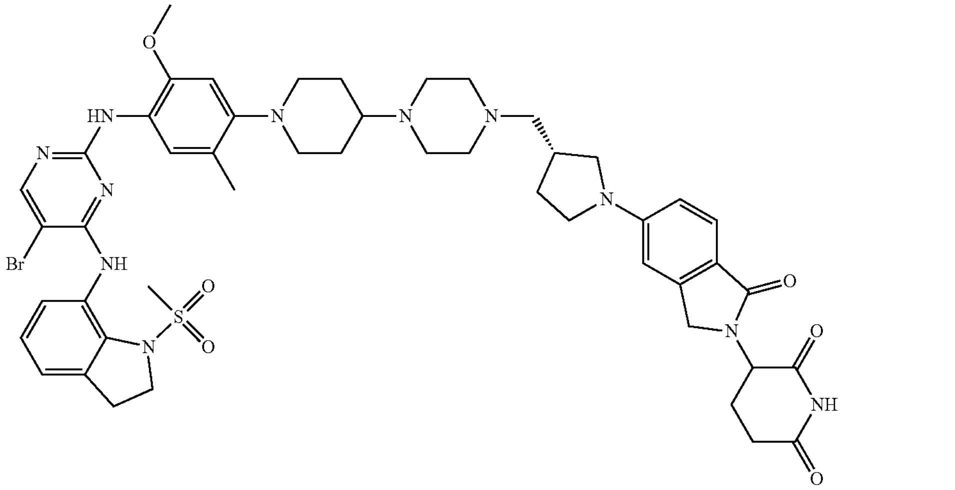

-continued
169
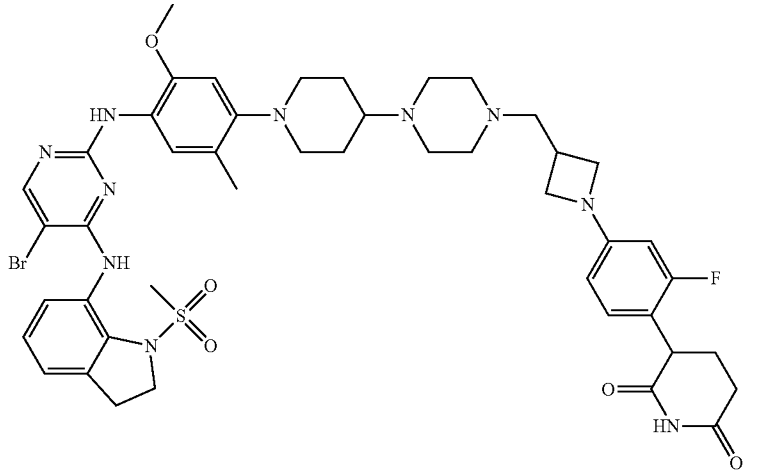
170
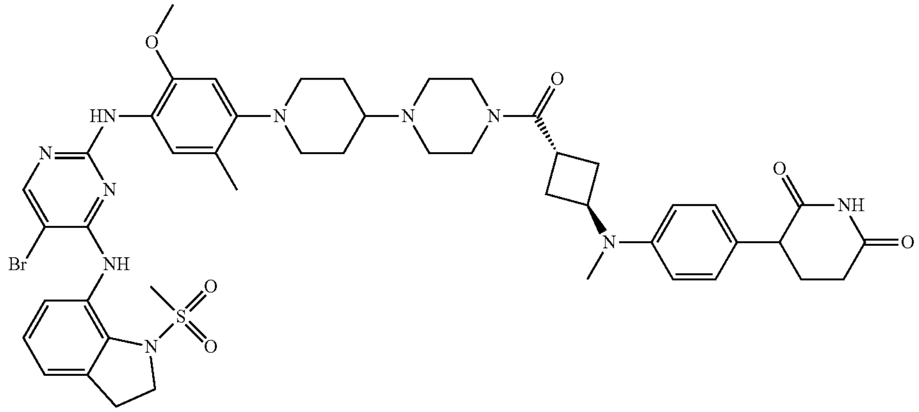
171
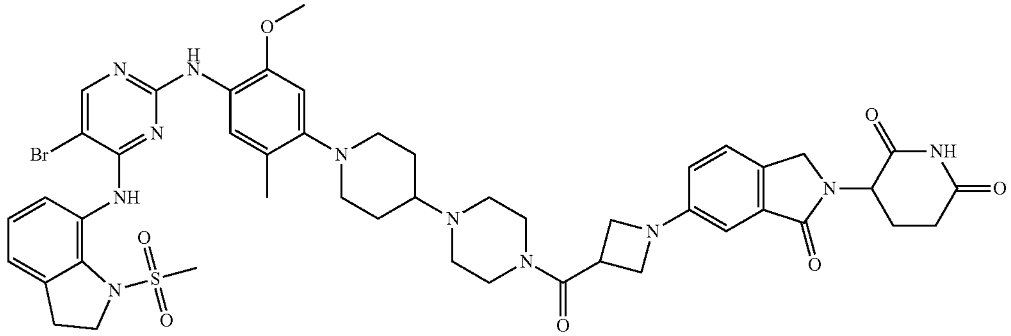
172
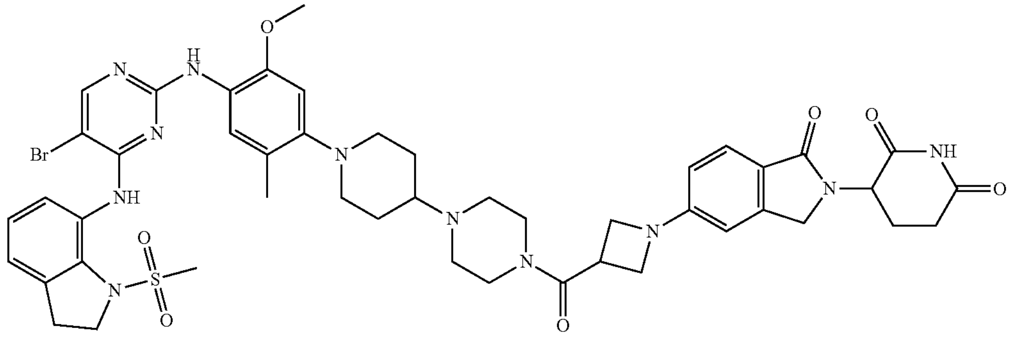

-continued
173
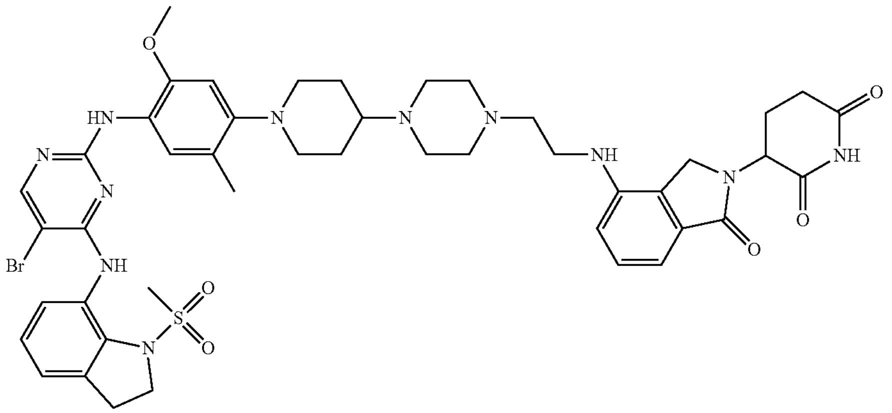
174
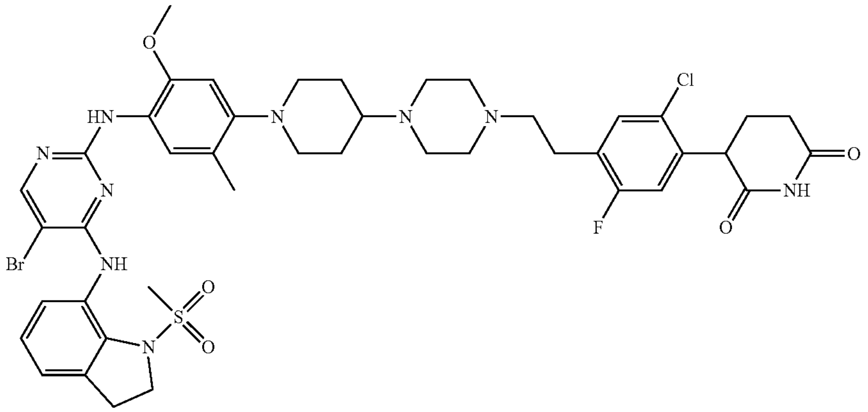
175
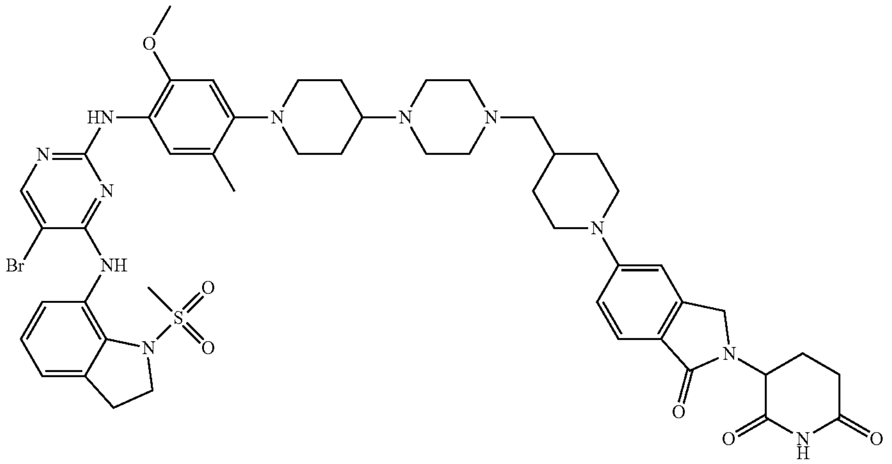

-continued
176
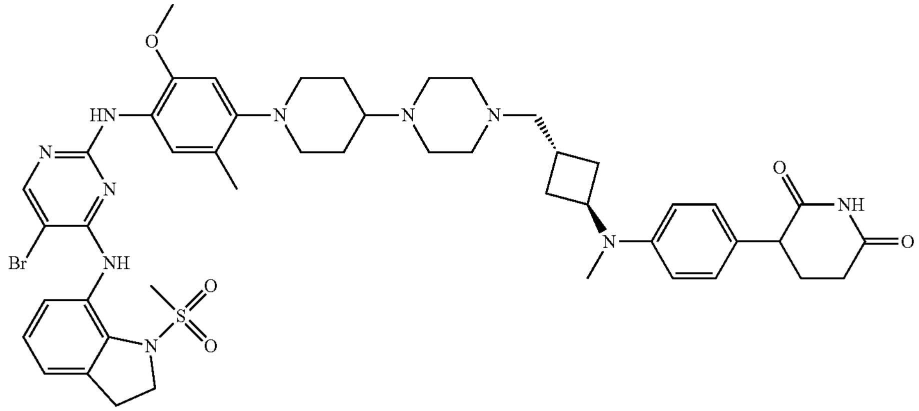
177
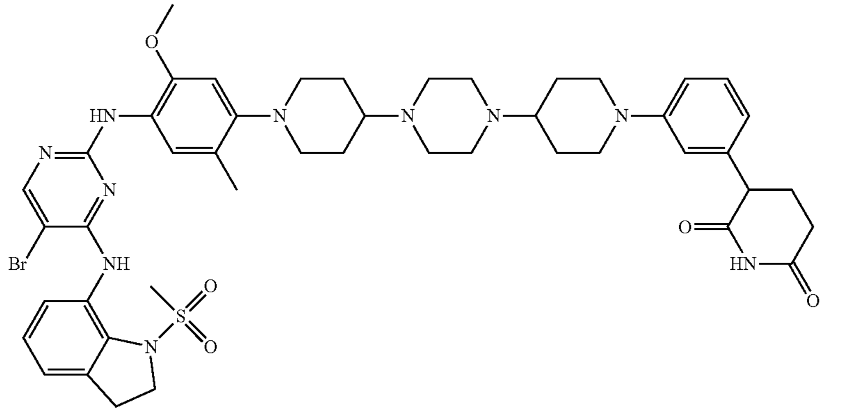
178
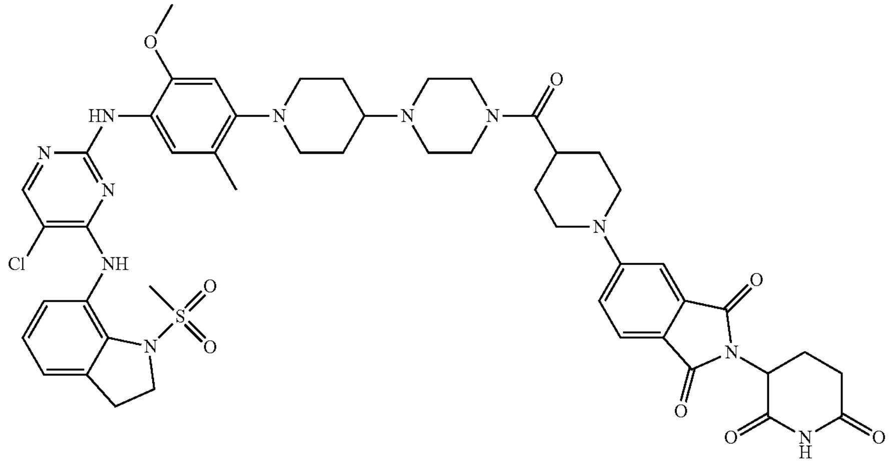
180
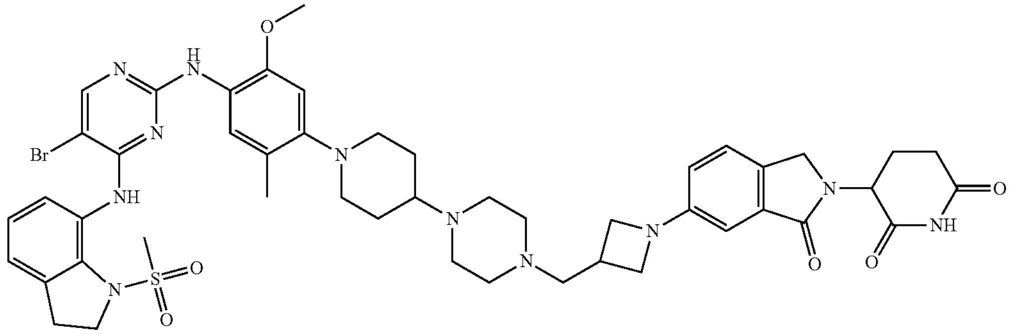

-continued
181
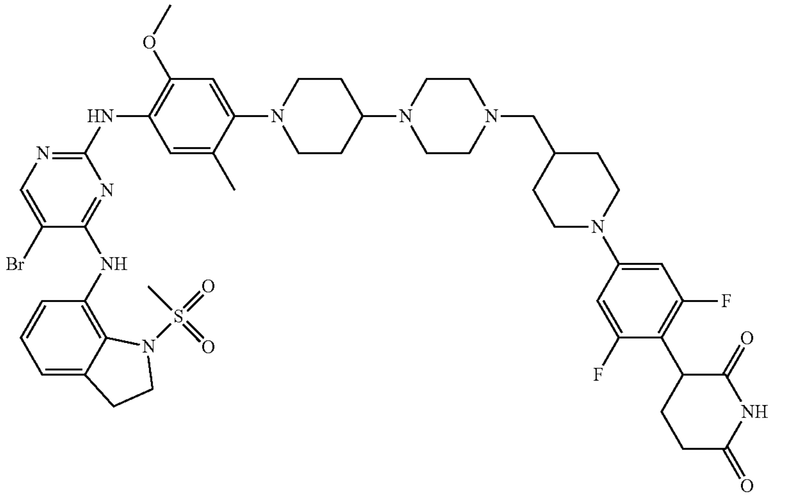
182
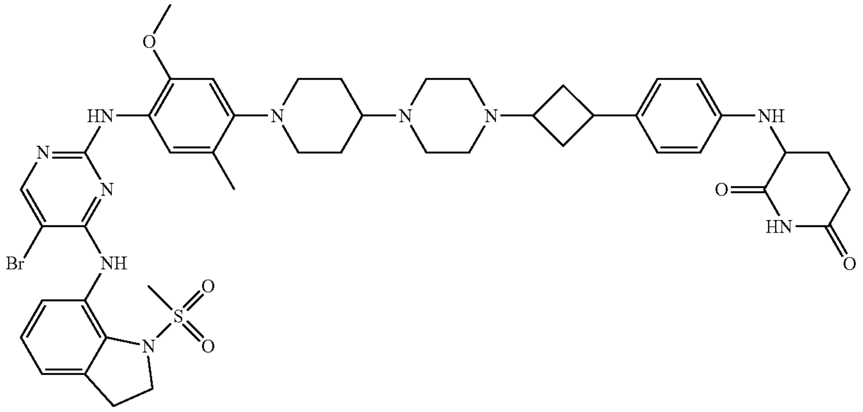
183
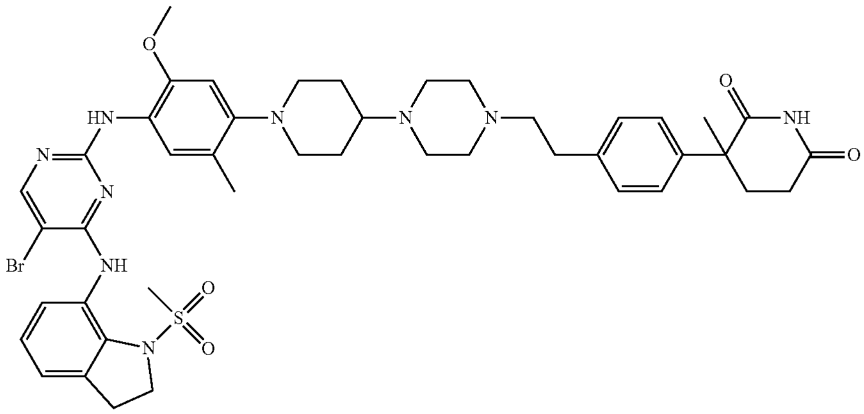

-continued
184
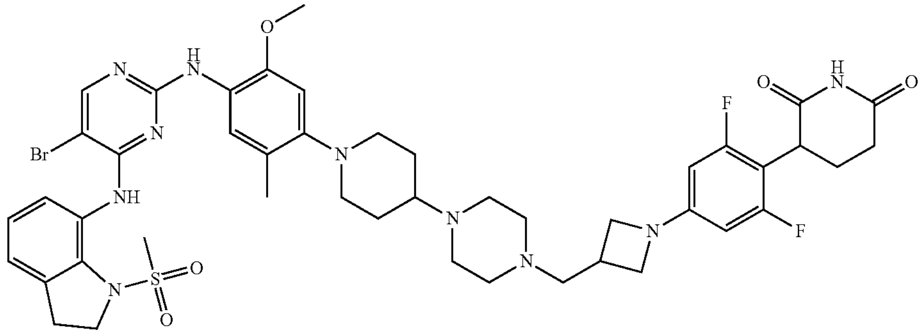
185
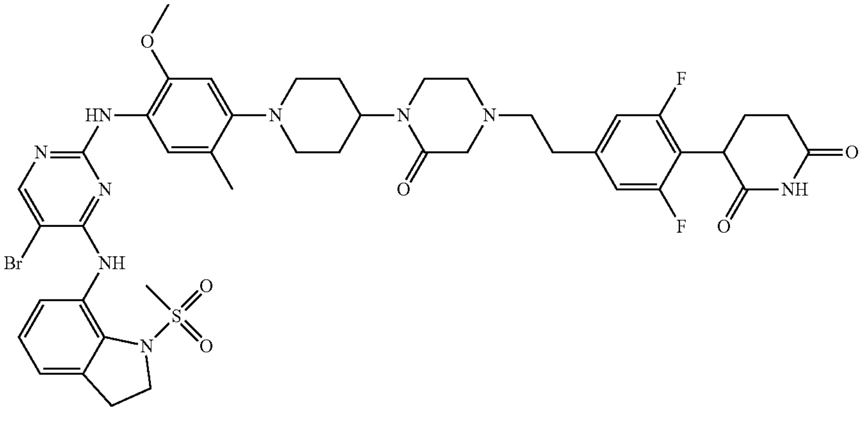
186
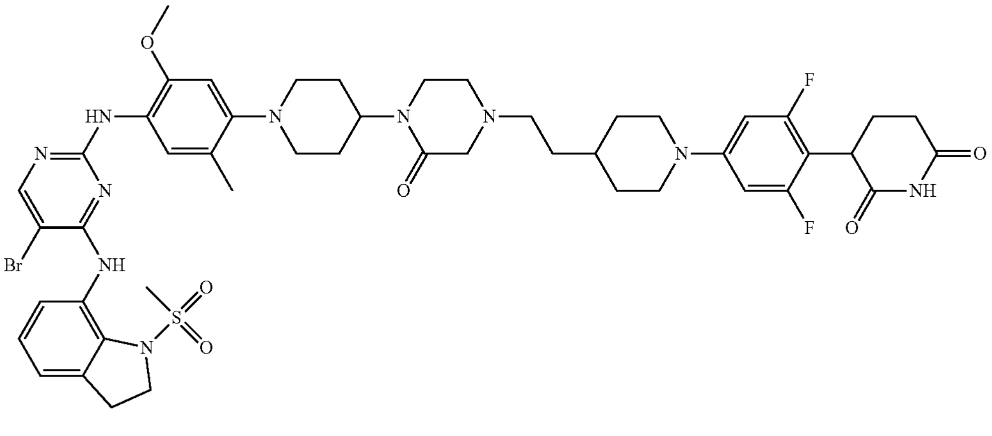

-continued
187
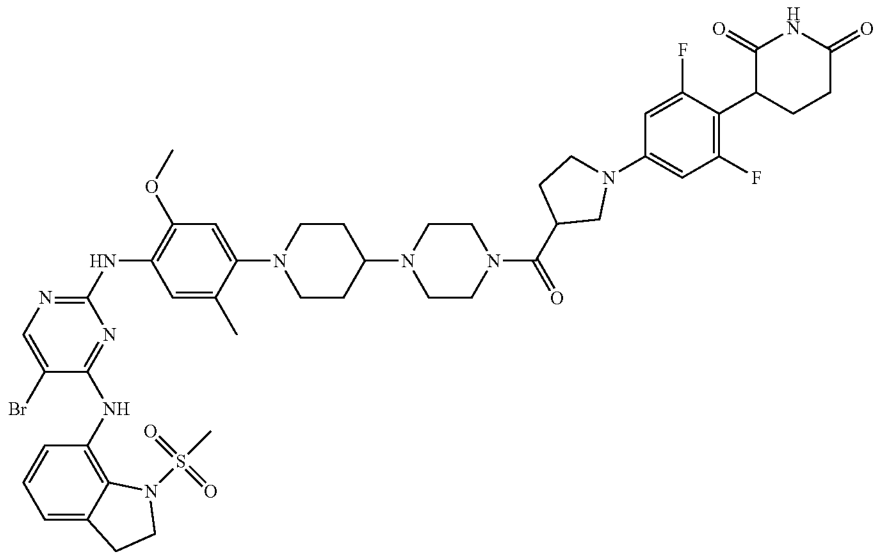
188
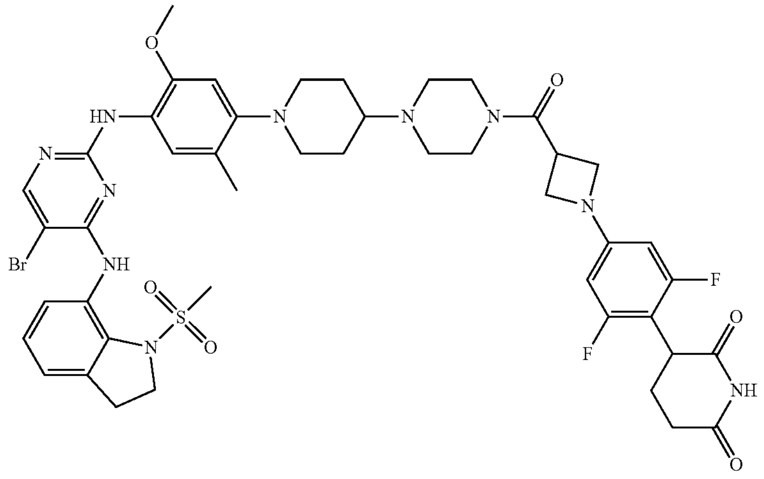
192
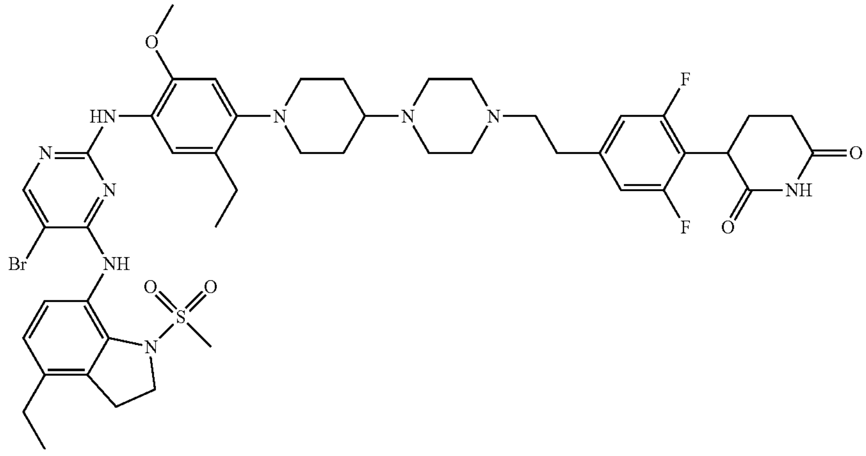

-continued
193
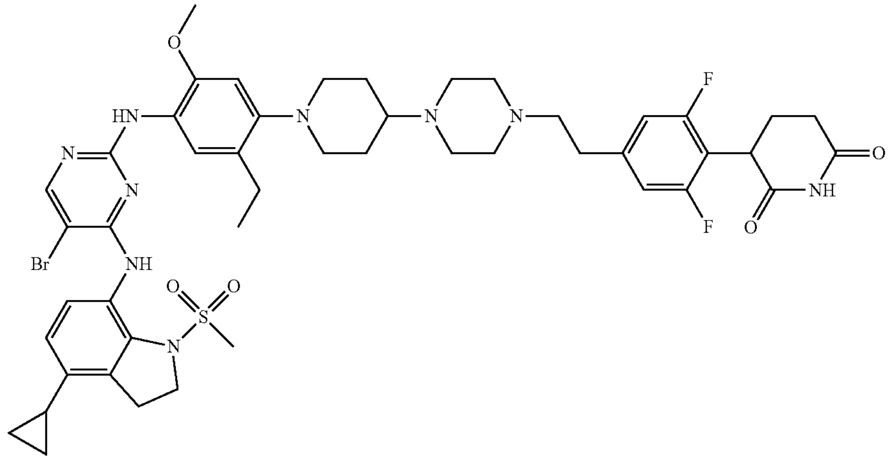
194
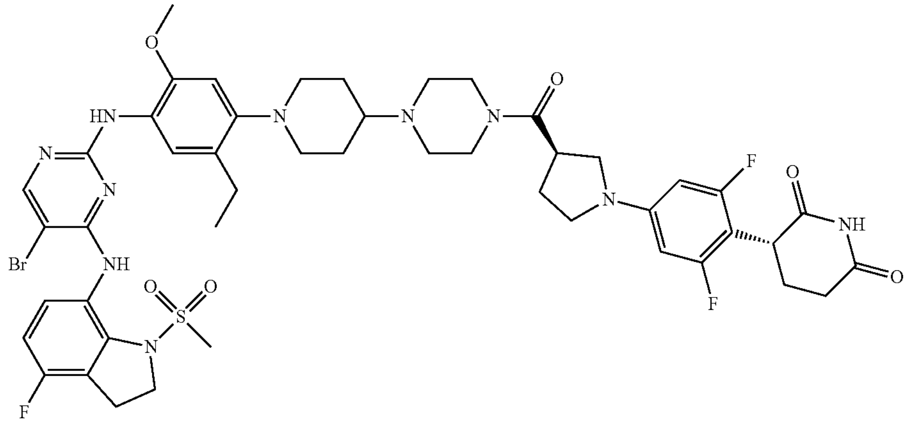
195
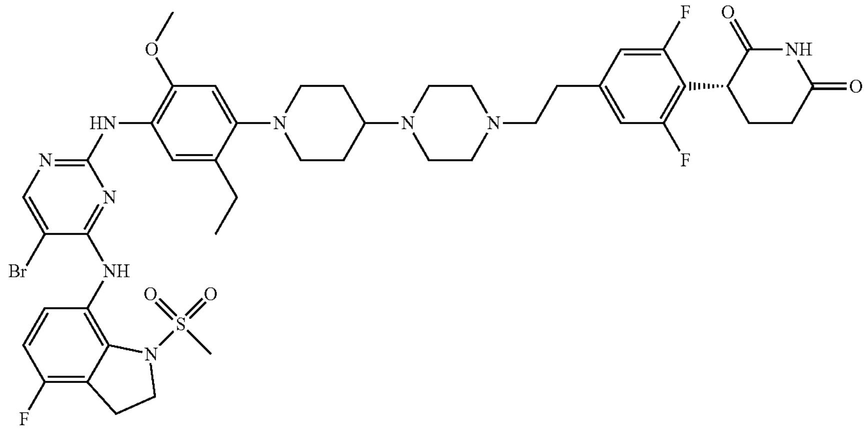

-continued
196
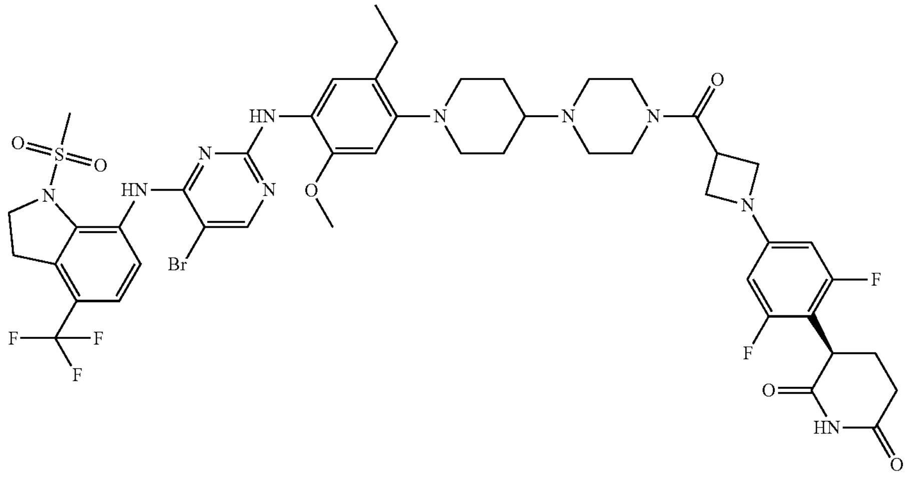
197
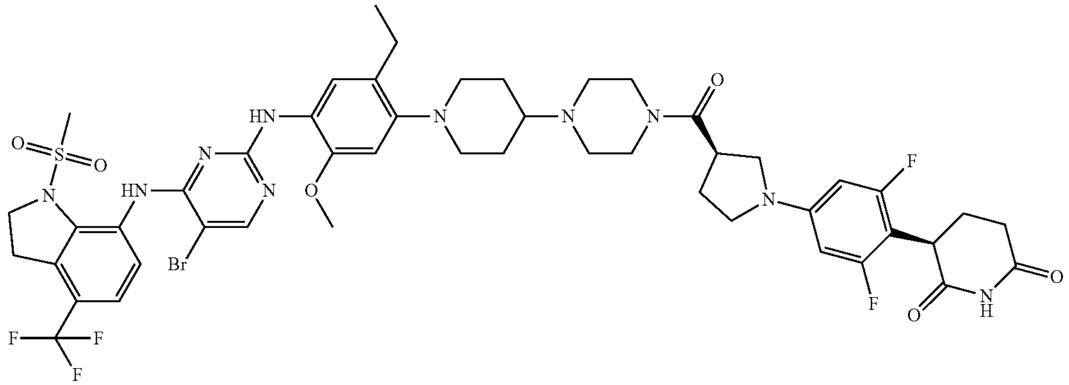
198
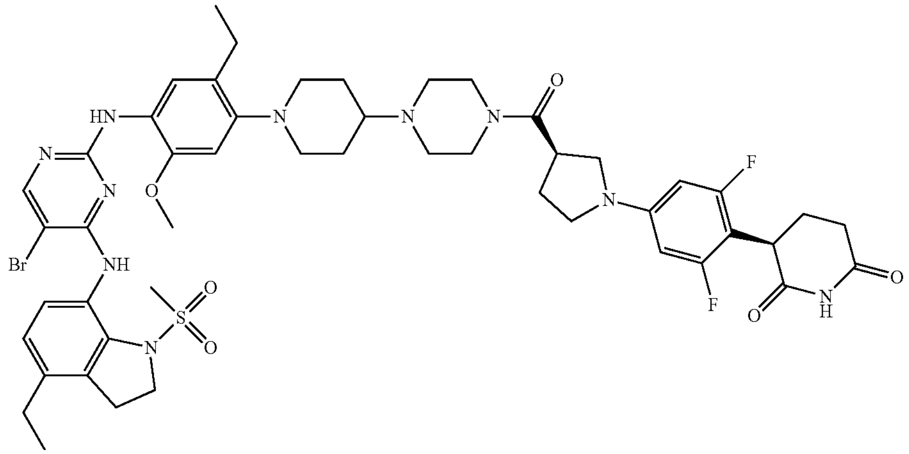

-continued

200

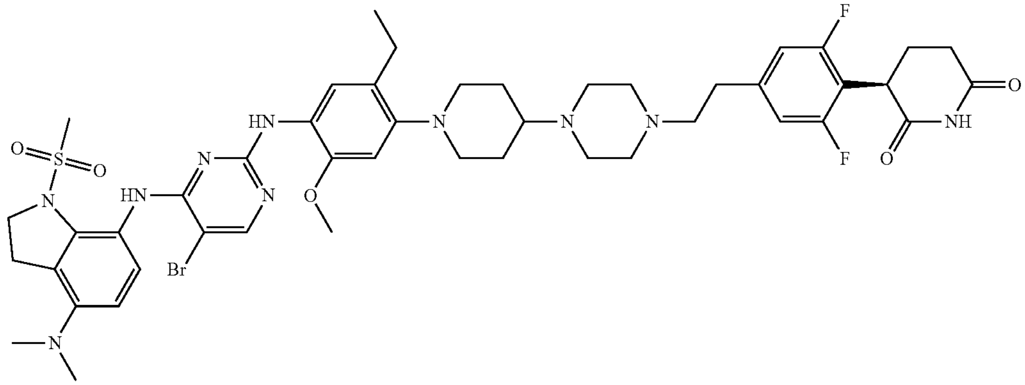

203

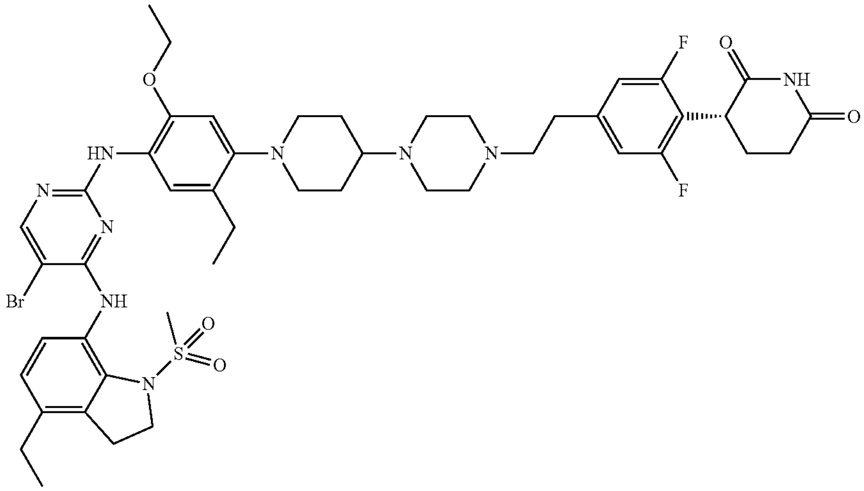

or an N-oxide thereof, or a pharmaceutically acceptable salt thereof, or a stereoisomer thereof, or a tautomer or a prodrug thereof.

27. A pharmaceutical composition comprising the compound of claim 1 or an N-oxide thereof, or a pharmaceutically acceptable salt thereof, or a stereoisomer thereof, or a tautomer or a prodrug thereof, together with a pharmaceutically acceptable excipient.

28. A method of treating a disease in which EGFR modulation is involved, comprising administrating to a subject in need thereof a therapeutically effective amount of the compound of claim 1 or an N-oxide thereof, or a pharmaceutically acceptable salt thereof, or a stereoisomer thereof, or a tautomer or a prodrug thereof; wherein the disease is selected from cancer.

29. The method of claim 28, wherein the disease is pancreatic cancer, breast cancer, glioblastoma multiforme, head and neck cancer, or non-small cell lung cancer.

30. The compound of claim 2, wherein $R^{1a}$ is selected from —$CH_3$, —$C_2H_5$, —$C_3H_7$, -tert-butyl, -n-butyl, -iso-butyl, —$C_5H_{11}$, -cyclopropyl,

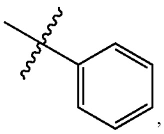, 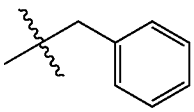,

-continued

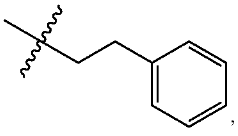, 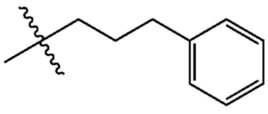,

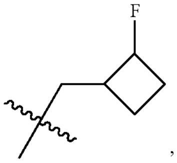, 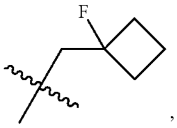,

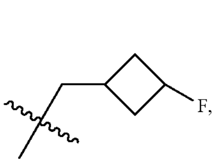 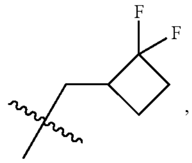,

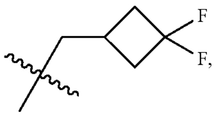

-$CHF_2$, —$CF_3$, —$N(CH_3)_2$, —$NHCH_3$, —$NHC_2H_5$, or —$NHC_3H_7$.

31. The compound of claim 3, wherein $R^2$ is selected from hydrogen, —F, —Cl, —Br, —I, methyl, ethyl, propyl, butyl, pentyl, hexyl, heptyl, or octyl; or two germinal $R^2$, together with the atom to which they are attached, form a spiro 3-, 4-membered cycloalkyl.

32. The compound of claim 3, wherein $R^2$ is selected from hydrogen, F, Cl, Br, I, —$CH_3$, —$C_2H_5$, —$C_3H_7$, —$C_4H_9$, or —$C_5H_{11}$; or two germinal $R^2$, together with the atom to which they are attached, form a spiro cyclopropyl or a spiro cyclobutyl.

33. The compound of claim 3, wherein $R^3$, $R^9$ and $R^{10}$ are each independently selected from H, F, Br, Cl, I, —$CH_3$, —$C_2H_5$, —$C_3H_7$, —$C_4H_9$, —$C_5H_{11}$, —$CF_3$, cyclopropyl, cyclobutyl, cyclopentyl, cyclohexyl, cycloheptyl, cyclooctyl, —$NH_2$, —$N(CH_3)_2$, —$N(CH_3)C_2H_5$, —$N(C_2H_5)_2$, —$OCH_3$, —$OC_2H_5$, —$OC_3H_7$, —$OC_4H_9$, or —$OC_5H_{11}$.

34. The compound of claim 5, wherein

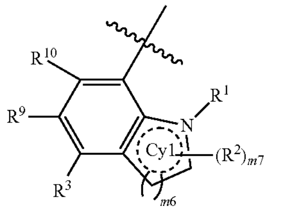

moiety is (a)

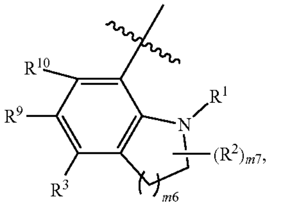

or (b),

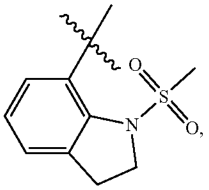
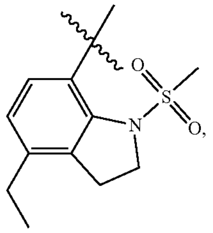
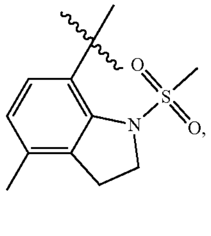
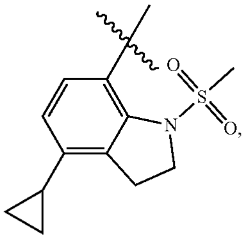
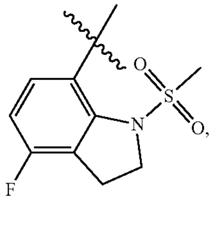
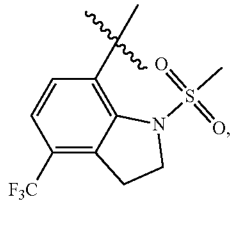

-continued

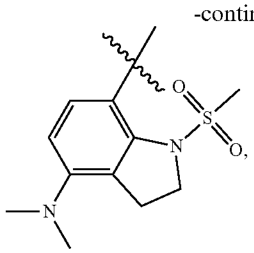
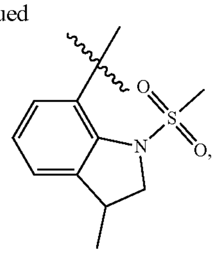
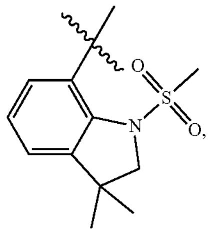
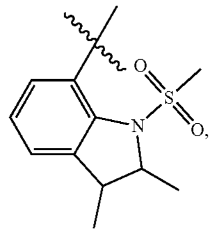
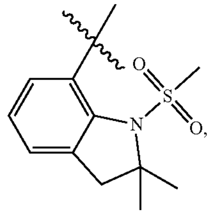
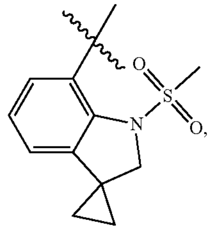
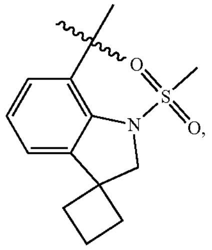
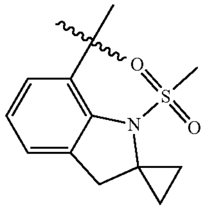

or

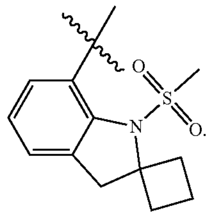

35. The compound of claim 6, wherein $R^4$ and $R^{11}$, together with the atom(s) to which they are attached, form a 3-, 4-, 5-, 6-, 7- or 8-membered ring, said ring comprising 0, 1 or 2 heteroatom(s) independently selected from nitrogen, oxygen, or optionally oxidized sulfur as ring member(s), said ring is optionally substituted with at least one substituent $R^{4e}$;

$R^{4e}$ is selected from —F, —Cl, —Br, —I, methyl, ethyl, propyl, butyl, pentyl, hexyl, heptyl, octyl, cyclopropyl, cyclobutyl, cyclopentyl, cyclohexyl, cycloheptyl, cyclooctyl, 3- to 8-membered heterocyclyl, phenyl, 5- to 12-membered heteroaryl, oxo, —CN, or —$OR^{4c}$;

$R^{4e}$ is independently hydrogen, —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl, or 5- to 12-membered heteroaryl.

36. The compound of claim 6, wherein $R^4$ and $R^{11}$, together with the atom(s) to which they are attached, form a 5- or 6-membered ring, said ring comprising 1 or 2 heteroatom(s) independently selected from nitrogen, oxygen, or optionally oxidized sulfur, said ring is optionally substituted with at least one substituent $R^{4e}$;

$R^{4e}$ is selected from —F, —Cl, —Br, —I, methyl, ethyl, propyl, butyl, pentyl, hexyl, heptyl, octyl, cyclopropyl, cyclobutyl, cyclopentyl, cyclohexyl, cycloheptyl, cyclooctyl, phenyl, 5- to 12-membered heteroaryl, oxo, —CN, $—OCH_3$, $—OC_2H_5$, $—OC_3H_7$, $—OC_4H_9$, and $—OC_5H_{11}$.

37. The compound of claim 10, wherein $Z^1$, $Z^2$, $Z^3$ and $Z^4$ are each independently $—CR^z$;

$R^z$, at each of its occurrences, is independently selected from hydrogen, —F, —Cl, —Br, —I, methyl, ethyl, propyl, butyl, pentyl, hexyl, heptyl, octyl, $—OCH_3$, $—OC_2H_5$, $—OC_3H_7$, $—OC_4H_9$, or $—OC_5H_{11}$; or two $R^z$, when attached to adjacent carbon atoms of the ring, together with the atoms to which they are attached, form a 4-, 5-, 6- or 7-membered ring, said ring comprising 0, 1 or 2 heteroatom(s) independently selected from nitrogen or oxygen, said ring is optionally substituted with at least one substituent $R^{Zc}$, wherein two germinal $R^{Zc}$, together with the atom to which they are attached, form a spiro 3-, 4-, 5- or 6-membered cycloalkyl or, two $R^{Zc}$ on different atoms, together with the atoms to which they are attached, form a 3-, 4-, 5- or 6-membered cycloalkyl.

38. The compound of claim 20, wherein $R^{14}$ is independently selected from H, F, Cl, Br, I, $CH_3$, $—OCH_3$, $CH_2F$, CN, $CHF_2$, or $CF_3$;

$X^8$ is independently selected from CF, CH, $C(CH_3)$, $C(C_2H_5)$, $C(C_3H_7)$, C(CN) or N;

$L^4$ is independently selected from a single bond, —O—, —NH—, $—CH_2—$, —CHF—, or $—CF_2—$;

$Y^1$, $Y^2$, and $Y^3$ are each independently selected from $CR^a$ or N, wherein $R^a$ is each independently selected from hydrogen, halogen, $—C_{1-8}$alkyl or $—C_{1-8}$alkoxy, wherein each of said $—C_{1-8}$alkyl or $—C_{1-8}$alkoxy is optionally substituted with at least one or more halogen, hydroxy, halogen, $—C_{1-8}$alkyl, or $—C_{1-8}$alkoxy;

$X^9$ is $CH_2$;

$n_6$ is independently 0, 1 or 2.

* * * * *